(12) United States Patent
Karol

(10) Patent No.: US 12,209,897 B2
(45) Date of Patent: Jan. 28, 2025

(54) MEDICAL TREATMENT SYSTEM AND METHODS USING A PLURALITY OF FLUID LINES

(71) Applicant: DEKA Products Limited Partnership, Manchester, NH (US)

(72) Inventor: Daniel S. Karol, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 18/787,166

(22) Filed: Jul. 29, 2024

(65) Prior Publication Data

US 2024/0385022 A1   Nov. 21, 2024

Related U.S. Application Data

(60) Continuation of application No. 18/606,446, filed on Mar. 15, 2024, which is a division of application No. (Continued)

(51) Int. Cl.
*A61M 1/28* (2006.01)
*A61M 1/14* (2006.01)
(Continued)

(52) U.S. Cl.
CPC ........... *G01F 22/02* (2013.01); *A61M 1/1524* (2022.05); *A61M 1/154* (2022.05); *A61M 1/155* (2022.05);
(Continued)

(58) Field of Classification Search
CPC .... A61M 1/155; A61M 1/1565; A61M 1/159; A61M 1/28; A61M 1/1561; A61M 1/1524; A61M 1/282
See application file for complete search history.

(56) References Cited

U.S. PATENT DOCUMENTS

| | | |
|---|---|---|
| 3,815,423 A | 6/1974 | Gearhart |
| 4,086,653 A | 4/1978 | Gernes |
| (Continued) | | |

FOREIGN PATENT DOCUMENTS

| | | |
|---|---|---|
| WO | WO1990013795 A2 | 11/1990 |
| WO | WO1995035124 A1 | 12/1995 |
| (Continued) | | |

OTHER PUBLICATIONS

File Wrapper of European Patent Publication No. EP 2 289 577 A1, Jun. 22, 2010 through Jul. 15, 2015, 147 pgs.

(Continued)

*Primary Examiner* — Courtney B Fredrickson
(74) *Attorney, Agent, or Firm* — Toohey Law Group, LLC; Kevin D. Mandro

(57) ABSTRACT

A system including a pumping cassette having a first side including number of valve wells and second side having a fluid bus. Each side may be covered by a flexible membrane. A control surface having a number of valve well control stations actuatable with respect to the flexible membrane covering the first side of the cassette to open and close the valve wells when the cassette is mated against the control surface may be included. A pressure distribution assembly having a positive and negative pressure source and a number of pneumatic valves may be included. A controller configured to selectively actuate the number of pneumatic valves to apply pressure against the valve well control stations in a valve pumping sequence until a volume displaced through the fluid bus of the pumping cassette from a source to a destination is within a range of a target volume may be included.

13 Claims, 214 Drawing Sheets

Related U.S. Application Data

16/384,082, filed on Apr. 15, 2019, now Pat. No. 11,965,766.

(60) Provisional application No. 62/658,731, filed on Apr. 17, 2018.

(51) Int. Cl.
*G01F 22/02* (2006.01)
*G16H 40/63* (2018.01)

(52) U.S. Cl.
CPC ........ *A61M 1/1561* (2022.05); *A61M 1/1565* (2022.05); *A61M 1/159* (2022.05); *A61M 1/282* (2014.02); *G16H 40/63* (2018.01); *A61M 2205/14* (2013.01); *A61M 2205/15* (2013.01); *A61M 2205/18* (2013.01); *A61M 2205/3306* (2013.01); *A61M 2205/3317* (2013.01); *A61M 2205/3327* (2013.01); *A61M 2205/3331* (2013.01); *A61M 2205/3368* (2013.01); *A61M 2205/3396* (2013.01); *A61M 2205/3584* (2013.01); *A61M 2205/366* (2013.01); *A61M 2205/42* (2013.01); *A61M 2205/50* (2013.01); *A61M 2205/502* (2013.01); *A61M 2205/505* (2013.01); *A61M 2205/52* (2013.01); *A61M 2205/581* (2013.01); *A61M 2205/6063* (2013.01); *A61M 2205/702* (2013.01); *A61M 2205/8206* (2013.01)

(56) References Cited

U.S. PATENT DOCUMENTS

| | | |
|---|---|---|
| 4,236,880 A | 12/1980 | Archibald |
| 4,265,601 A | 5/1981 | Mandroian |
| 4,411,649 A | 10/1983 | Kamen |
| 4,429,700 A | 2/1984 | Thees et al. |
| 4,456,030 A | 6/1984 | Bogossian |
| 4,468,219 A | 8/1984 | George et al. |
| 4,479,760 A | 10/1984 | Bilstad et al. |
| 4,519,239 A | 5/1985 | Kiesewetter et al. |
| 4,586,920 A | 5/1986 | Peabody |
| 4,593,561 A | 6/1986 | Gavrilovic |
| 4,611,578 A | 9/1986 | Heimes |
| 4,691,709 A | 9/1987 | Cohen |
| 4,778,449 A | 10/1988 | Weber et al. |
| 4,778,451 A | 10/1988 | Kamen |
| 4,826,482 A | 5/1989 | Kamen |
| 4,922,805 A | 5/1990 | Beswick |
| 4,927,411 A | 5/1990 | Pastrone et al. |
| 4,950,134 A | 8/1990 | Bailey et al. |
| 4,976,162 A | 12/1990 | Kamen |
| 5,088,515 A | 2/1992 | Kamen |
| 5,167,837 A | 12/1992 | Snodgrass et al. |
| 5,178,182 A | 1/1993 | Kamen |
| 5,193,990 A | 3/1993 | Kamen et al. |
| 5,195,986 A | 3/1993 | Kamen |
| 5,197,787 A | 3/1993 | Matsuda et al. |
| 5,207,645 A | 5/1993 | Ross et al. |
| 5,211,201 A | 5/1993 | Kamen et al. |
| 5,213,477 A | 5/1993 | Watanabe et al. |
| 5,222,946 A | 6/1993 | Kamen |
| 5,250,027 A | 10/1993 | Lewis et al. |
| 5,253,982 A | 10/1993 | Niemiec et al. |
| 5,275,724 A | 1/1994 | Bucchianeri et al. |
| 5,302,093 A | 4/1994 | Owens et al. |
| 5,336,051 A | 8/1994 | Tamari |
| 5,349,852 A | 9/1994 | Kamen et al. |
| 5,350,357 A | 9/1994 | Kamen et al. |
| 5,429,483 A | 7/1995 | Tamari |
| 5,431,626 A | 7/1995 | Bryant et al. |
| 5,431,629 A | 7/1995 | Lampropoulos et al. |
| 5,437,673 A | 8/1995 | Baust et al. |
| 5,438,510 A | 8/1995 | Bryant et al. |
| 5,447,286 A | 9/1995 | Kamen et al. |
| 5,461,901 A | 10/1995 | Ottestad |
| 5,474,683 A | 12/1995 | Bryant et al. |
| 5,514,102 A | 5/1996 | Winterer et al. |
| 5,542,919 A | 8/1996 | Simon et al. |
| 5,620,604 A | 4/1997 | Stone |
| 5,628,908 A | 5/1997 | Kamen et al. |
| 5,641,405 A | 6/1997 | Keshaviah et al. |
| 5,641,892 A | 6/1997 | Larkins et al. |
| 5,711,483 A | 1/1998 | Hays |
| 5,755,683 A | 5/1998 | Houle |
| 5,792,367 A | 8/1998 | Mattisson et al. |
| 5,795,328 A | 8/1998 | Barnitz et al. |
| 5,813,842 A | 9/1998 | Tamari |
| 5,814,004 A | 9/1998 | Tamari |
| 5,820,582 A | 10/1998 | Keilman |
| 5,902,336 A | 5/1999 | Mishkin |
| 5,938,634 A | 8/1999 | Packard |
| 5,980,481 A | 11/1999 | Grosuch |
| 6,041,801 A | 3/2000 | Gray et al. |
| 6,049,699 A | 4/2000 | Javitt |
| 6,070,761 A | 6/2000 | Bloom et al. |
| 6,074,359 A | 6/2000 | Keshaviah et al. |
| 6,132,405 A | 10/2000 | Nilsson et al. |
| 6,165,154 A | 12/2000 | Gray et al. |
| 6,167,837 B1 | 1/2001 | Cook |
| 6,210,361 B1 | 4/2001 | Kamen et al. |
| 6,223,130 B1 | 4/2001 | Gray et al. |
| 6,228,047 B1 | 5/2001 | Dadson |
| 6,302,653 B1 | 10/2001 | Bryant et al. |
| 6,343,614 B1 | 2/2002 | Gray et al. |
| 6,382,923 B1 | 5/2002 | Gray |
| 6,406,276 B1 | 7/2002 | Normand et al. |
| 6,416,293 B1 | 7/2002 | Bouchard et al. |
| 6,464,667 B1 | 10/2002 | Kamen et al. |
| 6,491,658 B1 | 12/2002 | Miura et al. |
| 6,497,676 B1 | 12/2002 | Childers et al. |
| 6,497,680 B1 | 12/2002 | Holst et al. |
| 6,503,062 B1 | 1/2003 | Gray et al. |
| 6,520,747 B2 | 2/2003 | Gray et al. |
| 6,558,343 B1 | 5/2003 | Neftel |
| 6,776,152 B2 | 8/2004 | Gray et al. |
| 6,808,369 B2 | 10/2004 | Gray et al. |
| 6,905,479 B1 | 7/2005 | Bouchard et al. |
| 7,354,190 B2 | 4/2008 | Demers et al. |
| 7,410,587 B2 | 8/2008 | Schick |
| 7,421,316 B2 | 9/2008 | Gray et al. |
| 7,461,968 B2 | 12/2008 | Demers et al. |
| 7,575,564 B2 | 8/2009 | Childers |
| 7,632,078 B2 | 12/2009 | Demers et al. |
| 7,632,080 B2 | 12/2009 | Tracey et al. |
| 7,662,139 B2 | 2/2010 | Demers et al. |
| 7,794,141 B2 | 9/2010 | Perry et al. |
| 7,853,362 B2 | 12/2010 | Gray et al. |
| 7,959,196 B2 | 7/2011 | Dale |
| 8,158,102 B2 | 4/2012 | Demers et al. |
| 8,197,439 B2 | 6/2012 | Wang et al. |
| 8,246,826 B2 | 8/2012 | Wilt et al. |
| 8,292,594 B2 | 10/2012 | Tracey et al. |
| 8,357,298 B2 | 1/2013 | Demers et al. |
| 8,393,690 B2 | 3/2013 | Grant et al. |
| 8,409,441 B2 | 4/2013 | Wilt |
| 8,485,800 B2 | 7/2013 | Lanigan et al. |
| 8,491,184 B2 | 7/2013 | Kamen et al. |
| 8,708,950 B2 | 4/2014 | Scarpaci et al. |
| 8,731,726 B2 | 5/2014 | Gray et al. |
| 8,821,475 B2 | 9/2014 | Distler et al. |
| 8,840,581 B2 | 9/2014 | McGill et al. |
| D728,779 S | 5/2015 | Sabin et al. |
| 8,989,906 B2 | 5/2015 | Gray et al. |
| 9,022,969 B2 | 5/2015 | Helmore et al. |
| 9,028,440 B2 | 5/2015 | Helmore et al. |
| D735,319 S | 7/2015 | Sabin et al. |
| 9,078,971 B2 | 7/2015 | Scarpaci et al. |
| D736,370 S | 8/2015 | Sabin et al. |
| 9,151,646 B2 | 10/2015 | Kamen et al. |
| D745,661 S | 12/2015 | Collins et al. |
| D749,206 S | 2/2016 | Johnson et al. |
| 9,248,225 B2 | 2/2016 | Demers et al. |

(56) References Cited

U.S. PATENT DOCUMENTS

| | | |
|---|---|---|
| D751,689 S | 3/2016 | Peret et al. |
| D751,690 S | 3/2016 | Peret et al. |
| D752,209 S | 3/2016 | Peret et al. |
| 9,295,778 B2 | 3/2016 | Kamen et al. |
| D754,065 S | 4/2016 | Gray et al. |
| 9,310,314 B2 | 4/2016 | Scarpaci et al. |
| D756,386 S | 5/2016 | Kendler et al. |
| D758,399 S | 6/2016 | Kendler et al. |
| D760,288 S | 6/2016 | Kendler et al. |
| D760,289 S | 6/2016 | Kendler et al. |
| 9,358,332 B2 | 6/2016 | McGill et al. |
| 9,364,394 B2 | 6/2016 | Demers et al. |
| 9,372,486 B2 | 6/2016 | Peret et al. |
| D760,782 S | 7/2016 | Kendler et al. |
| D760,888 S | 7/2016 | Gill et al. |
| 9,400,873 B2 | 7/2016 | Kamen et al. |
| 9,408,966 B2 | 8/2016 | Kamen |
| D767,756 S | 9/2016 | Sabin |
| 9,435,455 B2 | 9/2016 | Peret et al. |
| D768,716 S | 10/2016 | Kendler et al. |
| 9,465,919 B2 | 10/2016 | Kamen et al. |
| 9,488,200 B2 | 11/2016 | Kamen et al. |
| D774,645 S | 12/2016 | Gill et al. |
| 9,518,958 B2 | 12/2016 | Wilt et al. |
| 9,636,455 B2 | 5/2017 | Kamen et al. |
| D789,516 S | 6/2017 | Gill et al. |
| 9,675,756 B2 | 6/2017 | Kamen et al. |
| 9,677,555 B2 | 6/2017 | Kamen et al. |
| 9,687,417 B2 | 6/2017 | Demers et al. |
| D792,963 S | 7/2017 | Gill |
| D795,424 S | 8/2017 | Sloss |
| D795,805 S | 8/2017 | Gray et al. |
| 9,719,964 B2 | 8/2017 | Blumberg |
| 9,724,465 B2 | 8/2017 | Peret et al. |
| 9,724,466 B2 | 8/2017 | Peret et al. |
| 9,724,467 B2 | 8/2017 | Peret et al. |
| 9,730,731 B2 | 8/2017 | Langenfeld et al. |
| 9,744,300 B2 | 8/2017 | Kamen et al. |
| 9,746,093 B2 | 8/2017 | Peret et al. |
| 9,746,094 B2 | 8/2017 | Peret et al. |
| 9,759,343 B2 | 9/2017 | Peret et al. |
| 9,759,369 B2 | 9/2017 | Gray et al. |
| 9,772,044 B2 | 9/2017 | Peret et al. |
| D799,025 S | 10/2017 | Johnson et al. |
| D801,519 S | 10/2017 | Sabin et al. |
| 9,789,247 B2 | 10/2017 | Kamen et al. |
| D802,118 S | 11/2017 | Peret et al. |
| D803,386 S | 11/2017 | Sabin et al. |
| D803,387 S | 11/2017 | Bodwell et al. |
| D804,017 S | 11/2017 | Sabin |
| 9,808,572 B2 | 11/2017 | Kamen et al. |
| D805,183 S | 12/2017 | Sabin et al. |
| 9,856,990 B2 | 1/2018 | Peret et al. |
| 9,861,732 B2 | 1/2018 | Scarpaci et al. |
| D813,376 S | 3/2018 | Peret et al. |
| D814,021 S | 3/2018 | Sabin |
| D815,730 S | 4/2018 | Collins et al. |
| D816,685 S | 5/2018 | Kendler et al. |
| D816,829 S | 5/2018 | Peret et al. |
| D817,479 S | 5/2018 | Sabin et al. |
| D817,480 S | 5/2018 | Sabin et al. |
| 9,968,730 B2 | 5/2018 | Blumberg, Jr. et al. |
| 9,976,665 B2 | 5/2018 | Peret et al. |
| 10,044,791 B2 | 8/2018 | Kamen et al. |
| 10,082,241 B2 | 9/2018 | Janway et al. |
| 10,088,346 B2 | 10/2018 | Kane et al. |
| 10,108,785 B2 | 10/2018 | Kamen et al. |
| 10,113,660 B2 | 10/2018 | Peret et al. |
| 10,126,267 B2 | 11/2018 | Blumberg, Jr. |
| 10,185,812 B2 | 1/2019 | Kamen et al. |
| 10,201,647 B2 | 2/2019 | Norris et al. |
| 10,202,970 B2 | 2/2019 | Kamen et al. |
| 10,202,971 B2 | 2/2019 | Kamen et al. |
| 10,220,135 B2 | 3/2019 | Kamen et al. |
| 10,228,683 B2 | 3/2019 | Peret et al. |
| 10,242,159 B2 | 3/2019 | Kamen et al. |
| 10,245,374 B2 | 4/2019 | Kamen et al. |
| 10,265,463 B2 | 4/2019 | Biasi et al. |
| 10,288,057 B2 | 5/2019 | Kamen et al. |
| 10,316,834 B2 | 6/2019 | Kamen et al. |
| D854,145 S | 7/2019 | Collins |
| 10,380,321 B2 | 8/2019 | Kamen et al. |
| 10,391,241 B2 | 8/2019 | Desch et al. |
| D860,437 S | 9/2019 | Collins |
| 10,426,517 B2 | 10/2019 | Langenfeld et al. |
| 10,436,342 B2 | 10/2019 | Peret et al. |
| 10,453,157 B2 | 10/2019 | Kamen et al. |
| 10,468,132 B2 | 11/2019 | Kamen et al. |
| 10,471,402 B2 | 11/2019 | Demers et al. |
| 10,478,261 B2 | 11/2019 | Demers et al. |
| 10,488,848 B2 | 11/2019 | Peret et al. |
| 10,561,787 B2 | 2/2020 | Kamen et al. |
| 10,563,681 B2 | 2/2020 | Kamen et al. |
| 10,571,070 B2 | 2/2020 | Gray et al. |
| 10,655,779 B2 | 5/2020 | Janway et al. |
| 10,670,182 B2 | 6/2020 | Janway et al. |
| 10,718,445 B2 | 7/2020 | Yoo |
| 10,722,645 B2 | 7/2020 | Kamen et al. |
| 10,739,759 B2 | 8/2020 | Peret et al. |
| 10,753,353 B2 | 8/2020 | Kamen et al. |
| 10,761,061 B2 | 9/2020 | Wilt et al. |
| 10,839,953 B2 | 11/2020 | Kamen et al. |
| 10,844,970 B2 | 11/2020 | Peret et al. |
| D905,848 S | 12/2020 | Sloss et al. |
| 10,857,293 B2 | 12/2020 | Kamen et al. |
| 10,872,685 B2 | 12/2020 | Blumberg, Jr. et al. |
| 10,876,868 B2 | 12/2020 | Kane et al. |
| 10,894,638 B2 | 1/2021 | Peret et al. |
| 10,911,515 B2 | 2/2021 | Biasi et al. |
| D914,195 S | 3/2021 | Gray et al. |
| D914,196 S | 3/2021 | Gray et al. |
| D914,197 S | 3/2021 | Gray et al. |
| D917,045 S | 4/2021 | Gray |
| D918,396 S | 5/2021 | Gray et al. |
| 10,994,074 B2 | 5/2021 | Blumberg, Jr. et al. |
| 11,024,409 B2 | 6/2021 | Kamen et al. |
| 11,024,419 B2 | 6/2021 | Kamen et al. |
| 11,109,934 B2 | 9/2021 | Demers et al. |
| 11,129,933 B2 | 9/2021 | Kamen et al. |
| D937,413 S | 11/2021 | Gray |
| 11,164,672 B2 | 11/2021 | Kamen et al. |
| 11,179,688 B2 | 11/2021 | Demers et al. |
| 11,210,611 B2 | 12/2021 | Kamen et al. |
| 11,217,340 B2 | 1/2022 | Desch et al. |
| 11,227,687 B2 | 1/2022 | Kamen et al. |
| D943,736 S | 2/2022 | Sloss et al. |
| 11,244,745 B2 | 2/2022 | Kamen et al. |
| 11,295,846 B2 | 4/2022 | Kamen et al. |
| 11,328,803 B2 | 5/2022 | Kamen et al. |
| 11,339,887 B2 | 5/2022 | Peret et al. |
| 11,339,918 B2 | 5/2022 | Gray et al. |
| 11,348,674 B2 | 5/2022 | Kamen et al. |
| 2002/0085952 A1 | 7/2002 | Ellingboe et al. |
| 2002/0107474 A1 | 8/2002 | Noack |
| 2002/0147423 A1 | 10/2002 | Burbank et al. |
| 2003/0029451 A1 | 2/2003 | Blair et al. |
| 2003/0136181 A1 | 7/2003 | Balschat et al. |
| 2003/0218623 A1 | 11/2003 | Krensky et al. |
| 2003/0220607 A1 | 11/2003 | Busby et al. |
| 2003/0220608 A1 | 11/2003 | Huitt et al. |
| 2004/0019313 A1 | 1/2004 | Childers et al. |
| 2004/0044302 A1 | 3/2004 | Bernard et al. |
| 2004/0082903 A1 | 4/2004 | Micheli |
| 2008/0125693 A1* | 5/2008 | Gavin .................. A61M 1/287 604/29 |
| 2011/0313789 A1 | 12/2011 | Kamen et al. |
| 2012/0185267 A1 | 7/2012 | Kamen |
| 2013/0177455 A1 | 7/2013 | Kamen |
| 2013/0182381 A1 | 7/2013 | Gray |
| 2013/0184676 A1 | 7/2013 | Kamen |
| 2013/0188040 A1 | 7/2013 | Kamen |
| 2013/0191513 A1 | 7/2013 | Kamen |
| 2013/0197693 A1 | 8/2013 | Kamen |
| 2013/0204188 A1 | 8/2013 | Kamen |

(56) References Cited

U.S. PATENT DOCUMENTS

| | | |
|---|---|---|
| 2013/0272773 A1 | 10/2013 | Kamen |
| 2013/0281965 A1 | 10/2013 | Kamen |
| 2013/0297330 A1 | 11/2013 | Kamen |
| 2013/0310990 A1 | 11/2013 | Peret et al. |
| 2013/0317753 A1 | 11/2013 | Kamen |
| 2013/0317837 A1 | 11/2013 | Ballantyne |
| 2013/0336814 A1 | 12/2013 | Kamen |
| 2013/0339049 A1 | 12/2013 | Blumberg, Jr. |
| 2013/0346108 A1 | 12/2013 | Kamen |
| 2014/0165703 A1 | 6/2014 | Wilt |
| 2014/0180711 A1 | 6/2014 | Kamen |
| 2014/0188076 A1 | 7/2014 | Kamen |
| 2014/0188516 A1 | 7/2014 | Kamen |
| 2014/0195639 A1 | 7/2014 | Kamen |
| 2014/0227021 A1 | 8/2014 | Kamen |
| 2014/0318639 A1 | 10/2014 | Peret |
| 2014/0343492 A1 | 11/2014 | Kamen |
| 2015/0002667 A1 | 1/2015 | Peret et al. |
| 2015/0002668 A1 | 1/2015 | Peret et al. |
| 2015/0002677 A1 | 1/2015 | Peret et al. |
| 2015/0033823 A1 | 2/2015 | Blumberg, Jr. |
| 2015/0314083 A1 | 4/2015 | Blumberg, Jr. et al. |
| 2015/0154364 A1 | 6/2015 | Biasi et al. |
| 2015/0157791 A1 | 6/2015 | Desch et al. |
| 2015/0238228 A1 | 8/2015 | Langenfeld et al. |
| 2015/0257974 A1 | 9/2015 | Demers et al. |
| 2015/0332009 A1 | 11/2015 | Kane et al. |
| 2016/0055397 A1 | 2/2016 | Peret et al. |
| 2016/0055649 A1 | 2/2016 | Peret et al. |
| 2016/0061641 A1 | 3/2016 | Peret et al. |
| 2016/0063353 A1 | 3/2016 | Peret et al. |
| 2016/0073063 A1 | 3/2016 | Peret et al. |
| 2016/0084434 A1 | 3/2016 | Janway et al. |
| 2016/0097382 A1 | 4/2016 | Kamen et al. |
| 2016/0101227 A1* | 4/2016 | Norris ............... A61M 1/155 604/29 |
| 2016/0131272 A1 | 5/2016 | Yoo |
| 2016/0158437 A1 | 6/2016 | Biasi et al. |
| 2016/0179086 A1 | 6/2016 | Peret et al. |
| 2016/0184510 A1 | 6/2016 | Kamen et al. |
| 2016/0203292 A1 | 7/2016 | Kamen et al. |
| 2016/0262977 A1 | 9/2016 | Demers et al. |
| 2016/0319850 A1 | 11/2016 | Kamen et al. |
| 2016/0346056 A1 | 12/2016 | Demers et al. |
| 2016/0362234 A1 | 12/2016 | Peret et al. |
| 2017/0011202 A1 | 1/2017 | Kamen et al. |
| 2017/0045478 A1 | 2/2017 | Wilt et al. |
| 2017/0216516 A1 | 8/2017 | Dale et al. |
| 2017/0224909 A1 | 8/2017 | Kamen et al. |
| 2017/0259230 A1 | 9/2017 | Demers et al. |
| 2017/0266378 A1 | 9/2017 | Kamen et al. |
| 2017/0268495 A1 | 9/2017 | Overson et al. |
| 2017/0268497 A1 | 9/2017 | Kamen et al. |
| 2017/0284968 A1 | 10/2017 | Blumberg, Jr. |
| 2017/0296745 A1 | 10/2017 | Kamen et al. |
| 2017/0303969 A1 | 10/2017 | Langenfeld et al. |
| 2017/0319768 A1 | 11/2017 | Szpara et al. |
| 2017/0319769 A1 | 11/2017 | Wieslander et al. |
| 2017/0319770 A1 | 11/2017 | Fitzgerald et al. |
| 2017/0321841 A1 | 11/2017 | Gray et al. |
| 2017/0333623 A1 | 11/2017 | Kamen et al. |
| 2017/0335988 A1 | 11/2017 | Peret et al. |
| 2018/0038501 A1 | 2/2018 | Peret et al. |
| 2018/0066648 A1 | 3/2018 | Janway et al. |
| 2018/0080605 A1 | 3/2018 | Janway et al. |
| 2018/0106246 A1 | 4/2018 | Kamen et al. |
| 2018/0128259 A1 | 5/2018 | Kamen et al. |
| 2018/0224012 A1 | 8/2018 | Peret et al. |
| 2018/0228964 A1 | 8/2018 | Blumberg, Jr. et al. |
| 2018/0252359 A1 | 9/2018 | Janway et al. |
| 2018/0278676 A1 | 9/2018 | Kamen et al. |
| 2019/0009018 A1 | 1/2019 | Kamen et al. |
| 2019/0033104 A1 | 1/2019 | Kane et al. |
| 2019/0041362 A1 | 2/2019 | Blumberg, Jr. |
| 2019/0049029 A1 | 2/2019 | Peret et al. |
| 2019/0134298 A1 | 5/2019 | Kamen et al. |
| 2019/0139640 A1 | 5/2019 | Kamen et al. |
| 2019/0154026 A1 | 5/2019 | Kamen et al. |
| 2019/0170134 A1 | 6/2019 | Kamen et al. |
| 2019/0175821 A1 | 6/2019 | Kamen et al. |
| 2019/0179289 A1 | 6/2019 | Peret et al. |
| 2019/0189272 A1 | 6/2019 | Kamen et al. |
| 2019/0219047 A1 | 7/2019 | Kamen et al. |
| 2019/0249657 A1 | 8/2019 | Kamen et al. |
| 2019/0298913 A1 | 10/2019 | Biasi et al. |
| 2019/0316948 A1 | 10/2019 | Karol et al. |
| 2019/0328964 A1 | 10/2019 | Desch et al. |
| 2019/0341146 A1 | 11/2019 | Kamen et al. |
| 2019/0365421 A1 | 12/2019 | Langenfeld et al. |
| 2020/0025305 A1 | 1/2020 | Peret et al. |
| 2020/0051190 A1 | 2/2020 | Kamen et al. |
| 2020/0054823 A1 | 2/2020 | Baier et al. |
| 2020/0066388 A1 | 2/2020 | Kamen et al. |
| 2020/0070113 A1 | 3/2020 | Demers et al. |
| 2020/0078127 A1 | 3/2020 | Demers et al. |
| 2020/0171241 A1 | 6/2020 | Kamen et al. |
| 2020/0173469 A1 | 6/2020 | Kamen et al. |
| 2020/0182400 A1 | 6/2020 | Gray et al. |
| 2020/0278078 A1 | 9/2020 | Janway et al. |
| 2020/0292127 A1 | 9/2020 | Janway et al. |
| 2020/0297909 A1 | 9/2020 | Suljevic et al. |
| 2020/0347949 A1 | 11/2020 | Yoo |
| 2020/0371497 A1 | 11/2020 | Peret et al. |
| 2020/0386220 A1 | 12/2020 | Kamen et al. |
| 2020/0393414 A1 | 12/2020 | Wilt et al. |
| 2021/0023296 A1 | 1/2021 | Langenfeld et al. |
| 2021/0062929 A1 | 3/2021 | Peret et al. |
| 2021/0065867 A1 | 3/2021 | Kamen et al. |
| 2021/0085858 A1 | 3/2021 | Kamen et al. |
| 2021/0098102 A1 | 4/2021 | Blumberg, Jr. et al. |
| 2021/0116271 A1 | 4/2021 | Kane et al. |
| 2021/0125719 A1 | 4/2021 | Peret et al. |
| 2021/0252211 A1 | 8/2021 | Blumberg, Jr. et al. |
| 2021/0287790 A1 | 9/2021 | Kamen et al. |
| 2021/0304864 A1 | 9/2021 | Kamen et al. |
| 2021/0308366 A1 | 10/2021 | Kamen et al. |
| 2021/0365849 A1 | 11/2021 | Kamen et al. |
| 2021/0378777 A1 | 12/2021 | Demers et al. |
| 2022/0008649 A1 | 1/2022 | Kamen et al. |
| 2022/0044796 A1 | 2/2022 | Kamen et al. |
| 2022/0062541 A1 | 3/2022 | Kamen et al. |
| 2022/0122002 A1 | 4/2022 | Kamen et al. |
| 2022/0122710 A1 | 4/2022 | Desch et al. |
| 2022/0130536 A1 | 4/2022 | Kamen et al. |
| 2022/0143564 A1 | 5/2022 | Demers et al. |

FOREIGN PATENT DOCUMENTS

| | | |
|---|---|---|
| WO | WO1999006082 A1 | 2/1999 |
| WO | WO2013095459 A9 | 6/2013 |
| WO | WO2013096713 A2 | 6/2013 |
| WO | WO2013096718 A2 | 6/2013 |
| WO | WO2013096722 A2 | 6/2013 |
| WO | WO2013096909 A2 | 6/2013 |
| WO | WO2013176770 A2 | 11/2013 |
| WO | WO2013177357 A1 | 11/2013 |
| WO | WO2014100557 A2 | 6/2014 |
| WO | WO2014100571 A2 | 6/2014 |
| WO | WO2014100658 A1 | 6/2014 |
| WO | WO2014100687 A2 | 6/2014 |
| WO | WO2014100736 A2 | 6/2014 |
| WO | WO2014100744 A2 | 6/2014 |
| WO | WO2014144557 A2 | 6/2014 |
| WO | WO2015017275 A1 | 2/2015 |
| WO | PCT/US2019/27467 | 4/2019 |

OTHER PUBLICATIONS

File Wrapper of European Patent Publication No. EP1357958A2, Feb. 11, 2002 through Oct. 10, 2014, 970 pgs.
International Search Report and Written Opinion dated Sep. 24, 2019 received in International patent application PCT/US2019/027467 from European Patent Office as International Searching

(56) References Cited

OTHER PUBLICATIONS

Authority, European Patent Office, P.B. 5818 Patentlaan 2 NL—2280 HV Rijswijk (13pgs).
U.S. Appl. No. 62/658,731, filed Apr. 17, 2018.
U.S. Appl. No. 18/606,446, filed Mar. 15, 2024.

* cited by examiner

FIG. 24

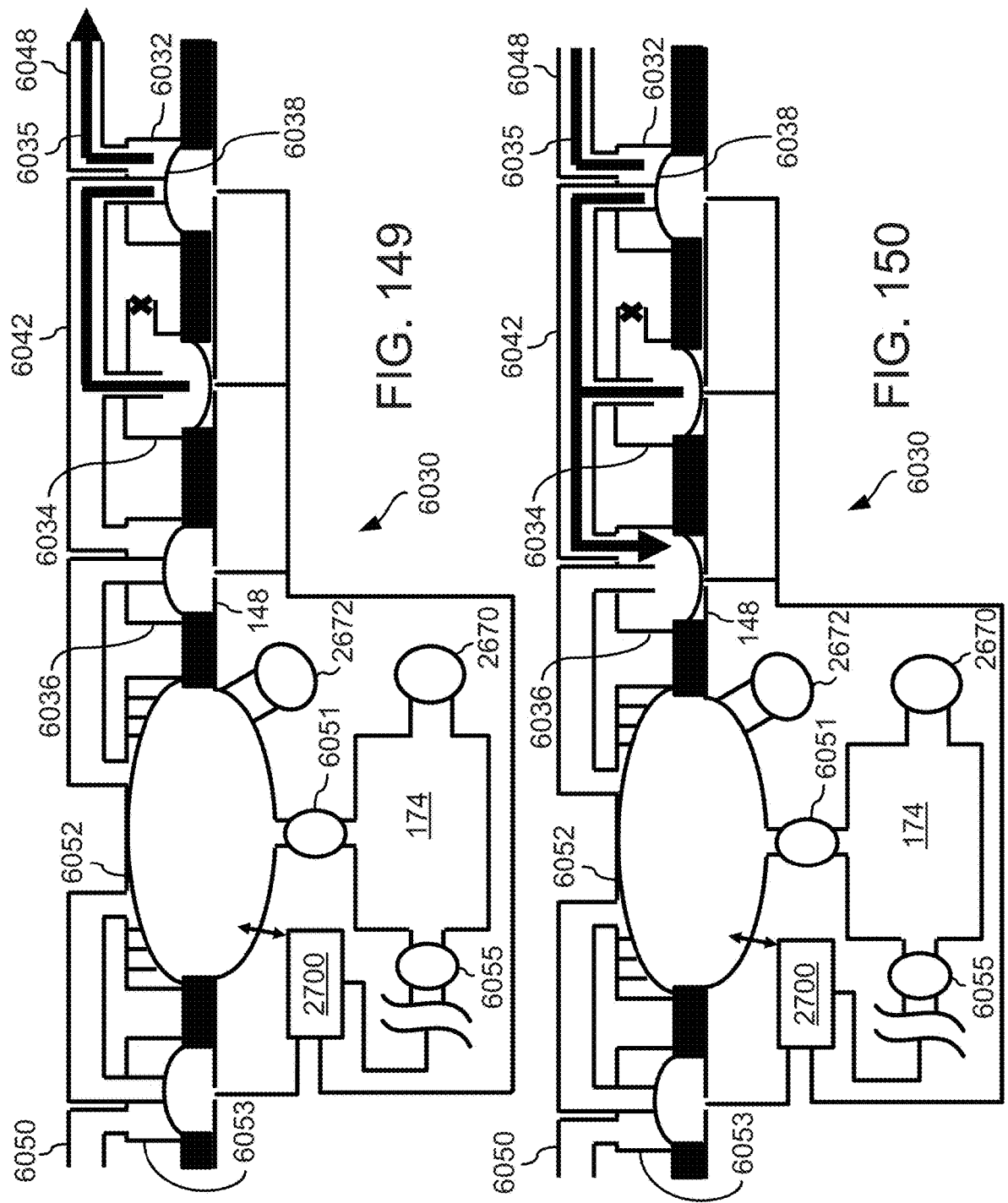

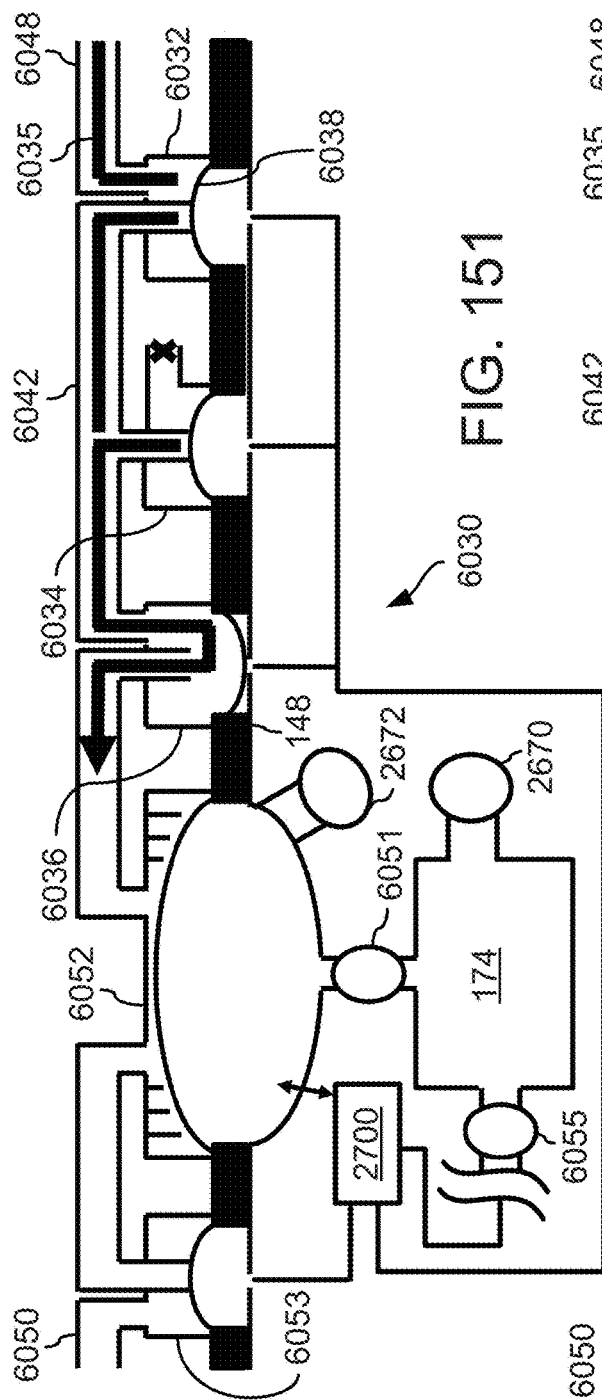
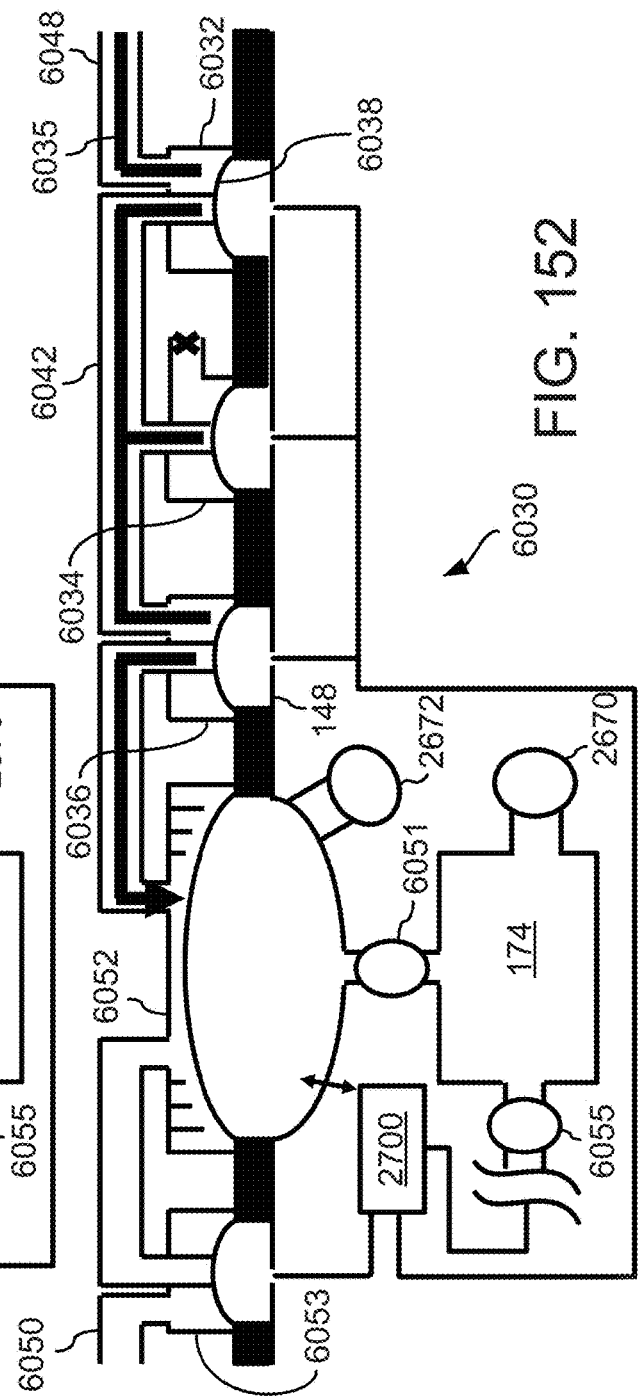

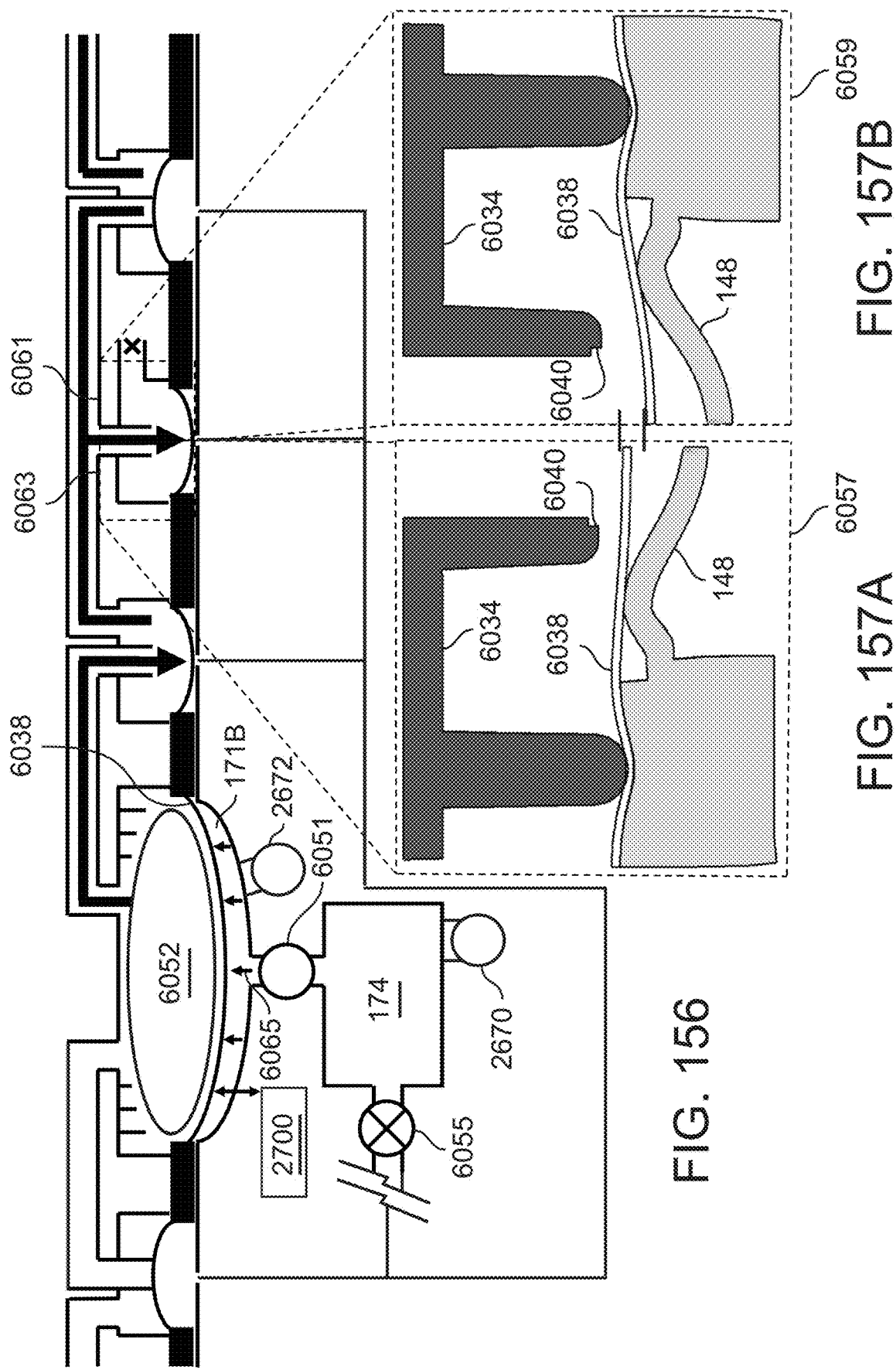

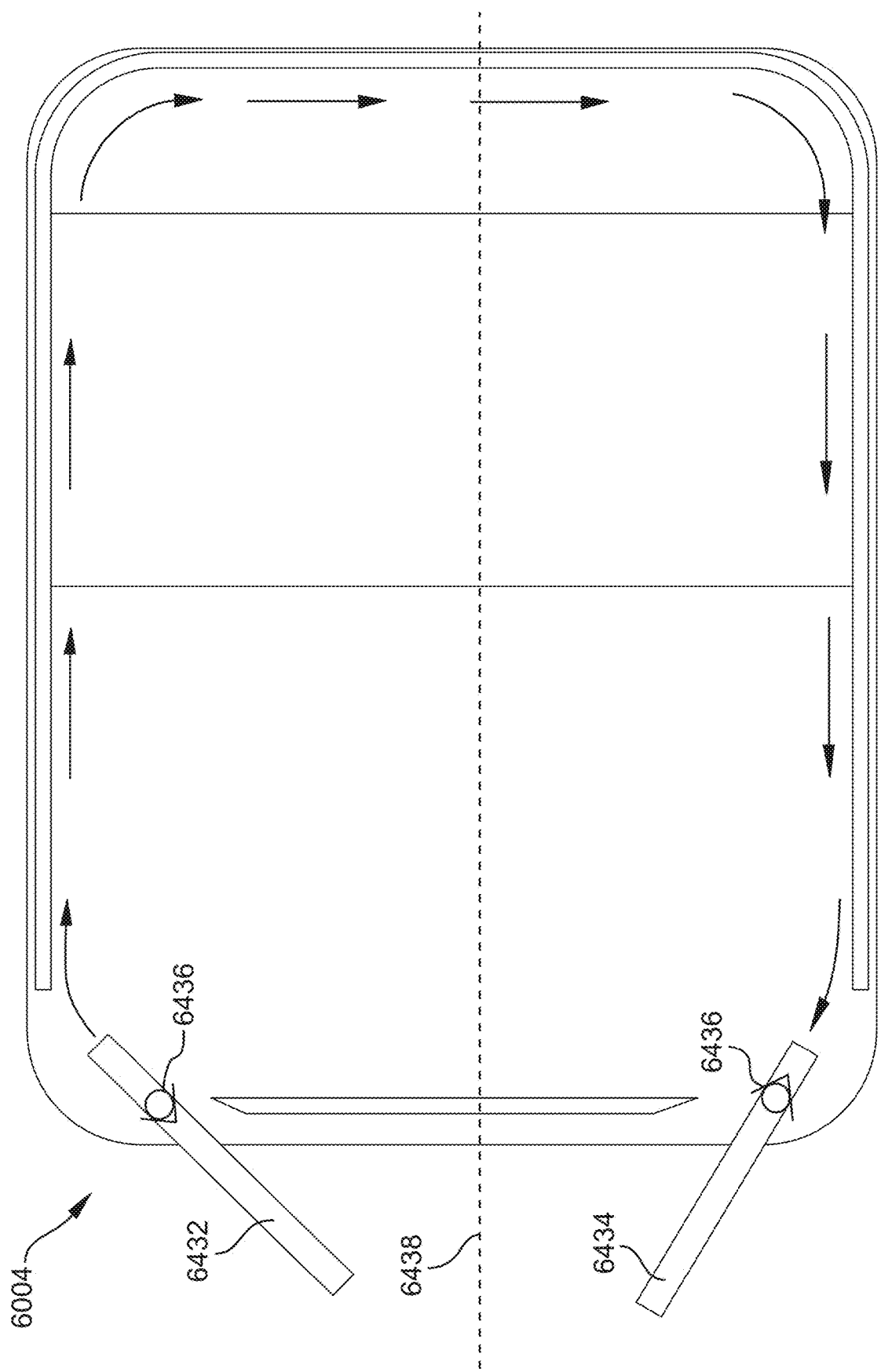

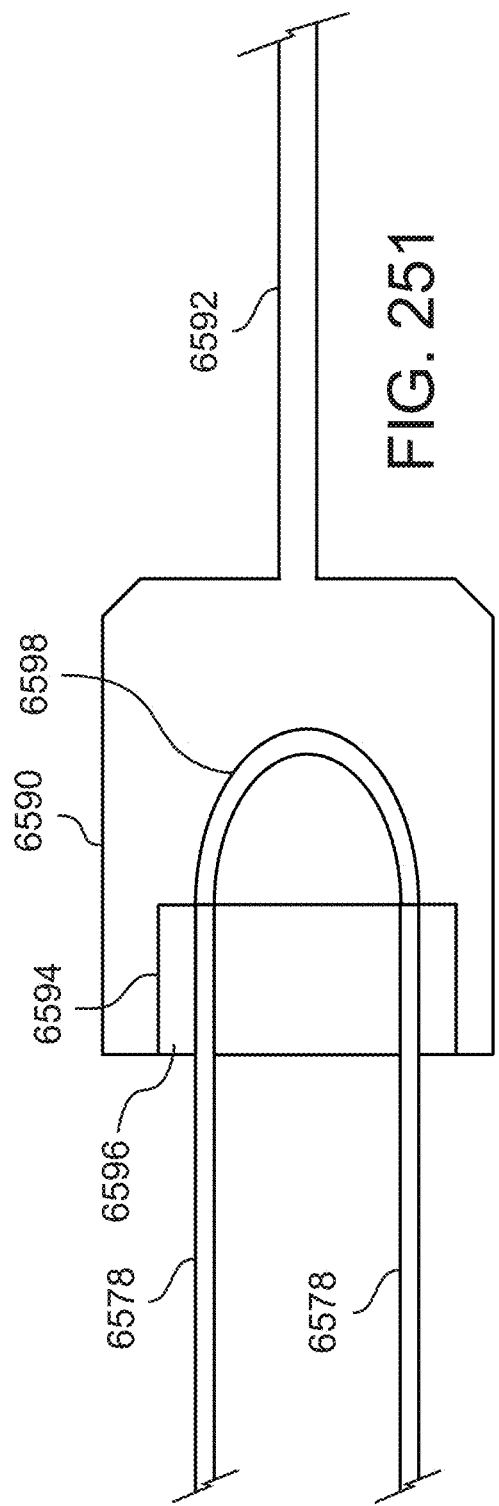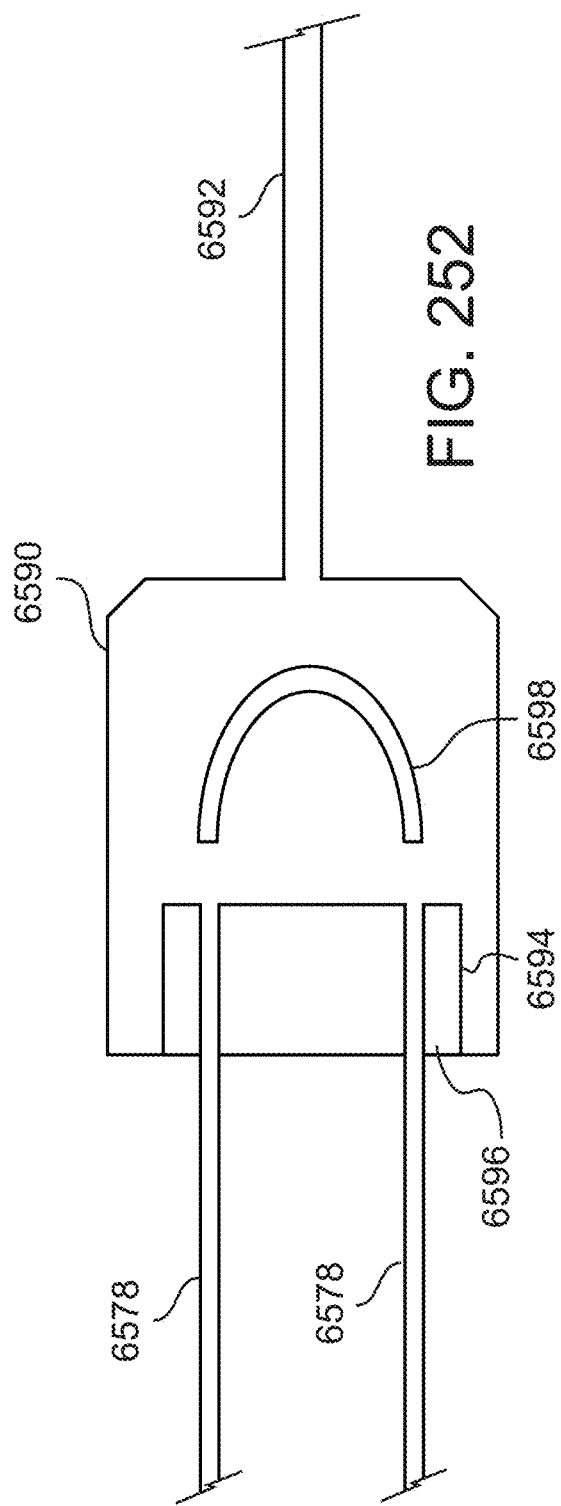

MEDICAL TREATMENT SYSTEM AND METHODS USING A PLURALITY OF FLUID LINES

CROSS-REFERENCE TO RELATED APPLICATIONS

The present application is a continuation of U.S. application Ser. No. 18/606,446, filed on Mar. 15, 2024, entitled Medical Treatment System and Methods Using a Plurality of Fluid Lines which is a Divisional of U.S. patent application Ser. No. 16/384,082, filed on Apr. 15, 2019, now U.S. Pat. No. 11,965,766, Issued Apr. 23, 2024, and entitled Medical Treatment System and Methods Using a Plurality of Fluid Lines which claims the benefit of U.S. Provisional Application Ser. No. 62/658,731 filed Apr. 17, 2018 and entitled Medical Treatment System and Methods Using a Plurality of Fluid Lines, each of which being hereby incorporated herein by reference in their entireties.

BACKGROUND

Peritoneal Dialysis (PD) involves the periodic infusion of sterile aqueous solution (called peritoneal dialysis solution, or dialysate) into the peritoneal cavity of a patient. Diffusion and osmosis exchanges take place between the solution and the bloodstream across the natural body membranes. These exchanges transfer waste products to the dialysate that the kidneys normally excrete. The waste products typically consist of solutes like sodium and chloride ions, and other compounds normally excreted through the kidneys like urea, creatinine, and water. The diffusion of water and solutes across the peritoneal membrane during dialysis is called ultrafiltration.

A popular form of PD is Automated Peritoneal Dialysis or APD. APD uses a machine, called a cycler, to automatically infuse, dwell, and drain peritoneal dialysis solution to and from the patient's peritoneal cavity. APD is particularly attractive to a PD patient, because it can be performed at home and at night while the patient is asleep. This frees the patient from the day-to-day demands of manually administered peritoneal dialysis (known as CAPD) during his/her waking and working hours.

The APD sequence or therapy typically lasts for several hours. It often begins with an initial drain phase to empty the peritoneal cavity of spent dialysate. The APD sequence then proceeds through a succession of fill, dwell, and drain phases that follow one after the other. Each sequencing including a fill/dwell/drain is called a cycle.

During the fill phase, the cycler transfers a predetermined volume of fresh, warmed dialysate into the peritoneal cavity of the patient. The dialysate remains (or "dwells") within the peritoneal cavity for a period of time. This is called the dwell phase. During the drain phase, the cycler removes the spent dialysate from the peritoneal cavity.

The number of cycles that are required during a given APD session depends upon the total volume of dialysate prescribed for the patient's APD regimen, and is either entered as part of the treatment prescription or calculated by the cycler.

Conventional peritoneal dialysis solutions typically come in the form of a premixed bag which contains electrolytes and dextrose in concentrations sufficient to generate the necessary osmotic pressure to remove water and solutes from the patient through ultrafiltration. These bags vary in size, but can range up to five or more liters. As several bags of dialysate are generally consumed during a therapy, the patient must maintain a stockpile of a large number of bags in their home to ensure appropriate supplies for continued therapy are available. It is recommended to keep about a month worth or more of supplies on hand. These bags may take up significant space. Additionally, these bags can be heavy making them difficult for patients to move about during set up.

More recently, there has been a focus on creating new PD solutions which are more physiologically biocompatible. This research is in progress and some solutions which are purported to be more physiologically biocompatible are currently on the market. Like conventional solutions, these are provided in bags which contain the full volume of fluid to be used during the therapy. Some of these bags may be compartmented and rely on the user manually manipulate the bag and to mix compartments prior to therapy. This is done since the mixed dialysate is intended for immediate use and does not have a long storage life in mixed state. Such a dialysate solution is evidenced to support better patient outcomes, but may contribute to increased waste, set-up burden, and introduce mixing variability from patient to patient.

Per the Center for Drug Evaluation and Research of the FDA, "manufacturing a sterile fluid like PD solution is highly specialized and complex, and there are limited numbers of manufacturing lines at each company that are capable of making these solutions." Expansion of production "can take months to years for a firm to complete necessary planning and development to initiate the new production lines successfully." Thus, as APD has become a modality of choice for dialysis patients, production of fluids has, in some instances, been unable to keep pace. It is projected that strong future growth in APD will outpace dialysate production capacity and will likely result in future shortfalls. Currently, the FDA states, "preventing and mitigating shortages of medically necessary drugs, like PD fluid, are top priorities for the FDA".

SUMMARY

In accordance with an embodiment of the present disclosure cassette based fluid pumping system may comprise a pumping cassette having a first side including number of valve wells and second side having a fluid bus. The first and second side may each be covered by a flexible membrane. The system may further comprise a control surface having a number of valve well control stations actuatable with respect to the flexible membrane covering the first side of the cassette to open and close the valve wells when the cassette is mated against the control surface. The system may further comprise a pressure distribution assembly having a positive and negative pressure source and a number of pneumatic valves. The system may further comprise a controller configured to selectively actuate the number of pneumatic valves to apply pressure against the valve well control stations in a valve pumping sequence until a volume displaced through the fluid bus of the pumping cassette from a source to a destination is within a range of a target volume.

In some embodiments the destination may be selected from a list consisting of a mixing reservoir in fluid communication with the cassette, a heater bag in fluid communication with the cassette, and a pump chamber disposed within the pumping cassette. In some embodiments, the source may be selected from a list consisting of a pump chamber disposed within the pumping cassette, and a source component in fluid communication with the cassette. In some embodiments, the source may be a source component containing one of component from a list consisting of a buffer solution, an acid solution, a purified water source, and a dialysate concentrate. In some embodiments, each valve pumping sequence may transfer under 150 microliters. In some embodiments, each valve pumping sequence may transfer a nominal volume of 70 microliters. In some embodiments, at least one of the number of valve wells may be a dedicated holding volume valve well. In some embodiments, the pumping cassette may include a pump chamber on the first side of the pumping cassette. The control surface may include a pump chamber control region adjacent the pump chamber when the cassette is mated against the control surface. The controller may be further configured apply negative pressure to the pump chamber control region via actuation of the pneumatic valves while selectively actuating the number of pneumatic valves to apply pressure against the valve well control stations in a valve pumping sequence. In some embodiments, the controller may be configured to monitor the volume of the pump chamber while selectively actuating the number of pneumatic valves to apply pressure against the valve well control stations in a valve pumping sequence via a pressure sensor disposed in a volume bounded at least partially by the pump chamber control region. In some embodiments, the pumping cassette may only include valve wells between the source reservoir and the destination. In some embodiments, all of the valve wells may include volcano valves. In some embodiments, the valve wells include a first valve well, a second valve well, and a third valve well. In some embodiments, the control surface may be configured to fluidly isolate the valve wells from each other when the control surface is mated against the flexible membrane covering the first side of the cassette.

In accordance with another embodiment of the present disclosure a fluid pumping system may comprise a pumping cassette having a first side and a second side. The first side may be covered by a first flexible membrane and the second side covered by a second flexible membrane. The pumping cassette may further including a midbody disposed between the first flexible membrane and the second flexible membrane. The midbody may form a plurality of valve wells on a first side of the midbody adjacent the first flexible membrane. The midbody may form a common fluid bus on a second side of the midbody adjacent to the second flexible membrane. The system may further comprise a control surface configured to mate against the first flexible membrane of the pumping cassette. The control surface may include valve-well control stations. Each valve-well control station of the valve-well control stations may be configured to engage with a respective valve well of the plurality of valve wells of the pumping cassette. The system may further comprise a positive pressure source configured to selectively apply a positive pressure to the first flexible membrane adjacent to one or more of the plurality of valve wells. The system may further comprise a negative pressure source configured to selectively apply a negative pressure to the first flexible membrane adjacent to one or more of the plurality of valve wells. The system may further comprise a controller configured to selectively control application of the positive pressure source and the negative pressure source to the valve-well control stations in order to displace the first flexible membrane to open and close the plurality of valve wells in a valve-pumping sequence. The controller may be configured to repeat the valve-pumping sequence until a volume transferred via the pumping cassette from a source reservoir to a destination is within a first range of a target volume.

In some embodiments, the destination may be a mixing reservoir. In some embodiments, the destination may be a heater bag. In some embodiments, the destination may be a pump chamber disposed within the pumping cassette. In some embodiments, the source reservoir may be a pump chamber disposed within the pumping cassette. In some embodiments, the source reservoir may be a source component connected to the pumping cassette via a fluid line. In some embodiments, the source component may be selected from one of a buffer solution, an acid solution, a purified water source, or a dialysate concentrate. In some embodiments, each valve pumping sequence may transfer under 150 microliters. In some embodiments, each valve pumping sequence may transfer a nominal volume of 70 microliters. In some embodiments, at least one of the plurality of valve wells may be a dedicated holding volume valve well. In some embodiments, the pumping cassette may include a pump chamber on the first side of the pumping cassette and the control surface may include a pump chamber control region which is in selective communication with the positive pressure and the negative pressure via pneumatic pump control valves. In some embodiments, the controller may be further configured to fill the pump chamber by applying the negative pressure to the flexible membrane adjacent to the pump chamber via actuation of one of the pneumatic pump control valves. In some embodiments, the controller may be configured to monitor the volume of the pump chamber and close the one of the pneumatic pump control valves when the volume of the pump chamber is within a second range of the target volume. In some embodiments, a difference between bounds of the second range may greater than a difference between bounds of the first range. In some embodiments, the positive pressure source and the negative pressure source may be in fluid communication with the plurality of valve wells through a pneumatic valve network. In some embodiments, the pumping cassette may only include valved-pumping chambers between the source reservoir and the destination. In some embodiments, all of the valve wells may include volcano valves. In some embodiments, the valve wells may include a first valve well, a second valve well, and a third valve well. In some embodiments, the control surface may be configured to fluidly isolate the first valve well, the second valve well, and the third valve well from each other when the control surface is mated against the first flexible membrane.

In accordance with an embodiment of the present disclosure a pneumatic peristaltic pumping system may comprise a pumping cassette having a cassette body with first and second side respectively covered by first and second flexible membranes. The pumping cassette may have a common fluid bus. The first side may have a plurality of translational elements. The system may further comprise, a pneumatic assembly including a positive and negative pressure reservoir, a pressure distribution module having a manifold, a plurality of pneumatic valves, and a control surface with a plurality of translational element control regions. The system may further comprise a cassette mount actuatable between a first position and a second position, the second position being a position in which the first flexible membrane is held against the control surface. The system may further comprise a controller configured to actuate the plurality of pneumatic valves and thereby apply positive and negative pressure to the translational element control regions in order to operate the translational elements in a pumping sequence. The controller may be configured to repeat the sequence until a volume transferred via the pumping cassette from a source reservoir to a destination is within a first range of a target volume.

In some embodiments, each translational element may be associated with a valve seat included in a translational element station. In some embodiments, the destination may be a pump chamber also included in the pumping cassette. In some embodiments, the source reservoir may be a pump chamber also included in the pumping cassette. In some embodiments, the destination may be a heater bag attached to an outlet of the pumping cassette via a fluid line. In some embodiments, each pump sequence may displace less than 100 microliters. In some embodiments, each pump sequence may displace a nominal volume of 70 microliters. In some embodiments, the common fluid bus may be disposed on the second side of the pumping cassette. In some embodiments, a portion of the pumping cassette body forms a platen toward and away from which the translational elements displace. In some embodiments, the platen may have a first side facing the first side of the pumping cassette and a second side facing the second side of the pumping cassette. In some embodiments, the pump sequence may displace the translational elements on one side of a platen of the pumping cassette body. In some embodiments, the displacement of the translational elements may cause fluid transfer through the common bus on an opposing side of the platen. In some embodiments, the platen may include at least one fluid flow channel in line with each of the translational elements and extending through the platen to the common fluid bus. In some embodiments, the pumping cassette may include a pump chamber on the first side of the pumping cassette and the control surface may include a pump chamber control region which is in selective communication with the positive and negative pressure reservoirs via pneumatic pump control valves. In some embodiments, the controller may be further configured to fill the pump chamber from the source reservoir by applying negative pressure to the pump chamber via actuation of one of the pneumatic pump control valves. The controller may be configured to monitor the volume of the pump chamber via at least one sensor and close the one of the pneumatic pump control valves when the volume of the pump chamber is within a second range of the target volume. In some embodiments, the difference between bounds of the second range is greater than the difference between bounds of the first range. In some embodiments, a nominal fill volume of the pump chamber may be at least 10 times greater than an amount of fluid displaced by each pumping sequence. In some embodiments, a nominal fill volume of the pump chamber may be at least 100 times greater than an amount of fluid displaced by each pumping sequence. In some embodiments, a nominal fill volume of the pump chamber may be at least 300 times greater than an amount of fluid displaced by each pumping sequence. In some embodiments, the controller may be configured to repeat the pumping sequence in an open loop manner until the volume transferred is within the first range of the target volume.

In accordance with another embodiment of the present disclosure a fluid pumping system may comprise a fluid handing set including a pumping cassette having a diaphragm overlaying at least one pump chamber and a plurality of fluid valves. The system may further comprise a pneumatic distribution assembly including a positive and a negative pressure reservoir. The system may further comprise a control surface, and a plurality of pneumatic valves actuatable to place regions of the control surface in selective communication with the positive and the negative pressure reservoir. The system may further comprise a controller configured to govern operation of the plurality of pneumatic valves to fill the at least one pump chamber from a source reservoir and to deliver the at least one pump chamber to a destination. Each fill may transfer close to a nominal pump stroke fill volume to the chamber. Each delivery may expel close to a nominal delivery stroke volume from the chamber. The controller may be configured to monitor a volume of the at least one pump chamber via at least one sensor. The controller may be configured to fill and deliver the at least one pump chamber until within a threshold of a total transfer target volume has been transferred and calculate a withholding volume to subtract from the nominal fill stroke volume on a number of subsequent pump chamber fills.

In some embodiments, the threshold may be an amount of volume remaining to be transferred. In some embodiments, the threshold may be a number of pump chamber fill and delivery strokes remaining. In some embodiments, the withholding volume may be no greater than a maximum withhold volume limit. In some embodiments, the number of subsequent pump chamber fills may be equal to one of the nominal pump stroke fill volume and nominal pump stroke delivery volume divided by a maximum withholding volume limit. In some embodiments, the controller may be further configured to add the withholding volume withheld on each of the number of subsequent pump chamber fills to a final stroke fill volume. In some embodiments, the withholding volume may be selected such that a final stroke fill volume is substantially equal to a nominal pump stroke fill volume. In some embodiments, the withholding volume may be selected such that a final stroke fill volume is no less than the nominal pump stroke fill volume less the withholding volume.

In accordance with another embodiment of the present disclosure a fluid pumping system may comprise a fluid handing set including a pumping cassette having at least one pump chamber and a plurality of fluid valves. The system may further comprise a pneumatic distribution assembly including a positive and negative pressure reservoir, a control surface including valve control regions and at least one pump control region, and a plurality of pneumatic valves actuatable to place the valve control regions and at least one pump control region in selective communication with the positive and negative pressure reservoir. The system may further comprise a controller configured to govern operation of the plurality of pneumatic valves to fill the at least one pump chamber from a source reservoir by applying negative pressure to the at least one pump chamber and at least one valve between the at least one pump chamber and source reservoir via actuation of the pneumatic pump control valves. The controller configured to monitor the volume of the at least one pump chamber via at least one sensor and to deliver the at least one pump chamber to a destination by applying positive pressure to the at least one pump chamber and negative pressure to at least one valve between the at least one pump chamber and destination via actuation of one of the pneumatic pump control valves. The controller may be configured to fill and deliver the at least one pump chamber and determine a volume remaining of a total transfer target volume. The controller may be configured calculate a withholding volume to subtract from a target volume of at least one pump chamber fill and add to a target volume of another pump chamber fill.

In some embodiments, the another pump chamber fill may be a final pump chamber fill which once delivered will bring the volume remaining to substantially zero. In some embodiments, the controller may be configured to calculate a withholding volume to subtract from each of a plurality of pump chamber fills. In some embodiments, the withholding volume may be limited by a maximum withholding volume limit. In some embodiments, the number of the at least one pump chamber fill from which a withholding volume is subtracted may be determined by dividing a nominal fill volume of the at least one pump chamber by the maximum withholding volume limit. In some embodiments, the another pump chamber fill may be a final pump chamber fill which once delivered will bring the volume remaining to substantially zero. In some embodiments, the withholding volume subtracted from the at least one pump chamber fill may be chosen such that a final pump fill volume on the final pump chamber fill is equal to a full pump chamber fill volume. In some embodiments, the another pump chamber fill may be a final pump chamber fill which once delivered will bring the volume remaining to substantially zero. In some embodiments, the withholding volume subtracted from each of the at least one pump chamber fill may be chosen such that a final pump fill volume on the final pump chamber fill is equal to no less than a full pump chamber fill volume less the withholding volume.

In accordance with an embodiment of the present disclosure a fluid pumping system may comprise a fluid handing set including a pumping cassette having a diaphragm overlaying a pump chamber and a plurality of fluid valves. The system may further comprise a pneumatic distribution assembly including a positive and negative pressure reservoir, a control surface, and a plurality of pneumatic valves actuatable to place regions of the control surface in selective communication with the positive and negative pressure reservoir. The system may further comprise a controller configured to govern operation of the plurality of pneumatic valves to fill the pump chamber from a source reservoir and to deliver the pump chamber to a destination. The controller may be configured to fill the pump chamber to a target volume based on data from at least one sensor, stop filling of the pump chamber and command a volume measurement of pump chamber be collected, and compare measurement data from the volume measurement to a target volume range criteria. The controller may further be configured to command delivery of the pump chamber to the destination if the measurement data is within the target volume range criteria and may be configured to command delivery of at least a portion of the pump chamber to a retry reservoir if the measurement data is outside the target volume range criteria.

In some embodiments, the target volume range criteria may be no greater than +/−3 ml of the target volume. In some embodiments, the at least one sensor may include a pressure sensor. In some embodiments, the at least one sensor may be configured to provide substantially continuous data to the controller as the pump chamber is filled. In some embodiments, the data provided from the at least one sensor may be pressure data and the controller may monitor a pressure decay in a control chamber associated with the pump chamber to determine when the pump chamber has been filled to the target volume. In some embodiments, the retry reservoir may be the source reservoir. In some embodiments, the volume measurement of the pump chamber may be based on ideal gas laws.

In accordance with another embodiment of the present disclosure a method of flushing a contaminating fluid from a fluid admixing cassette may comprise pumping fluid with the fluid admixing cassette, based on a formulation prescription, from a plurality of source reservoirs to a mixing reservoir to admix a prescribed solution. The method may further comprise drawing fluid into a first pump chamber of the fluid admixing cassette from the mixing reservoir. The method may further comprise transferring fluid, via a first contaminated flow path of the fluid admixing cassette, in the first pump chamber into a second pump chamber of the fluid admixing cassette. The method may further comprise delivering to a first port at a terminus of the first contaminated flow path fluid from the first pump chamber. The method may further comprise delivering fluid, via a second contaminated flow path, in the first and second pump chamber to a discard destination in fluid communication with the fluid admixing cassette.

In some embodiments, the first pump chamber may be disposed more distal to a second fluid port of the pumping cassette than the second pump chamber. In some embodiments, the second port may be a patient line outlet connected to a patient line. In some embodiments, the first port and the second port may be disposed on opposing termini of the first contaminated flow path. In some embodiments, delivering fluid to the first port of the first contaminated flow path may comprise monitoring the volume delivered with at least one sensor and halting delivery when the volume delivered reaches a target volume. In some embodiments, the target volume may be no less than a hold up volume of the first contaminated flow path, the hold up volume being equal to a volume of a portion of the first contaminated flow path disposed between the first port and an access port to the first pump chamber. In some embodiments, delivering fluid to the first port of the first contaminated flow path may comprise fully delivering the first pump chamber to the first port. In some embodiments, the contaminating fluid may be selected from a group consisting of: purified water, dialysate concentrate, acid solution, and buffer solution. In some embodiments, the first contaminated flow path may be a common fluid bus of the pumping cassette. In some embodiments, the second contaminated flow path may be a common fluid bus of the pumping cassette. In some embodiments, the discard destination may be a drain port of the fluid admixing cassette. In some embodiments, transferring fluid in the first pump chamber into the second pump chamber may comprise drawing a vacuum on the second pump chamber and subjecting the first chamber to ambient pressure.

In accordance with another embodiment of the present disclosure a system for use with a fluid handling set having a first fluid handling set portion and a second fluid handling set portion operated at a higher pressure than a maximum toleration pressure of the first fluid handling set portion may comprise a pumping cassette included in first the fluid handling set portion having a first pump chamber and a fluid valve leading to a port connected to a fluid line from the second fluid handling set portion. The system may further comprise a pressure distribution assembly having a control surface against which the pumping cassette is held, and including at least one pressure transducer configured to output data indicative of the pressure of the first pump chamber. The system may further comprise a controller configured to command the pressure distribution module to apply pressure to the control surface to establish a path from the port to the first pump chamber, receive the data, and generate a failsafe command signal upon determination that the data indicates a pressure rise in the pump chamber greater than a predetermined threshold.

In some embodiments, the higher pressure of the second fluid handling set portion may be at least 100% greater than the maximum toleration pressure of the first fluid handling set portion. In some embodiments, the higher pressure may be at least 500% greater than the maximum toleration pressure of the first fluid handling set portion. In some embodiments, the higher pressure may be greater than or equal to 100 kPa and less than 300 kPa. In some embodiments, the maximum toleration pressure may be between 20 and 70 kPa. In some embodiments, the system further may comprise a positive pressure reservoir and at least one pressure distribution valve actuatable between an open and closed position, a valve of the at least one pressure distribution valve establishing a positive pressure application path between the positive pressure reservoir and the first pump chamber via the control surface in the open position. In some embodiments, the controller may be configured to maintain the first pump chamber at a positive pressure set point lower than the threshold via a valve control signal supplied to the valve of the at least one pressure distribution valve. In some embodiments, the positive pressure set point may be 10 kPa. In some embodiments, the positive pressure set point may be less than 60% of a set point of the positive pressure reservoir. In some embodiments, the failsafe command signal may be a deploy command for an occluder between the pumping cassette and a source generating the higher pressure. In some embodiments, the failsafe command signal may be a shutdown command signal for a source generating the higher pressure. In some embodiments, the pumping cassette includes a second pump chamber and the controller may be configured to command the pressure distribution module to establish a path from the port to both the first pump chamber and a second pump chamber of the cassette. In some embodiments, the at least one pressure transducer may include a first pressure transducer disposed in a pump control chamber of the pressure distribution assembly and a second pressure transducer disposed in another chamber of the pressure distribution.

In accordance with another embodiment of the present disclosure a fluid admixture system for admixing a solution specified in a formulation prescription may comprise a fluid handing set including a pumping cassette having a diaphragm overlaying a pump chamber and a plurality of fluid valves. The system may further comprise a pneumatic distribution assembly including a positive and negative pressure reservoir, a control surface, and a plurality of pneumatic valves actuatable to place regions of the control surface in selective communication with the positive and negative pressure reservoir. The system may further comprise at least one mass transfer sensor configured to generate a data signal. The system may further comprise a controller configured to govern operation of the plurality of pneumatic valves to apply pressure to the pumping cassette via the control surface to fill the pump chamber from a plurality of source reservoirs and to deliver the pump chamber to a mixing reservoir in a number of pump strokes. The controller may be configured to analyze at least the data signal to determine a mass of a source component transferred from the plurality of source reservoirs to the mixing reservoir during each pump stroke of the number of pump strokes. The controller may select a source reservoir from the plurality of source reservoirs for each pump stroke based on a mass transfer parameter defined in the formulation prescription.

In some embodiments, the at least one mass transfer sensor may include a temperature sensor. In some embodiments, the at least one mass transfer sensor may include an infrared sensitive imager. In some embodiments, the at least one mass transfer sensor may include a scale. In some embodiments, the at least one mass transfer sensor may include a Wheatstone bridge. In some embodiments, the at least one mass transfer sensor may include an electromagnetic force restoration scale.

In accordance with an embodiment of the present disclosure a fluid admixture system for admixing a solution may comprise a heater. The system may further comprise a pressure distribution module including a positive and negative pressure reservoir, a control surface, and a plurality of pressure distribution valves actuatable to place regions of the control surface in selective communication with the positive and negative pressure reservoir. The system may further comprise a fluid handling set. The fluid handling set may include a plurality of source flow conduits connected to respective source components, a fluid pumping cassette, and a heater bag configured to be disposed on the heater and connected to the pumping cassette via a heater bag fluid line. At least one of the plurality of source flow conduits may be at least partially integral with the heater bag and in heat exchange relationship with the heater bag. The at least one of the plurality of source flow conduits extending from a first point on the heater bag to a second point on the heater bag in a predetermined path. The system may further comprise a controller configured to issue valve actuation signals to the plurality of pressure distribution valves to pump and route a start up volume of fluid from a first source component of the source components through the pumping cassette to the mixing reservoir and subsequently pump and route fluid from the source component reservoirs to the mixing reservoir in ratios specified by a therapy formulation to admix the solution.

In some embodiments, the at least one of the plurality of source flow conduits may be attached to an exterior surface of the heater bag. In some embodiments, the at least one of the plurality of source flow conduits may be partially disposed within an interior volume of the heater bag. In some embodiments, the predetermined path may be a switchback like pattern. In some embodiments, the heater may include a heater pan the heater pan shaped to cradle the heater bag, the heater pan including a recess mimicking the predetermined pattern and sized to accept a portion of the source line at least partially integral with the heater bag. In some embodiments, at least one source flow conduit of the plurality of sources flow conduits may be independent of the heater bag and free of direct physical attachment to the heater bag. In some embodiments, the start up volume may be between 300 ml-500 ml. In some embodiments, the first source component may supply fluid at a temperature above 30° C. In some embodiments, the first source component may be a water purification device. In some embodiments, the at least one of the plurality of source flow conduits being at least partially integral with the heater bag may be constructed of at least two different materials. In some embodiments, at least one of the two different materials may be the same material as the heater bag. In some embodiments, the predetermined path may be a meandering path. In some embodiments, the heater bag may be constructed of three layers of material and may include a first interior volume and a second interior volume. In some embodiments, the second interior volume may be a portion of the at least one of the plurality of source flow conduits being at least partially integral with the heater bag.

In accordance with another embodiment of the present disclosure, a fluid admixture set for admixing a solution may comprise a plurality of fluid reservoirs including a mixing reservoir, and a number of source component reservoirs. The set may further comprise a fluid pumping cassette including a membrane overlaying at least one pump chamber and a plurality of fluid valves actuatable by displacement of the membrane between an open position and a closed position. The set may further comprise a plurality of source flow conduits each fluidically connecting respective source component reservoirs of the number of source component reservoirs to the pumping cassette via respective cassette ports. A heat exchange source flow conduit of the plurality of source flow conduits may be at least partially integral with a select reservoir of the plurality of fluid reservoirs other than the source component reservoirs. The heat exchange source flow conduit may be fluidically coupled to the pumping cassette and in heat exchange relationship with the select reservoir. The set may further comprise at least one mixing line extending from a mixing port of the pumping cassette to the mixing reservoir.

In some embodiments, the heat exchange source flow conduit may extend form a first point on the select reservoir to a second point on the select reservoir in a predetermined path. In some embodiments, the predetermined path may be an indirect path from the first point to the second point. In some embodiments, the predetermined path may be a switchback like path. In some embodiments, the select reservoir may be a bag. In some embodiments, the heat exchange source flow conduit may fluidically connect a water purification device to the pumping cassette. In some embodiments, the heat exchange source flow conduit may fluidically connect a source component reservoir at a temperature greater than 30° C. to the pumping cassette. In some embodiments, the select reservoir may be the mixing reservoir. In some embodiments, the select reservoir may be a source component reservoir of the plurality of source component reservoirs.

In accordance with another embodiments of the present disclosure a fluid admixture system for admixing a solution may comprise a fluid handing set including a pumping cassette having a diaphragm overlaying a pump chamber and a plurality of fluid valves. The fluid handling cassette may include a plurality of fluid lines each attached to a respective port of the pumping cassette. The system may further comprise a pneumatic distribution assembly including a positive and negative pressure reservoir, a control surface against which the diaphragm is pressed, and a plurality of pneumatic valves actuatable to place regions of the control surface in selective communication with the positive and negative pressure reservoir to route fluid through the pumping cassette and execute a number of pump strokes. The system may further comprise a volume displacement sensing assembly including at least one pressure transducer configured to generate pressure data. The system may further comprise a temperature sensing assembly including an infrared sensitive imager having a field of view inclusive of a monitored portion of the fluid handling set. The infrared sensitive imager may be configured to generate thermal data of the monitored portion. The system may further comprise a controller configured to receive the thermal data and pressure data and analyze the thermal data and pressure data to determine a mass transferred during each pump stroke of the number of pump strokes.

In some embodiments, the system further may comprise a fluid line guide constraining a constrained portion of at least one of the fluid lines to a known location. In some embodiments, the monitored portion may include the constrained portion of the at least one fluid line. In some embodiments, the temperature sensing assembly may include a window intermediate the infrared sensitive imager and the monitored portion. In some embodiments, the monitored portion may be the pump chamber of the pumping cassette. In some embodiments, the monitored portion may be a fluid pathway of the pumping cassette. In some embodiments, the monitored portion may be a common fluid bus of the pumping cassette. In some embodiments, the infrared sensitive imager may be disposed in a pressure delivery module of the pressure distribution module. In some embodiments, the pressure delivery module may include a pump chamber control chamber and fluid valve control chambers pressurizable to cause displacement of the regions of the control surface. In some embodiments, the control surface may include an infrared transparent window disposed intermediate the infrared sensitive imager and the monitored portion. In some embodiments, the infrared sensitive imager may be disposed in a door actuatable between an open position and a closed position in which the door presses the pumping cassette and the diaphragm against the control surface. In some embodiments, the infrared sensitive imager may be included in an infra imager array of a plurality of imagers.

In accordance with an embodiment of the present disclosure, a flow composition detector for detecting the composition of a fluid in a fluid line segment may comprise a fluid line holder including a fluid line segment accepting channel, the channel configured to constrain the fluid line segment into a retained configuration. The detector may further comprise a light emission assembly disposed in a first cavity located at a first bend region of the channel. The light emission assembly may have at least one light emitter with a light emission axis directed through a portion of a flow conduit of the fluid line segment when the fluid line segment is in the retained configuration. The light emission assembly may include a reference detector configured for detecting an intensity of light emitted from the at least one light emitter and generating a reference signal proportional to the intensity. The detector may further comprise a light detection assembly positioned in a second cavity located at second bend region of the channel opposite the first bend region and arranged to receive light emitted by the light emission assembly and generate a transmittance signal proportional to a received light intensity. The light detection assembly positioned along the light emission axis. The detector may further comprise a controller configured to receive the reference signal and transmittance signal to determine an absorption characteristic of the fluid and determine a composition of the fluid based at least in part on the absorption characteristic.

In some embodiments, the fluid line holder may be attached to a dialysis machine. In some embodiments, the fluid line holder may include a base and a retainer which mates into a receiving structure of the base. In some embodiments, the retainer may attach to the base via a coupler. In some embodiments, a first portion of the channel may be included in the base and a second portion of the channel may be included in the retainer. In some embodiments, wherein the retainer may be physically connected to the base with a connector. In some embodiments, the channel may be U shaped. In some embodiments, the at least one light emitter may emit ultraviolet light. In some embodiments, the at least one light emitter may emit light at a wavelength of 405 nm. In some embodiments, the at least one light emitter may be an LED. In some embodiments, the composition of the fluid may be determined as a percent composition of an osmotic agent. In some embodiments, wherein the distance between the light emission assembly and the light detection assembly may be greater than 2.5 inches.

In accordance with another embodiment of the present disclosure a system for determining a characteristic correlated to a heightwise location of a component of interest relative to a pumping chamber of a fluid handling set may comprise a pumping cassette including the pumping chamber and having at least a first fluid valve, and a second a fluid valve leading to a port connected to a fluid line coupled to the component of interest. The system may further comprise a pressure distribution module having a control surface against which the pumping cassette is held. The pressure distribution module may include at least one sensor configured to output data indicative of the pressure of the pumping chamber. The system may further comprise a controller configured to command the pressure distribution module to establish a path from the port to the pumping chamber, receive the data, and detect a feature profile in the data. The controller may further be configured to predict the characteristic of the component of interest based on the feature profile and temporal data associated with the feature profile.

In some embodiments, the controller may be further configured to actuate one or more pneumatic valve of the pressure distribution module to apply pressure to the control surface and consequentially place the pumping chamber in an intermediary state between a fully filled and fully delivered state before establishing the path from the port to the pumping chamber. In some embodiments, the intermediate state may be a state that allows for the detection of a maximum positive and maximum negative head height of about the same absolute value. In some embodiments, the controller may be further configured to actuate one or more pneumatic valve of the pressure distribution module to apply pressure to the control surface and consequentially place the pumping chamber in a negative head height detection biased state before establishing the path from the port to the pumping chamber. In some embodiments, the controller may be further configured to actuate one or more pneumatic valve of the pressure distribution module to apply pressure to the control surface and consequentially place the pumping chamber in a positive head height detection biased state before establishing the path from the port to the pumping chamber. In some embodiments, the controller may compare the predicted characteristic to an expected characteristic range and generate an error signal when the predicted characteristic is outside of the expected range. In some embodiments, the controller may be configured to predict the characteristic using a behavior model. In some embodiments, the behavior model may be based off an ideal second order undampened system. In some embodiments, the feature profile may include one or more pressure peak. In some embodiments, the feature profile may include a first pressure peak and a second pressure peak lower in magnitude than the first peak. In some embodiments, the controller may be configured to set an adjusted pumping pressure value based on the predicted characteristic. In some embodiments, while the controller is detecting the feature profile, the controller may also be configured to orchestrate pumping of fluid through the pumping cassette via actuation of one or more pneumatic valves in the pressure distribution module associated with a second pump chamber in the pumping cassette.

In accordance with an embodiment of the present disclosure a fluid admixing set may comprise a fluid handling cassette having at least one pump chamber, a plurality of fluid flow control valves, and a plurality of ports. The set may further comprise a plurality of fluid conduits, each of the plurality of fluid conduits connected a port of the plurality of ports. The system may further comprise a first concentrate reservoir connector at an end of a first of the plurality of fluid conduits. The system may further comprise a second concentrate reservoir connector at an end of a second of the plurality of fluid conduits. The system may further comprise a mixing reservoir in fluid communication with an end of a third fluid conduit of the plurality of fluid conduits. The mixing reservoir may be flaccid and configured to inflate and deflate with the introduction and removal of fluid via actuation of the at least one pump chamber of the pumping cassette. The mixing reservoir may include at least one dispersal element configured to increase mixing of fluid occurring within the mixing reservoir at least as fluid is transferred to the mixing reservoir.

In some embodiments, the at least one dispersal element may be a turbulence generator. In some embodiments, the at least one dispersal element may be a diffuser. In some embodiments, the at least one dispersal element may be a laminar flow director. In some embodiments, the mixing reservoir may include an inlet line which extends into the interior volume of the mixing reservoir through a first side of the mixing reservoir. In some embodiments, the inlet line may have a span enclosed by the mixing reservoir extending at least one third of the way through the interior volume of the mixing reservoir toward a side opposing the first side, the at least one dispersal element being included in the span. In some embodiments, the at least one dispersal element may comprise a number of perforations extending radially through a wall of the span. In some embodiments, the perforations may have a size gradient from a first size proximal to the first side of the mixing reservoir to a second size more proximal to the opposing side. In some embodiments, wherein the first size may be smaller than the second size. In some embodiments, the perforations may have a density gradient from a first density proximal to the first side of the mixing reservoir to a second density more proximal to the opposing side. In some embodiments, the second density may be more dense than the first density. In some embodiments, the at least one dispersal element may be a venturi ejector on a portion of an inlet line which extends through the mixing reservoir and into the interior volume of the mixing reservoir. In some embodiments, the at least one dispersal element may include a flow director including one of a float or sinker element. In some embodiments, the at least one dispersal element may comprise at least one baffle. In some embodiments, the at least one baffle may include at least one passthrough. In some embodiments, the at least one baffle may include a plurality of passthroughs of different dimensions. In some embodiments, the at least one baffle may comprise a plurality of baffles arranged in an echelon formation within the interior of the mixing reservoir. In some embodiments, the at least one baffle may be chevron shaped. In some embodiments, the at least one baffle may be constructed of a flexible material. In some embodiments, the at least one dispersal element may comprise an inlet line and outlet line each having a longitudinal axis disposed transverse to the other. In some embodiments, the inlet line and outlet line each having a check valve to prevent two directional flow. In some embodiments, the at least one dispersal element may include a number of scalloped features disposed on an end face of an inlet line extending into the interior volume of the mixing reservoir.

In accordance with an embodiment of the present disclosure a fluid admixture system for admixing a solution specified in a formulation prescription may comprise a fluid handing set including a pumping cassette having a diaphragm overlaying a pump chamber and a plurality of fluid valves. The system may further comprise a pneumatic distribution assembly including a positive and negative pressure reservoir, a control surface, and a plurality of pneumatic valves actuatable to place regions of the control surface in selective communication with the positive and negative pressure reservoir. The system may further comprise a plurality of source component reservoirs in fluid communication with the pumping cassette via a fluid line. Each of the plurality of source component reservoirs including a thermal well configured to accept a respective temperature sensor probe. The system may further comprise a controller configured to govern operation of the plurality of pneumatic valves to apply pressure to the pumping cassette via the control surface to fill the pump chamber from the plurality of source reservoirs and to deliver the pump chamber to a mixing reservoir over a number of pump strokes. The controller may be in data communication with the respective temperature sensor probes and configured to analyze data signals from the respective temperature sensor probes to determine a density of a source component transferred from one of the plurality of source component reservoirs to the mixing reservoir during at least one pump stroke of the number of pump strokes where that source component is transferred.

In some embodiments, the controller may be configured to select a source reservoir from the plurality of source reservoirs for each pump stroke based on a mass transfer parameter defined in the formulation prescription. In some embodiments, the controller may be configured to determine when the mass transfer parameter has been satisfied based at least in part on the density. In some embodiments, the controller may be configured to determine when the mass transfer parameter has been satisfied based on the density and a volume pumped for each stroke of the number of pump strokes. In some embodiments, the plurality of source component reservoirs may include a first and second concentrate source. In some embodiments, the plurality of source components may include an acid concentrate and a buffer solution. In some embodiments, the fluid handling set may be in fluid communication with a diluent source. In some embodiments, the diluent source may be a water purification device. In some embodiments, the water purification device may be selected from either a reverse osmosis purifier or a distillation purifier. In some embodiments, the mixing reservoir may be a flaccid reservoir which inflates or collapses in relation to an amount of fluid held within its interior volume.

In accordance with another embodiment of the present disclosure a fluid admixing set may comprise a fluid handling cassette having at least one pump chamber, a plurality of fluid flow control valves, and a plurality of ports. The set may further comprise a plurality of fluid conduits, each of the plurality of fluid conduits connected a port of the plurality of ports. The set may further comprise a mixing reservoir disposed at an end of a first of the plurality of fluid conduits. The set may further comprise a source component reservoir configured to be connected to an end of a second of the plurality of fluid conduits, the source component reservoir having an interior volume divided into a first section, a second section, and a third section, the first and second section each including a different liquid concentrate and being segregated from one another via a first temporary barrier, the third section being segregated from both the first and second sections by a second temporary barrier, the first temporary barrier having a first strength and the second barrier having a second strength greater than the first.

In some embodiments, at least one of the first and second temporary barriers may include a frangible. In some embodiments, at least one of the first and second temporary barriers may be a peelable barrier. In some embodiments, the different liquid concentrates may include an acid concentrate and a buffer concentrate. In some embodiments, one of the different liquid concentrates may include an osmotic agent concentrate for use in dialysis therapy. In some embodiments, a third of the plurality of fluid lines may include a connector configured to interface with a diluent source. In some embodiments, the diluent source may be a water purification device. In some embodiments, the third section of the interior volume may be liquid free when the second temporary barrier is intact. In some embodiments, the second temporary barrier may include a number of tiers of seals.

In accordance with an embodiment of the present disclosure a system for use with a fluid handing set having a first fluid handling set portion and a second fluid handling set portion subjected to a higher pressure than a maximum toleration pressure of the first fluid handling set portion may comprise a pumping cassette included in first the fluid handling set portion having a first pump chamber and a fluid valve leading to a port connected to a fluid line from the second fluid handling set portion. The system may further comprise a pressure distribution assembly having a control surface against which the pumping cassette is held, and including at least one pressure transducer configured to output data indicative of the pressure of the first pump chamber. The system may further comprise a high pressure source coupled to the second fluid handling set portion. The system may further comprise a controller configured to receive the data, and generate a failsafe command signal upon determination that the data indicates a pressure rise greater than a predetermined threshold when a fluid flow path between the first pump chamber and the high pressure source is open.

In some embodiments, the higher pressure of the second fluid handling set portion may be at least 100% greater than the maximum toleration pressure of the first fluid handling set portion. In some embodiments, the higher pressure may be at least 500% greater than the maximum toleration pressure of the first fluid handling set portion. In some embodiments, the higher pressure may be greater than or equal to 100 kPa and less than 300 kPa. In some embodiments, the maximum toleration pressure may be between 20 and 70 kPa. In some embodiments, the system may further comprise a positive pressure reservoir and at least one pressure distribution valve actuatable between an open and closed position, a valve of the at least one pressure distribution valve establishing a positive pressure application path between the positive pressure reservoir and the first pump chamber via the control surface in the open position. In some embodiments, the controller may be configured to maintain the first pump chamber at a positive pressure set point lower than the threshold via a valve control signal supplied to the valve of the at least one pressure distribution valve. In some embodiments, the positive pressure set point may be 10 kPa. In some embodiments, the positive pressure set point may be less than 60% of a set point of the positive pressure reservoir. In some embodiments, the failsafe command signal may be a deploy command for an occluder between the pumping cassette and the high pressure source. In some embodiments, the failsafe command signal may be a shutdown command signal for the high pressure source. In some embodiments, the failsafe command may be a release command for an occluder between the pumping cassette and the high pressure source. In some embodiments, the pumping cassette includes a second pump chamber and the controller may be configured to command the pressure distribution module to actuate the control surface the to open a fluid communication pathway within the cassette between the first pump chamber and a second pump chamber of the cassette. In some embodiments, the at least one pressure transducer may include a first pressure transducer disposed in a pump control chamber of the pressure distribution assembly and a second pressure transducer disposed in another chamber of the pressure distribution assembly.

In accordance with another embodiment of the present disclosure, a method for determining a characteristic correlated to a heightwise location of a component of interest of a fluid handling set portion relative to a pumping chamber in a cassette of the fluid handling set may comprise establishing a flow path from the pumping chamber to a port of the cassette coupled to a fluid line coupled to the component of interest. The method may further comprise monitoring data indicative of a pressure in the pump chamber from at least one pressure sensor. The method may further comprise detecting a feature profile in the data. The method may further comprise predicting the characteristic of the component of interest based on the feature profile and temporal data associated with the feature profile.

In some embodiments, the method may further comprise actuating one or more pneumatic valve to apply pressure to cassette and consequentially place the pumping chamber in an intermediary state between a fully filled and fully delivered state before establishing the flow path from the pumping chamber to the port. In some embodiments, the intermediate state may be a state that allows for the detection of a maximum positive and maximum negative head height of about the same absolute value. In some embodiments, the method may further comprise actuating one or more pneumatic valve to apply pressure cassette and consequentially place the pumping chamber in a negative head height detection biased state before establishing the path from pumping chamber to the port. In some embodiments, wherein the method may further comprise actuating one or more pneumatic valve to apply pressure cassette and consequentially place the pumping chamber in a positive head height detection biased state before establishing the path from the pumping chamber to the port. In some embodiments, the method may further comprise comparing the predicted characteristic to an expected characteristic range. In some embodiments, the method may further comprise generating an error signal when the predicted characteristic is outside of the expected range. In some embodiments, predicting the characteristic may comprise applying a behavior model. In some embodiments, the behavior model may be based off an ideal second order undampened system. In some embodiments, detecting the feature profile may comprise detecting one or more pressure peak. In some embodiments, detecting the feature profile may comprise detecting a first pressure peak and a second pressure peak lower in magnitude than the first peak. In some embodiments, the method may further comprise setting an adjusted pumping pressure value based on the predicted characteristic. In some embodiments, the method may further comprise orchestrating pumping of fluid through the pumping cassette via actuation of a second pump chamber in the pumping cassette while detecting the feature profile.

In accordance with an embodiment of the present disclosure a cassette based fluid pumping system may comprise a pumping cassette a number of valve wells, a pump chamber and a fluid bus. The system may further comprise an actuation assembly having a control surface with a number of valve well control stations actuatable to open and close the number of valve wells of the cassette when the cassette is mated against the control surface, a control chamber separated from the pump chamber by a pump chamber control region of the control surface when the cassette is mated against the control surface, and a control chamber volume measurement assembly. The system may further comprise a controller configured to selectively actuate the number of valve well control stations in a valve pumping sequence to deliver fluid from a source through the fluid bus and into the pump chamber and collect control chamber volume data from the control chamber volume measurement assembly until the control chamber volume data indicates a target volume of fluid is present in the pump chamber.

In some embodiments, the number of valve wells and the pump chamber may be included on a first side of the cassette and the fluid bus may be included on a second side of the cassette. In some embodiments, the first and second side of the cassette may be covered by cassette sheeting. In some embodiments the cassette sheeting of the first side of the cassette and second side of the cassette may be sealed to a periphery of the cassette. In some embodiments, the actuation assembly may be a pneumatic pressure distribution assembly. In some embodiments, the source may be a source component connected to the pumping cassette via a fluid line. In some embodiments, the source component may be selected from one of a buffer solution, an acid solution, a purified water source, or a dialysate concentrate. In some embodiments, each valve pumping sequence may transfer under 150 microliters. In some embodiments, each valve pumping sequence may transfer a nominal volume of 70 microliters. In some embodiments, at least one of the plurality of valve wells may be a dedicated holding volume valve well. In some embodiments, the controller may be configured to check the control chamber volume data against a valve pumping criteria to detect a potentially full chamber containing liquid and air when the control chamber volume data is in breach of the valve pumping criteria. In some embodiments, the controller may be configured to collect a measurement indicative of a volume of air in the pump chamber via the control chamber volume measurement assembly when the valve pumping criteria is breached. In some embodiments, the control chamber volume data may be compared to the measurement indicative of a volume of air in the pump chamber to determine whether the volume of air in the pump chamber is greater than a threshold. In some embodiments, the valve pumping criteria may be a minimum volume displacement into the pumping chamber per valve pumping sequence. In some embodiments, the valve pumping criteria may be a minimum volume displacement into the pumping chamber for a plurality of valve pumping sequence actuations. In some embodiments, the valve pumping criteria may be a maximum number of valve pumping sequence actuations. In some embodiments, the control chamber volume measurement assembly may include a pressure sensor in communication with the control chamber, a reference chamber having a known volume separated from the control chamber via a valve, and a pressure sensor in communication with the reference chamber.

In accordance with another embodiment of the present disclosure a pneumatic peristaltic pumping system may comprise a pumping cassette having a cassette body with first and second side respectively covered by first and second flexible membranes. The pumping cassette may have a common fluid bus and a plurality of translational elements. The system may further comprise a pneumatic actuation assembly having a control surface with a plurality of translational element control regions actuatable to displace the plurality of translational elements of the cassette when the cassette is mated against the control surface. The system may further comprise a cassette mount actuatable between a first position and a second position, the second position being a position in which the first flexible membrane is held against the control surface. The system may further comprise a controller configured to actuate the translational element control regions in order to operate the translational elements in a pumping sequence. The controller may be configured to repeat the sequence until a volume transferred via the pumping cassette from a source to a destination is within a range of a target volume.

In some embodiments, each translational element may be associated with a valve seat included in a translational element station. In some embodiments, the destination may be a pump chamber. In some embodiments, the pump chamber may also be included in the pumping cassette. In some embodiments, the source may be a pump chamber also included in the pumping cassette. In some embodiments, the destination may be a mixing reservoir attached to an outlet of the pumping cassette via a fluid line. In some embodiments, each pump sequence may displace less than 100 microliters. In some embodiments, each pump sequence may displace a nominal volume of 70 microliters. In some embodiments, the common fluid bus may be disposed on the second side of the pumping cassette and the plurality of translational element may be disposed on the first side of the pumping cassette. In some embodiments, a portion of the pumping cassette body may form a platen stationary with respect to the translational elements. In some embodiments, the platen may have a first side facing the first side of the pumping cassette and a second side facing the second side of the pumping cassette. In some embodiments, the pump sequence may displace the translational elements on one side of a platen of the pumping cassette body. In some embodiments, the displacement of the translational elements may cause fluid transfer through the common bus on an opposing side of the platen. In some embodiments, the platen may include at least one respective fluid flow channel in line with each of the translational elements and extending through the platen to the common fluid bus. In some embodiments, the pumping cassette may include a pump chamber on the first side of the pumping cassette and the control surface may include a pump chamber control region. In some embodiments, the controller may be configured to fill deliver the pump chamber from the source by governing application of negative and positive pressure to the pump chamber. The controller may be configured to monitor the volume of the pump chamber via at least one sensor and begin actuating the translational element control regions in the pumping sequence when the volume of the pump chamber is within a second range of the target volume. In some embodiments, the difference between bounds of the second range may be greater than the difference between bounds of the first range. In some embodiments, a nominal fill volume of the pump chamber may be at least 10 times greater than an amount of fluid displaced by each pumping sequence. In some embodiments, a nominal fill volume of the pump chamber may be at least 100 times greater than an amount of fluid displaced by each pumping sequence. In some embodiments, a nominal fill volume of the pump chamber may be at least 300 times greater than an amount of fluid displaced by each pumping sequence. In some embodiments, the controller may be configured to repeat the pumping sequence in an open loop manner until the volume transferred is within the first range of the target volume. In some embodiments, the controller may be configured to repeat the pumping sequence in a semi-closed loop manner until the volume transferred is within the first range of the target volume. In some embodiments, the controller may be configured to repeat the pumping sequence in a closed loop manner until the volume transferred is within the first range of the target volume.

In accordance with another embodiment of the present disclosure a fluid pumping system may comprise a fluid handing set including a pumping cassette having a diaphragm overlaying a pump chamber and a plurality of fluid valves. The system may further comprise a pneumatic distribution assembly including a control surface having actuatable control regions for the pump chamber and plurality of fluid valves. The system may further comprise a controller configured to govern operation of the pneumatic distribution assembly to fill the pump chamber from a source and to deliver the pump chamber to a destination. The controller may be configured to fill the pump chamber to a target volume based on data from at least one sensor of the pneumatic distribution assembly, stop filling of the pump chamber and command a volume measurement of pump chamber be collected via a measurement assembly included in the pneumatic distribution assembly, and compare measurement data from the volume measurement to a target volume range criteria. The controller may be configured to command delivery of the pump chamber to the destination if the measurement data is within the target volume range criteria and may be configured to command delivery of at least a portion of the pump chamber to a retry reservoir if the measurement data is outside the target volume range criteria.

In some embodiments, the target volume range criteria may be no greater than +/−2 ml of the target volume. In some embodiments, the at least one sensor may include a pressure sensor. In some embodiments, the at least one sensor may be configured to provide substantially continuous data to the controller as the pump chamber is filled. In some embodiments, the data provided from the at least one sensor may be pressure data and the controller may be configured to monitor a pressure decay in a control chamber associated with the pump chamber to determine when the pump chamber has been filled to the target volume. In some embodiments, the retry reservoir may be the source. In some embodiments, the at least one sensor may be included in the measurement assembly. In some embodiments, the volume measurement of the pump chamber may be based on ideal gas laws.

In accordance with an embodiment of the present disclosure a method of determining a heightwise location of a component of interest relative to a pumping chamber of a fluid handling set, may comprise establishing a flow path between the pumping chamber and the component of interest. The method may further comprise receiving, with a controller, data from a pressure sensor indicative of pressure in the pump chamber. The method may further comprise detecting, with the controller, a feature profile in the data. The method may further comprise determining, with the controller, the heightwise location of the component of interest using the data and temporal data associated with the feature profile before the data indicates that the pressure in the pump chamber is stable.

In some embodiments, the method may further comprise actuating one or more pneumatic valve of the pressure distribution module to apply pressure to the control surface and consequentially place the pumping chamber in an intermediary state between a fully filled and fully delivered state before establishing the path from the pump chamber to the component of interest. in some embodiments, the intermediate state may be a state that allows for the detection of a maximum positive and maximum negative head height of about the same absolute value. In some embodiments, the method may further comprise actuating one or more pneumatic valve of the pressure distribution module to apply pressure to the control surface and consequentially place the pumping chamber in a negative head height detection biased state before establishing the path from the pumping chamber to the component of interest. In some embodiments, the method may further comprise actuating one or more pneumatic valve of the pressure distribution module to apply pressure to the control surface and consequentially place the pumping chamber in a positive head height detection biased state before establishing the path from the pump chamber to the component of interest. In some embodiments, the method may further comprise comparing the determined height wise location to an expected range and generating an error signal when the predicted characteristic is outside of the expected range. In some embodiments, the method may further comprise using a behavior model. In some embodiments, the behavior model may be based off an ideal second order undampened system. In some embodiments, detecting the feature profile may comprise detecting one or more pressure peak. In some embodiments, detecting the feature profile may comprise detecting a first pressure peak and a second pressure peak lower in magnitude than the first peak. In some embodiments, the method may further comprise setting an adjusted pumping pressure value based on the heightwise location of the component of interest. In some embodiments, the method may further comprise orchestrating pumping of fluid through the pumping cassette via actuation of one or more pneumatic valves in the pressure distribution module associated with a second pump chamber in the pumping cassette while detecting the feature profile.

In accordance with another embodiment of the present disclosure a fluid pumping system for providing a medical therapy may comprise a fluid handling set including a cassette having at least one pump chamber and a number of fluid lines coupled to the cassette. The system may further comprise a pressure distribution assembly having a pneumatically actuated control surface against which the pumping cassette is held and at least one pressure transducer configured to output data indicative of the pressure of the at least one pump chamber. The system may further comprise a liquid dispensing device in fluid communication with the cassette via a flow path provided by at least one of the number of fluid lines. The system may further comprise a controller configured to command delivery of a liquid into the flow path from the liquid dispensing device to place the flow path in a semi-dry state and govern application of pressure to actuate the pump chamber and pressurize the flow path. The controller may be configured prohibit use of the cassette for the medical therapy when the data indicates a breach of a pressurization criteria.

In some embodiments, the liquid may be purified water. In some embodiments, the liquid dispensing device may be a water purification device. In some embodiments, the flow path may include an accumulator. In some embodiments, the flow path may include at least one filter. In some embodiments, the flow path may include an accumulator and the semi-dry state may a state in which a portion of the flow path between the liquid dispensing device and the accumulator is filled with liquid. In some embodiments, the controller may be configured to actuate the pump chamber to pressurize the flow path to a positive pressure. In some embodiments, the pressurization criteria may be a positive pressurization check which is breached in the event a reduced flow condition is detected based on the data. In some embodiments, the controller may be configured to actuate the pump chamber to pressurize the flow path to a negative pressure. In some embodiments, the pressurization criteria may be a negative pressurization which is breached in the event that more than an expected amount of gas is pumped from the flow path.

In accordance with another embodiment of the present disclosure a method of performing a semi-dry set integrity test may comprise filling a portion of a flow path of a fluid handling set most distal to a cassette of the fluid handling set with a liquid. The method may further comprise pumping a gas, via the cassette, to pressurize the flow path. The method may further comprise monitoring, with a controller, data from at least one sensor indicative of a pressure in the flow path. The method may further comprise determining, with a controller, if the data conforms with at least one pressurization criteria. The method may further comprise prohibiting use of the fluid handling set when the data breaches any of the at least one pressurization criteria.

In some embodiments, prohibiting use of the fluid handling set may comprise generating a message for display on a user interface. In some embodiments, filling the portion of the flow path may comprise dispensing a volume of fluid from a liquid dispensing device coupled to the flow path. In some embodiments, filling the portion of the flow path may comprise dispensing a volume of purified water from a water purification device coupled to the flow path. In some embodiments, filling the portion of the flow path may comprise dispensing a volume of fluid from a liquid dispensing device to fill a portion of the flow path between the liquid dispensing device and an accumulator included in the flow path. In some embodiments, pumping the gas may comprise delivering a volume of gas from a pump chamber of the cassette to the flow path. In some embodiments, determining if the data conforms to the at least one pressurization criteria may comprise performing a positive pressurization check which is breached when a reduced flow condition for fluid pumped from the pump chamber is detected. In some embodiments, pumping the gas may comprise filling the pump chamber with gas from the flow path. In some embodiments, determining if the data conforms to the at least one pressurization criteria may comprise performing a negative pressurization check which is breached when more than an expected amount of gas is pumped from the flow path before a reduce flow condition is detected based on the data. In some embodiments, filling the portion of the flow path may comprise wetting at least one filter included in the flow path.

In some embodiments, a method for checking the integrity of a fluid handling set may comprise performing a dry fluid handling set integrity check. The method may further comprise partially priming the fluid handling set. The method may further comprise performing a semi-dry set integrity check on an unprimed section of the set. The method may further comprise fully priming the fluid handling set. The method may further comprise performing a wetted fluid handling set integrity check. The method may further comprise prohibiting use of the fluid handling set when any of the dry, semi-dry, or wetted, fluid handling set integrity checks fails.

In some embodiments, partially priming the fluid handling set may comprise priming a portion of a flow path located at a point most distal to a cassette in fluid communication with the flow path. In some embodiments, partially priming the fluid handling set may comprise dispensing a volume of water from a water purification device. In some embodiments, partially priming the fluid handling set may comprise wetting at least one filter in a flow path of the fluid handling set. In some embodiments, partially priming the fluid handling set may comprise filling a portion of a flow path between a terminal end of the flow path and an accumulator in the flow path with liquid. In some embodiments, prohibiting use of the fluid handling set may comprise generating a message for display on a user interface of a pumping device. In some embodiments, performing the semi-dry set integrity test may comprise delivering a pumping chamber of gas from a cassette included in the fluid handling set to a semi-dry flow path of the fluid handling set and monitoring for conformance to a pressurization criteria. In some embodiments, performing the semi-dry set integrity test may comprise filling a pumping chamber of a cassette included in the fluid handling set with fluid from a semi-dry flow path of the fluid handling set and monitoring for conformance to a pressurization criteria.

In accordance with another embodiment of the present disclosure a cassette based fluid pumping system may comprise a fluid handling set including a cassette and a number of flow paths. The system may further comprise a pressure distribution assembly having a control surface configured to mate against the cassette and at least one sensor configured to output data indicative of pressure in the fluid handling set. The system may further comprise a controller configured to orchestrate application of pressure to the cassette via the pressure distribution assembly to conduct a plurality of fluid handling set integrity tests including a dry fluid handling set integrity test, a semi-dry fluid handling set integrity test, and a wetted fluid handling set integrity test. The controller may be configured to prohibit further use of the fluid handling set when any of the plurality of fluid handling set integrity tests fails.

In some embodiments, the controller may be configured to communicate a partial priming command to a liquid dispensing device coupled to a flow path of the fluid handling set at a point on the flow path most distal to the cassette during the semi-dry fluid handling set integrity test. In some embodiments, the liquid dispensing device may be a water purification device. In some embodiments, the fluid handling set may include at least one filter which is in a wetted state during the semi-dry fluid handling set integrity test. In some embodiments, the fluid handling set may include an accumulator and a portion of a flow path between a terminal end of the flow path and the accumulator in the flow path is filled with liquid during the semi-dry fluid handling set integrity test. In some embodiments, the controller may be configured to generating a message for display on a user interface of the system when any of the plurality of fluid handling set integrity tests fail. In some embodiments, the controller may be configured to orchestrate delivery of a pumping chamber of gas from the cassette to a semi-dry flow path of the number of flow paths and monitor the data for conformance to a pressurization criteria during the semi-dry fluid handling set integrity test. In some embodiments, the controller may be configured to orchestrate filling of a pumping chamber of the cassette with fluid from a semi-dry flow path of the number of flow paths and monitor the data for conformance to a pressurization criteria during the semi-dry cassette integrity test.

BRIEF DESCRIPTION OF THE DRAWINGS

These and other aspects will become more apparent from the following detailed description of the various embodiments of the present disclosure with reference to the drawings in which like numerals reference like elements, and wherein:

FIG. 24 shows an example screen depicting a result of an identification tag analysis generated for display on a user interface;

FIG. 120 is an illustration of the implementation of an adaptive tidal mode during a tidal therapy;

FIG. 121 is an illustration showing peritoneal volume over time for a tidal therapy;

FIG. 122 is another illustration showing peritoneal volume over time for a tidal therapy;

FIG. 123 is an illustration of peritoneal volume over time for a tidal therapy which includes an adapted fill;

FIG. 124 shows a flowchart outlining steps which may be used to replenish a heater bag with dialysate solution;

FIG. 125 shows a flowchart outlining steps which may be employed by a cycler which uses solution expiration timers;

FIG. 126 shows an example screen which may be generated by a processor for display on a user interface of a cycler indicating a solution expiration timer;

FIG. 127A and FIG. 127B are flowcharts of a cycler performing an initial drain that starts with a flow check;

FIG. 128 shows a screen shot which may be generated for display on a user interface of a cycler during a drain that includes a soft drain option;

FIG. 129 shows a flowchart outlining steps which may be used to program and collected an automated effluent sample using a cycler;

FIG. 130 shows a flowchart outlining steps which may be used to program and collected an automated effluent sample using a cycler;

FIG. 131 shows a flowchart detailing a number of example actions which may be executed to detect a head height of a component of interest of the system;

Figure 132:
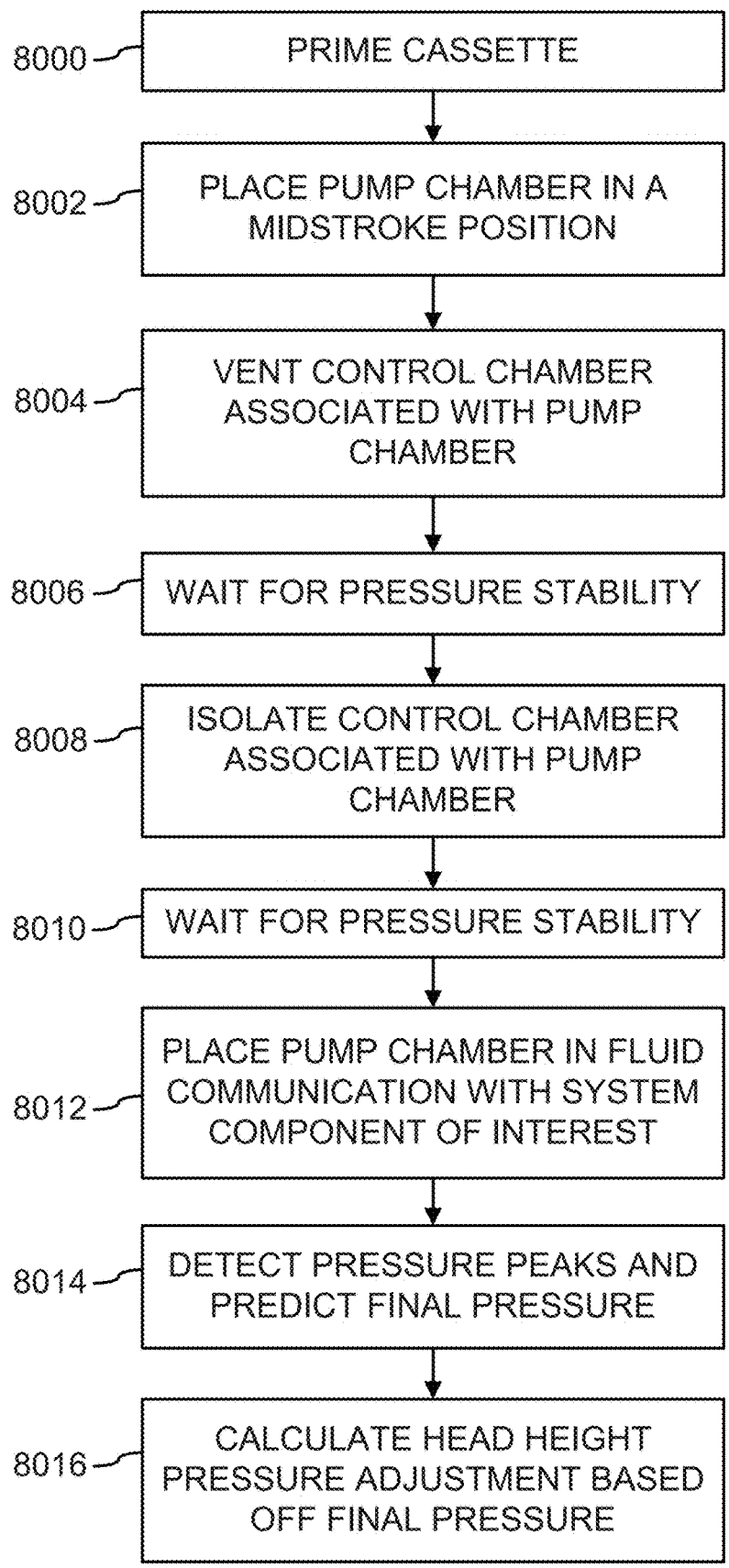
Figure 133:
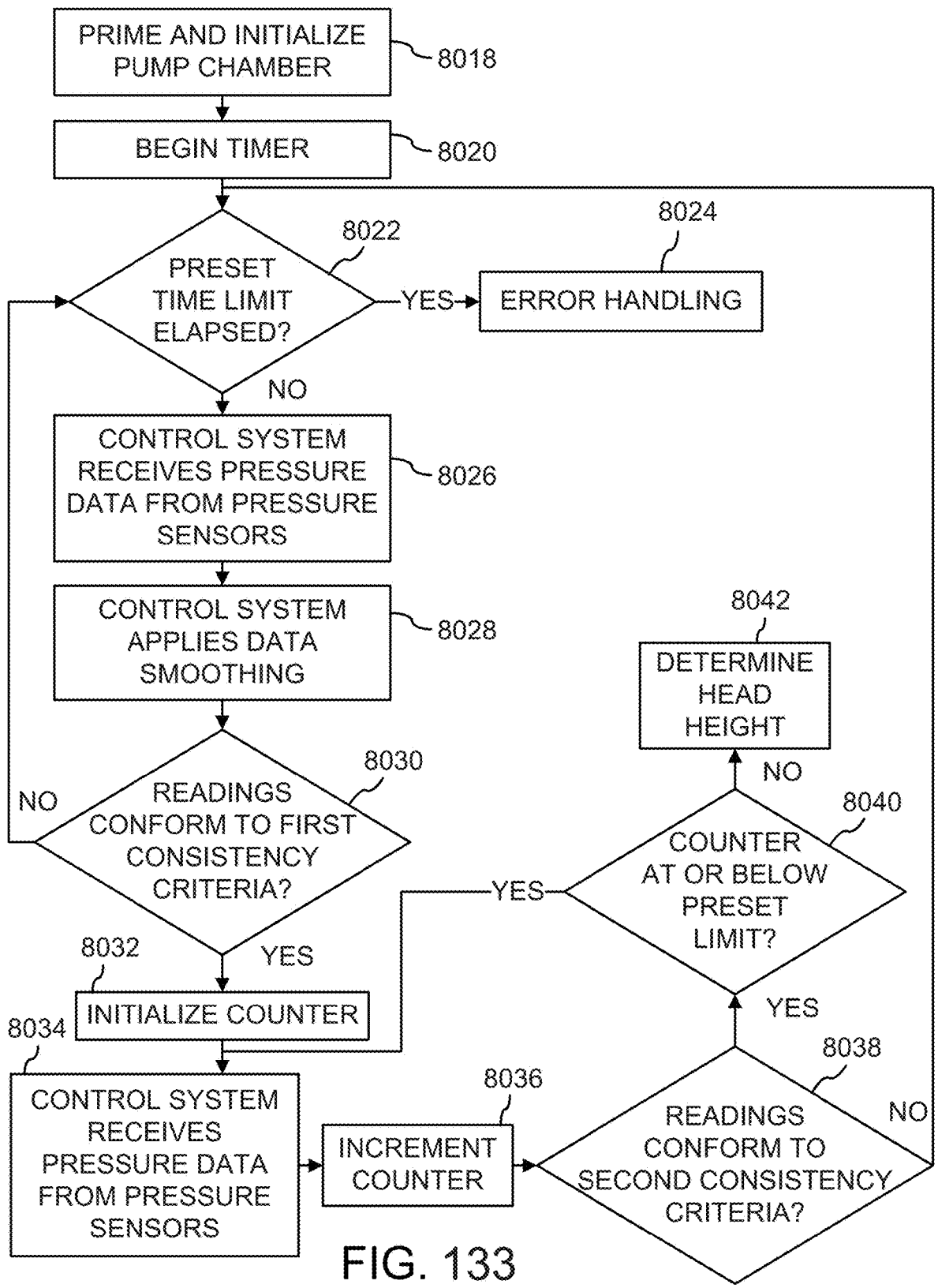
Figure 134:
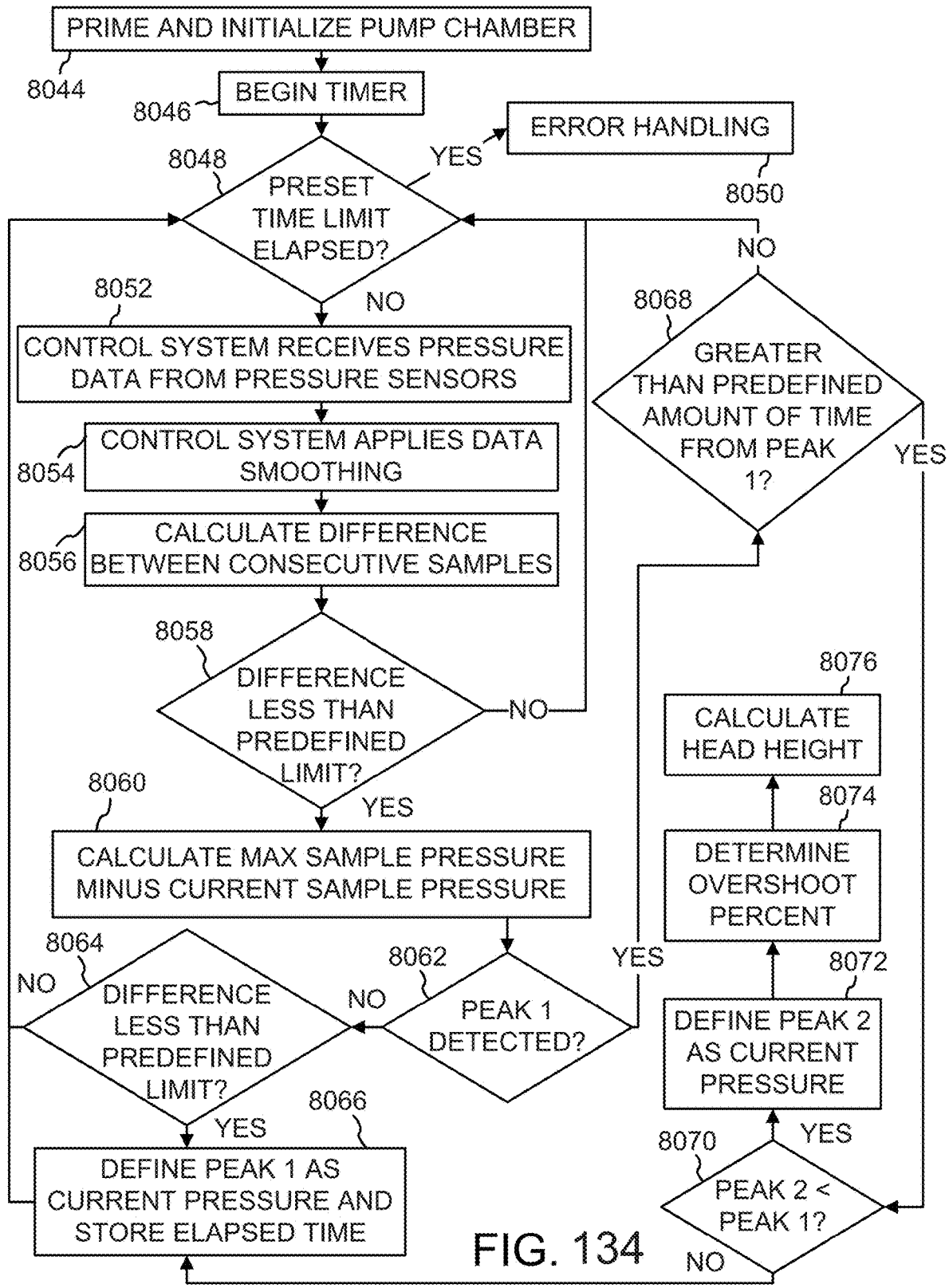
Figure 135:
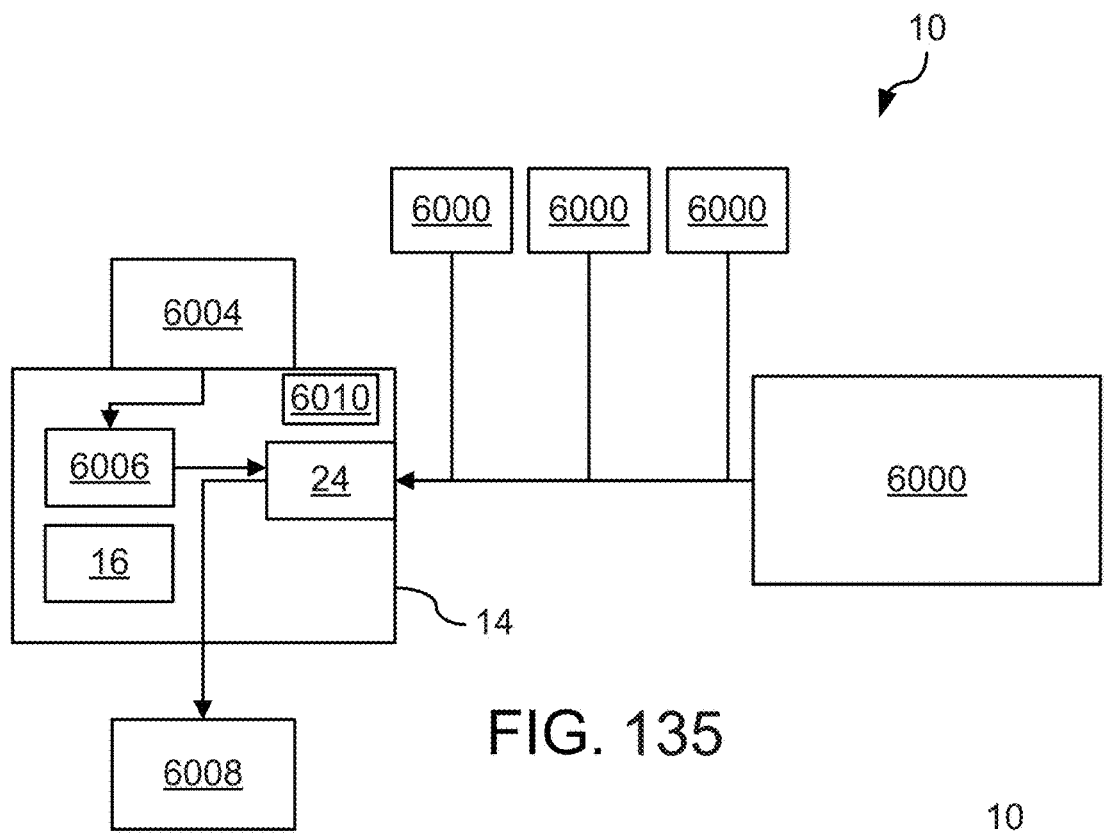
Figure 136:
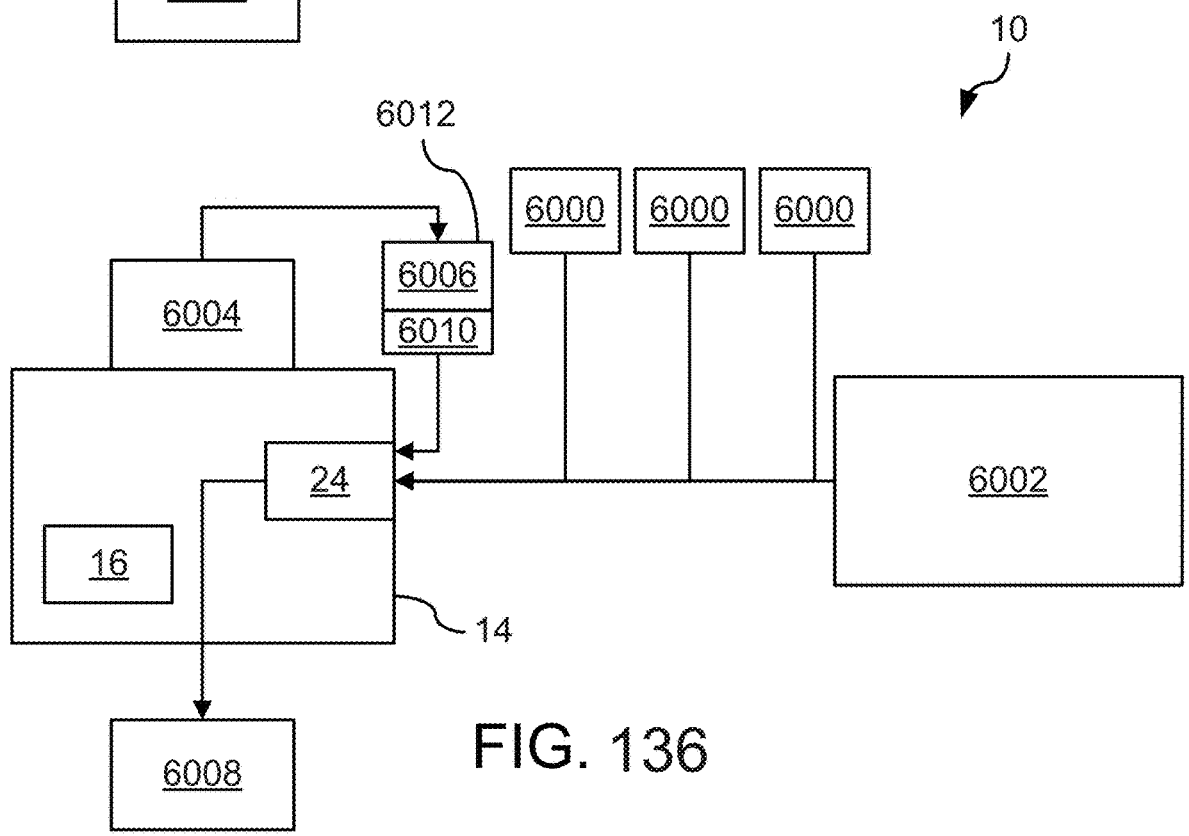
Figure 153:
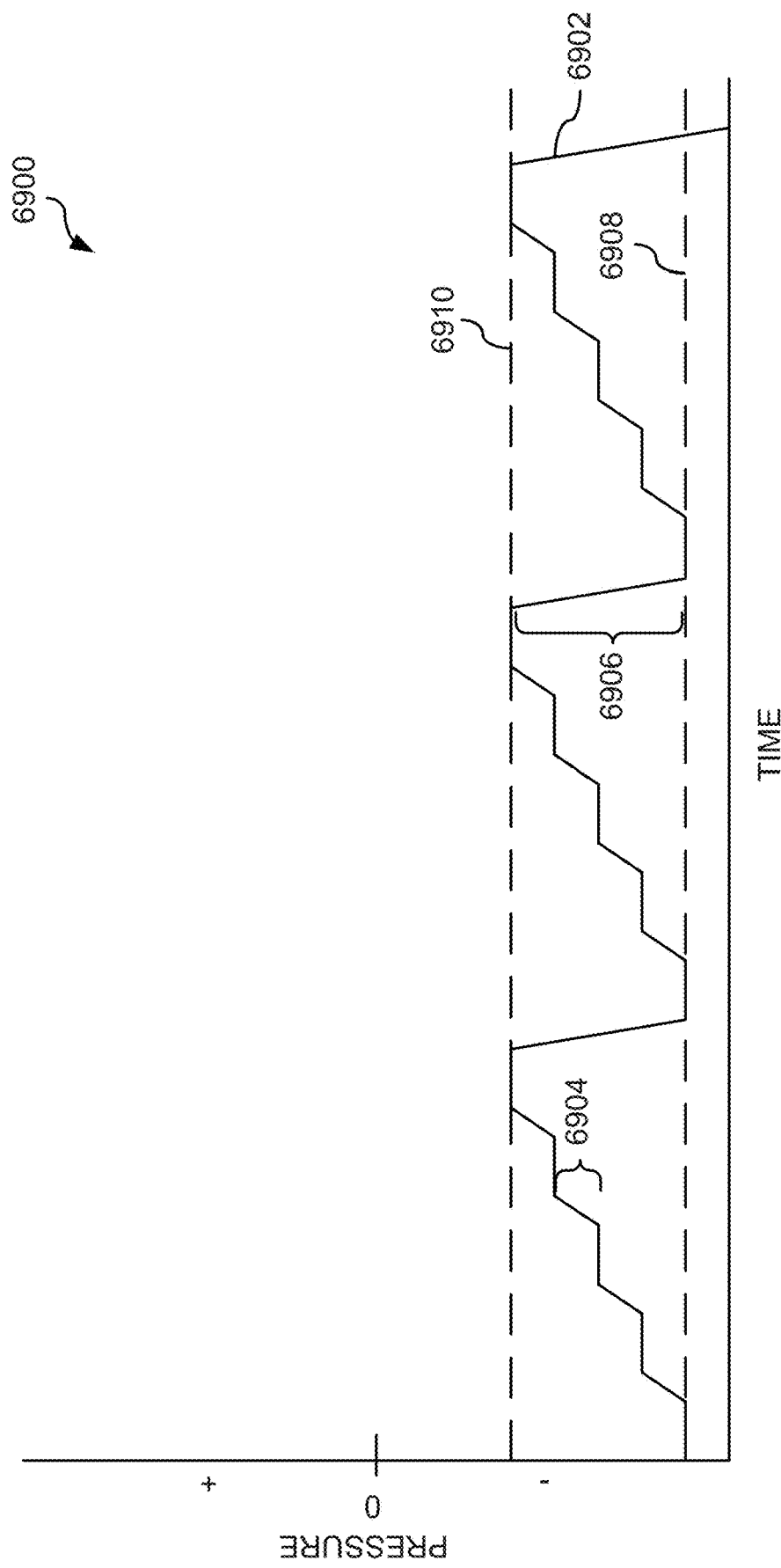
Figure 154:
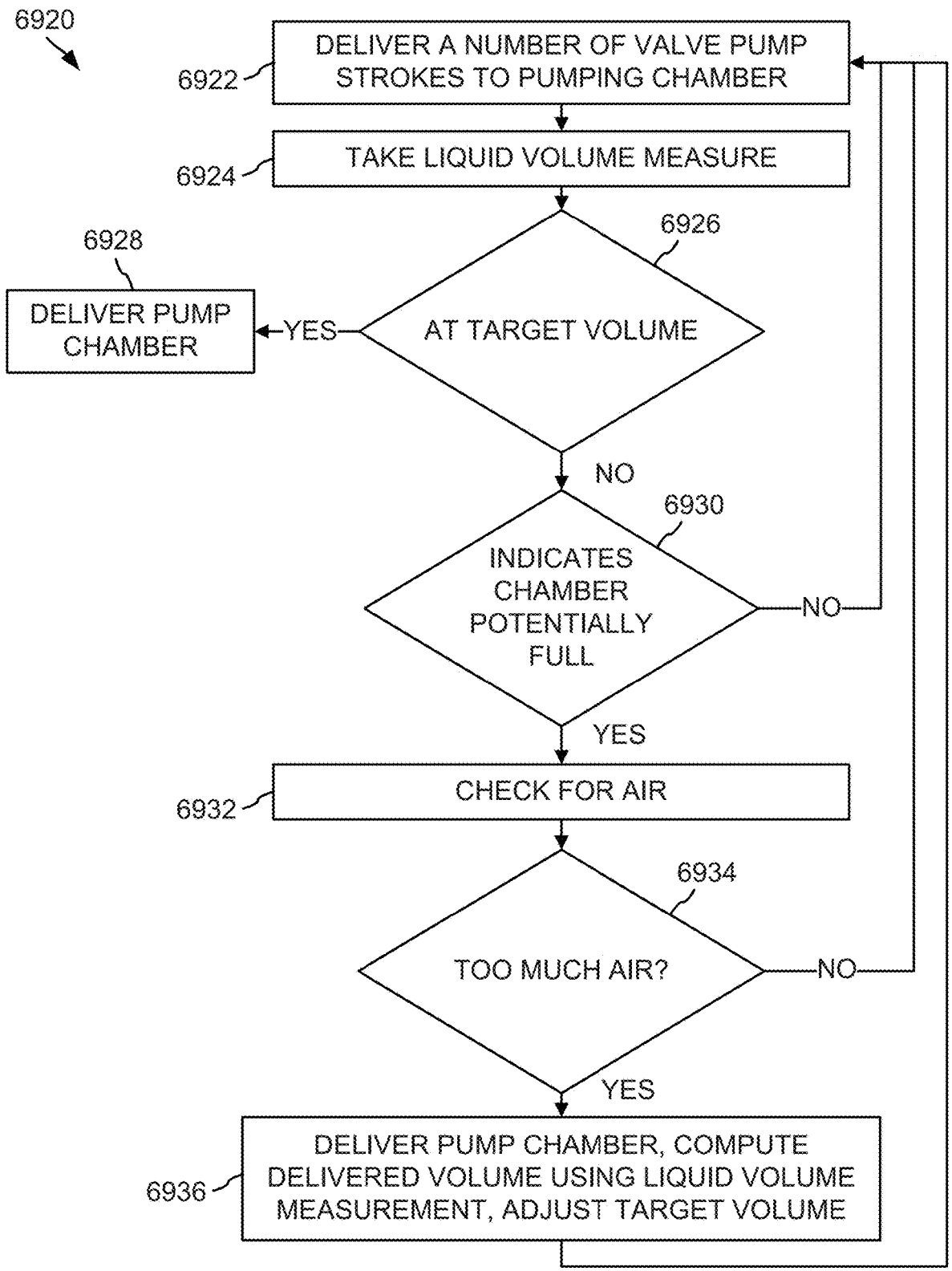
Figure 155A:
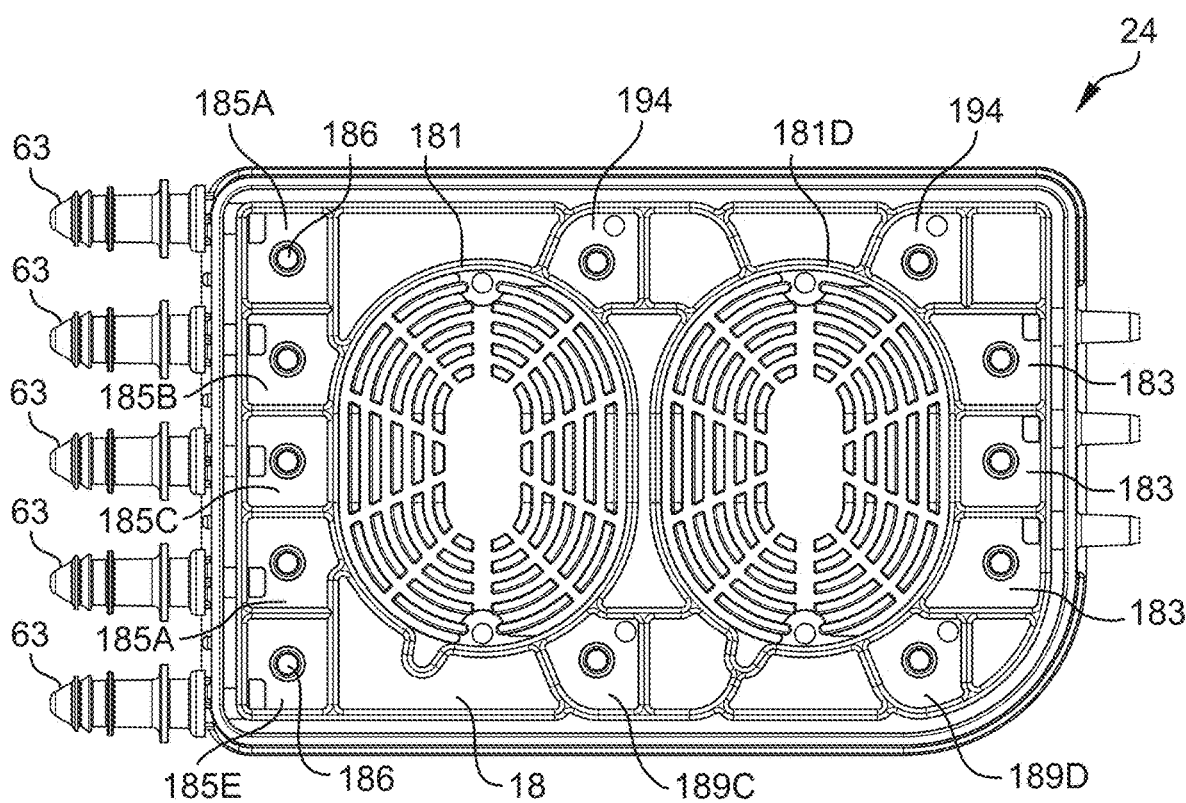
Figure 155B:
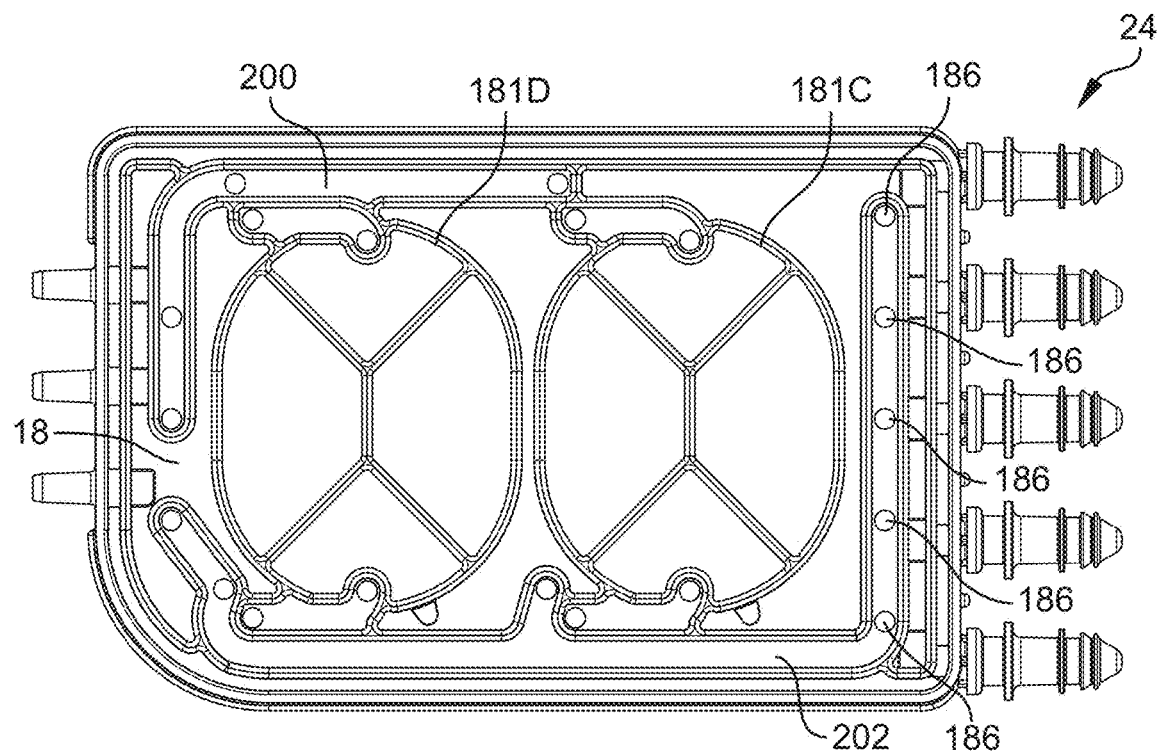
Figure 158:
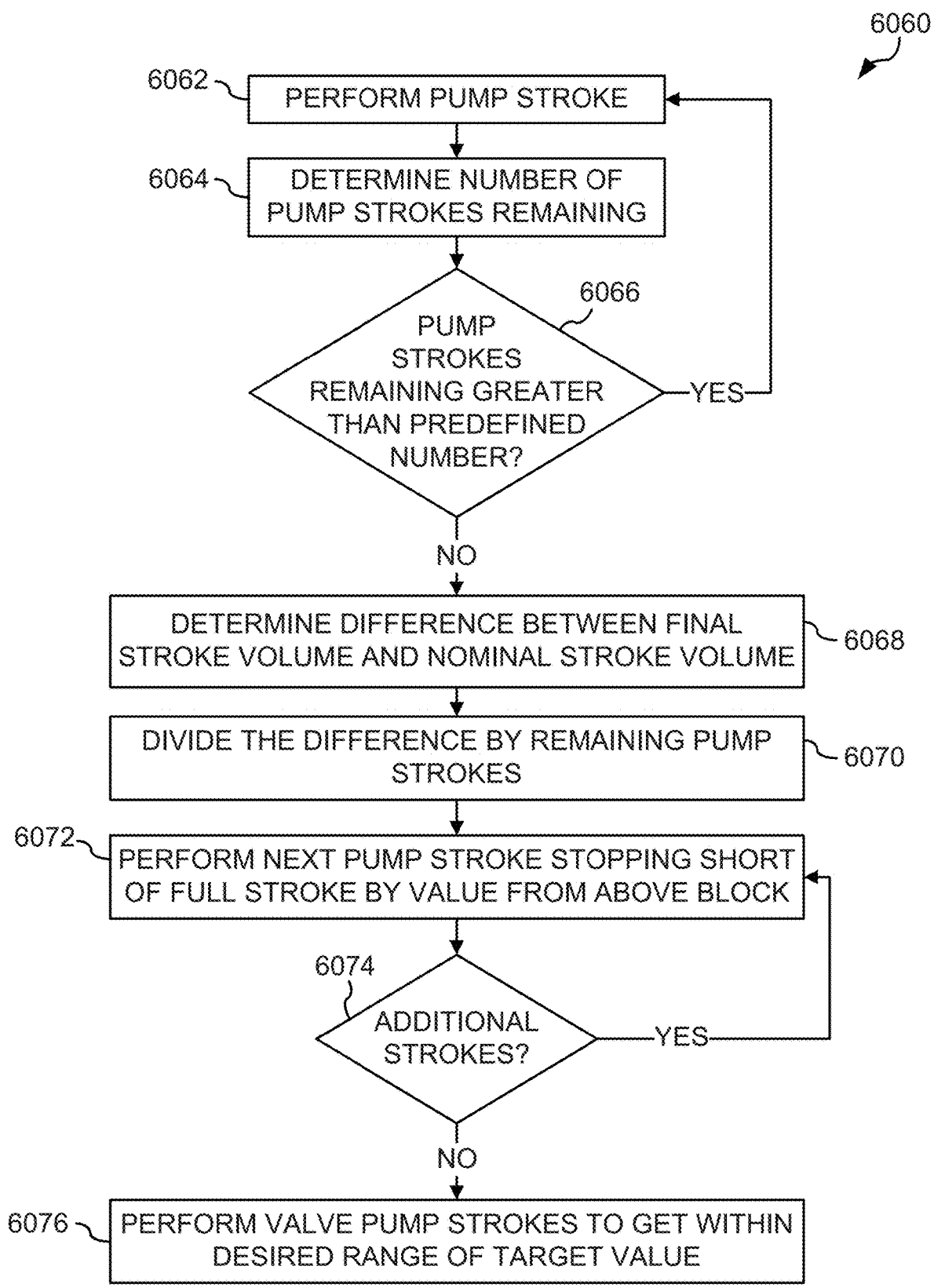
Figure 159:
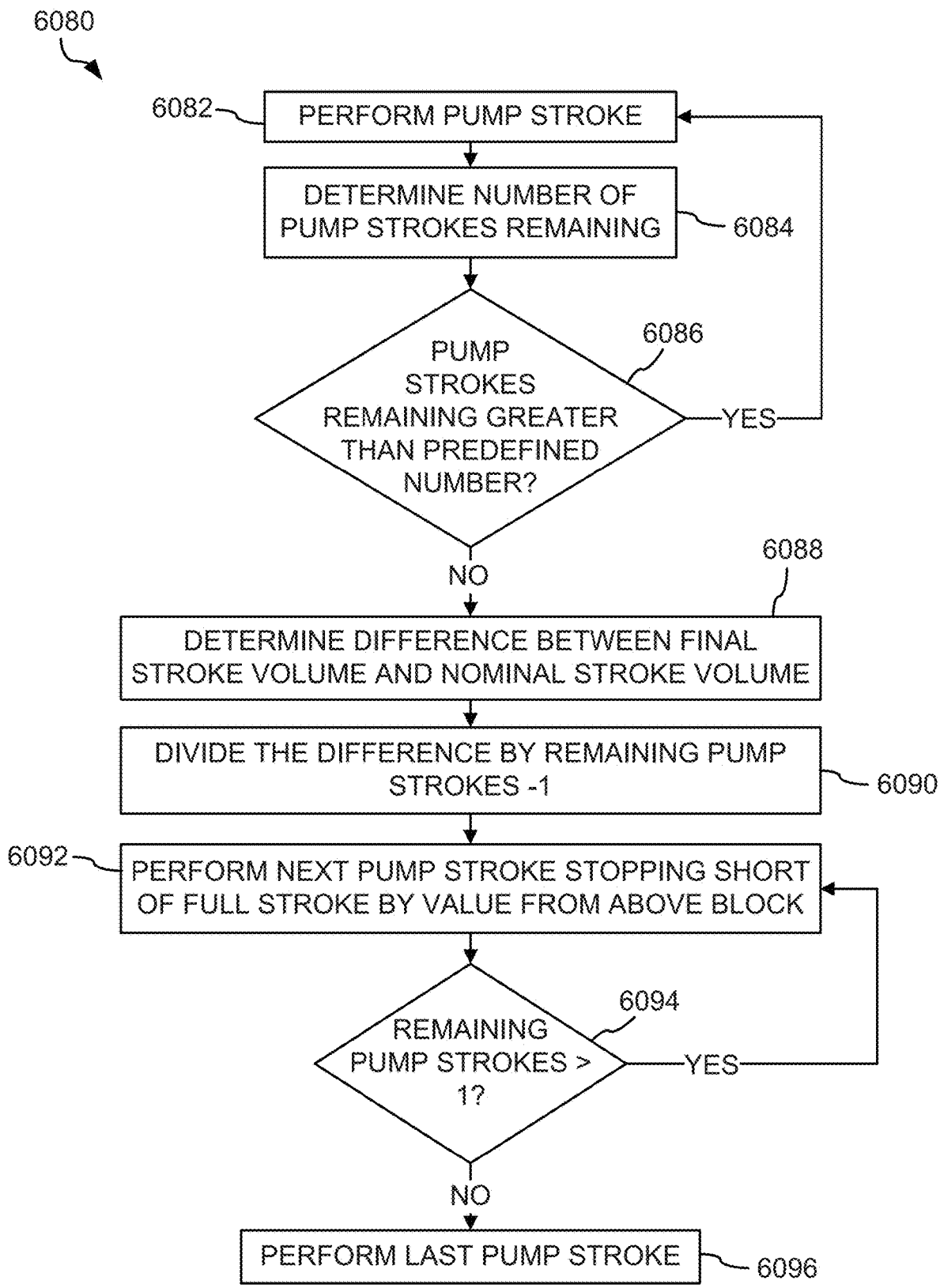
Figure 160:
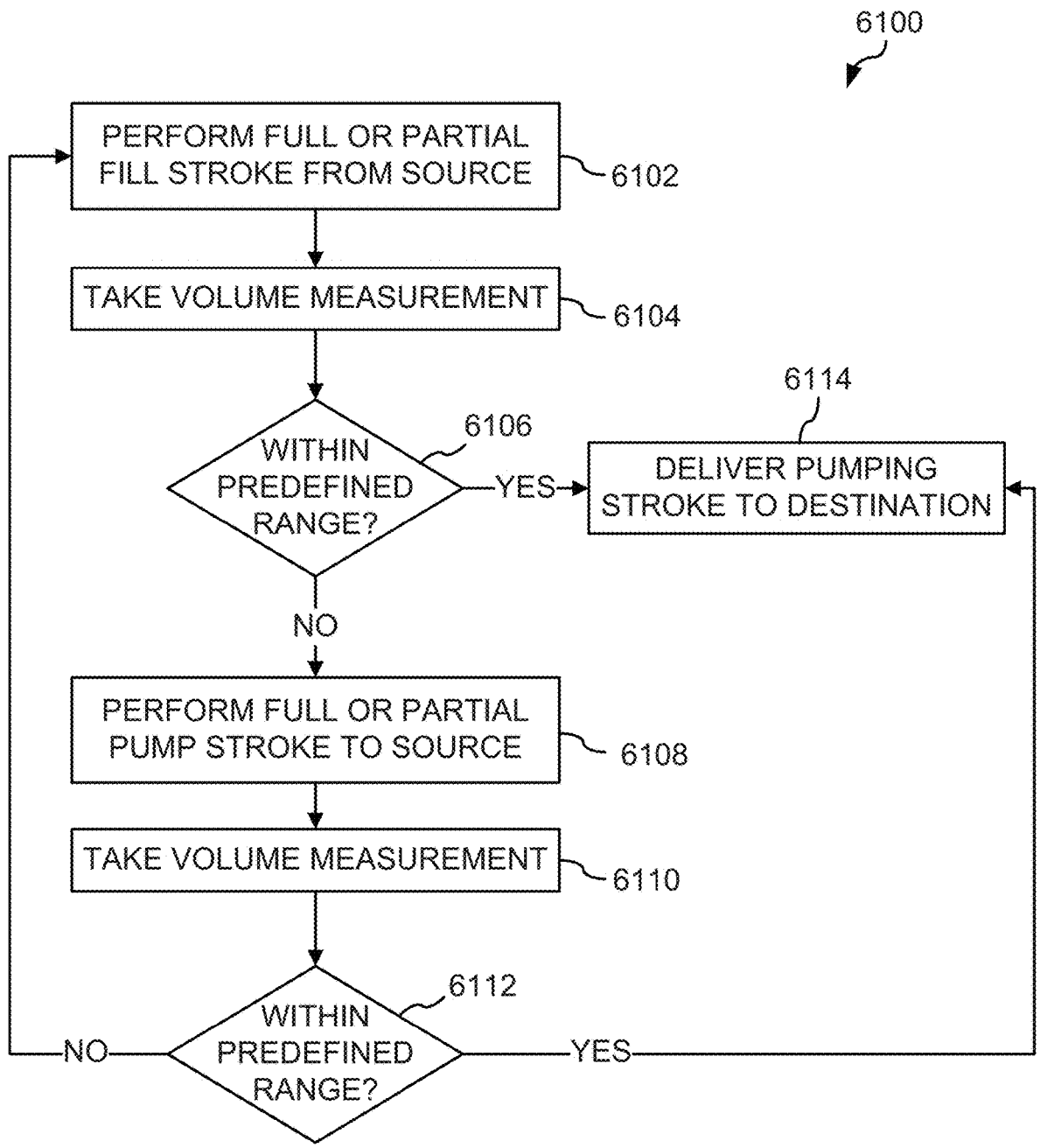
Figure 161:
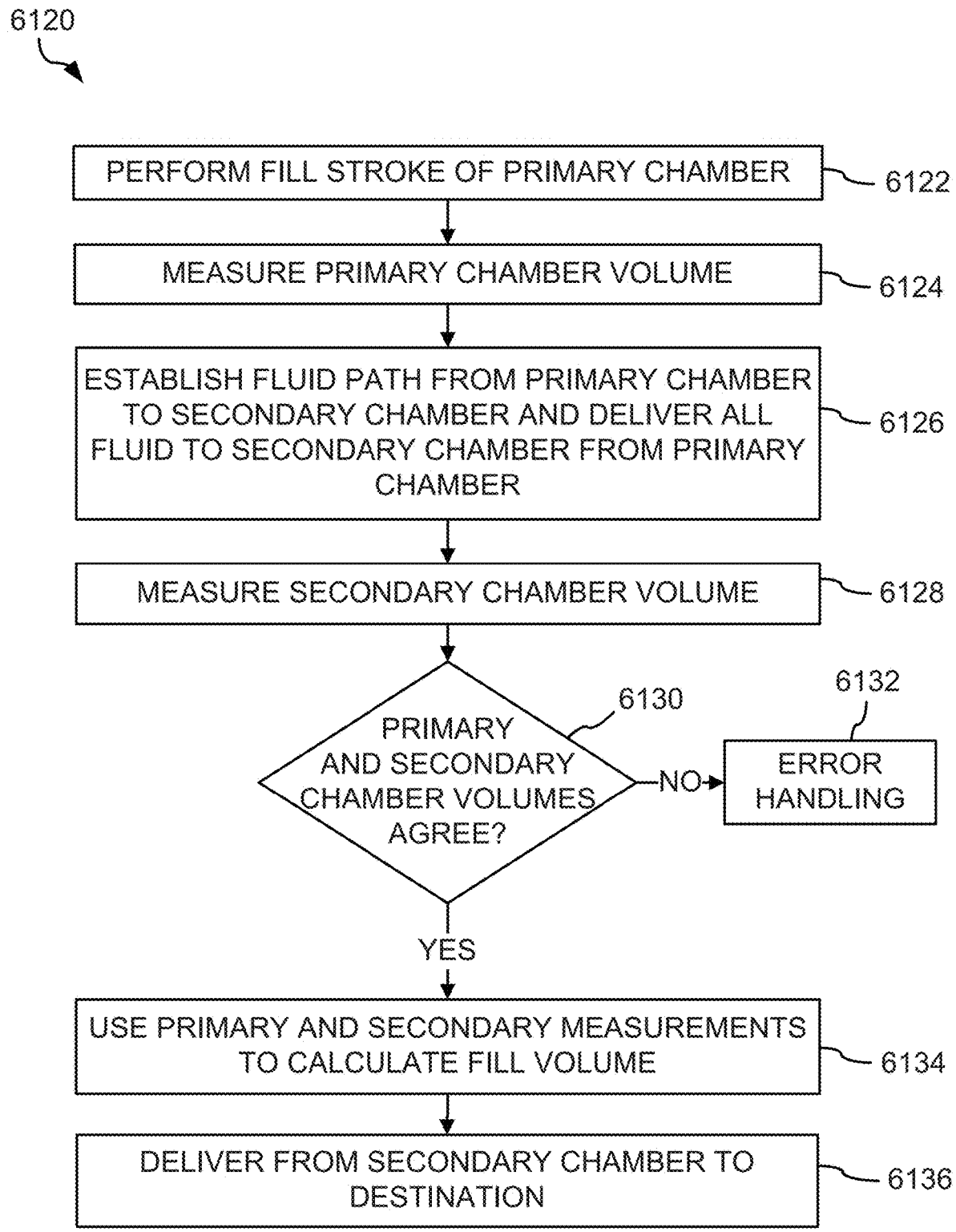
Figure 162:
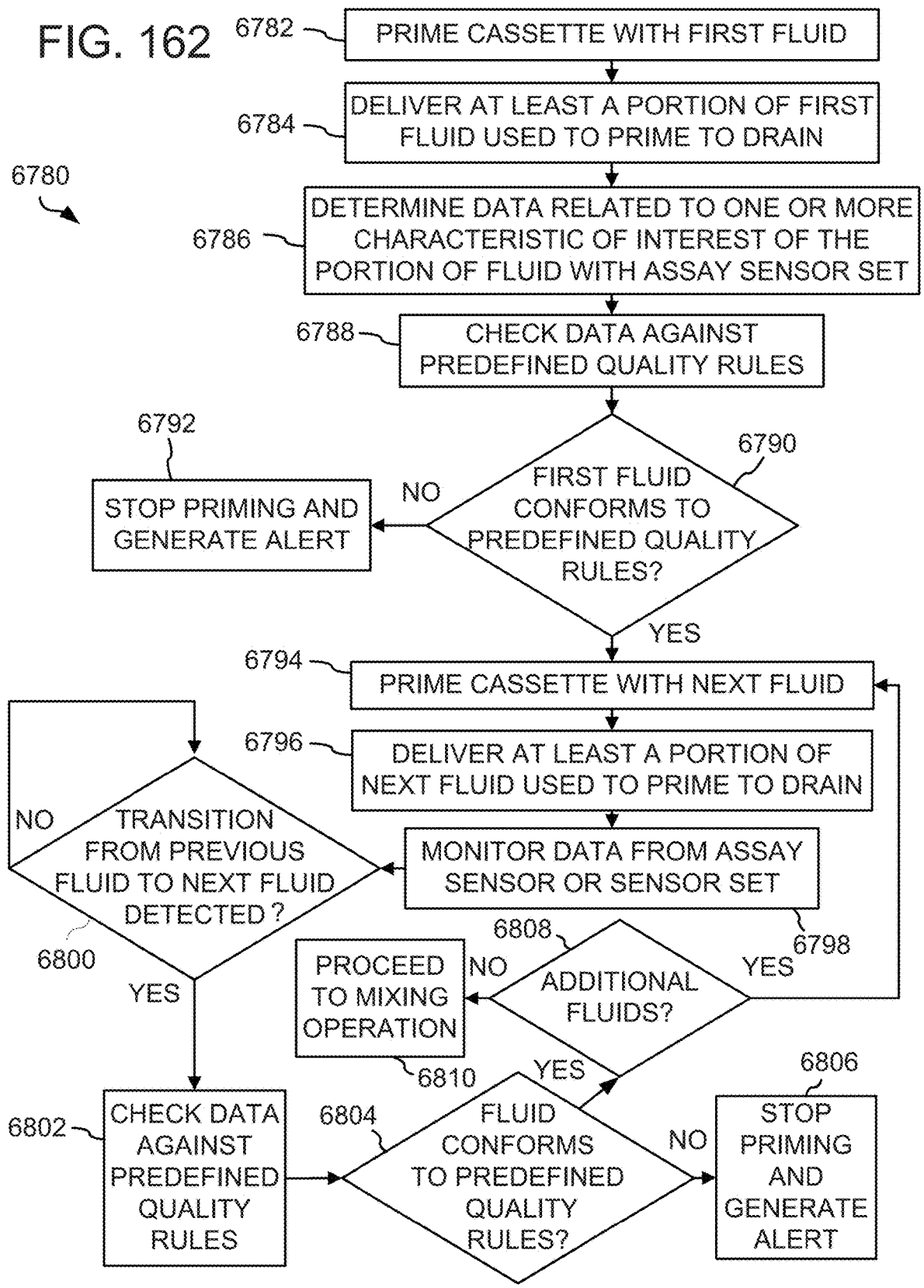
Figure 163:
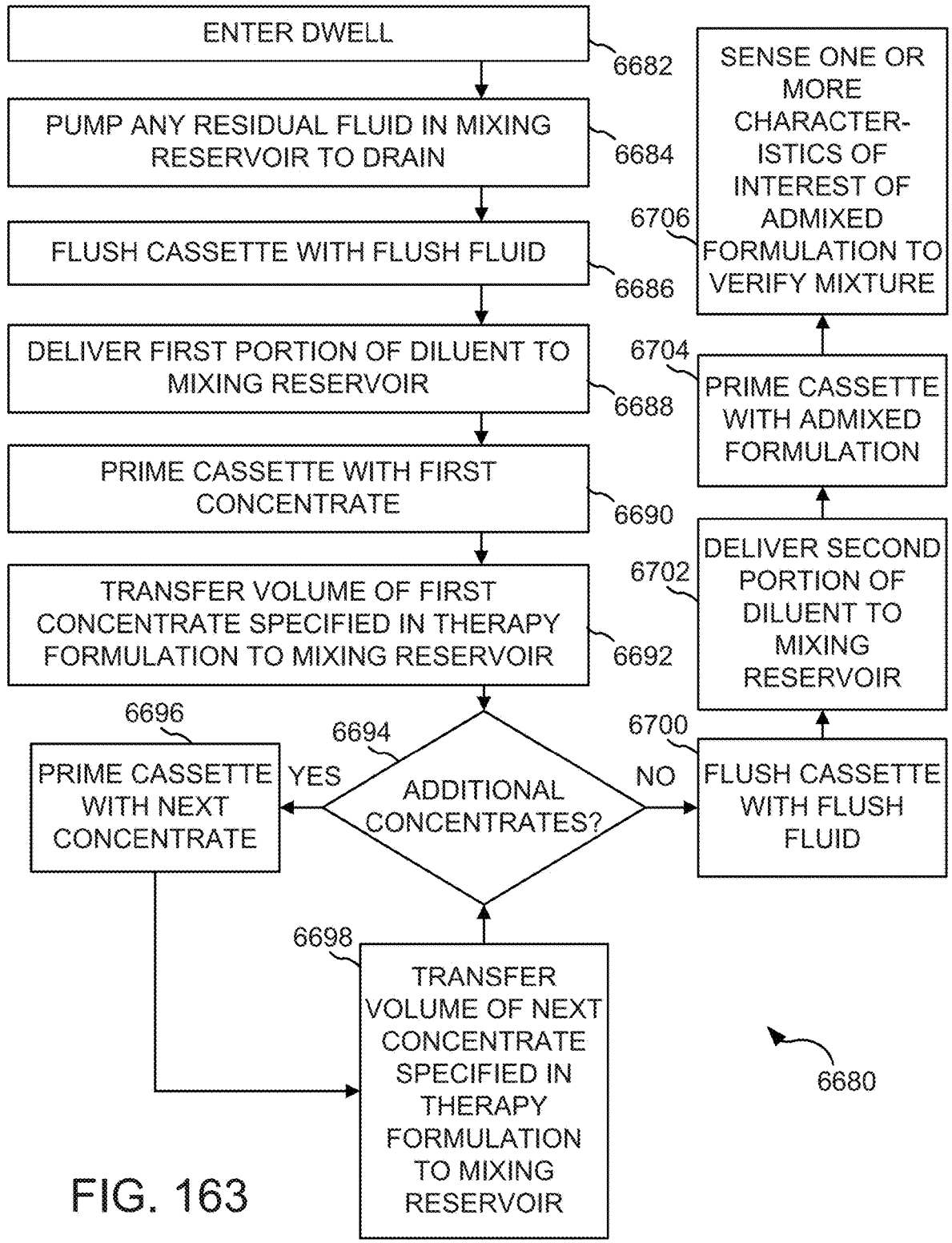
Figure 164A:
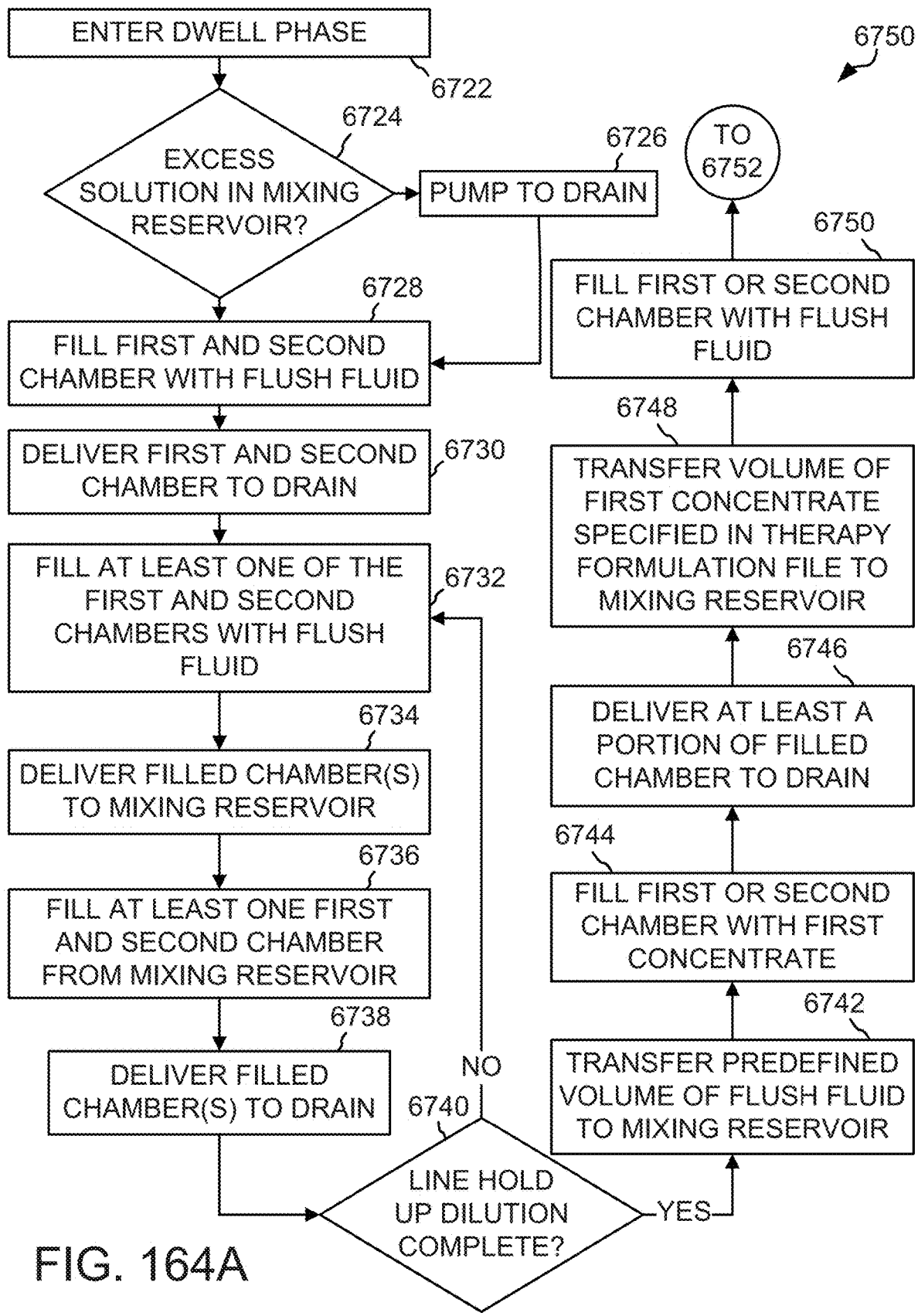
Figure 164B:
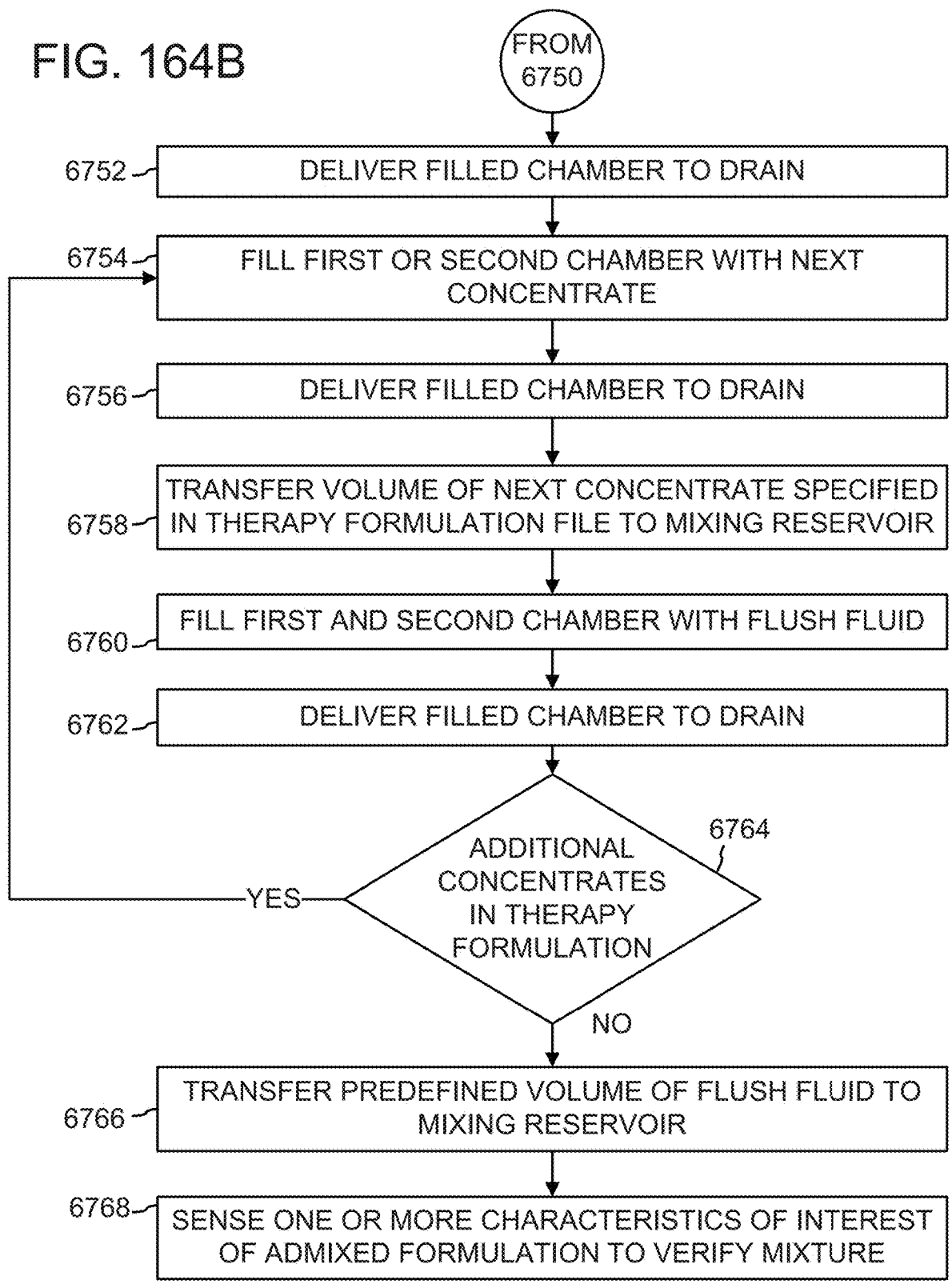
Figure 165:
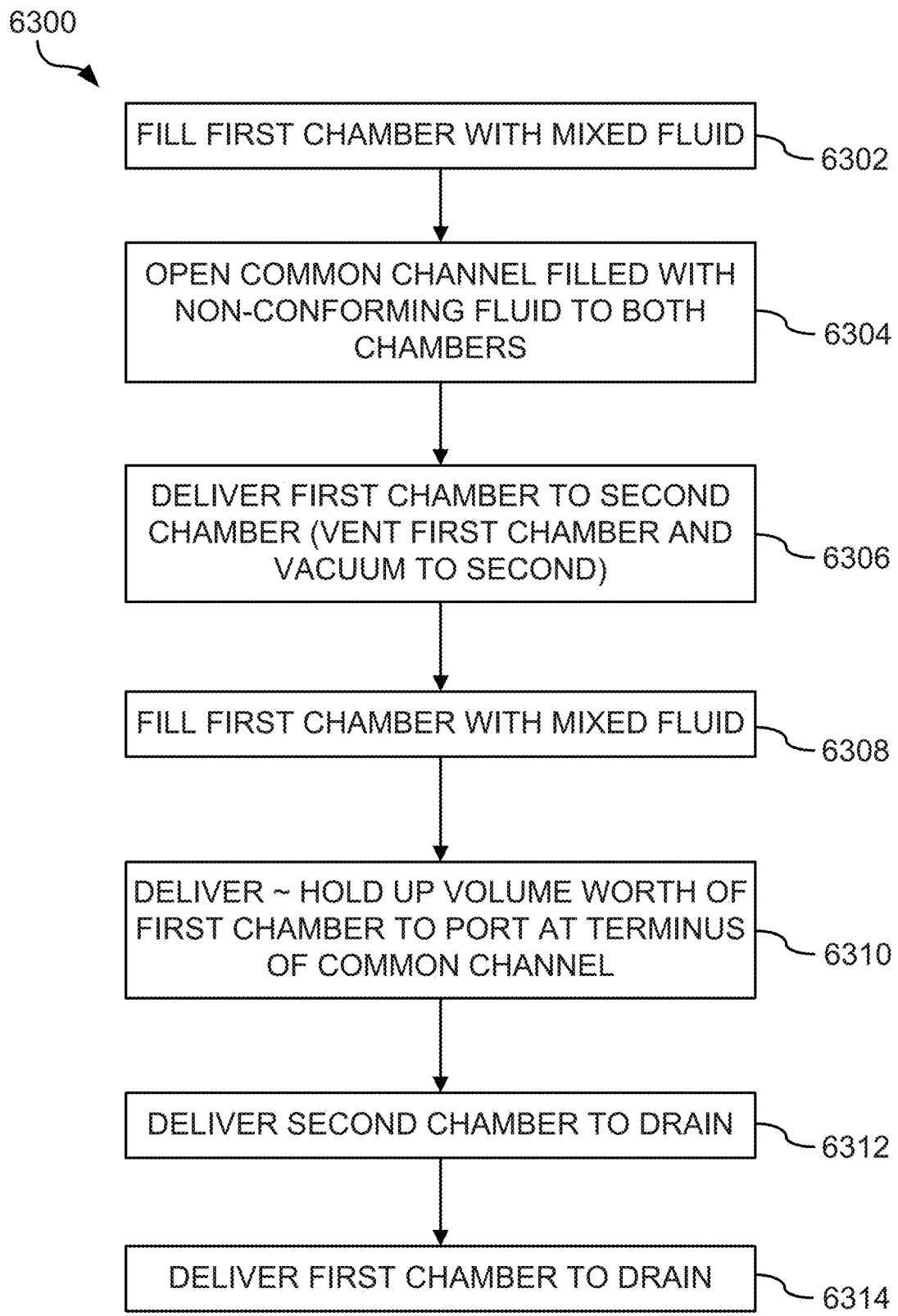
Figure 166:
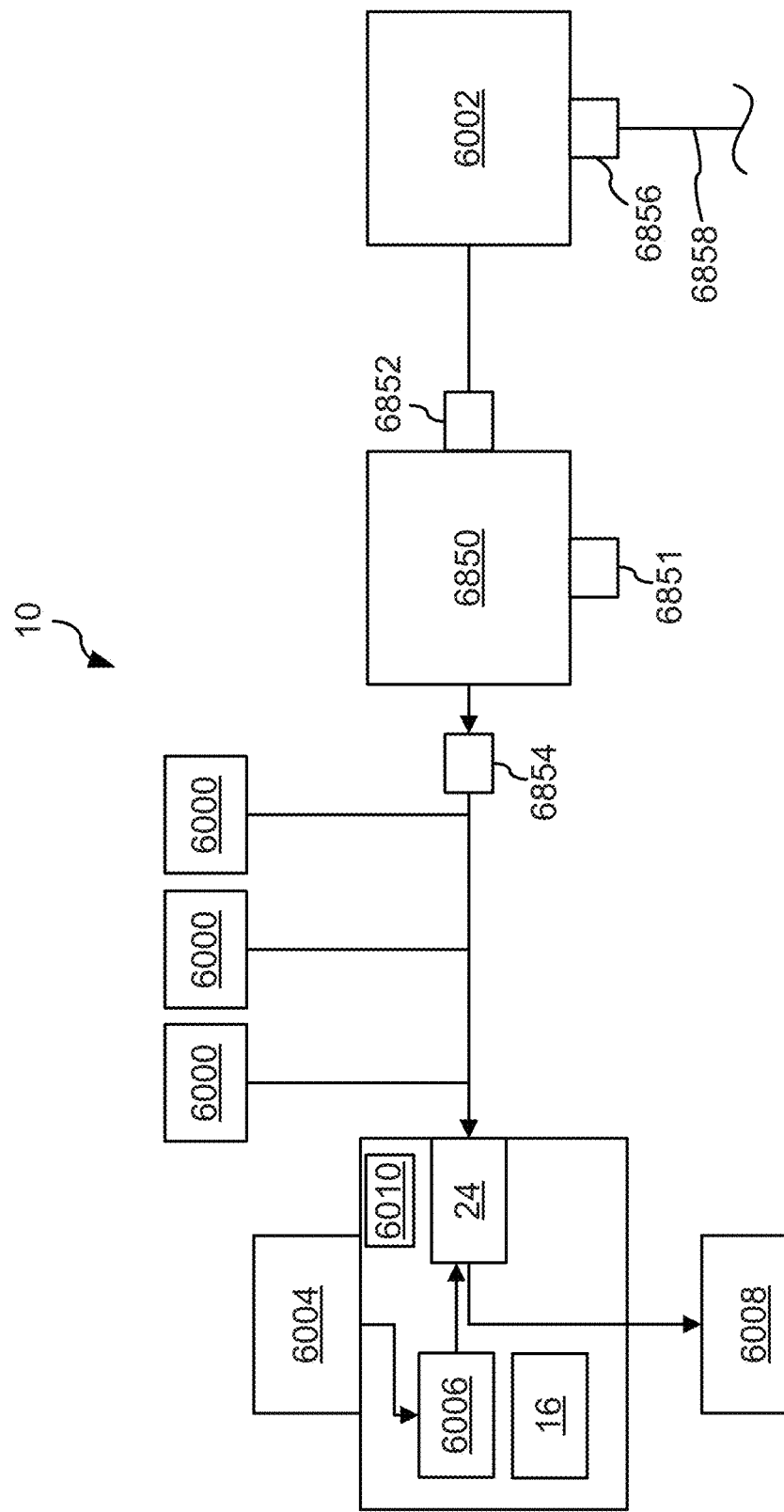
Figure 167:
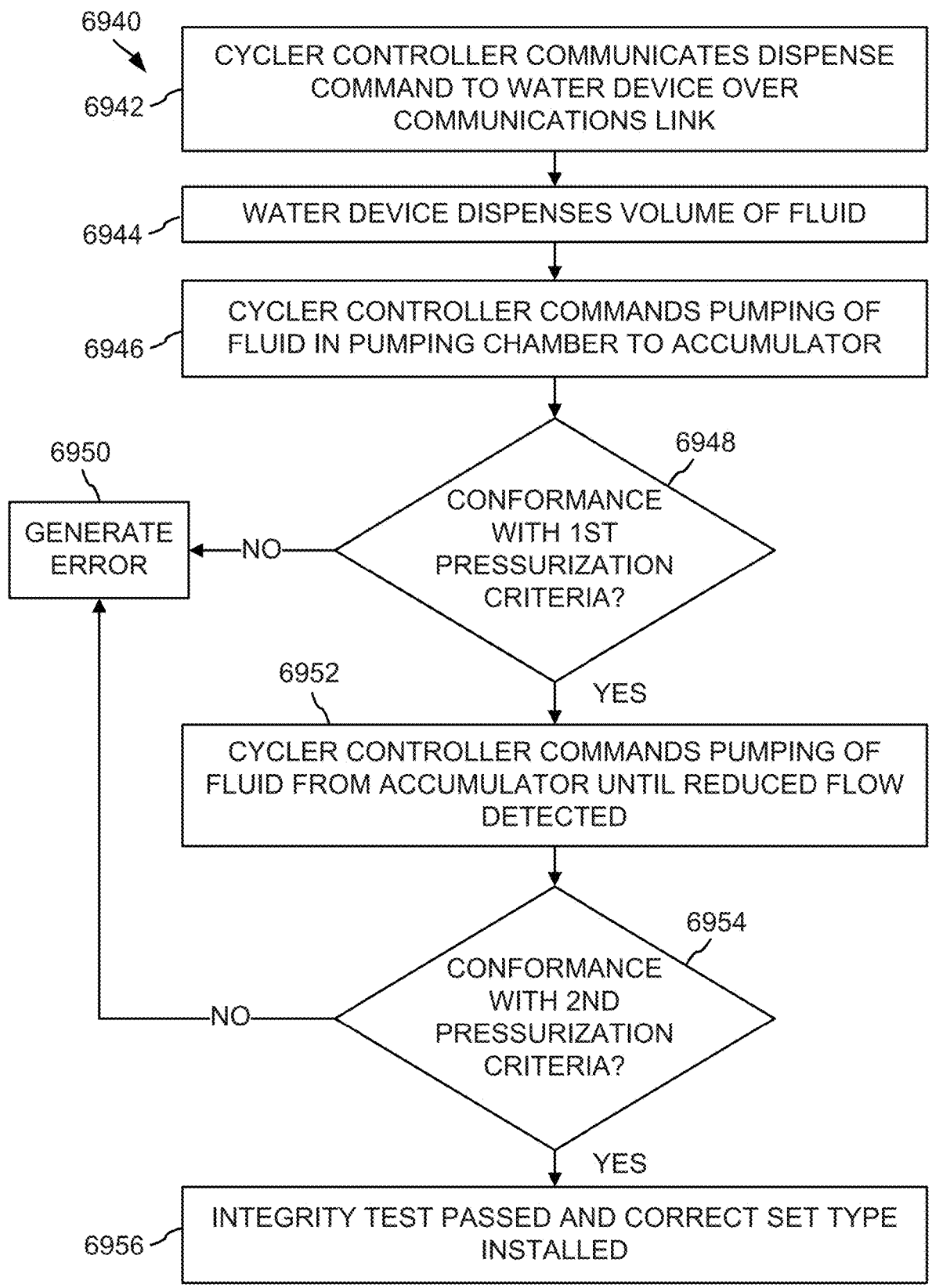
Figure 168A:
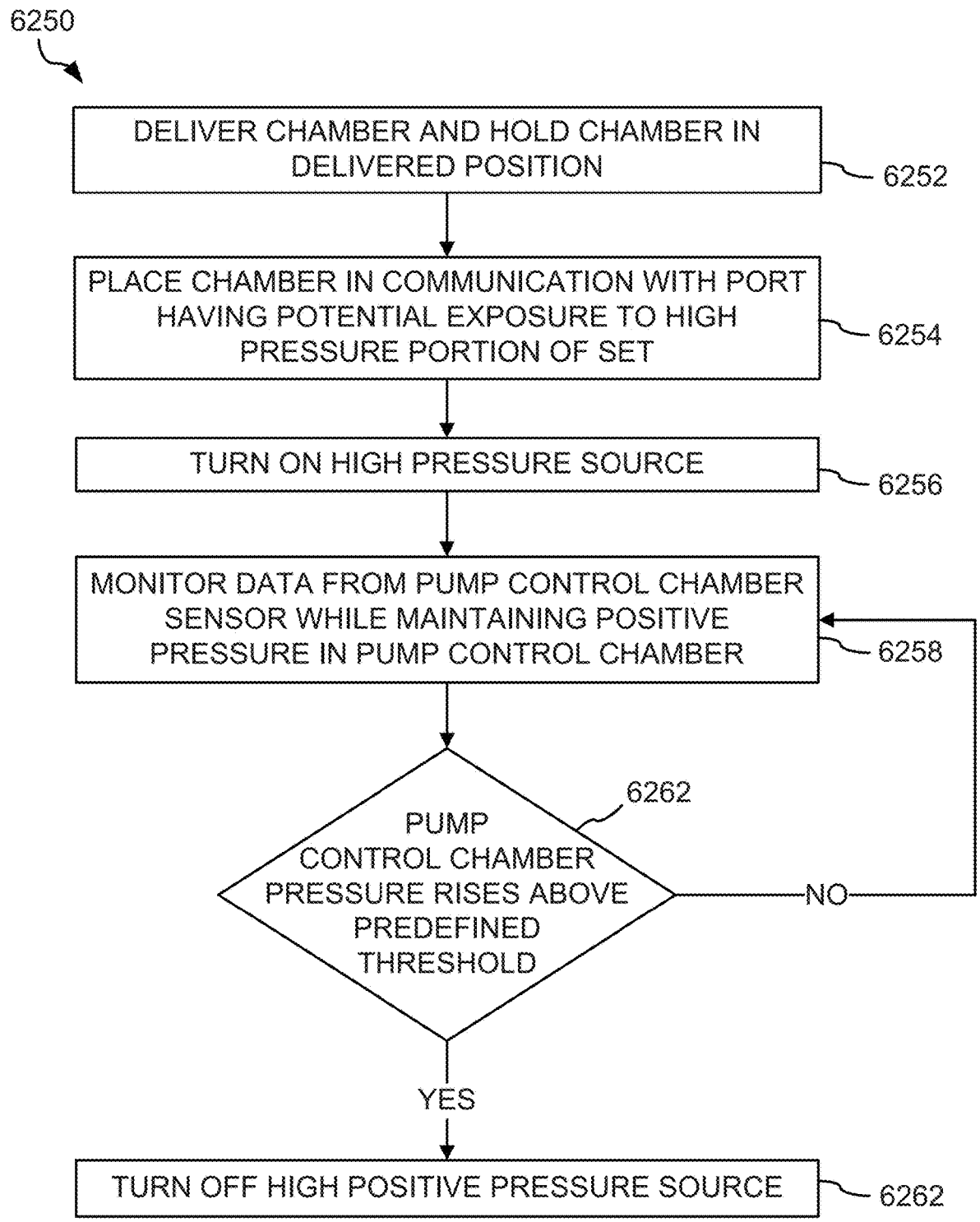
Figure 168B:
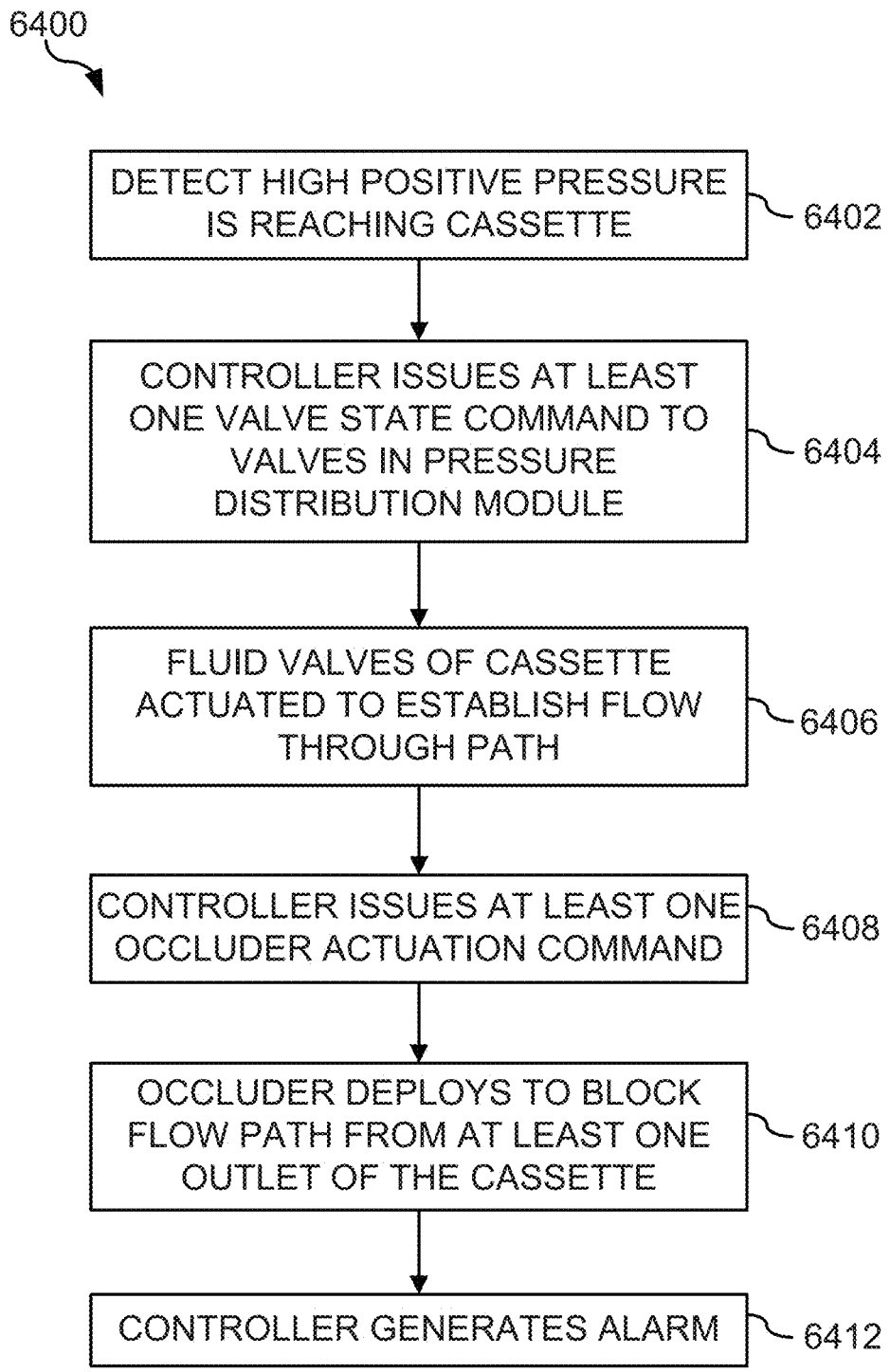
Figure 169:
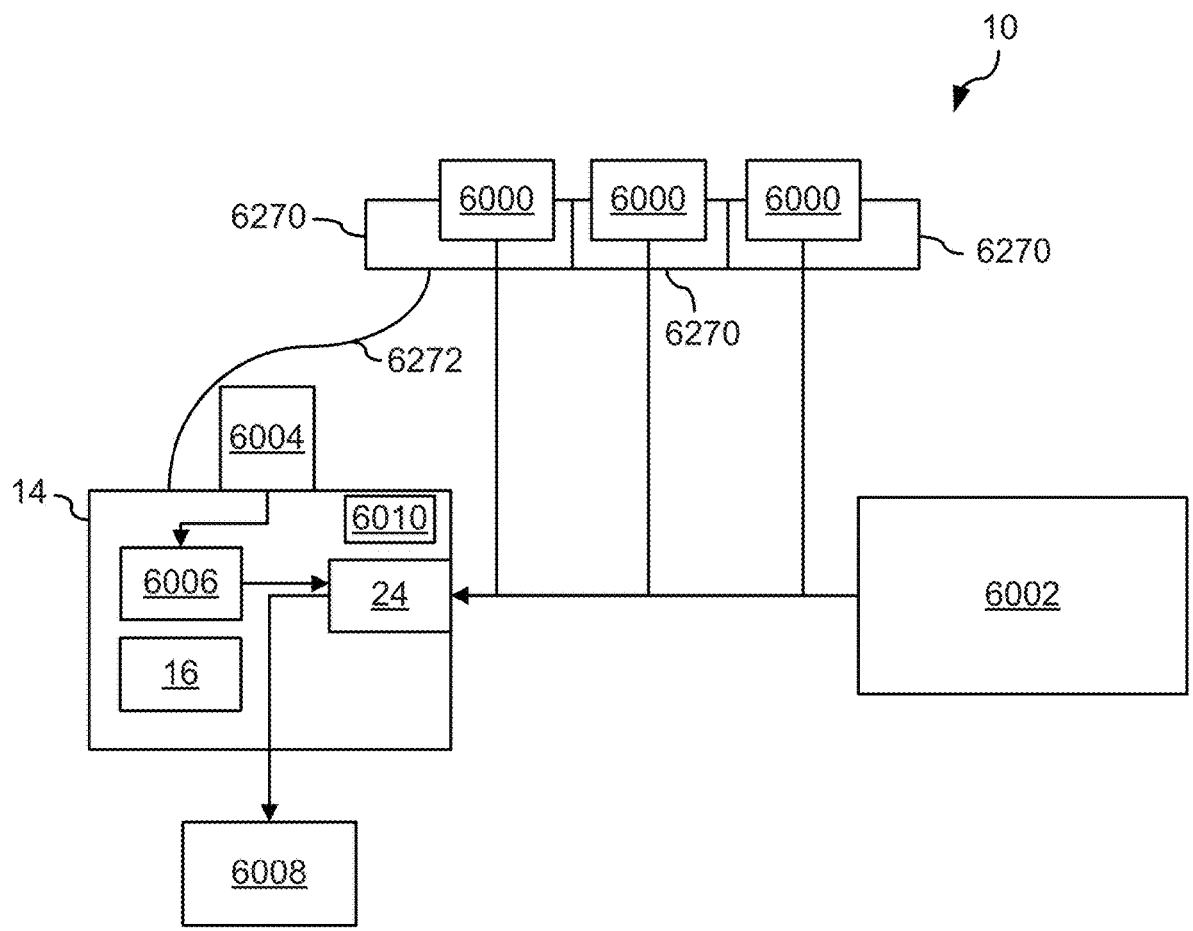
Figure 170:
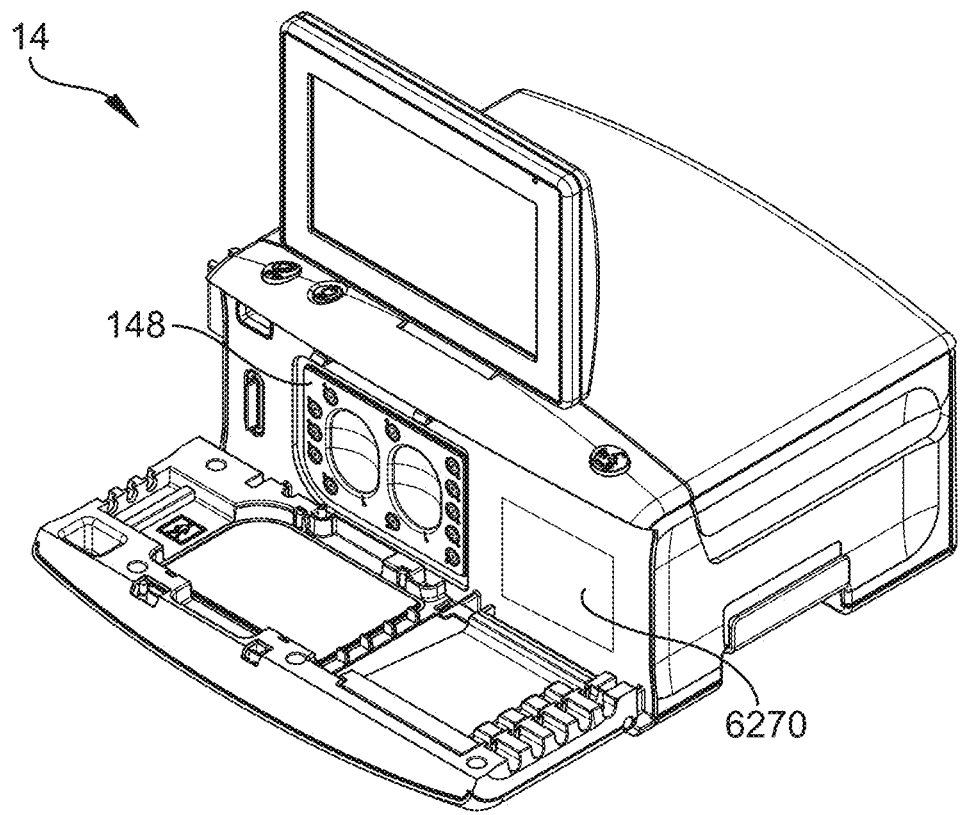
Figure 171:
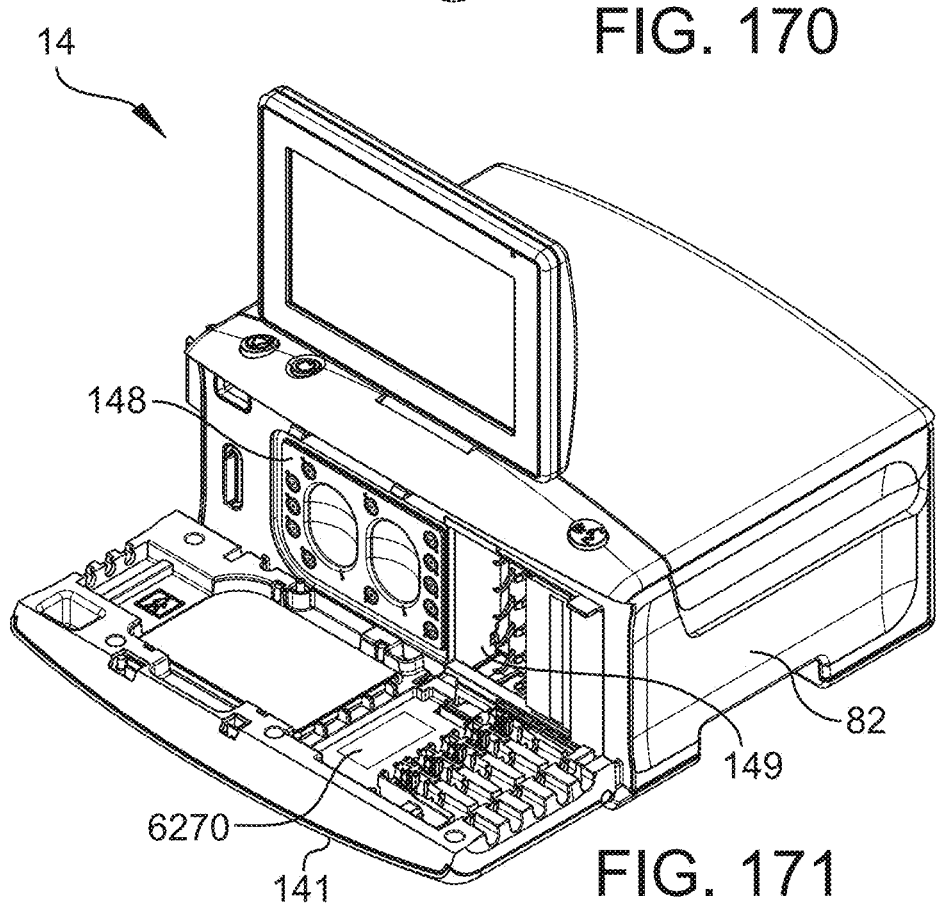
Figure 172:
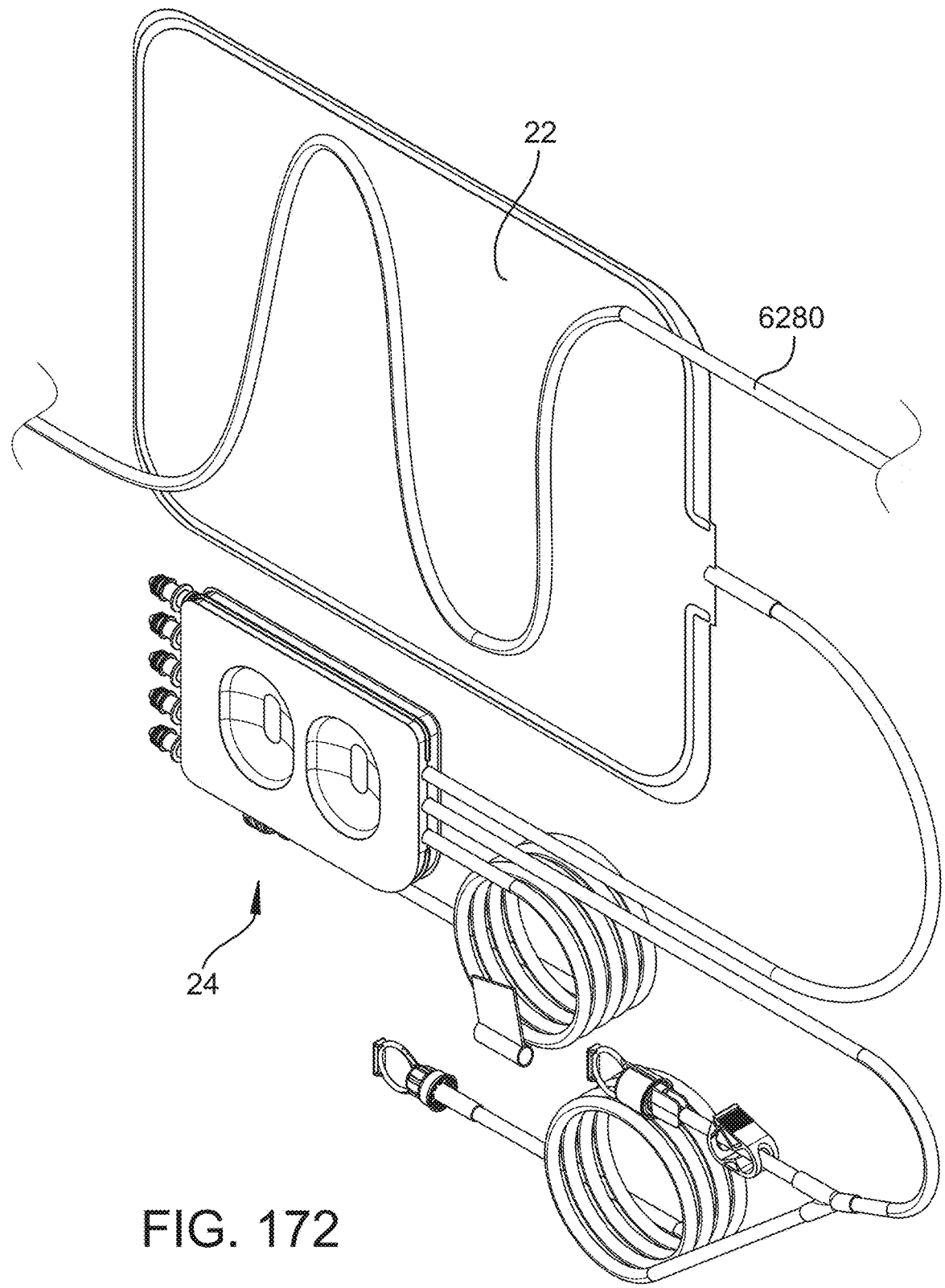
Figure 173:
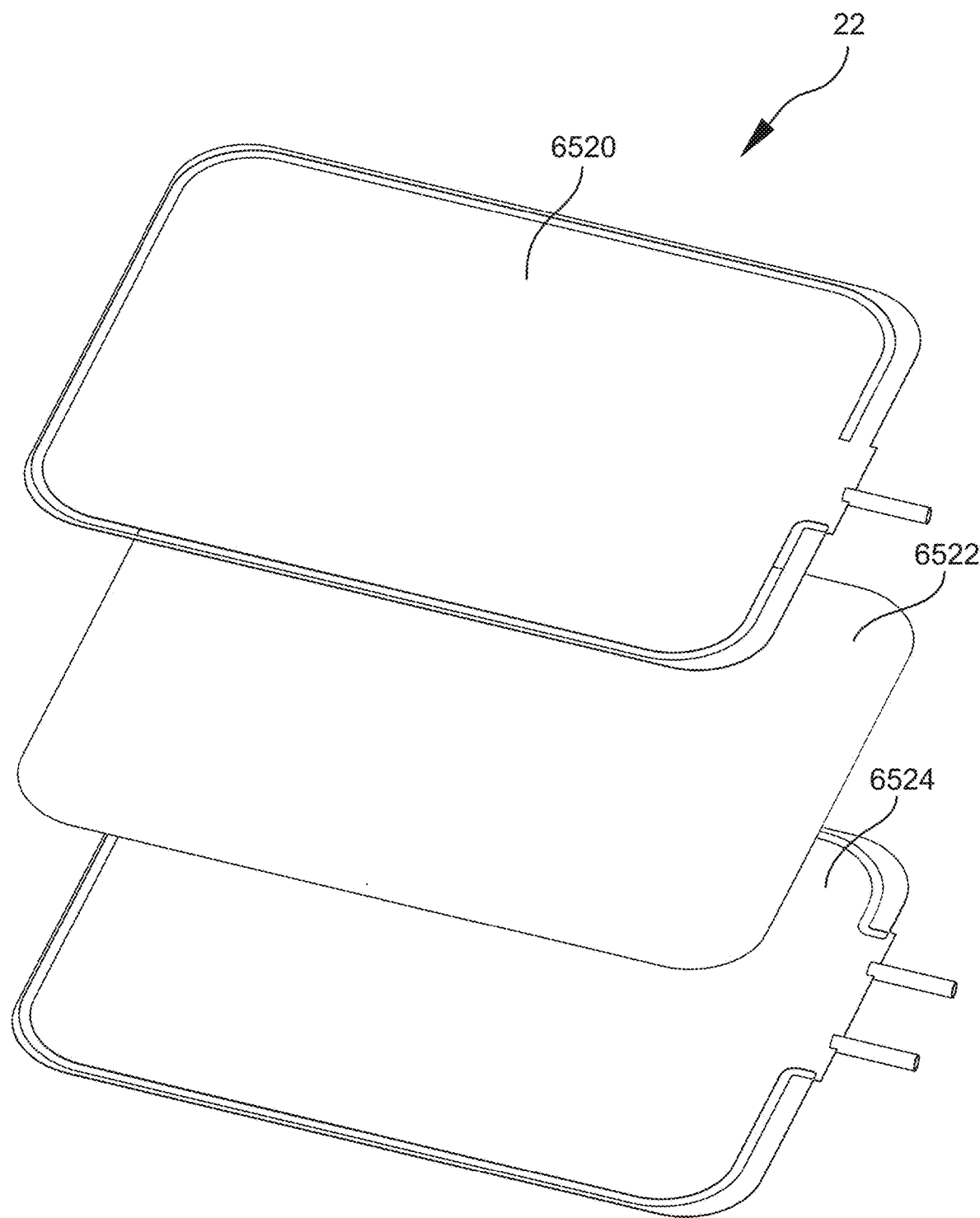
Figure 174:
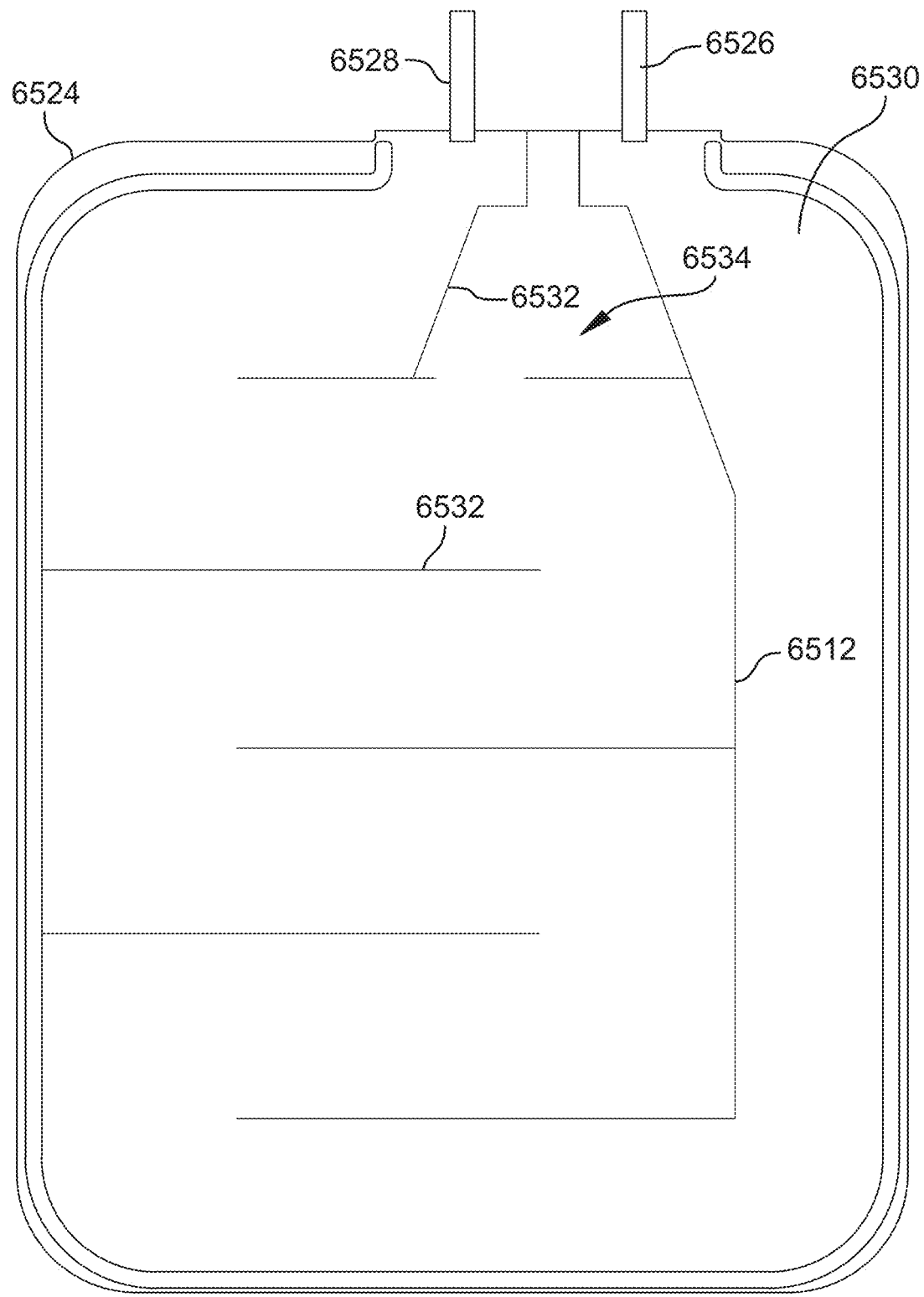
Figure 175:
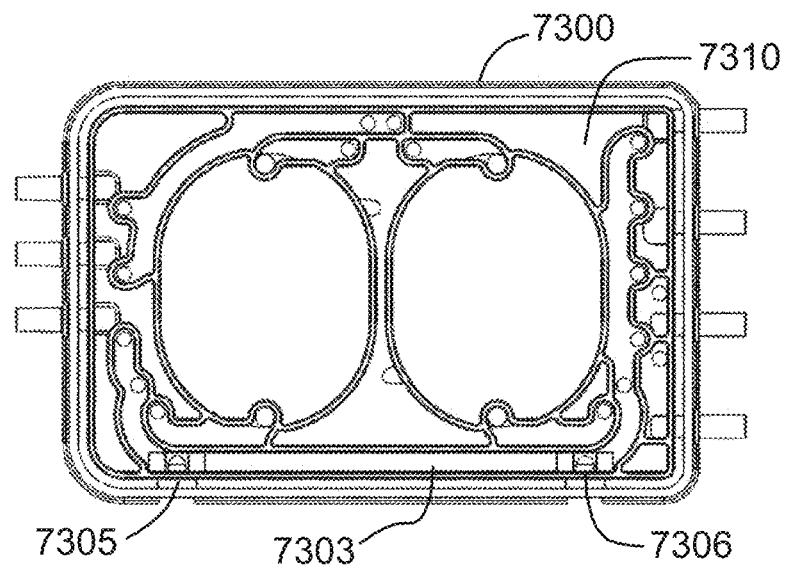
Figure 176:
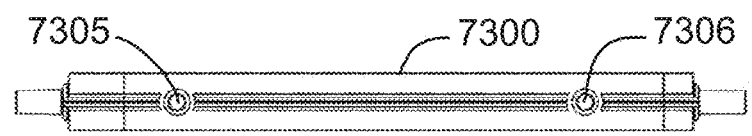
Figure 177:
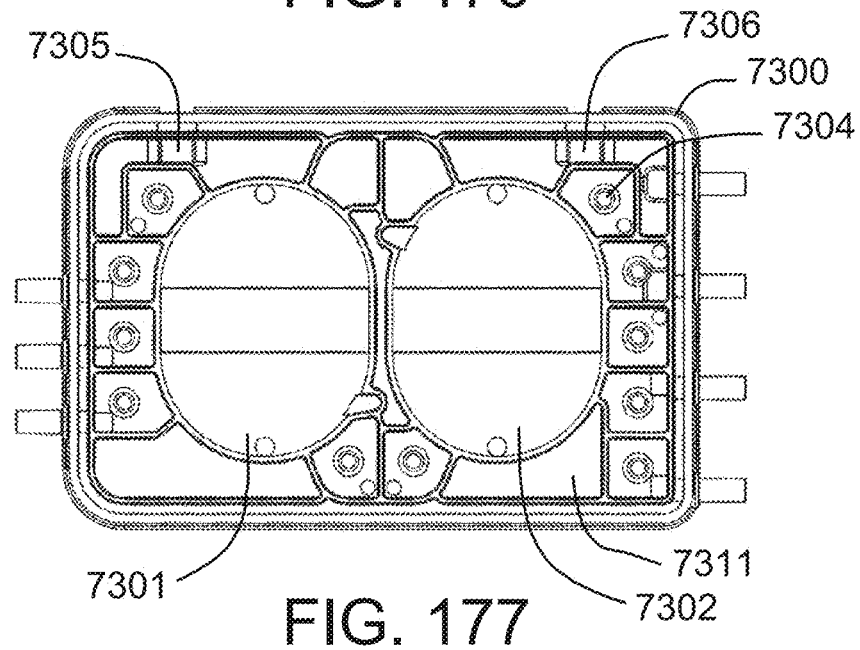
Figure 178:
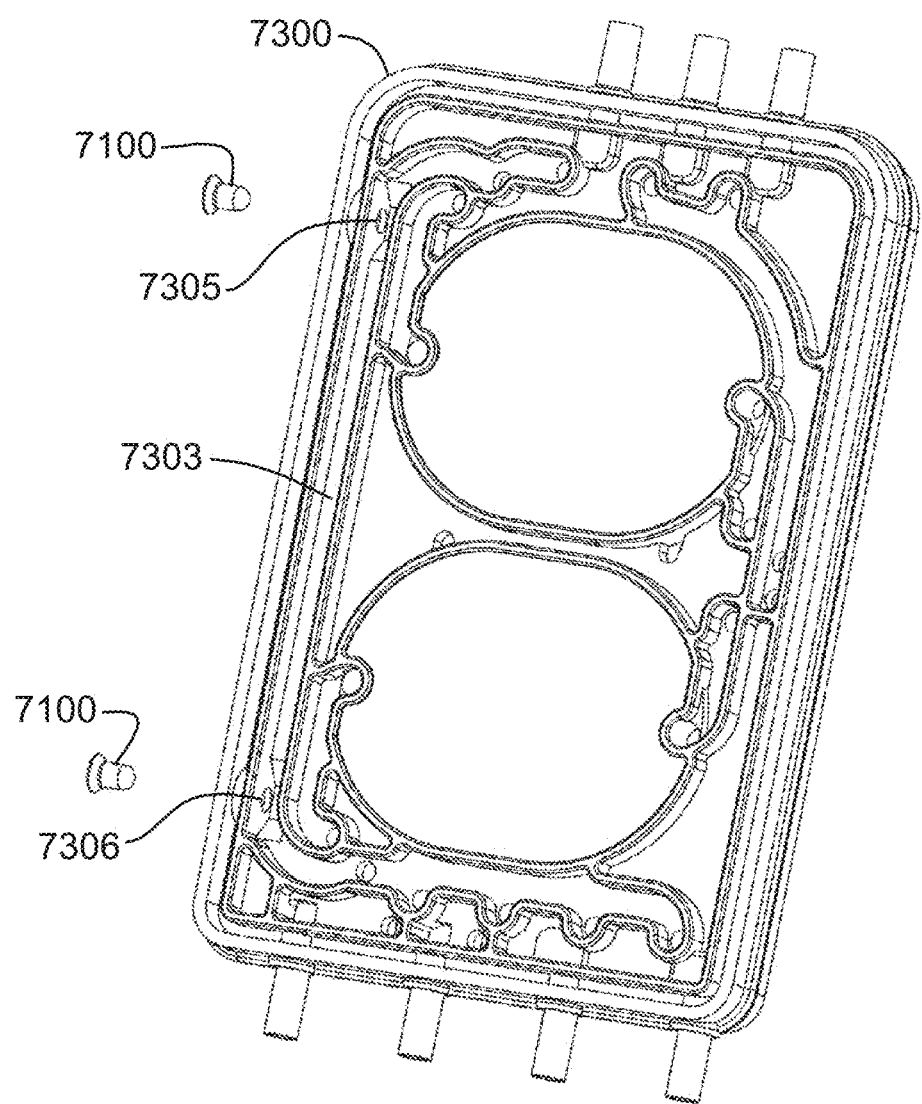
Figure 179:
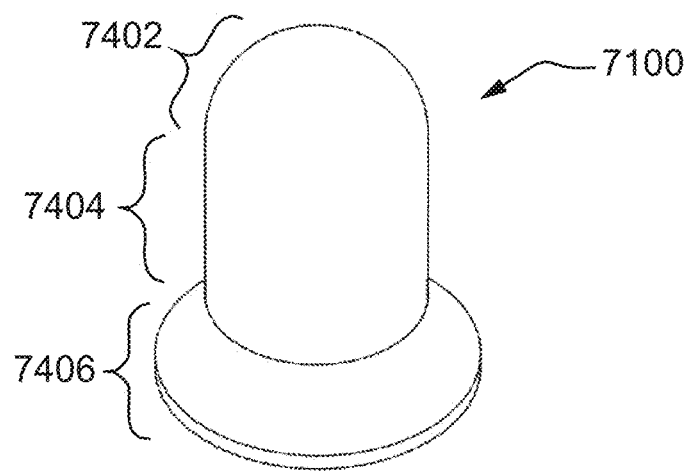
Figure 180:
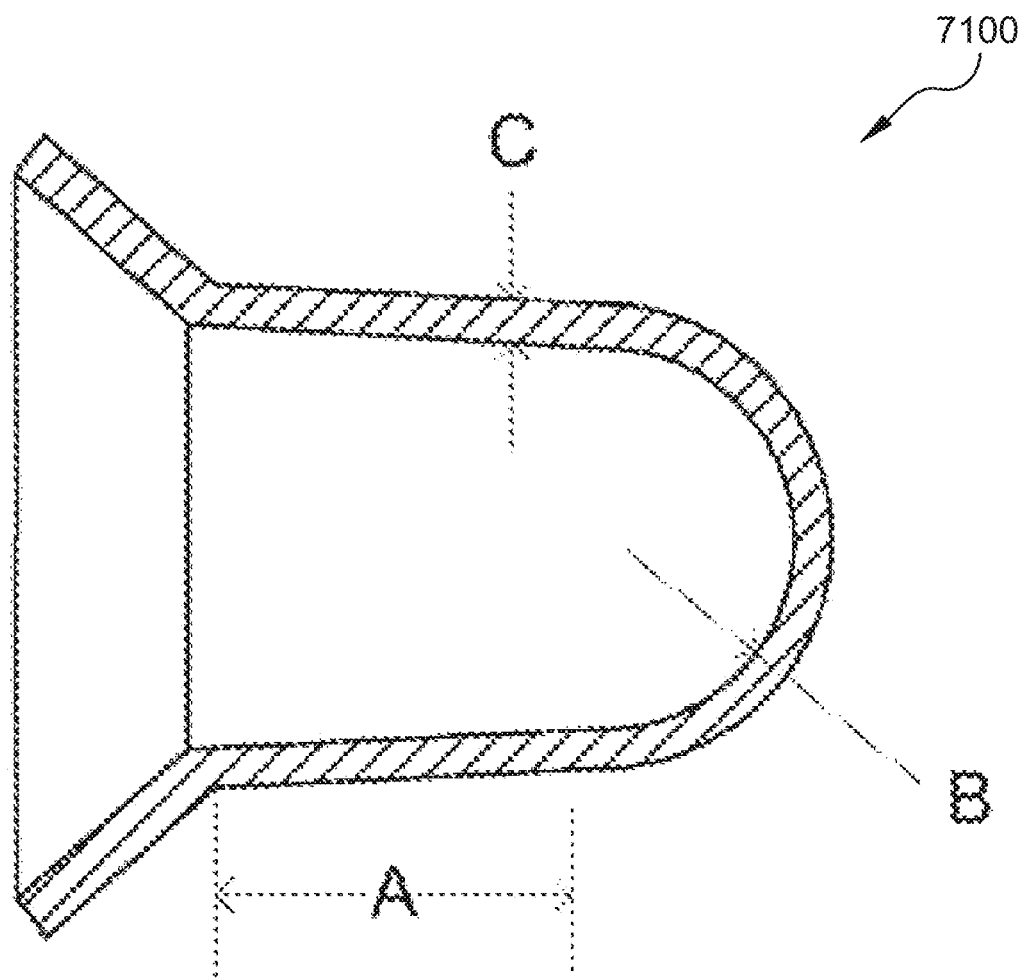
Figure 181:
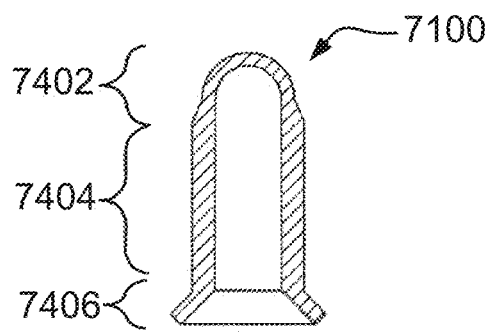
Figure 182:
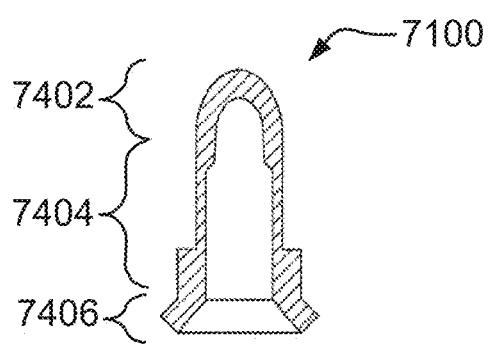
Figure 183:
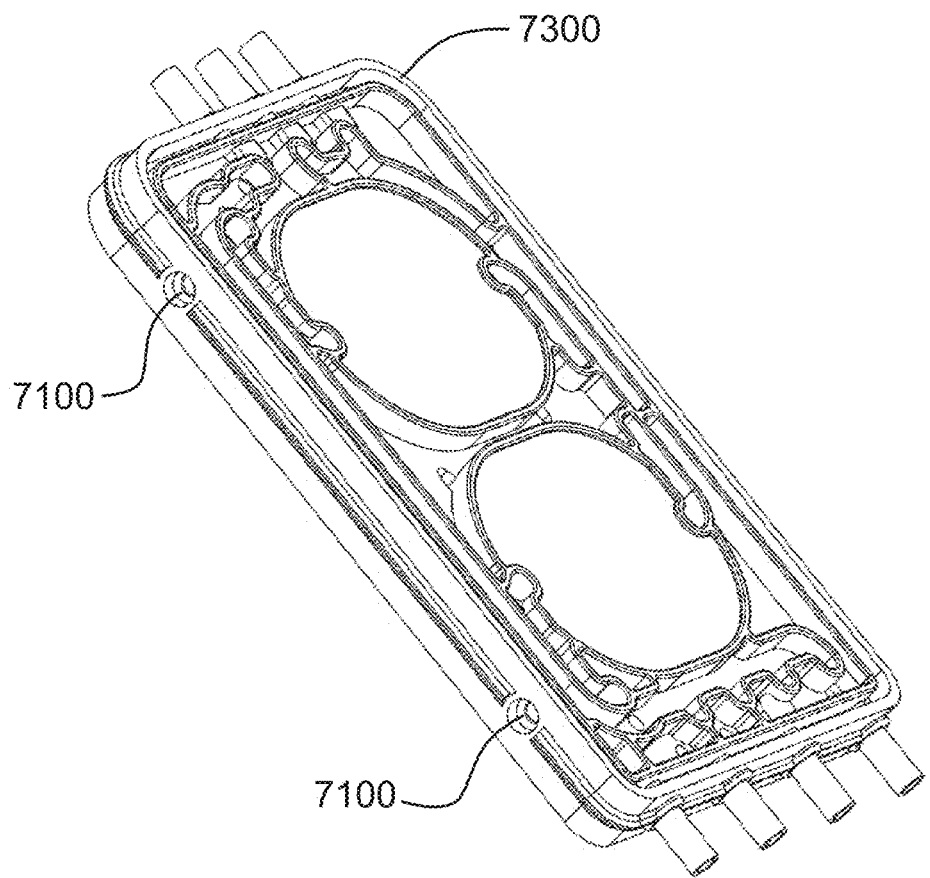
Figure 184:
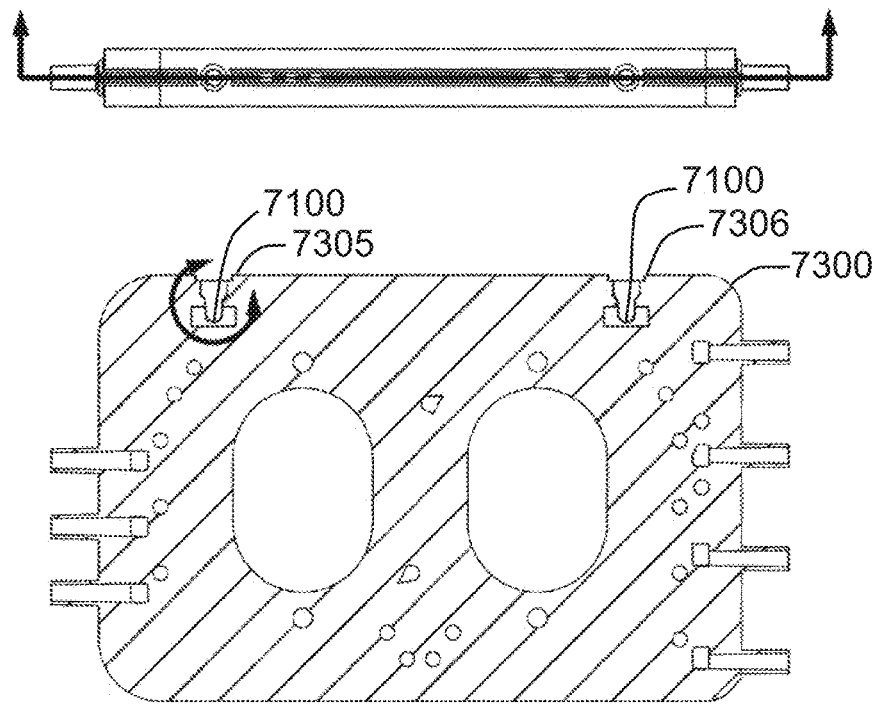
Figure 185:
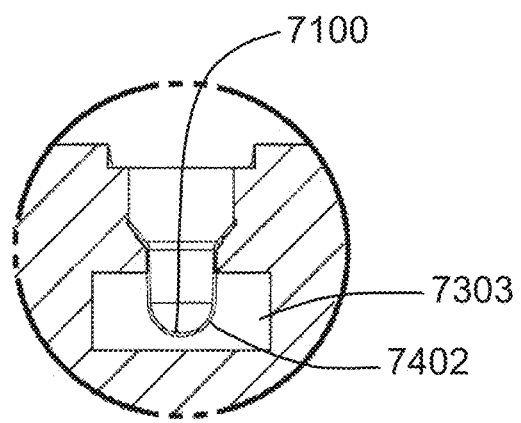
Figure 186:
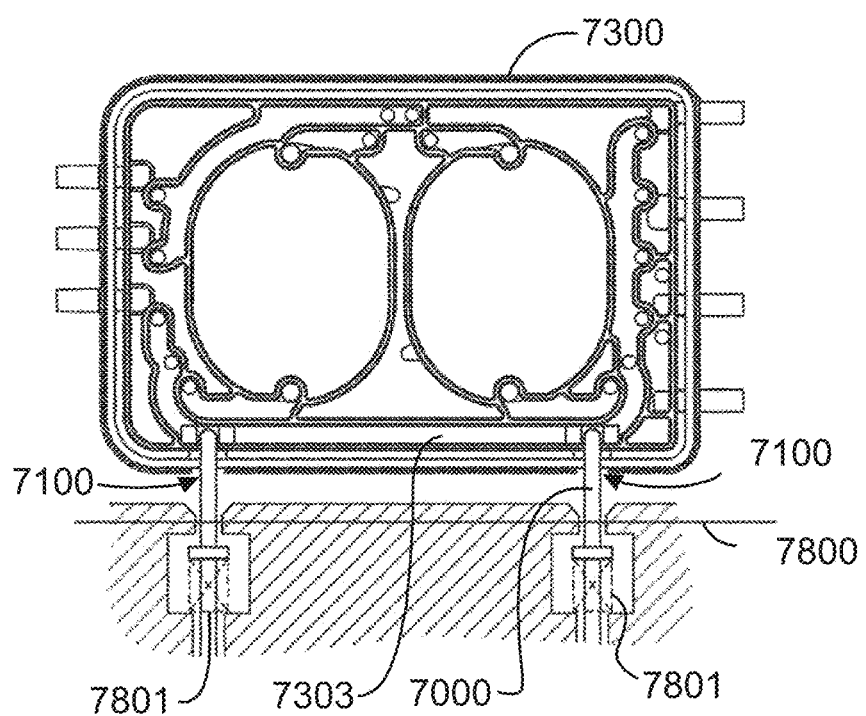
Figure 187:
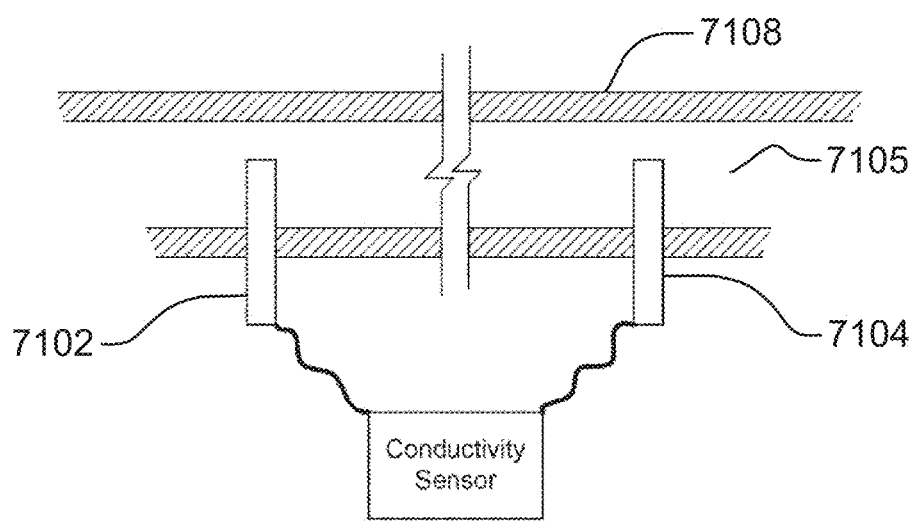
Figure 188:
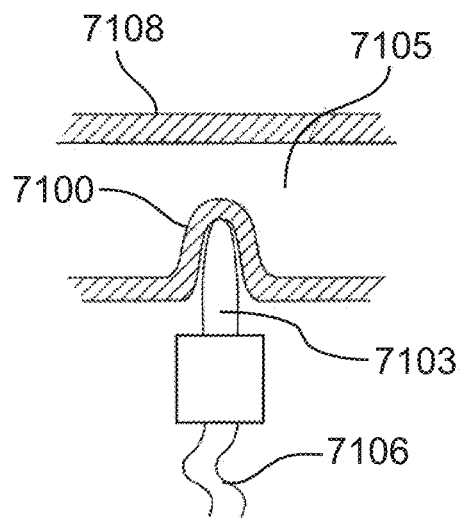
Figure 189:
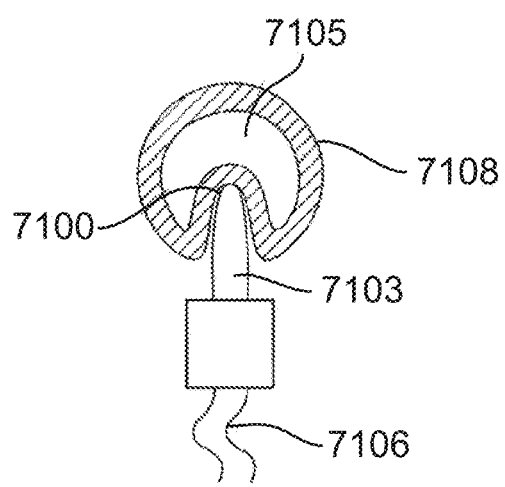
Figure 190:
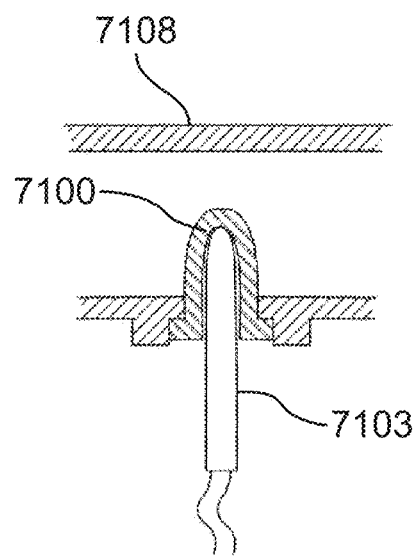
Figure 191:
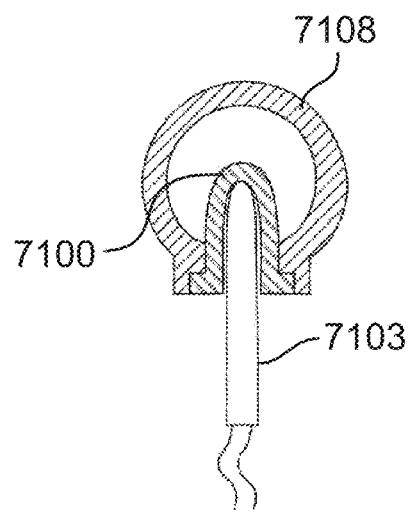
Figure 192:
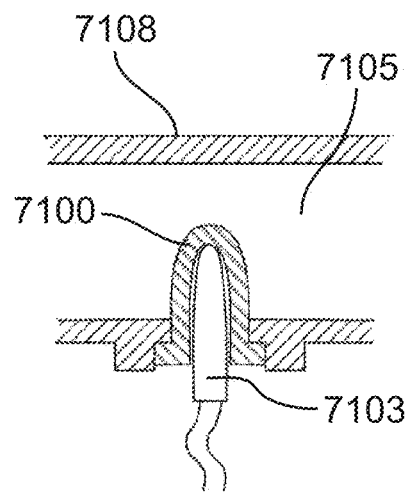
Figure 193:
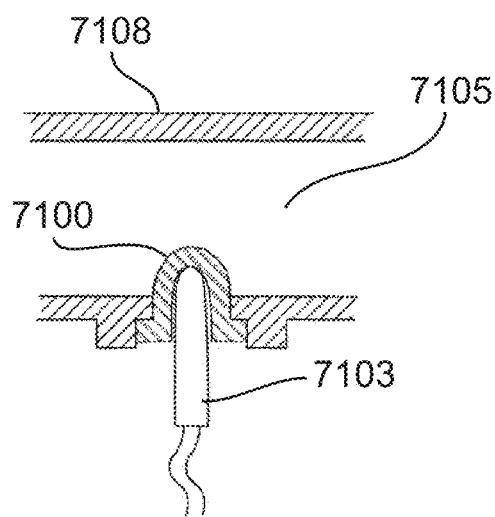
Figure 212:
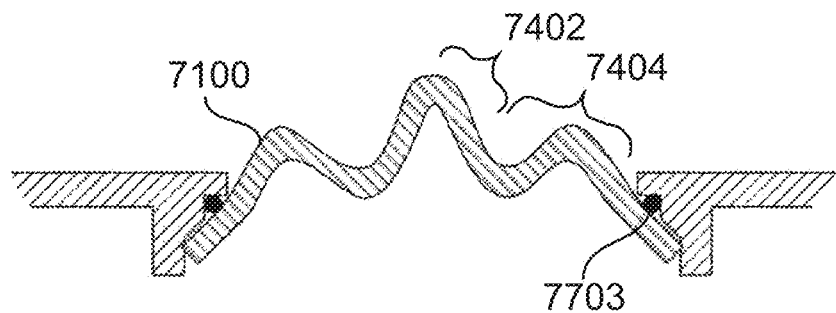
Figure 213:
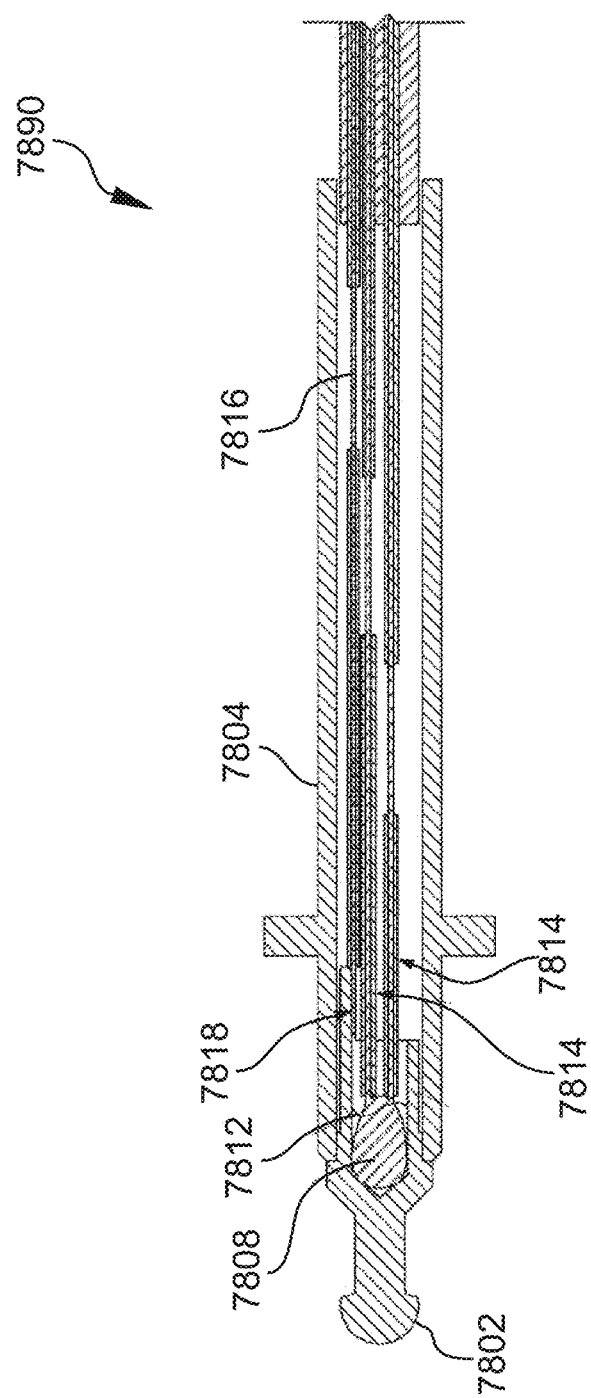
Figure 214:
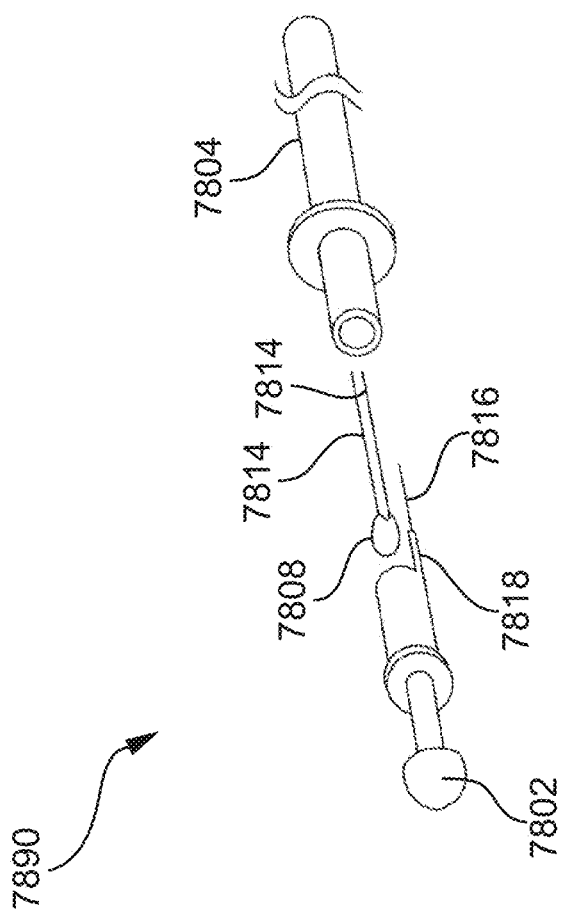
Figure 215:
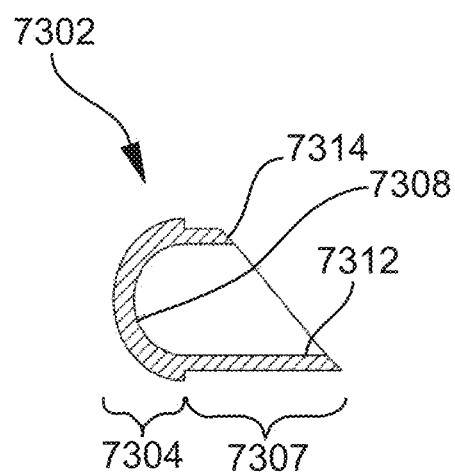
Figure 216:
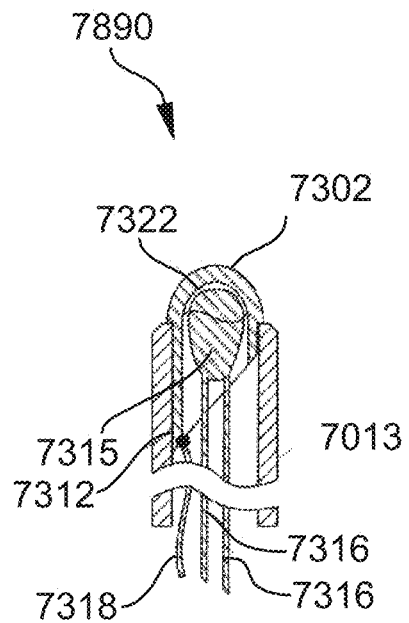
Figure 217:
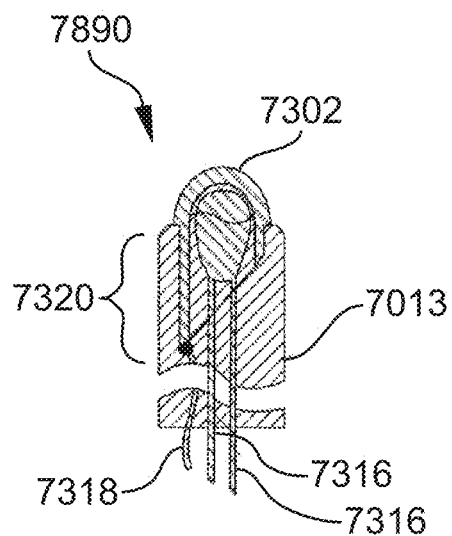
Figure 218:
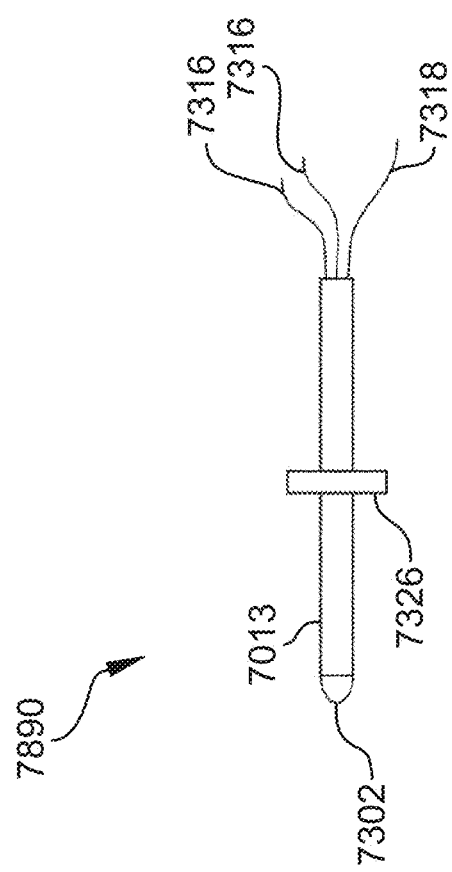
Figure 219:
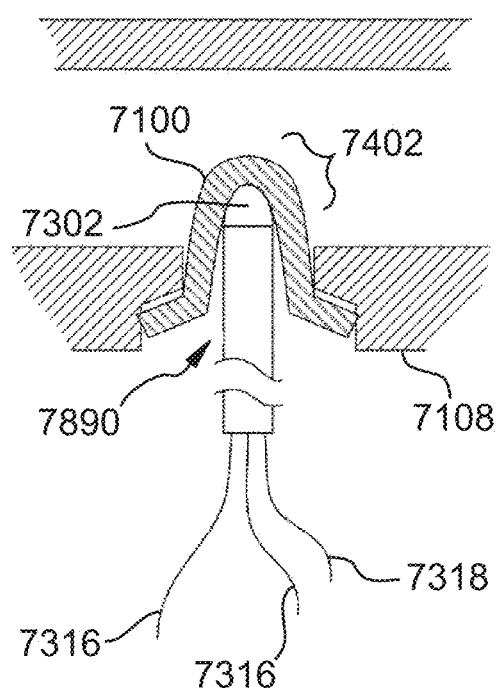
Figure 220:
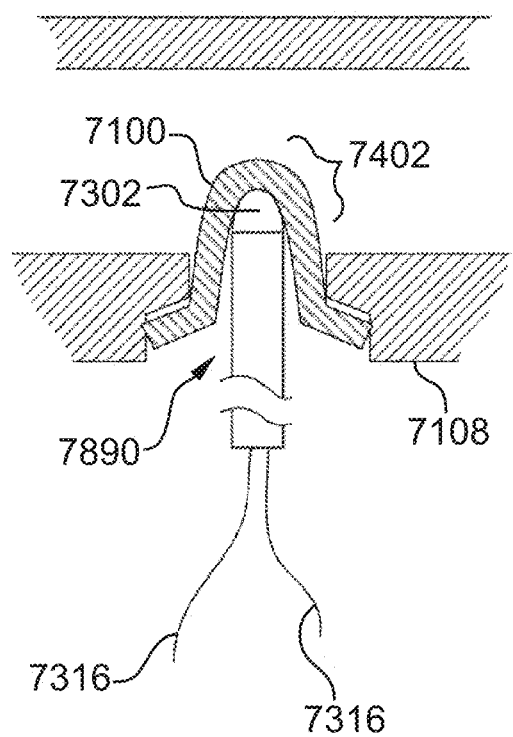
Figure 221:
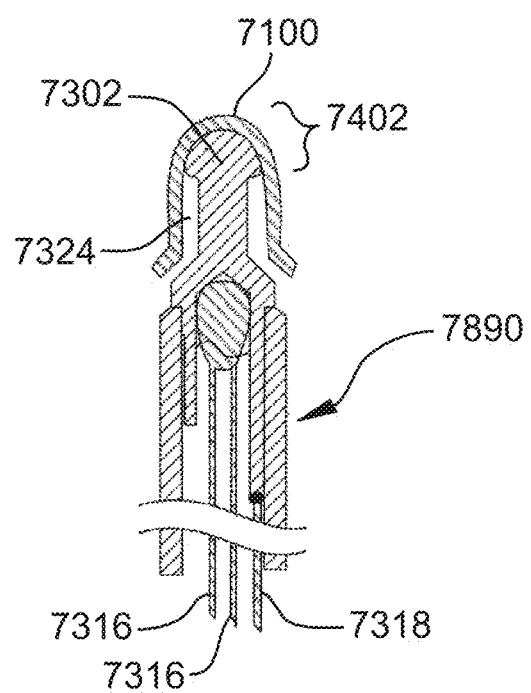
Figure 222:
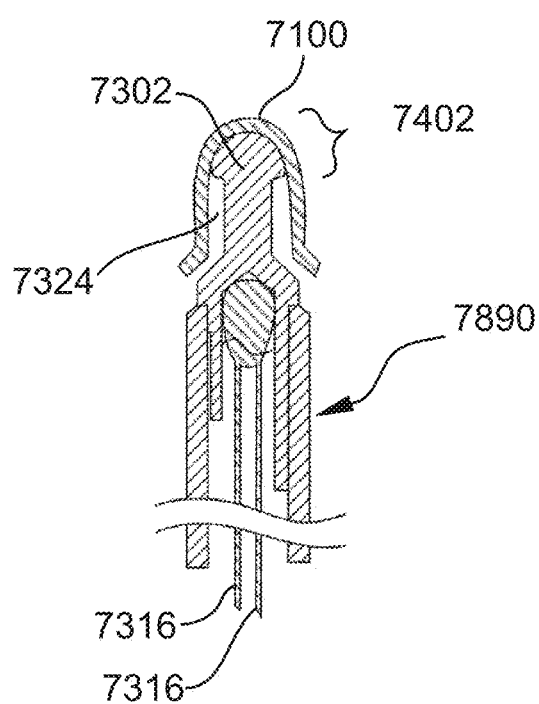
Figure 223:
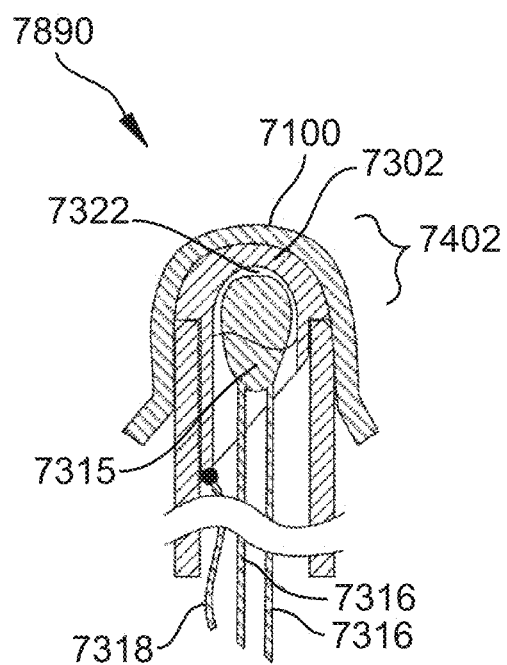
Figure 224:
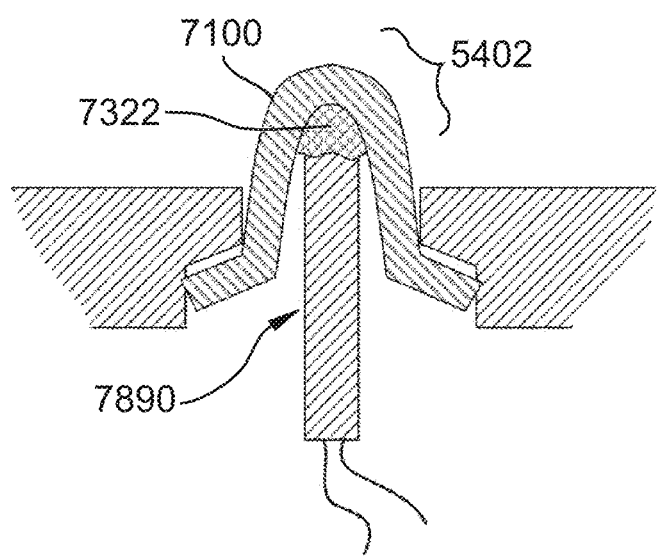
Figure 225:
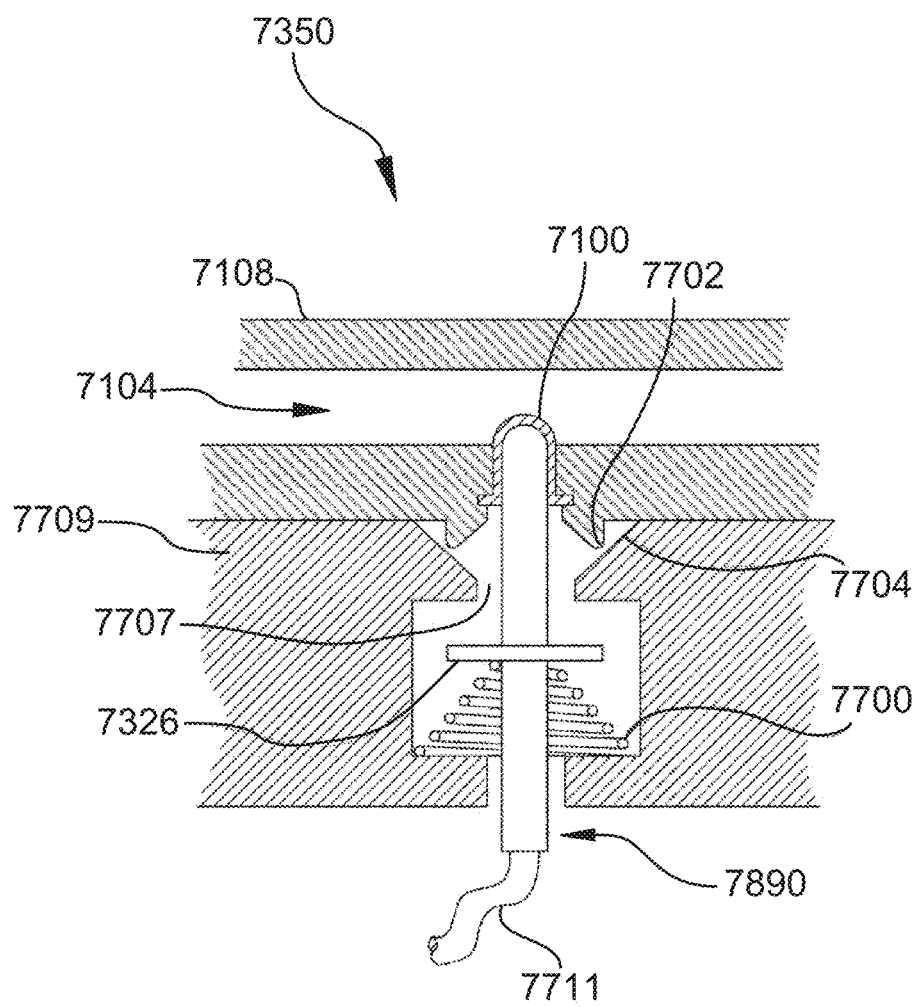
Figure 226:
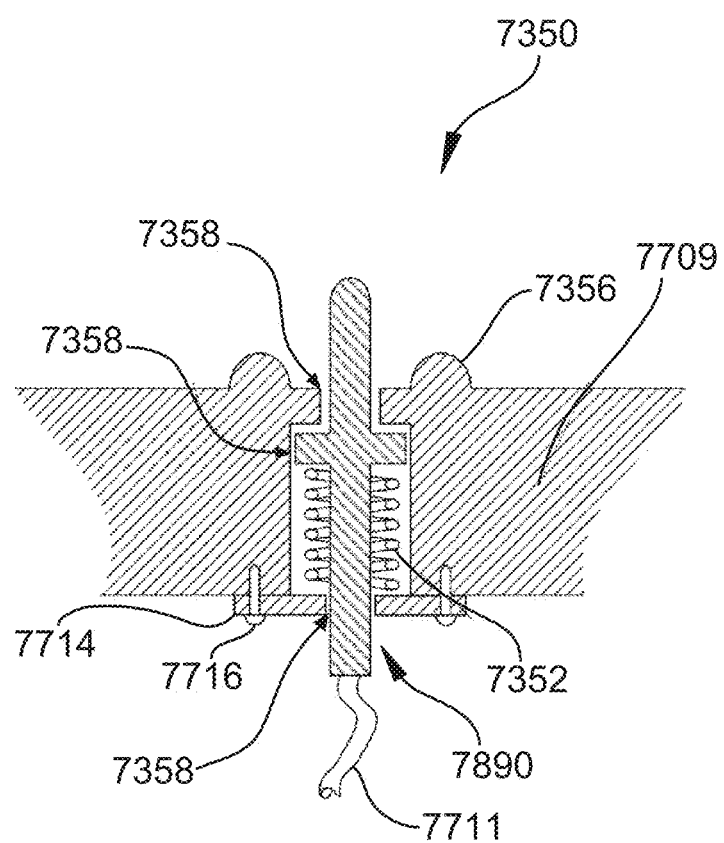
Figure 227:
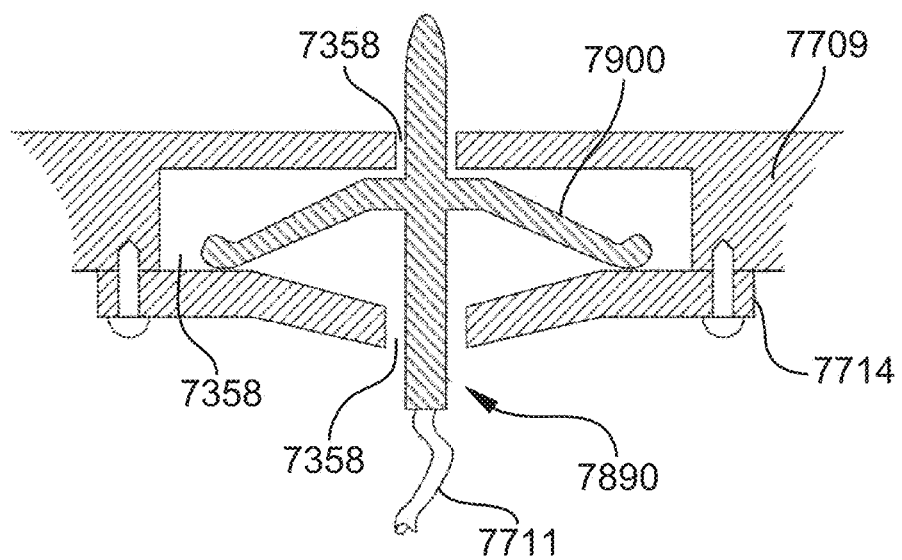
Figure 228:
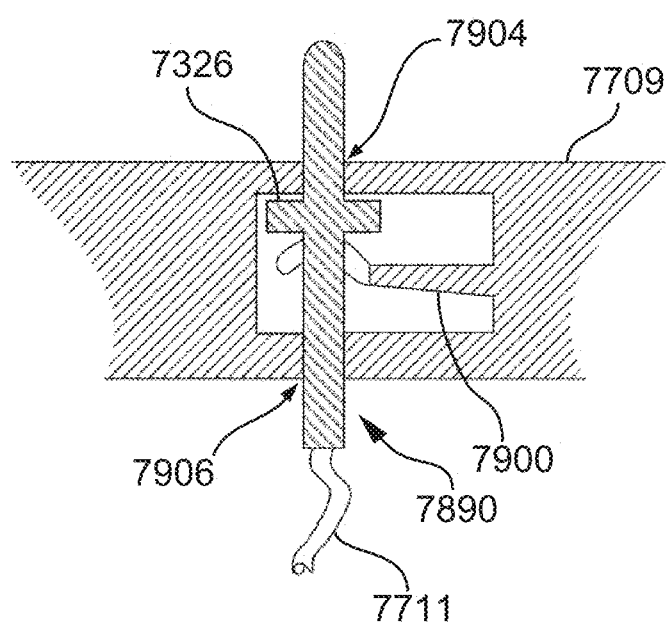
Figure 229:
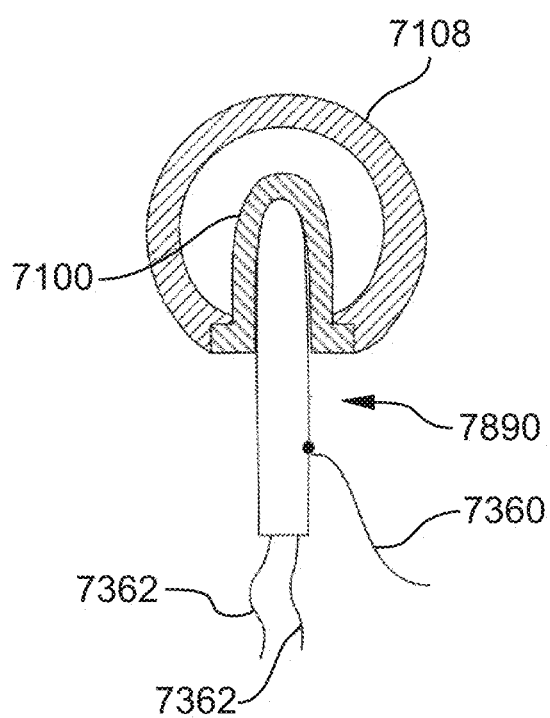
Figure 230:
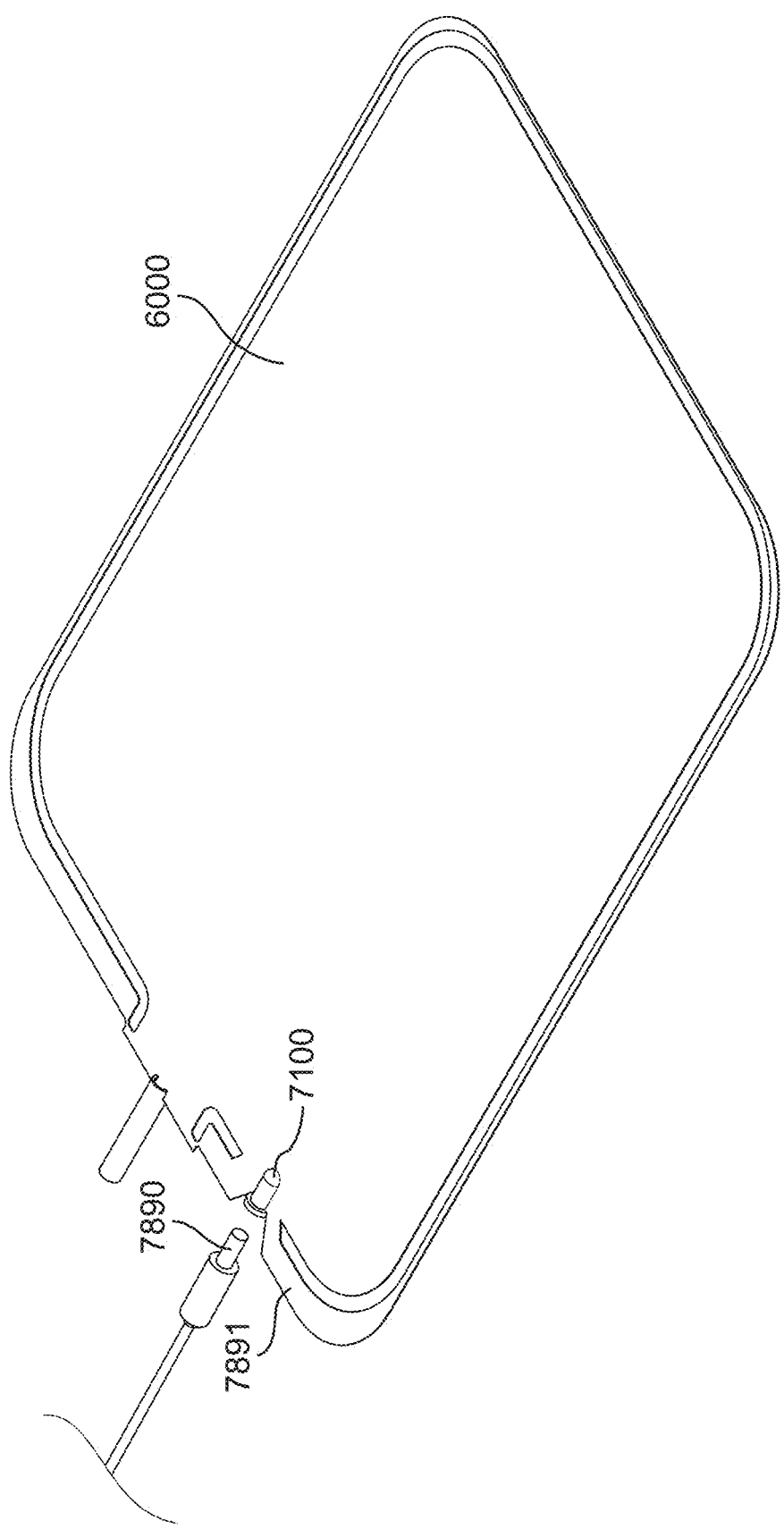
Figure 231A:
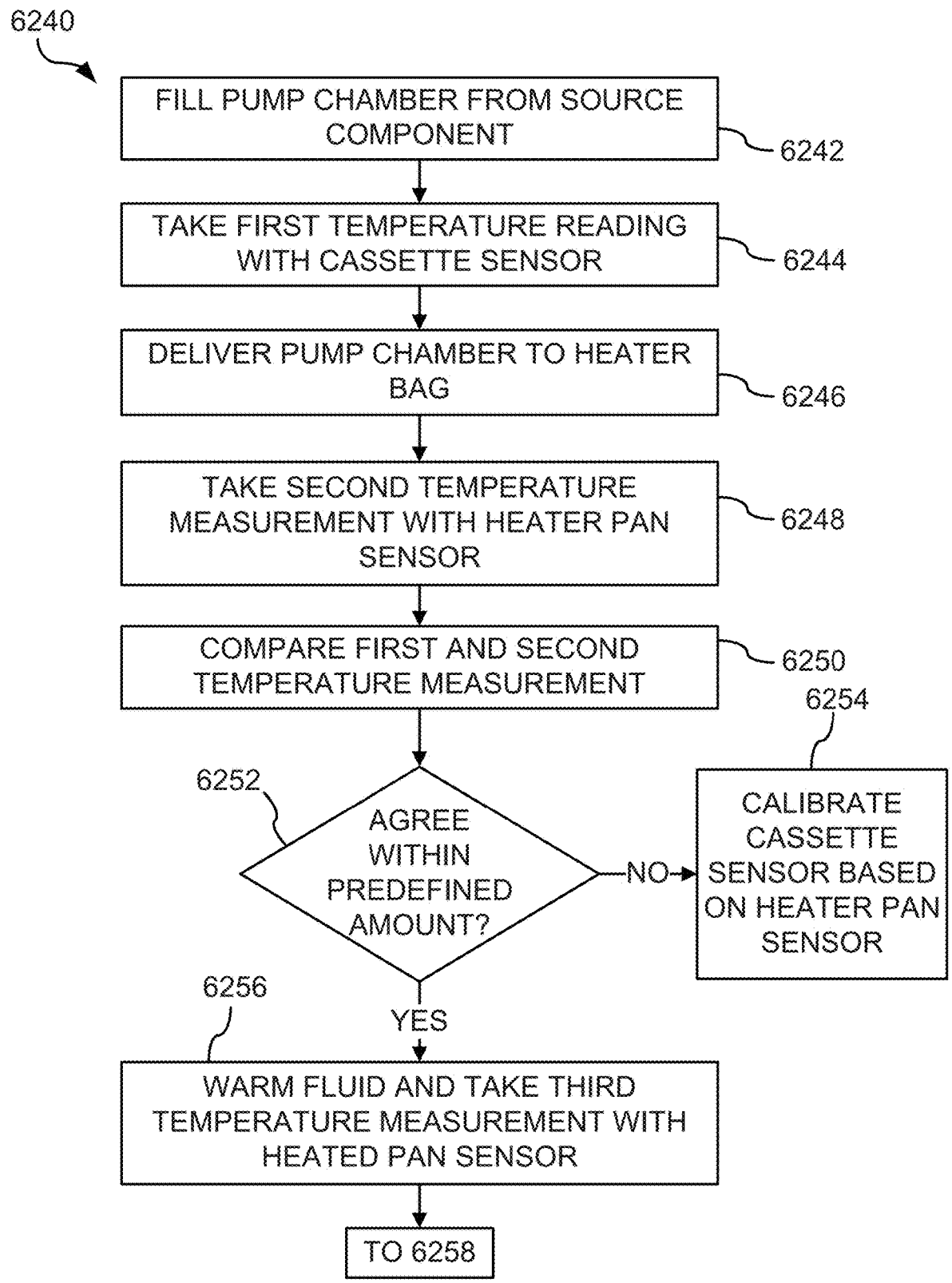
Figure 231B:
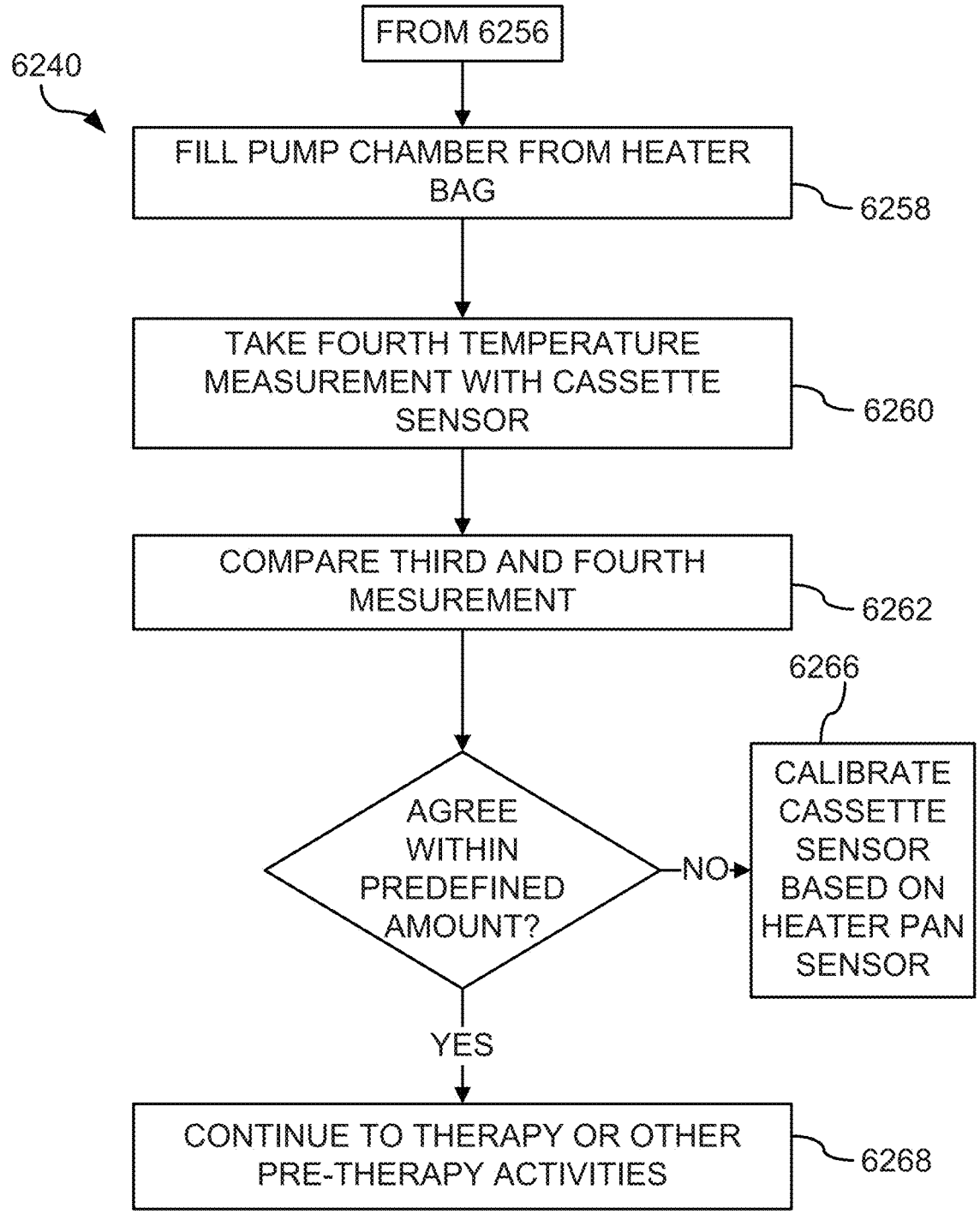
Figure 232:
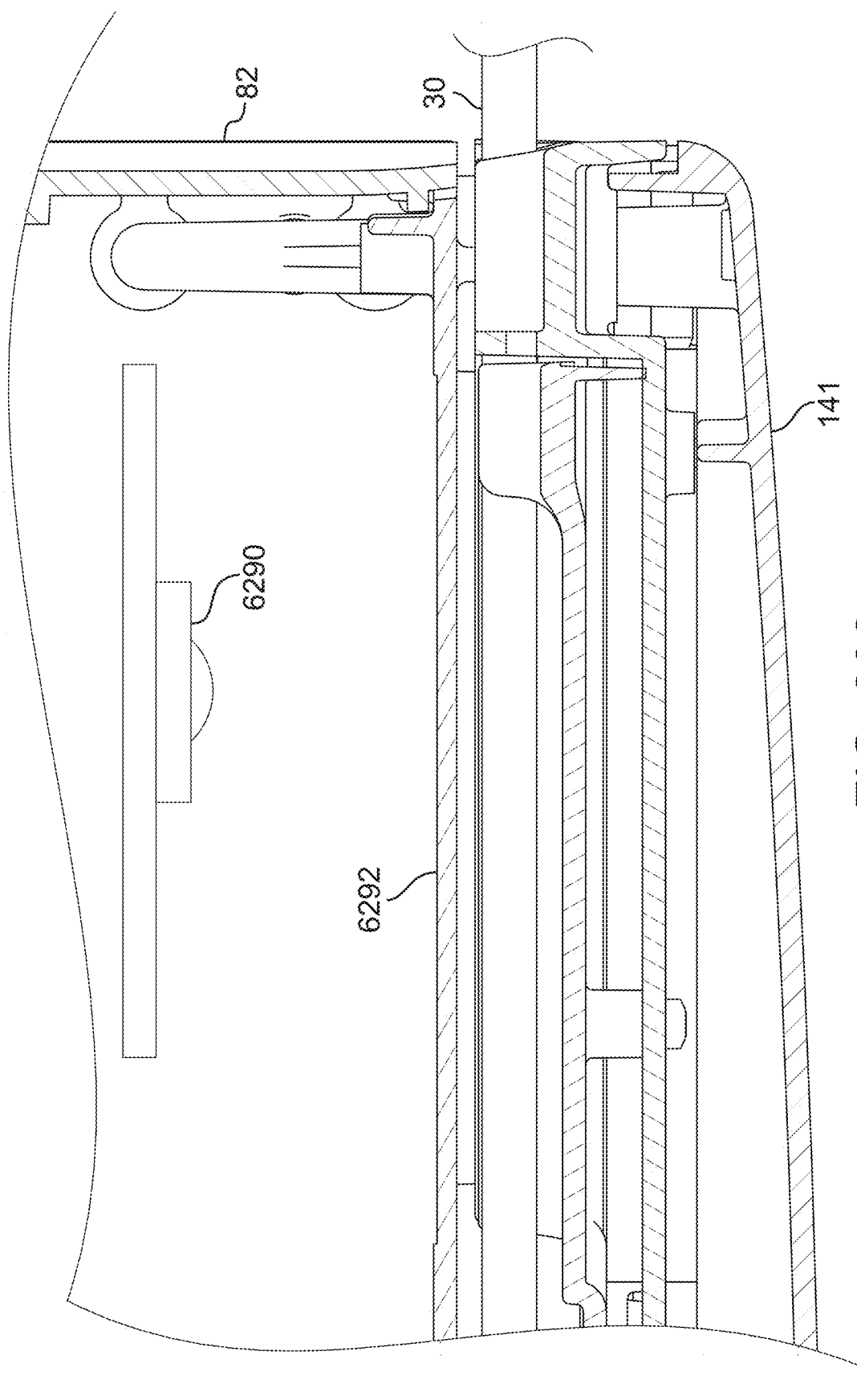
Figure 233:
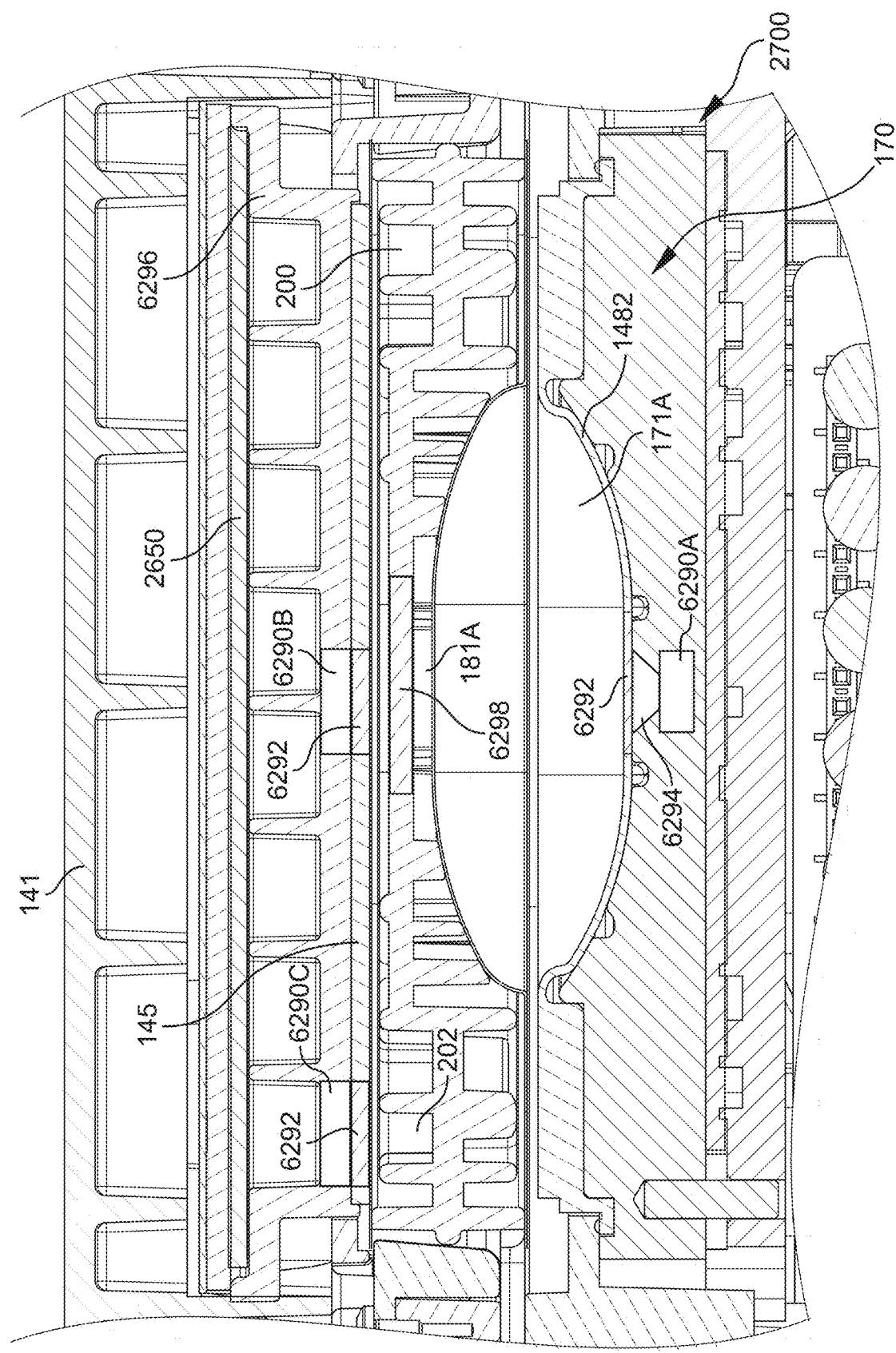
Figure 234:
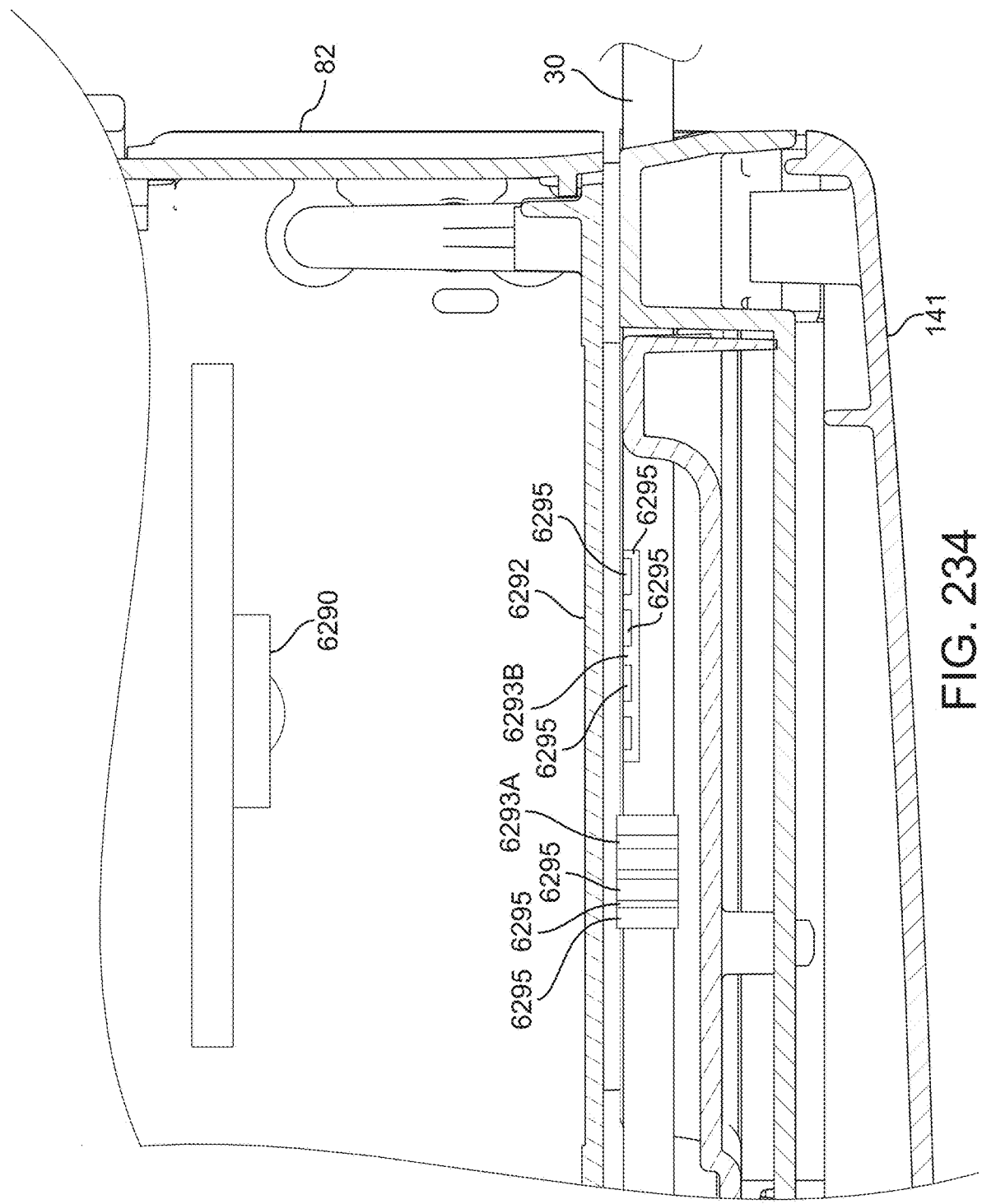
Figure 235:
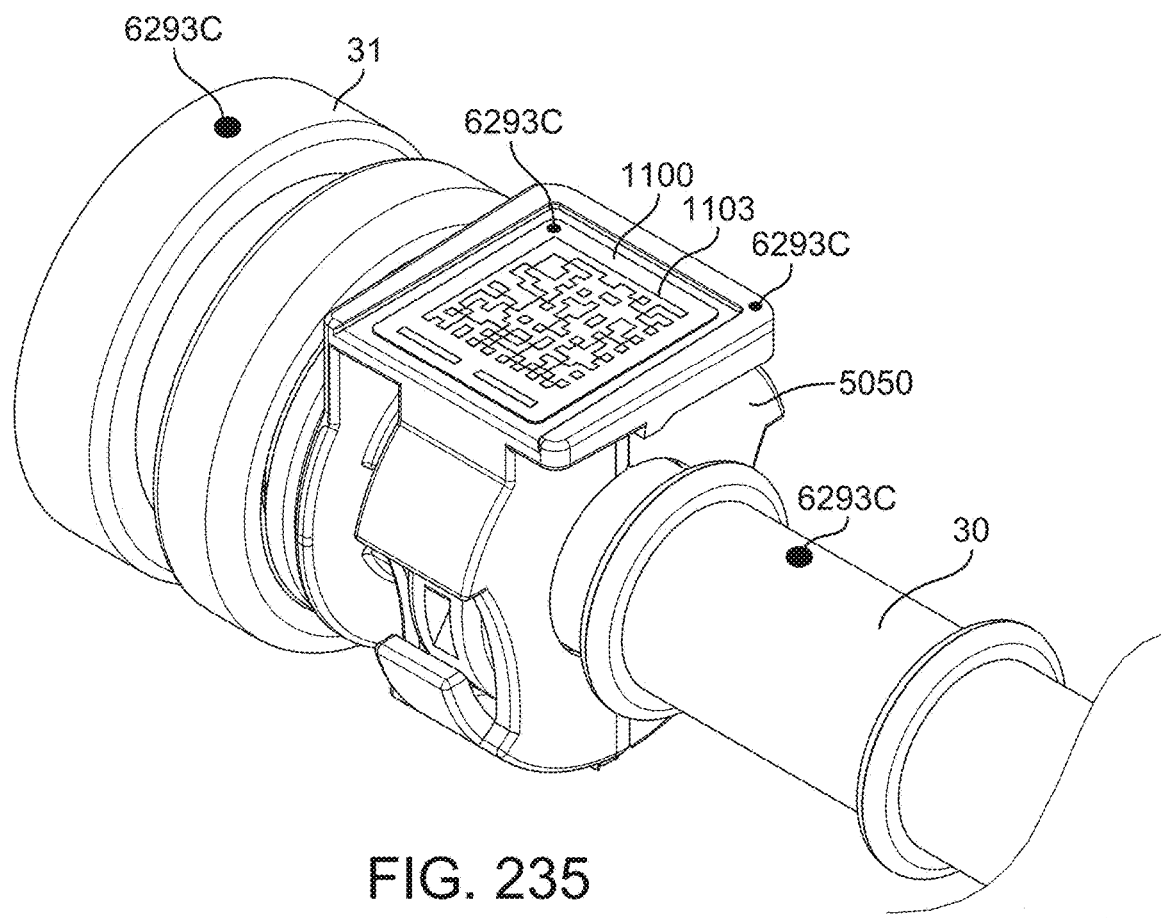
Figure 236:
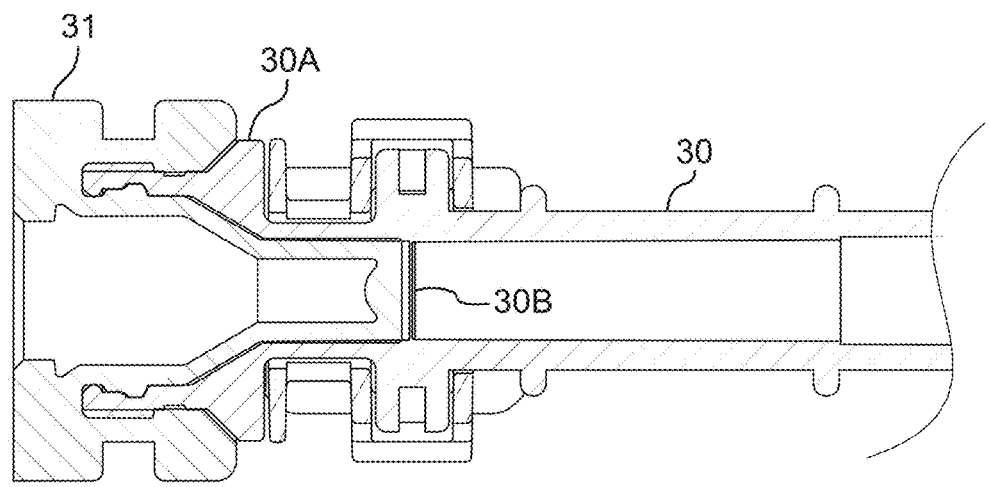
Figure 237:
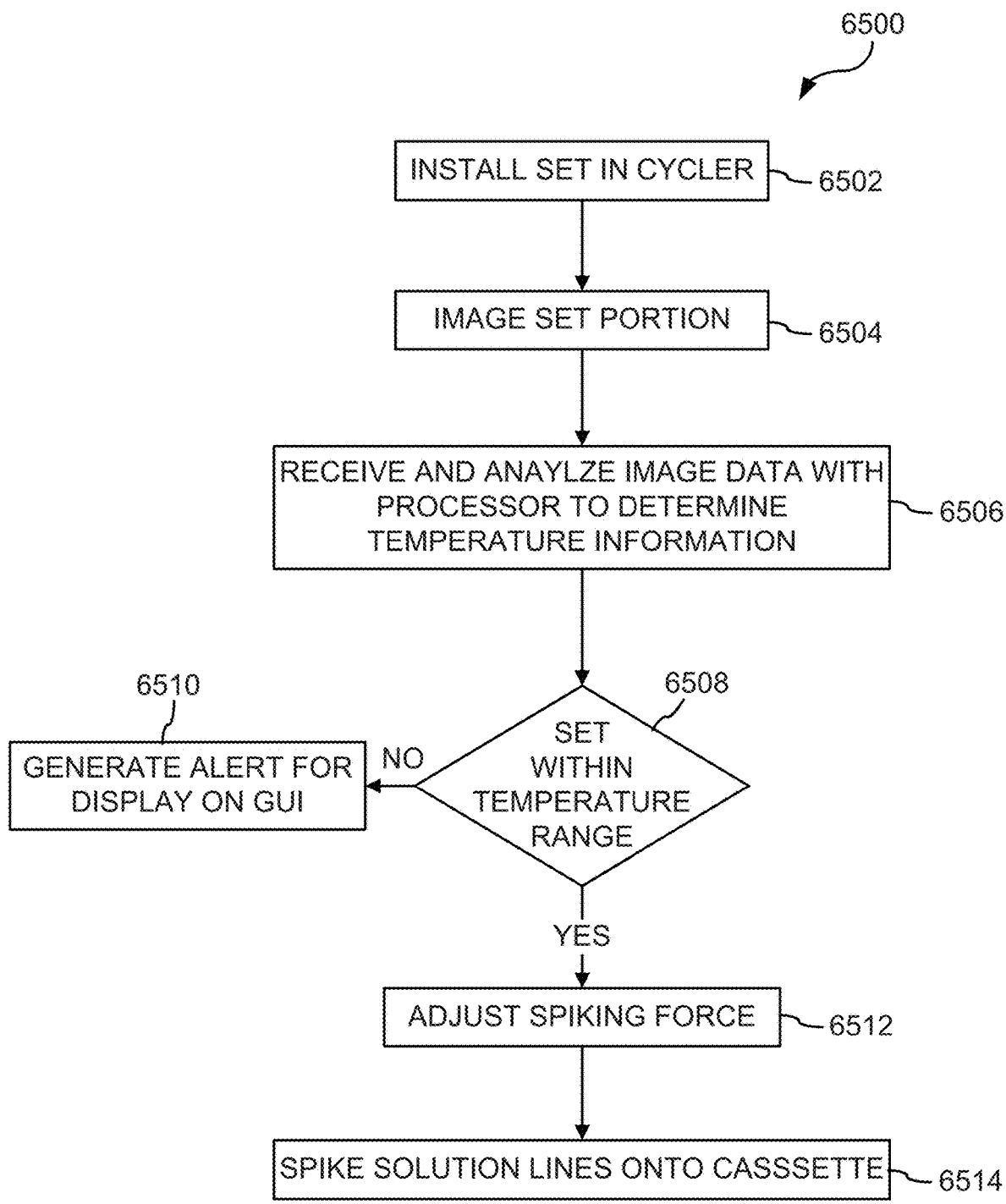
Figure 238:
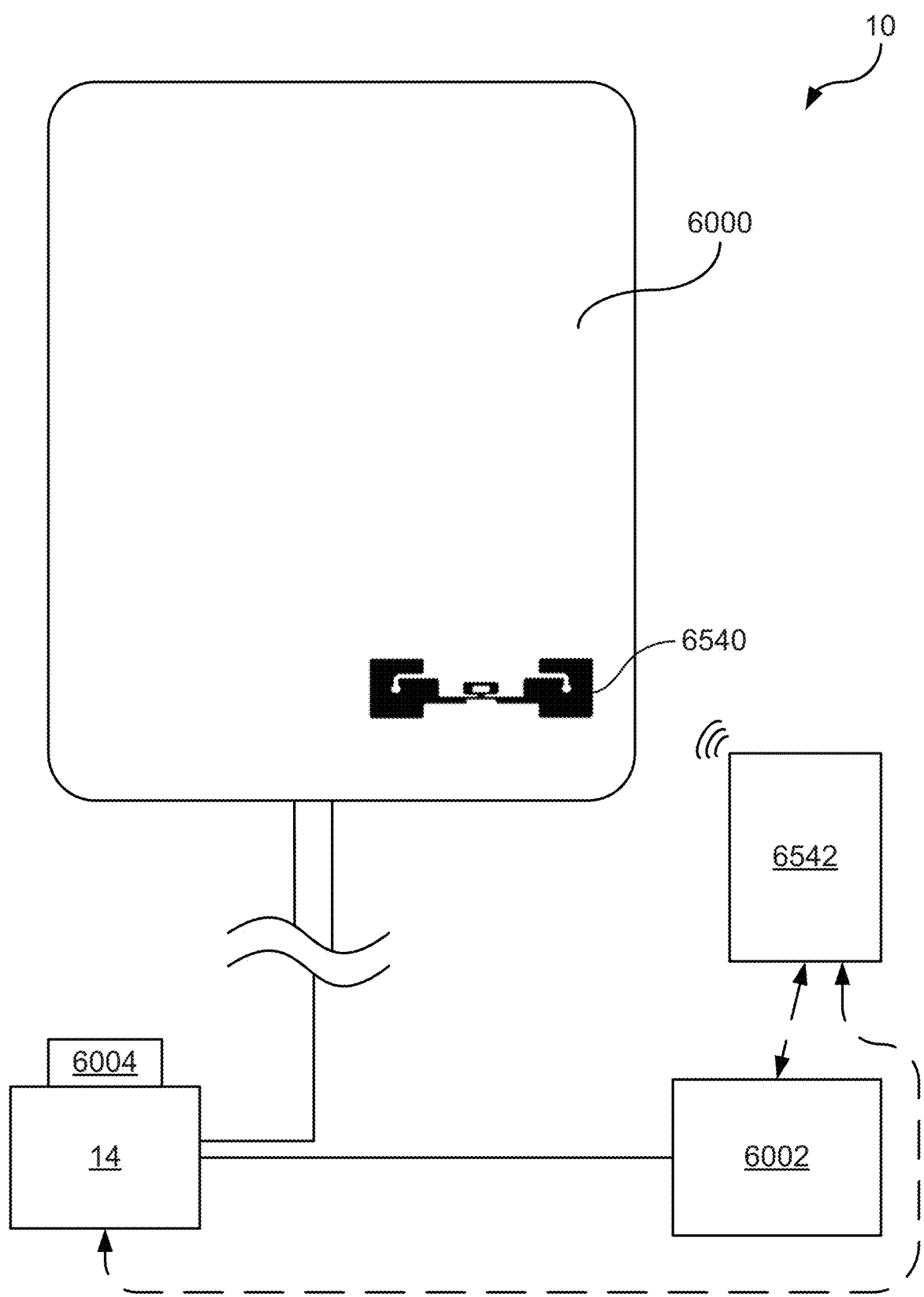
Figure 239:
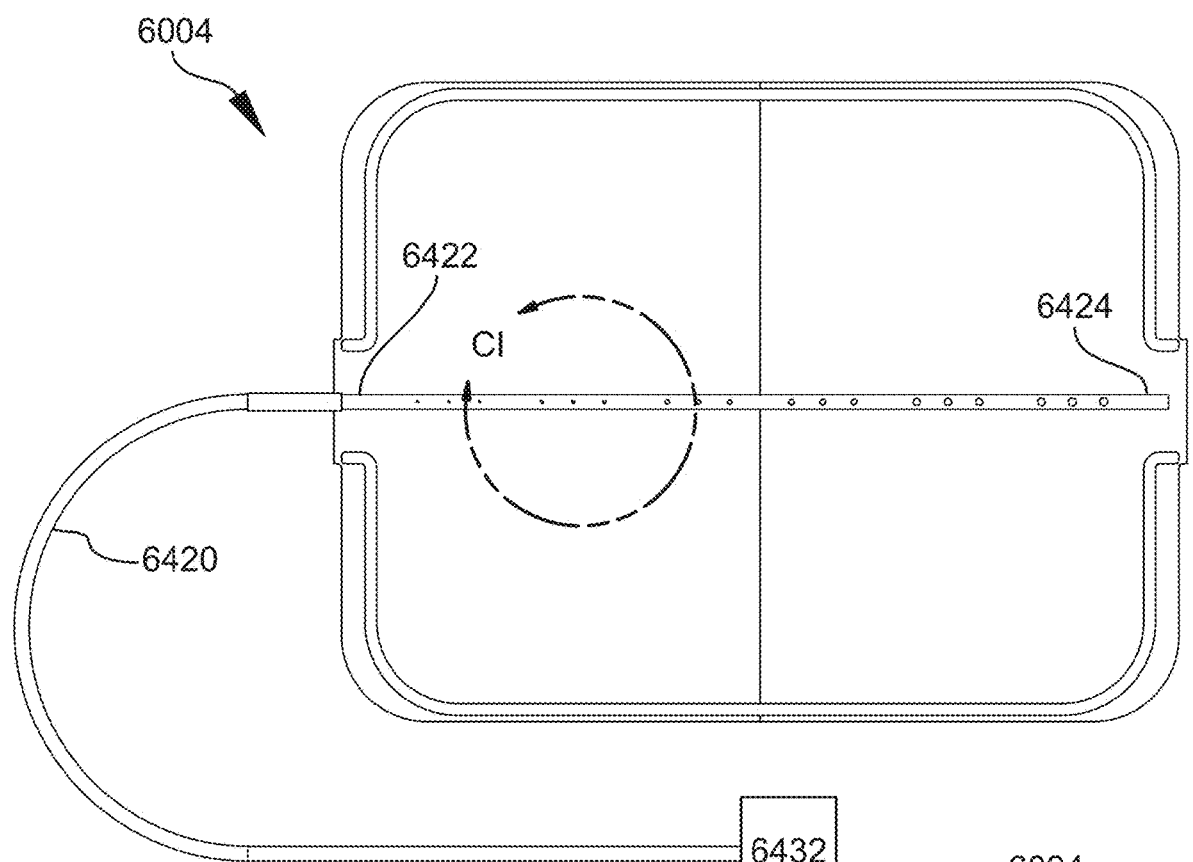
Figure 240:
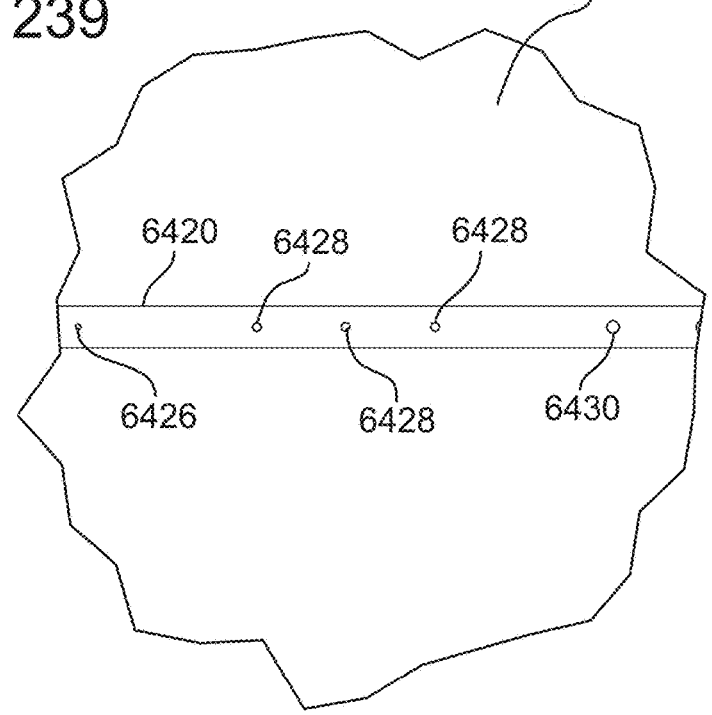
Figure 241:
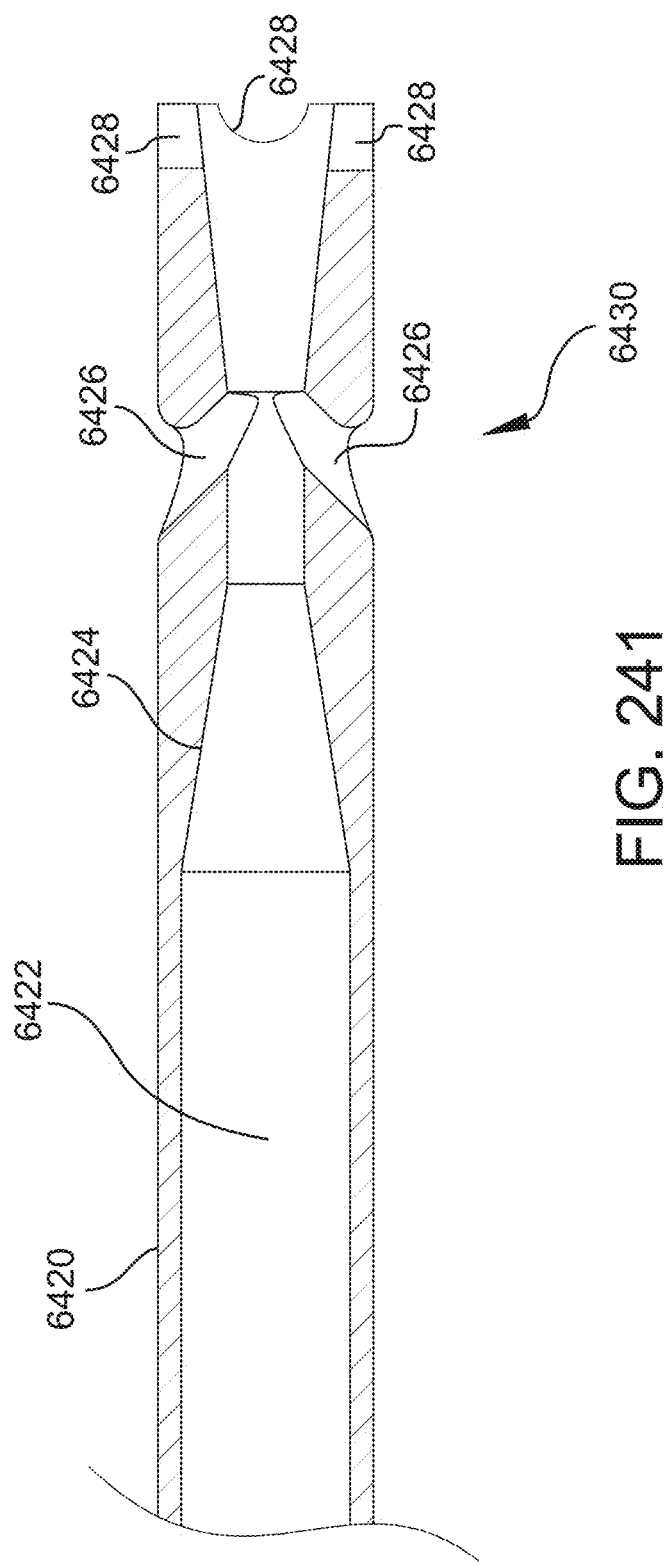
Figure 243A:
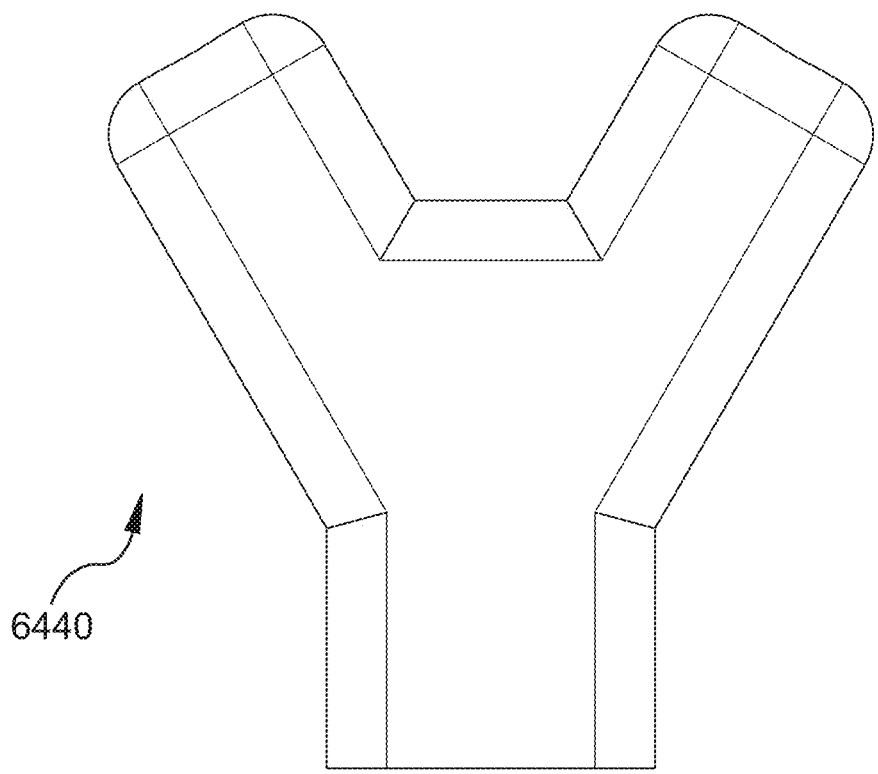
Figure 243B:
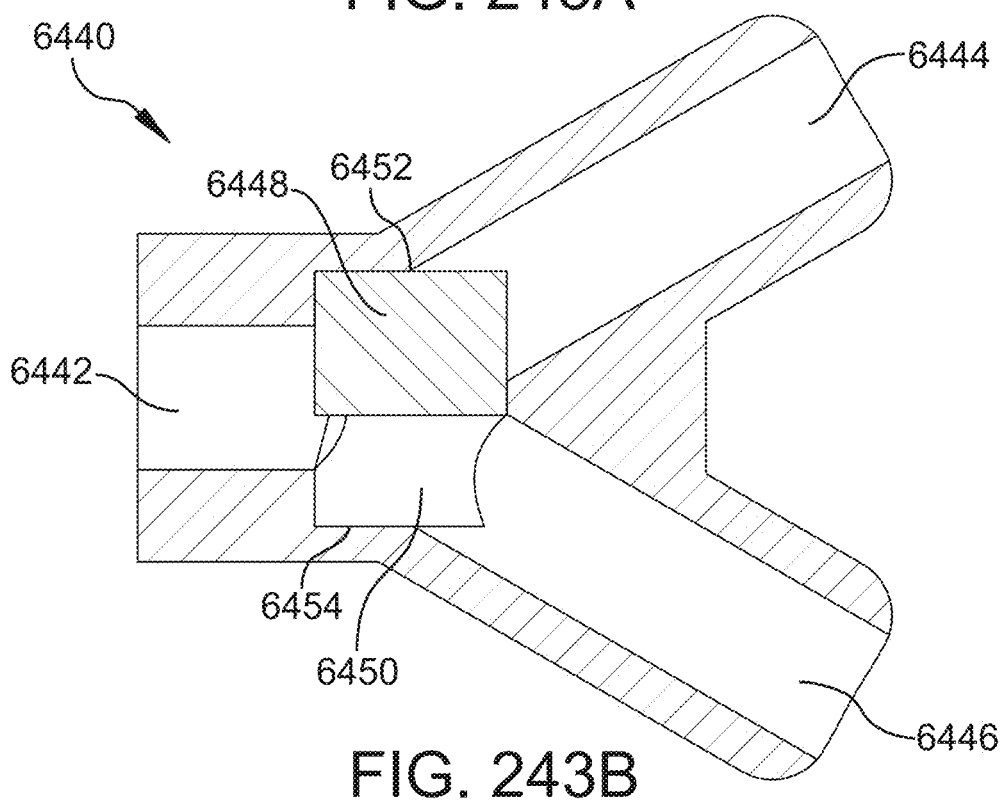
Figure 244A:
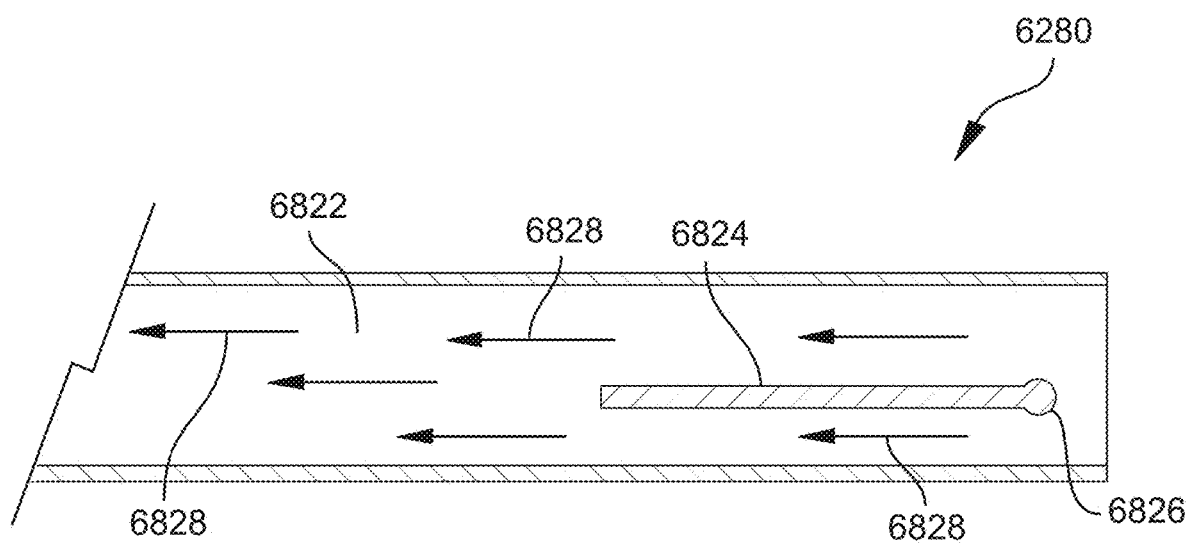
Figure 244B:
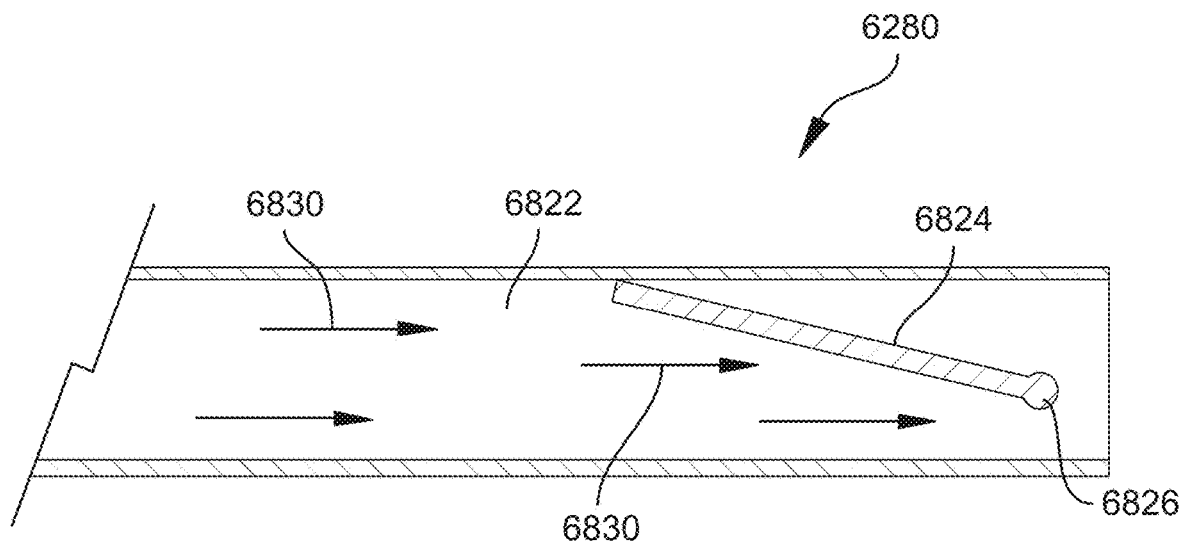
Figure 245:
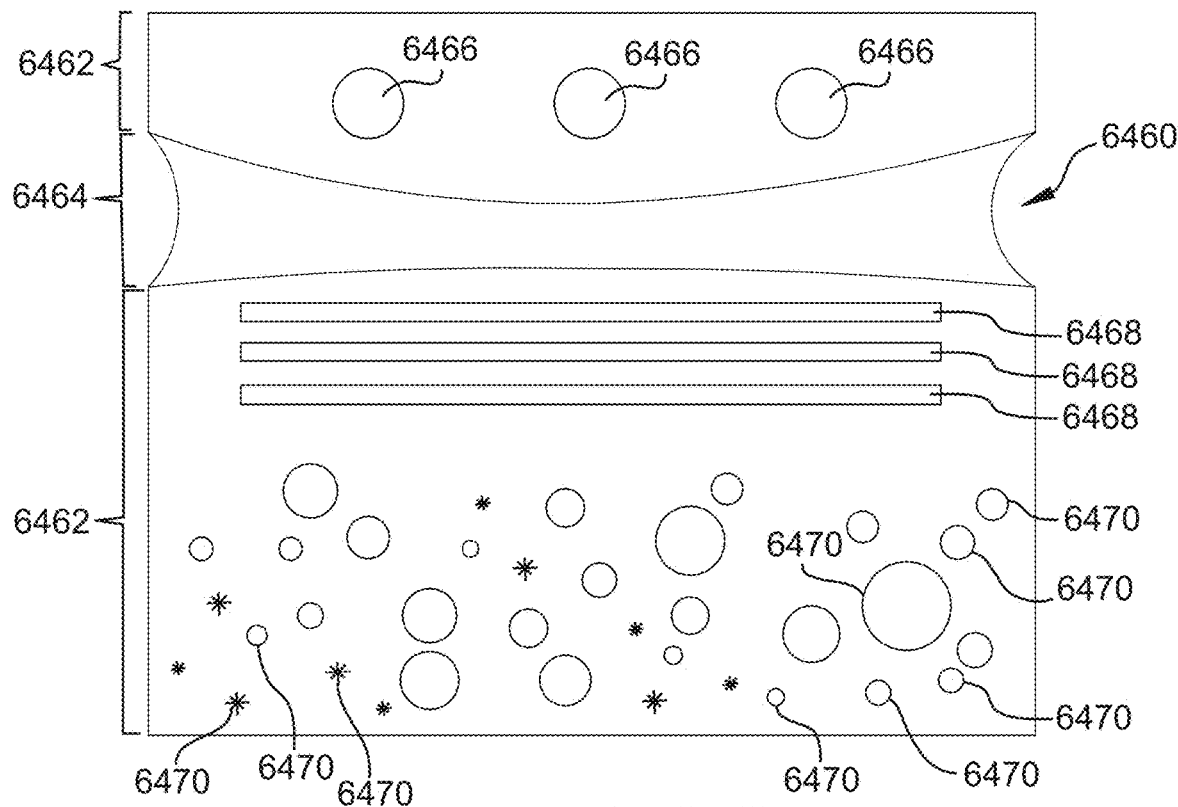
Figure 246:
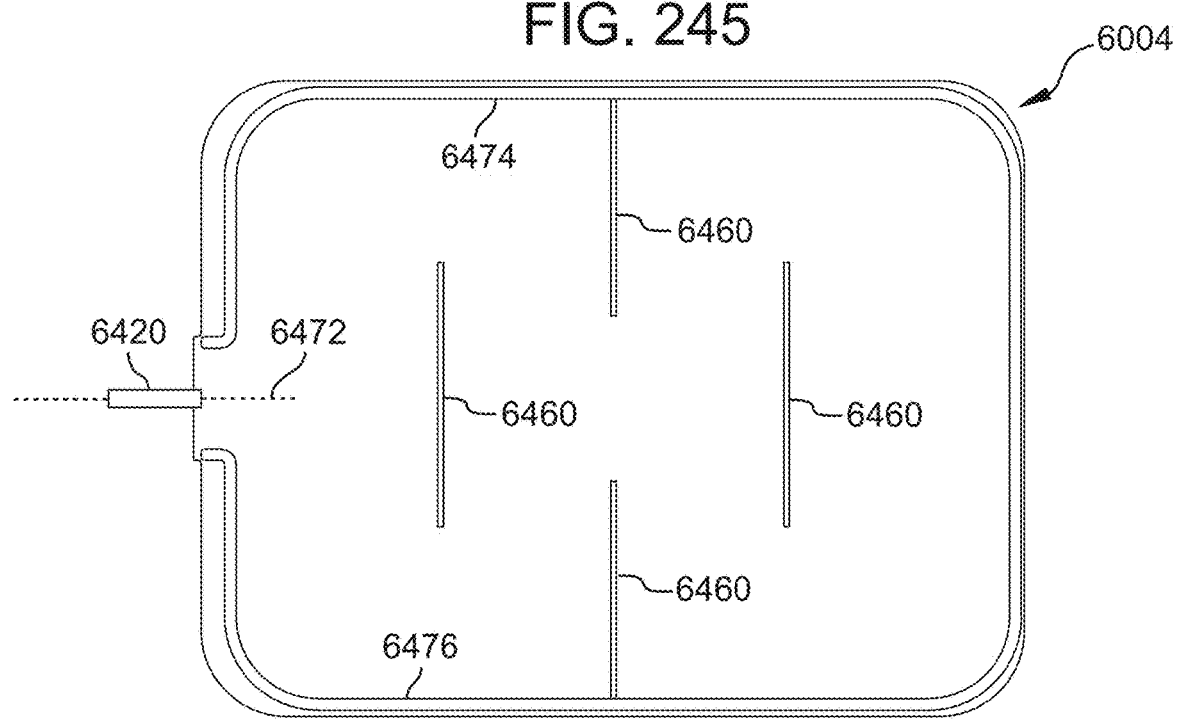
Figure 247:
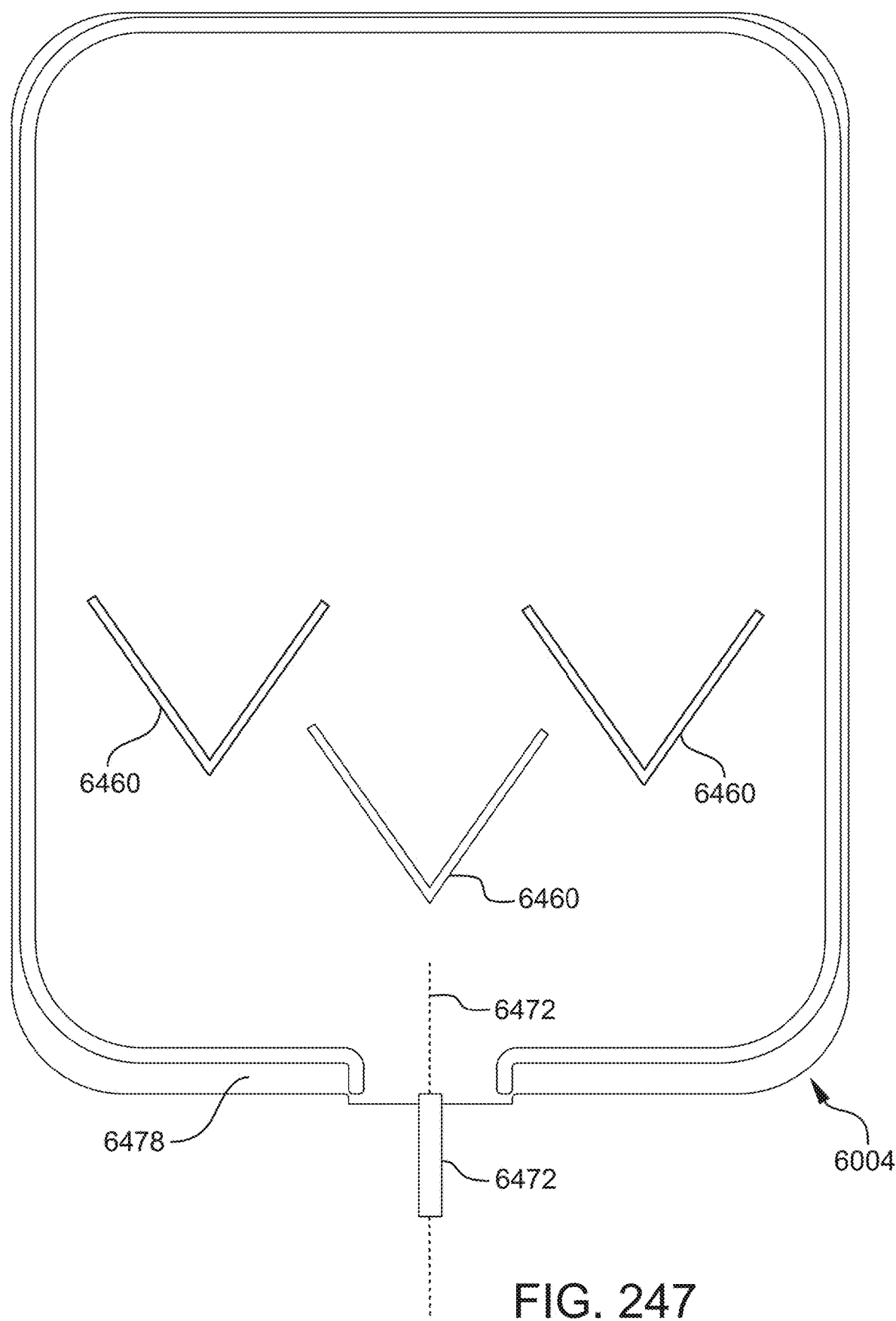
Figure 248:
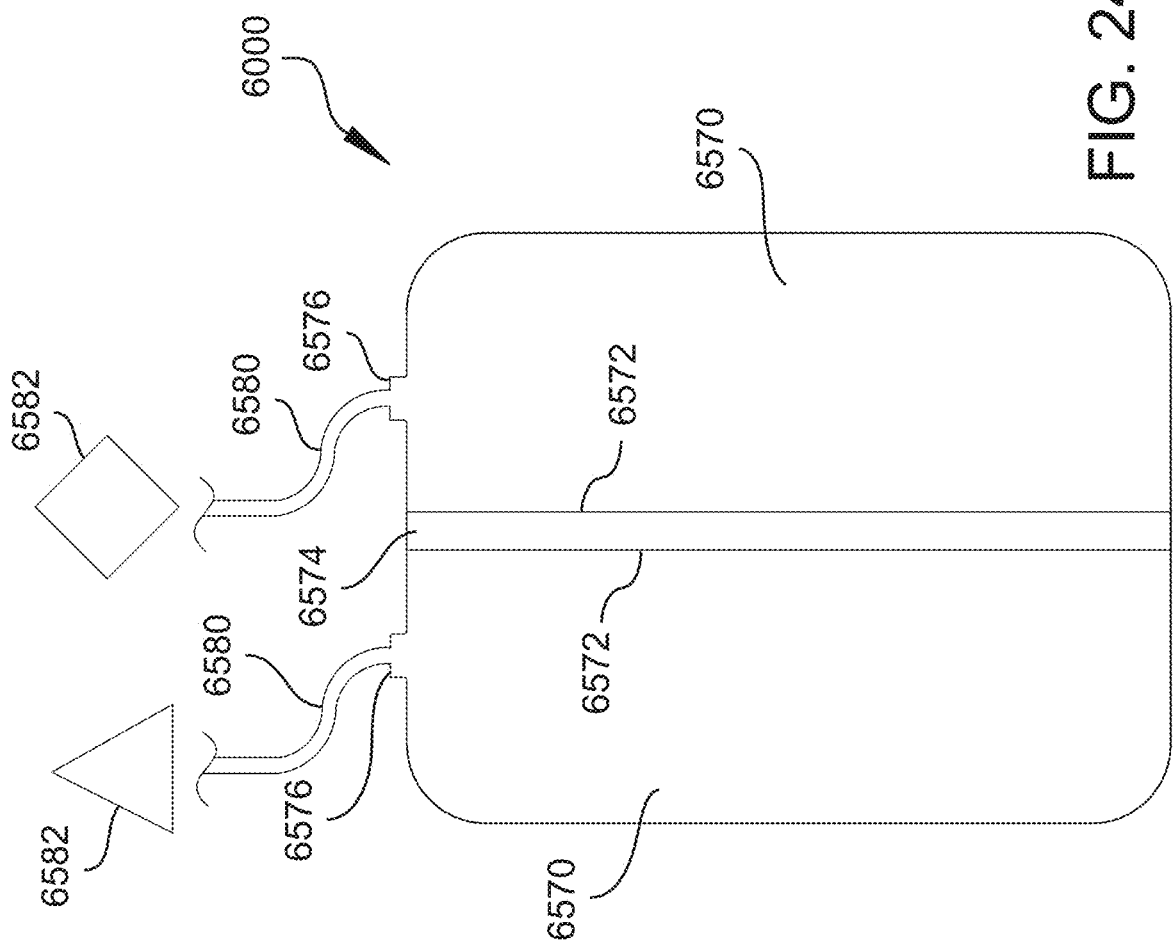
Figure 250:
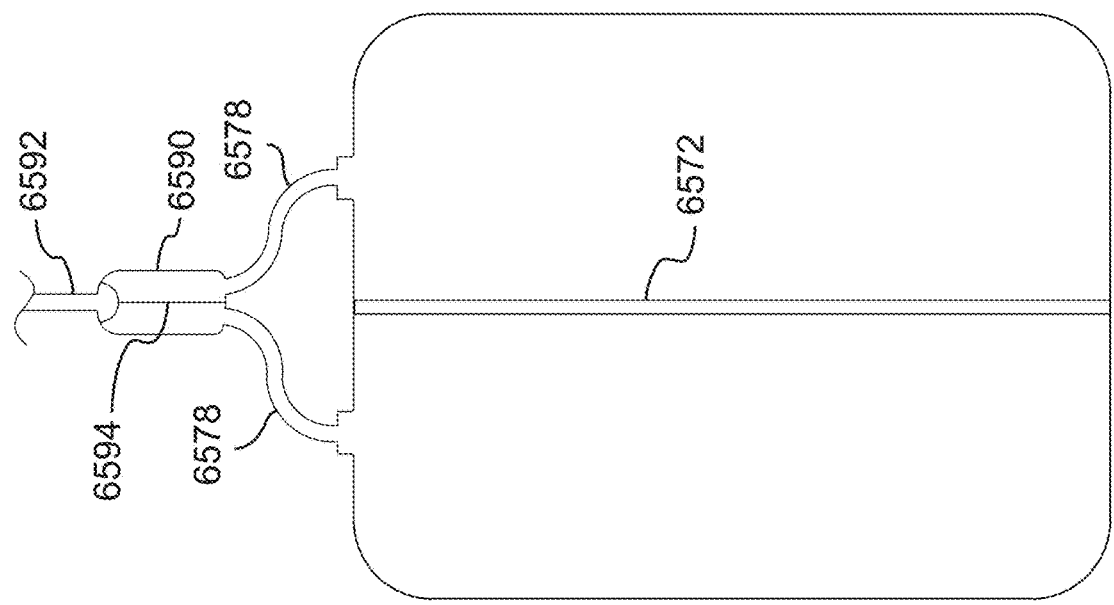
Figure 249:
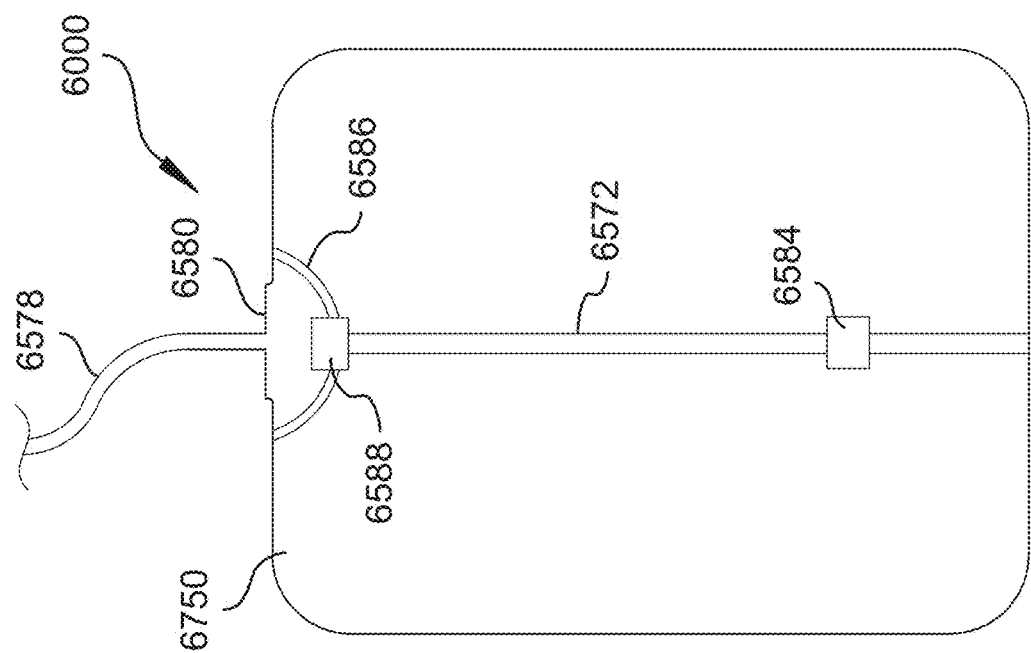
Figure 253:
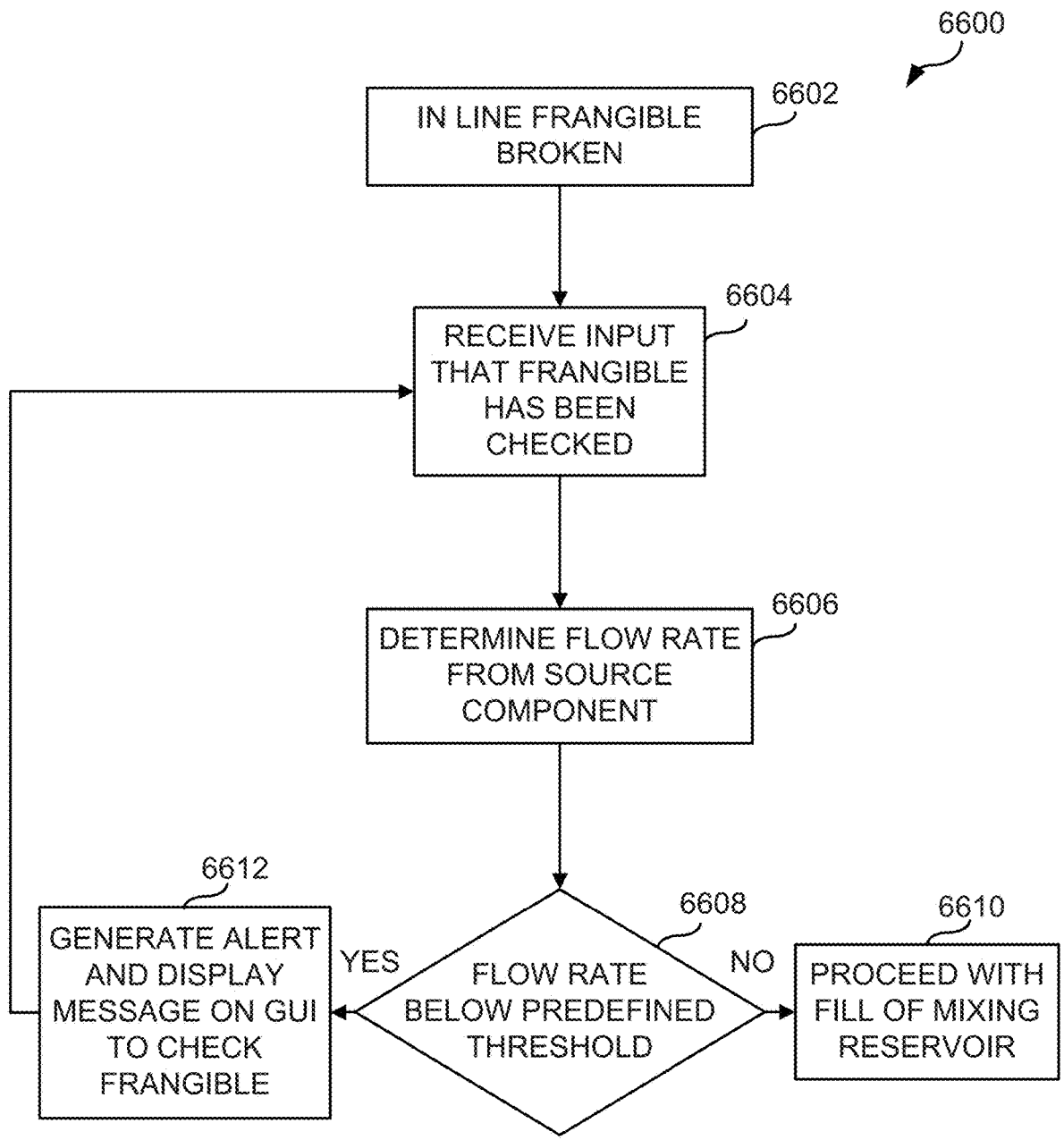
Figure 254:
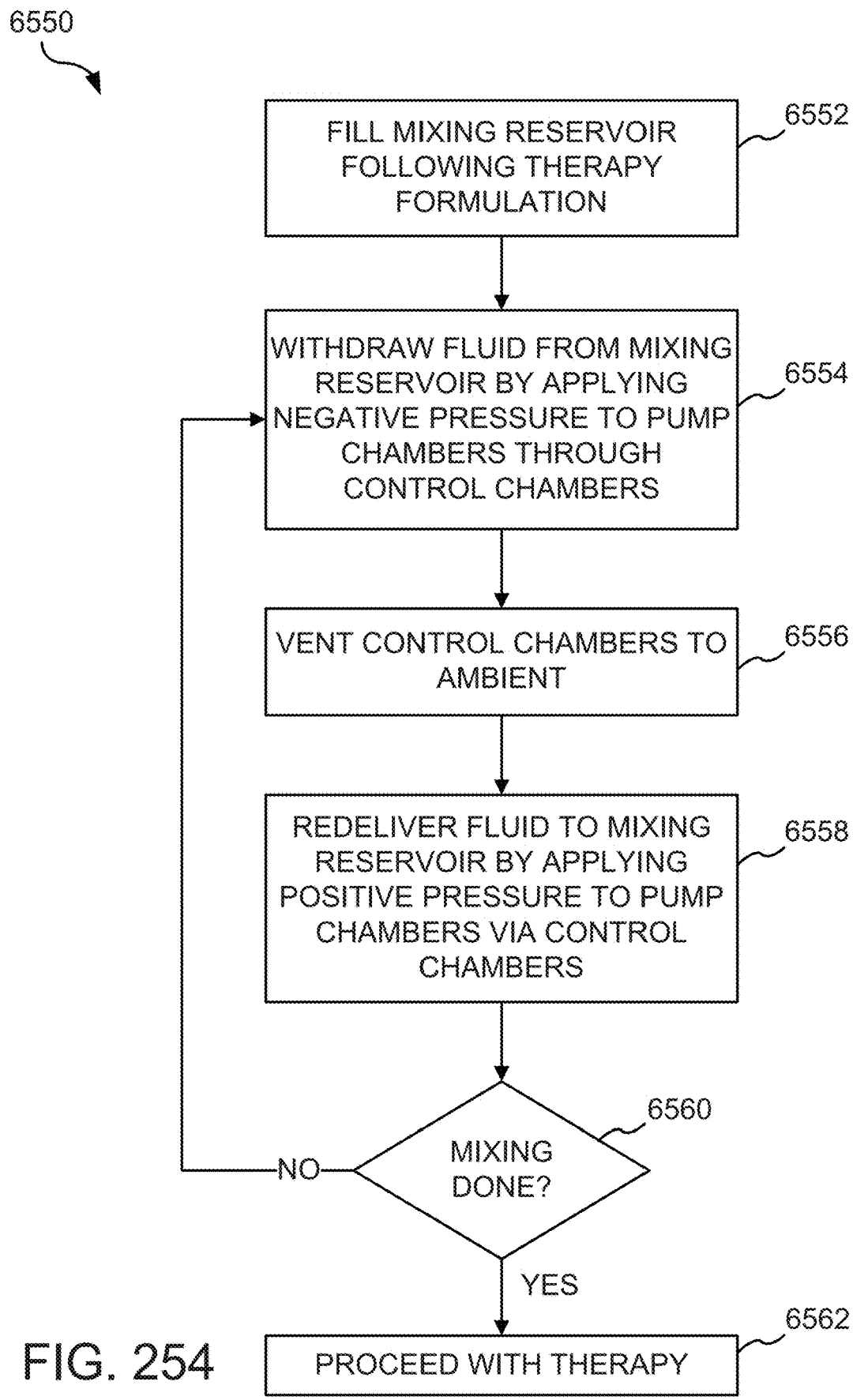
Figure 255:
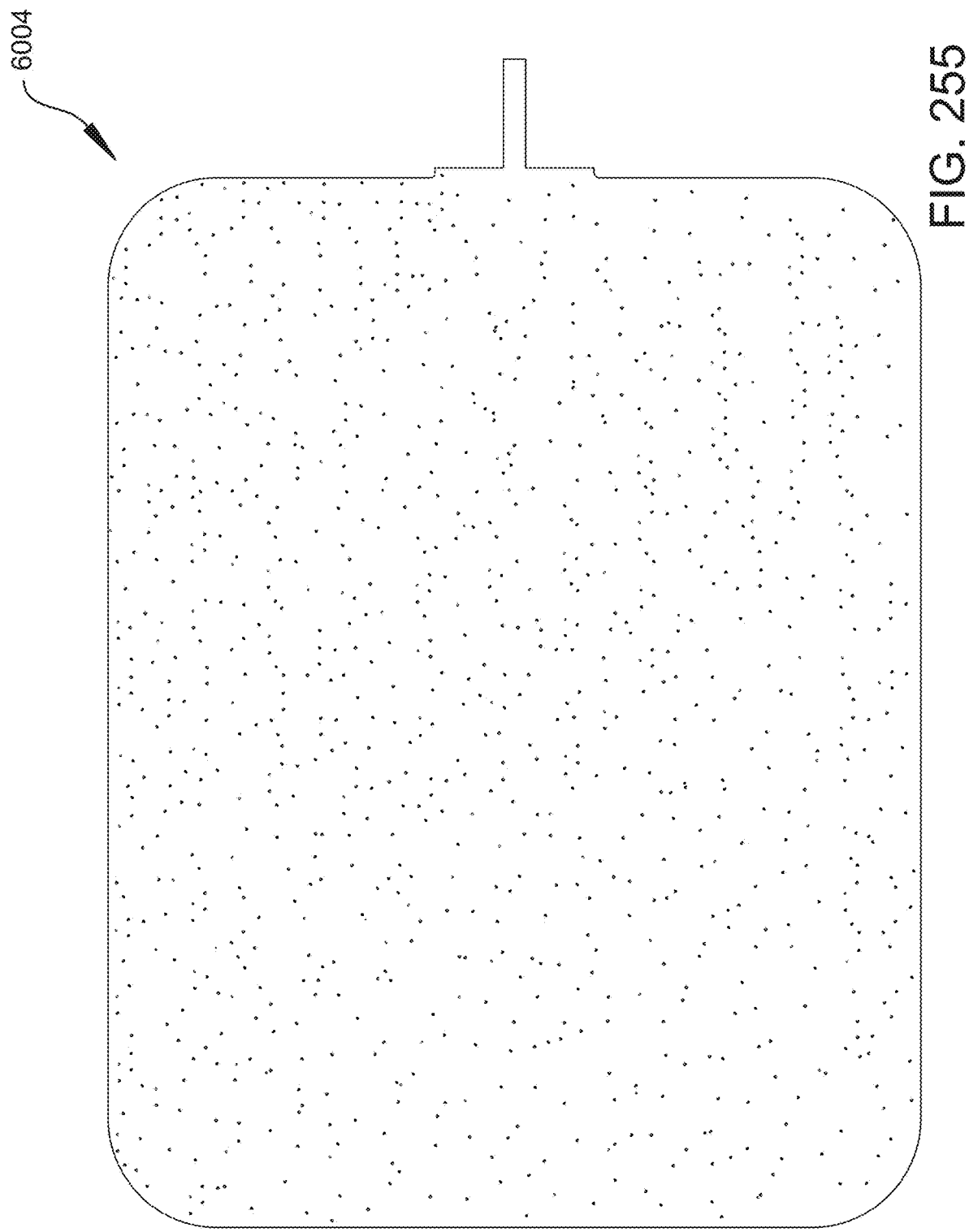
Figure 256A:
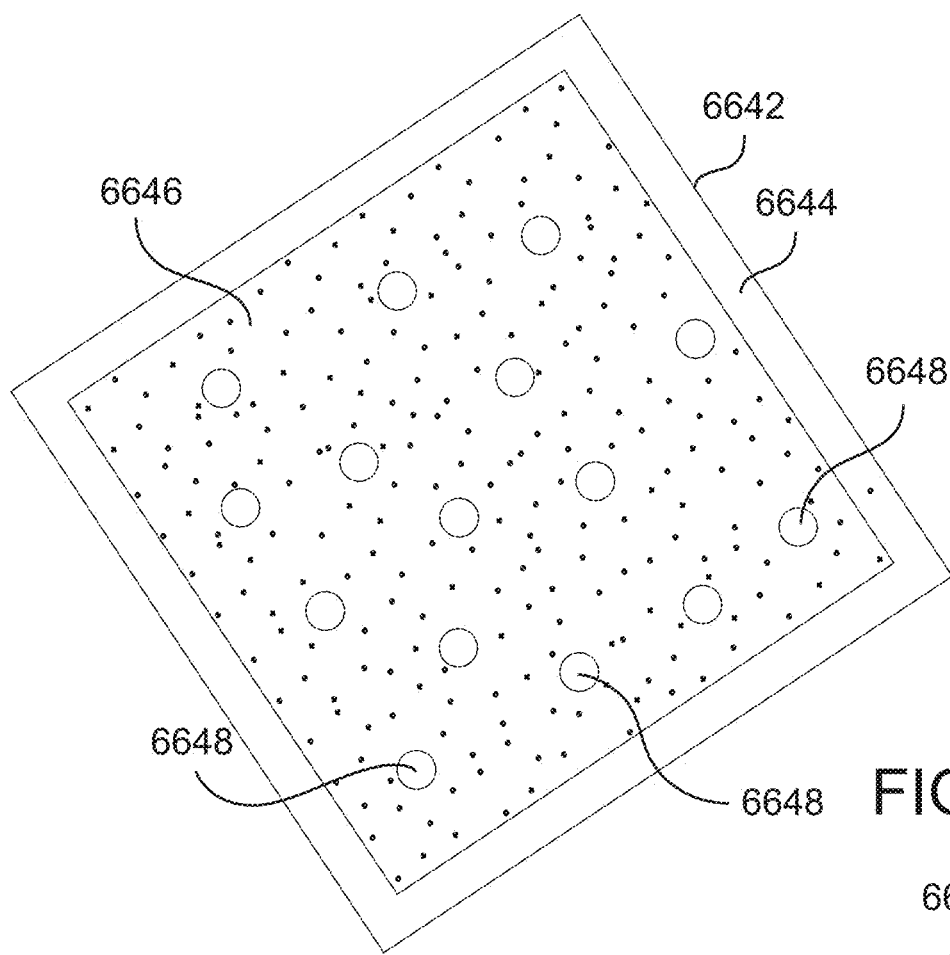
Figure 256B:
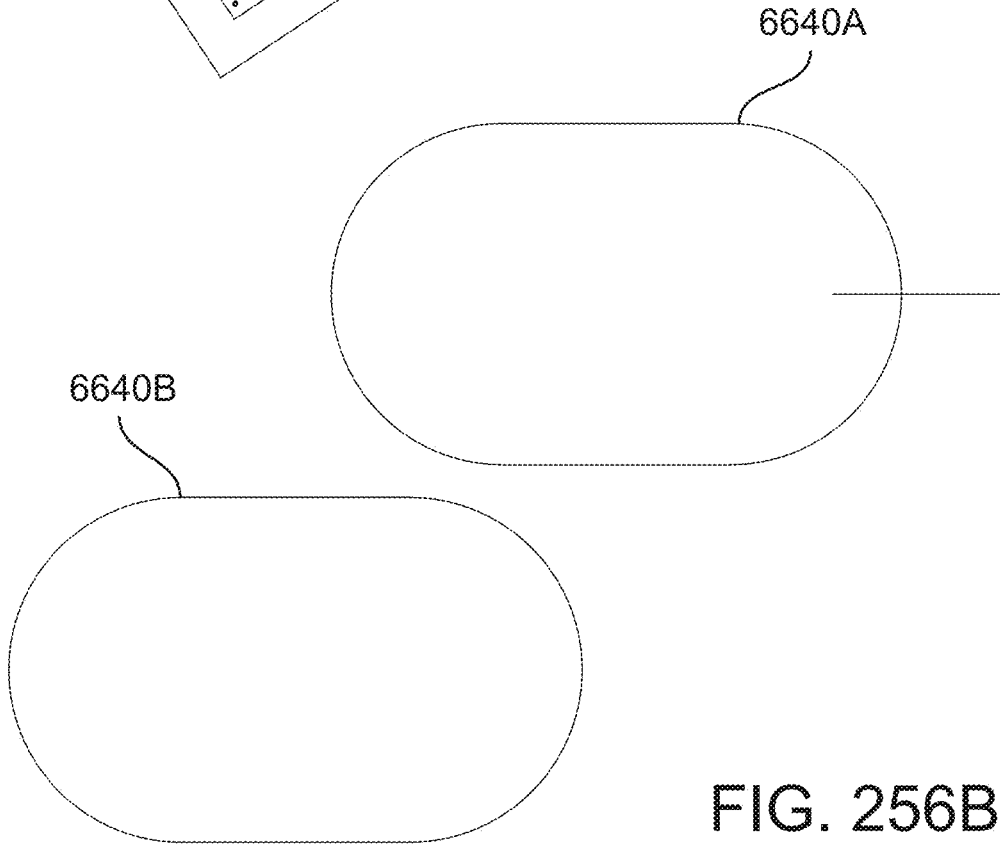
Figure 257:
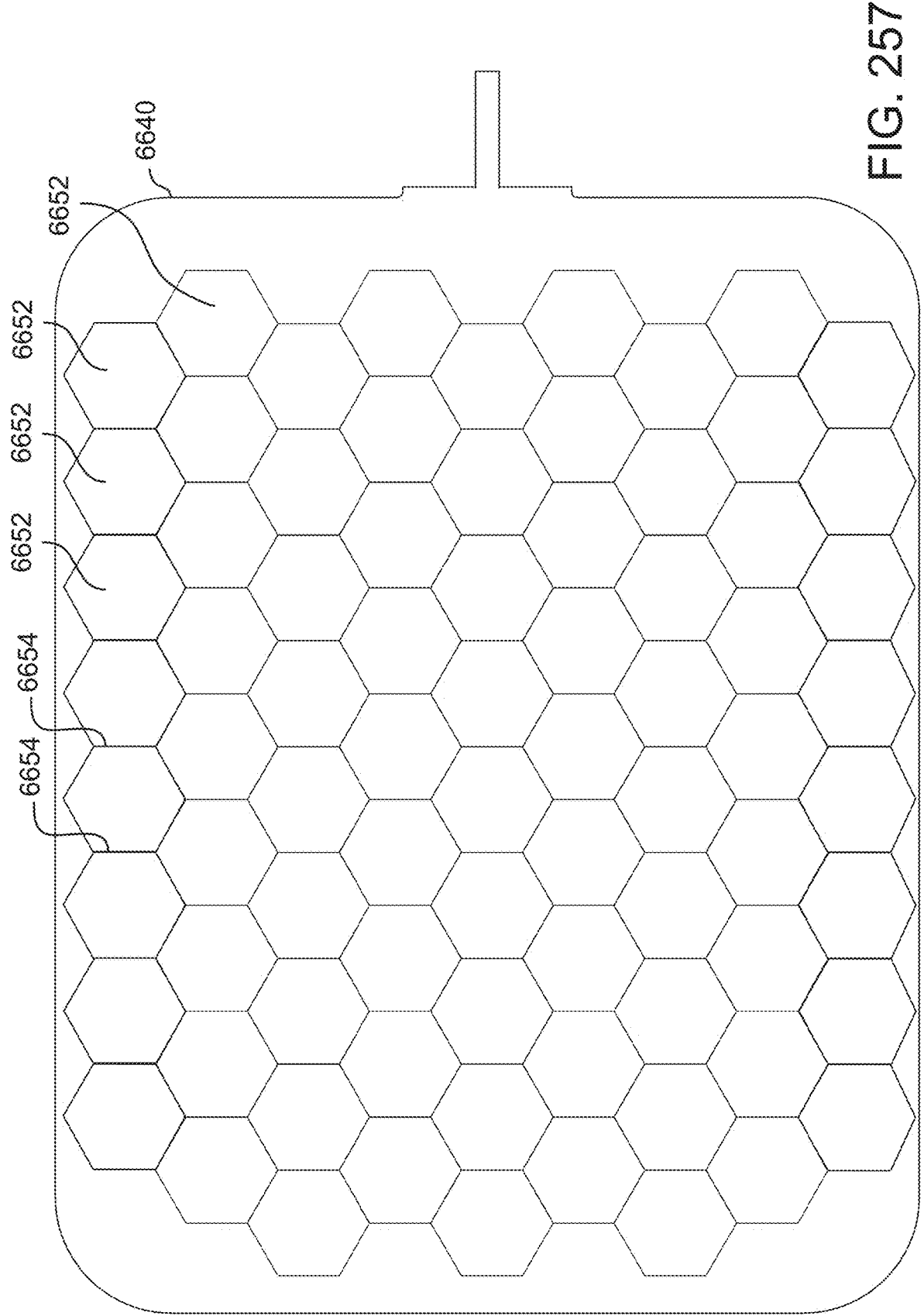
Figure 258:
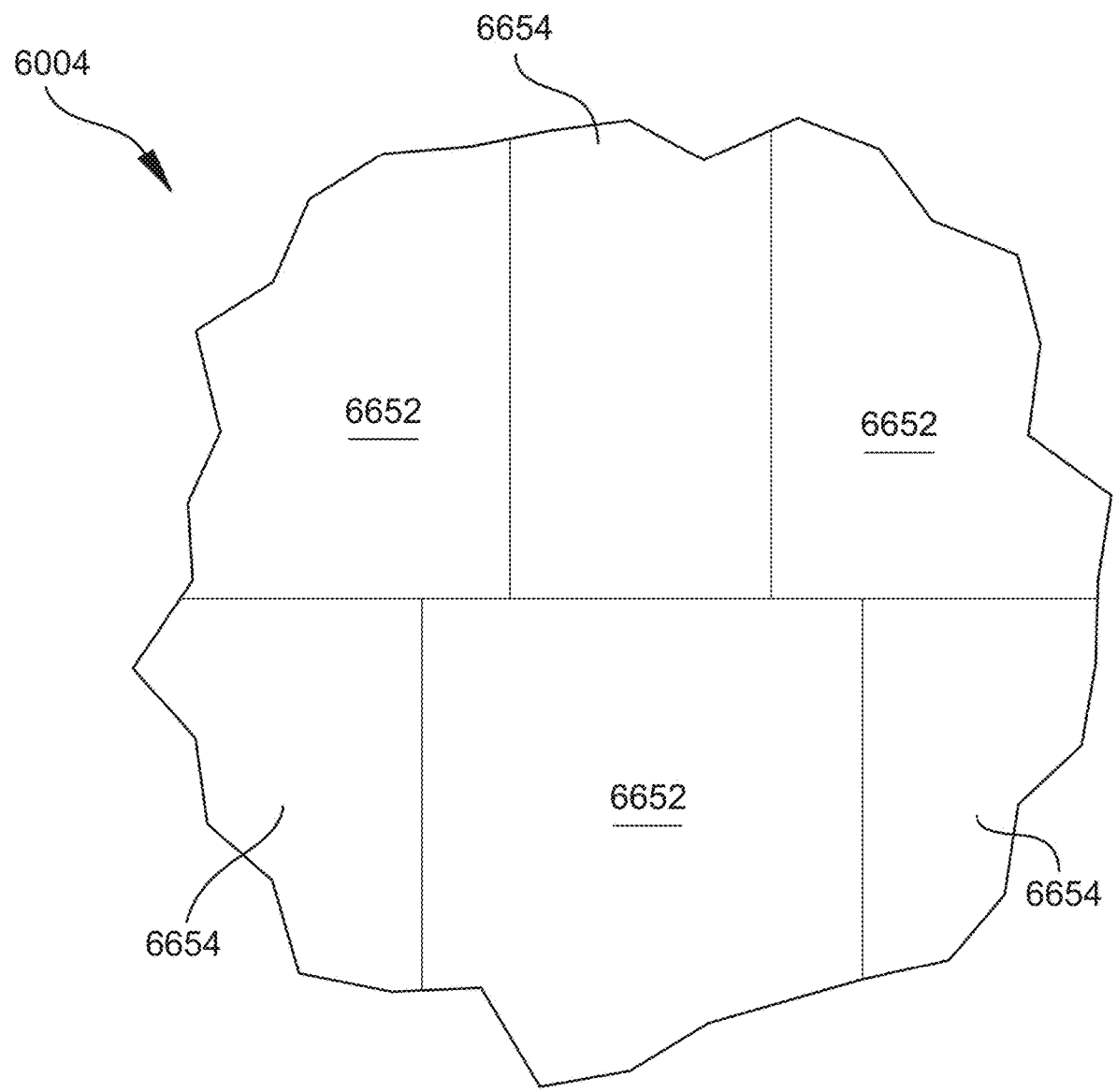
Figure 259:
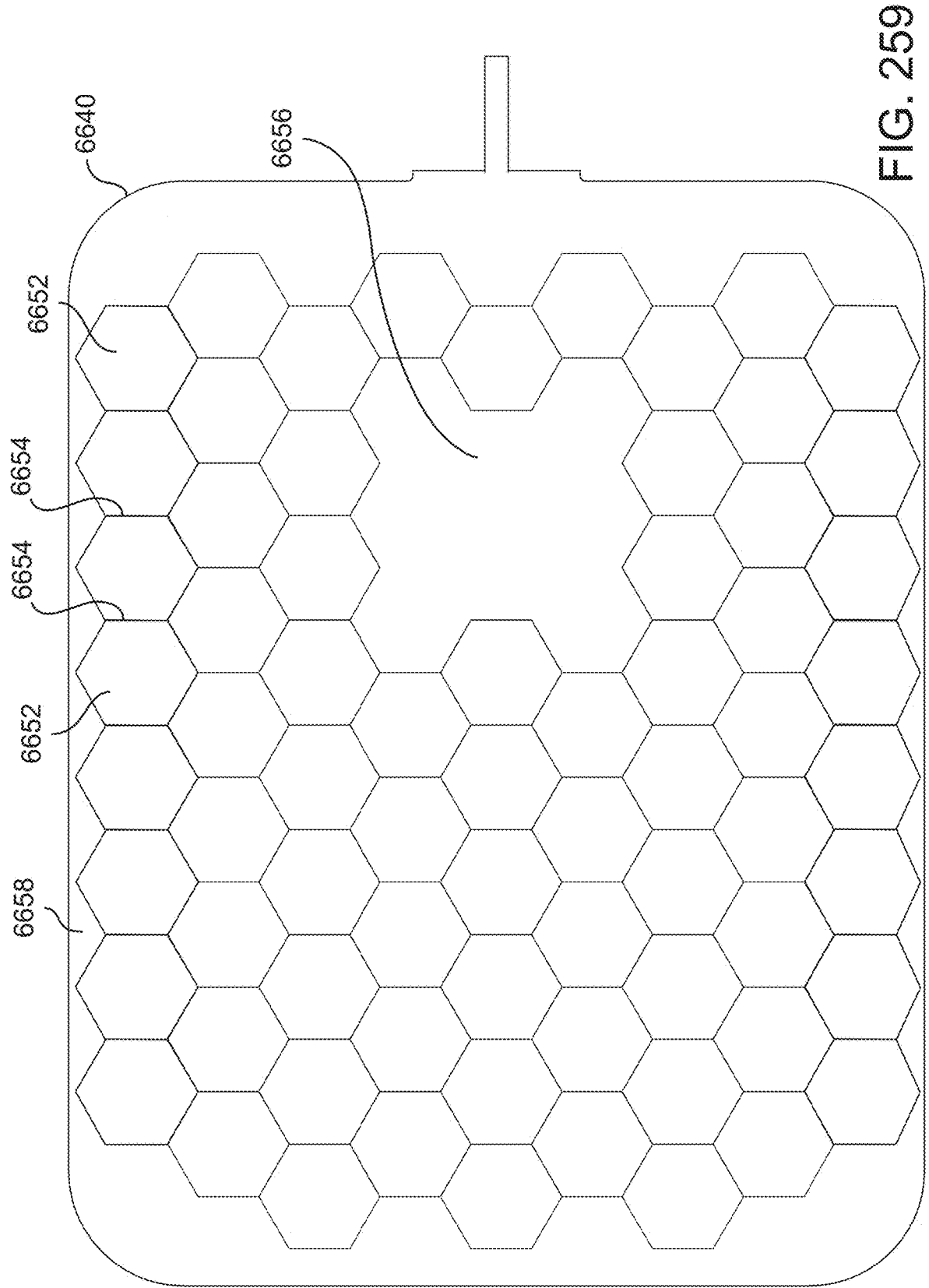
Figure 260:
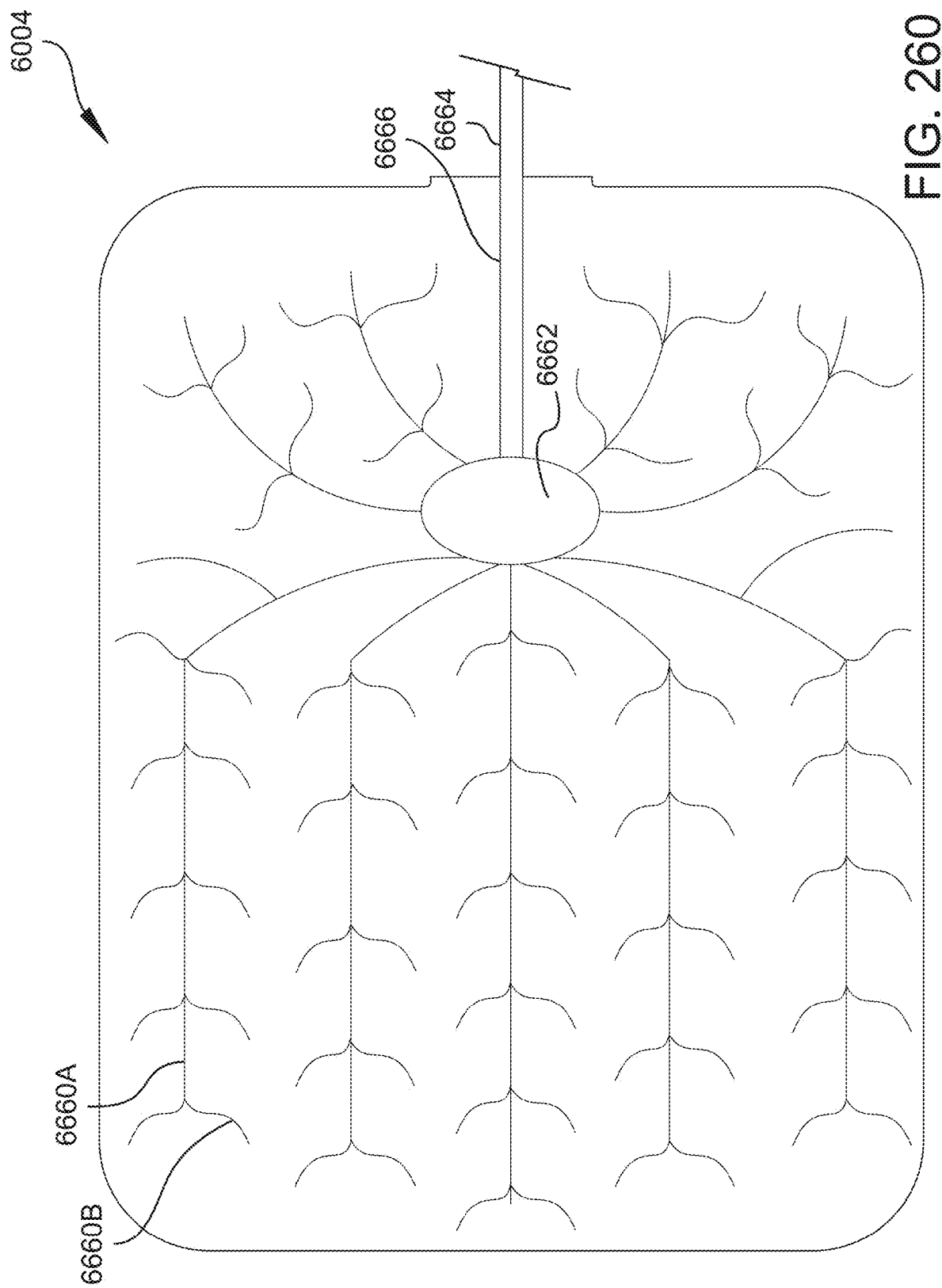
Figure 261:
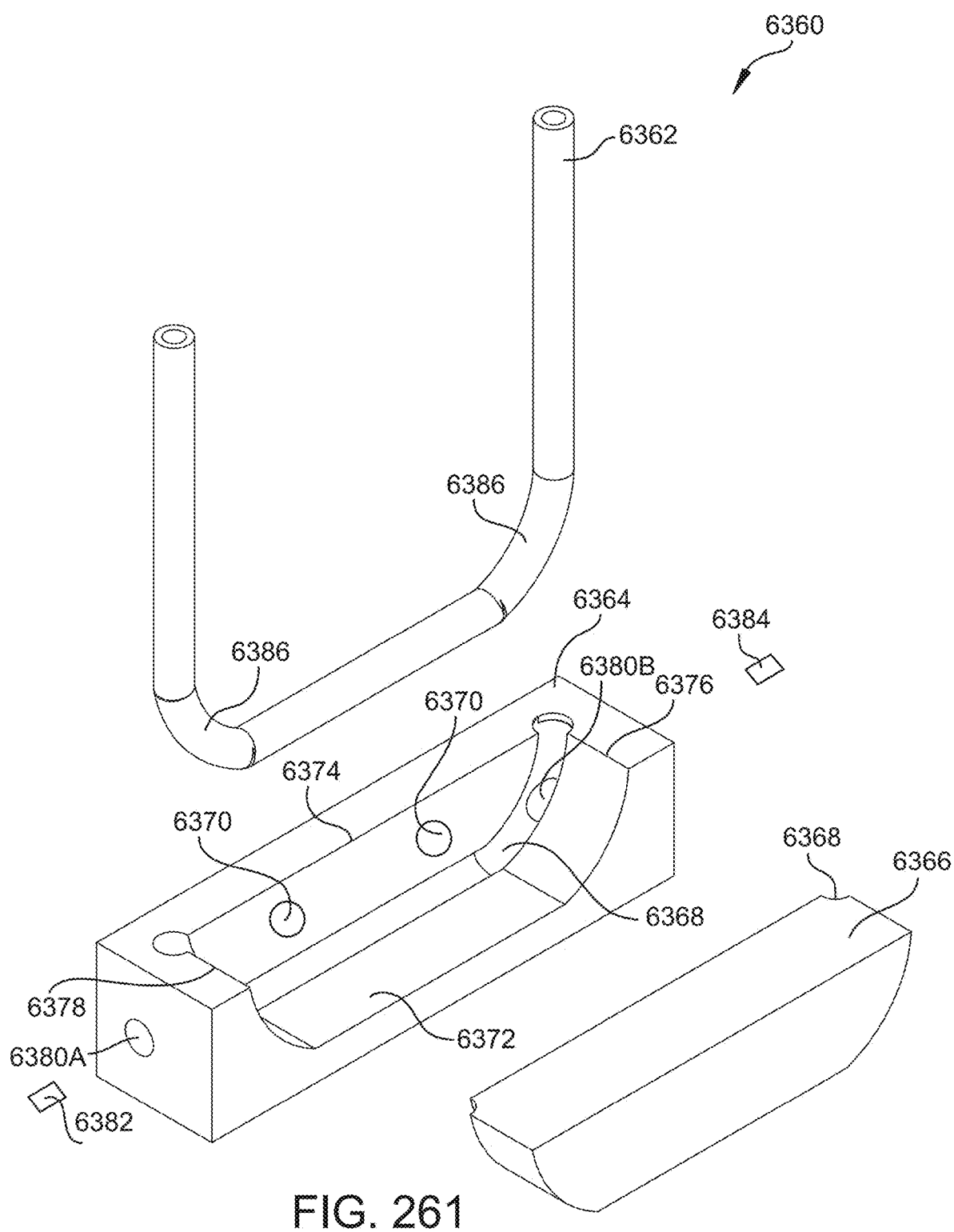

FIG. 132 shows a flowchart detailing a number of example actions which may be executed to adjust a pumping pressure based of a determined head height of a component of interest;

FIG. 133 shows a flowchart detailing a number of example actions which may be executed during a head height detection of a component of interest of the system;

FIG. 134 shows a flowchart detailing a number of example actions which may be executed during a head height detection of a component of interest of the system;

FIG. 135 depicts an example system for mixing dialysate solution from a number of component sources;

FIG. 136 depicts an example system for mixing dialysate solution from a number of component sources;

FIGS. 137-142 depict a number of cross-sectional views of an example cassette in which fluid is pumped through the cassette via actuation of cassette valves;

FIGS. 143-146 depict a number of cross-sectional views of an example cassette in which fluid is pumped through the cassette via actuation of cassette valves;

FIGS. 147-152 depict a number of schematized views of an example cassette in which fluid is pumped through the cassette via actuation of cassette valves;

FIG. 153 depicts an illustrative graph showing a conceptualized pressure trace of control chamber pressure as a number of valve pump strokes are delivered to a pump chamber;

FIG. 154, depicts a flowchart detailing a number of example actions which may be used when delivering valve pump strokes to a pump chamber of a cassette;

FIG. 155A depicts a view of an example cassette;

FIG. 155B depicts a view of an opposing side of the example cassette shown in FIG. 154A;

FIG. 156 depicts a schematized view of an example cassette;

FIGS. 157A-157B depict detailed views of indicated regions of the example cassette shown in FIG. 156;

FIG. 158 depicts a flowchart detailing a number of example actions which may be executed to deliver a volume of a fluid using both pump chamber and valve pump strokes;

FIG. 159 depicts a flowchart detailing a number of example actions which may be executed to deliver a volume of fluid using pump chamber strokes;

FIG. 160 depicts a flowchart detailing a number of example actions which may be executed to deliver a volume of fluid to a destination using a pump chamber;

FIG. 161 depicts a flowchart detailing a number of example actions which may be executed to deliver a volume of fluid to a destination using multiple pump chambers of a cassette;

FIG. 162 depicts a flowchart detailing a number of example actions which may be executed to prime a cassette prior to a mixing operation;

FIG. 163 depicts a flowchart detailing a number of example actions which may be executed to mix a solution defined in a therapy formulation using the system;

FIGS. 164A and 164B depicts a flowchart detailing a number of example actions which may be executed to mix a solution defined in a therapy formulation using the system;

FIG. 165 depicts a flowchart detailing a number of example actions which may be executed to flush non-conforming fluid from a cassette;

FIG. 166 depicts an example system for mixing dialysate solution from a number of component sources;

FIG. 167 depicts a flowchart detailing number of example actions which may be executed to confirm installation and integrity of an appropriate fluid handling set type;

FIG. 168A depicts a flowchart detailing a number of example actions which may be executed to monitor for pressure in a high pressure portion of a set reaching a cassette included in the set;

FIG. 168B depicts a flowchart detailing a number of example actions which may be executed to react to a detection of pressure in a high pressure portion of a set reaching a cassette of the set;

FIG. 169 depicts an example system for mixing dialysate solution from a number of component sources having a source heater;

FIGS. 170 and 171 depict views of exemplary cyclers having source heaters;

FIG. 172 depicts a view of portions of an example set having a fluid line routed under a heater bag;

FIG. 173 depicts an exploded view of an example mixing reservoir;

FIG. 174 depicts a plan view of an example mixing reservoir;

FIG. 175 is a section view of the back side of an exemplary cassette;

FIG. 176 is a side view of the side of an exemplary cassette;

FIG. 177 is a section view of the front of an exemplary cassette;

FIG. 178 is a view of an exemplary cassette and exemplary thermal wells;

FIG. 179 is a pictorial view of an example thermal well;

FIG. 180 is a cross sectional view of an exemplary embodiment of a thermal well;

FIGS. 181 and 182 show section views of embodiments of thermal wells having variable wall thickness;

FIG. 183 is a view of an exemplary cassette with exemplary thermal wells installed;

FIG. 184 is a view of example thermal wells extending into a fluid line of an exemplary cassette;

FIG. 185 is a close up certain features of FIG. 184;

FIG. 186 is a section view showing an embodiment of the cassette engaged with a housing and illustrating engagement of sensing probes located in the housing with sensor ports of the cassette;

FIG. 187 depicts a schematized view of two sensor probed extending into a fluid line;

FIGS. 188 and 189 show embodiments of a sensing apparatus where the thermal well is a continuous part of the fluid line;

FIGS. 190 and 191 are embodiments of a sensing apparatus where the thermal well is a separate part from the fluid line;

FIGS. 192 and 193 are embodiments of a sensing apparatus showing various lengths and widths of the thermal well;

FIGS. 194-212 are sectional views of various embodiments of exemplary thermal wells embedded in a fluid line;

FIG. 213 is a section side view of one embodiment of a sensing probe;

FIG. 214 is an exploded view of the embodiment shown in FIG. 212;

FIG. 215 is a sectional view of an alternate embodiment of a tip of a sensing probe;

FIG. 216 is an alternate embodiment of a sensing probe;

FIG. 217 is an alternate embodiment of a sensing probe;

FIG. 218 is a side view of an alternate embodiment of a sensing probe;

FIG. 219 is a section view of a sensing probe coupled to a thermal well;

FIG. 220 is an alternate embodiment of a sensing probe;

FIG. 221 is a section view of a sensing probe coupled to a thermal well;

FIG. 222 is an alternate embodiment of a sensing probe;

FIG. 223 is a sectional view of one exemplary embodiment of a sensor apparatus;

FIG. 224 shows an alternate embodiment of a sensing probe coupled to a thermal well;

FIG. 225 is a section view of one embodiment of a sensing probe coupled to a thermal well and suspended by a spring;

FIG. 226 is a section view of one embodiment of a sensing probe in a housing;

FIG. 227 is a section view of one embodiment of a sensing probe in a housing;

FIG. 228 is a section view of one embodiment of a sensing probe in a housing;

FIG. 229 is a section view of a fluid line with a sensor apparatus;

FIG. 230 shows an exemplary source component including an example sensing probe;

FIGS. 231A-231B depict a flowchart detailing a number of example actions which may be executed to calibrate a temperature sensor monitoring a cassette;

FIG. 232 depicts an example cross-sectional view of a portion of an example cycler including a contactless temperature sensor;

FIG. 233 depicts an example cross-sectional view of a portion of an example cycler including a contactless temperature sensor;

FIG. 234 depicts an example cross-sectional view of a portion of an example cycler including a contactless temperature sensor;

FIG. 235-236 depict views of a portion of a solution line including thermochromic elements;

FIG. 237 depicts a flowchart detailing a number of example actions which may be executed to adjust spiking force in an automated line spiking system of a cycler based at least in part on temperature information related to a set installed in the cycler;

FIG. 238 depicts an example system having a source component including an RFID tag;

FIG. 239 depicts a top down view of an example mixing reservoir including an inlet/outlet line having a number of orifices;

FIG. 240 depicts a detailed view of an indicated region of FIG. 239;

FIG. 241 depicts a cross-sectional view of an example inlet/outlet line of a mixing reservoir including a venturi ejector;

FIG. 242 depicts a top down view of an example mixing reservoir including separate inlet and outlet lines;

FIGS. 243A-243B depict views of an example flow director which may be included in a mixing reservoir;

FIGS. 244A-244B depict views of another example flow director which may be included in a mixing reservoir;

FIG. 245 depicts a view of an example baffle which may be included in a mixing reservoir;

FIG. 246 depicts a top down view of an example mixing reservoir including a number of baffles;

FIG. 247 depicts a top down view of an example mixing reservoir including a number of baffles;

FIG. 248 depicts an example source component having an embodiment of a temporary barrier;

FIG. 249 depicts an example source component having an embodiment of a temporary barrier;

FIG. 250 depicts an example source component having an embodiment of a temporary barrier and a fluid line including a line junction;

FIGS. 251 and 252 show a schematized embodiment of an exemplary line junction;

FIG. 253 depicts a flowchart detailing a number of example actions which may be executed to determine if a temporary barrier in a part of a fluid handling set has been properly disrupted;

FIG. 254 depicts a flowchart detailing a number of example actions which may be executed to mix fluid within a source component via pumping action with the cycler;

FIG. 255 depicts an example mixing reservoir including a textured surface on the walls defining the interior volume of the mixing reservoir;

FIGS. 256A-256B depict an example of a form which may be used to apply a texture to sheets used to construct a mixing reservoir;

FIG. 257 depicts an example sheet of a mixing reservoir having texture formed from a geometric pattern;

FIG. 258 depicts a cross sectional view of a portion of an mixing reservoir in a collapsed state where the mixing reservoir includes a texture formed from a geometric pattern on the walls defining the interior volume of the mixing reservoir;

FIG. 259 depicts an example sheet of a mixing reservoir having texture formed from a geometric pattern;

FIG. 260 depicts an example sheet of a mixing reservoir having texture formed as a branching structure;

FIG. 261 depicts an example concentration sensor; and

Figure 262:
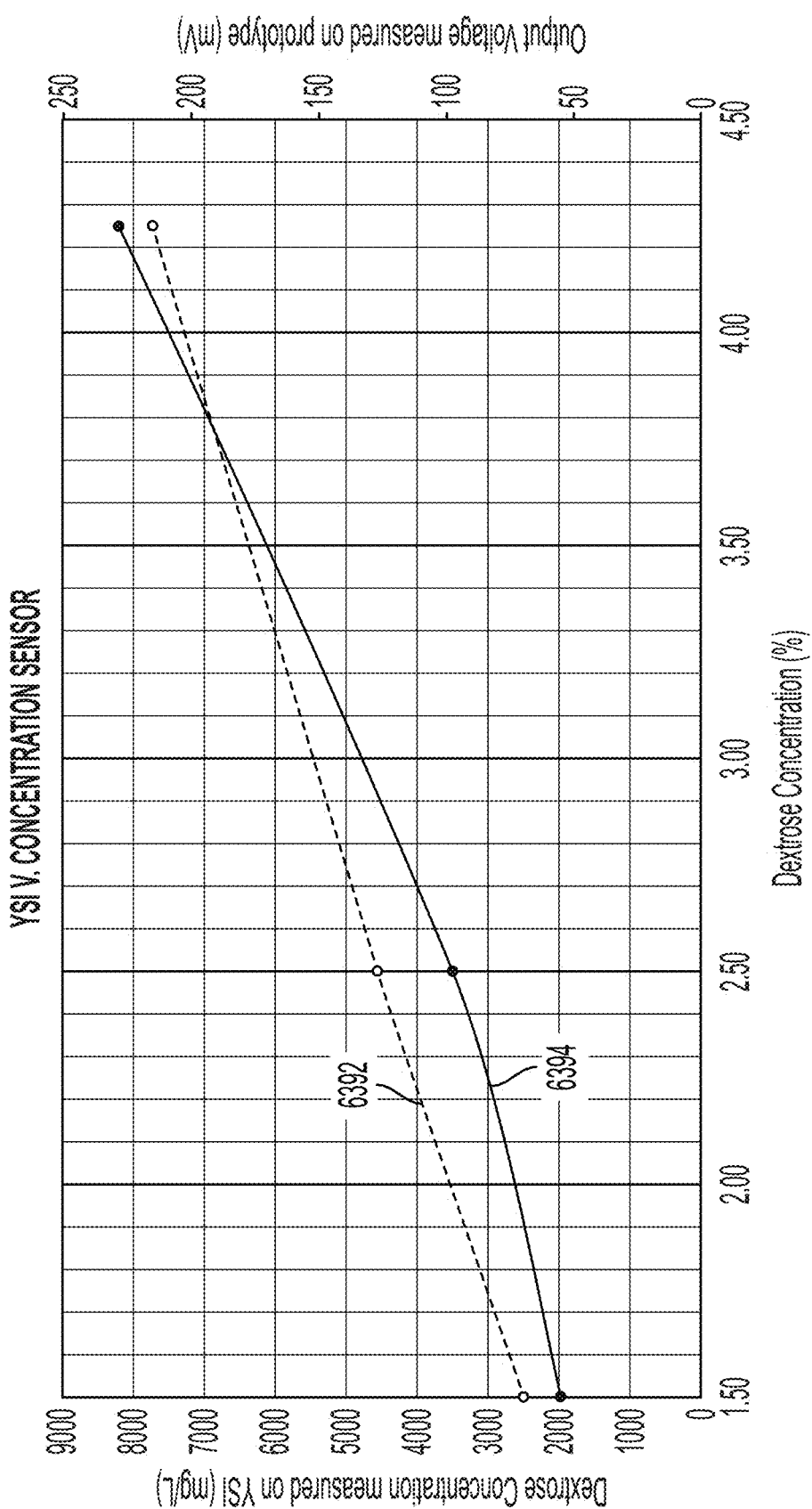

FIG. 262 depicts a graph of output voltage from a sensor similar to that shown in FIG. 261 compared to dextrose concentration of a solution in the sensor.

DETAILED DESCRIPTION

Although aspects of the disclosure are described in relation to a peritoneal dialysis system, certain aspects of the disclosure can be used in other medical applications, including infusion systems such as intravenous infusion systems or extracorporeal blood flow systems, and irrigation and/or fluid exchange systems for the stomach, intestinal tract, urinary bladder, pleural space or other body or organ cavity. Thus, aspects of the disclosure are not limited to use in peritoneal dialysis in particular, or dialysis in general.

APD System

Figure 1:
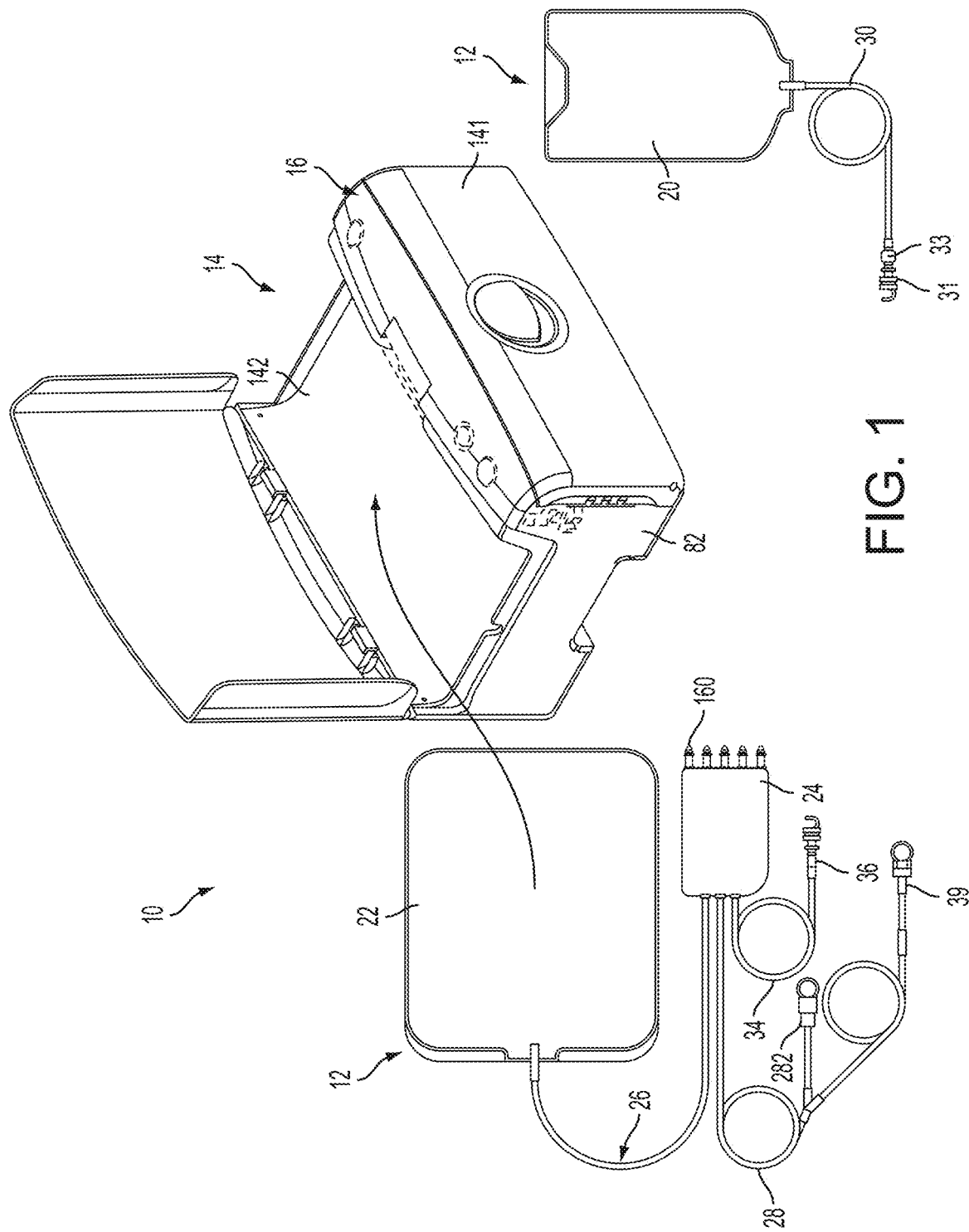
FIG. 1 shows a schematic view of an automated peritoneal dialysis (APD) system that incorporates one or more aspects of the disclosure.

FIG. 1 shows an automated peritoneal dialysis (APD) system 10 that may incorporate one or more aspects of the disclosure. As shown in FIG. 1, for example, the system 10 in this illustrative embodiment includes a dialysate delivery set 12 (which, in certain embodiments, can be a disposable set), a cycler 14 that interacts with the delivery set 12 to pump liquid provided by a solution container 20 (e.g., a bag), and a control system 16 (e.g., including a programmed computer or other data processor, computer memory, an interface to provide information to and receive input from a user or other device, one or more sensors, actuators, relays, pneumatic pumps, tanks, a power supply, and/or other suitable components-only a few buttons for receiving user control input are shown in FIG. 1, but further details regarding the control system components are provided below) that governs the process to perform an APD procedure. In this illustrative embodiment, the cycler 14 and the control system 16 are associated with a common housing 82, but may be associated with two or more housings and/or may be separate from each other. The cycler 14 may have a compact footprint, suited for operation upon a table top or other relatively small surface normally found in the home. The cycler 14 may be lightweight and portable, e.g., carried by hand via handles at opposite sides of the housing 82.

The set 12 in this embodiment is intended to be a single use, disposable item, but instead may have one or more reusable components, or may be reusable in its entirety. The user associates the set 12 with the cycler 14 before beginning each APD therapy session, e.g., by mounting a cassette 24 within a front door 141 of the cycler 14. The cycler 14 then interacts with the cassette 24 to pump and control fluid flow in the various lines of the set 12. For example, dialysate may be pumped both to and from the patient to affect APD. Post therapy, the user may remove all or part of the components of the set 12 from the cycler 14.

As is known in the art, prior to use, the user may connect a patient line 34 of the set 12 to his/her indwelling peritoneal catheter (not shown) at a connection 36. In one embodiment, the cycler 14 may be configured to operate with one or more different types of cassettes 24, such as those having differently sized patient lines 34. For example, the cycler 14 may be arranged to operate with a first type of cassette 24 with a patient line 34 sized for use with an adult patient, and a second type of cassette 24 with a patient line 34 sized for an infant or pediatric use. The pediatric patient line 34 may be shorter and have a smaller inner diameter than the adult line so as to minimize the volume of the line, allowing for more controlled delivery of dialysate and helping to avoid returning a relatively large volume of used dialysate to the pediatric patient when the set 12 is used for consecutive drain and fill cycles. A heater bag 22, which is connected to the cassette 24 by a line 26, may be placed on a heater container receiving portion (in this case, a tray) 142 of the cycler 14. The cycler 14 may pump fresh dialysate (via the cassette 24) into the heater bag 22 so that the dialysate may be heated by the heater tray 142, e.g., by electric resistance heating elements associated with the tray 142 to a temperature of about 37 degrees C. Heated dialysate may be provided from the heater bag 22 to the patient via the cassette 24 and the patient line 34. In an alternative embodiment, the dialysate can be heated on its way to the patient as it enters, or after it exits, the cassette 24 by passing the dialysate through tubing in contact with the heater tray 142, or through an in-line fluid heater (which may be provided in the cassette 24). Used dialysate may be pumped from the patient via the patient line 34 to the cassette 24 and into a drain line 28, which may include one or more clamps to control flow through one or more branches of the drain line 28. In this illustrative embodiment, the drain line 28 may include a connector 39 for connecting the drain line 28 to a dedicated drain receptacle, and an effluent sample port 282 for taking a sample of used dialysate for testing or other analysis. The user may also mount the lines 30 of one or more containers 20 within the door 141. The lines 30 may also be connected to a continuous or real-time dialysate preparation system. The lines 26, 28, 30, 34 may include a flexible tubing and/or suitable connectors and other components (such as pinch valves, etc.) as desired. The containers 20 may contain sterile peritoneal dialysis solution for infusion or other materials, e.g., materials used by the cycler 14 to formulate dialysate by mixing with water, or admixing different types of dialysate solutions. The lines 30 may be connected to spikes 160 of the cassette 24, which are shown in FIG. 1 covered by removable caps. In one aspect of the disclosure described in more detail below, the cycler 14 may automatically remove caps from one or more spikes 160 of the cassette 24 and connect lines 30 of solution containers 20 to respective spikes 160. This feature may help reduce the possibility of infection or contamination by reducing the chance of contact of non-sterile items with the spikes 160.

Figure 1A:
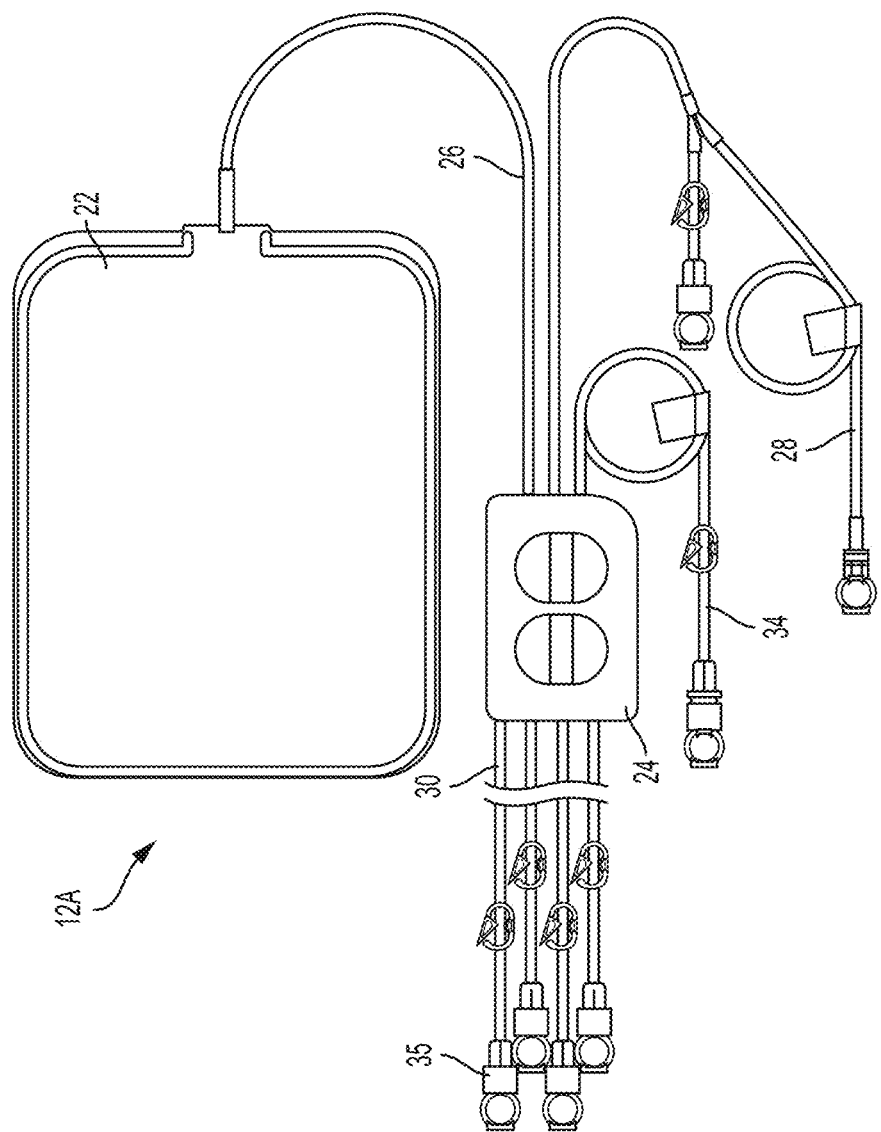
FIG. 1A shows an alternative arrangement for a dialysate delivery set shown in FIG. 1.

In another aspect, a dialysate delivery set 12a may not have cassette spikes 160. Instead, one or more solution lines 30 may be permanently affixed to the inlet ports of cassette 24, as shown in FIG. 1A. In this case, each solution line 30 may have a (capped) spike connector 35 for manual connection to a solution container or dialysate bag 20.

With various connections made, the control system 16 may pace the cycler 14 through a series of fill, dwell, and/or drain cycles typical of an APD procedure. For example, during a fill phase, the cycler 14 may pump dialysate (by way of the cassette 24) from one or more containers 20 (or other source of dialysate supply) into the heater bag 22 for heating. Thereafter, the cycler 14 may infuse heated dialysate from the heater bag 22 through the cassette 24 and into the patient's peritoneal cavity via the patient line 34. Following a dwell phase, the cycler 14 may institute a drain phase, during which the cycler 14 pumps used dialysate from the patient via the line 34 (again by way of the cassette 24), and discharges spent dialysis solution into a nearby drain (not shown) via the drain line 28.

The cycler 14 does not necessarily require the solution containers 20 and/or the heater bag 22 to be positioned at a prescribed head height above the cycler 14, e.g., because the cycler 14 is not necessarily a gravity flow system. Instead, the cycler 14 may emulate gravity flow, or otherwise suitably control flow of dialysate solution, even with the source solution containers 20 above, below or at a same height as the cycler 14, with the patient above or below the cycler 14, etc. For example, the cycler 14 can emulate a fixed head height during a given procedure, or the cycler 14 can change the effective head height to either increase or decrease pressure applied to the dialysate during a procedure. The cycler 14 may also adjust the rate of flow of dialysate. In one aspect of the disclosure, the cycler 14 may adjust the pressure and/or flow rate of dialysate when provided to the patient or drawn from the patient so as to reduce the patient's sensation of the fill or drain operation. Such adjustment may occur during a single fill and/or drain cycle, or may be adjusted across different fill and/or drain cycles. In one embodiment, the cycler 14 may taper the pressure used to draw used dialysate from the patient near the end of a drain operation. Because the cycler 14 may establish an artificial head height, it may have the flexibility to interact with and adapt to the particular physiology or changes in the relative elevation of the patient.

Cassette

In one aspect of the disclosure, a cassette 24 may include patient and drain lines that are separately occludable with respect to solution supply lines. That is, safety critical flow to and from patient line may be controlled, e.g., by pinching the lines to stop flow, without the need to occlude flow through one or more solution supply lines. This feature may allow for a simplified occluder device since occlusion may be performed with respect to only two lines as opposed to occluding other lines that have little or no effect on patient safety. For example, in a circumstance where a patient or drain connection becomes disconnected, the patient and drain lines may be occluded. However, the solution supply and/or heater bag lines may remain open for flow, allowing the cycler 14 to prepare for a next dialysis cycle; e.g., separate occlusion of patient and drain lines may help ensure patient safety while permitting the cycler 14 to continue to pump dialysate from one or more containers 20 to the heater bag 22 or to other solution containers 20.

In another aspect of the disclosure, the cassette 24 may have patient, drain and heater bag lines at one side or portion of the cassette and one or more solution supply lines at another side or portion of the cassette 24, e.g., an opposite side of the cassette 24. Such an arrangement may allow for separate occlusion of patient, drain or heater bag lines with respect to solution lines as discussed above. Physically separating the lines attached to the cassette 24 by type or function allows for more efficient control of interaction with lines of a certain type or function. For example, such an arrangement may allow for a simplified occluder design because less force is required to occlude one, two or three of these lines than all lines leading to or away from the cassette 24. Alternately, this arrangement may allow for more effective automated connection of solution supply lines to the cassette 24, as discussed in more detail below. That is, with solution supply lines and their respective connections located apart from patient, drain and/or heater bag lines, an automated de-capping and connection device may remove caps from spikes 160 on the cassette 24 as well as caps on solution supply lines, and connect the lines to respective spikes 160 without interference by the patient, drain or heater bag lines.

Figure 2:
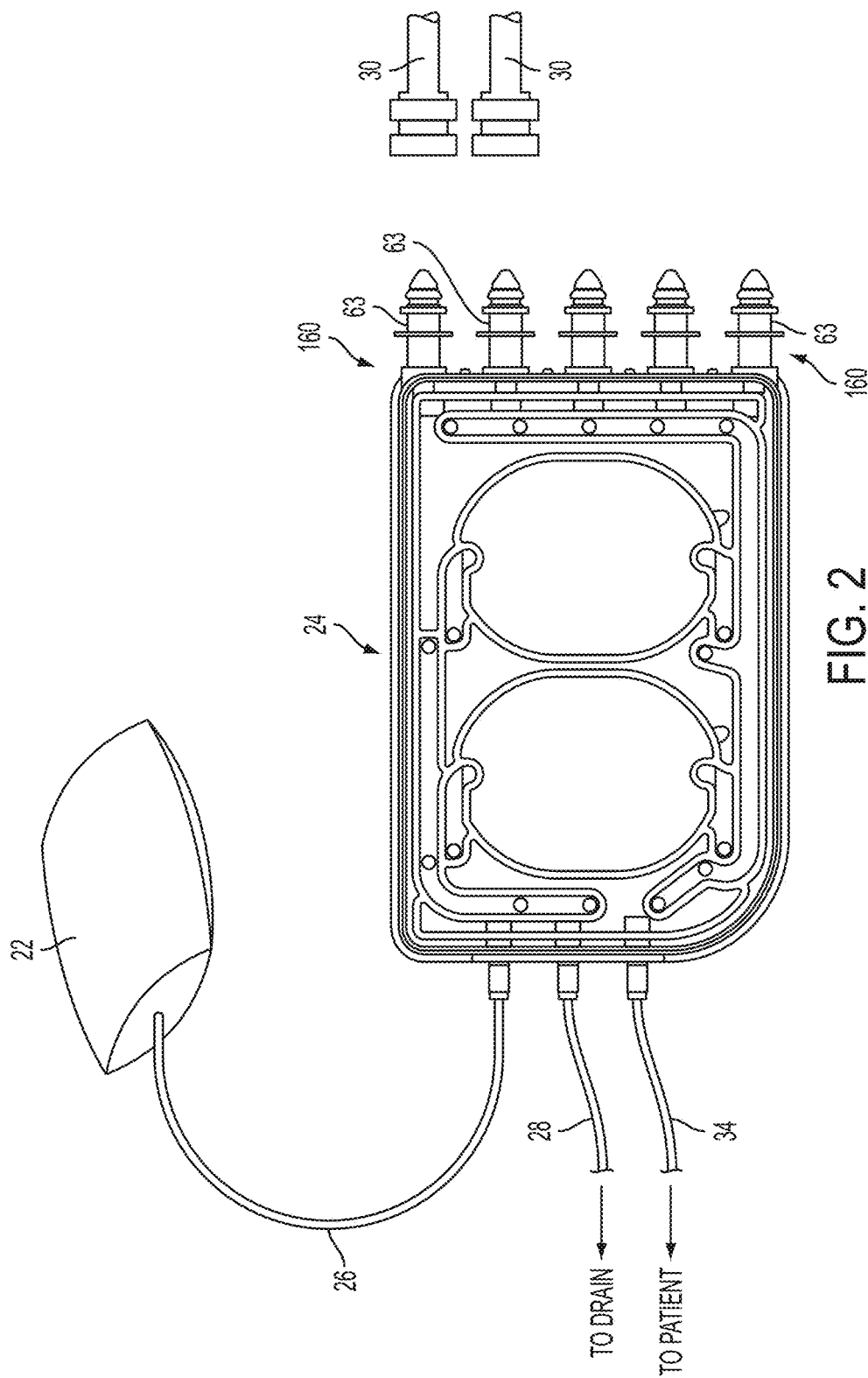
FIG. 2 is a schematic view of an illustrative set for use with the APD system of FIG. 1.

FIG. 2 shows an illustrative embodiment of a cassette 24 that incorporates aspects of the disclosure described above. In this embodiment, the cassette 24 has a generally planar body and the heater bag line 26, the drain line 28 and the patient line 34 are connected at respective ports on the left end of the cassette body, while the right end of the cassette body may include five spikes 160 to which solution supply lines 30 may be connected. In the arrangement shown in FIG. 2, each of the spikes 160 is covered by a spike cap 63, which may be removed, exposing the respective spike 160 and allowing connection to a respective line 30. As described above, the lines 30 may be attached to one or more solution containers or other sources of material, e.g., for use in dialysis and/or the formulation of dialysate, or connected to one or more collection bags for sampling purposes or for peritoneal equilibration testing (PET test).

Figure 3:
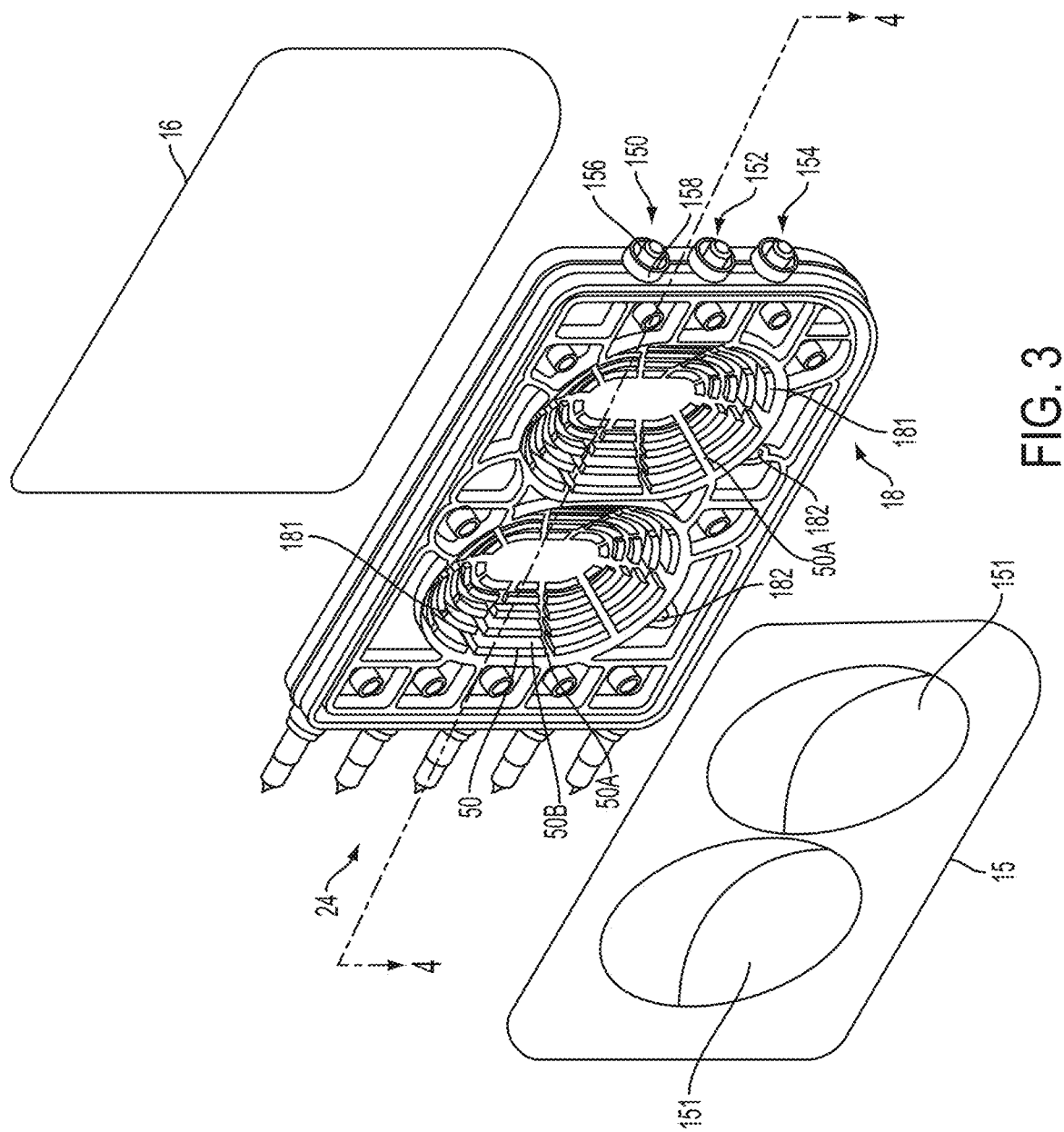
FIG. 3 is an exploded perspective view of a cassette in a first embodiment.
Figure 4:
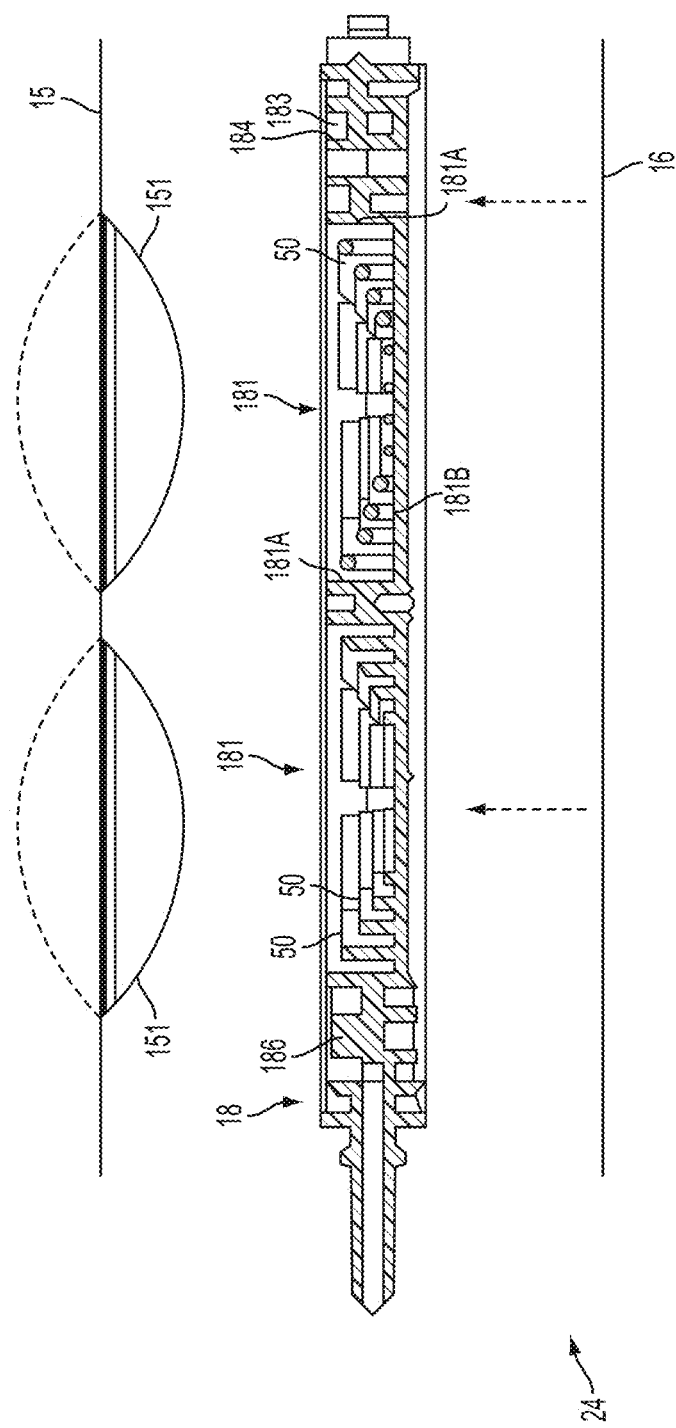
FIG. 4 is a cross sectional view of the cassette along the line 4-4 in FIG. 3.

FIGS. 3 and 4 show exploded views (perspective and top views, respectively) of the cassette 24 in this illustrative embodiment. The cassette 24 is formed as a relatively thin and flat member having a generally planar shape, e.g., may include components that are molded, extruded or otherwise formed from a suitable plastic. In this embodiment, the cassette 24 includes a base member 18 that functions as a frame or structural member for the cassette 24 as well as forming, at least in part, various flow channels, ports, valve portions, etc. The base member 18 may be molded or otherwise formed from a suitable plastic or other material, such as a polymethyl methacrylate (PMMA) acrylic, or a cyclic olefin copolymer/ultra low density polyethylene (COC/ULDPE), and may be relatively rigid. In an embodiment, the ratio of COC to ULDPE can be approximately 85%/15%. FIG. 3 also shows the ports for the heater bag (port 150), drain (port 152) and the patient (port 154) that are formed in the base member 18. Each of these ports 150, 152, 154 may be arranged in any suitable way, such as, for example, a central tube 156 extending from an outer ring or skirt 158, or a central tube alone. Flexible tubing for each of the heater bag, drain and patient lines 26, 28, 34 may be connected to the central tube 156 and engaged by the outer ring 158, if present.

Both sides of the base member 18 may be covered, at least in part, by a membrane 15 and 16, e.g., a flexible polymer film made from, for example, polyvinyl chloride (PVC), that is cast, extruded or otherwise formed. Alternatively, the sheet may be formed as a laminate of two or more layers of poly-cyclohexylene dimethylene cyclohexanedicarboxylate (PCCE) and/or ULDPE, held together, for example, by a coextrudable adhesive (CXA). In some embodiments, the membrane thickness may be in the range of approximately 0.002 to 0.020 inches thick. In a preferred embodiment, the thickness of a PVC-based membrane may be in the range of approximately 0.012 to 0.016 inches thick, and more preferably approximately 0.014 inches thick. In another preferred embodiment, such as, for example, for laminate sheets, the thickness of the laminate may be in the range of approximately 0.006 to 0.010 inches thick, and more preferably approximately 0.008 inches thick.

Both membranes 15 and 16 may function not only to close or otherwise form a part of flowpaths of the cassette 24, but also may be moved or otherwise manipulated to open/close valve ports and/or to function as part of a pump diaphragm, septum or wall that moves fluid in the cassette 24. For example, the membranes 15 and 16 may be positioned on the base member 18 and sealed (e.g., by heat, adhesive, ultrasonic welding or other means) to a rim around the periphery of the base member 18 to prevent fluid from leaking from the cassette 24. The membrane 15 may also be bonded to other, inner walls of the base member 18, e.g., those that form various channels, or may be pressed into sealing contact with the walls and other features of the base member 18 when the cassette 24 is suitably mounted in the cycler 14. Thus, both of the membranes 15 and 16 may be sealed to a peripheral rim of the base member 18, e.g., to help prevent leaking of fluid from the cassette 24 upon its removal from the cycler 14 after use, yet be arranged to lie, unattached, over other portions of the base member 18. Once placed in the cycler 14, the cassette 24 may be squeezed between opposed gaskets or other members so that the membranes 15 and 16 are pressed into sealing contact with the base member 18 at regions inside of the periphery, thereby suitably sealing channels, valve ports, etc., from each other.

Other arrangements for the membranes 15 and 16 are possible. For example, the membrane 16 may be formed by a rigid sheet of material that is bonded or otherwise made integral with the body 18. Thus, the membrane 16 need not necessarily be, or include, a flexible member. Similarly, the membrane 15 need not be flexible over its entire surface, but instead may include one or more flexible portions to permit pump and/or valve operation, and one or more rigid portions, e.g., to close flowpaths of the cassette 24. It is also possible that the cassette 24 may not include the membrane 16 or the membrane 15, e.g., where the cycler 14 includes a suitable member to seal pathways of the cassette 24, control valve and pump function, etc.

Figure 5:
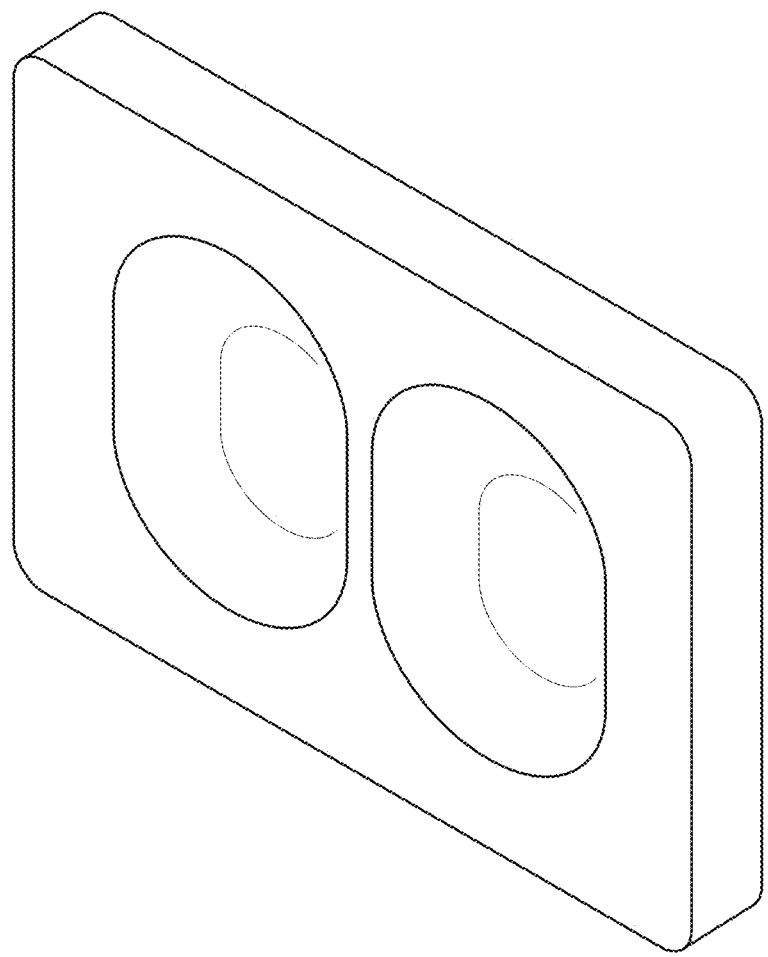
FIG. 5 is a perspective view of a vacuum mold that may be used to form a membrane having pre-formed pump chamber portions in an illustrative embodiment.

In accordance with another aspect of the disclosure, the membrane 15 may include a pump chamber portion 151 ("pump membrane") that is formed to have a shape that closely conforms to the shape of a corresponding pump chamber 181 depression in the base 18. For example, the membrane 15 may be generally formed as a flat member with thermoformed (or otherwise formed) dome-like shapes 151 that conform to the pump chamber depressions of the base member 18. The dome-like shape of the pre-formed pump chamber portions 151 may be constructed, for example, by heating and forming the membrane over a vacuum form mold of the type shown in FIG. 5. As shown in FIG. 5, the vacuum may be applied through a collection of holes along the wall of the mold. Alternatively, the wall of the mold can be constructed of a porous gas-permeable material, which may result in a more uniformly smooth surface of the molded membrane. In one example, the molded membrane sheet 15 is trimmed while attached to the vacuum form mold. The vacuum form mold then presses the trimmed membrane sheet 15 against the cassette body 18 and bonds them together. In one embodiment the membrane sheets 15, 16 are heat-welded to the cassette body 18. In this way, the membrane 15 may move relative to the pump chambers 181 to effect pumping action without requiring stretching of the membrane 15 (or at least minimal stretching of the membrane 15), both when the membrane 15 is moved maximally into the pump chambers 181 and (potentially) into contact with spacer elements 50 (e.g., as shown in solid line in FIG. 4 while pumping fluid out of the pump chamber 181), and when the membrane 15 is maximally withdrawn from the pump chamber 181 (e.g., as shown in dashed line in FIG. 4 when drawing fluid into the pump chamber 181). Avoiding stretching of the membrane 15 may help prevent pressure surges or other changes in fluid delivery pressure due to sheet stretch and/or help simplify control of the pump when seeking to minimize pressure variation during pump operation. Other benefits may be found, including reduced likelihood of membrane 15 failure (e.g., due to tears in the membrane 15 resulting from stresses place on the membrane 15 during stretching), and/or improved accuracy in pump delivery volume measurement, as described in more detail below. In one embodiment, the pump chamber portions 151 may be formed to have a size (e.g., a define a volume) that is about 85-110% of the pump chamber 181, e.g., if the pump chamber portions 151 define a volume that is about 100% of the pump chamber volume, the pump chamber portion 151 may lie in the pump chamber 181 and in contact with the spacers 50 while at rest and without being stressed.

Providing greater control of the pressure used to generate a fill and delivery stroke of liquid into and out of a pump chamber may have several advantages. For example, it may be desirable to apply the minimum negative pressure possible when the pump chamber draws fluid from the patient's peritoneal cavity during a drain cycle. A patient may experience discomfort during the drain cycle of a treatment in part because of the negative pressure being applied by the pumps during a fill stroke. The added control that a pre-formed membrane can provide to the negative pressure being applied during a fill stroke may help to reduce the patient's discomfort.

A number of other benefits may be realized by using pump membranes pre-formed to the contour of the cassette pump chamber. For example, the flow rate of liquid through the pump chamber can be made more uniform, because a constant pressure or vacuum can be applied throughout the pump stroke, which in turn may simplify the process of regulating the heating of the liquid. Moreover, temperature changes in the cassette pump may have a smaller effect on the dynamics of displacing the membrane, as well as the accuracy of measuring pressures within the pump chambers. In addition, pressure spikes within the fluid lines can be minimized. Also, correlating the pressures measured by pressure transducers on the control (e.g. pneumatic) side of the membrane with the actual pressure of the liquid on the pump chamber side of the membrane may be used. This in turn may permit more accurate head height measurements of the patient and fluid source bags prior to therapy, improve the sensitivity of detecting air in the pump chamber, and improve the accuracy of volumetric measurements. Furthermore, eliminating the need to stretch the membrane may allow for the construction and use of pump chambers having greater volumes.

In this embodiment, the cassette 24 includes a pair of pump chambers 181 that are formed in the base member 18, although one pump chamber or more than two pump chambers are possible. In accordance with an aspect of the disclosure, the inner wall of pump chambers 181 includes spacer elements 50 that are spaced from each other and extend from the inner wall of pump chamber 18 to help prevent portions of the membrane 15 from contacting the inner wall of pump chamber 181. As shown on the right-side pump chamber 181 in FIG. 4, the inner wall is defined by side portions 181a and a bottom portion 181b. The spacers 50 extend upwardly from the bottom portion 181b in this embodiment, but could extend from the side portions 181a or be formed in other ways. By preventing contact of the membrane 15 with the pump chamber inner wall, the spacer elements 50 may provide a dead space (or trap volume) which may help trap air or other gas in the pump chamber 181 and inhibit the gas from being pumped out of the pump chamber 181 in some circumstances. In other cases, the spacers 50 may help the gas move to an outlet of the pump chamber 181 so that the gas may be removed from the pump chamber 181, e.g., during priming. Also, the spacers 50 may help prevent the membrane 15 from sticking to the pump chamber inner wall and/or allow flow to continue through the pump chamber 181, even if the membrane 15 is pressed into contact with the spacer elements 50. In addition, the spacers 50 help to prevent premature closure of the outlet port of the pump chamber (openings 187 and/or 191) if the sheet happens to contact the pump chamber inner wall in a non-uniform manner. Further details regarding the arrangement and/or function of spacers 50 are provided in U.S. Pat. No. 6,302,653 to Bryant et al., issued Oct. 16, 2001, entitled "Methods and Systems for Detecting the Presence of a Gas in a Pump and Preventing a Gas from Being Pumped from a Pump," and U.S. Pat. No. 6,382,923 to Gray, issued May 7, 2002, entitled "Pump Chamber Having at Least one Spacer for Inhibiting the Pumping of a Gas,", both of which are incorporated herein by reference in their entireties.

In this embodiment, the spacer elements 50 are arranged in a kind of "stadium seating" arrangement such that the spacer elements 50 are arranged in a concentric elliptical pattern with ends of the spacer elements 50 increasing in height from the bottom portion 181b of the inner wall with distance away from the center of the pump chamber 181 to form a semi-elliptical domed shaped region (shown by dotted line in FIG. 4). Positioning spacer elements 50 such that the ends of the spacer elements 50 form a semi-elliptical region that defines the domed region intended to be swept by the pump chamber portion 151 of the membrane 15 may allow for a desired volume of dead space that minimizes any reduction to the intended stroke capacity of pump chambers 181. As can be seen in FIG. 3 (and FIG. 6), the "stadium seating" arrangement in which spacer elements 50 are arranged may include "aisles" or breaks 50a in the elliptical pattern. Breaks (or aisles) 50a help to maintain an equal gas level throughout the rows (voids or dead space) 50b between spacer elements 50 as fluid is delivered from the pump chamber 181. For example, if the spacer elements 50 were arranged in the stadium seating arrangement shown in FIG. 6 without breaks (or aisles) 50a or other means of allowing liquid and air to flow between spacer elements 50, the membrane 15 might bottom out on the spacer element 50 located at the outermost periphery of the pump chamber 181, trapping whatever gas or liquid is present in the void between this outermost spacer element 50 and the side portions 181a of the pump chamber wall. Similarly, if the membrane 15 bottomed out on any two adjacent spacer elements 50, any gas and liquid in the void between the elements 50 may become trapped. In such an arrangement, at the end of the pump stroke, air or other gas at the center of pump chamber 181 could be delivered while liquid remains in the outer rows. Supplying breaks (or aisles) 50a or other means of fluidic communication between the voids between spacer elements 50 helps to maintain an equal gas level throughout the voids during the pump stroke, such that air or other gas may be inhibited from leaving the pump chamber 181 unless the liquid volume has been substantially delivered.

In certain embodiments, spacer elements 50 and/or the membrane 15 may be arranged so that the membrane 15 generally does not wrap or otherwise deform around individual spacers 50 when pressed into contact with them, or otherwise extend significantly into the voids between spacers 50. Such an arrangement may lessen any stretching or damage to membrane 15 caused by wrapping or otherwise deforming around one or more individual spacer elements 50. For example, it has also been found to be advantageous in this embodiment to make the size of the voids between spacers 50 approximately equal in width to the width of the spacers 50. This feature has shown to help prevent deformation of the membrane 15, e.g., sagging of the membrane into the voids between spacers 50, when the membrane 15 is forced into contact with the spacers 50 during a pumping operation.

In accordance with another aspect of the disclosure, the inner wall of pump chambers 181 may define a depression that is larger than the space, for example a semi-elliptical or domed space, intended to be swept by the pump chamber portion 151 of the membrane 15. In such instances, one or more spacer elements 50 may be positioned below the domed region intended to be swept by the membrane portion 151 rather than extending into that domed region. In certain instances, the ends of spacer elements 50 may define the periphery of the domed region intended to be swept by the membrane 15. Positioning spacer elements 50 outside of, or adjacent to, the periphery of the domed region intended to be swept by the membrane portion 151 may have a number of advantages. For example, positioning one or more spacer elements 50 such that the spacer elements 50 are outside of, or adjacent to, the domed region intended to be swept by the flexible membrane provides a dead space between the spacers and the membrane 15, such as described above, while minimizing any reduction to the intended stroke capacity of pump chambers 181.

Figure 6:
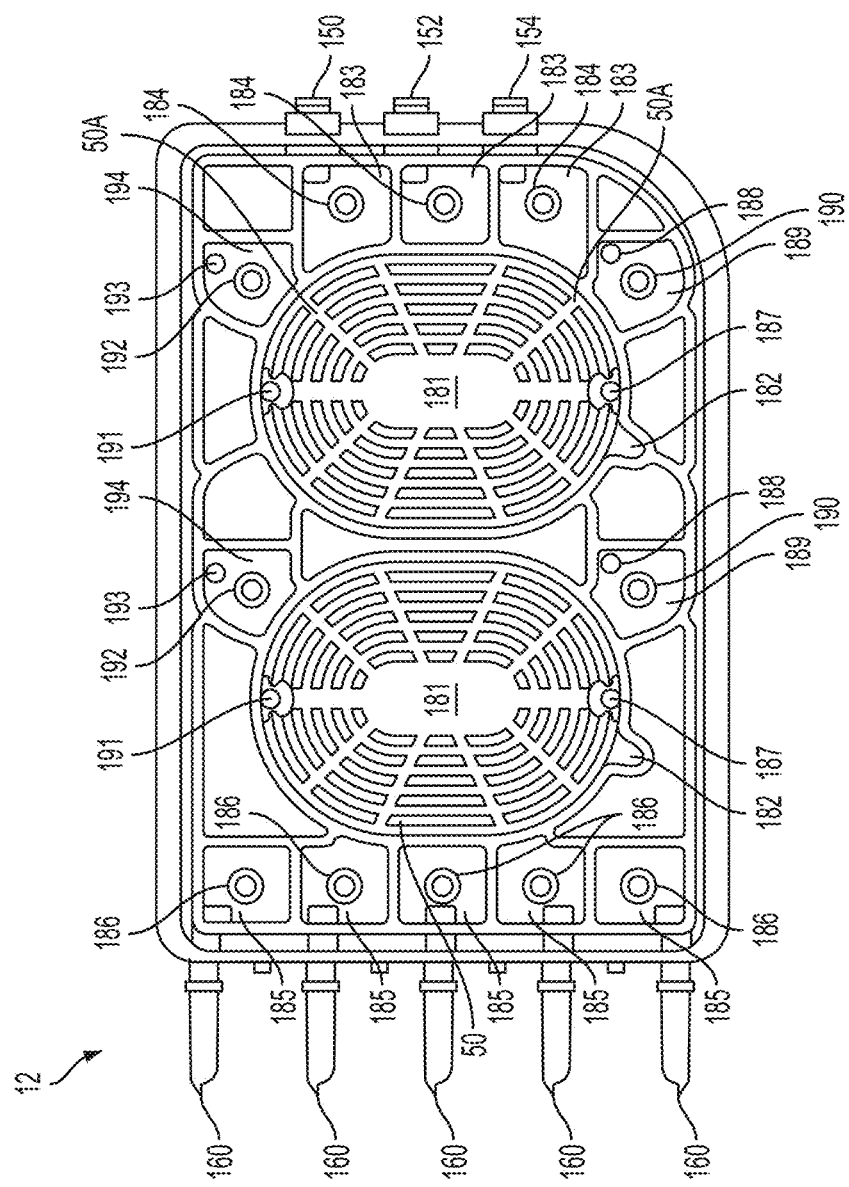
FIG. 6 shows a front view of the cassette body of FIG. 3.
Figure 7:
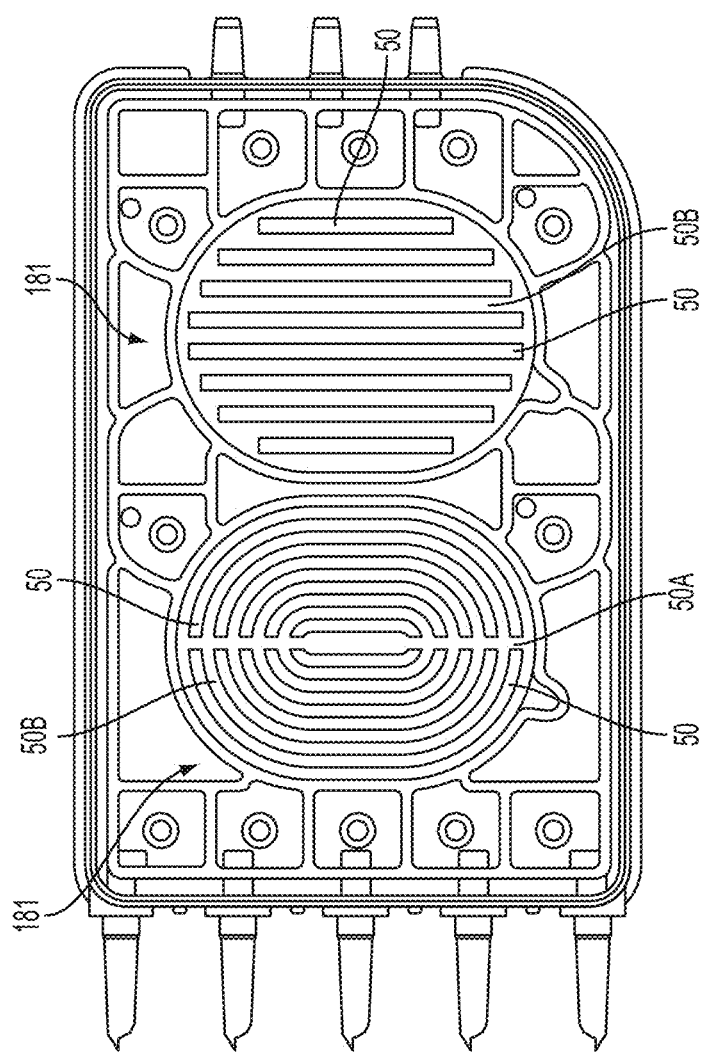
FIG. 7 is a front view of a cassette body including two different spacer arrangements in an illustrative embodiment.

It should be understood that the spacer elements 50, if present, in a pump chamber 181 may be arranged in any other suitable way, such as for example, shown in FIG. 7. The left side pump chamber 181 in FIG. 7 includes spacers 50 arranged similarly to that in FIG. 6, but there is only one break or aisle 50a that runs vertically through the approximate center of the pump chamber 181. The spacers 50 may be arranged to define a concave shape similar to that in FIG. 6 (i.e., the tops of the spacers 50 may form the semi-elliptical shape shown in FIGS. 3 and 4), or may be arranged in other suitable ways, such as to form a spherical shape, a box-like shape, and so on. The right-side pump chamber 181 in FIG. 7 shows an embodiment in which the spacers 50 are arranged vertically with voids 50b between spacers 50 also arranged vertically. As with the left-side pump chamber, the spacers 50 in the right-side pump chamber 181 may define a semi-elliptical, spherical, box-like or any other suitably shaped depression. It should be understood, however, that the spacer elements 50 may have a fixed height, a different spatial pattern than those shown, and so on.

Also, the membrane 15 may itself have spacer elements or other features, such as ribs, bumps, tabs, grooves, channels, etc., in addition to, or in place of the spacer elements 50. Such features on the membrane 15 may help prevent sticking of the membrane 15, etc., and/or provide other features, such as helping to control how the sheet folds or otherwise deforms when moving during pumping action. For example, bumps or other features on the membrane 15 may help the sheet to deform consistently and avoid folding at the same area(s) during repeated cycles. Folding of a same area of the membrane 15 at repeated cycles may cause the membrane 15 to prematurely fail at the fold area, and thus features on the membrane 15 may help control the way in which folds occur and where.

Figure 8:
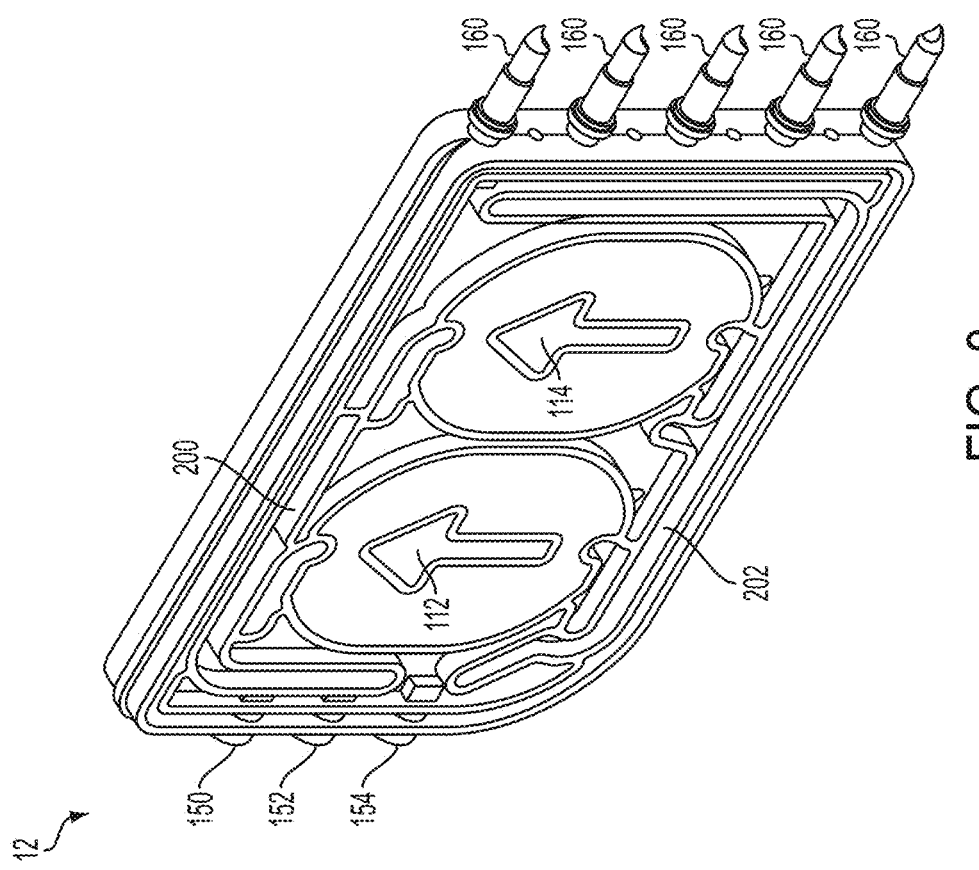
FIG. 8 is a rear perspective view of the cassette body of FIG. 3.
Figure 9:
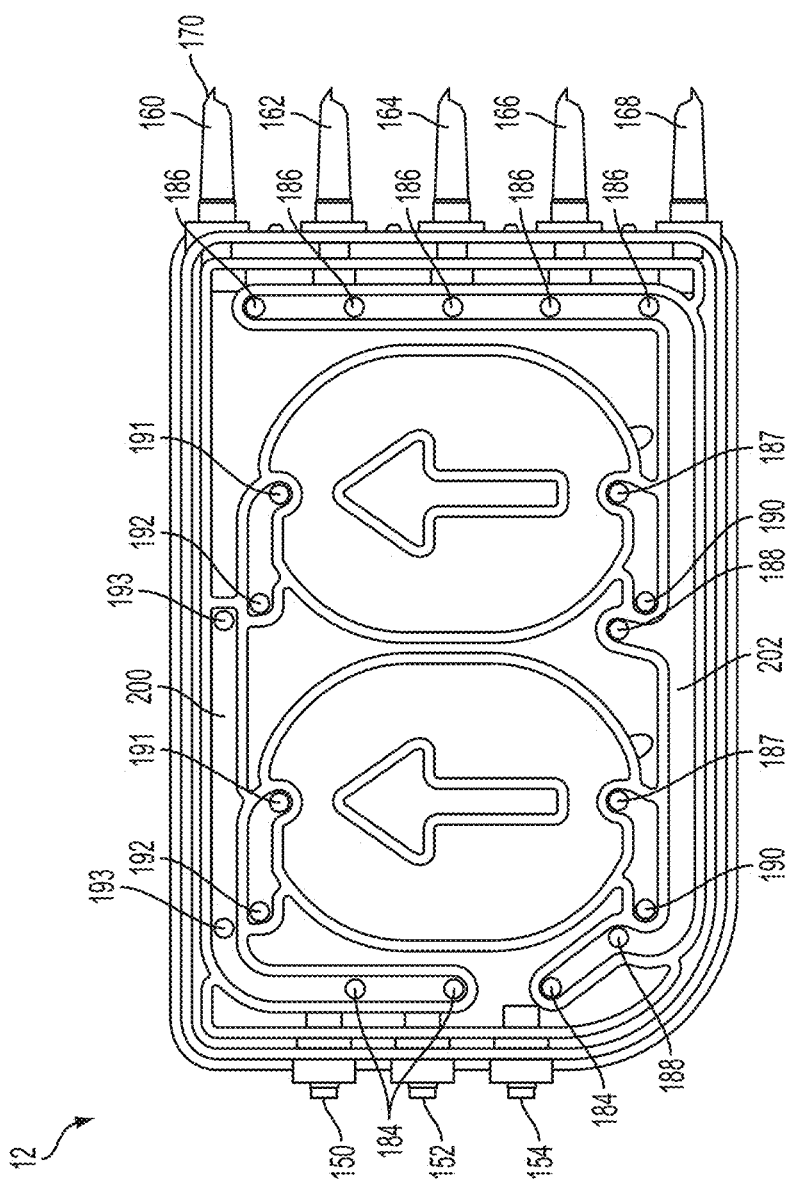
FIG. 9 is a rear view of the cassette body of FIG. 3.

In this illustrative embodiment, the base member 18 of the cassette 24 defines a plurality of controllable valve features, fluid pathways and other structures to guide the movement of fluid in the cassette 24. FIG. 6 shows a plan view of the pump chamber side of the base member 18, which is also seen in perspective view in FIG. 3. FIG. 8 shows a perspective view of a back side of the base member 18, and FIG. 9 shows a plan view of the back side of the base member 18. The tube 156 for each of the ports 150, 152 and 154 fluidly communicates with a respective valve well 183 that is formed in the base member 18. The valve wells 183 are fluidly isolated from each other by walls surrounding each valve well 183 and by sealing engagement of the membrane 15 with the walls around the wells 183. As mentioned above, the membrane 15 may sealingly engage the walls around each valve well 183 (and other walls of the base member 18) by being pressed into contact with the walls, e.g., when loaded into the cycler 14. Fluid in the valve wells 183 may flow into a respective valve port 184, if the membrane 15 is not pressed into sealing engagement with the valve port 184. Thus, each valve port 184 defines a valve (e.g., a "volcano valve") that can be opened and closed by selectively moving a portion of the membrane 15 associated with the valve port 184. As will be described in more detail below, the cycler 14 may selectively control the position of portions of the membrane 15 so that valve ports (such as ports 184) may be opened or closed so as to control flow through the various fluid channels and other pathways in the cassette 24. Flow through the valve ports 184 leads to the back side of the base member 18. For the valve ports 184 associated with the heater bag and the drain (ports 150 and 152), the valve ports 184 lead to a common channel 200 formed at the back side of the base member 18. As with the valve wells 183, the channel 200 is isolated from other channels and pathways of the cassette 24 by the sheet 16 making sealing contact with the walls of the base member 18 that form the channel 200. For the valve port 184 associated with the patient line port 154, flow through the port 184 leads to a common channel 202 on the back side of the base member 18. Common channel 200 may also be referred to herein as an upper fluidic bus and common channel 202 may also be referred to herein as a lower fluidic bus.

Returning to FIG. 6, each of the spikes 160 (shown uncapped in FIG. 6) fluidly communicates with a respective valve well 185. The valve wells 185 are isolated from each other by walls and sealing engagement of the membrane 15 with the walls that form the wells 185. Fluid in the valve wells 185 may flow into a respective valve port 186, if the membrane 15 is not in sealing engagement with the port 186. Again, the position of portions of the membrane 15 over each valve port 186 can be controlled by the cycler 14 to open and close the valve ports 186. Flow through the valve ports 186 leads to the back side of the base member 18 and into the common channel 202.

Thus, in accordance with one aspect of the disclosure, a cassette 24 may have a plurality of solution supply lines (or other lines that provide materials for providing dialysate) that are connected to a common manifold or channel of the cassette 24, and each line may have a corresponding valve to control flow from/to the line with respect to the common manifold or channel. Fluid in the channel 202 may flow into lower openings 187 of the pump chambers 181 by way of openings 188 that lead to lower pump valve wells 189 (see FIG. 6). Flow from the lower pump valve wells 189 may pass through a respective lower pump valve port 190 if a respective portion of the membrane 15 is not pressed in sealing engagement with the port 190. As can be seen in FIG. 9, the lower pump valve ports 190 lead to a channel that communicates with the lower openings 187 of the pump chambers 181. Flow out of the pump chambers 181 may pass through the upper openings 191 and into a channel that communicates with an upper valve port 192. Flow from the upper valve port 192 (if the membrane 15 is not in sealing engagement with the port 192) may pass into a respective upper valve well 194 and into an opening 193 that communicates with the common channel 200 on the back side of the base member 18.

As will be appreciated, the cassette 24 may be controlled so that the pump chambers 181 can pump fluid from and/or into any of the ports 150, 152 and 154 and/or any of the spikes 160. For example, fresh dialysate provided by one of the containers 20 that is connected by a line 30 to one of the spikes 160 may be drawn into the common channel 202 by opening the appropriate valve port 186 for the proper spike 160 and possibly closing other valve ports 186 for other spikes 160. Also, the lower pump valve ports 190 may be opened and the upper pump valve ports 192 may be closed. Thereafter, the portions of the membrane 15 associated with the pump chambers 181 (i.e., pump membranes 151) may be moved (e.g., away from the base member 18 and the pump chamber inner wall) so as to lower the pressure in the pump chambers 181, thereby drawing fluid in through the selected spike 160 through the corresponding valve port 186, into the common channel 202, through the openings 188 and into the lower pump valve wells 189, through the (open) lower pump valve ports 190 and into the pump chambers 181 through the lower openings 187. The valve ports 186 are independently operable, allowing for the option to draw fluid through any one or a combination of spikes 160 and associated source containers 20, in any desired sequence, or simultaneously. Of course, only one pump chamber 181 need be operable to draw fluid into itself. The other pump chamber may be left inoperable and closed off to flow by closing the appropriate lower pump valve port 190.

With fluid in the pump chambers 181, the lower pump valve ports 190 may be closed, and the upper pump valve ports 192 opened. When the membrane 15 is moved toward the base member 18, the pressure in the pump chambers 181 may rise, causing fluid in the pump chambers 181 to pass through the upper openings 191, through the (open) upper pump valve ports 192 and into the upper pump valve wells 194, through the openings 193 and into the common channel 200. Fluid in the channel 200 may be routed to the heater bag port 150 and/or the drain port 152 and into the corresponding heater bag line or drain line by opening the appropriate valve port 184. In this way, for example, fluid in one or more of the containers 20 may be drawn into the cassette 24, and pumped out to the heater bag 22 and/or the drain.

Fluid in the heater bag 22 (e.g., after having been suitably heated on the heater tray for introduction into the patient) may be drawn into the cassette 24 by opening the valve port 184 for the heater bag port 150, closing the lower pump valve ports 190, and opening the upper pump valve ports 192. By moving the portions of the membrane 15 associated with the pump chambers 181 away from the base member 18, the pressure in the pump chambers 181 may be lowered, causing fluid flow from the heater bag 22 and into the pump chambers 181. With the pump chambers 181 filled with heated fluid from the heater bag 22, the upper pump valve ports 192 may be closed and the lower pump valve ports 190 opened. To route the heated dialysate to the patient, the valve port 184 for the patient port 154 may be opened and valve ports 186 for the spikes 160 closed. Movement of the membrane 15 in the pump chambers 181 toward the base member 18 may raise the pressure in the pump chambers 181 causing fluid to flow through the lower pump valve ports 190, through the openings 188 and into the common channel 202 to, and through, the (open) valve port 184 for the patient port 154. This operation may be repeated a suitable number of times to transfer a desired volume of heated dialysate to the patient.

When draining the patient, the valve port 184 for the patient port 154 may be opened, the upper pump valve ports 192 closed, and the lower pump valve ports 190 opened (with the spike valve ports 186 closed). The membrane 15 may be moved to draw fluid from the patient port 154 and into the pump chambers 181. Thereafter, the lower pump valve ports 190 may be closed, the upper valve ports 192 opened, and the valve port 184 for the drain port 152 opened. Fluid from the pump chambers 181 may then be pumped into the drain line for disposal or for sampling into a drain or collection container. Alternatively, fluid may also be routed to one or more spikes 160/lines 30 for sampling or drain purposes. This operation may be repeated until sufficient dialysate is removed from the patient and pumped to the drain.

The heater bag 22 may also serve as a mixing container. Depending on the specific treatment requirements for an individual patient, dialysate or other solutions having different compositions can be connected to the cassette 24 via suitable solution lines 30 and spikes 160. Measured quantities of each solution can be added to heater bag 22 using cassette 24, and admixed according to one or more predetermined formulae stored in microprocessor memory and accessible by control system 16. Alternatively, specific treatment parameters can be entered by the user via user interface 144. The control system 16 can be programmed to compute the proper admixture requirements based on the type of dialysate or solution containers connected to spikes 160, and can then control the admixture and delivery of the prescribed mixture to the patient. Admixture of fluids is further described later in the specification.

Patient Line State Detection Apparatus

In one aspect, a fluid line state detector detects when a fluid line to a patient, such as patient line 34, is adequately primed with fluid before it is connected to the patient. It should be understood that although a fluid line state detector is described in connection with a patient line 34, it may be used for the detection of the presence any suitable tubing segment or other conduit and/or a fill state of the tubing segment or other conduit. In some embodiments, a fluid line state detector can be used to detect adequate priming of a tubing segment of the patient-connecting end of a fluid line. The patient line 34 may be connected to an indwelling catheter in a patient's blood vessel, in a body cavity, subcutaneously, or in another organ. In one embodiment, the patient line 34 may be a component of a peritoneal dialysis system 10, delivering dialysate to and receiving fluid from a patient's peritoneal cavity. A tubing segment near the distal end of the line may be placed in an upright position in a cradle within which the sensor elements of the detector are located. The fluid line state detector may be any of those described in U.S. Pat. No. 10,201,647, to Norris et al., issued Feb. 12, 2019, filed Jun. 5, 2015, and entitled "Medical Treatment System and Methods Using a Plurality of Fluid Lines" which is incorporated herein by reference in its entirety.

Solution Line Organizer

Figure 10:
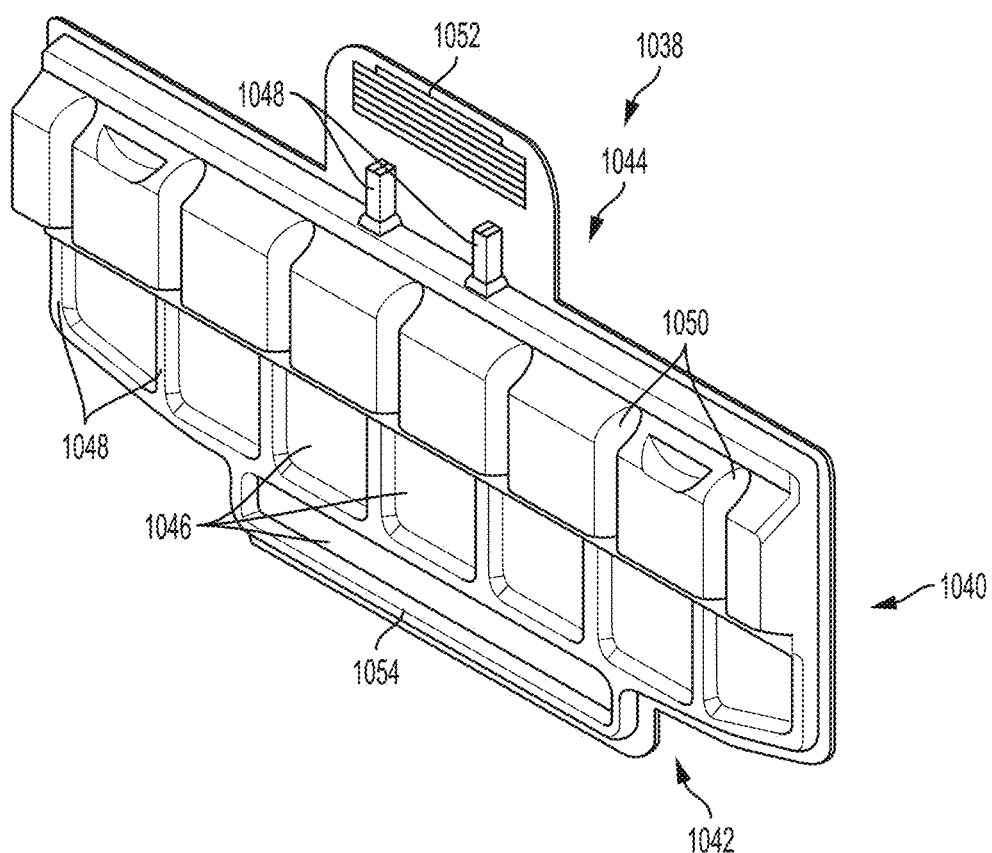
FIG. 10 is a perspective view of the front of an unloaded organizer (absent any solution lines)
Figure 11:
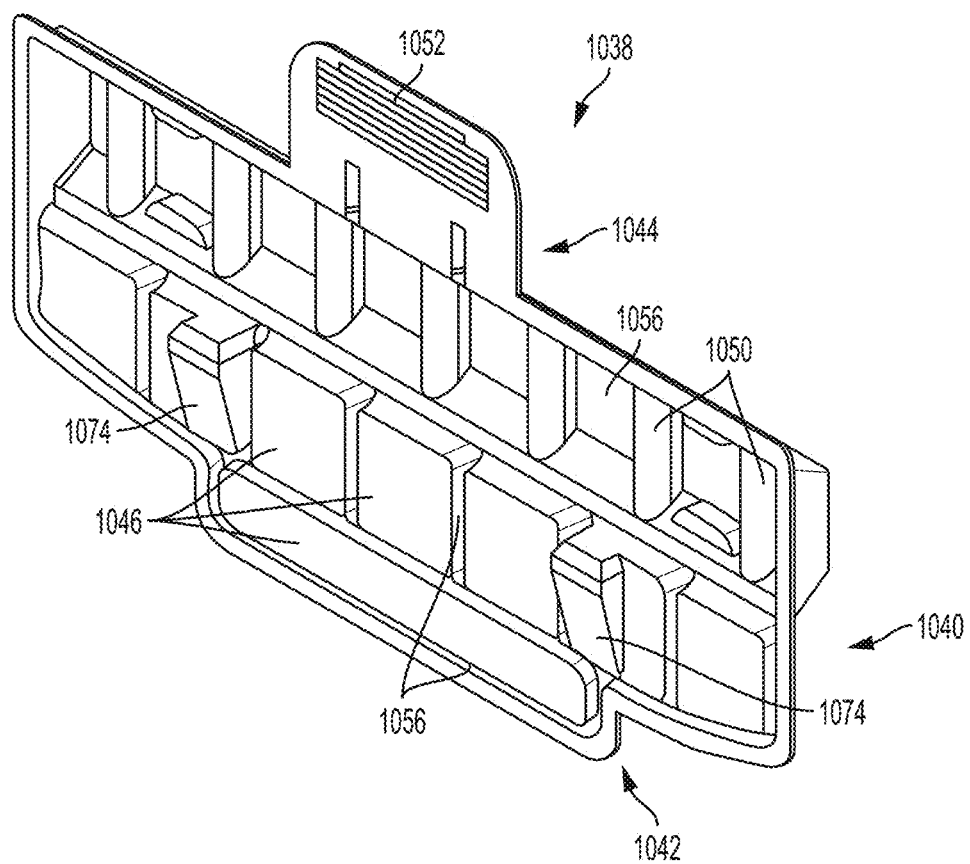
FIG. 11 is a back view of the organizer of FIG. 10.
Figure 12:
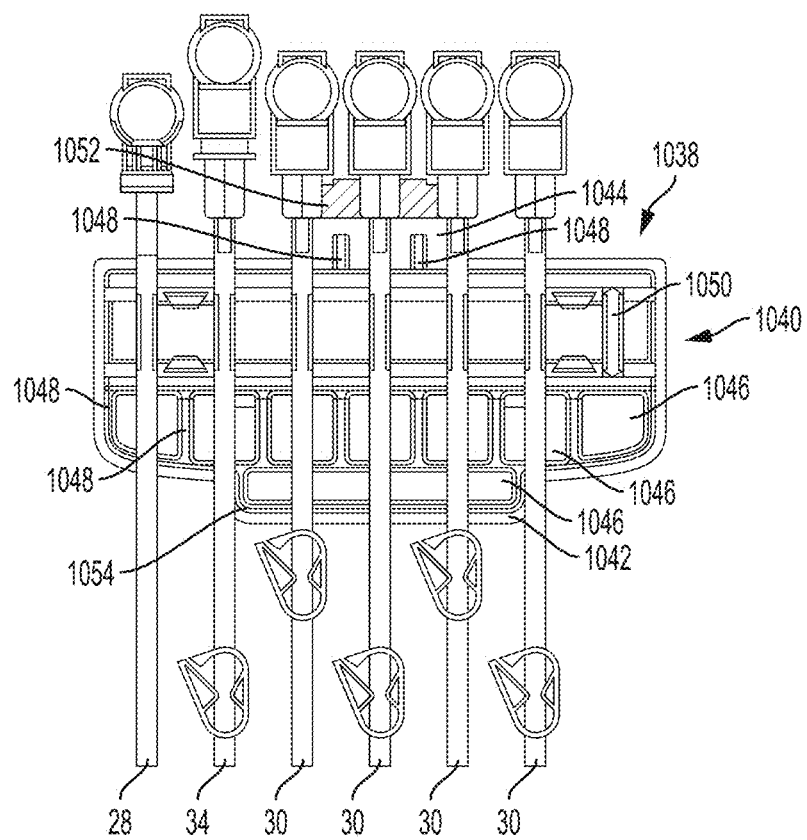
FIG. 12 is a perspective view of an organizer including a plurality of solution lines, a fluid line, and a drain line.

FIGS. 10-12 show a perspective view of the front of an unloaded organizer 1038, a perspective view of the back of an unloaded organizer 1038, and a front view of a loaded organizer 1038 respectively. In this embodiment, the organizer 1038 may be substantially formed from a moderately flexible material (such as, e.g., PAXON AL55-003 HDPE resin). Forming the organizer 1038 from this or another relatively flexible polymer material increases the organizer's 1038 durability when attaching and removing solution lines or solution line connectors.

The organizer 1038 may conveniently be mounted or attached to an outer wall of the cycler housing 82. The organizer 1038 may include a tube holder section 1040, a base 1042, and a tab 1044. The tube holder section 1040, the base 1042, and the tab 1044 may all be flexibly connected, and may be substantially formed from the same HDPE-based material. The tube holder section 1040 may have a generally rectangular shape, and may include a generally flat top edge and a bottom edge that may be slightly curved in an outwardly direction. The tube holder section 1040 may include a series of recessed segments 1046 that extend horizontally along the bottom edge of the tube holder section 1040. Each of the recessed segments 1046 may be separated by a series of support columns 1048, which may also define the shape and size of the segments 1046. The tube holder section 1040 may also include a raised area that extends horizontally along the top edge of the tube holder section 1040. The raised area may include a plurality of slots 1050. The slots 1050 may be defined in a vertical orientation, and may extend from the top edge of the tube holder section 1040 to the top of the recessed segments 1046. The slots 1050 may have a generally cylindrical shape so as to conform to the shape of a drain line 28, solution line 30, or patient line 34. The depth of the slots 1050 may be such that the opening of the slot 1050 is narrower then the inner region of the slot 1050. Therefore, once a line is placed into the slot 1050 it becomes locked or snap-fit into place. The line may then require a pre-determined minimum amount of force to be removed from the slot 1050. This ensures that the lines are not unintentionally removed from the organizer 1050.

In one aspect, the tab 1044 may be flexibly connected to the top edge of the tube holder section 1040. The tab 1044 may have a generally rectangular shape. In another embodiment, the tab 1044 may also include two slightly larger radius corners. The tab 1044 may also include two vertically extending support columns 1048. The support columns 1048 may be connected to the top edge of the tube holder section 1040, and may extend in an upward direction into the tab 1044. In alternative embodiment, the length and number of the support columns 1048 may vary depending on the desired degree of flexibility of the tab 1044. In another aspect, the tab 1044 may include a ribbed area 1052. The purpose of the tab 1044 and the ribbed area 1052 is to allow the organizer 1038 to be easily grasped by a user so that the user can easily install, transport, or remove the solution lines 30 from the organizer 1038. Also, the tab 1044 provides an additional area of support when removing and loading the lines into the organizer 1038.

In another aspect, the base 1042 may be flexibly connected to the bottom edge of the tube holder section 1040. The base 1042 may have a generally rectangular shape. In another embodiment, the base 1042 may also include two slightly larger radius corners. The base 1042 may include an elongated recessed segment 1046, which may be defined by a support ring 1054 that surrounds the recessed segment 1046. The support columns 1050, the support ring 1054, and the raised area may all create a series of voids 1056 along the back of the organizer 1038 (shown, e.g., in FIG. 11).

Figure 13:
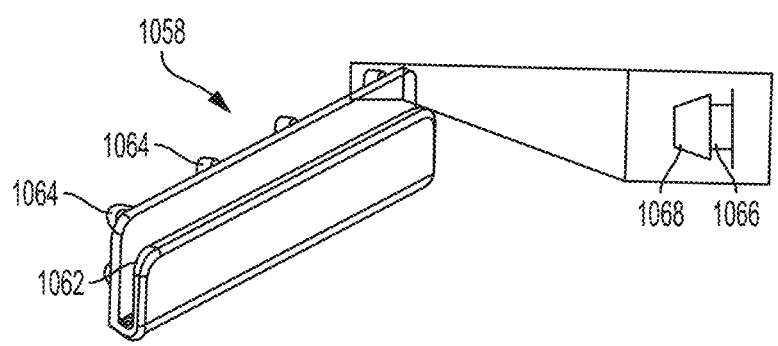
FIG. 13 is a perspective view of an organizer clip.
Figure 14:
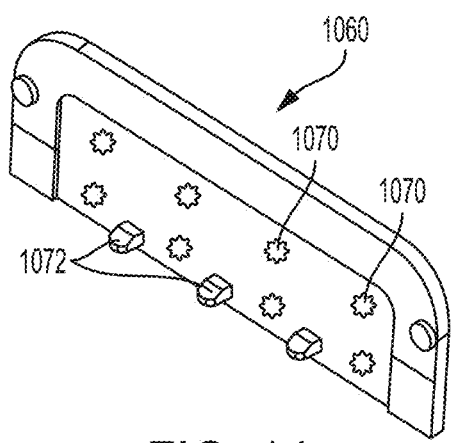
FIG. 14 is a perspective view of an organizer clip receiver.

FIG. 13 and FIG. 14 show a perspective view of an organizer clip 1058, and a perspective view of an organizer clip receiver 1060 respectively. In these illustrative embodiments, the clip 1058 may be made from a relatively high durometer polyurethane elastomer, such as, for example, 80 Shore A durometer urethane. In an alternative embodiment, the clip 1058 may be made from any type of flexible and durable material that would allow the organizer 1038 to flex and pivot along the base 1042 when positioned in the clip 1058. The clip 1058 may be "U-shaped", and may include a back portion that extends slightly higher than a front portion. Additionally, there may be a lip 1062 that extends along the top edge of the front portion of the clip 1058. The lip 1062 extends slightly into the cavity of the clip 1058. The back portion of the clip 1058 may also include a plurality of elastomeric pegs 1064 connected to (or formed from) and extending away from the back portion of the clip 1058. The pegs 1064 may include both a cylindrical section 1066 and a cone 1068. The cylindrical section 1066 may connect to the back portion of the clip 1058, and the cone 1068 may be attached to an open end of the cylindrical section 1066. The pegs 1064 allow the clip 1058 to be permanently connected to the organizer clip receiver 1060, by engaging the pegs 1064 within a plurality of holes 1070 in the organizer clip receiver 1060.

The organizer clip receiver 1060 may include a plurality of chamfered tabs 1072. The chamfered tabs 1072 may mate with corresponding slots on the back portion of the clip 1058 when the pegs 1064 are engaged with the organizer clip receiver 1060. Once the chamfered tabs 1072 engage the slots, they can extend through the back portion of the clip 1058, and act as locking mechanisms to hold the organizer 1038 in place when positioned into the clip 1058. When the organizer 1038 is positioned within the clip 1058, the chamfers 1072 fit into the void 1056 on the back of the base 1042, which was created by the raised support ring 1054.

Referring again to FIG. 11, and in accordance with another aspect of the present disclosure, there may be a plurality of ramps 1074 extending outwardly from the back of the organizer 1038. The ramps 1074 may be generally shaped as inclined planes. This allows the organizer 1038 to angle away from the cycler 14 when placed into the clip 1058, which provides numerous advantages over previous designs. For example, in this illustrative embodiment, the angle of the organizer 1038 ensures that neither the tab 1044, nor any of the lines (or line caps) connected to the organizer 1038 are allowed to interfere with the heater lid 143 when the lid 143 is being opened and closed. Additionally, the angle of the organizer 1038 in relation to the cycler 14, coupled with the flexibility of the organizer 1038, both encourage the user to remove the solution lines 30 from the bottom instead of from the connector end 30*a* of the solution lines. Preferably, the user should not remove the solution lines 30 by grasping the connector ends 30*a*, because in doing so the user could inadvertently remove one or more caps 31, which could cause contamination and spills. Another advantage of the organizer 1038 is that it aids the user in connecting color coded solution lines 30 to the correct containers 20 by helping to separate the color coded lines 30.

Door Latch Sensor

A door latch sensor may be included and may be any of those described in U.S. Pat. No. 10,201,647 to Norris et al., filed Jun. 5, 2015, entitled "Medical Treatment System and Methods Using a Plurality of Fluid Lines," which is incorporated herein by reference in its entirety.

Set Loading and Operation

Figure 16:
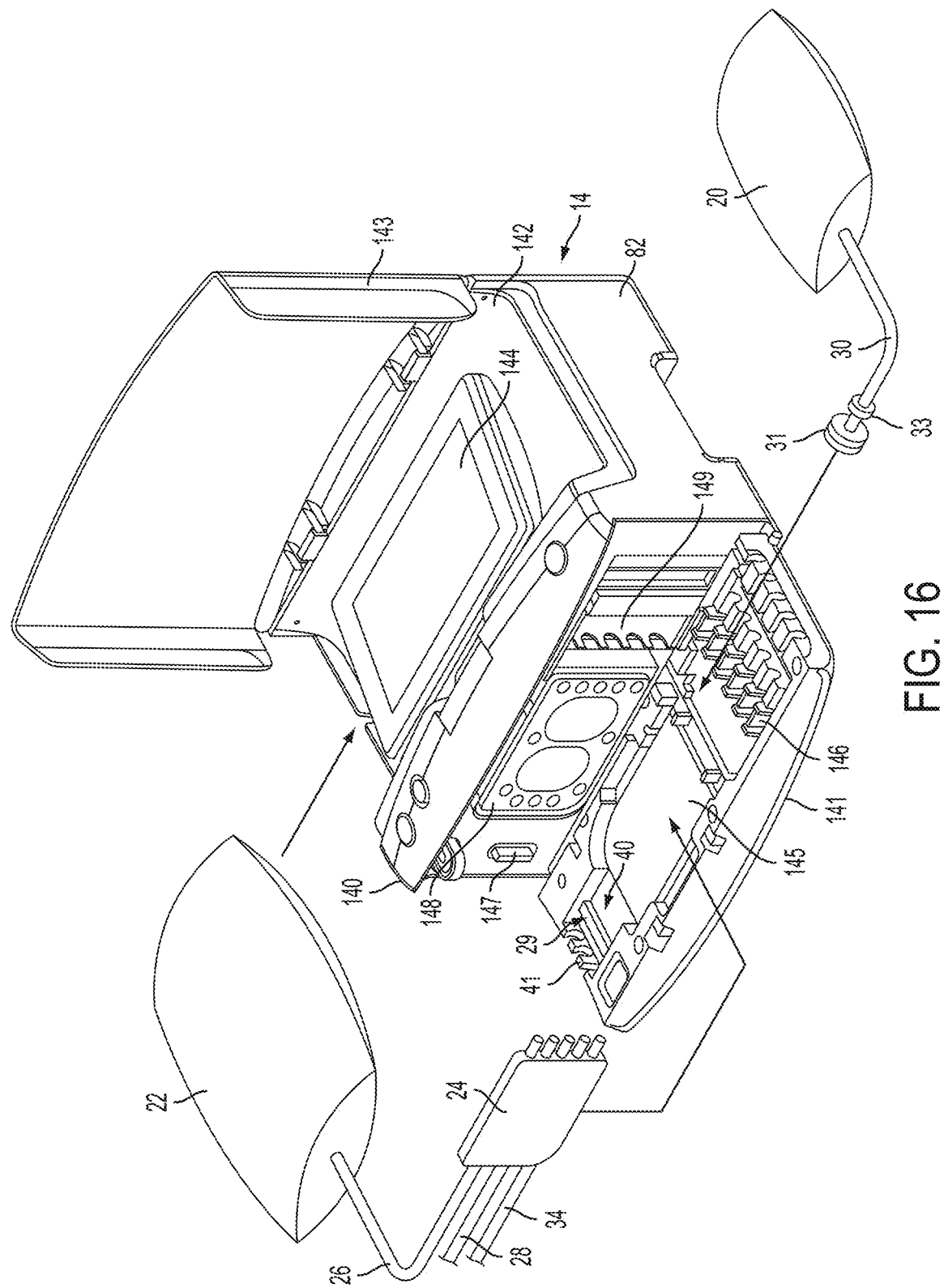
FIG. 16 is a perspective view of the APD system of FIG. 1 with the door of the cycler in an open position.

FIG. 16 shows a perspective view of the APD system 10 of FIG. 1 with the door 141 of the cycler 14 lowered into an open position, exposing a mounting location 145 for the cassette 24 and a carriage 146 for the solution lines 30. In this embodiment, the door 141 is mounted by a hinge at a lower part of the door 141 to the cycler housing 82. When loading the set 12, the cassette 24 is placed in the mounting location 145 with the membrane 15 and the pump chamber side of the cassette 24 facing upwardly, allowing the portions of the membrane 15 associated with the pump chambers 181 and the valve ports to interact with a control surface 148 of the cycler 14 when the door 141 is closed. The mounting location 145 may be shaped so as to match the shape of the base member 18, thereby ensuring proper orientation of the cassette 24 in the mounting location 145. In this illustrative embodiment, the cassette 24 and mounting location 145 have a generally rectangular shape with a single larger radius corner which requires the user to place the cassette 24 in a proper orientation into the mounting location 145 or the door 141 will not close. It should be understood, however, that other shapes or orientation features for the cassette 24 and/or the mounting location 145 are possible.

In accordance with an aspect of the disclosure, when the cassette 24 is placed in the mounting location 145, the patient, drain and heater bag lines 34, 28 and 26 are routed through a channel 40 in the door 141 to the left as shown in FIG. 16. The channel 40, which may include guides 41 or other features, may hold the patient, drain and heater bag lines 34, 28 and 26 so that an occluder 147 may selectively close/open the lines for flow. Upon closing of door 141, occluder 147 can compress one or more of patient, drain and heater bag lines 34, 28 and 26 against occluder stop 29. Generally, the occluder 147 may allow flow through the lines 34, 28 and 26 when the cycler 14 is operating (and operating properly), yet occlude the lines when the cycler 14 is powered down (and/or not operating properly). Occlusion of the lines may be performed by pressing on the lines, or otherwise pinching the lines to close off the flow path in the lines. Preferably, the occluder 147 may selectively occlude at least the patient and drain lines 34 and 28.

When the cassette 24 is mounted and the door 141 is closed, the pump chamber side of the cassette 24 and the membrane 15 may be pressed into contact with the control surface 148, e.g., by an air bladder, spring or other suitable arrangement in the door 141 behind the mounting location 145 that squeezes the cassette 24 between the mounting location 145 and the control surface 148. This containment of the cassette 24 may press the membranes 15 and 16 into contact with walls and other features of the base member 18, thereby isolating channels and other flow paths of the cassette 24 as desired. The control surface 148 may include a flexible gasket or membrane, e.g., a sheet of silicone rubber or other material that is associated with the membrane 15 and can selectively move portions of the membrane 15 to cause pumping action in the pump chambers 181 and opening/closing of valve ports of the cassette 24. The control surface 148 may be associated with the various portions of the membrane 15, e.g., placed into intimate contact with each other, so that portions of the membrane 15 move in response to movement of corresponding portions of the control surface 148. For example, the membrane 15 and control surface 148 may be positioned close together, and a suitable vacuum (or pressure that is lower relative to ambient) may be introduced through vacuum ports suitably located in the control surface 148, and maintained, between the membrane 15 and the control surface 148 so that the membrane 15 and the control surface 148 are essentially stuck together, at least in regions of the membrane 15 that require movement to open/close valve ports and/or to cause pumping action. In another embodiment, the membrane 15 and control surface 148 may be adhered together, or otherwise suitably associated.

In some embodiments, the surface of the control surface 148 or gasket facing the corresponding cassette membrane overlying the pump chambers and/or valves is textured or roughened. The texturing creates a plurality of small passages horizontally or tangentially along the surface of the gasket 148 when the gasket 148 is pulled against the surface of the corresponding cassette membrane. This may improve evacuation of air between the gasket surface and the cassette membrane surface in the textured locations. It may also improve the accuracy of pump chamber volume determinations using pressure-volume relationships (such as, for example, in the FMS procedures described elsewhere), by minimizing trapped pockets of air between the gasket 148 and the membrane. It may also improve the detection of any liquid that may leak into the potential space between the gasket 148 and the cassette membrane. In an embodiment, the texturing may be accomplished by masking the portions of the gasket mold that do not form the portions of the gasket 148 corresponding to the pump membrane and valve membrane locations. A chemical engraving process such as the Mold-Tech® texturing and chemical engraving process may then be applied to the unmasked portions of the gasket mold. Texturing may also be accomplished by any of a number of other processes, such as, for example, sand blasting, laser etching, or utilizing a mold manufacturing process using electrical discharge machining.

Before closing the door 141 with the cassette 24 loaded, one or more solution lines 30 may be loaded into the carriage 146. The end of each solution line 30 may include a cap 31 and a region 33 for labeling or attaching an indicator or identifier. The indicator, for example, can be an identification tag that snaps onto the tubing at indicator region 33. In accordance with an aspect of the disclosure and as will be discussed in more detail below, the carriage 146 and other components of the cycler 14 may be operated to remove the cap(s) 31 from lines 30, recognize the indicator for each line 30 (which may provide an indication as to the type of solution associated with the line, an amount of solution, etc.) and fluidly engage the lines 30 with a respective spike 160 of the cassette 24. This process may be done in an automated way, e.g., after the door 141 is closed and the caps 31 and spikes 160 are enclosed in a space protected from human touch, potentially reducing the risk of contamination of the lines 30 and/or the spikes 160 when connecting the two together. For example, upon closing of the door 141, the indicator regions 33 may be assessed (e.g., visually by a suitable imaging device and software-based image recognition, by RFID techniques, etc.) to identify what solutions are associated with which lines 30. The ability to detect features of a line 30 by way of an indicator at indicator region 33 may provide benefits such as allowing a user to position lines 30 in any location of the carriage 146 without having an affect on system operation. That is, since the cycler 14 can automatically detect solution line features, there is no need to ensure that specific lines are positioned in particular locations on the carriage 146 for the system to function properly. Instead, the cycler 14 may identify which lines 30 are where, and control the cassette 24 and other system features appropriately. For example, one line 30 and connected container may be intended to receive used dialysate, e.g., for later testing. Since the cycler 14 can identify the presence of the sample supply line 30, the cycler 14 can route used dialysate to the appropriate spike 160 and line 30. As discussed above, since the spikes 160 of the cassette 24 all feed into a common channel, the input from any particular spike 160 can be routed in the cassette 24 in any desired way by controlling valves and other cassette features.

With lines 30 mounted, the carriage 146 may be moved to the left (again, while the door 141 is closed), positioning the caps 31 over a respective spike cap 63 on a spike 160 of the cassette 24 and adjacent a cap stripper 149. The cap stripper 149 may extend outwardly (toward the door 141 from within a recess in the cycler 14 housing) to engage the caps 31. For example, the cap stripper 149 may include five fork-shaped elements that engage with a corresponding groove in the caps 31, allowing the cap stripper 149 to resist left/right movement of the cap 31 relative to the cap stripper 149. By engaging the caps 31 with the cap stripper 149, the caps 31 may also grip the corresponding spike cap 63. Thereafter, with the caps 31 engaged with corresponding spike caps 63, the carriage 146 and cap stripper 149 may move to the right, removing the spike caps 63 from the spikes 160 that are engaged with a corresponding cap 31. One possible advantage of this arrangement is that spike caps 63 are not removed in locations where no solution line 30 is loaded because engagement of the cap 31 from a solution line 30 is required to remove a spike cap 63. Thus, if a solution line 30 will not be connected to a spike 160, the cap on the spike 160 is left in place. The cap stripper 149 may then stop rightward movement (e.g., by contacting a stop), while the carriage 146 continues movement to the right. As a result, the carriage 146 may pull the terminal ends of the lines 30 from the caps 31, which remain attached to the cap stripper 149. With the caps 31 removed from the lines 30 (and the spike caps 63 still attached to the caps 31), the cap stripper 149 may again retract with the caps 31 into the recess in the cycler 14 housing, clearing a path for movement of the carriage 146 and the uncapped ends of the lines 30 toward the spikes 160. The carriage 146 then moves left again, attaching the terminal ends of the lines 30 with a respective spike 160 of the cassette 24. This connection may be made by the spikes 160 piercing an otherwise closed end of the lines 30 (e.g., the spikes 160 may pierce a closed septum or wall in the terminal end), permitting fluid flow from the respective containers 20 to the cassette 24. In an embodiment, the wall or septum may be constructed of a flexible and/or self-sealing material such as, for example, PVC, polypropylene, or silicone rubber.

In accordance with an aspect of the disclosure, the heater bag 22 may be placed in the heater bag receiving section (e.g., a tray) 142, which is exposed by lifting a lid 143. In this embodiment, the cycler 14 includes a user or operator interface 144 that is pivotally mounted to the housing 82, as discussed below. To allow the heater bag 22 to be placed into the tray 142, the interface 144 may be pivoted upwardly out of the tray 142. As is known in the art, the heater tray 142 may heat the dialysate in the heater bag 22 to a suitable temperature, e.g., a temperature appropriate for introduction into the patient. In accordance with an aspect of the disclosure, the lid 143 may be closed after placement of the heater bag 22 in the tray 142, e.g., to help trap heat to speed the heating process, and/or help prevent touching or other contact with a relatively warm portion of the heater tray 142, such as its heating surfaces. In one embodiment, the lid 143 may be locked in a closed position to prevent touching of heated portions of the tray 142, e.g., in the circumstance that portions of the tray 142 are heated to temperatures that may cause burning of the skin. Opening of the lid 143 may be prevented, e.g., by a lock, until temperatures under the lid 143 are suitably low.

In accordance with another aspect of the disclosure, the cycler 14 includes a user or operator interface 144 that is pivotally mounted to the cycler 14 housing and may be folded down into the heater tray 142. With the interface 144 folded down, the lid 143 may be closed to conceal the interface 144 and/or prevent contact with the interface 144. The interface 144 may be arranged to display information, e.g., in graphical form, to a user, and receive input from the user, e.g., by using a touch screen and graphical user interface. The interface 144 may include other input devices, such as buttons, dials, knobs, pointing devices, etc. With the set 12 connected, and containers 20 appropriately placed, the user may interact with the interface 144 and cause the cycler 14 to start a treatment and/or perform other functions.

However, prior to initiating a dialysis treatment cycle, the cycler 14 must at least prime the cassette 24, the patient line 34, heater bag 22, etc., unless the set 12 is provided in a pre-primed condition (e.g., at the manufacturing facility or otherwise before being put into use with the cycler 14). Priming may be performed in a variety of ways, such as controlling the cassette 24 (namely the pumps and valves) to draw liquid from one or more solution containers 20 via a line 30 and pump the liquid through the various pathways of the cassette 24 so as to remove air from the cassette 24. Dialysate may be pumped into the heater bag 22, e.g., for heating prior to delivery to the patient. Once the cassette 24 and heater bag line 26 are primed, the cycler 14 may next prime the patient line 34. In one embodiment, the patient line 34 may be primed by connecting the line 34 (e.g., by the connector 36) to a suitable port or other connection point on the cycler 14 and causing the cassette 24 to pump liquid into the patient line 34. The port or connection point on the cycler 14 may be arranged to detect the arrival of liquid at the end of the patient line 34 (e.g., optically, by conductive sensor, or other), thus detecting that the patient line 34 is primed. As discussed above, different types of sets 12 may have differently sized patient lines 34, e.g., adult or pediatric size. In accordance with an aspect of the disclosure, the cycler 14 may detect the type of cassette 24 (or at least the type of patient line 34) and control the cycler 14 and cassette 24 accordingly. For example, the cycler 14 may determine a volume of liquid delivered by a pump in the cassette 24 needed to prime the patient line 34, and based on the volume, determine the size of the patient line 34. Other techniques may be used, such as recognizing a barcode or other indicator on the cassette 24, patient line 34 or other component that indicates the patient line type.

Figure 17:
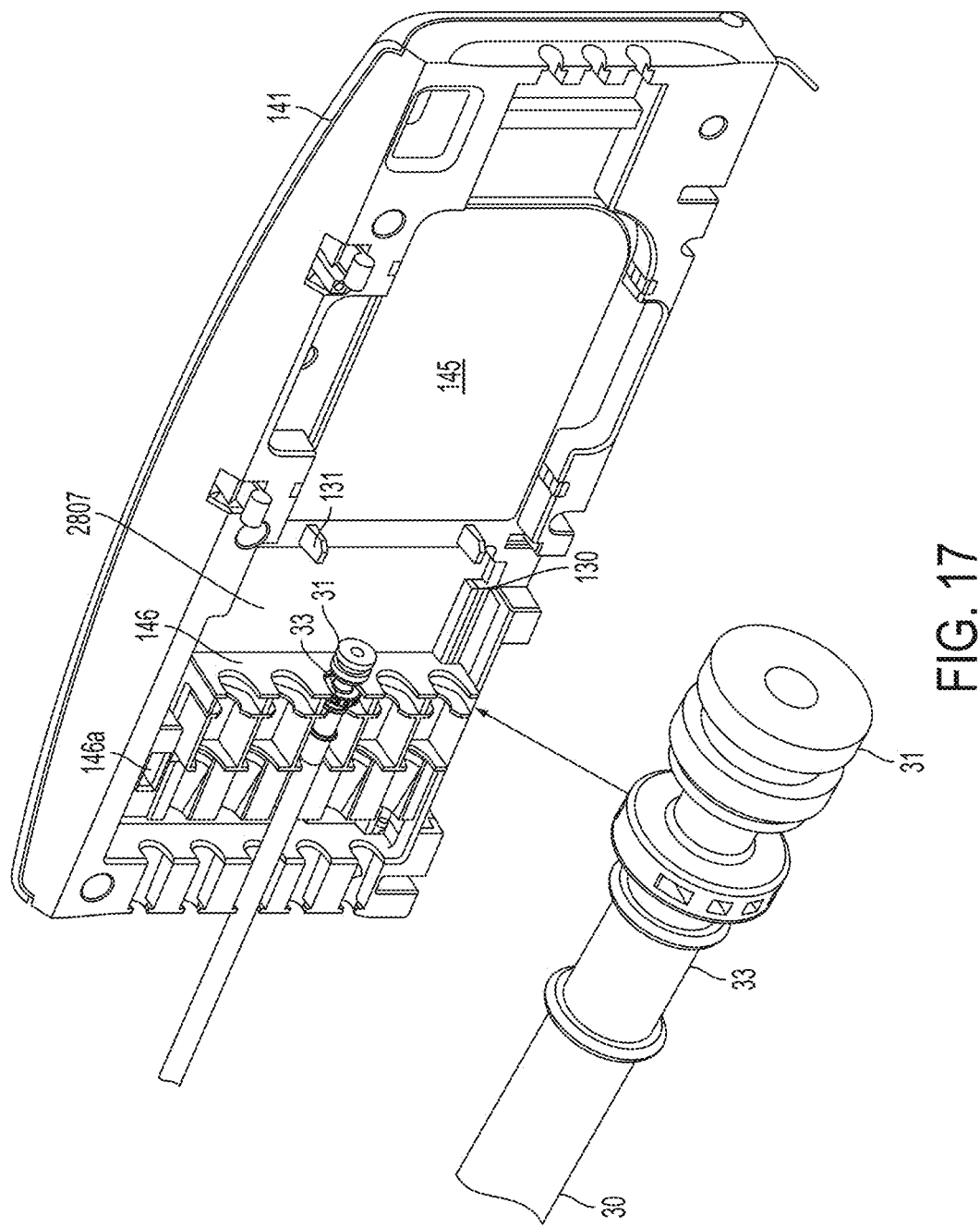
FIG. 17 is a perspective view of the inner side of the door of the cycler show in FIG. 16.

FIG. 17 shows a perspective view of the inner side of the door 141 disconnected from the housing 82 of the cycler 14. This view more clearly shows how the lines 30 are received in corresponding grooves in the door 141 and the carriage 146 such that the indicator region 33 is captured in a specific slot of the carriage 146. With the indicator at indicator region 33 positioned appropriately when the tubing is mounted to the carriage 146, a reader or other device can identify indicia of the indicator, e.g., representing a type of solution in the container 20 connected to the line 30, an amount of solution, a date of manufacture, an identity of the manufacturer, and so on. The carriage 146 is mounted on a pair of guides 130 at top and bottom ends of the carriage 146 (only the lower guide 130 is shown in FIG. 17). Thus, the carriage 146 can move left to right on the door 141 along the guides 130. When moving toward the cassette mounting location 145 (to the right in FIG. 17), the carriage 146 can move until it contacts stops 131.

Figure 18:
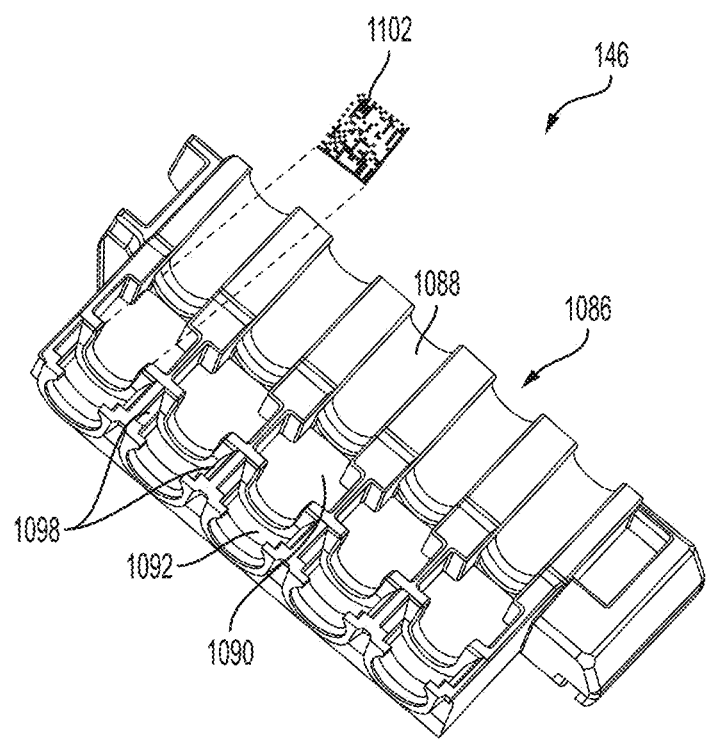
FIG. 18 is a perspective view of a carriage in a first embodiment.
Figure 19:
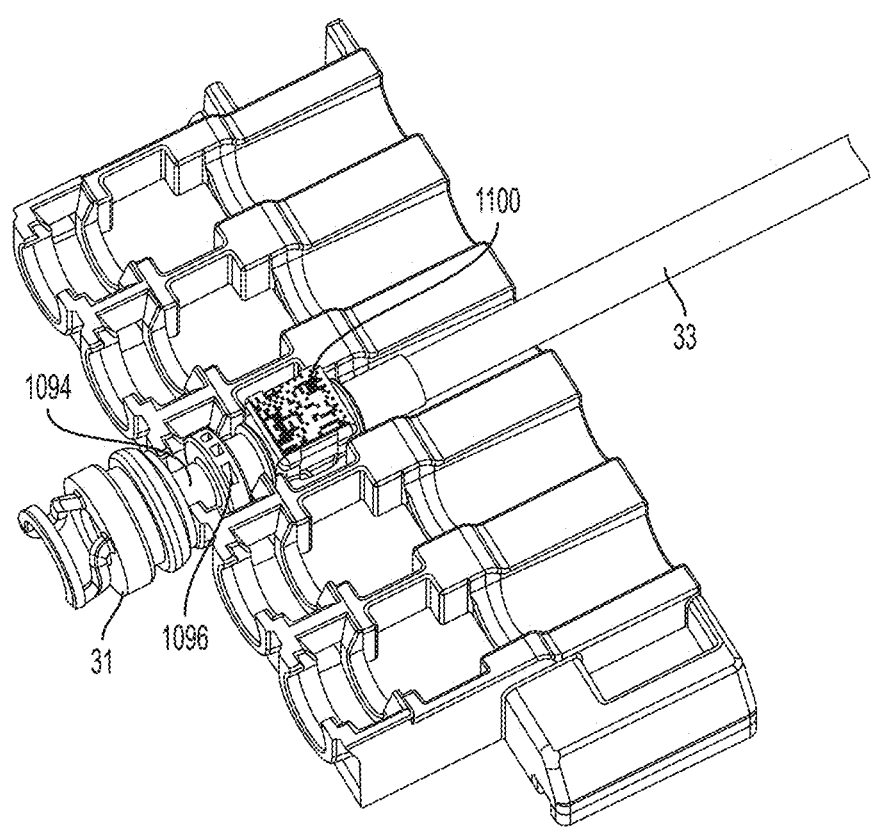
FIG. 19 is an enlarged perspective view of a solution line loaded into the carriage of FIG. 18.

FIG. 18 and FIG. 19 show a perspective view of a carriage 146, and an enlarged perspective view of a solution line 30 loaded into the carriage 146. In these illustrative embodiments, the carriage 146 may have the ability to move on the door 141 along the guide 130. The carriage 146 may include five slots 1086, and therefore may have the ability to support up to five solution lines 30. Each slot 1086 may include three different sections; a solution line section 1088, an ID section 1090, and a clip 1092. The solution line section 1088 may have a generally cylindrical shaped cavity that allows the solution lines 30 to remain organized and untangled when loaded into the carriage 146. The clip 1092 may be located at the opposite end of each of the slots 1086, relative to the solution line section 1088. The purpose of the clip 1092 is to provide a secure housing for a membrane port 1094 located at the connector end 30a of the solution line 30, and to prevent the solution line 30 from moving during treatment.

In one embodiment of the present disclosure, the clip 1092 may have a semicircular shape, and may include a middle region that extends slightly deeper than the two surrounding edge regions. The purpose of including the deeper middle region is to accommodate a membrane port flange 1096. The flange 1096 may have a substantially greater radius than the rest of the membrane port. Therefore, the deeper middle region is designed to fit the wider flange 1096, while the two edge regions provide support so that the membrane port 1094 is immobilized. Additionally, the deep middle region may have two cutouts 1098 positioned on opposite sides of the semicircle. The cutouts 1098 may have a generally rectangular shape so as to allow a small portion of the flange 1096 to extend into each of the cutouts 1098 when positioned in the clip 1092. The cutouts 1098 may be formed so that the distance between the top edges of each cutout 1098 is slightly less than the radius of the flange 1096. Therefore, a sufficient amount of force is required to snap the flange 1096 into the clip 1092. Also, allowing for the distance between the top edges of the two cutouts 1098 to be less than the radius of the flange 1096 helps to keep the solution line 30 from inadvertently becoming dislodged during treatment.

In this illustrative embodiment, the carriage 146 may provide superior performance over previous designs because of its ability to counteract any deformation of the membrane ports 1094. The carriage 146 is designed to stretch the membrane ports 1094 between the front of the flange 1096 and the back of the sleeve. If the membrane port 1094 is further stretched at any point during treatment, a wall in the carriage 146 may support the flange 1096.

In accordance with another aspect of the present disclosure, the ID section 1090 may be positioned between the solution line section 1088 and the clip 1092. The ID section 1090 may have a generally rectangular shape, thus having the ability to house an identification tag 1100 that may snap onto the solution line 30 at the indicator region 33. The indicator region 33 may have an annular shape that is sized and configured to fit within the ID section 1090 when mounted in the carriage 146. The identification tag 1100 may provide an indication as to the type of solution associated with each line 30, the amount of solution, a date of manufacture, and an identity of the manufacturer. As shown in FIG. 18, the ID section 1090 may include a two dimensional (2-D) barcode 1102, which may be imprinted on the bottom of the ID section 1090. The barcode 1102 may be a Data Matrix symbol with 10 blocks per side, and may include an "empty" Data Matrix code. The barcode 1102 may be positioned on the carriage 146 underneath the identification tag 1100, when the solution lines 30 are loaded into the carriage 146. However, in an alternative embodiment, the barcode 1102 may be added to the ID section 1090 of the carriage 146 by way of a sticker or laser engraving. Also, in another embodiment, the barcode 1102 may include a Data Matrix that consists of varying dimensions of length and width, as well as varying numbers of blocks per side.

In this illustrative embodiment, however, the specific number of blocks per side, and the specific length and width of each barcode 1102 was specifically chosen in order to provide the most robust design under a variety of conditions. Using only 10 blocks per side may result in the barcode 1102 having larger blocks, which therefore ensures that the barcode 1102 is easily readable, even under the dark conditions that exist inside of the cycler housing 82.

Figure 20:
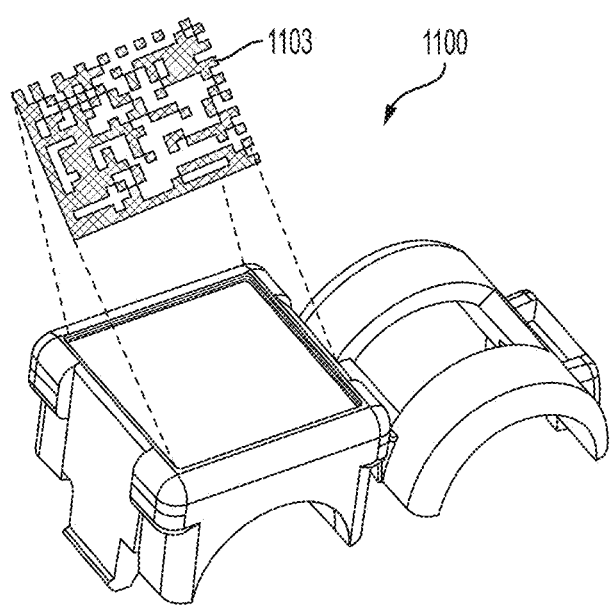
FIG. 20 is a perspective view of an open identification tag.
Figure 21:
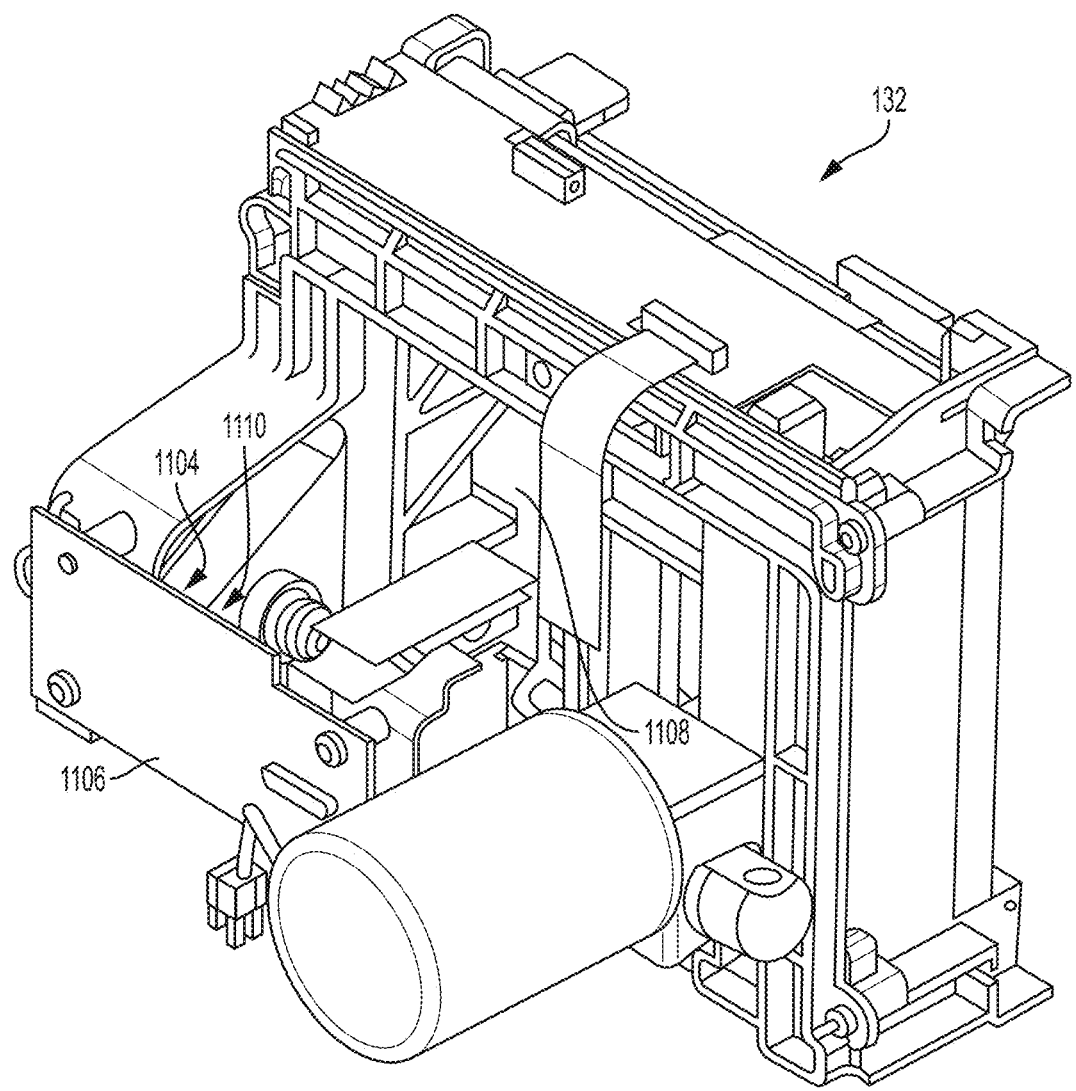
FIG. 21 is a perspective view of a carriage drive assembly including an AutoID camera mounted to an AutoID camera board.

FIG. 20 and FIG. 21 show a perspective view of a foldable identification tag 1100, and a perspective view of a carriage drive assembly 132 including an AutoID camera 1104 mounted to an AutoID camera board 1106 respectively. In accordance with an aspect of the present disclosure, the identification tag 1100 may be formed from an injection mold, and it may then fold to snap around the indicator region 33. The identification tag 1100 may include edges that are rounded, which may prevent damage to the solution containers 20 during shipping. The identification tag 1100 may also include an 8×8 mm two dimensional (2-D) Data Matrix symbol 1103 with 18 blocks per side plus a quiet zone, which may be added by way of a sticker. The information contained in these Data Matrix symbols 1103 may be provided from the camera 1104 to the control system 16, which may then obtain indicia, through various processes such as by way of image analysis. Therefore, the AutoID camera 1104 will have the ability to detect slots 1086 that contain a solution line 30 that is correctly installed, a line 30 that is incorrectly installed, or the absence of a line 30. A solution line 30 that is correctly installed will allow the camera 1104 to detect the Data Matrix symbol 1103 located on the identification tag 1100, the absence of a solution line 30 will allow the camera 1104 to detect an "empty" Data Matrix barcode 1102 located on the carriage 146 underneath the membrane port 1094, and a solution line 30 that is incorrectly loaded will occlude the "empty" Data Matrix barcode 1102, resulting in no Data Matrix being decoded by the camera 1104 for that slot. Thus, the camera 1104 should always decode a Data Matrix in every slot 1086 on the carriage 146, baring an incorrectly loaded solution line 30.

In this illustrative embodiment, ability to detect features of a solution line 30 by way of an identification tag 1100 located at indicator region 33 may provide benefits such as allowing a user to position lines 30 in any location of the carriage 146 without having an effect on system operation. Additionally, since the cycler 14 can automatically detect solution line features, there is no need to ensure that specific lines 30 are positioned in particular locations on the carriage 146 for the system to function properly. Instead, the cycler 14 may identify which lines 30 are where, and control the cassette 24 and other system features appropriately.

In accordance with another aspect of the disclosure, the identification tag 1100 must face into the carriage drive assembly 132 in order to be decoded by the camera 1104. To ensure this, the solution line receiving structures on the holder for the solution lines and the identification tag 1100 may have complementary alignment features. With reference to the example embodiments of the carriage 146 described herein, the carriage 146 and identification tag 1100 may have complementary alignment features. Additionally, the solution lines 30 with identification tags 1100 should also fit within the Cleanflash machine, thus, the solution line 30 with identification tag 1100 may be constructed to fit within a 0.53 inch diameter cylinder. In an embodiment, the alignment feature may be a flat bottomed bill on the identification tag 1100 and matching rib in the carriage 146. In one embodiment of the present disclosure, the bill and rib may slightly interfere, forcing the back of the identification tag 1100 in an upward direction. While this configuration may create a small amount of misalignment, it reduces misalignment in the other axis. Finally, to ensure that the identification tag 1100 is properly seated, the front of the carriage drive assembly 132 can be designed with only about 0.02 inch of clearance over the present carriage 146 and identification tag 1100 alignment.

In accordance with another aspect of the disclosure, the AutoID camera board 1106 may be mounted to the back of the carriage drive assembly 132. Additionally, the AutoID camera 1104 may be mounted to the camera board 1106. The camera board 1106 may be placed approximately 4.19 inches from the identification tag 1100. However, in an alternative embodiment, the camera board 1106 may be moved backward without any serious consequences. A plastic window 1108 may also be attached to the front of the carriage drive assembly 132, which may allow the identification tags 1100 to be imaged while also preventing fluid and finger ingress. The AutoID camera 1104 may include a camera lens, which may be any type of lens, such as those used for security applications, or lenses intended for camera phones with the IR filter removed. In accordance with an aspect of the present disclosure, the camera lens may consist of a small size, light weight, low cost, and high image quality.

Additionally, a single SMD IR LED 1110 may be attached to the camera board 1106. The LED 1110 may then illuminate the identification tags 1100 so that the camera 1104 may easily decode the Data Matrices 1103. It is important that the identification tags 1100 be illuminated because the environment inside of the cycler housing 82 is mostly absent of light. Therefore, without the LED 1110 to illuminate the identification tags 1100 the camera 1104 would be unable to decode the Data Matrices 1103. Furthermore, to avoid creating glare in front of the identification tags 1100, the LED 1110 may be mounted 0.75 inch away from the camera 1104. An FPGA may also be mounted to the camera board 1106, and may act as an intermediary between the OV3640 image sensor and a cycler's 14 UI processor. In addition to making the processor's job easier, this architecture may allow for a different image sensor to be used without a change to any other cycler hardware or software. Finally, image decoding is handled by the open source package libdmtx, which is addressable from a number of programming languages and can run from a command line for testing.

In some embodiments, a processor associated with the camera 1104 may be capable of decoding barcodes, data matrices, or the like outside of an indicator region 33 of a solution line installed in a carriage 146. For example, a processor associated with camera 1104 may be capable of decoding an identifying marking on the packaging or overpack of a set or on the set itself before the set is installed in the cycler 14. For example, during setup, the user interface of a cycler 14 may instruct a user to hold the set packaging in front of or a certain distance away from a window such as window 1108, such that an identifying marking on the packing is facing the window. In this position, the identifying marking will be in the field of the view of the image sensor of the camera 1104. The camera 1104 may then image the packing and the identifying marking may be decoded by a processor associated with the camera 1104. In some embodiments, after the identifying marking has been decoded, the user interface may prompt the user to confirm various information about the set 12.

The information encoded in the identifying marking on the set or set packaging may be the same as or different from that included on the indicator for each solution line 30. For example, the information on the set packing may be stored for logging purposes (e.g. lot number identification etc.). In some embodiments, the information decoded from the set packing may be compared to the information included on the solution lines 30 to ensure that the information matches or corresponds. This may provide for some redundancy allowing the device to double check that the lines have been identified correctly and that the correct set 12 was installed.

Figure 22:
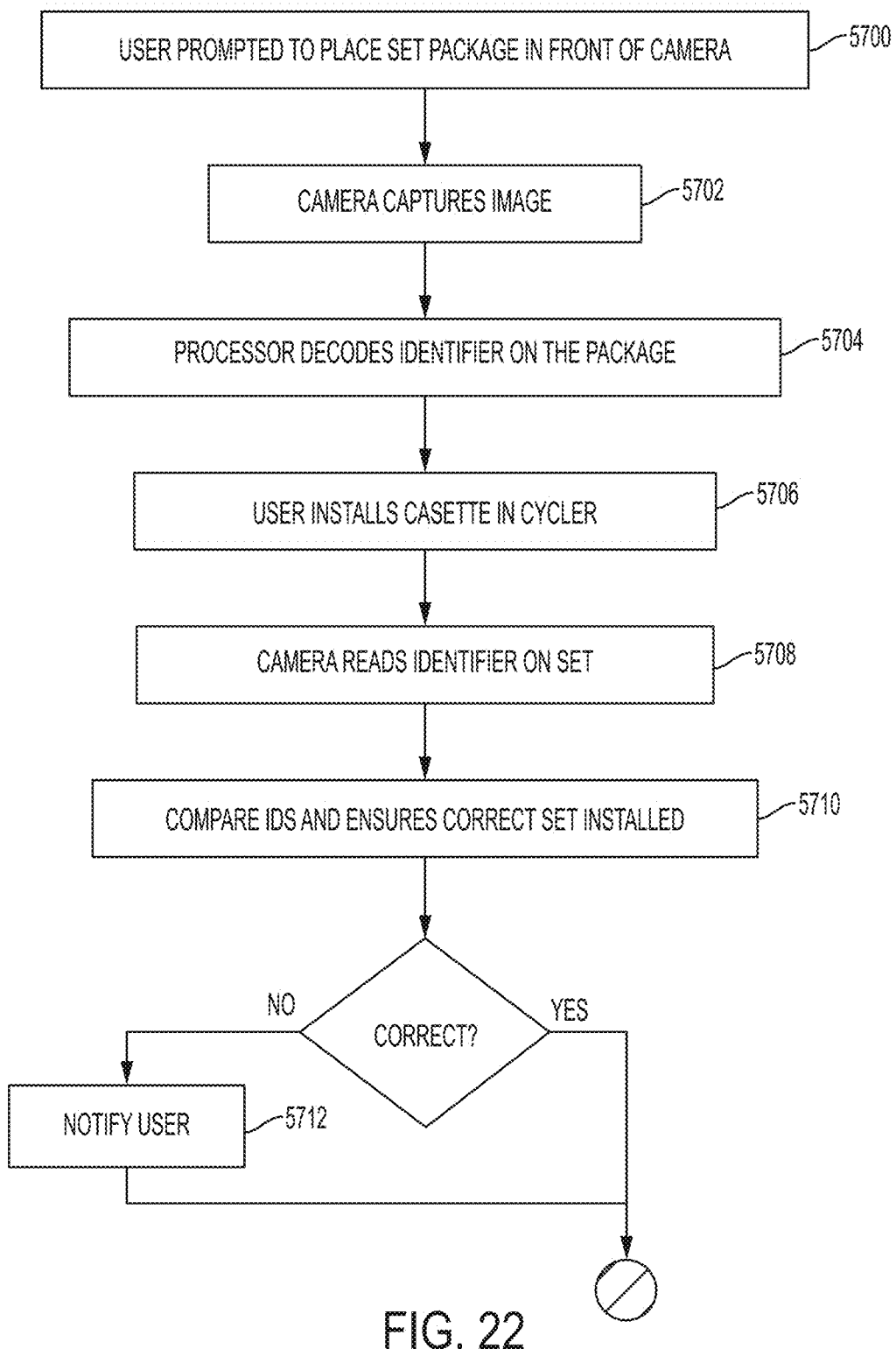
FIG. 22 shows a flowchart outlining a number of steps which may be used to determine information about a set to be installed in a cycler.

FIG. 22 depicts a flowchart detailing a number of example steps which may be used to determine information about a set to be installed in a cycler 14 by reading an identification marking on the packaging for the set 12. As shown, in step 5700, a user may be instructed to place a set package in front of a camera in the cycler. This may be accomplished via a prompt generated by a processor of the cycler for display on a user interface of the cycler. The cycler may then capture an image of the identification marking on the set packaging or overpack in step 5702. In some embodiments, the user may be required to interact with the user interface of the cycler to notify the cycler processor that the set packaging has been properly positioned. This interaction may generate a signal which is recognized by a processor that then commands the image to be captured.

In step 5704, a processor of the cycler may decode the identifier on the packaging. The user may then install the cassette in the cycler in step 5706. In some embodiments, before the user installs the cassette, the user interface of the cycler may display a notification which asks a user to confirm that the set was correctly identified in step 5704. In one aspect, the cycler may display a message if the packaging is identified to be for a cassette that would be incompatible with a selected or programmed therapy.

Once the set is installed a camera in the cycler may read one or more identifying markings on the set in step 5708. In some embodiments, the identifying marking read in step 5708 may be an identification tag 1100 on each solution line of the set. A processor of the cycler may compare the information about the set gathered in step 5702 and 5708 to ensure that the correct set was installed in step 5710. In the event that the information does not match, the user may be notified in step 5712.

In some embodiments, to avoid deleterious effects of glare from visible light, the data matrices 1103 of the identification tags 1100 may include a fluorescent ink or dye which emits light of a first wavelength or spectrum in response to absorption of light of a second wavelength or spectrum shone upon it. Such an identification system can be used in any fluid handling medical device in which fluid containers or bags may have fluids of different compositions, expiration dates, or in which manufacturing lot numbers need to be recorded by the device. In an example embodiment, the system can be used in an automated peritoneal dialysis apparatus. The system comprises an image sensor or camera 1104 configured to read an image generated by fluorescent light, the image comprising a pattern of coded information characterizing the fluid in the container, the age of the container, its lot number, etc. The fluid line 33 to which the container is attached can be mounted in a mount, cradle or carriage 1088 to fix its location relative to the image sensor. The fluid line can have an attached identification tag 1100 on or near the mount, onto which a fluorescent identifying marking 1103 has been applied. The marking fluoresces a pattern of light that contains the coded information upon absorption of light having a non-visible wavelength emitted by an emitter nearby. The image sensor can be connected to a controller adapted to receive electronic signals from the image sensor board 1106 representing the image pattern containing the coded information.

For example, the data matrices 1103 may include an ink or dye which fluoresces in the visible spectrum when it absorbs light in the ultraviolet spectrum. The data matrices 1103 may be printed with such an ink or dye and applied to the identification tags 1100 as a sticker, for example. Any other suitable means of attaching a data matrix 1103 to an identification tag 1100 may also be used. In addition to an image sensor, the camera 1104 may include a camera lens which includes a filter that filters out light of the second wavelength or spectrum (e.g. a UV filter). One or more lighting elements, such as LED 1110 (e.g. an SMD LED) that generates light at the second wavelength or spectrum (e.g. UV light) may be attached or connected to the camera board 1106. The LED 1110 may then illuminate the data matrices 1103 on the identification tags 1100. In such embodiments, the data matrices 1103 will emit light in the first wavelength or spectrum (e.g. in the visible spectrum) in response to illumination by light of the second wavelength or spectrum. The camera 1104 may then receive the emitted light of the first wavelength for decoding of the data matrices 1103. The decoding of the data matrices 1103 may be accomplished as described above. The effects of glare from reflected light from the LED may be reduced in this fashion, since the camera 1104 can be configured to filter out light at the LED's emitting wavelength/spectrum.

Figure 23:
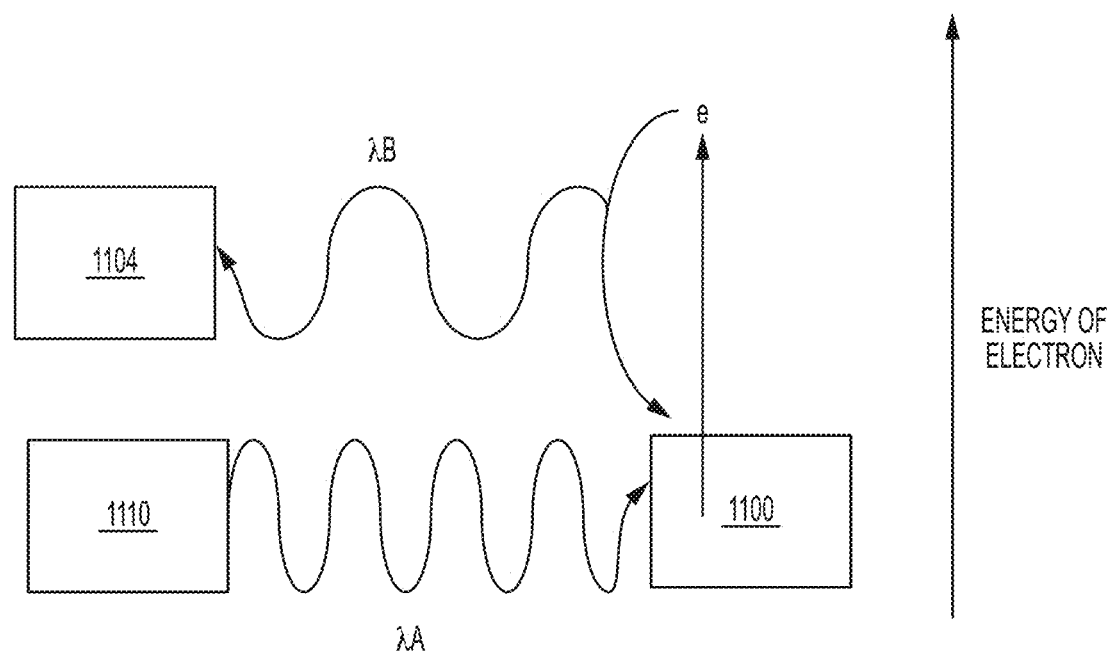
FIG. 23 shows a system including an identification tag having a code printed in a fluorescent material.

FIG. 23 depicts an illustration of a system in which the identification tag 1100 has a code printed in a fluorescent material. As shown, one or more LED's 1110 may illuminate the identification tag 1100 using light at a wavelength A. The light generated by fluorescence at wavelength B is received by the camera 1104. As mentioned above, the fluorescence may be in the visible spectrum and the wavelength emitted by the LED may be a wavelength outside of the visible spectrum such as ultraviolet light. The camera 1104 may optionally include a filter which filters out the wavelength emitted by the LED Once the identification tags 1100 of each line have been imaged by the camera 1104 and analyzed, a processor of the cycler may generate a screen for display on a user interface which displays the results. The display may indicate various characteristics about the solution identified. In other embodiments, the display may disclose characteristics of the solutions programmed for use during the therapy, and indicate whether these solutions have been detected by the camera. In an embodiment in which the controller is programmed to perform image recognition, and in which the solution line caps are in the field of view of the image sensor or camera 1104, a results screen may display whether the lines were detected in a capped or uncapped state. In the event that the programmed solutions are not all present or that a line is uncapped, the controller may be programmed to prevent the user from proceeding with therapy and to display on a screen the needed corrective actions. The screen may also optionally display information about the type of set (e.g. pediatric, adult, extended patient line, etc.) installed in the cycler if such information is collected. Preferably, this action is performed and the screen display is shown prior to the connection of the solution lines to a cassette so as not to waste any solution.

Figure 24:
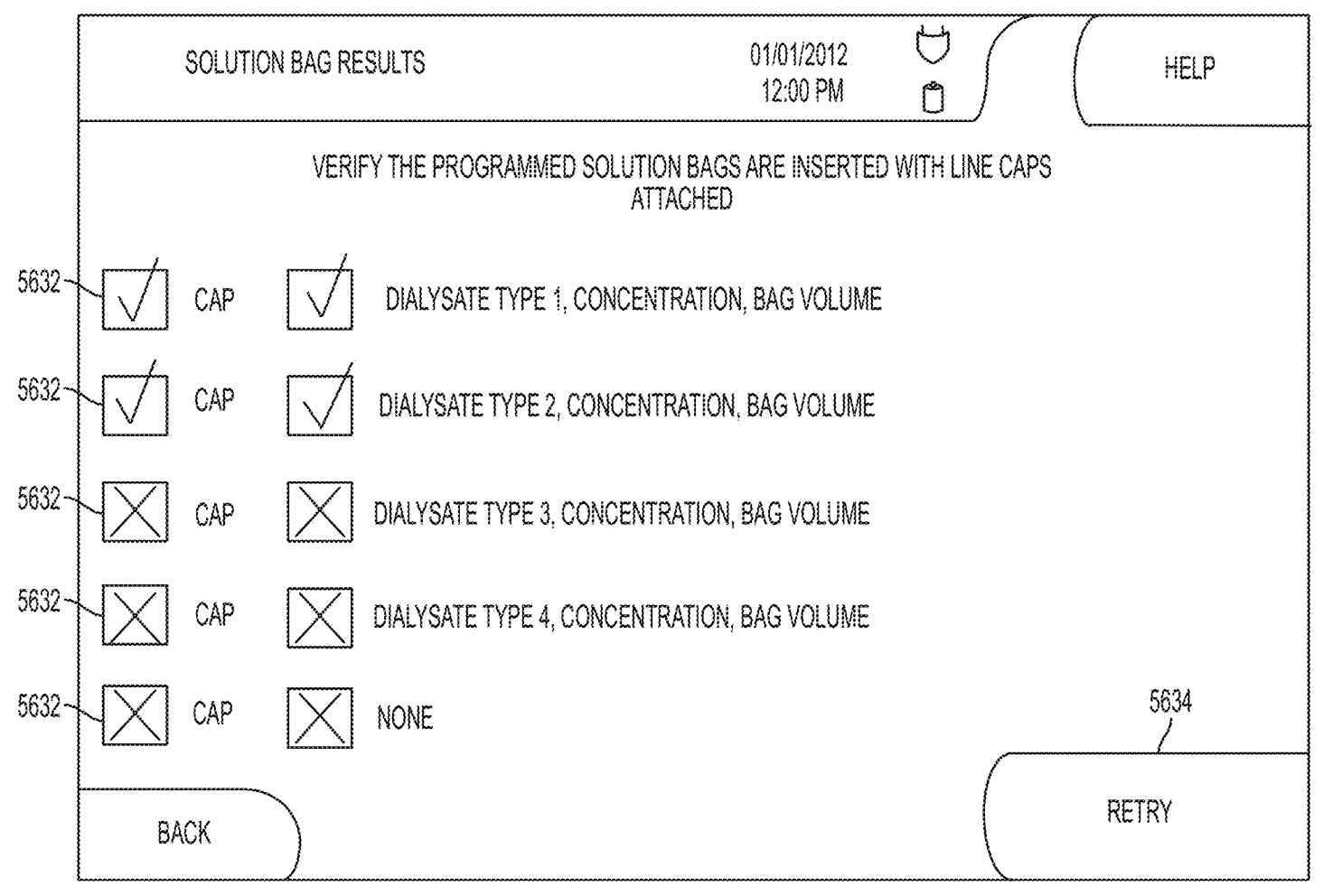

FIG. 24 depicts an example of a screen shot 5630 which may be generated for display on the user interface of a cycler. The example screen 5630 shows the results of identification tag 1100 analysis. In the example screen 5630, the characteristics of the solutions programmed for use in the therapy are shown. These characteristics may include (but are not limited to): dialysate type or name, concentration of dialysate, volume of dialysate bag, osmotic agent of the dialysate, other composition information (e.g. buffer information, ionic content information), bag type, etc. The characteristics shown may differ if the cycler is set up for at-home use or for use in a dialysis clinic. If there are fewer solution bags programmed for use in the therapy than the maximum allowed for the cycler, unused solution line or solution line cap locations may be labeled "none", "no solution", or the like.

A number of indicators 5362 may also be included on the example screen 5630. These indicators 5632 indicate to a user whether the solution has been identified as installed in the cycler. For example, a checkmark may appear in an indicator 5632 next to a listed solution type if present. An 'X' may appear if the listed item is not detected.

The example screen 5630 shown in FIG. 24 also includes an indicator 5632 associated with each solution that indicates whether a cap has been detected on the installed line. As above, any suitable method may be used to display whether a capped or uncapped line is detected.

In some embodiments, it may be desirable to include a brace, brace member or stiffener for placement on the distal end of a solution line. It may be configured to surround a portion of the line and/or an attached connector. A carriage 146 may also include retaining features 1092 configured to accept a solution line. Any of those described in U.S. Pat. No. 10,201,647 to Norris et al., issued Feb. 12, 2019, filed Jun. 5, 2015, entitled "Medical Treatment System and Methods Using a Plurality of Fluid Lines," which is incorporated herein by reference in its entirety.

Figure 25:
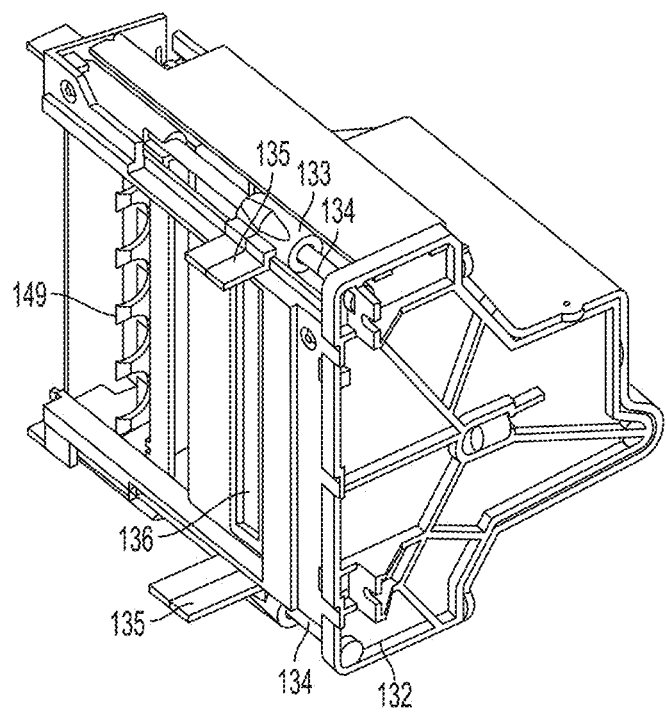
FIG. 25 is a right front perspective view of a carriage drive assembly and cap stripper in a first embodiment.

FIG. 25 shows a perspective view of a carriage drive assembly 132 in a first embodiment that functions to move the carriage 146 to remove the caps from spikes 160 on the cassette 24, remove caps 31 on the solution lines 30 and connect solution lines 30 to the spikes 160. A drive element 133 is arranged to move left to right along rods 134. In this illustrative embodiment, an air bladder powers the movement of the drive element 133 along the rods 134, but any suitable drive mechanism may be used, including motors, hydraulic systems, etc. The drive element 133 has forwardly extending tabs 135 that engage with corresponding slots 146*a* on the carriage 146 (see FIG. 17, which shows a top slot 146*a* on the carriage 146). Engagement of the tabs 135 with the slots 146*a* allows the drive element 133 to move the carriage 146 along the guides 130. The drive element 133 also includes a window 136, through which an imaging device, such as a CCD or CMOS imager, may capture image information of the indicators at indicator regions 33 on the lines 30 mounted to the carriage 146. Image information regarding the indicators at indicator regions 33 may be provided from the imaging device to the control system 16, which may obtain indicia, e.g., by image analysis. The drive element 133 can selectively move the cap stripper 149 both to the left and right along the rods 134. The cap stripper 149 extends forward and back using a separate drive mechanism, such as a pneumatic bladder.

Figure 26:
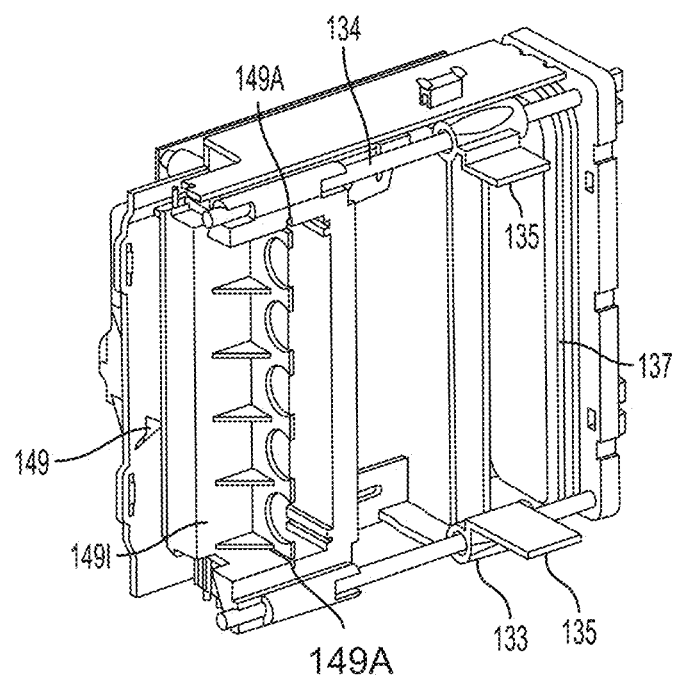
FIG. 26 a left front perspective view of the carriage drive assembly and cap stripper of FIG. 25.

FIG. 26 shows a left side perspective view of the carriage drive assembly 132, which more clearly shows how a stripper element of the cap stripper 149 is arranged to move in and out (a direction generally perpendicular to the rods 134) along grooves 149*a* in the housing of the cap stripper 149. Each of the semicircular cut outs of the stripper element may engage a corresponding groove of a cap 31 on a line 30 by extending forwardly when the cap 31 is appropriately positioned in front of the stripper 149 by the drive element 133 and the carriage 146. With the stripper element engaged with the caps 31, the cap stripper 149 may move with the carriage 146 as the drive element 133 moves.

Figure 27:
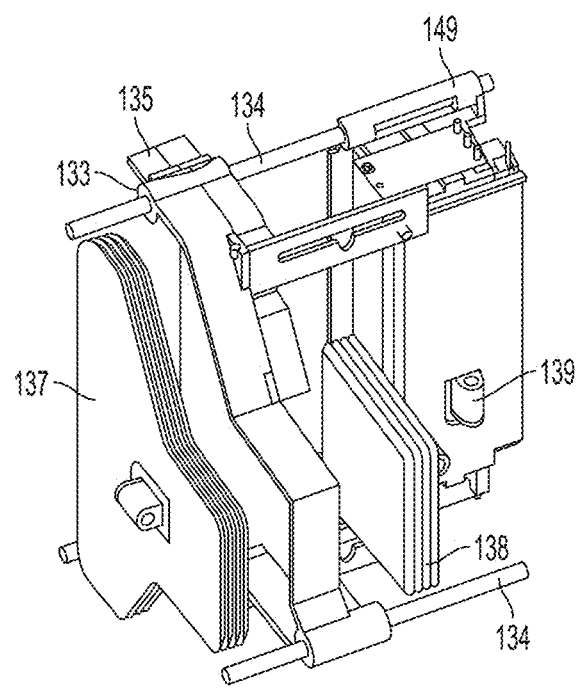
FIG. 27 is a rear perspective view of a carriage drive.
Figure 28:
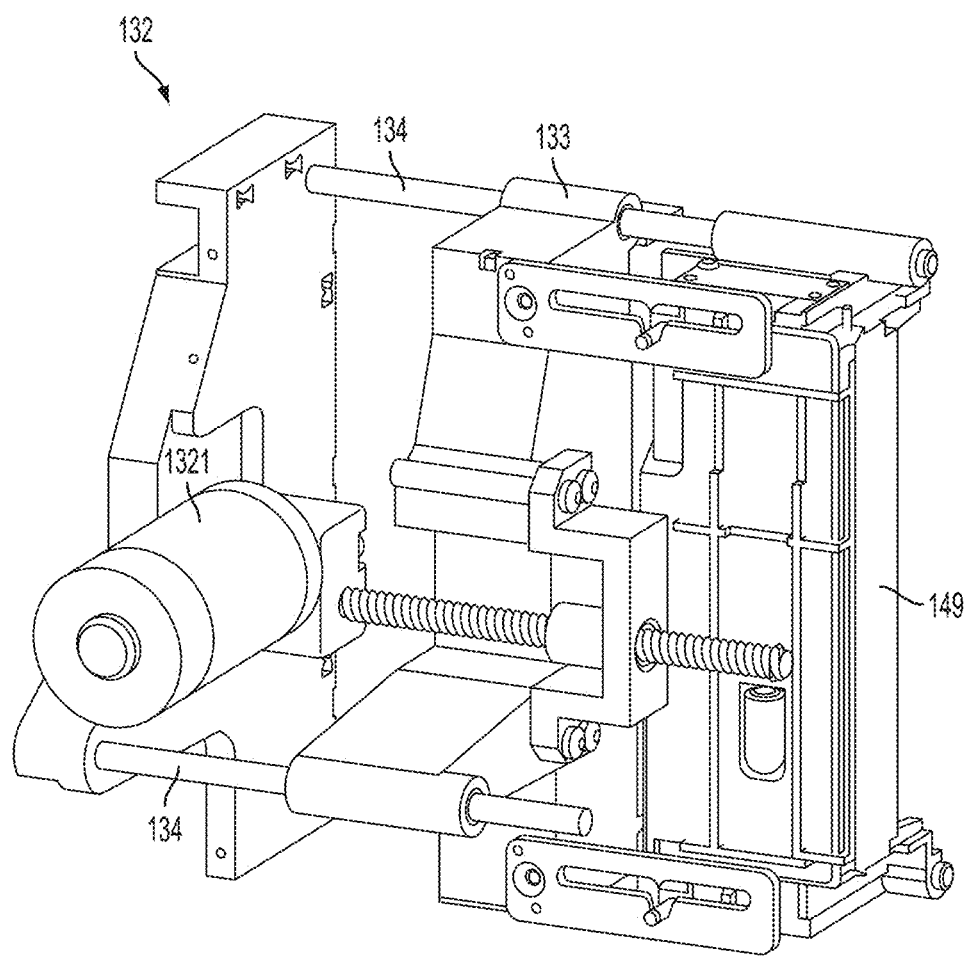
FIG. 28 is a left rear perspective view of the carriage drive assembly and cap stripper of FIG. 27.
Figure 29:
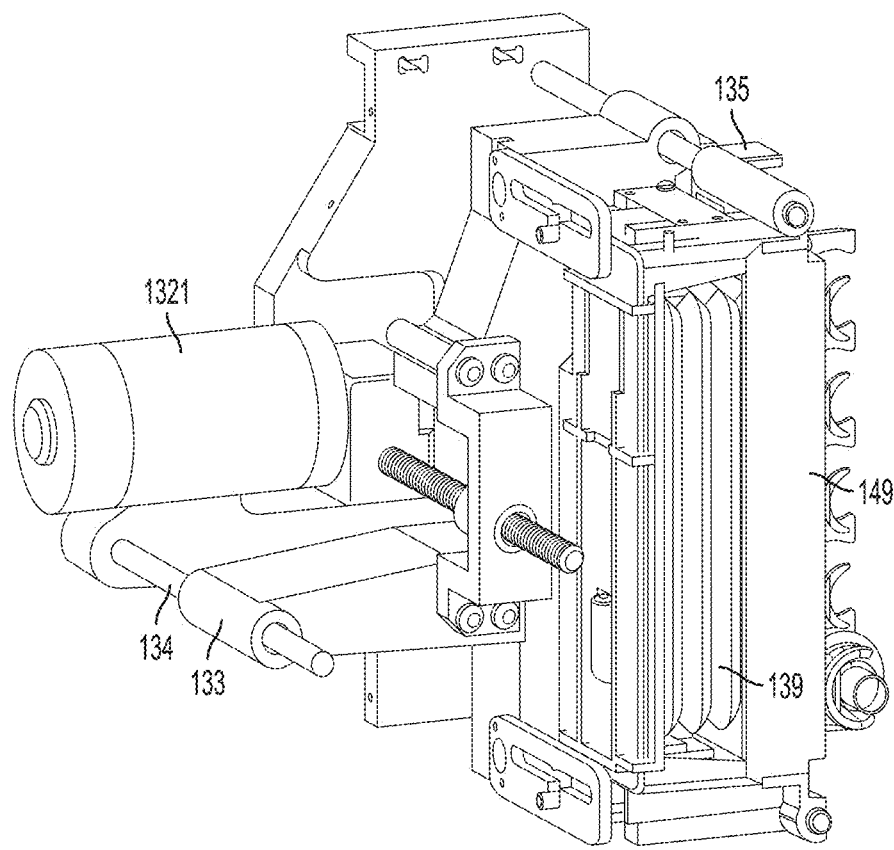
FIG. 29 is a left rear perspective view of a carriage drive assembly and cap stripper element.

FIG. 27 shows a partial rear view of the carriage drive assembly 132. In this embodiment, the drive element 133 is moved toward the cassette 24 mounting location 145 by a first air bladder 137 which expands to force the drive element 133 to move to the right in FIG. 27. The drive element can be moved to the left by a second air bladder 138. Alternatively, drive element 133 can be moved back and forth by means of one or more motors coupled to a linear drive gear assembly, such as a ball screw assembly (in which the carriage drive assembly is attached to a ball nut), or a rack and pinion assembly, for example. The stripper element 1491 of the cap stripper 149 can be moved in and out of the cap stripper housing by a third bladder, or alternatively, by a motor coupled to a linear drive assembly, as described previously.

FIGS. 28-30B show another embodiment of a carriage drive assembly 132 and cap stripper 149. As can be seen in the rear view of the carriage drive assembly 132 in FIG. 28, in this embodiment the drive element 133 is moved right and left by a screw drive mechanism 1321. As can be seen in the right rear perspective view of the carriage drive assembly 132 in FIG. 29, the stripper element is moved outwardly and inwardly by an air bladder 139, although other arrangements are possible as described above.

Figure 30A:
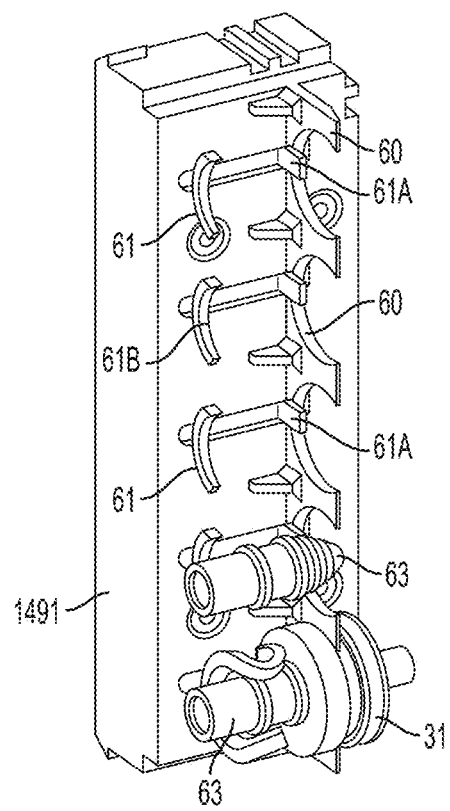
FIG. 30A is a left front perspective view of the cap stripper element of FIG. 29.
Figure 30B:
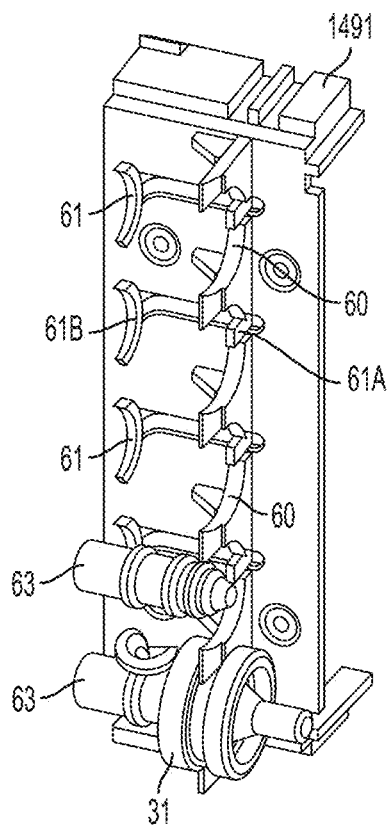
FIG. 30B is a right front perspective view of the cap stripper element of FIG. 29.

FIGS. 30A and 30B show left and right front perspective views of another embodiment for the stripper element 1491 of the cap stripper 149. The stripper element 1491 in the embodiment shown in FIG. 26 included only fork-shaped elements arranged to engage with a cap 31 of a solution line 30. In the FIGS. 30A and 30B embodiment, the stripper element 1491 not only includes the fork-shaped elements 60, but also rocker arms 61 that are pivotally mounted to the stripper element 1491. As will be explained in more detail below, the rocker arms 61 assist in removing spike caps 63 from the cassette 24. Each of the rocker arms 61 includes a solution line cap engagement portion 61a and a spike cap engagement portion 61b. The rocker arms 61 are normally biased to move so that the spike cap engagement portions 61b are positioned near the stripper element 1491, as shown in the rocker arms 61 in FIG. 30B. However, when a cap 31 is received by a corresponding fork-shaped element 60, the solution line cap engagement portion 61a contacts the cap 31, which causes the rocker arm 61 to pivot so that the spike cap engagement portion 61b moves away from the stripper element 1491, as shown in FIG. 30A. This position enables the spike cap engagement portion 61b to contact a spike cap 63, specifically a flange on the spike cap 63.

Figure 31:
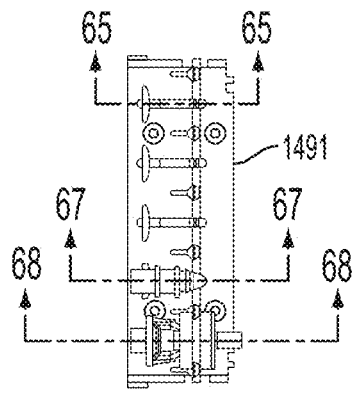
FIG. 31 is a front view of the cap stripper element of FIG. 29.
Figure 32:
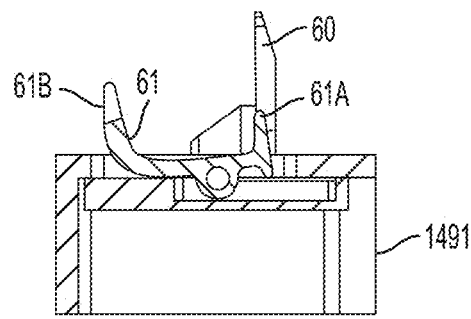
FIG. 32 is a cross sectional view along the line 65-65 in FIG. 31.
Figure 33:
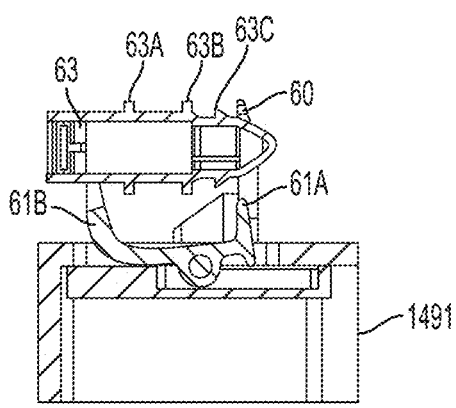
FIG. 33 is a cross sectional view along the line 66-66 in FIG. 31.
Figure 34:
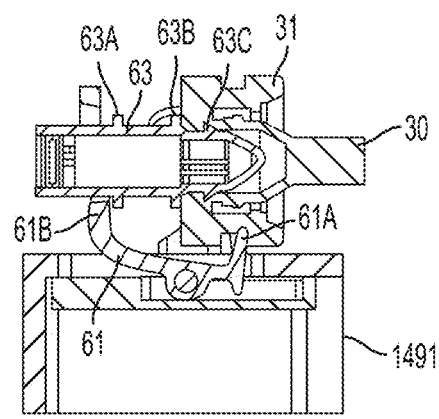
FIG. 34 is a cross sectional view along the line 67-67 in FIG. 31.

FIG. 31 shows a front view of the stripper element 1491 and the location of several cross-sectional views shown in FIGS. 32-34. FIG. 32 shows the rocker arm 61 with no spike cap 63 or solution line cap 31 positioned near the stripper element 1491. The rocker arm 61 is pivotally mounted to the stripper element 1491 at a point approximately midway between the spike cap engagement portion 61b and the solution cap engagement portion 61a. As mentioned above, the rocker arm 61 is normally biased to rotate in a counter-clockwise direction as shown in FIG. 32 so that the spike cap engagement portion 61b is positioned near the stripper element 1491. FIG. 33 shows that the rocker arm 61 maintains this position (i.e., with the spike cap engagement portion 61b located near the stripper element 1491) even when the stripper element 1491 advances toward a spike cap 63 in the absence of a solution line cap 31 engaging with the fork-shaped element 60. As a result, the rocker arm 61 will not rotate clockwise or engage the spike cap 63 unless a solution line cap 31 is present. Thus, a spike cap 63 that does not engage with a solution line cap 31 will not be removed from the cassette 24.

FIG. 34 shows an example in which a solution line cap 31 is engaged with the fork-shaped element 60 and contacts the solution line cap engagement portion 61a of the rocker arm 61. This causes the rocker arm 61 to rotate in a clockwise direction and the spike cap engagement portion 61b to engage with the spike cap 63. In this embodiment, engagement of the portion 61b includes positioning the portion 61b adjacent a second flange 63a on the spike cap 63 so that when the stripper element 1491 moves to the right (as shown in FIG. 34), the spike cap engagement portion 61b will contact the second flange 63a and help pull the spike cap 63 from the corresponding spike 160. Note that the solution line cap 31 is made of a flexible material, such as silicone rubber, to allow a barb 63c of the spike cap 63 to stretch the hole 31b of cap 31 (see FIG. 38) and be captured by a circumferential inner groove or recess within cap 31. A first flange 63b on the spike cap 63 acts as a stop for the end of solution line cap 31. In another example, the spike cap 63 does not include a first flange 63b. The walls defining the groove or recess in the cap 31 hole 31b may be symmetrical, or preferably asymmetrically arranged to conform to the shape of the barb 63c (see FIG. 51 for a cross sectional view of the cap 31 and the groove or recess). The second flange 63a on spike cap 63 acts as a tooth with which the spike cap engagement portion 61b of the rocker arm 61 engages in order to provide an additional pulling force to disengage the spike cap 63 from the spike 160, if necessary.

Figure 35:
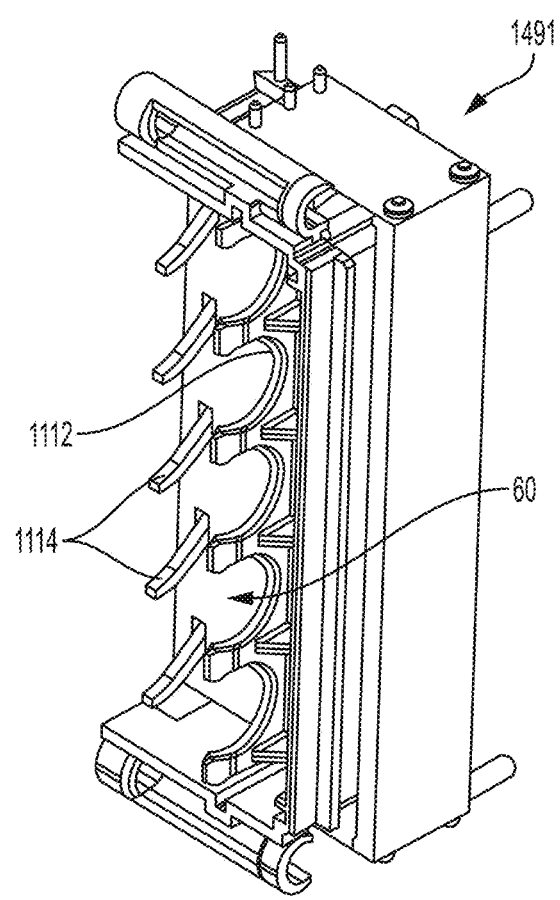
FIG. 35 is a perspective view of an embodiment for a stripper element of a cap stripper.
Figure 36:
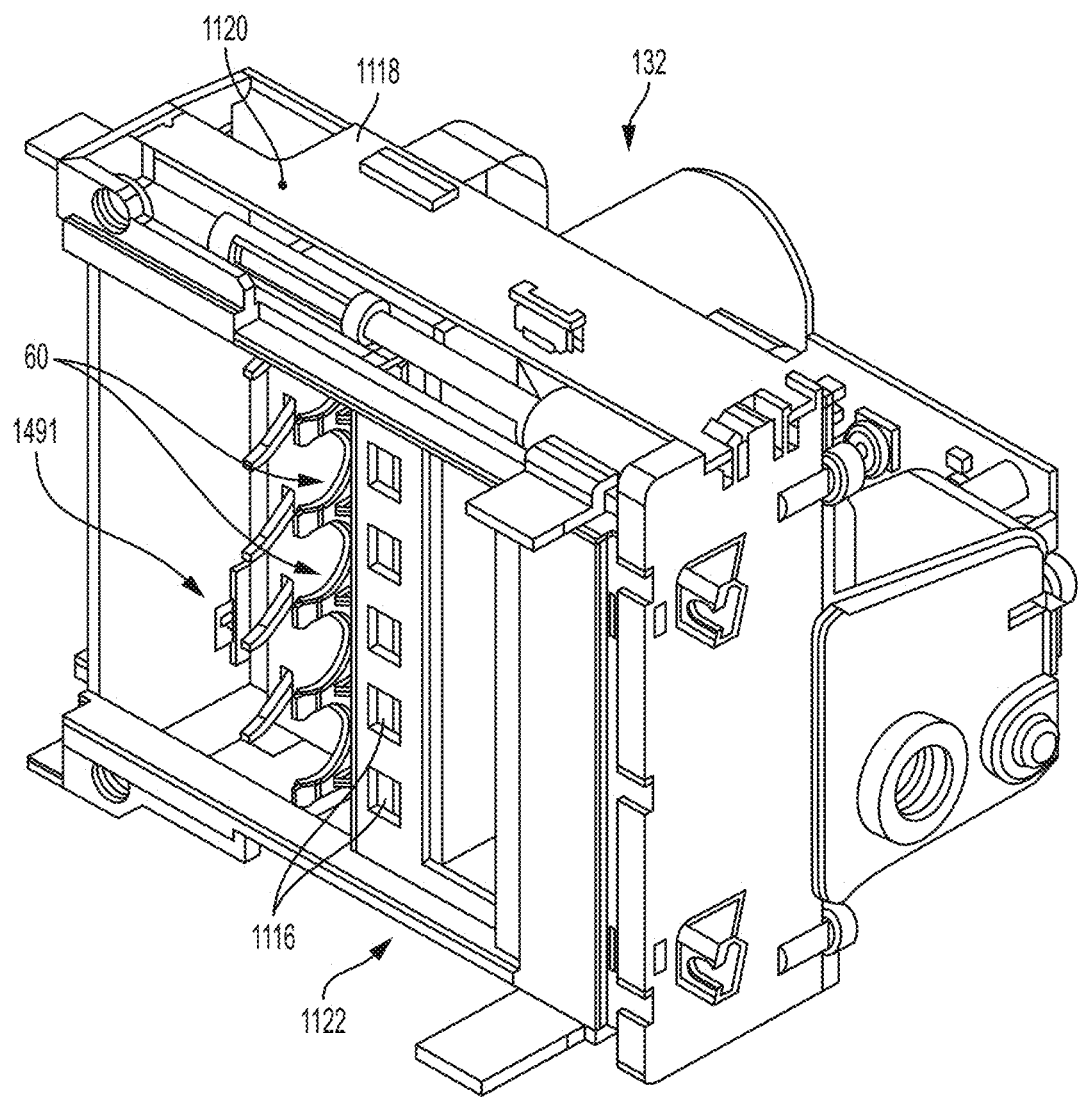
FIG. 36 is a front perspective view of the carriage drive assembly of FIG. 21 showing the position of the stripper element of FIG. 35 within the carriage drive assembly.

FIG. 35 and FIG. 36 show two different perspective views of another embodiment for the stripper element 1491 of the cap stripper 149. The stripper element 1491 in the embodiment shown in FIG. 26 uses fork-shaped elements 60 arranged to engage with a cap 31 of a solution line 30. In the embodiment shown in FIG. 35, the stripper element 1491 not only includes the fork-shaped elements 60, but may also include a plurality of sensing elements 1112, and a plurality of rocker arms 1114. The sensing elements 1112 and rocker arms 1114 may be arranged in two parallel columns that run vertically along the stripper element 1491. In an embodiment, each vertical column may contain five individual sensing elements 1112 and rocker arms 1114, each being positioned to generally align in a row corresponding with each of the fork-shaped elements 60. Each sensing element 1112 may be mechanically connected or linked to one of the corresponding rocker arms 1114. In addition, the assembly comprising each sensing element 1112 and rocker arm 1114 may include a biasing spring (not shown) that keeps each rocker arm 1114 biased toward a non-engagement position and sensing element 1112 in a position to be contacted and moved by the presence of a solution line cap 31 in fork-shaped element 60. Each sensing element 1112 can be displaced and tilted toward the back of the stripper element 1491 by contact with a corresponding solution line cap 31 in forked-shaped element 60. Through the mechanical connection between sensing element 1112 and rocker arm 1114, rocker arm 1114 can pivotally rotate or tilt laterally toward spike cap 63 upon contact between solution line cap 31 and sensing element 1112. As rocker arm 1114 rotates or tilts toward spike cap 63, it can engage second flange 63a on spike cap 63, allowing the stripper assembly to remove spike cap 63 from its corresponding spike.

Figures 37A, 37B, 37C:
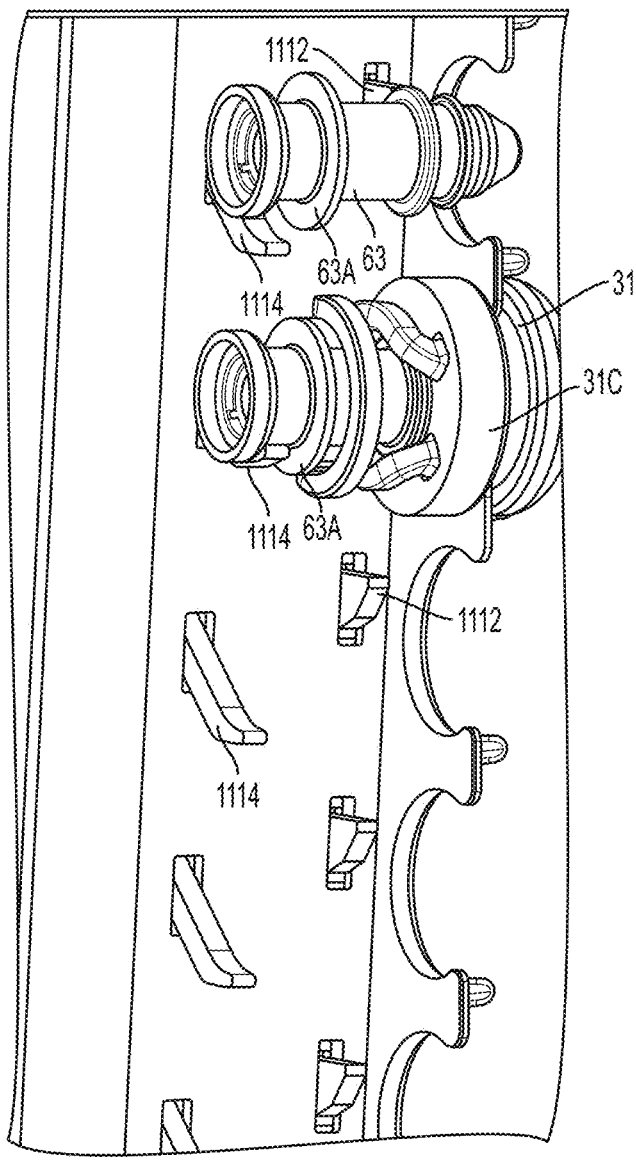
FIG. 37A is a perspective view of a portion of the stripper element of FIG. 35, in which a spike cap is positioned.
FIG. 37B is a perspective view of a portion of the stripper element of FIG. 35, in which a solution line cap is positioned over a spike cap.
FIG. 37C is a perspective view of a portion of the stripper element of FIG. 35, showing a sensor element and rocker arm in the absence of a spike cap.

FIGS. 37A-37C illustrate the relationship between sensing element 1112 and a solution line cap 31, and between rocker arm 1114 and spike cap 63. FIG. 37C shows the sensing element 1112 and rocker arm 1114 in the absence of a spike cap 63 and solution line cap 31. As shown in FIG. 37B, an outer flange 31c of solution line cap 31 has a diameter sufficiently large to make contact with sensing element 1112. As shown in FIG. 37A, in the absence of a solution line cap 31, the mere presence of spike cap 63 alone does not contact sensing element 1112 sufficiently enough to displace it and cause it to rotate away from spike cap 63. As shown in FIG. 37B, the displacement of sensing element 1112 causes rotation or tilting of rocker arm 1114 toward spike cap 63, ultimately to the point of being positioned adjacent flange 63a of spike cap 63. As shown in FIG. 37A, when rocker arm 1114 is in a non-deployed position, it can clear the outer circumference of second flange 63a of spike cap 63 by a pre-determined amount (e.g., 0.040 inch). Upon movement of rocker arm 1114 into a deployed position, its range of travel may be configured so as to provide a slight compression force against its corresponding spike cap 63 to ensure a secure engagement.

Once a rocker arm 1114 is positioned adjacent flange 63a of a spike cap 63, movement of stripper element 1491 to the right will engage spike cap 63 via flange 63a and help to pull spike cap 63 from its corresponding spike 160. In the absence of a solution line 30 and its associated solution line cap 31, stripper element 1491 will not remove the corresponding spike cap 63, keeping its associated spike 160 sealed. Thus, fewer than the maximum number of cassette spikes 161 may be accessed when fewer than the maximum number of solution lines need to be used.

Figure 38:
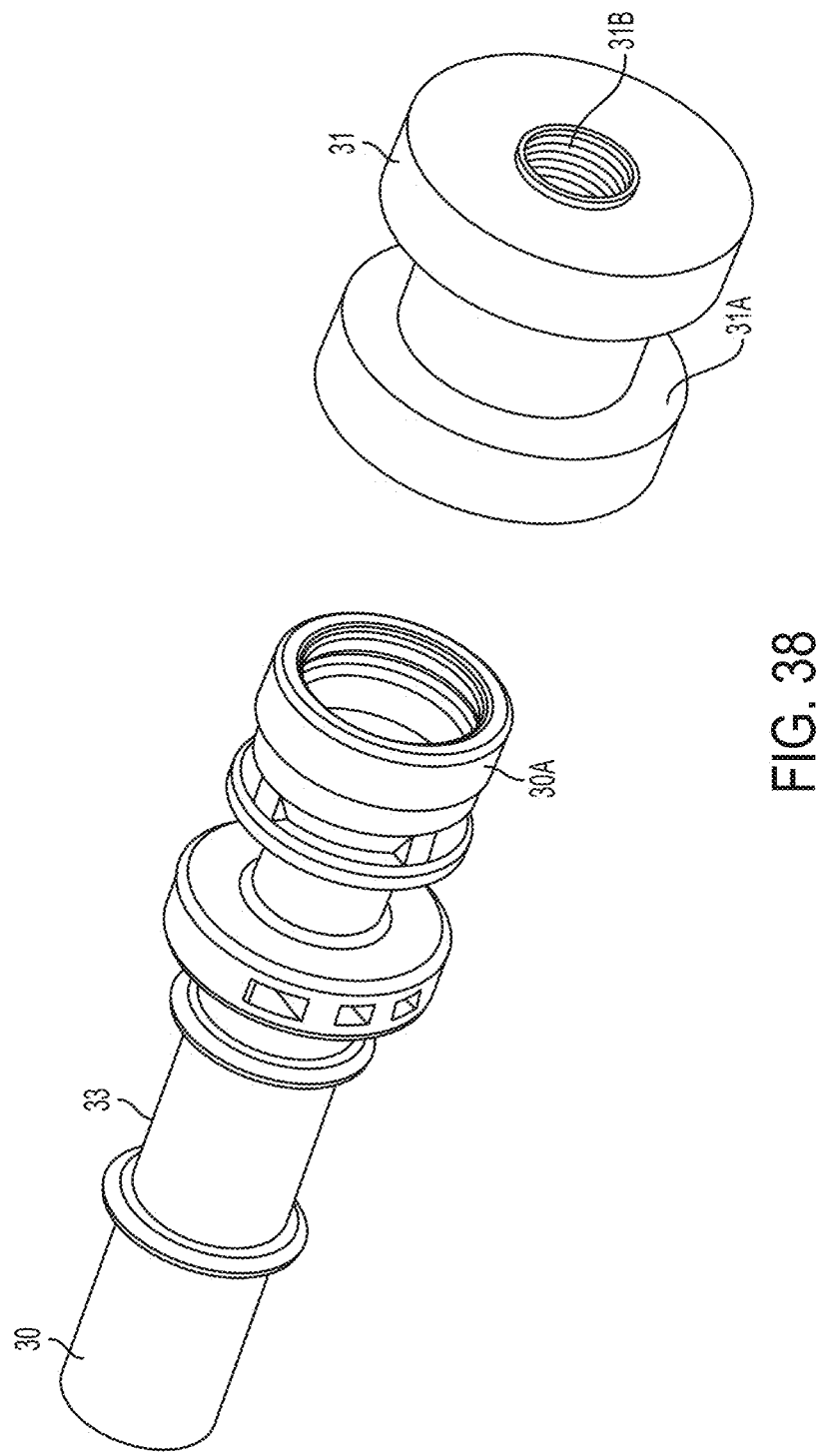
FIG. 38 is a close-up exploded view of the connector end of a solution line in an illustrative embodiment.

FIG. 38 shows a close-up exploded view of the connector end 30a of a solution line 30 with the cap 31 removed. In FIG. 38, the caps 31 are shown without a finger pull ring like that shown in FIG. 39 for clarity. A pull ring need not be present for operation of the cap 31 with the cycler 14. It may be useful, however, in allowing an operator to manually remove the cap 31 from the terminal end of solution line 30, if necessary. In this illustrative embodiment, the indicator at indicator region 33 has an annular shape that is sized and configured to fit within a corresponding slot of the carriage 146 when mounted as shown in FIGS. 16 and 17. Of course, the indicator may take any suitable form. The cap 31 is arranged to fit over the extreme distal end of the connector end 30a, which has an internal bore, seals, and/or other features to enable a leak-free connection with a spike 160 on a cassette 24. The connector end 30a may include a pierceable wall or septum (see FIG. 51 item 30b) that prevents leakage of solution in the line 30 from the connector end 30a, even if the cap 31 is removed. The wall or septum may be pierced by the spike 160 when the connector end 30a is attached to the cassette 24, allowing flow from the line 30 to the cassette 24. As discussed above, the cap 31 may include a groove 31a that is engaged by a fork-shaped element 60 of the cap stripper 149. The cap 31 may also include a hole 31b that is arranged to receive a spike cap 63. The hole 31b and the cap 31 may be arranged so that, with the cap stripper 149 engaged with the groove 31a and the spike cap 63 of a spike 160 received in the hole 31b, the cap 31 may grip the spike cap 63 suitably so that when the carriage 146/cap stripper 149 pulls the cap 31 away from the cassette 24, the spike cap 63 is removed from the spike 160 and is carried by the cap 31. This removal may be assisted by the rocker arm 61 engaging with the second flange 63a or other feature on the spike cap 63, as described above. Thereafter, the cap 31 and spike cap 63 may be removed from the connector end 30a and the line 30 attached to the spike 160 by the carriage 146.

Solution Line Connector Heater

In one embodiment, a connector heater may be provided near the indicator region 33 of the solution lines 30. The connector heater may control the temperature of the connector end 30a and in particular the pierceable wall or septum 30b in order to limit the carriage force required attach the solution lines to the spikes 160 on the cassette 24. There may be enough variation in ambient (room) temperature to affect the hardness of the pierceable wall or septum 30b of the connector end 30a of the solution line, which may in turn affect the performance of the carriage 146 in joining the spike 160 to the connector end 30a of the solution line 30. For example, at lower ambient temperatures, the increased hardness of the pierceable wall or septum 30b may require a greater force for spike 160 to penetrate it. On the other hand, at higher ambient temperatures, the pierceable wall or septum may be so soft as to deform rather than separate when contacted by the spike 160.

The temperature of the connector ends 30a may be controlled in a number of ways, which may include placing a heating element in an appropriate location (e.g., at or near location 2807 on the door 141), installing a temperature sensor to monitor the temperature of connector ends 30a, and using a controller to receive temperature data and modulate the operation of the heating element. The temperature may be measured by a temperature sensor element mounted on the stripper element 1491 or on the carriage 146. Alternatively, the temperature of the connector end 30a may be determined using an infrared (IR) sensor tuned to measure surface temperature of the connector end 30a.

The controller may be a software process in the automation computer 300. Alternatively, the controller may be implemented in the hardware interface 310. The controller may modulate the power sent to a resistance heater, for example, in one of a number of ways. For example, the controller may send a PWM signal to a MOSFET that can modulate the flow of electrical power to the resistance heater. The controller may control the measured temperature to the desired temperature through a number of algorithms. One exemplary algorithm includes a proportional-integral (PI) feedback loop on the measured temperature to set the heater power. Alternatively, the heater power can be modulated in an open loop algorithm that sets the heater power based on the measured ambient temperature.

In another embodiment, the temperature of the connector end 30a may be controlled by mounting a radiant heater in the door 141 at location 2807, for example, and aimed at the connector ends. Alternatively, the temperature of the connector ends may be controlled by mounting a thermo-electric element at location 2807, for example, on the door 141. The thermo-electric element may provide either heating or cooling to the area surrounding the connector ends when mounted on the carriage 146. The radiant heater or thermo-electric element may be modulated by a controller to maintain the temperature within a given range. The preferred temperature range for the connector end 30a depends on the material comprising the pierceable wall or septum, and may be determined empirically. In one embodiment, the piercable wall is PVC and the preferred temperature range is set at about 10° C. to 30° C., or more preferably to a temperature range of about 20° C. to 30° C.

In an embodiment, the connector heater near the indicator region 33 may be used after the door is closed and before the solution lines 30 are attached to the cassette 24. The automation computer 300 or a controller enables the connector heater if the measured temperature near the connector 30a is outside a preferred range. The automation computer 300 or a controller may delay the auto-connection process until the measured temperature is within the preferred range. The connector heater may be disabled after the auto-connection process is completed.

Set Loading and Operation Continued

Once treatment is complete, or the line 30 and/or the cassette 24 are ready for removal from cycler 14, the cap 31 and attached spike cap 63 may be re-mounted on the spike 160 and the line 30 before the door 141 is permitted to be opened and the cassette 24 and line 30 removed from the cycler 14. Alternatively, the cassette 24 and solution containers with lines 30 can be removed en bloc from cycler 14 without re-mounting cap 31 and the attached spike cap 63. An advantage of this approach includes a simplified removal process, and avoidance of any possible fluid leaks onto the cycler 14 or surrounding area from improperly re-mounted or inadequately sealing caps.

Figure 39:
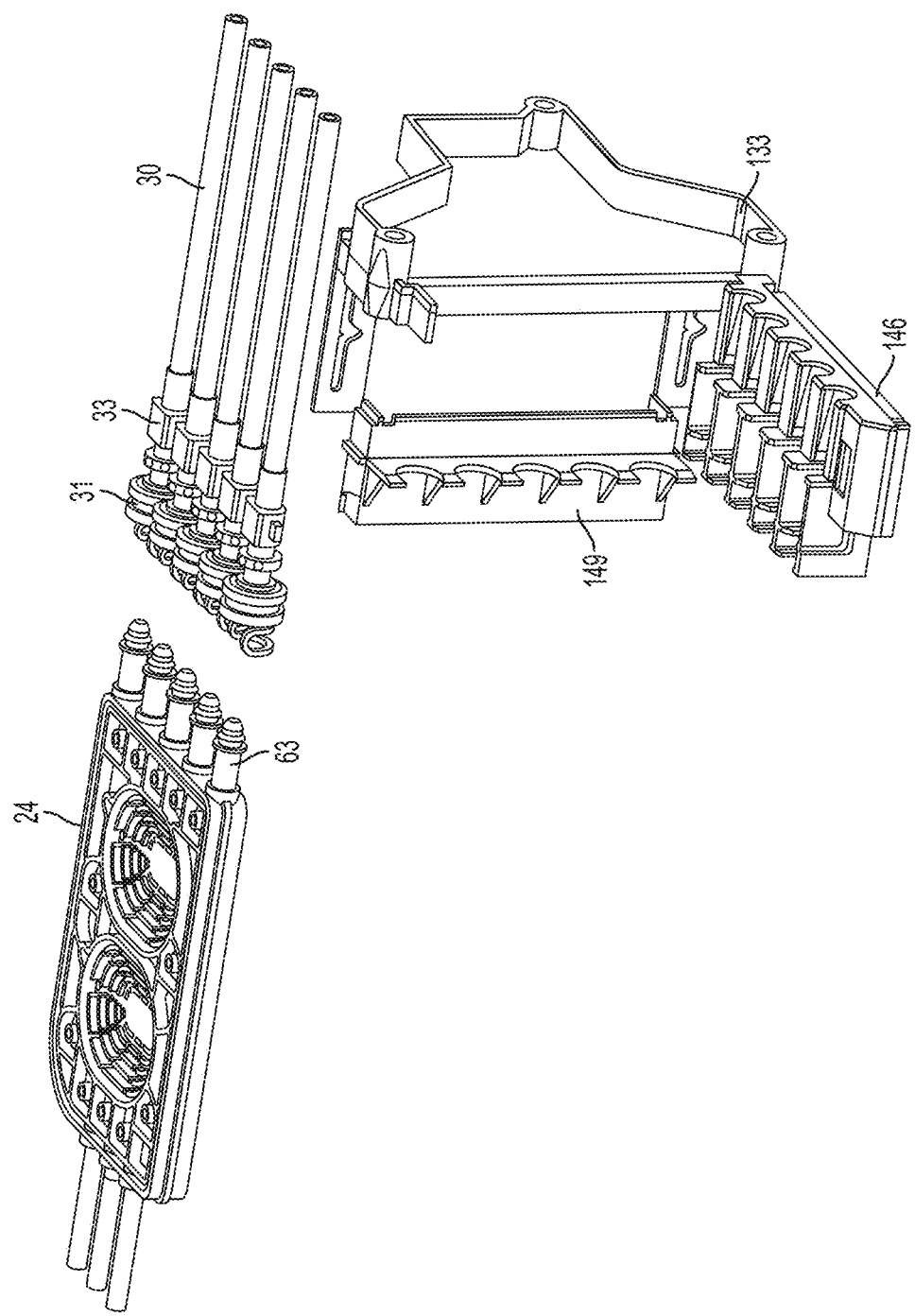
FIG. 39 is a schematic view of a cassette and solution lines being loaded into the cycler of FIG. 16.
Figure 40:
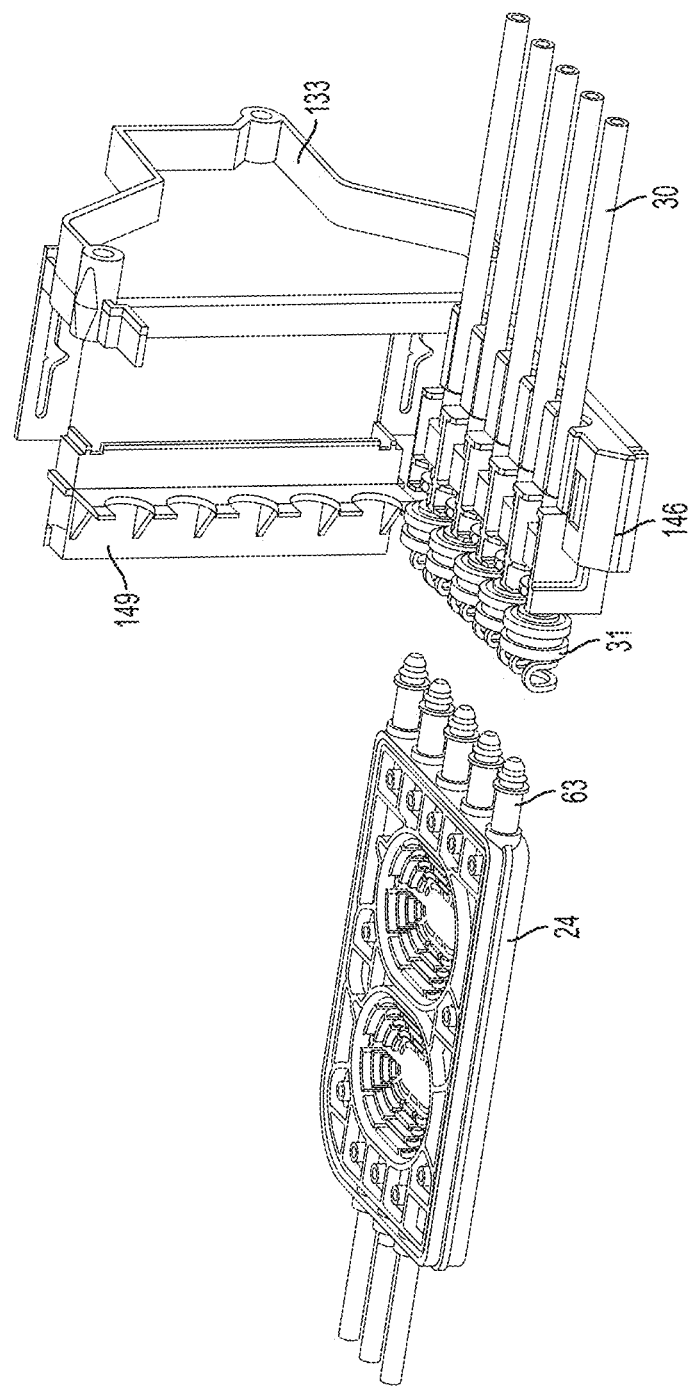
FIG. 40 is a schematic view of the cassette and solution lines after placement in respective locations of the door of the cycler of FIG. 16.
Figure 41:
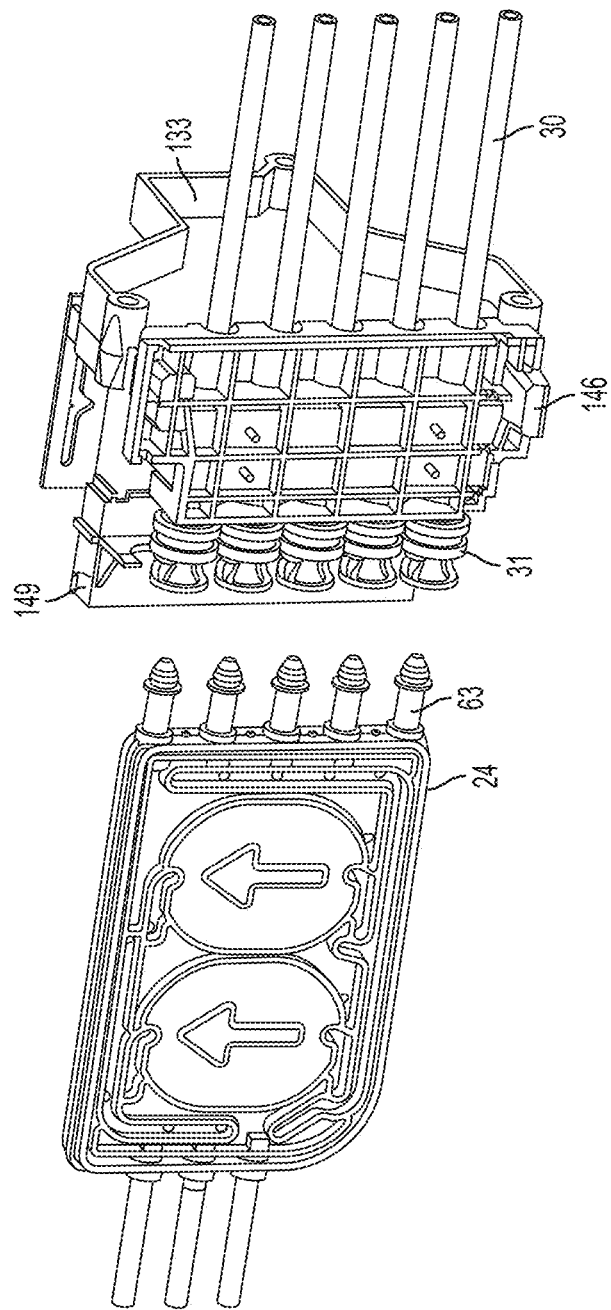
FIG. 41 is a schematic view of the cassette and solution lines after the door of the cycler is closed.
Figure 42:
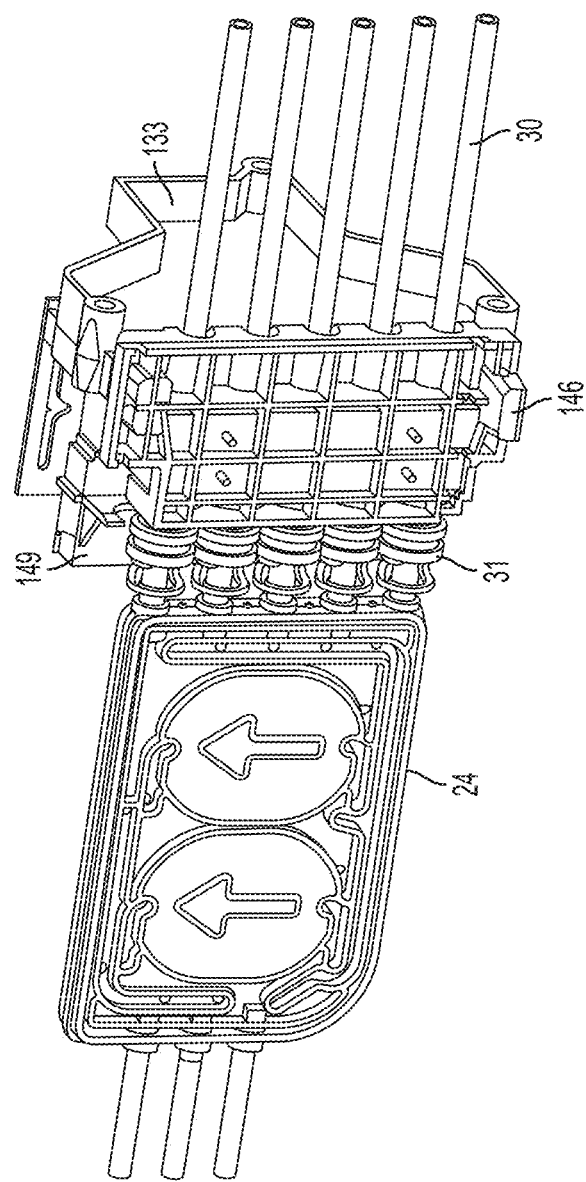
FIG. 42 is a schematic view of the solution lines being engaged with spike caps.
Figure 43:
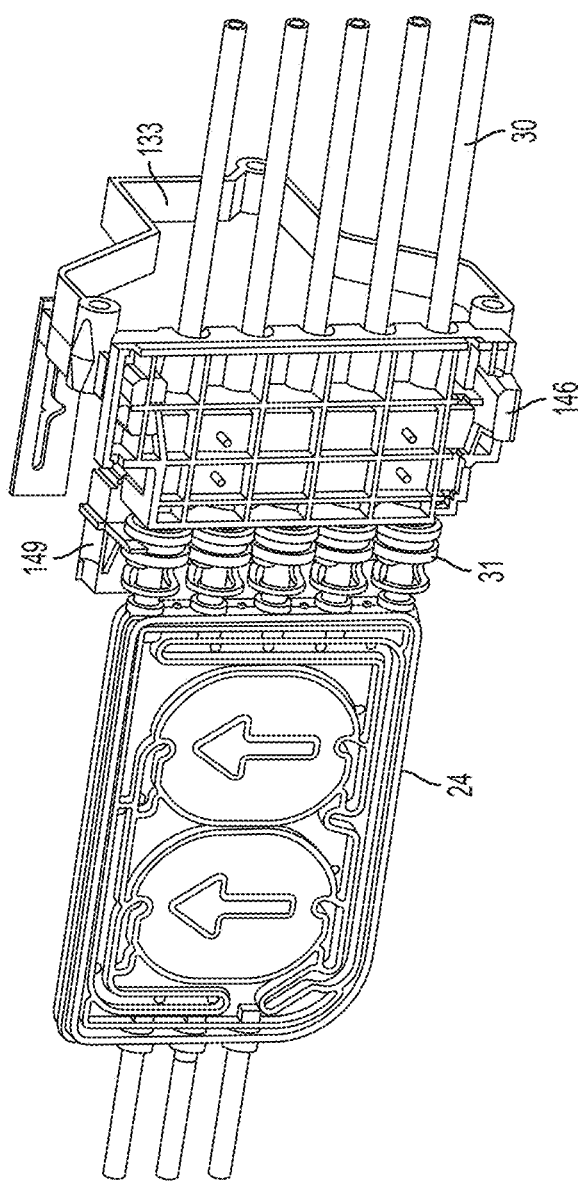
FIG. 43 is a schematic view of the cap stripper engaging with spike caps and solution line caps.
Figure 44:
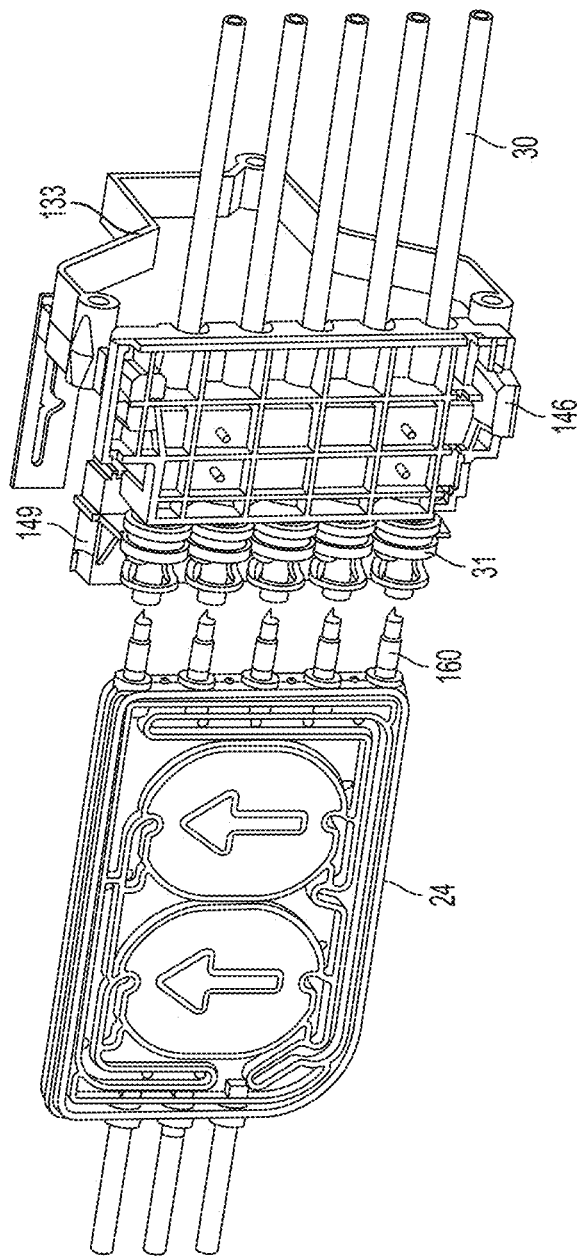
FIG. 44 is a schematic view of the solution lines with attached caps and spike caps after movement away from the cassette.
Figure 45:
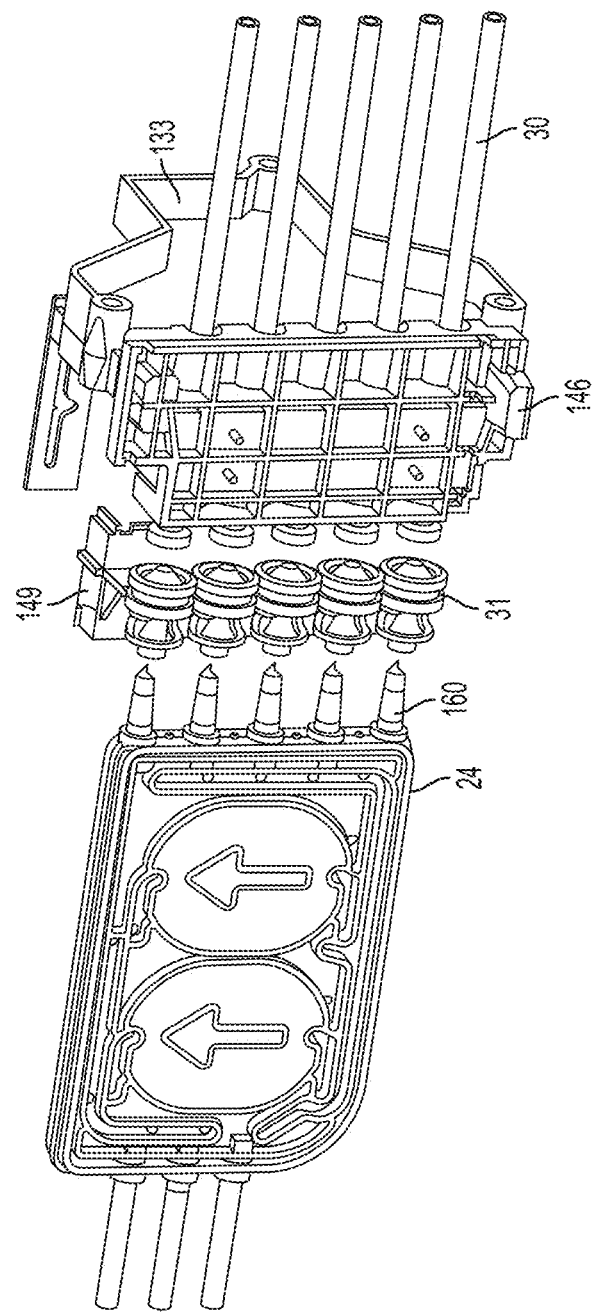
FIG. 45 is a schematic view of the solution lines after movement away from the solution line caps and spike caps.
Figure 46:
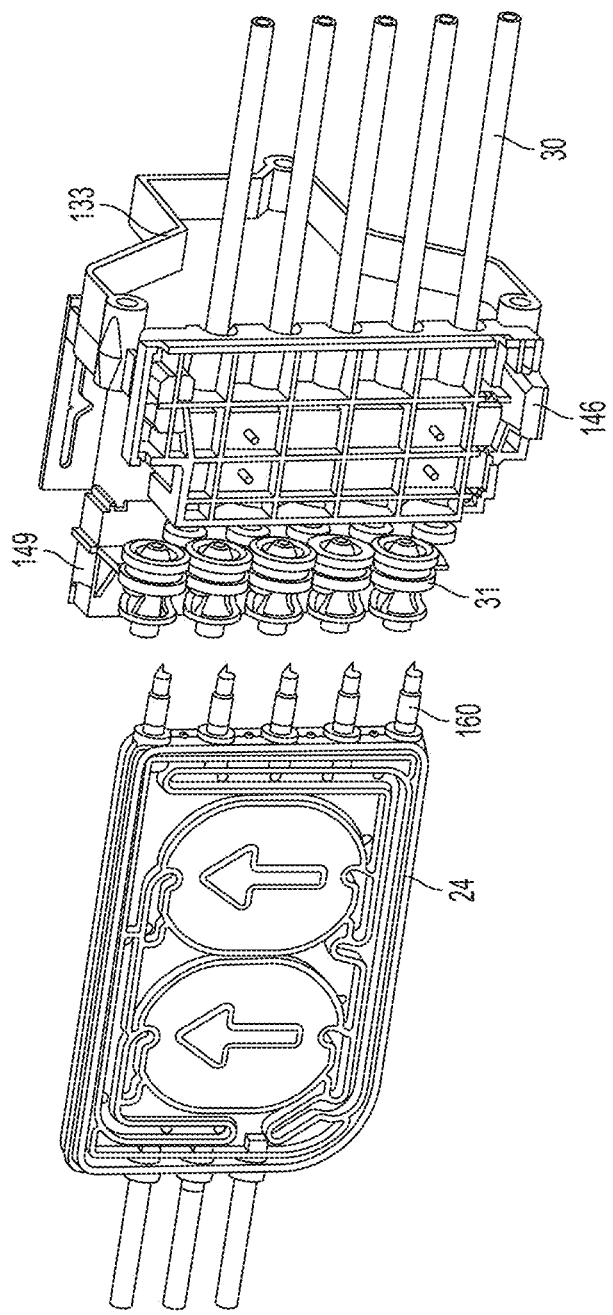
FIG. 46 is a schematic view of the cap stripper retracting with the solution line caps and spike caps.
Figure 47:
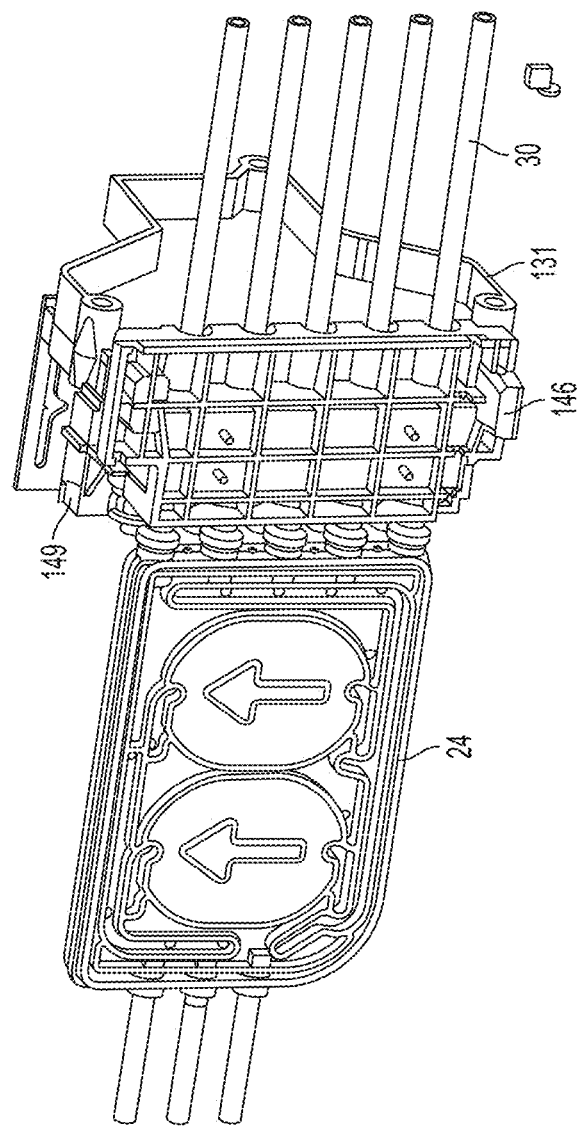
FIG. 47 is a schematic view of the solution lines being engaged with the spikes of the cassette.

FIGS. 39-47 show a perspective view of the carriage 146, cap stripper 149 and cassette 24 during a line mounting and automatic connection operation. The door 141 and other cycler 14 components are not shown for clarity. In FIG. 39, the carriage 146 is shown in a folded down position, as if the door 141 is open in the position shown in FIG. 16. The lines 30 and cassette 24 are positioned to be lowered onto the door 141. In FIG. 40, the lines 30 are loaded into the carriage 146 and the cassette 24 is loaded into the mounting location 145. At this point the door 141 can be closed to ready the cycler for operation. In FIG. 41, the door 141 is closed. Identifiers or indicators located at indicator region 33 on the lines 30 may be read to identify various line characteristics so that the cycler 14 can determine what solutions, how much solution, etc., are loaded. In FIG. 42, the carriage 146 has moved to the left, engaging the caps 31 on the lines 30 with corresponding spike caps 63 on the cassette 24. During the motion, the drive element 133 engages the cap stripper 149 and moves the cap stripper 149 to the left as well. However, the cap stripper 149 remains in a retracted position. In FIG. 43, the cap stripper 149 moves forward to engage the fork-shaped elements 60 with the caps 31, thereby engaging the caps 31 that have been coupled to the spike caps 63. If present, the rocker arms 61 may move to an engagement position with respect to the spike caps 63. Next, as shown in FIG. 44, the carriage 146 and the cap stripper 149 move to the right, away from the cassette 24 so as to pull the caps 31 and spike caps 63 from the corresponding spikes 160 on the cassette 24. It is during this motion that the rocker arms 61, if present, may assist in pulling spike caps 63 from the cassette 24. In FIG. 45, the cap stripper 149 has stopped its movement to the right, while the carriage 146 continues to move away from the cassette 24. This causes the connector ends 30a of the lines 30 to be pulled from the caps 31, leaving the caps 31 and spike caps 63 mounted on the cap stripper 149 by way of the fork-shaped elements 60. In FIG. 46, the cap stripper 149 retracts, clearing a path for the carriage 146 to move again toward the cassette 24. In FIG. 47, the carriage 146 moves toward the cassette 24 to engage the connector ends 30a of the lines 30 with the corresponding spikes 160 of the cassette 24. The carriage 146 may remain in this position during cycler 14 operation. Once treatment is complete, the movements shown in FIGS. 39-47 may be reversed to recap the spikes 160 and the solution lines 30 and remove the cassette 24 and/or lines 30 from the cycler 14.

The cycler 14 can be configured to verify that all caps 31 have been removed from the cap stripper 149 before any attempt is made to start a new therapy using the cycler 14. In an embodiment, this may be performed before a new cassette 24 and solution line set have been installed in the cycler 14—either at the end of a therapy or during the startup period preceding a new therapy. Alternatively or additionally, a residual cap detection procedure can be performed after the installation of a new cassette and solution line set, but preferably before any cassette spike caps have been engaged with solution line caps 31.

The cap detection system comprises a sensor to detect the position of the cap stripper relative to a plane in which an installed cassette and set of one or more solution lines reside when mounted in the cycler. Movement of the cap stripper forward or aft (i.e. toward or away from the plane) can be monitored by a cycler controller using a position sensor (e.g., Hall sensor). If a solution line cap/spike cap has not been removed from the cap stripper by the user, its presence will interfere with movement of the cap stripper toward the plane to a pre-determined position corresponding to full deployment of the cap stripper. The presence of a cap on the cap stripper, interfering with full deployment of the cap stripper toward the plane can cause the controller to issue an alert to the user. If one or more solution lines 30 have been mounted in the cycler 14, the interference will likely be between the remaining one or more caps on the cap stripper and the one or more caps of the solution lines. If no solution lines have been mounted in the cycler, the controller can command the cap stripper to move laterally in a direction parallel to the plane to a point at which a raised feature of the carriage (e.g., walls 5510a or 5510b) provided an interference with any remaining cap in the cap stripper during a commanded movement of the cap stripper toward the plane.

In an embodiment, position sensors for the cap stripper 149 are configured to detect the extent of forward deployment of the cap stripper toward the carriage when the door 141 is closed. After the door 141 is closed (FIG. 41) and before any lateral movement of the carriage 146, the cycler controller initiates a forward deployment of the cap stripper 149. The position of the cap stripper 149 may be monitored by one or more displacement sensors or by a camera aimed at the appropriate location. For example, one or more Hall effect sensors can be configured to sense a magnet embedded in or attached to the cap stripper 149. If one or more cap(s) 31 from a previous mounting operation remain in the cap stripper 149, the leftover cap 31 will be pushed against a newly installed solution line and cap 31 on the carriage 146, preventing the cap stripper 149 from displacing to a fully deployed position. If no new cassette or solution line set have been installed, the cycler controller can direct the movement of the carriage 146 laterally to a pre-determined location that causes one or more features of the carriage 146 to act as an interference element against a residual cap 31 on the cap stripper 149, but that allows the cap stripper 149 to fully deploy if it is not holding a residual cap 31. In some embodiments, the cap stripper 149 may be required to move beyond a predetermined threshold location for the auto-connect process to be allowed to continue. The predetermined threshold location may be chosen such that it is sufficiently beyond the point at which deployment of the cap stripper 149 would be impeded if a leftover cap 31 is present.

The Hall effect sensor may be installed in a location that is protected, separate, partitioned from, or fluidically isolated from the cap stripper 149 while still being able to sense a magnet on the cap stripper 149.

If the cap stripper 149 is deployed by means of an inflatable bladder, the bladder can optionally not be inflated to maximum pressure when checking for leftover caps 31. Instead an inflation pressure need only be sufficient to cause to cap stripper 149 to displace toward the carriage 146, but less than a pressure needed to actually engage a solution line cap installed in the carriage. This pressure may, for example, be a predetermined pressure; or it may be variable, reaching a level necessary to move the cap stripper 149. In such embodiments, once the position sensor detects movement the controller may either cease bladder inflation or limit inflation pressure. In some embodiments, the controller may require the cap stripper 149 to deploy by a predetermined amount before the bladder inflation pressure is limited.

In embodiments in which a mechanism other than an inflatable bladder is used to move the cap stripper 149, other devices may be introduced to limit the force applied by the deployment mechanism during this pre-therapy cap detection test. For example, a torque or pressure sensor or strain gauge may be connected to a gear and motor assembly to feed back similar information to the controller to limit the force applied by the assembly.

Other position sensors may be used, including but not limited to, an optical sensor, contact sensor (e.g. microswitch), rangefinding sensor, etc. In other embodiments, the cycler may use sensing elements 1112 (see, for example, FIG. 35) to determine if caps 31 are present in the cap stripper 149. A camera can be used to identify a characteristic of a cap 31 on the cap stripper 149, such as its shape, color, opacity, light absorption or reflection characteristics, etc.

Figure 48:
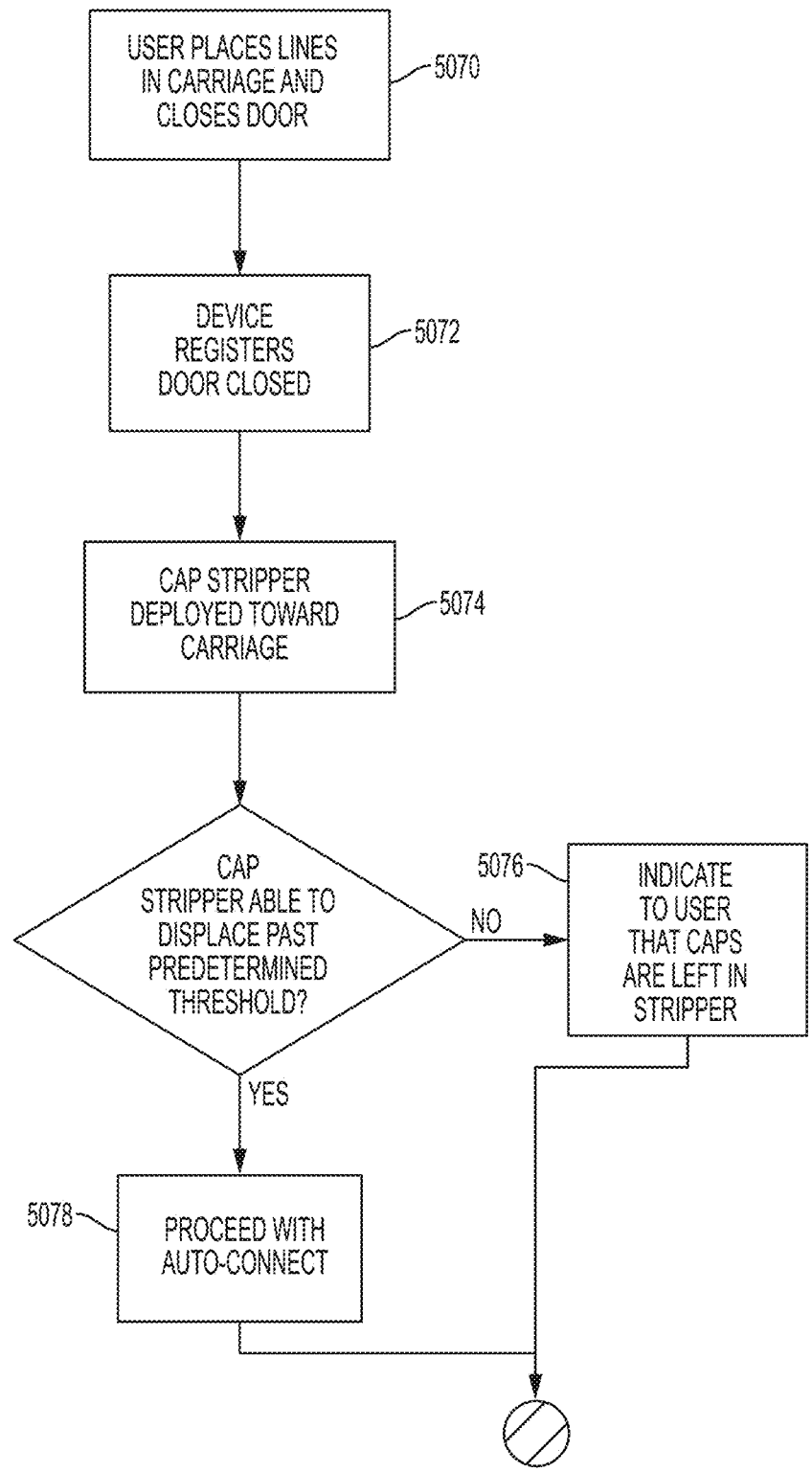
FIG. 48 depicts a flowchart detailing a number of example steps which may be used to detect the presence of leftover caps in a cap stripper.

FIG. 48 depicts a flowchart detailing an example of a number of steps that may be used to detect the presence of leftover caps 31 in a cap stripper 149. The steps shown in FIG. 48 detect the presence of leftover caps 31 by deploying the cap stripper 149 and monitoring its displacement. Additionally, the flowchart shown in FIG. 48 checks for the presences of caps 31 in the cap stripper 149 after a set has been installed in the cycler. The test may be performed before and/or after a cassette and solution lines have been installed.

As shown, in step 5070, a user may place the solution lines in the carriage 146 and close the door of the cycler. In step 5072, the cycler may register that the door of the cycler has been closed. After the cycler registers that the door has been closed, the cycler may deploy the cap stripper 149 toward the carriage 146 in step 5074.

The procedure may be performed before installation of a new cassette and solution line set. In such an embodiment, the steps 5070 and 5072 may not be performed. Instead, a step in which the carriage 149 is moved laterally to a pre-determined position may be performed. The predetermined position may be selected such that the carriage 149 acts as an interference element for the cap-bearing cap stripper 149.

The cycler may then check to see if the cap stripper 149 is able to displace past a predetermined threshold location. In the event that the cap stripper 149 is unable to displace beyond the predetermined location, a user may be notified of the presence of caps 31 left in the cap stripper 149 in step 5076. If the cap stripper 149 is able to displace beyond the predetermined threshold, a cycler may proceed with later steps of a solution line connection process in step 5078. In this step, the cycler may, for example, connect the cassette spike caps to the solution line caps installed in the carriage.

Figure 49:
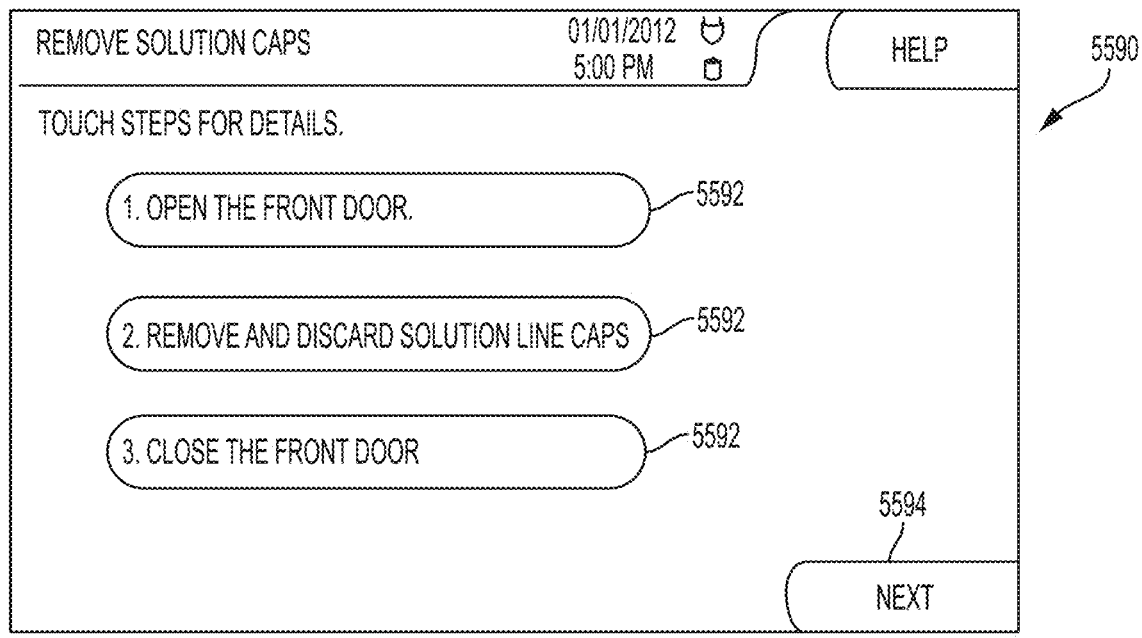
FIG. 49 depicts an example screen which may be generated for display on a user interface of a cycler by a processor of the cycler the displays instructions on how to remove caps from a cap stripper.

FIG. 49 depicts an example screen shot 5590 which may be generated for display on a user interface of a cycler by a processor of the cycler. The example screen 5590 shown in FIG. 49 may for example, be displayed in step 5076 of FIG. 48. As shown, the example screen 5590 informs a user that there are solution line caps present in the cap stripper of the cycler. The screen 5590 also includes instructions on how to remove the solution line caps from the cap stripper. In the example embodiment, the instructions are text instructions, though in other embodiments, the instructions may include any combination of text, graphics, and/or animations.

The instructions are divided into a number of steps which may be associated with user selectable buttons 5592 on the user interface. For example, the user interface of the cycler may be a touch screen. A user may touch, tap, double tap, etc. one of the selectable buttons 5592 on the screen 5590 to get more detailed instructions on how to perform the associated step. For example, when the processor of the cycler detects that a user has interacted with one of the buttons 5592, the processor may generate a message for display on the screen 5590 with additional detail, or may display a new screen with additional information. Alternatively, when the processor of the cycler detects that a user has interacted with one of the buttons 5592, the processor may generate another screen for display that provides additional detail.

The screen 5590 also includes a next button 5594. A user may interact with the next button 5594 to inform the processor of the cycler that the residual caps have been removed from the cap stripper. In some embodiments, the cycler may re-check for caps to verify that they have been removed from the cap stripper. Optionally, the next button may be disabled until the cycler processor detects that the door of the cycler has been opened and closed.

Figure 50:
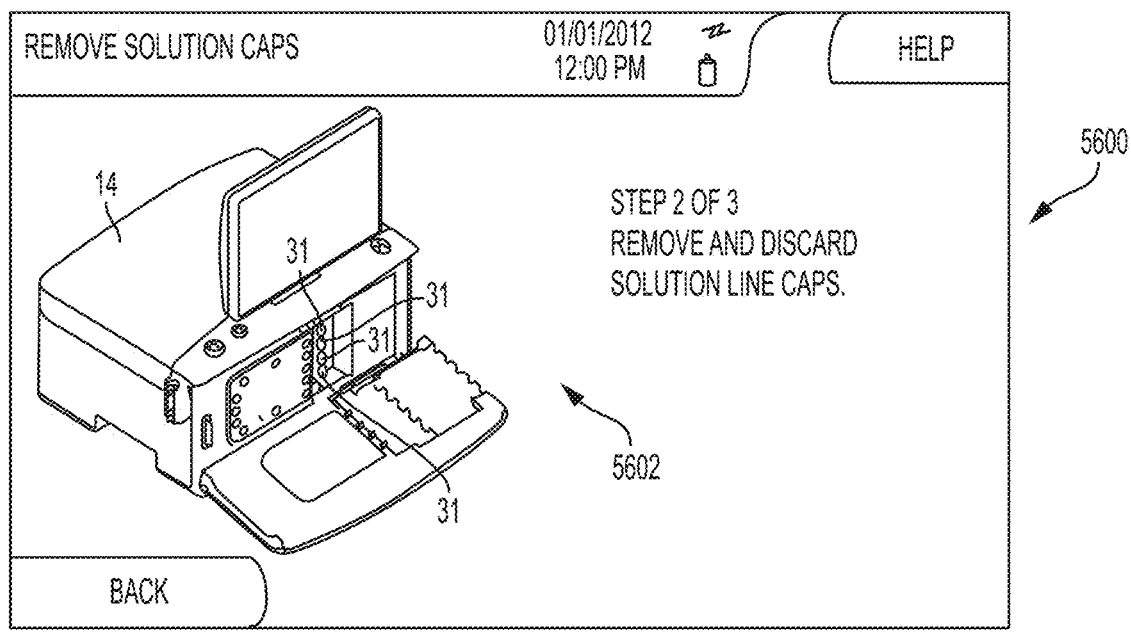
FIG. 50 depicts an example screen which may be generated for display on a user interface of a cycler by a processor of the cycler that displays instructions on how to remove caps from a cap stripper.

FIG. 50 depicts an example screen 5600 which may be generated for display on a user interface of a cycler by a processor of the cycler. The example screen 5600 shown in FIG. 50 may for example, be displayed in response to a user interacting with the button 5592 labeled "Remove and discard solution line caps." in FIG. 49. The example screen 5600 includes text describing how the user may complete the step. Additionally, the example screen 5600 includes a graphic 5602 of a cycler 14. The graphic 5602 may indicate to a user where the solution line cap 31 or caps 31 are located. In some embodiments, the screen 5600 may optionally include an animation which demonstrates to the user how to remove the solution line caps 31.

Figure 51:
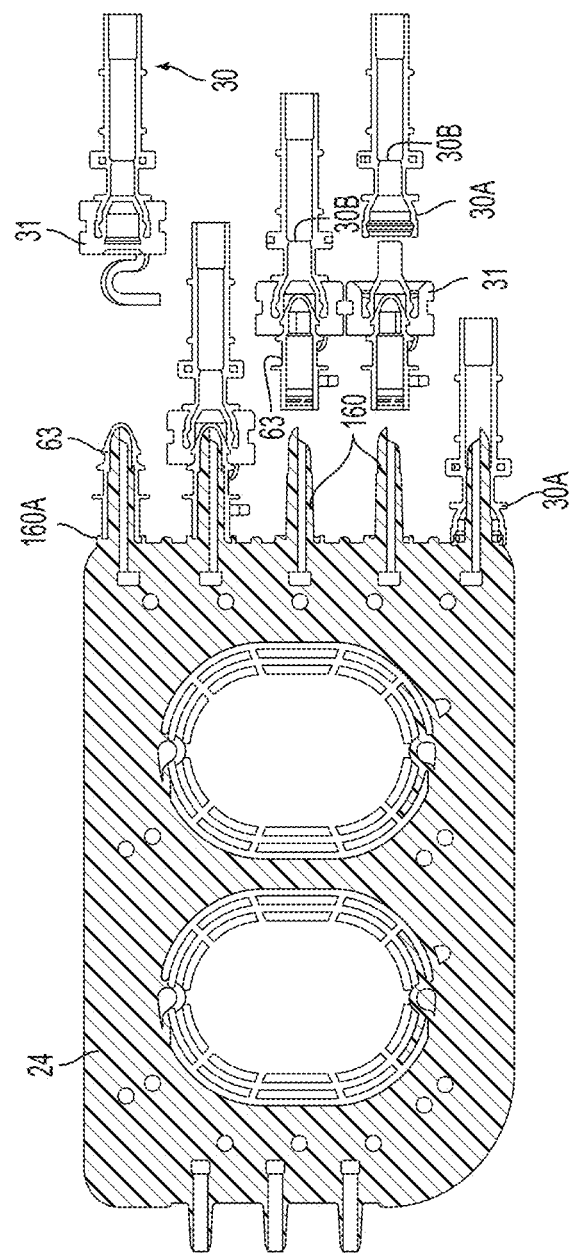
FIG. 51 is a cross sectional view of a cassette with five stages of a solution line connection operation shown with respect to corresponding spikes of the cassette.

To further illustrate the removal of caps 31 and spike caps 63, FIG. 51 shows a cross-sectional view of the cassette 24 at five different stages of line 30 connection. At the top spike 160, the spike cap 63 is still in place on the spike 160 and the solution line 30 is positioned away from the cassette 24, as in FIG. 41. At the second spike 160 down from the top, the solution line 30 and cap 31 are engaged over the spike cap 63, as in FIGS. 42 and 43. At this point, the cap stripper 149 may engage the cap 31 and spike cap 63. At the third spike 160 from the top, the solution line 30, cap 31 and spike cap 63 have moved away from the cassette 24, as in FIG. 44. At this point, the cap stripper 149 may stop movement to the right. At the fourth spike 160 from the top, the solution line 30 continues movement to the right, removing the cap 31 from the line 30, as in FIG. 45. Once the caps 31 and 63 are retracted, the solution line 30 moves to the left to fluidly connect the connector end 30a of the line 30 to the spike 160, as in FIG. 47.

Various sensors can be used to help verify that the carriage 146 and cap stripper 149 move fully to their expected positions. In an embodiment, the carriage drive assembly 132 can be equipped with six Hall effect sensors (not shown): four for the carriage 146 and two for the cap stripper 149. A first cap stripper sensor may be located to detect when the cap stripper 149 is fully retracted. A second cap stripper sensor may be located to detect when the cap stripper 149 is fully extended. A first carriage sensor may be located to detect when the carriage 146 is in the "home" position, i.e. in position to permit loading the cassette 24 and lines 30. A second carriage sensor may be located to detect when the carriage 146 is in position to have engaged the spike caps 63. A third carriage sensor may be located to detect when the carriage 146 has reached a position to have removed the caps 31 from the lines 30. A fourth carriage sensor may be located to detect when the carriage 146 has moved to a position to have engaged the connector ends 30a of the lines 30 with the corresponding spikes 160 of the cassette 24. In other embodiments, a single sensor can be used to detect more than one of the carriage positions described above. The cap stripper and carriage sensors can provide input signals to an electronic control board ("autoconnect board"), which in turn can communicate specific confirmation or error codes to the user via the user interface 144.

FIG. 36 shows a perspective view of an alternative embodiment of the carriage drive assembly 132. The carriage drive assembly 132 in the embodiment shown in FIG. 25 included only the drive element 133, the rods 134, the tabs 135 and the window 136. In the FIG. 36 embodiment, the carriage drive assembly 132 not only includes the drive element 133, the rods 134, the tabs 135, and the window 136, but may also include a vertical column of AutoID view boxes 1116. The view boxes 1116 may be positioned directly adjacent to the window 136. Also, the view boxes 1116 may be positioned and shaped so that the horizontal axis of each of the five slots 1086 located on the carriage 146 run through the center of a corresponding view box 1116, when the carriage 146 moves either right or left along the guides 130. The view boxes 1116 may allow for the AutoID camera 1104, which is attached to the camera board 1106, to detect if the solution line caps 31 are positioned on the lines 30 prior to the engaging of the solution lines with the spike cap 63. Alternatively, in some embodiments, the individual view boxes may not be necessary. Instead, the window 136 may be enlarged so that the caps 31 may be seen through the single window 136. Checking for the solution line 30 caps 31 may allow for confirmation that the user hasn't removed the caps 31 prematurely. Once the presence or absence of the caps 31 is determined, the camera 1104 can provide a corresponding input signal to an electronic control board (referred to as the autoconnect board elsewhere in the specification), which in turn can communicate specific confirmation or error codes, relating to the presence of the caps 31 on the lines 30, to the user via the user interface 144.

In accordance with another aspect of the disclosure, the carriage drive assembly 132 may include an autoconnect board 1118. The autoconnect board 1118 may be attached to the top of the carriage drive assembly 132, and may extend the entire length of the assembly 132. In this illustrative embodiment, there may also be an LED 1120 mounted to the autoconnect board 1118. The LED 1120 may be located in a fixed position directly above the fork-shaped elements 60. Also, the LED 1120 may be directed is a fashion so that the light being emitted from the LED 1120 travels downward across the stripper element 1491. In accordance with another aspect of the present disclosure, the carriage drive assembly 132 may also include a fluid board 1122. The fluid board 1122 may be attached to the bottom of the carriage drive assembly 132, and may also extent the length of the assembly 132. In this illustrative embodiment, there may be a receiver 1124 (not pictured) mounted to the fluid board 1122 at a location directly below the LED 1120, which is mounted to the autoconnect board 1118. Therefore, the LED 1120 can emit light across the fork-shaped elements 60, and if the light it detected by the receiver 1124 then there are no solution line caps 31 left in the stripper element 1491, however, if the light is interrupted on its way towards the receiver 1124 then there may be a cap 31 left in the stripper element 1491. This LED 1120 and receiver 1124 combination allows for the detection of caps 31 that may have been inadvertently left in the stripper element 1491 either by the user or by the cycler 14. In accordance with an aspect of the disclosure, the fluid board 1122 may also have the ability to detect humidity, moisture, or any other liquid that may be present inside of the carriage drive assembly 132, which could potentially cause the cycler 14 to fail.

There may be an advantage in adjusting the force with which the carriage 146 engages the spike caps 63, depending on how many lines 30 are being installed. The force required to complete a connection to the cassette 24 increases with the number of caps 31 that must be coupled to spike caps 63. The sensing device for detecting and reading information from the line indicators at indicator regions 33 can also be used to provide the data required to adjust the force applied to drive element 133. The force can be generated by a number of devices, including, for example, the first air bladder 137, or a linear actuator such as a motor/ball screw. An electronic control board (such as, for example, the autoconnect board) can be programmed to receive input from the line detection sensor(s), and send an appropriate control signal either to the motor of a linear actuator, or to the pneumatic valve that controls inflation of air bladder 137. The controller 16 can control the degree or rate of movement of drive element 133, for example by modulating the voltage applied to the motor of a linear actuator, or by modulating the pneumatic valve controlling the inflation of bladder 137.

In accordance with an aspect of the present disclosure, it may be necessary for the carriage drive assembly 132 to be capable of generating a force of at least 550 N (124 lbf) on carriage 146, in order to engage the membrane ports with spikes 160. This force is to be measured in the carriage direction of the membrane port spiking onto the cassette 24. The maximum force required to spike a sterilized PVC membrane port onto the spike 160 may be 110 N. Additionally, the maximum force required to spike a sterilized JPOC membrane port onto the spike 160 may be 110 N. These force requirements ensure carriage drive assembly 132 is able to spike five JPOC ports. In an alternative embodiment, the PVC port force requirement may be lowered further based on current insertion forces.

The aspect of the disclosure by which caps 31 on lines 30 are removed together with caps 63 on spikes 160 of the cassette 24 may provide other advantages aside from simplicity of operation. For example, since spike caps 63 are removed by way of their engagement with a cap 31 on a line 30, if there is no line 30 mounted at a particular slot on the carriage 146, the spike cap 63 at that position will not be removed. For example, although the cassette 24 includes five spikes 160 and corresponding spike caps 63, the cycler 14 can operate with four or less (even no) lines 30 associated with the cycler 14. For those slots on the carriage 146 where no line 30 is present, there will be no cap 31, and thus no mechanism by which a spike cap 63 at that position can be removed. Thus, if no line 30 will be connected to a particular spike 160, the cap 63 on that spike 160 may remain in place during use of the cassette 24. This may help prevent leakage at the spike 160 and/or contamination at the spike 160.

Figure 52:
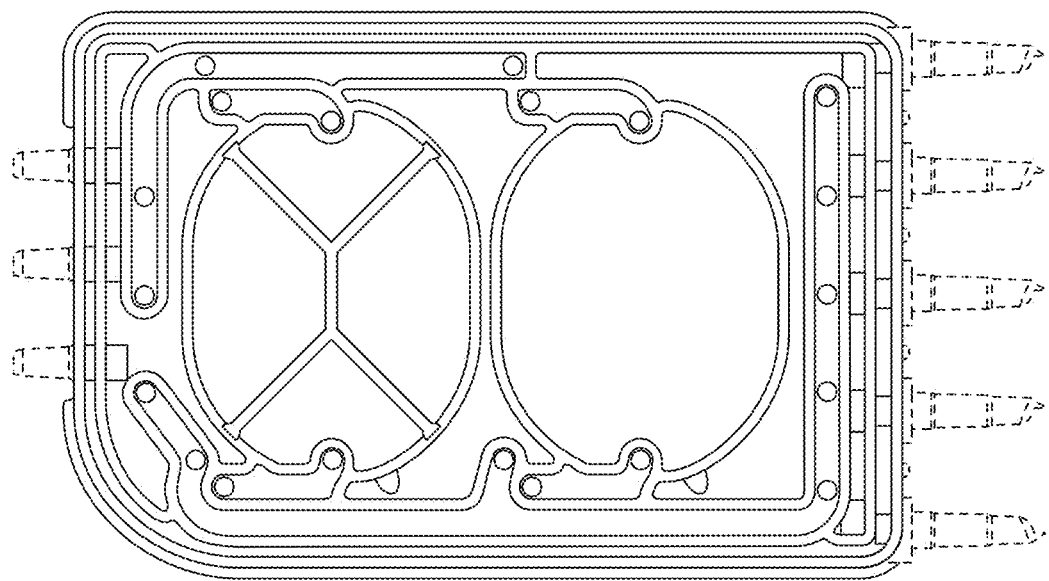
FIG. 52 is a rear view of a cassette in another illustrative embodiment including different arrangements for a rear side of the cassette adjacent the pump chambers.

The cassette 24 in FIG. 51 includes a few features that are different from those shown, for example, in the embodiment shown in FIGS. 3, 4 and 6. In the FIGS. 3, 4 and 6 embodiment, the heater bag port 150, drain line port 152 and patient line port 154 are arranged to have a central tube 156 and a skirt 158. However, as mentioned above and shown in FIG. 51, the ports 150, 152, 154 may include only the central tube 156 and no skirt 158. This is also shown in FIG. 52. The embodiment depicted in FIG. 52 includes raised ribs formed on the outside surface of the left-side pump chamber 181. The raised ribs may also be provided on the right-side pump chamber 181, and may provide additional contact points of the outside walls of pump chambers 181 with the mechanism in the door 141 at the cassette mounting location 145, which presses the cassette 24 against the control surface 148 when the door 141 is closed. The raised ribs are not required, and instead the pump chambers 181 may have no rib or other features, as shown for the right-side pump chamber 181 in FIG. 52. Similarly, the spikes 160 in FIGS. 3, 4 and 6 embodiments include no skirt or similar feature at the base of the spike 160, whereas the embodiment in FIG. 51 includes a skirt 160*a*. This is also shown in FIG. 52. The skirt 160*a* may be arranged to receive the end of the spike cap 63 in a recess between the skirt 160*a* and the spike 160, helping to form a seal between the spike 160 and the spike cap 63.

Figure 53:
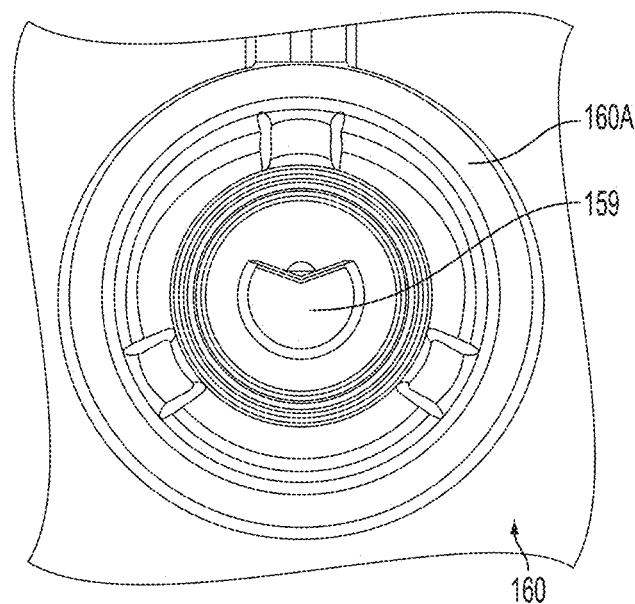
FIG. 53 is an end view of a spike of a cassette in an illustrative embodiment.

Another inventive feature shown in FIG. 51 relates to the arrangement of the distal tip of the spike 163 and the lumen 159 through the spike 160. In this aspect, the distal tip of the spike 160 is positioned at or near the longitudinal axis of the spike 160, which runs generally along the geometric center of the spike 160. Positioning the distal tip of the spike 160 at or near the longitudinal axis may help case alignment tolerances when engaging the spike 160 with a corresponding solution line 30 and help the spike 160 puncture a septum or membrane 30b in the connector end 30a of the line 30. As a result, the lumen 159 of the spike 160 is located generally off of the longitudinal axis of the spike 160, e.g., near a bottom of the spike 160 as shown in FIG. 51 and as shown in an end view of a spike 160 in FIG. 53. Also, the distal end of the spike 160 has a somewhat reduced diameter as compared to more proximal portions of the spike 160 (in this embodiment, the spike 160 actually has a step change in diameter at about ⅔ of the length of the spike 160 from the body 18). The reduced diameter of the spike 160 at the distal end may provide clearance between the spike 160 and the inner wall of the line 30, thus allowing the septum 30b a space to fold back to be positioned between the spike 160 and the line 30 when pierced by the spike 160. The stepped feature 160b on the spike 160 (shown, e.g., in FIG. 54) may also be arranged to engage the line 30 at the location where the septum 30b is connected to the inner wall of the line 30, thus enhancing a seal formed between the line 30 and the spike 160.

Figure 54:
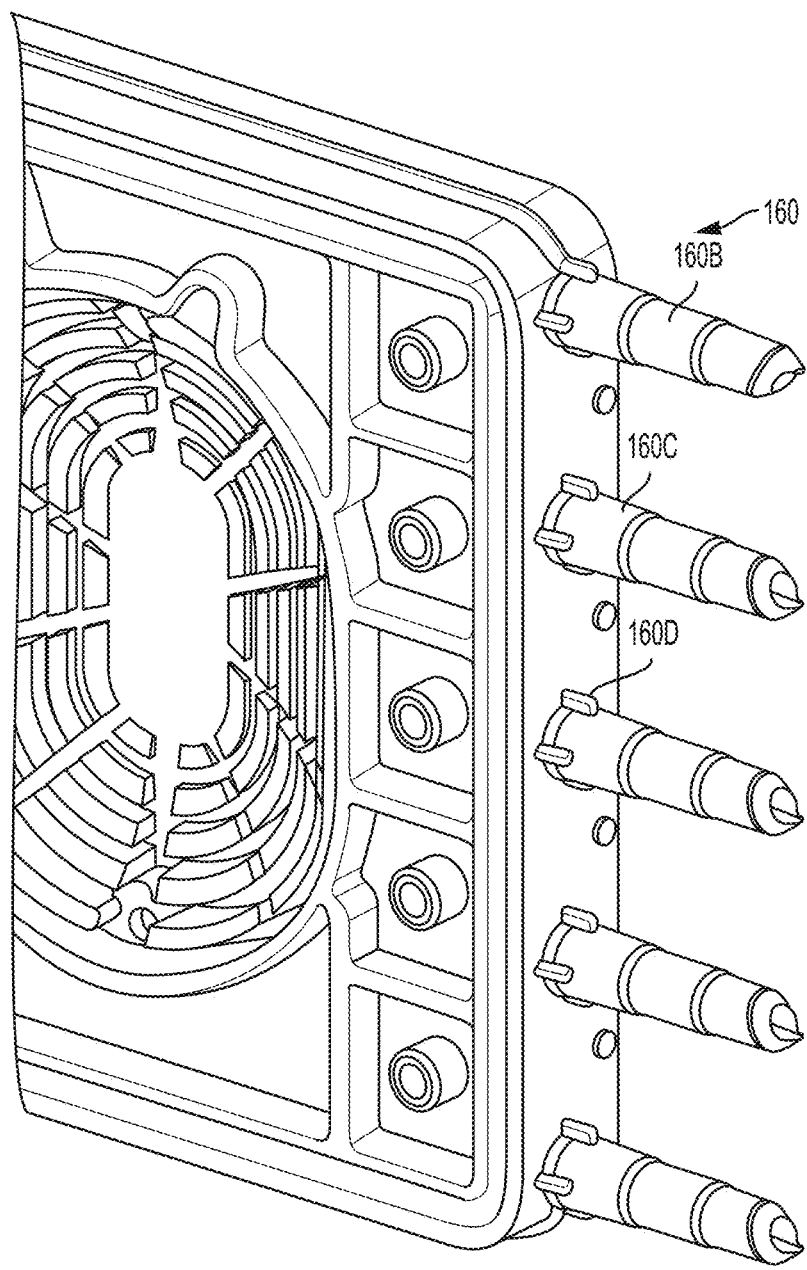
FIG. 54 is a perspective view of an alternative embodiment of the spikes of a cassette.

In another embodiment, as shown in FIG. 54, the length of the base 160c of spike 160 may be shortened to reduce the force required to remove the spike cap 63 from spike 160, or to reduce the force required to spike the connector end 30a of solution line 30. Shortening the base 160c reduces the area of frictional contact between spike 160 and its cap 63, or between spike 160 and the internal surface of connector end 30a. In addition, the skirt 160a at the base of spike 160 may be replaced by individual posts 160d. The posts 160d allow the spike cap 63 to be properly seated onto spike 160 while also allowing for more thorough circulation of sterilization fluid or gas around spike 160 during the sterilization process prior to or after packaging of the dialysate delivery set 12.

Figure 55:
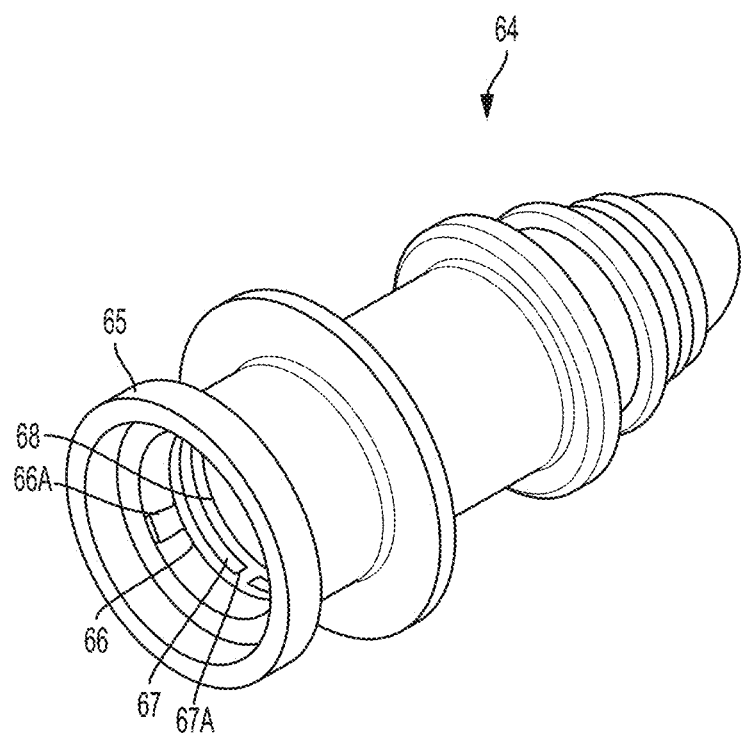
FIG. 55 shows an embodiment of a spike cap configured to fit over the spikes shown in FIG. 54.

A spike cap 64, as shown in FIG. 55 may be used with the embodiment shown in FIG. 54. A skirt 65 on the base of spike cap 64 is constructed to fit snugly over the posts 160d of the base of spike 160 shown in FIG. 54. In addition, interrupted ribs 66, 67 within the inner circumference of the base of spike 160 may provide a snug fit between spike cap 64 and the base 160c of spike 160, while also permitting sterilizing gas or fluid to penetrate more distally over the base of a capped spike 160.

Figure 56:
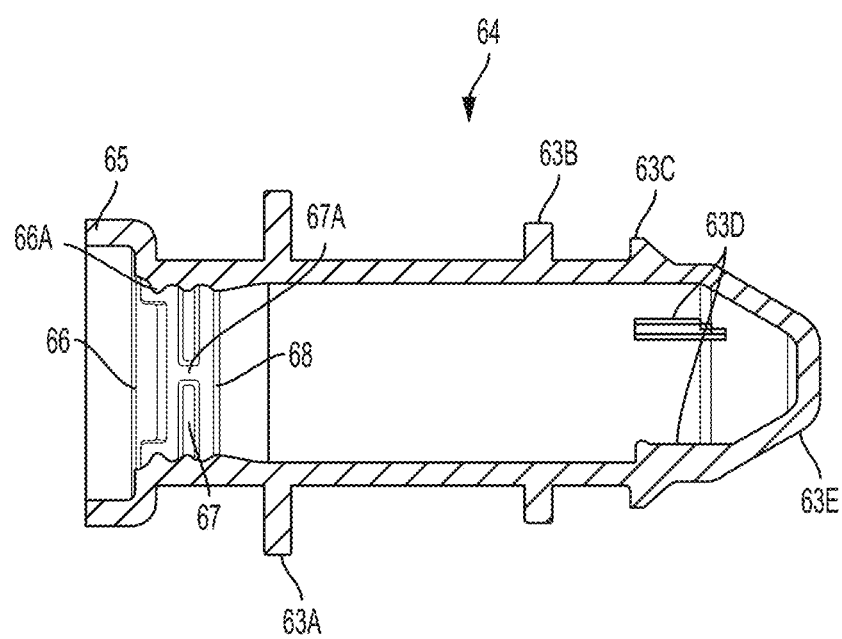
FIG. 56 is a cross-sectional view of a spike cap shown in FIG. 55.

As shown in FIG. 56, in a cross-sectional view of spike cap 64, a set of three inner ribs 66, 67, 68 may be used to provide a snug fit between spike cap 64 and the base 160c of spike 160. In an embodiment, rib 66 and rib 67 have interruptions or gaps 66a and 67a along their circumference to permit gas or fluid external to the cassette to flow over the base 160c of spike 160. A third rib 68 may be circumferentially intact in order to make a sealing engagement between spike cap 64 and the base 160c of spike 160, sealing off the base 160c from rest of the external surface of spike 160. In other embodiments, ribs within spike cap 64 may be oriented longitudinally rather than circumferentially, or in any other orientation to provide a snug fit between spike cap 64 and spike 160, while also permitting an external gas or fluid to make contact with the outside of the base 160c of spike 160. In the embodiment shown, for example, the outer surface of the cassette 24, spike cap and most of the base 160c of spike 160 can be sterilized by exposing the cassette 24 externally to ethylene oxide gas. Because the diameter of the stepped feature 160b and the distal end of spike 160 are smaller than the inner diameter of the overlying portion of spike cap 64, any gas or fluid entering the spike lumen from within the cassette 24 can reach the outer surface of spike 160 up to the sealing rib 68. Thus any sterilizing gas such as ethylene oxide entering the fluid passages of the cassette 24 may reach the remainder of the external surface of spike 160. In an embodiment, the gas may enter the cassette 24 through a vented cap, for example, on the end of patient line 34 or drain line 28.

The spike cap 34 may include three or more centering ribs 64D that contact the end of the spike 160. The ribs 64D are oriented along the major access of spike cap 34 and located near the closed end of the spike cap 34. Preferably there are at least three ribs 63D to center the closed end of the cap on the spike without over constraining the cap/spike orientation. The spike cap 64 includes a tapered end with a blunt tip to facilitate the penetration of the spike cap 34 into the hole 31b of the solution cap 31. The tapered end will guide the spike cap 34 if it misaligned with the hole 31b. The blunt tip avoids snagging the solution cap 31 unlike a sharp tip that might catch the inside edge of the hole 31b and dig into the solution cap 31 material. In contrast a blunt tip can slide past the edges of the hole 31b.

Figure 57:
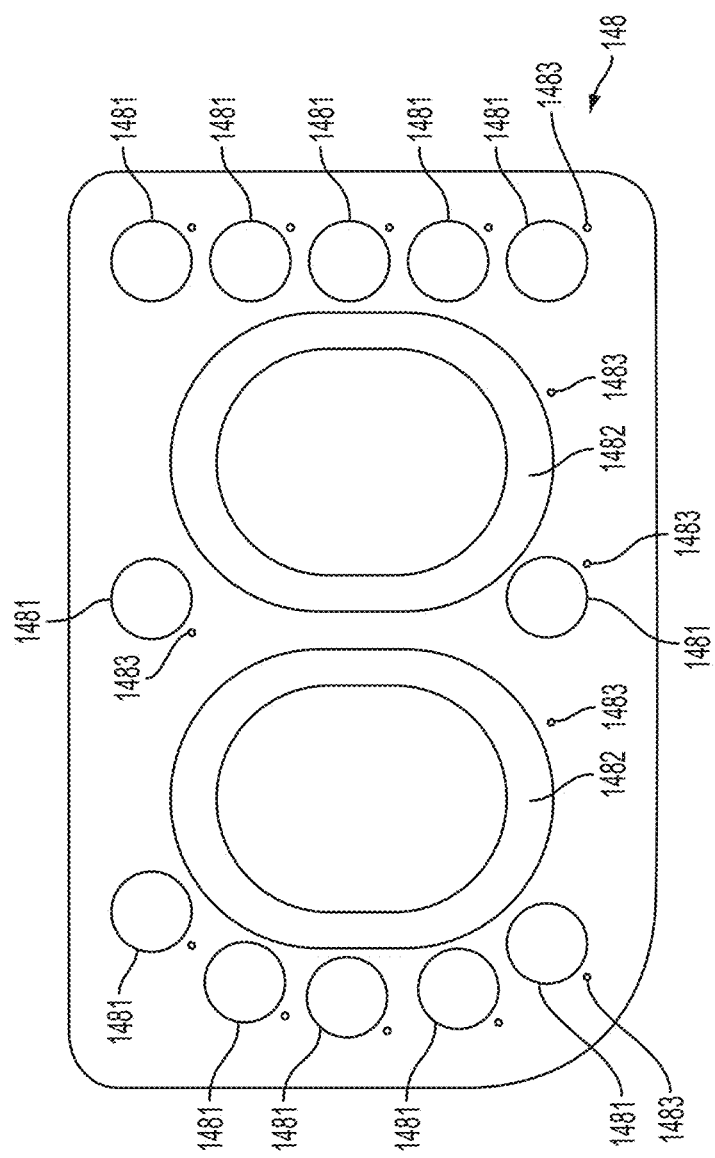
FIG. 57 is a front view of a control surface of the cycler for interaction with a cassette in the FIG. 16 embodiment.

FIG. 57 shows a plan view of the control surface 148 of the cycler 14 that interacts with the pump chamber side of the cassette 24 (e.g., shown in FIG. 6) to cause fluid pumping and flow path control in the cassette 24. When at rest, the control surface 148, which may be described as a type of gasket, and comprise a sheet of silicone rubber, may be generally flat. Valve control regions 1481 may (or may not) be defined in the control surface 148, e.g., by a scoring, groove, rib or other feature in or on the sheet surface, and be arranged to be movable in a direction generally transverse to the plane of the sheet. By moving inwardly/outwardly, the valve control regions 1481 can move associated portions of the membrane 15 on the cassette 24 so as to open and close respective valve ports 184, 186, 190 and 192 of the cassette 24, and thus control flow in the cassette 24. Two larger regions, pump control regions 1482, may likewise be movable so as to move associated shaped portions 151 of the membrane 15 that cooperate with the pump chambers 181. Like the shaped portions 151 of the membrane 15, the pump control regions 1482 may be shaped in a way to correspond to the shape of the pump chambers 181 when the control regions 1482 are extended into the pump chambers 181. In this way, the portion of the control sheet 148 at the pump control regions 1482 need not necessarily be stretched or otherwise resiliently deformed during pumping operation.

Each of the regions 1481 and 1482 may have an associated vacuum or evacuation port 1483 that may be used to remove all or substantially all of any air or other fluid that may be present between the membrane 15 of cassette 24, and the control surface 148 of cycler 14, e.g., after the cassette 24 is loaded into the cycler 14 and the door 141 closed. This may help ensure close contact of the membrane 15 with the control regions 1481 and 1482, and help control the delivery of desired volumes with pump operation and/or the open/closed state of the various valve ports. Note that the vacuum ports 1482 are formed in locations where the control surface 148 will not be pressed into contact with a wall or other relatively rigid feature of the cassette 24. For example, in accordance with one aspect of the disclosure, one or both of the pump chambers 181 of the cassette 24 may include a vacuum vent clearance region formed adjacent the pump chamber. In this illustrative embodiment as shown in FIGS.

3 and 6, the base member 18 may include vacuum vent port clearance or extension features 182 (e.g., recessed areas that are fluidly connected to the pump chambers 181) adjacent and outside the oval-shaped depressions forming the pump chambers 181 to allow the vacuum vent port 1483 for the pump control region 1482 to remove any air or fluid from between membrane 15 and control surface 148 (e.g., due to rupture of the membrane 15) without obstruction. The extension feature may also be located within the perimeter of pump chamber 181. However, locating vent port feature 182 outside the perimeter of pump chamber 181 may preserve more of the pumping chamber 181 volume for pumping liquids, e.g., allows for the full footprint of pump chamber 181 to be used for pumping dialysate. Preferably, extension feature 182 is located in a vertically lower position in relation to pump chamber 181, so that any liquid that leaks between membrane 15 and control surface 148 is drawn out through vacuum port 1483 at the earliest opportunity. Similarly, vacuum ports 1483 associated with valves 1481 are preferably located in a vertically inferior position with respect to valves 1481.

Figure 58:
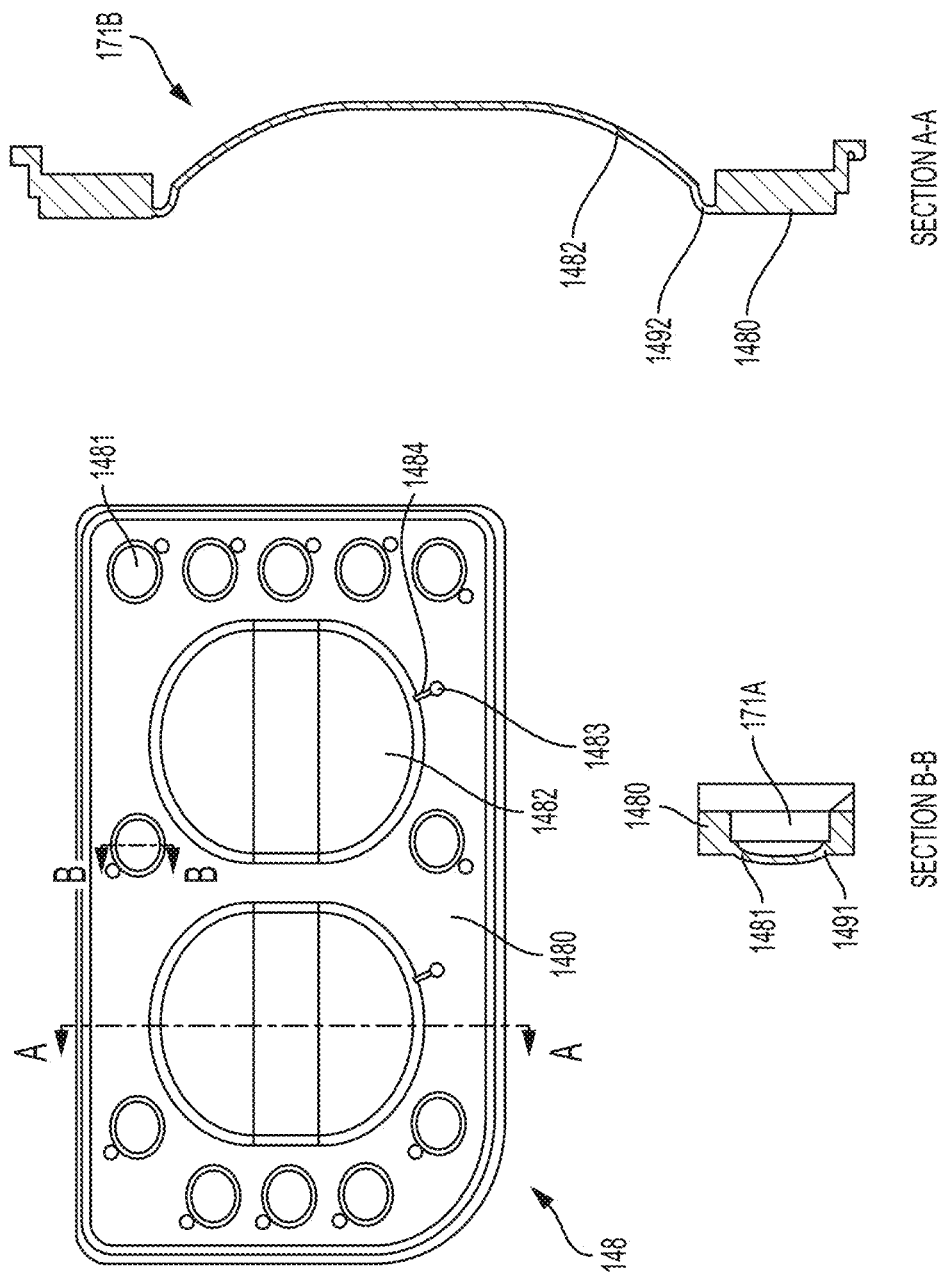
FIG. 58 is a front view and selected cross-sectional views of an embodiment of a control surface of the cycler.

FIG. 58 shows that control surface 148 may be constructed or molded to have a rounded transition between the base element 1480 of control surface 148 and its valve and pump control regions 1481, 1482. The junctions 1491 and 1492 may be molded with a small radius to transition from base element 1480 to valve control region 1481 and pump control region 1482, respectively. A rounded or smooth transition helps to prevent premature fatigue and fracture of the material comprising control surface 148, and may improve its longevity. In this embodiment, channels 1484 leading from vacuum ports 1483 to the pump control regions 1482 and valve control regions 1481 may need to be lengthened somewhat to accommodate the transition feature.

Figure 59:
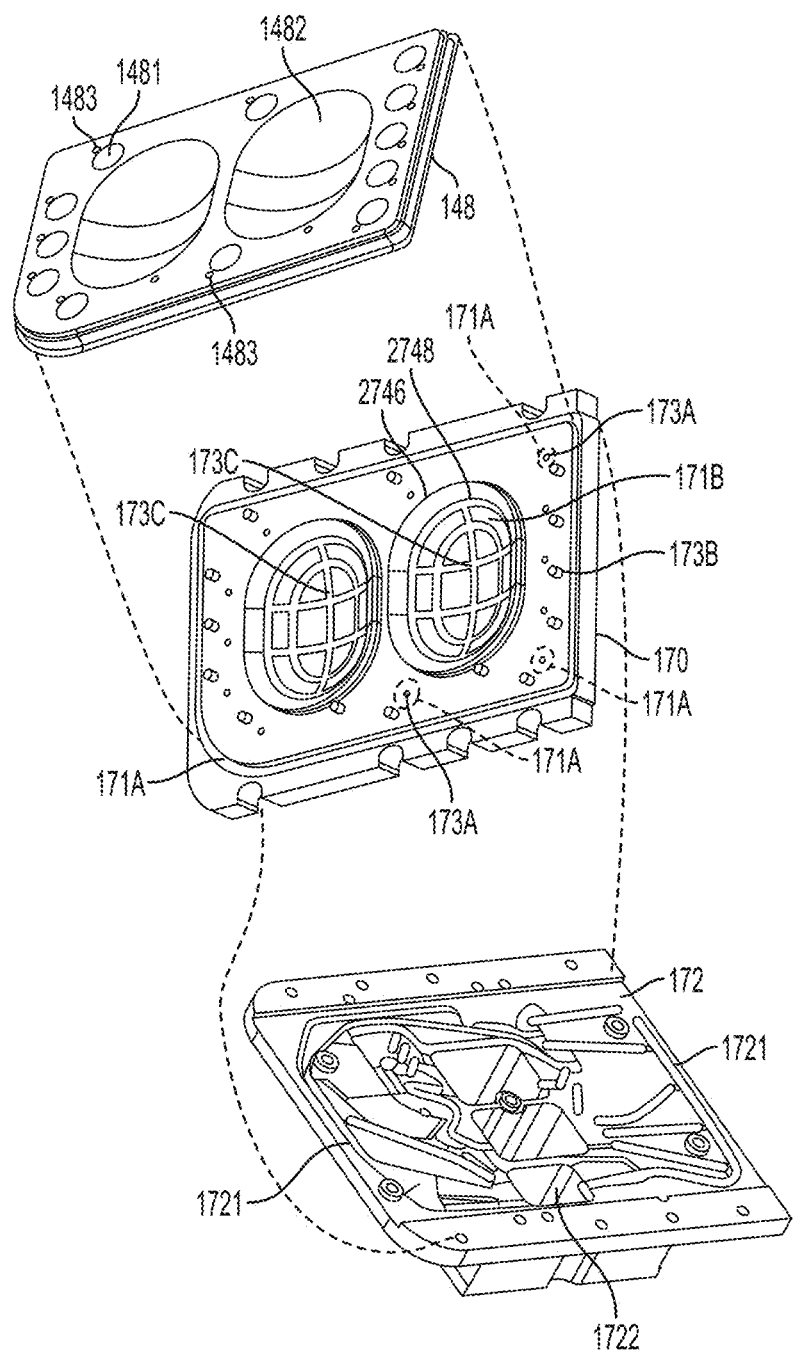
FIG. 59 is an exploded view of an assembly for the interface surface of FIG. 57, with the mating pressure delivery block and pressure distribution module.

The control regions 1481 and 1482 may be moved by controlling a pneumatic pressure and/or volume on a side of the control surface 148 opposite the cassette 24, e.g., on a back side of the rubber sheet that forms the control surface 148. For example, as shown in FIG. 59, the control surface 148 may be backed by a mating or pressure delivery block 170 that includes control chambers or depressions 171A located in association with each control region 1481, and control chambers or depressions 171B, located in association with each control region 1482, and that are isolated from each other or at least can be controlled independently of each other if desired. The surface of mating or pressure delivery block 170 forms a mating interface with cassette 24 when cassette 24 is pressed into operative association with control surface 148 backed by mating block 170. The control chambers or depressions of mating block 170 are thus coupled to complementary valve or pumping chambers 181 of cassette 24, sandwiching control regions 1481 and 1482 of control surface 148 adjacent to mating block 170, and the associated regions of membrane 15 (such as shaped portion 151) adjacent to cassette 24. Air or other control fluid may be moved into or out of the control chambers or depressions 171A, 171B of mating block 170 for the regions 1481, 1482, thereby moving the control regions 1481, 1482 as desired to open/close valve ports of the cassette 24 and/or effect pumping action at the pump chambers 181. In one illustrative embodiment shown in FIG. 59, the control chambers 171A may be arranged as cylindrically-shaped regions backing each of the valve control regions 1481. The control chambers or depressions 171B may comprise ellipsoid, ovoid or hemi-spheroid voids or depressions backing the pump control regions 1482. Fluid control ports 173A may be provided for each control chamber 171A so that the cycler 14 can control the volume of fluid and/or the pressure of fluid in each of the valve control chambers 1481. Fluid control ports 173C may be provided for each control chamber 171B so that the cycler 14 can control the volume of fluid and/or the pressure of fluid in each of the volume control chambers 1482. For example, the mating block 170 may be mated with a manifold 172 that includes various ports, channels, openings, voids and/or other features that communicate with the control chambers 171 and allow suitable pneumatic pressure/vacuum to be applied to the control chambers 171. Although not shown, control of the pneumatic pressure/vacuum may be performed in any suitable way, such as through the use of controllable valves, pumps, pressure sensors, accumulators, and so on. Of course, it should be understood that the control regions 1481, 1482 may be moved in other ways, such as by gravity-based systems, hydraulic systems, and/or mechanical systems (such as by linear motors, etc.), or by a combination of systems including pneumatic, hydraulic, gravity-based and mechanical systems.

Figure 60:
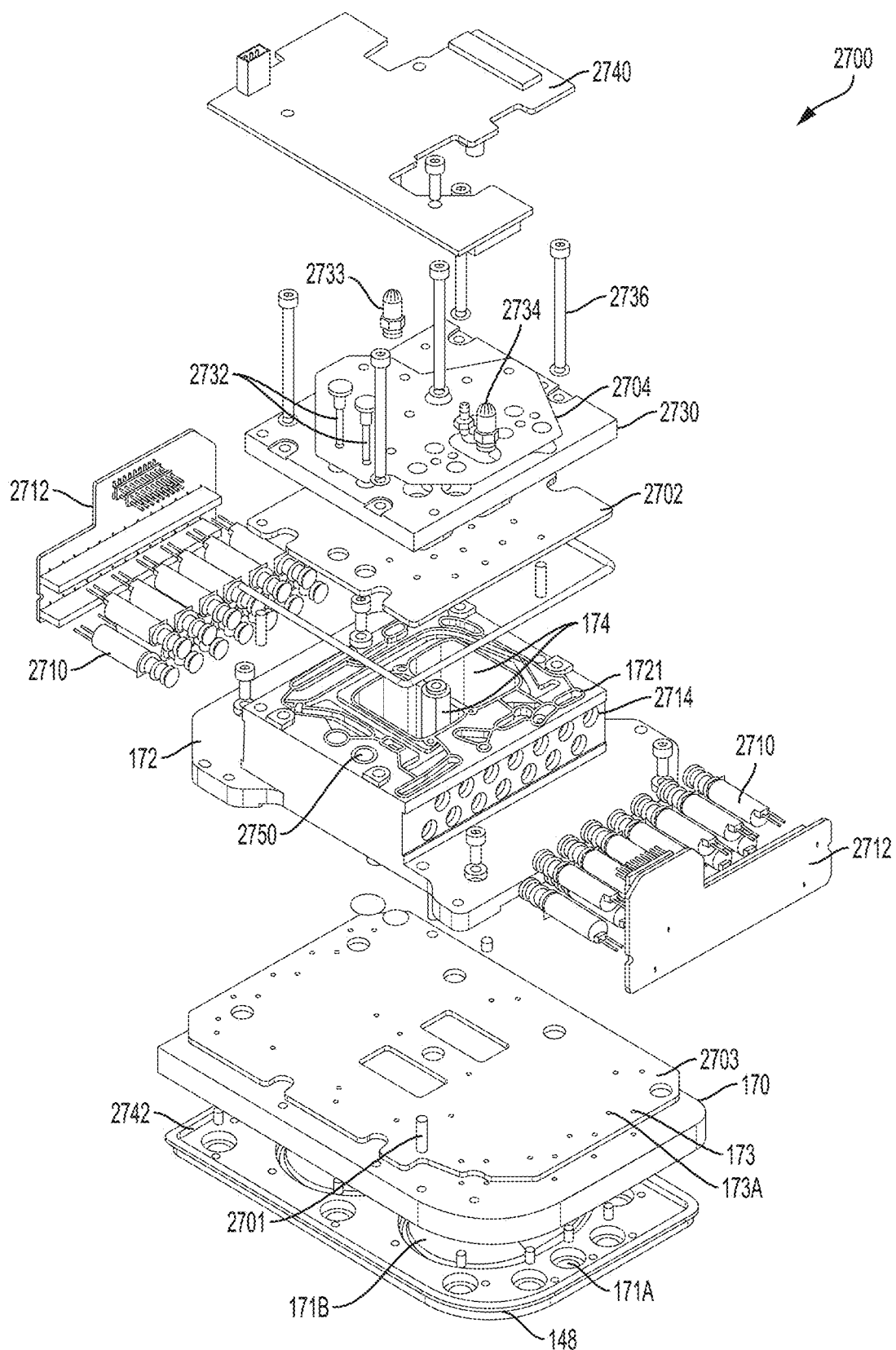
FIG. 60 is an exploded view of the integrated manifold.
Figure 61:
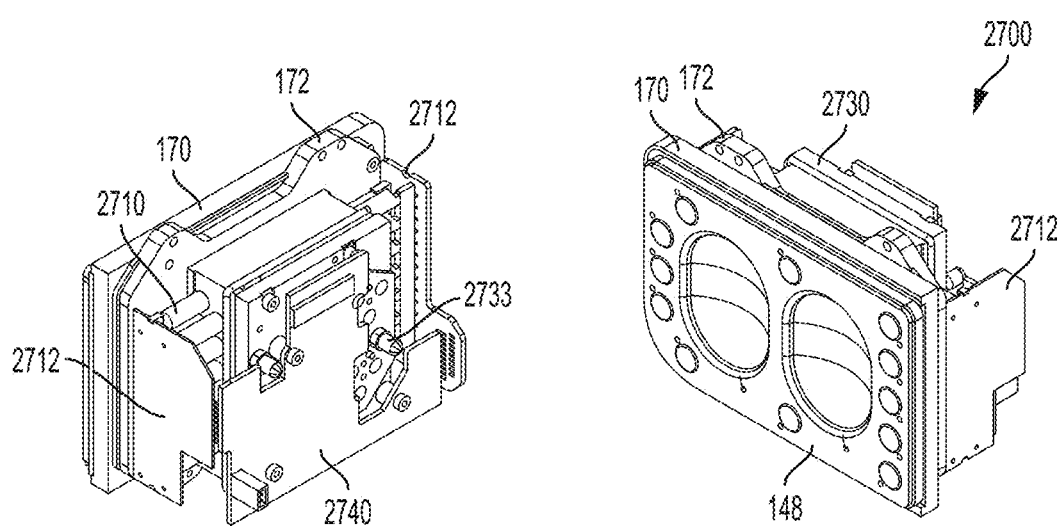
FIG. 61 shows two isometric views of the integrated manifold.

FIG. 60 shows an exploded view of an integrated pressure distribution module or assembly 2700 for use in a fluid flow control apparatus for operating a pumping cassette, and suitable for use as pressure distribution manifold 172 and mating block 170 of cycler 14. FIG. 61 shows a view of an integrated module 2700 comprising a pneumatic manifold or block, ports for supply pressures, pneumatic control valves, pressure sensors, a pressure delivery or mating block and a control surface or actuator that includes regions comprising flexible membranes for actuating pumps and valves on a pumping cassette. The integrated module 2700 may also include reference chambers within the pneumatic manifold for an FMS volume measurement process for determining the volume of fluid present in a pumping chamber of a pumping cassette. The integrated module may also comprise a vacuum port, and a set of pathways or channels from interfaces between the actuator and flexible pump and valve membranes of a pumping cassette to a fluid trap and liquid detection system. In some embodiments, the pneumatic manifold may be formed as a single block. In other embodiments, the pneumatic manifold may be formed from two or more manifold blocks mated together with gaskets positioned between the manifold blocks. The integrated module 2700 occupies a relatively small space in a fluid flow control apparatus, and eliminates the use of tubes or flexible conduits connecting the manifold ports with corresponding ports of a pressure delivery module or block mated to a pumping cassette. Among other possible advantages, the integrated module 2700 reduces the size and assembly cost of the pneumatic actuation assembly of a peritoneal dialysis cycler, which may result in a smaller and less expensive cycler. Additionally, the short distances between pressure or vacuum distribution ports on the pressure distribution manifold block and corresponding pressure or vacuum delivery ports on a mating pressure delivery block, together with the rigidity of the conduits connecting the ports, may improve the responsiveness of an attached pumping cassette and the accuracy of cassette pump volume measurement processes. When used in a peritoneal dialysis cycler 14, in an embodiment, an integrated module comprising a metallic pressure distribution manifold mated directly to a metallic pressure delivery block may also reduce any temperature differences between the control volume 171B and the reference chamber 174 of the cycler 14, which may improve the accuracy of the pump volume measurement process.

An exploded view of the integrated module 2700 is presented in FIG. 60. The actuator surface, mounted on a mating block or pressure delivery block, is analogous or equivalent to the gasket or control surface 148, that includes flexible regions arranged to move back and forth to pump fluid and/or open and close valves by pushing or pulling on a membrane 15 of a pump cassette 24. With respect to cycler 14, the control surface 148 is actuated by the positive and negative pneumatic pressure supplied to the control volumes 171A, 171B behind the control regions 1481, 1482. The control surface 148 attaches to the pressure delivery block or mating block 170 by fitting tightly on a raised surface 2744 on the front surface of the mating block 170 with a lip 2742. The mating block 170 may include one or more surface depressions 2746 to align with and support the oval curved shape of one or more corresponding pump control surfaces 1482, forming a pump control chamber. A similar arrangement, with or without a surface depression, may be included in forming a valve control region 171A to align with a corresponding control surface 1481 for controlling one or more valves of a pumping cassette. The mating block 170 may further include grooves 2748 on the surface of depression 2746 of mating block 170 behind the pump control surface 1482 to facilitate the flow of control fluid or gas from the port 173C to the entire back surface the pump control surface 1482. Alternatively, rather than having grooves 2748, the depression 2746 may be formed with a roughened surface or a tangentially porous surface.

The mating block 170 connects the pressure distribution manifold 172 to the control surface 148, and delivers pressure or vacuum to various control regions on control surface 148. The mating block 170 may also be referred to as a pressure delivery block in that it provides pneumatic conduits to supply pressure and vacuum to the valve control regions 1481 and the pump control regions 1482, vacuum to the vacuum ports 1483 and connections from the pump control volumes 171B to the pressure sensors. The ports 173A connect the valve control volumes 171A to the pressure distribution manifold 172. The ports 173C connect the pump control volume 171B to the pressure distribution manifold 172. The vacuum ports 1483 are connected to the pressure distribution manifold 172 via ports 173B. In one embodiment, the ports 173B extend above the surface of the pressure delivery block 170 to pass through the control surface 148 to provide vacuum at port 1483 without pulling the control surface 148 onto the port 173B and blocking flow.

The pressure delivery block 170 is attached to the front face of the pressure distribution manifold 172. The ports 173A, 173B, 173C line up with pneumatic circuits on the pressure distribution manifold 172 that connect to valve ports 2714. In one example, the pressure delivery block 170 is mated to the pressure distribution manifold 172 with a front flat gasket 2703 clamped between them. The block 170 and manifold 172 are held together mechanically, which in an embodiment is through the use of bolts 2736 or other types of fasteners. In another example, rather than a flat gasket 2703, compliant elements are placed in or molded in either the pressure delivery block 170 or the pressure distribution manifold 172. Alternatively, the pressure delivery block 170 may be bonded to the pressure distribution manifold 172 by an adhesive, double sided tape, friction welding, laser welding, or other bonding method. The block 170 and manifold 172 may be formed of metal or plastic and the bonding methods will vary depending on the material.

The pressure distribution manifold 172 contains ports for the pneumatic valves 2710, reference chambers 174, a fluid trap 1722 and pneumatic circuitry or of the integrated module 2700 connections provides pneumatic connections between the pressure reservoirs, valves, and contains ports 2714 that receive multiple cartridge valves 2710. The cartridge valves 2710 include but are not limited to the binary valves 2660 controlling flow to valve control volumes 171A, the binary valves X1A, X1B, X2, X3 controlling flow to pump control volumes 171B, and the binary valves 2661-2667 controlling flow to the bladders 2630, 2640, 2650 and pressure reservoirs 2610, 2620. The cartridge valves 2710 are pressed into the valve ports 2714 and electrically connected to the hardware interface 310 via circuit board 2712.

The pneumatic circuitry in the pressure distribution manifold 172 may be formed with a combination of grooves or slots 1721 on the front and back faces and approximately perpendicular holes that connect the grooves 1721 on one face to valve ports 2714, the fluid trap 1722 and to grooves and ports on the opposite face. Some grooves 1721 may connect directly to the reference chambers 174. A single perpendicular hole may connect a groove 1721 to multiple valve ports 174 that are closely spaced and staggered. Sealed pneumatic conduits are formed when the grooves 1721 are isolated from one another by, in one example, the front flat gasket 2703 as shown in FIG. 60.

The presence of liquid in the fluid trap 1722 may be detected by a pair of conductivity probes 2732. The conductivity probes 2732 slide through a back gasket 2704, a back plate 2730 and holes 2750 before entering the fluid trap 1722 in the pressure distribution manifold 172.

The back plate 2730 seals the reference volumes 174, the grooves 1721 on the back face of the pressure distribution manifold 172 and provides ports for the pressure sensors 2740 and ports for pressure and vacuum lines 2734 and vents to the atmosphere 2733. In one example, the pressure sensors may be IC chips soldered to a single board 2740 and pressed as a group against the back gasket 2704 on the back plate 2730. In one example, bolts 2736 clamp the back plate 2730, pressure distribution manifold 172 and pressure delivery block 170 together with gaskets 2703, 2702 between them. In another example, the back plate 2730 may be bonded to the pressure delivery manifold 172 as described above. The assembled integrated module 2700 is presented in FIG. 61.

Figure 62:
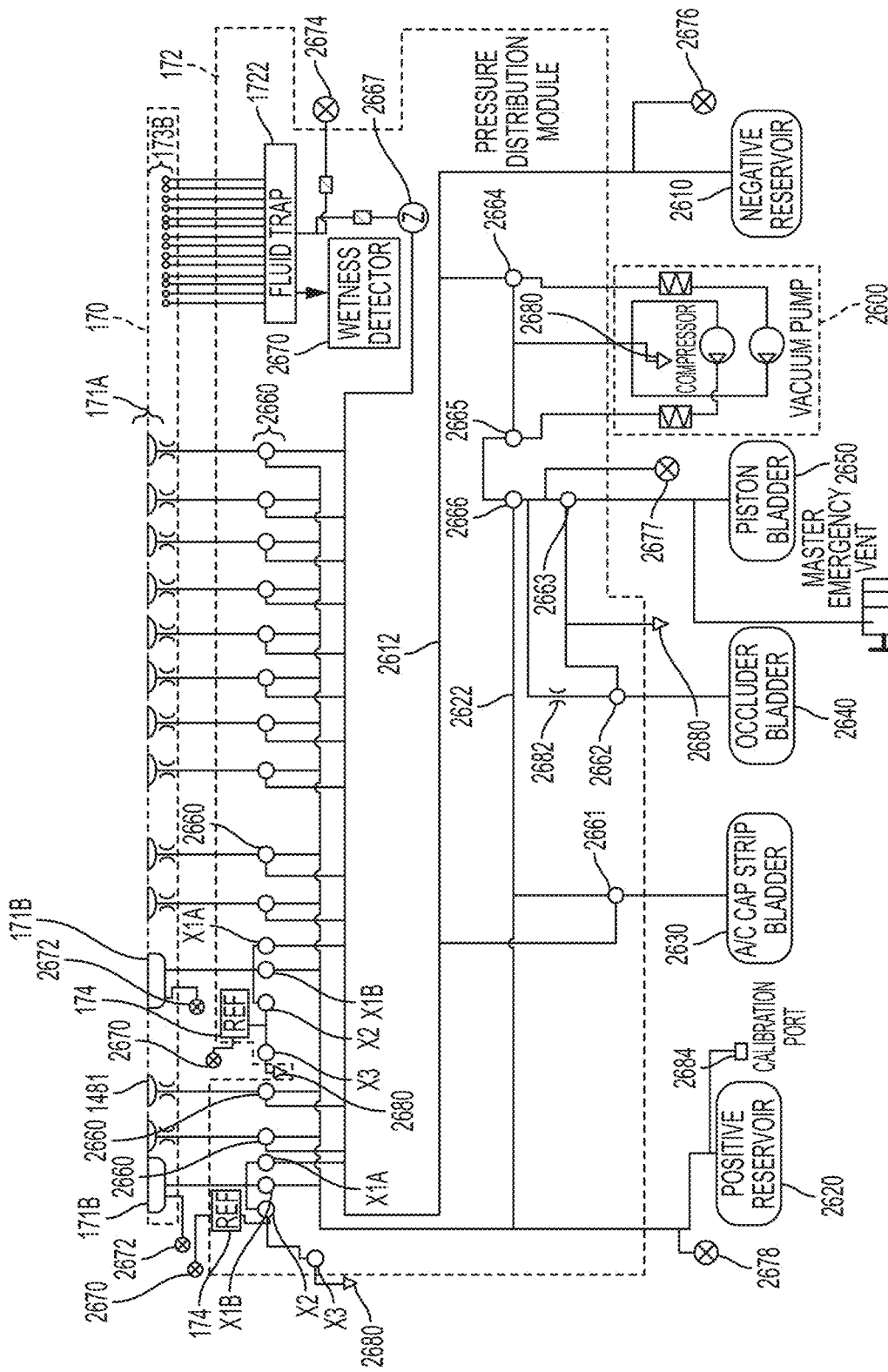
FIG. 62 shows a schematic of the pneumatic system that controls fluid flow through the cycler.

FIG. 62 presents a schematic of the pneumatic circuit in the integrated manifold 2700 and pneumatic elements outside the manifold. The pump 2600 produces vacuum and pressure. The pump 2600 is connected via 3 way valves 2664 and 2665 to a vent 2680 and the negative or vacuum reservoir 2610 and the positive reservoir 2620. The pressure in the positive and negative reservoirs 2620, 2610 are measured respectively by pressure sensors 2678, 2676. The hardware interface 310 controls the speed of the pump 2600 and the position of 3-way valves 2664, 2665, 2666 to control the pressure in each reservoir. The auto-connect stripper element bladder 2630 is connected via 3-way valve 2661 to either the positive pressure line 2622 or the negative or vacuum line 2612. The automation computer 300 commands the position of valve 2661 to control the location of the stripper element 1461. The occluder bladder 2640 and piston bladder 2650 are connected via 3-way valves 2662 and 2663 to either the pressure line 2622 or vent 2680. The automation computer 300 commands valve 2663 to connect the piston bladder 2650 to the pressure line 2622 after the door 141 is closed to securely engage the cassette 24 against the control surface 148. The occluder bladder 2640 is connected to the pressure line 2622 via valve 2662 and restriction 2682. The occluder bladder 2640 is connected to the vent 2680 via valve 2662. The orifice 2682 advantageously slows the filling of the occluder bladder 2640 that retracts the occluder 147 in order to maintain the pressure in the pressure line 2622. The high pressure in the pressure line 2622 keeps the various valve control surfaces 171A and the piston bladder 2650 actuated against the cassette 24, which prevents flow to or from the patient as the occluder 147 opens. Conversely the connection from the occluder bladder 2640 to the vent 2680 is unrestricted, so that occluder 147 can quickly close.

The valve control surfaces 1481 are controlled by the pressure in the valve control volume 171A, which in turn is controlled by the position of the 3-way valves 2660. The valves 2660 can be controlled individually via commands from the automation computer 300 passed to the hardware interface 310. The valves controlling the pumping pressures in the pump control volumes 171B are controlled with 2-way valves X1A, X1B. The valves X1A, X1B in one example may be controlled by the hardware interface 310 to achieve a pressure commanded by the automation computer 300. The pressure in each pump control chamber 171B is measured by sensors 2672. The pressure in the reference chambers is measured by sensors 2670. The 2-way valves X2, X3 respectively connect the reference chamber 174 to the pump control chamber 171B and the vent 2680.

The fluid trap 1722 is in fluid communication with the vacuum line 2612 during operation as explained elsewhere in this application. The fluid trap 1722 is connected by several lines to the ports 173B in the pressure delivery block 170. The pressure in the fluid trap 1722 is monitored by pressure sensor 2674 that is mounted on the back plate 2730.

The vacuum ports 1483 may be employed to separate the membrane 15 from the control surface 148 at the end of therapy before or during the opening the door. The vacuum provided by the negative pressure source to the vacuum ports 1483 sealingly engages the membrane 15 to the control surface 148 during therapy. In some instances a substantial amount of force may be needed to separate the control surface 148 from the cassette membrane 15, preventing the door 141 from freely rotating into the open position, even when the application of vacuum is discontinued. Thus, in an embodiment, the pressure distribution module 2700 is configured to provide a valved channel between the positive pressure source and the vacuum ports 1483. Supplying positive pressure at the vacuum ports 1483 may aid in separating the membrane 15 from the control surface 148, thereby allowing the cassette 24 to separate more easily from the control surface 148 and allow the door 141 to open freely. The pneumatic valves in the cycler 14 may be controlled by the automation computer 300 to provide a positive pressure to the vacuum ports 1483. The manifold 172 may include a separately valved channel dedicated for this purpose, or alternatively it may employ the existing channel configurations and valves, operated in a particular sequence.

In one example the vacuum ports 1483 may be supplied with positive pressure by temporarily connecting the vacuum ports 1483 to the positive pressure reservoir 2620. The vacuum ports 1483 are normally connected to the vacuum reservoir 2610 via a common fluid collection chamber or fluid trap 1722 in the manifold 172 during therapy. In one example, the controller or automation computer may open valve X1B between the positive pressure reservoir and the volume control chamber 171B and the valve X1A between the negative pressure reservoir and the same volume control chamber 171B simultaneously, which will pressurize the air in the fluid trap 1722 and the vacuum ports 1483. The pressurized air will flow through the vacuum ports 1483 and between the membrane 15 and the control surface 148, breaking any vacuum bond between the membrane 15 and control surface 148. However, in the illustrated manifold, the stripper element 1491 of the cap stripper 149 may extend while the positive pressure is supplied to common fluid collection chamber 1722 fluid, because the stripper bladder 2630 is connected to a the vacuum supply line 2612. In this example, in a subsequent step, the fluid trap 1722 may be valved off from the now-pressurized vacuum line and the two valves X1A, X1B connecting the positive and vacuum reservoirs to the volume control chamber 171B may be closed. The vacuum pump 2600 is then operated to reduce the pressure in the vacuum reservoir 2610 and the vacuum supply line 2612, which in turn allows the stripper element 1491 to be withdrawn. The door 141 may then be opened after detaching the cassette 24 from the control surface 148 and retracting the stripper element 1491.

In accordance with an aspect of the disclosure, the vacuum ports 1483 may be used to detect leaks in the membrane 15, e.g., a liquid sensor in a conduit or chamber connected to a vacuum port 1483 may detect liquid if the membrane 15 is perforated or liquid otherwise is introduced between the membrane 15 and the control surface 148. For example, vacuum ports 1483 may align with and be sealingly associated with complementary vacuum ports 173B in mating block 170, which in turn may be sealingly associated with fluid passages 1721 leading to a common fluid collection chamber 1722 in manifold 172. The fluid collection chamber 1722 may contain an inlet through which vacuum can be applied and distributed to all vacuum ports 1483 of a control surface 148. By applying vacuum to the fluid collection chamber 1722, fluid may be drawn from each of the vacuum ports 173B and 1483, thus removing fluid from any space between the membrane 15 and the control surface 148 at the various control regions. However, if there is liquid present at one or more of the regions, the associated vacuum port 1483 may draw the liquid into the vacuum ports 173B and into the lines 1721 leading to the fluid collection chamber 1722. Any such liquid may collect in the fluid collection chamber 1722, and be detected by one or more suitable sensors, e.g., a pair of conductivity sensors that detect a change in conductivity in the chamber 1722 indicating the presence of liquid. In this embodiment, the sensors may be located at a bottom side of the fluid collection chamber 1722, while a vacuum source connects to the chamber 1722 at an upper end of the chamber 1722. Therefore, if liquid is drawn into the fluid collection chamber 1722, the liquid may be detected before the liquid level reaches the vacuum source. Optionally, a hydrophobic filter, valve or other component may be placed at the vacuum source connection point into the chamber 1722 to help further resist the entry of liquid into the vacuum source. In this way, a liquid leak may be detected and acted upon by controller 16 (e.g., generating an alert, closing liquid inlet valves and ceasing pumping operations) before the vacuum source valve is placed at risk of being contaminated by the liquid.

In the example schematic shown in FIG. 62, a calibration port 2684 is depicted. The calibration port 2684 may be used to calibrate the various pressure sensors 2670, 2672, 2674, 2676, 2677, 2678 in the pneumatic system. For example, a pressure reference may be connected to the pneumatic circuit of the cycler via the calibration port 2684. With the pressure reference connected, the valves of the pneumatic system may be actuated so as to connect all of the pressure sensors 2670, 2672, 2674, 2676, 2677, 2678 to the same fluid volume. A known pressure may then be established in the pneumatic system using the pressure reference. The pressure readings from each of the pressure sensors 2670, 2672, 2674, 2676, 2677, 2678 may be compared to the known pressure of the pressure reference and the pressure sensors 2670, 2672, 2674, 2676, 2677, 2678 may then be calibrated accordingly. In some embodiments, selected pressure sensors of the pressure sensors 2672, 2674, 2676, 2677, 2678 may be connected and brought to the pressure of the reference for calibration in groups or individually.

Any fluid handling device (i.e. base unit) that is configured to actuate diaphragm-based pumps and valves on a removable cassette can take advantage of its pneumatic (or hydraulic) cassette interface to receive a calibrating reference pressure via a specialized calibrating cassette (or 'cassette fixture'). A calibrating cassette can have the same overall dimensions as a standard fluid pumping cassette, so that it can provide a sealing interface with the cassette interface or control surface of the base unit. One or more of the pump or valve regions can be allowed to communicate with a corresponding region of the interface to which it mates, so that a reference pneumatic or hydraulic pressure can be introduced through the calibrating cassette and into the pneumatic or hydraulic flow paths of the base unit (e.g. via a pneumatic or hydraulic manifold).

For example, in a pneumatically operated peritoneal dialysis cycler, the pneumatic circuitry of the cycler may be accessed directly through the cassette interface of the cycler 14. This may for example, be accomplished using a modified cassette or cassette fixture which allows the control surface 148 to create a seal against the cassette fixture. Additionally, the cassette fixture may be constructed to include at least one access port in fluid communication with a vacuum port 173B of the cassette interface. In the absence of a vacuum port (e.g. in embodiments having slits or perforations in the control surface) the access port may instead be placed in communication with the vacuum vent feature of the cassette interface or control surface.

The cassette fixture (or calibrating cassette) may be constructed to have a direct flow path from an external cassette port to the access port facing the device interface, the external cassette port then being available for connection to a pressure reference. As described above, all or some of the pressure sensors 2670, 2672, 2674, 2676, 2677, 2678 may be placed into fluid communication with a common volume, through the appropriate actuation of pneumatic control valves in the pressure distribution manifold. A known pressure may be established in that volume using the pressure reference. The pressure readings from each of the pressure sensors 2670, 2672, 2674, 2676, 2677, 2678 may be compared to the known pressure of the pressure reference and the pressure sensors 2670, 2672, 2674, 2676, 2677, 2678 may then be calibrated accordingly.

In some embodiments of a pressure distribution manifold, it may not be possible for all of the pressure sensors 2670, 2672, 2674, 2676, 2677, 2678 to be connected to a common volume at one time. In that case, the flow paths to the individual pressure sensors 2670, 2672, 2674, 2676, 2677, 2678 may need to be opened in a sequential manner to ensure calibration of all sensors. Additionally, it should be noted that once calibrated, one or more of the pressure sensors 2670, 2672, 2674, 2676, 2677, 2678 may be used to calibrate other pressure sensors 2670, 2672, 2674, 2676, 2677, 2678 in a pressure distribution manifold of a base unit or cycler 14. The previously calibrated pressure sensor or sensors may be placed into a common volume with the uncalibrated pressure sensor (e.g. via suitable valve actuations). The pressure of the common volume may be known via the calibrated pressure sensor(s). The uncalibrated pressure sensor's reading may be compared to the known pressure of the common volume and then calibrated accordingly.

In one embodiment, the inner wall of the control chambers 171B can include raised elements somewhat analogous to the spacer elements 50 of the pump chamber, e.g., as shown in FIG. 59 for the control chambers 171B associated with the pump control regions 1482. These raised elements can take the form of plateau features, ribs, or other protrusions that keep the control ports recessed away from the fully retracted control regions 1482. This arrangement may allow for a more uniform distribution of pressure or vacuum in the control chamber 171B, and prevent premature blocking of any control port by the control surface 148. A pre-formed control surface 148 (at least in the pump control regions) may not be under a significant stretching force when fully extended against either the inner wall of the pump chamber of the cassette 24 during a delivery stroke, or the inner wall of the control chamber 171 during a fill stroke. It may therefore be possible for the control region 1482 to extend asymmetrically into the control chamber 171B, causing the control region 1482 to prematurely close off one or more ports of the control chamber 171B before the chamber is fully evacuated. Having features on the inner surface of the control chamber 171B that prevent contact between the control region 1482 and the control ports may help to assure that the control region 1482 can make uniform contact with the control chamber inner wall during a fill stroke.

As suggested above, the cycler 14 may include a control system 16 with a data processor in electrical communication with the various valves, pressure sensors, motors, etc., of the system and is preferably configured to control such components according to a desired operating sequence or protocol. The control system 16 may include appropriate circuitry, programming, computer memory, electrical connections, and/or other components to perform a specified task. The system may include pumps, tanks, manifolds, valves or other components to generate desired air or other fluid pressure (whether positive pressure—above atmospheric pressure or some other reference—or negative pressure or vacuum—below atmospheric pressure or some other reference) to control operation of the regions of the control surface 148, and other pneumatically-operated components. Further details regarding the control system 16 (or at least portions of it) are provided below.

In one illustrative embodiment, the pressure in the pump control chambers 171B may be controlled by a binary valve, e.g., which opens to expose the control chamber 171 to a suitable pressure/vacuum and closes to cut off the pressure/vacuum source. The binary valve may be controlled using a saw tooth-shaped control signal which may be modulated to control pressure in the pump control chamber 171B. For example, during a pump delivery stroke (i.e., in which positive pressure is introduced into the pump control chamber 171B to move the membrane 15/control surface 148 and force liquid out of the pump chamber 181), the binary valve may be driven by the saw tooth signal so as to open and close at a relatively rapid rate to establish a suitable pressure in the control chamber 171B (e.g., a pressure between about 70-90 mmHg). If the pressure in the control chamber 171B rises above about 90 mmHg, the saw tooth signal may be adjusted to close the binary valve for a more extended period. If the pressure drops below about 70 mmHg in the control chamber 171B, the saw tooth control signal may again be applied to the binary valve to raise the pressure in the control chamber 171. Thus, during a typical pump operation, the binary valve will be opened and closed multiple times, and may be closed for one or more extended periods, so that the pressure at which the liquid is forced from the pump chamber 181 is maintained at a desired level or range (e.g., about 70-90 mmHg).

In some embodiments and in accordance with an aspect of the disclosure, it may be useful to detect an "end of stroke" of the membrane 15/pump control region 1482, e.g., when the membrane 15 contacts the spacers 50 in the pump chamber 181 or the pump control region 1482 contacts the wall of the pump control chamber 171B. For example, during a pumping operation, detection of the "end of stroke" may indicate that the membrane 15/pump control region 1482 movement should be reversed to initiate a new pump cycle (to fill the pump chamber 181 or drive fluid from the pump chamber 181). In one illustrative embodiment in which the pressure in the control chamber 171B for a pump is controlled by a binary valve driven by a saw tooth control signal, the pressure in the pump chamber 181 will fluctuate at a relatively high frequency, e.g., a frequency at or near the frequency at which the binary valve is opened and closed. A pressure sensor in the control chamber 171B may detect this fluctuation, which generally has a higher amplitude when the membrane 15/pump control region 1482 are not in contact with the inner wall of the pump chamber 181 or the wall of the pump control chamber 171B. However, once the membrane 15/pump control region 1482 contacts the inner wall of the pump chamber 181 or the wall of the pump control chamber 171B (i.e., the "end of stroke"), the pressure fluctuation is generally damped or otherwise changes in a way that is detectable by the pressure sensor in the pump control chamber 171B. This change in pressure fluctuation can be used to identify the end of stroke, and the pump and other components of the cassette 24 and/or cycler 14 may be controlled accordingly.

Figure 69:
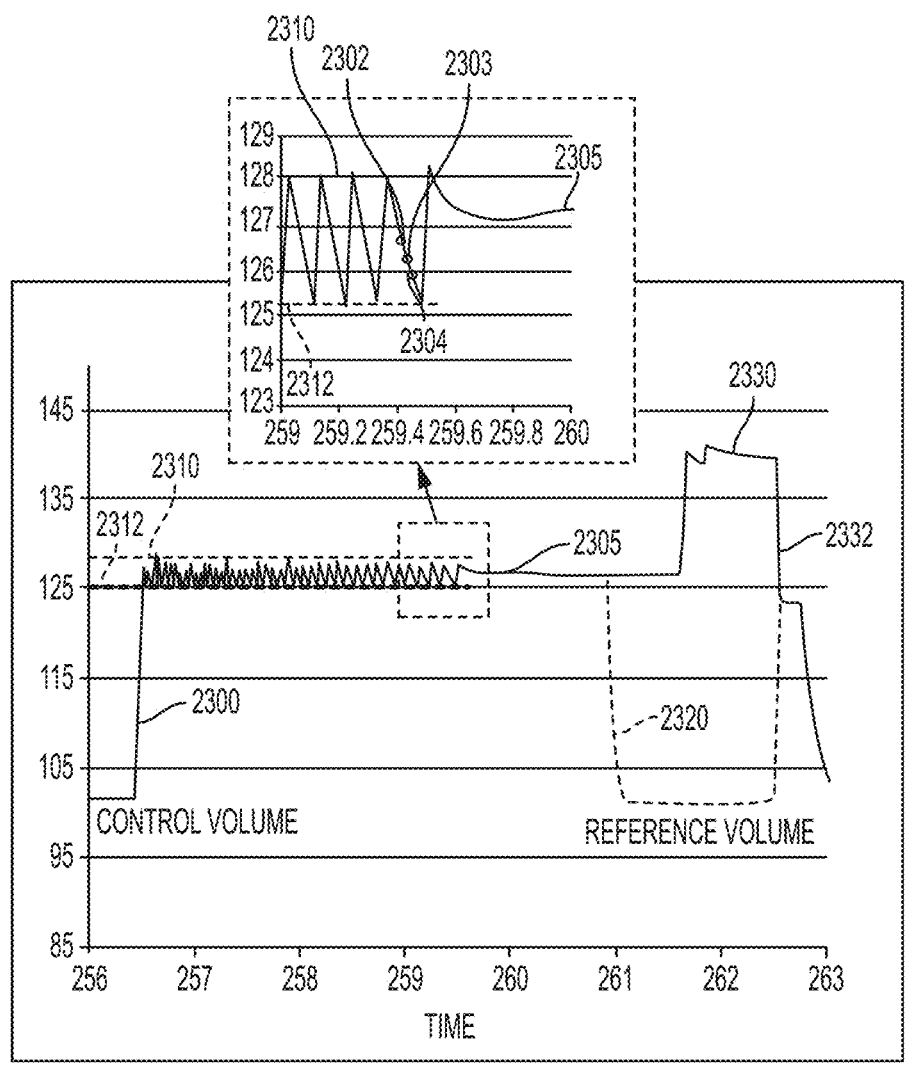
FIG. 69 shows a pressure tracing from a control or actuation chamber of a pumping cassette during a liquid delivery stroke.

In one embodiment, the pneumatic pressure applied to the control chamber 171B is actively controlled by a processor receiving a signal from a pressure transducer 2672 (FIG. 62) connected to the control chamber 171B and a fast acting binary valve X1A, X1B between a pressure reservoir 2620, 2610 and the control chamber 171B. The processor may control the pressure with a variety of control algorithms including closed loop proportional or proportional-integrator feedback control that varies the valve duty cycle to achieve the desired pressure in the control volume 171B. In one embodiment, the processor controls the pressure in the control chamber 171B with an on-off controller often called a bang-bang controller. The on-off controller monitors the pressure in the control volume or chamber 171B during a deliver stroke and open the binary valve X1B connecting the control volume 171B to the positive reservoir 2620 when the pressure is less than a lower first limit and closes the binary valve X1B when the pressure is above a higher second limit. During a fill stroke, the on-off controller opens the binary valve X1A connecting the control volume 171B to the negative reservoir 2610 when the pressure is greater than a third limit and closes the binary valve X1A when the pressure is less than a fourth limit, where the forth limit is lower than the third limit and both the third and forth limits are less than the first limit. A plot of the pressure over time as during a deliver stroke and the subsequent FMS measurement is shown in FIG. 69. The control chamber pressure 2300 oscillates between the lower first limit 2312 and the higher second limit 2310 as the membrane 15 moves across the control chamber 171B. The pressure stops oscillating between the limits when the membrane 15 stops moving. The membrane 15 typically stops moving when it contacts either the stadium steps 50 of the cassette or it contacts the control chamber surface 171B. The membrane 15 may also stop moving if the outlet fluid line is occluded.

The automation computer (AC) 300 detects the end of stroke by evaluating the pressure signals. There are many possible algorithms to detect the end of pressure oscillation that indicate the end-of-stroke (EOS). The algorithms and methods to detect EOS in the section labeled "Detailed Description of the system and Method of Measuring Change Fluid Flow Rate" in U.S. Pat. No. 6,520,747 to Gray et al., issued Feb. 18, 2003, entitled "System for Measuring Change in Fluid Flow Rate within a Line," and the section describing the filtering to detect end of stroke in U.S. Pat. No. 8,292,594 to Tracey et al., issued Oct. 23, 2012, entitled "Fluid Pumping Systems, Devices and Methods," both of which are herein incorporated by reference in their entirety along with the entirety of the references within which they are contained.

One example of an algorithm to detect EOS, the AC 300 evaluates the time between the pressure crossing the first and second limits during a deliver stroke or third and fourth limits during a fill stroke. The on-off controller opens and closes the valves X1A, X1B in response to the pressure oscillating between the two limits as the control chamber 171B volume changes during the fill or deliver stroke. When the membrane 15 stops moving at the end-of-stroke, the pressure changes will significantly diminish so that the pressure no longer exceeds one or both limits. The AC 300 may detect EOS by measuring the time between the pressure exceeding alternating limits. If the time since the pressure crossed the last limit exceeds a predefined threshold, then the AC 300 may declare an EOS. The algorithm may further include an initial period during which the AC 300 does not measure the time between limit crossings.

In another example algorithm, the AC 300 evaluates the derivative of the pressure signal with respect to time. The AC 300 may declare an EOS, if the derivative remains below a minimum threshold for a minimum length of time. In a further example, the minimum threshold is the average of the absolute value of the average pressure derivative during the stroke. The algorithm calculates the slope (derivative with respect to time) of a curve fit to a set of data points, where the data points are taken from a moving window. The absolute value of each slope is then averaged over the stroke to calculate the absolute value of the average pressure derivative. In another example of an EOS algorithm, the AC 300 may not include the pressure data until after an initial delay. The AC 300 ignores the initial pressure data to avoid false EOS detections due to irregular pressure traces that occasionally occur during the early part of the stroke. In another example, the AC 300 declares an EOS only after the second derivative of the pressure in the later part of the stroke has remained below a threshold for a minimum time and a wait period of time has past.

The criteria to declare an EOS may be optimized for different pumping conditions. The optimized EOS detection conditions include the second pressure derivative threshold, the minimum time to remain below the second derivative threshold, the duration of the initial delay and a length of the wait period. These EOS detection criteria may be optimized differently, for example, the fill stroke from the bags 20, 22, the deliver stroke to the patient, the fill stroke from the patient, and the deliver stroke to the bags 20, 22. Alternatively each EOS detection criteria may be a function of the pumping pressure in the control chamber 171B.

Occluder

In one aspect of the disclosure, an occluder for opening/closing one or more flexible lines may include a pair of opposed occluding members, which may be configured as resilient elements, such as flat plates made of a spring steel (e.g., leaf springs), having a force actuator configured to apply a force to one or both of the occluding members to operate the occluder. In certain embodiments, the force actuator may comprise an expandable or enlargeable member positioned between the resilient elements. With the expandable member in a reduced size condition, the resilient elements may be in a flat or nearly flat condition and urge a pinch head to engage with one or more lines so as to pinch the lines closed. However, when the expandable member urges the resilient elements apart, the resilient elements may bend and withdraw the pinch head, releasing the lines and allowing flow through the lines. In other embodiments, the occluding members could be essentially rigid with respect to the levels of force applied by the force actuator. In certain embodiments, the force actuator may apply a force to one or both opposed occluding members to increase the distance between the occluding members in at least a portion of the region where they are opposed to effect opening or closing of the flexible tubing.

Figure 63:
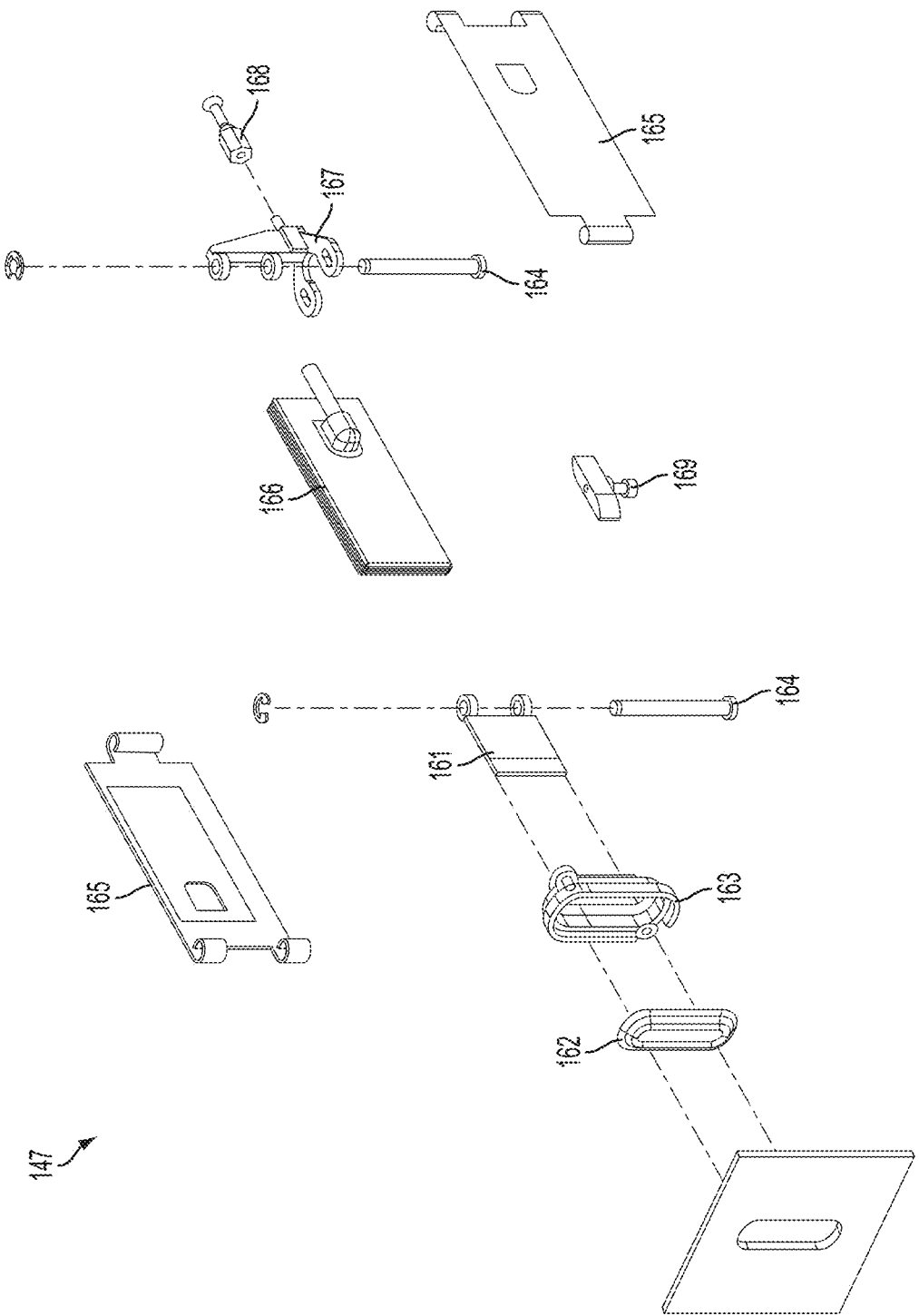
FIG. 63 is an exploded perspective view of an occluder in an illustrative embodiment.
Figure 64:
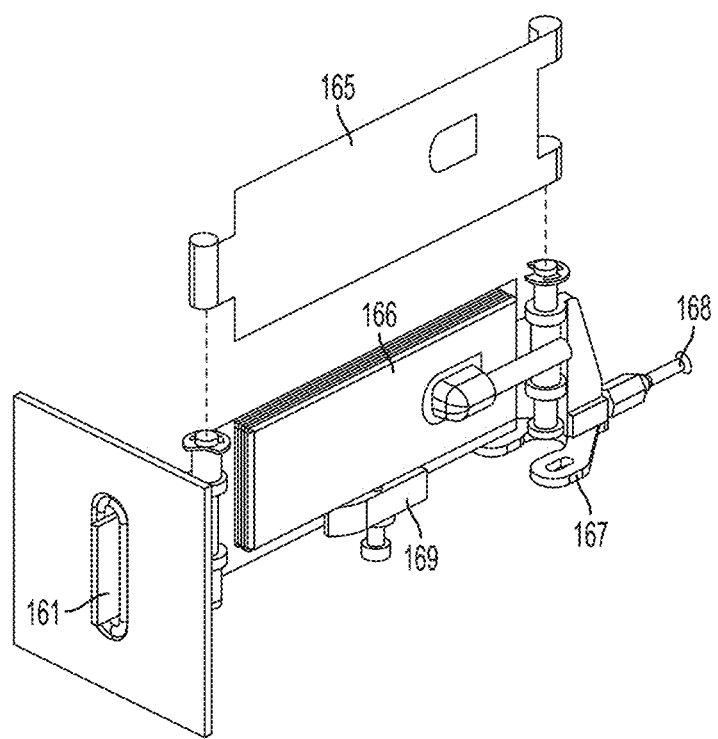
FIG. 64 is a partially exploded perspective view of the occluder of FIG. 63.

FIG. 63 shows an exploded view and FIG. 64 shows a partially assembled view of an illustrative embodiment of an occluder 147 that may be used to close, or occlude, the patient and drain lines 34 and 28, and/or other lines in the cycler 14 or the set 12 (such as, for example, the heater bag line 26). The occluder 147 includes an optional pinch head 161, e.g., a generally flat blade-like element that contacts the tubes to press the tubes against the door 141 and pinch the tubes closed. In other embodiments, the function of the pinch head could be replaced by an extending edge of one or both of occluding members 165. The pinch head 161 includes a gasket 162, such as an O-ring or other member, that cooperates with the pinch head 161 to help resist entry of fluid (air or liquid for example) into the cycler 14 housing, e.g., in case of leakage in one of the occluded lines. The bellows gasket 162 is mounted to, and pinch head 161 passes through, a pinch head guide 163 that is mounted to the front panel of the cycler housing, i.e., the panel exposed by opening the door 141. The pinch head guide 163 allows the pinch head 161 to move in and out of the pinch head guide 163 without binding and/or substantial resistance to sliding motion of the pinch head 161. A pivot shaft 164 attaches a pair of opposed occluder spring members, comprising in the illustrated embodiment spring plates 165, that each include a hook-shaped pivot shaft bearing, e.g., like that found on standard door hinges, to the pinch head 161. That is, the openings of shaft guides on the pinch head 161, and the openings formed by the hook-shaped bearings on the spring plates 165 are aligned with each other and the pivot shaft 164 is inserted through the openings so the pinch head 161 and the spring plates 165 are pivotally connected together. The spring plates 165 may be made of any suitable material, such as steel, and may be arranged to be generally flat when unstressed. The opposite end of the spring plates 165 includes similar hook-shaped bearings, which are pivotally connected to a linear adjustor 167 by a second pivot shaft 164. In this embodiment, the force actuator comprises a bladder 166 positioned between the spring plates 165 and arranged so that when fluid (e.g., air under pressure) is introduced into the bladder 166, the bladder 166 may expand and push the spring plates 165 away from each other in a region between the pivot shafts 164. The bladder 166 may be attached to one or both spring plates 165 by pressure sensitive adhesive (PSA) tape. A linear adjustor 167 is fixed to the cycler housing 82 while the pinch head 161 is allowed to float, although its movement is guided by the pinch head guide 163. The linear adjustor 167 includes slot holes at its lower end, allowing the entire assembly to be adjusted in position and thus permitting the pinch head to be appropriately positioned when the occluder 147 is installed in the cycler 14. A turnbuckle 168 or other arrangement may be used to help adjust the position of the linear adjustor 167 relative to the housing 82. That is, the pinch head 161 generally needs to be properly positioned so that with the spring plates 165 located near each other and the bladder 166 substantially emptied or at ambient pressure, the pinch head 161 suitably presses on the patient and drain lines so as to pinch the lines closed to flow without cutting, kinking or otherwise damaging the lines. The slot openings in the linear adjustor 167 allows for this fine positioning and fixing of the occluder 147 in place. An override release device, such as provided by release blade 169 is optionally positioned between the spring plates 165, and as is discussed in more detail below, may be rotated so as to push the spring plates 165 apart, thereby withdrawing the pinch head 161 into the pinch head guide 163. The release blade 169 may be manually operated, e.g., to disable the occluder 147 in case of power loss, bladder 166 failure or other circumstance.

The spring plates 165 may be constructed from any material that is elastically resistant to bending forces and which has sufficient longitudinal stiffness (resistance to bending) to provide sufficient restoring force, in response to a bending displacement, to occlude a desired number of collapsible tubes. In the illustrated embodiment, each spring plate is essentially flat when unstressed and in the shape of a sheet or plate. In alternative embodiments utilizing one or more resilient occluding members (spring members), any occluding member(s) that is elastically resistant to bending forces and which has sufficient longitudinal stiffness (resistance to bending) to provide sufficient restoring force, in response to a bending displacement to occlude a desired number of collapsible tubes may be utilized. Potentially suitable spring members can have a wide variety of shapes as apparent to those of ordinary skill in the art, including, but not limited to cylindrical, prism-shaped, trapezoidal, square, or rectangular bars or beams, I-beams, elliptical beams, bowl-shaped surfaces, and others. Those of ordinary skill in the art can readily select proper materials and dimensions for spring plates 165 based on the present teachings and the requirements of a particular application.

Figure 65:
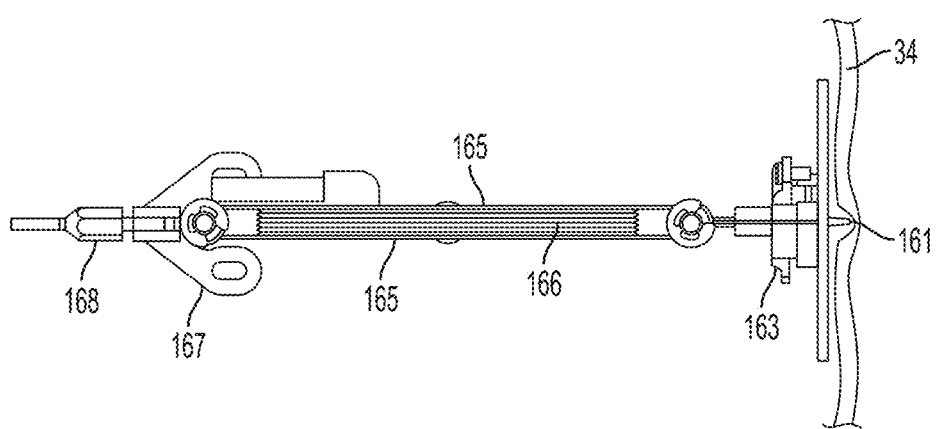
FIG. 65 is a top view of the occluder of FIG. 63 with the bladder in a deflated state.
Figure 66:
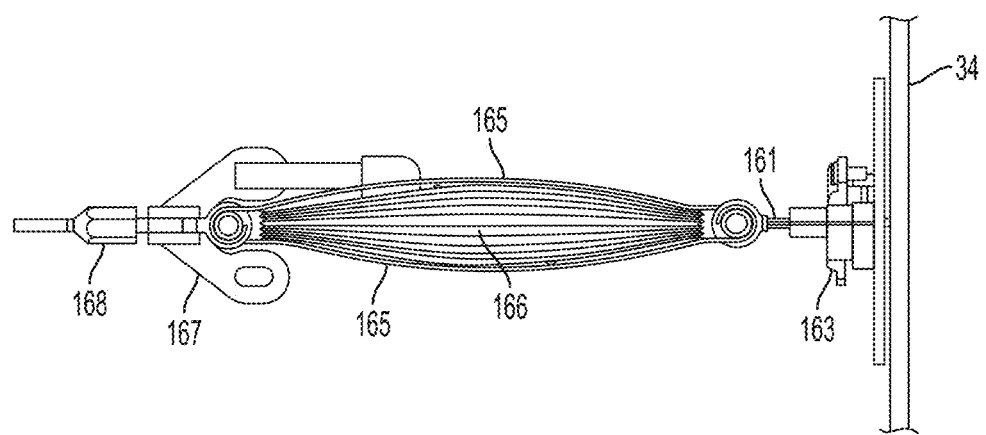
FIG. 66 is a top view of the occluder of FIG. 63 with the bladder in an inflated state.

FIG. 65 shows a top view of the occluder 147 with the bladder 166 deflated and the spring plates 165 located near each other and in a flat or nearly flat condition. In this position, the pinch head 161 is fully extended from the pinch head guide and the front panel of the cycler 14 (i.e., the panel inside of the door 141) and enabled to occlude the patient and drain lines. FIG. 66, on the other hand, shows the bladder 166 in an inflated state in which the spring plates 165 are pushed apart, thereby retracting the pinch head 161 into the pinch head guide 163. Note that the linear adjustor 167 is fixed in place relative to the cycler housing 82 and thus fixed relative to the front panel of the housing 82. As the spring plates 165 are moved apart, the pinch head 161 moves rearward relative to the front panel since the pinch head 161 is arranged to move freely in and out of the pinch head guide 163. This condition prevents the pinch head 161 from occluding the patient and drain lines and is the condition in which the occluder 147 remains during normal operation of the cycler 14. That is, as discussed above, various components of the cycler 14 may operate using air pressure/vacuum, e.g., the control surface 148 may operate under the drive of suitable air pressure/vacuum to cause fluid pumping and valve operation for the cassette 24. Thus, when the cycler 14 is operating normally, the cycler 14 may produce sufficient air pressure to not only control system operation, but also to inflate the bladder 166 to retract the pinch head 161 and prevent occlusion of the patient and drain lines. However, in the case of system shut down, failure, fault or other condition, air pressure to the bladder 166 may be terminated, causing the bladder 166 to deflate and the spring plates 165 to straighten and extend the pinch head 161 to occlude the lines. One possible advantage of the arrangement shown is that the return force of the spring plates 165 is balanced such that the pinch head 161 generally will not bind in the pinch head guide 163 when moving relative to the pinch head guide 163. In addition, the opposing forces of the spring plates 165 will tend to reduce the amount of asymmetrical frictional wear of the pivot shafts and bushings of the assembly. Also, once the spring plates 165 are in an approximately straight position, the spring plates 165 can exert a force in a direction generally along the length of the pinch head 161 that is several times larger than the force exerted by the bladder 166 on the spring plates 165 to separate the spring plates 165 from each other and retract the pinch head 161. Further, with the spring plates 165 in a flat or nearly flat condition, the force needed to be exerted by fluid in the collapsed tubing to overcome the pinching force exerted by the pinch head 161 approaches a relatively high force required, when applied to the spring plates 165 at their ends and essentially parallel to the plane of the flattened spring plates 165, to buckle the spring plates 165 by breaking the column stability of the flattened spring plates 165. As a result, the occluder 147 can be very effective in occluding the lines with a reduced chance of failure while also requiring a relatively small force be applied by the bladder 166 to retract the pinch head 161. The dual spring plate 165 arrangement of the illustrative embodiment may have the additional advantage of significantly increasing the pinching force provided by the pinch head 161, for any given force needed to bend the spring plate 165, and/or for any given size and thickness of spring plate 165.

In some circumstances, the force of the occluder 147 on the lines may be relatively large and may cause the door 141 to be difficult to open. That is, the door 141 must oppose the force of the occluder 147 when the pinch head 161 is in contact with and occluding lines, and in some cases this may cause the latch that maintains the door 141 in a closed state to be difficult or impossible to operate by hand. Of course, if the cycler 14 is started and produces air pressure to operate, the occluder bladder 166 can be inflated and the occluder pinch head 161 retracted. However, in some cases, such as with a pump failure in the cycler 14, inflation of the bladder 166 may be impossible or difficult. To allow opening of the door 141, the occluder 147 may include a manual release. In this illustrative embodiment, the occluder 147 may include a release blade 169 as shown in FIGS. 63 and 64 which includes a pair of wings pivotally mounted for rotary movement between the spring plates 165. When at rest, the release blade wings may be aligned with the spring plates 165 as shown in FIG. 64, allowing the occluder 147 to operate normally. However, if the spring plates 165 are in a flat condition and the pinch head 161 needs to be retracted manually, the release blade 169 may be rotated, e.g., by engaging a hex key or other tool with the release blade 169 and turning the release blade 169, so that the wings push the spring plates 165 apart. The hex key or other tool may be inserted through an opening in the housing 82 of the cycler 14, e.g., an opening near the left side handle depression in the cycler housing 82, and operated to disengage the occluder 147 and allow the door 141 to be opened.

Pump Volume Delivery Measurement

In another aspect of the disclosure, the cycler 14 may determine a volume of fluid delivered in various lines of the system 10 without the use of a flowmeter, weight scale or other direct measurement of fluid volume or weight. For example, in one embodiment, a volume of fluid moved by a pump, such as a pump in the cassette 24, may be determined based on pressure measurements of a gas used to drive the pump. In one embodiment, a volume determination can be made by isolating two chambers from each other, measuring the respective pressures in the isolated chambers, allowing the pressures in the chambers to partially or substantially equalize (by fluidly connecting the two chambers) and measuring the pressures. Using the measured pressures, the known volume of one of the chambers, and an assumption that the equalization occurs in an adiabatic way, the volume of the other chamber (e.g., a pump chamber) can be calculated. In one embodiment, the pressures measured after the chambers are fluidly connected may be substantially unequal to each other, i.e., the pressures in the chambers may not have yet completely equalized. However, these substantially unequal pressures may be used to determine a volume of the pump control chamber, as explained below.

Figure 67:
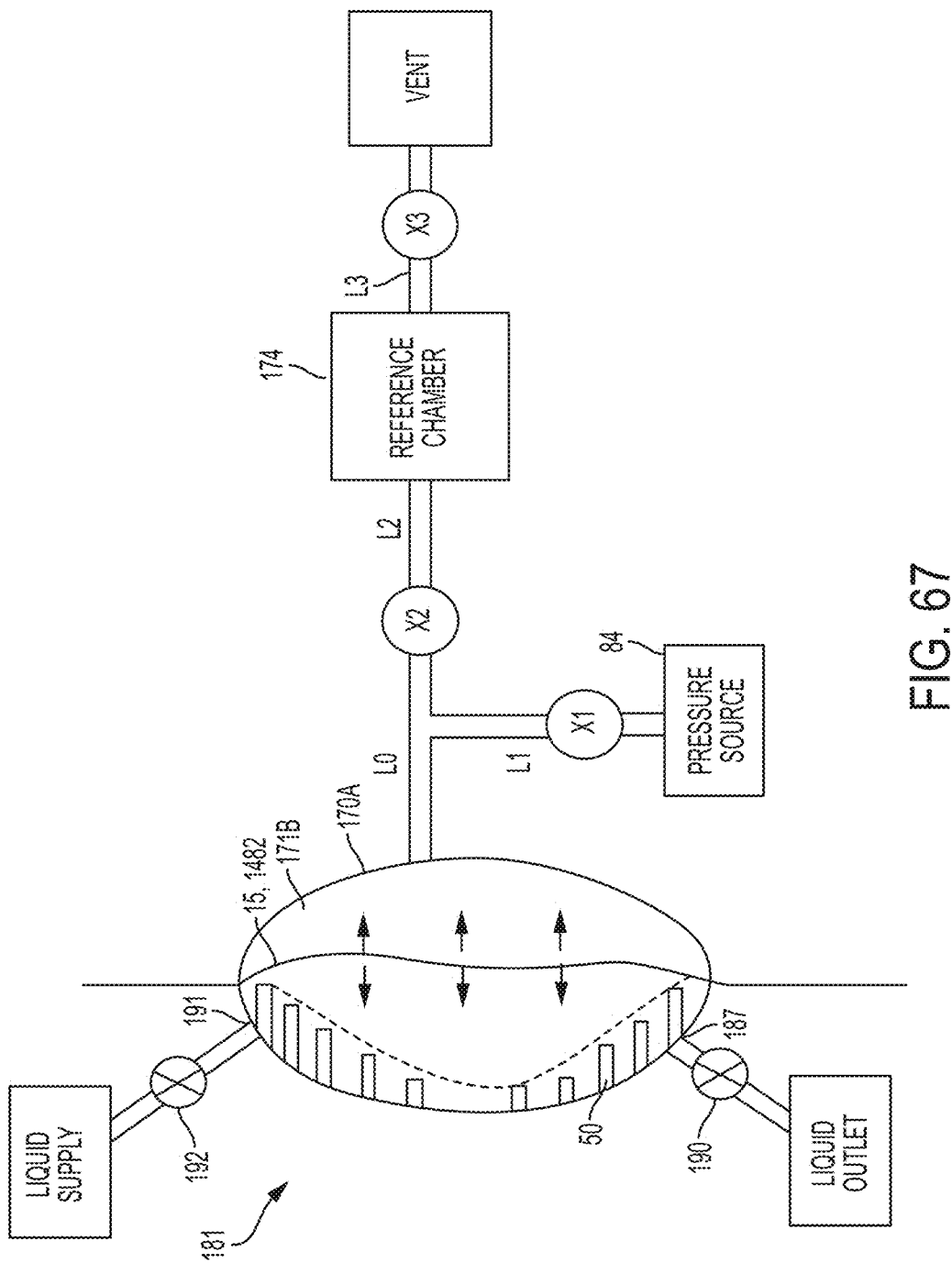
FIG. 67 is a schematic view of a pump chamber of a cassette and associated control components and inflow/outflow paths in an illustrative embodiment.

For example, FIG. 67 shows a schematic view of a pump chamber 181 of the cassette 24 and associated control components and inflow/outflow paths. In this illustrative example, a liquid supply, which may include the heater bag 22, heater bag line 26 and a flow path through the cassette 24, is shown providing a liquid input at the upper opening 191 of the pump chamber 181. The liquid outlet is shown in this example as receiving liquid from the lower opening 187 of the pump chamber 181, and may include a flow path of the cassette 24 and the patient line 34, for example. The liquid supply may include a valve, e.g., including the valve port 192, that can be opened and closed to permit/impede flow to or from the pump chamber 181. Similarly, the liquid outlet may include a valve, e.g., including the valve port 190, that can be opened and closed to permit/impede flow to or from the pump chamber 181. Of course, the liquid supply could include any suitable arrangement, such as one or more solution containers 30, the patient line 34, one or more flow paths in the cassette 24 or other liquid source, and the liquid outlet could likewise include any suitable arrangement, such as the drain line, the heater bag 22 and heater bag line 26, one or more flow paths in the cassette 24 or other liquid outlet. Generally speaking, the pump chamber 181 (i.e., on the left side of the membrane 14 in FIG. 67) will be filled with an incompressible liquid, such as water or dialysate, during operation. However, air or other gas may be present in the pump chamber 181 in some circumstances, such as during initial operation, priming, or other situations as discussed below. Also, it should be understood that although aspects of the disclosure relating to volume and/or pressure detection for a pump are described with reference to the pump arrangement of the cassette 24, aspects of the disclosure may be used with any suitable pump or fluid movement system.

FIG. 67 also shows schematically to the right of the membrane 15 and the control surface 1482 (which are adjacent each other) a control chamber 171B, which may be formed as a void or other space in the mating block 170A associated with the pump control region 1482 of the control surface 1482 for the pump chamber 181, as discussed above. It is in the control chamber 171B that suitable air pressure is introduced to cause the membrane 15/control region 1482 to move and effect pumping of liquid in the pump chamber 181. The control chamber 171B may communicate with a line L0 that branches to another line L1 and a first valve X1 that communicates with a pressure source 84 (e.g., a source of air pressure or vacuum). The pressure source 84 may include a piston pump in which the piston is moved in a chamber to control a pressure delivered to the control chamber 171B, or may include a different type of pressure pump and/or tank(s) to deliver suitable gas pressure to move the membrane 15/control region 1482 and perform pumping action. The line L0 also leads to a second valve X2 that communicates with another line L2 and a reference chamber 174 (e.g., a space suitably configured for performing the measurements described below). The reference chamber 174 also communicates with a line L3 having a valve X3 that leads to a vent or other reference pressure (e.g., a source of atmospheric pressure or other reference pressure). Each of the valves X1, X2 and X3 may be independently controlled. Pressure sensors may be arranged, e.g., one sensor at the control chamber 171B and another sensor at the reference chamber 174, to measure pressure associated with the control chamber and the reference chamber. These pressure sensors may be positioned and may operate to detect pressure in any suitable way. The pressure sensors may communicate with the control system 16 for the cycler 14 or other suitable processor for determining a volume delivered by the pump or other features.

As mentioned above, the valves and other components of the pump system shown in FIG. 67 can be controlled so as to measure pressures in the pump chamber 181, the liquid supply and/or liquid outlet, and/or to measure a volume of fluid delivered from the pump chamber 181 to the liquid supply or liquid outlet. Regarding volume measurement, one technique used to determine a volume of fluid delivered from the pump chamber 181 is to compare the relative pressures at the control chamber 171B to that of the reference chamber 174 in two different pump states. By comparing the relative pressures, a change in volume at the control chamber 171B can be determined, which corresponds to a change in volume in the pump chamber 181 and reflects a volume delivered from/received into the pump chamber 181. For example, after the pressure is reduced in the control chamber 171B during a pump chamber fill cycle (e.g., by applying negative pressure from the pressure source through open valve X1) so as to draw the membrane 15 and pump control region 1482 into contact with at least a portion of the control chamber wall (or to another suitable position for the membrane 15/region 1482), valve X1 may be closed to isolate the control chamber from the pressure source, and valve X2 may be closed, thereby isolating the reference chamber 174 from the control chamber 171B. Valve X3 may be opened to vent the reference chamber to ambient pressure, then closed to isolate the reference chamber. With valve X1 closed and the pressures in the control chamber and reference chamber measured, valve X2 is then opened to allow the pressure in the control chamber 171B and the reference chamber 174 to start to equalize. The initial pressures of the reference chamber 174 and the control chamber 171B, together with the known volume of the reference chamber 174 and pressures measured after equalization has been initiated (but not yet necessarily completed) can be used to determine a volume for the control chamber 171B. This process may be repeated at the end of the pump delivery cycle when the sheet 15/control region 1482 are pushed into contact with the spacer elements 50 of the pump chamber 181. By comparing the control chamber volume 171B at the end of the fill cycle to the volume at the end of the delivery cycle, a volume of liquid delivered from the pump can be determined.

Conceptually, the pressure equalization process (e.g., at opening of the valve X2) is viewed as happening in an adiabatic way, i.e., without heat transfer occurring between air in the control and reference chambers 171B, 174 and its environment. The conceptual notion is that there is an imaginary piston located initially at the valve X2 when the valve X2 is closed, and that the imaginary piston moves in the line L0 or L2 when the valve X2 is opened to equalize the pressure in the control and reference chambers 171B, 174. Since (a) the pressure equalization process happens relatively quickly, (b) the air in the control chamber 171B and the reference chamber 174 has approximately the same concentrations of elements, and (c) the temperatures are similar, the assumption that the pressure equalization happens in an adiabatic way may introduce only small error into the volume measurements. Also, in one embodiment, the pressures taken after equalization has been initiated may be measured before substantial equalization has occurred-further reducing the time between measuring the initial pressures and the final pressures used to determine the pump chamber 181 volume. Error can be further reduced, for example, by using low thermal conductivity materials for the membrane 15/control surface 1482, the cassette 24, the control chamber 171B, the lines, the reference chamber 174, etc., so as to reduce heat transfer.

Given the assumption that an adiabatic system exists between the state when the valve X2 is closed until after the valve X2 is opened and the pressures equalize, the following applies:

$$PV^\gamma = \text{Constant} \qquad (1)$$

where P is pressure, V is volume and $\gamma$ is equal to a constant (e.g., about 1.4 where the gas is diatomic, such as air). Thus, the following equation can be written to relate the pressures and volumes in the control chamber 171B and the reference chamber 174 before and after the opening of valve X2 and pressure equalization occurs:

$$PrVr^\gamma + PdVd^\gamma = \text{Constant} = PfVf^\gamma \qquad (2)$$

where Pr is the pressure in the reference chamber 174 and lines L2 and L3 prior to the valve X2 opening, Vr is the volume of the reference chamber 174 and lines L2 and L3 prior to the valve X2 opening, Pd is the pressure in the control chamber 171B and the lines L0 and L1 prior to the valve X2 opening, Vd is the volume of the control chamber 171B and the lines L0 and L1 prior to the valve X2 opening, Pf is the equalized pressure in the reference chamber 174 and the control chamber 171B after opening of the valve X2, and Vf is the volume of the entire system including the control chamber 171B, the reference chamber 174 and the lines L0, L1, L2, and L3, i.e., Vf=Vd+Vr. Since Pr, Vr, Pd, Pf and $\gamma$ are known, and Vf=Vr+Vd, this equation can be used to solve for Vd. Although reference is made herein to use of a "measured pressure" in determining volume values, etc., it should be understood that such a measured pressure value need not necessarily be any particular form, such as in psi units. Instead, a "measured pressure" or "determined pressure" may include any value that is representative of a pressure, such as a voltage level, a resistance value, a multibit digital number, etc. For example, a pressure transducer used to measure pressure in the pump control chamber 171B may output an analog voltage level, resistance or other indication that is representative of the pressure in the pump control chamber 171B. The raw output from the transducer may be used as a measured pressure, and/or some modified form of the output, such as a digital number generated using an analog output from the transducer, a psi or other value that is generated based on the transducer output, and so on. The same is true of other values, such as a determined volume, which need not necessarily be in a particular form such as cubic centimeters. Instead, a determined volume may include any value that is representative of the volume, e.g., could be used to generate an actual volume in, say, cubic centimeters.

In an embodiment of a fluid management system ("FMS") technique to determine a volume delivered by the pump, it is assumed that pressure equalization upon opening of the valve X2 occurs in an adiabatic system. Thus, Equation 3 below gives the relationship of the volume of the reference chamber system before and after pressure equalization:

$$Vrf = Vri(Pf/Patm)^{-(1/\gamma)} \quad (3)$$

where Vrf is the final (post-equalization) volume of the reference chamber system including the volume of the reference chamber 174, the volume of the lines L2 and L3 and the volume adjustment resulting from movement of the "piston", which may move to the left or right of the valve X2 after opening, Vri is the initial (pre-equalization) volume of the reference chamber 174 and the lines L2 and L3 with the "piston" located at the valve X2, Pf is the final equalized pressure after the valve X2 is opened, and Patm is the initial pressure of the reference chamber 174 before valve X2 opening (in this example, atmospheric pressure). Similarly, Equation 4 gives the relationship of the volume of the control chamber system before and after pressure equalization:

$$Vdf = Vdi(Pf/Pdi)^{-(1/\gamma)} \quad (4)$$

where Vdf is the final volume of the control chamber system including the volume of the control chamber 171B, the volume of the lines L0 and L1, and the volume adjustment resulting from movement of the "piston", which may move to the left or right of the valve X2 after opening, Vdi is the initial volume of the control chamber 171B and the lines L0 and L1 with the "piston" located at the valve X2, Pf is the final pressure after the valve X2 is opened, and Pdi is the initial pressure of the control chamber 171B before valve X2 opening.

The volumes of the reference chamber system and the control chamber system will change by the same absolute amount after the valve X2 is opened and the pressure equalizes, but will differ in sign (e.g., because the change in volume is caused by movement of the "piston" left or right when the valve X2 opens), as shown in Equation 5:

$$\Delta Vr = (-1)\Delta Vd \quad (5)$$

Note that this change in volume for the reference chamber 174 and the control chamber 171B is due only to movement of the imaginary piston. The reference chamber 174 and control chamber 171B will not actually change in volume during the equalization process under normal conditions. Also, using the relationship from Equation 3, the change in volume of the reference chamber system is given by:

$$\Delta Vr = Vrf - Vri = Vri\left(-1 + (Pf/Patm)^{-(1/\gamma)}\right) \quad (6)$$

Similarly, using Equation 4, the change in volume of the control chamber system is given by:

$$\Delta Vd = Vdf - Vdi = Vdi\left(-1 + (Pf/Pdi)^{-(1/\gamma)}\right) \quad (7)$$

Because Vri is known, and Pf and Patm are measured or known, ΔVr can be calculated, which according to Equation 5 is assumed to be equal to (−)ΔVd. Therefore, Vdi (the volume of the control chamber system before pressure equalization with the reference chamber 174) can be calculated using Equation 7. In this embodiment, Vdi represents the volume of the control chamber 171B plus lines L0 and L1, of which L0 and L1 are fixed and known quantities. Subtracting L0 and L1 from Vdi yields the volume of the control chamber 171B alone. By using Equation 7 above, for example, both before (Vdi1) and after (Vdi2) a pump operation (e.g., at the end of a fill cycle and at the end of a discharge cycle), the change in volume of the control chamber 171B can be determined, thus providing a measurement of the volume of fluid delivered by (or taken in by) the pump. For example, if Vdi1 is the volume of the control chamber 171B at the end of a fill stroke, and Vdi2 is the volume of the control chamber 171B at the end of the subsequent delivery stroke, the volume of fluid delivered by the pump may be estimated by subtracting Vdi1 from Vdi2. Since this measurement is made based on pressure, the volume determination can be made for nearly any position of the membrane 15/pump control region 1482 in the pump chamber 181, whether for a full or partial pump stroke. However, measurement made at the ends of fill and delivery strokes can be accomplished with little or no impact on pump operation and/or flow rate.

One aspect of the disclosure involves a technique for identifying pressure measurement values that are to be used in determining a volume for the control chamber 171B and/or other purposes. For example, although pressure sensors may be used to detect a pressure in the control chamber 171B and a pressure in the reference chamber 174, the sensed pressure values may vary with opening/closing of valves, introduction of pressure to the control chamber 171B, venting of the reference chamber 174 to atmospheric pressure or other reference pressure, etc. Also, since in one embodiment, an adiabatic system is assumed to exist from a time before pressure equalization between the control chamber 171B and the reference chamber 174 until after equalization, identifying appropriate pressure values that were measured as close together in time may help to reduce error (e.g., because a shorter time elapsed between pressure measurements may reduce the amount of heat that is exchanged in the system). Thus, the measured pressure values may need to be chosen carefully to help ensure appropriate pressures are used for determining a volume delivered by the pump, etc.

As mentioned, L3 of FIG. 67 may have a valve X3 which leads to a vent. In some embodiments, this vent may communicate with the atmosphere or, in other embodiments, another reference pressure. In some embodiments, this vent may be connected via a valve to the control chamber 171B such that the control chamber 171B may be vented (see, e.g., FIG. 62). In prior devices the vent has been used to bring a control chamber 171B from a negative pressure after a fill stroke to ambient pressure before positive pressurization of the control chamber 171B. This brings the control chamber 171B to a higher starting pressure before connection to the pressure source 84 and consequently minimizes the depletion of pressure in a positive pressure source or reservoir 84. As a result a pump supplying a positive pressure reservoir 84 would be required to run less frequently.

On the other hand, it has since been determined that venting a control chamber 171B which is already at a positive pressure to a lower pressure before subsequently positively repressurizing the chamber for an FMS measurement may be advantageous in some scenarios. Though this new step requires additional work (e.g. pump runtime) to keep the pressure source 84 at its pressure set point, it may be done to help mitigate any possible undesirable effects from back pressure (e.g. due to an occluded line leading to or from the associated pumping chamber 181, or due to a partial occlusion). Additionally, this may help to increase the overall accuracy of volume measurement and fluid accounting. One possible reason for this is that a pump chamber outlet valve 190—in this case a pneumatically operated membrane valve—may not close as efficiently when the control chamber 171B remains positively pressurized.

In some embodiments, a control system 16 of a cycler 14 may vent the control chamber 171B before taking a measurement to determine fluid volume delivered or filled. Additionally, in some embodiments, the control system 16 of a cycler 14 may vent a first control chamber 171B before performing a pumping operation with a second control chamber included in the installed cassette 24.

In the example embodiment shown in FIG. 67, this venting or back pressure relief may be accomplished by opening valves X2 and X3 and closing valve X1. Thus, the control chamber 171B may be placed into communication with the vent via the reference chamber 174. In other embodiments, of course, a control chamber 171B may be placed into more direct communication with a vent. For example, an additional valve associated with a fluid path in direct communication with the vent may be included. Any other suitable configuration may also be used.

In some embodiments, the control chamber 171B may be vented by placing the control chamber 171B into fluid communication with the vent for a suitable or predetermined period of time. In other embodiments, to control venting of a control chamber 171B, the control system 16 of the cycler 14 may use data from a pressure sensor associated with one or both of the control chambers 171B or reference chamber 174 (or in a location fluidly connectable to the control chamber, such as, for example, a pressure distribution module). In such embodiments, data from the pressure sensor(s) may be used to determine whether or not the control chamber 171B has been sufficiently vented. Once a determination is made that the control chamber 171B has been sufficiently vented, the control system 16 of the cycler 14 may close the appropriate valve to isolate the control chamber 171B from the vent. In order for the control system 16 to determine that the control chamber 171B has been sufficiently vented, the control chamber 171B pressure need not necessarily fully equalize with that of the vent.

In some embodiments, in order to relieve back pressure in a control chamber 171B, it may instead be subjected to a negative pressure source for an appropriate or predetermined period of time. In such embodiments, the control chamber 171B may be placed into communication with a pressure source 84. In the example embodiment shown in FIG. 67, this may be accomplished by opening valve X1 and closing at least valve X3. In the case of a positively pressurized control chamber 171B, the pressure source to which the control chamber 171B is connected may be a negative pressure source. In some embodiments, the control system 16 of the cycler 14 may only open a valve to the negative pressure source for a brief period of time. The brief period of time may be of a duration sufficient to bring the pressure in the control chamber 171B to within a pre-determined range of a predetermined value (in an example, this may be approximately atmospheric pressure), before it is allowed to equalize with the pressure source. In other embodiments, the valve X1 may be modulated to produce the same effect. If it is a vari-valve, its orifice opening may be modulated by the controller; whereas if it is a binary valve, the controller may modulate the rate and magnitude of pressure delivery across the valve using, for example, pulse-width-modulation.

Figure 68:
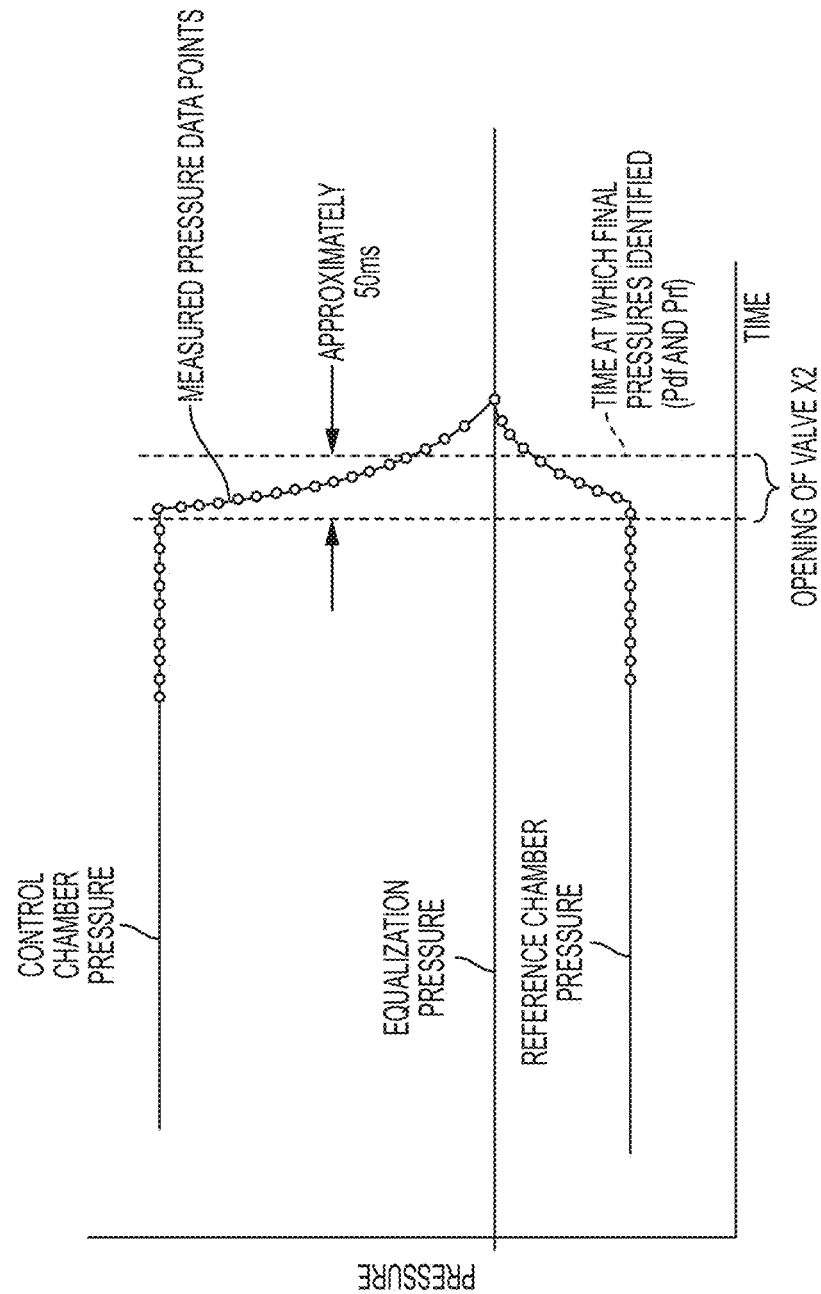
FIG. 68 is a plot of illustrative pressure values for the control chamber and the reference chamber from a point in time before opening of the valve X2 until some time after the valve X2 is opened for the embodiment of FIG. 67.

For purposes of explanation, FIG. 68 shows a plot of illustrative pressure values for the control chamber and the reference chamber from a point in time before opening of the valve X2 until some time after the valve X2 is opened to allow the pressure in the chambers to equalize. In this illustrative embodiment, the pressure in the control chamber 171B is higher than the pressure in the reference chamber 174 before equalization, but it should be understood that the control chamber 171B pressure may be lower than the reference chamber 174 pressure before equalization in some arrangements, such as during and/or at the end of a fill stroke. Also, the plot in FIG. 68 shows a horizontal line marking the equalization pressure, but it should be understood that this line is shown for clarity only. The equalization pressure in general will not be known prior to opening of the valve X2. In this embodiment, the pressure sensors sense pressure at a rate of about 2000 Hz for both the control chamber 171B and the reference chamber 174, although other suitable sampling rates could be used. Before opening of the valve X2, the pressures in the control chamber 171B and the reference chamber 174 are approximately constant, there being no air or other fluid being introduced into the chambers. Thus, the valves X1 and X3 will generally be closed at a time before opening of the valve X2. Also, valves leading into the pump chamber 181, such as the valve ports 190 and 192, may be closed to prevent influence of pressure variations in the pump chamber 181, the liquid supply or liquid outlet.

At first, the measured pressure data is processed to identify the initial pressures for the control chamber 171B and reference chambers 174, i.e., Pd and Pr. In one illustrative embodiment, the initial pressures are identified based on analysis of a 10-point sliding window used on the measured pressure data. This analysis involves generating a best fit line for the data in each window (or set), e.g., using a least squares technique, and determining a slope for the best fit line. For example, each time a new pressure is measured for the control chamber 171B or the reference chamber 174, a least squares fit line may be determined for a data set including the latest measurement and the 9 prior pressure measurements. This process may be repeated for several sets of pressure data, and a determination may be made as to when the slope of the least squares fit lines first becomes negative (or otherwise non-zero) and continues to grow more negative for subsequent data sets (or otherwise deviates from a zero slope). The point at which the least squares fit lines begin to have a suitable, and increasing, non-zero slope may be used to identify the initial pressure of the chambers, i.e., at a time before the valve X2 is opened.

In one embodiment, the initial pressure value for the reference chamber 174 and the control chamber 171B may be determined to be in the last of 5 consecutive data sets, where the slope of the best fit line for the data sets increases from the first data set to the fifth data set, and the slope of the best fit line for the first data set first becomes non-zero (i.e., the slope of best fit lines for data sets preceding the first data set is zero or otherwise not sufficiently non-zero). For example, the pressure sensor may take samples every ½ millisecond (or other sampling rate) starting at a time before the valve X2 opens. Every time a pressure measurement is made, the cycler 14 may take the most recent measurement together with the prior 9 measurements, and generate a best fit line to the 10 data points in the set. Upon taking the next pressure measurement (e.g., ½ millisecond later), the cycler 14 may take the measurement together with the 9 prior measurements, and again generate a best fit line to the 10 points in the set. This process may be repeated, and the cycler 14 may determine when the slope of the best fit line for a set of 10 data points first turns non-zero (or otherwise suitably sloped) and, for example, that the slope of the best fit line for 5 subsequent sets of 10 data points increases with each later data set. To identify the specific pressure measurement to use, one technique is to select the third measurement in the $5^{th}$ data set (i.e., the $5^{th}$ data set with which it was found that the best fit line has been consistently increasing in slope and the $1^{st}$ measurement is the pressure measurement that was taken earliest in time) as the measurement to be used as the initial pressure for the control chamber 171B or the reference chamber 174, i.e., Pd or Pr. This selection was chosen using empirical methods, e.g., plotting the pressure measurement values and then selecting which point best represents the time when the pressure began the equalization process. Of course, other techniques could be used to select the appropriate initial pressure.

In one illustrative embodiment, a check may be made that the times at which the selected Pd and Pr measurements occurred were within a desired time threshold, e.g., within 1-2 milliseconds of each other. For example, if the technique described above is used to analyze the control chamber 171B pressure and the reference chamber 174 pressure and identify a pressure measurement (and thus a point in time) just before pressure equalization began, the times at which the pressures were measured should be relatively close to each other. Otherwise, there may have been an error or other fault condition that invalidates one or both of the pressure measurements. By confirming that the time at which Pd and Pr occurred are suitably close together, the cycler 14 may confirm that the initial pressures were properly identified.

To identify when the pressures in the control chamber 171B and the reference chamber 174 have equalized such that measured pressures for the chamber can be used to reliably determine pump chamber 181 volume, the cycler 14 may analyze data sets including a series of data points from pressure measurements for both the control chamber 171B and the reference chamber 174, determine a best fit line for each of the data sets (e.g., using a least squares method), and identify when the slopes of the best fit lines for a data set for the control chamber 171B and a data set for the reference chamber 174 are first suitably similar to each other, e.g., the slopes are both close to zero or have values that are within a threshold of each other. When the slopes of the best fit lines are similar or close to zero, the pressure may be determined to be equalized. The first pressure measurement value for either data set may be used as the final equalized pressure, i.e., Pf. In one illustrative embodiment, it was found that pressure equalization occurred generally within about 200-400 milliseconds after valve X2 is opened, with the bulk of equalization occurring within about 50 milliseconds. Accordingly, the pressure in the control and reference chambers 171B, 174 may be sampled approximately 400-800 times or more during the entire equalization process from a time before the valve X2 is opened until a time when equalization has been achieved.

In some cases, it may be desirable to increase the accuracy of the control chamber 171B volume measurement using an alternate FMS technique. Substantial differences in temperature between the liquid being pumped, the control chamber gas, and the reference chamber gas may introduce significant errors in calculations based on the assumption that pressure equalization occurs adiabatically. Waiting to make pressure measurements until full equalization of pressure between the control chamber 171B and the reference chamber 174 may allow an excessive amount of heat transfer to occur. In one aspect of the disclosure, pressure values for the pump chamber 181 and reference chamber 174 that are substantially unequal to each other, i.e., that are measured before complete equalization has occurred, may be used to determine pump chamber 181 volume.

In one embodiment, heat transfer may be minimized, and adiabatic calculation error reduced, by measuring the chamber pressures throughout the equalization period from the opening of valve X2 through full pressure equalization, and selecting a sampling point during the equalization period for the adiabatic calculations. In one embodiment of an APD system, measured chamber pressures that are taken prior to complete pressure equalization between the control chamber 171B and the reference chamber 174 can be used to determine pump chamber 181 volume. In one embodiment, these pressure values may be measured about 50 ms after the chambers are first fluidly connected and equalization is initiated. As mentioned above, in one embodiment, complete equalization may occur about 200-400 ms after the valve X2 is opened. Thus, the measured pressures may be taken at a point in time after the valve X2 is opened (or equalization is initiated) that is about 10% to 50% or less of the total equalization time period. Said another way, the measured pressures may be taken at a point in time at which 50-70% of pressure equalization has occurred (i.e., the reference and pump chamber pressures have changed by about 50-70% of the difference between the initial chamber pressure and the final equalized pressure). Using a computer-enabled controller, a substantial number of pressure measurements in the control and reference chambers 171B, 174 can be made, stored and analyzed during the equalization period (for example, 40-100 individual pressure measurements). Among the time points sampled during the first 50 ms of the equalization period, there is a theoretically optimized sampling point for conducting the adiabatic calculations (e.g., see FIG. 68 in which the optimized sampling point occurs at about 50 ms after opening of the valve X2). The optimized sampling point may occur at a time early enough after valve X2 opening to minimize thermal transfer between the gas volumes of the two chambers, but not so early as to introduce significant errors in pressure measurements due to the properties of the pressure sensors and delays in valve actuation. However, as can be seen in FIG. 68, the pressures for the control chamber 171B and reference chambers 174 may be substantially unequal to each other at this point, and thus equalization may not be complete. Note that in some cases, it may be technically difficult to take reliable pressure measurements immediately after the opening of valve X2, for example, because of the inherent inaccuracies of the pressure sensors, the time required for valve X2 to fully open, and the rapid initial change in the pressure of either the control chamber 171B or the reference chamber 174 immediately after the opening of valve X2.

During pressure equalization, when the final pressure for the control chamber 171B and reference chambers 174 are not the same, Equation 2 becomes:

$$\_PriVri^{\gamma} + PdiVdi^{\gamma} = \text{Constant} = PrfVrf^{\gamma} + PdfVdf^{\gamma} \qquad (8)$$

where: Pri=pressure in the reference chamber 174 prior to opening valve X2, Pdi=pressure in the control chamber 171B prior to opening valve X2, Prf=final reference chamber 174 pressure, Pdf=final control chamber 171B pressure.

An optimization algorithm can be used to select a point in time during the pressure equalization period at which the difference between the absolute values of $\Delta Vd$ and $\Delta Vr$ is minimized (or below a desired threshold) over the equalization period. In an adiabatic process, this difference should ideally be zero, as indicated by Equation 5. In FIG. 68 the point in time at which the difference between the absolute values of $\Delta Vd$ and $\Delta Vr$ is minimized occurs at the 50 ms line, marked "time at which final pressures identified." First, pressure data can be collected from the control and reference chambers 171B, 174 at multiple points j=1 through n between the opening of valve X2 and final pressure equalization. Since Vri, the fixed volume of the reference chamber system before pressure equalization, is known, a subsequent value for Vrj (reference chamber system volume at sampling point j after valve X2 has opened) can be calculated using Equation 3 at each sampling point Prj along the equalization curve. For each such value of Vrj, a value for $\Delta Vd$ can be calculated using Equations 5 and 7, each value of Vrj thus yielding Vdij, a putative value for Vdi, the volume of the control chamber system prior to pressure equalization. Using each value of Vrj and its corresponding value of Vdij, and using Equations 3 and 4, the difference in the absolute values of $\Delta Vd$ and $\Delta Vr$ can be calculated at each pressure measurement point along the equalization curve. The sum of these differences squared provides a measure of the error in the calculated value of Vdi during pressure equalization for each value of Vrj and its corresponding value Vdij. Denoting the reference chamber 174 pressure that yields the least sum of the squared differences of $|\Delta Vd|$ and $|\Delta Vr|$ as Prf, and its associated reference chamber 174 volume as Vrf, the data points Prf and Pdf corresponding to Vrf can then be used to calculate an optimized estimate of Vdi, the initial volume of the control chamber system.

One method for determining where on the equalization curve to capture an optimized value for Pdf and Prf is as follows:

1) Acquire a series of pressure data sets from the control and reference chambers 171B, 174 starting just before the opening of valve X2 and ending with Pr and Pd becoming close to equal. If Pri is the first reference chamber 174 pressure captured, then the subsequent sampling points in FIG. 68 will be referred to as Prj=Pr1, Pr2, .... Prn.

2) Using Equation 6, for each Prj after Pri, calculate the corresponding $\Delta Vrj$ where j represents the jth pressure data point after Pri.

$$\Delta Vrj = Vrj - Vri = Vri\left(-1 + (Prj/Pri)^{-(1/\gamma)}\right) \qquad 65$$

3) For each such $\Delta Vrj$ calculate the corresponding Vdij using Equation 7. For example:

$$\Delta Vr1 = Vri*\left(-1 + (Pr1/Pri)^{-(1/\gamma)}\right)$$

$$\Delta Vd1 = -\Delta Vr1$$

Therefore, $$Vdi1 = \Delta Vd1/\left(-1 + (Pd1/Pdi)^{-(1/\gamma)}\right)$$

$$Vdin = \Delta Vdn/\left(-1 + (Pdn/Pdi)^{-(1/\gamma)}\right)$$

Having calculated a set of n control chamber system initial volumes (Vdi1 to Vdin) based on the set of reference chamber 174 pressure data points Pr1 to Prn during pressure equalization, it is now possible to select the point in time (f) that yields an optimized measure of the control chamber system initial volume (Vdi) over the entire pressure equalization period.

4) Using Equation 7, for each Vdi1 through Vdin, calculate all $\Delta Vdj,k$ using control chamber 171B pressure measurements Pd for time points k=1 to n.

For the Vdi corresponding to Pr1:

$$\Delta Vd1,1 = Vdi1*\left(-1 + (Pd1/Pdi)^{-(1/\gamma)}\right)$$

$$\Delta Vd1,2 = Vdi1*\left(-1 + (Pd2/Pdi)^{-(1/\gamma)}\right)$$

$$\Delta Vd1,n = Vdi1*\left(-1 + (Pdn/Pdi)^{-(1/\gamma)}\right)$$

For the Vdi corresponding to Prn:

$$\Delta Vdn,1 = Vdin*\left(-1 + (Pd1/Pdi)^{-(1/\gamma)}\right)$$

$$\Delta Vdn,2 = Vdin*\left(-1 + (Pd2/Pdi)^{-(1/\gamma)}\right)$$

$$\Delta Vdn,n = Vdin*\left(-1 + (Pdn/Pdi)^{-(1/\gamma)}\right)$$

5) Take the sum-square error between the absolute values of the $\Delta Vr$'s and $\Delta Vdj,k$'s $$S_1 = \sum_{k=1}^{n}(|\Delta V_{d1,k}| - |\Delta V_{rk}|)^2$$

S1 represents the sum-square error of $|\Delta Vd|$ minus $|\Delta Vr|$ over all data points during the equalization period when using the first data point Pr1 to determine Vdi, the control chamber system initial volume, from Vr1 and $\Delta Vr$.

$$S_2 = \sum_{k=1}^{n}(|\Delta V_{d2,k}| - |\Delta V_{rk}|)^2$$

S2 represents the sum-square error of |ΔVr| minus |ΔVd| over all data points during the equalization period when using the second data point Pr2 to determine Vdi, the control chamber system initial volume, from Vr2 and ΔVr.

$$S_n = \sum_{k=1}^{n}(|\Delta V_{dn,k}| - |\Delta V_{rk}|)^2$$

6) The Pr data point between Pr1 and Prn that generates the minimum sum-square error S from step 5 (or a value that is below a desired threshold) then becomes the chosen Prf, from which Pdf and an optimized estimate of Vdi, the control chamber 171B initial volume, can then be determined. In this example, Pdf occurs at, or about, the same time as Prf.
7) The above procedure can be applied any time that an estimate of the control chamber 171B volume is desired, but can preferably be applied at the end of each fill stroke and each delivery stroke. The difference between the optimized Vdi at the end of a fill stroke and the optimized Vdi at the end of a corresponding delivery stroke can be used to estimate the volume of liquid delivered by the pump.

Air Detection

Another aspect of the disclosure involves the determination of a presence of air in the pump chamber 181, and if present, a volume of air present. Such a determination can be important, e.g., to help ensure that a priming sequence is adequately performed to remove air from the cassette 24 and/or to help ensure that air is not delivered to the patient. In certain embodiments, for example, when delivering fluid to the patient through the lower opening 187 at the bottom of the pump chamber 181, air or other gas that is trapped in the pump chamber 181 may tend to remain in the pump chamber 181 and will be inhibited from being pumped to the patient unless the volume of the gas is larger than the volume of the effective dead space of pump chamber 181. As discussed below, the volume of the air or other gas contained in pump chambers 181 can be determined and the gas can be purged from pump chamber 181 before the volume of the gas is larger than the volume of the effective dead space of pump chamber 181.

A determination of an amount of air in the pump chamber 181 may be made at the end of a fill stroke, and thus, may be performed without interrupting a pumping process. For example, at the end of a fill stroke during which the membrane 15 and the pump control region 1482 are drawn away from the cassette 24 such that the membrane 15/region 1482 are brought into contact with the wall of the control chamber 171, the valve X2 may be closed, and the reference chamber 174 vented to atmospheric pressure, e.g., by opening the valve X3. Thereafter, the valves X1 and X3 may be closed, fixing the imaginary "piston" at the valve X2. The valve X2 may then be opened, allowing the pressure in the control chamber 171B and the reference chamber 174 to equalize, as was described above when performing pressure measurements to determine a volume for the control chamber 171B.

If there is no air bubble in the pump chamber 181, the change in volume of the reference chamber, i.e., due to the movement of the imaginary "piston," determined using the known initial volume of the reference chamber system and the initial pressure in the reference chamber 174, will be equal to the change in volume of the control chamber 171B determined using the known initial volume of the control chamber system and the initial pressure in the control chamber 171B. The initial volume of the control chamber may be known in conditions where the membrane 15/control region 1482 are in contact with the wall of the control chamber 171B or in contact with the spacer elements 50 of the pump chamber 181. However, if air is present in the pump chamber 181, the change in volume of the control chamber 171B will actually be distributed between the control chamber 171B volume and the air bubble(s) in the pump chamber 181. As a result, the calculated change in volume for the control chamber 171B using the known initial volume of the control chamber system will not be equal to the calculated change in volume for the reference chamber 174, thus signaling the presence of air in the pump chamber 181.

If there is air in the pump chamber 181, the initial volume of the control chamber system Vdi is actually equal to the sum of the volume of the control chamber 171B and lines L0 and L1 (referred to as Vdfix) plus the initial volume of the air bubble in the pump chamber 181, (referred to as Vbi), as shown in Equation 9:

$$Vdi = Vbi + Vdfix \quad (9)$$

With the membrane 15/control region 1482 pressed against the wall of the control chamber 171B at the end of a fill stroke, the volume of any air space in the control chamber 171B, e.g., due to the presence of grooves or other features in the control chamber wall, and the volume of the lines L0 and L1—together Vdfix—can be known quite accurately. Similarly, with the membrane 15/control region 1482 pressed against the spacer elements 50 of the pump chamber 181, the volume of the control chamber 171B and the lines L0 and L1 can be known accurately. After a fill stroke, the volume of the control chamber system is tested using a positive pressure control chamber 171B precharge. Any discrepancy between this tested volume and the tested volume at the end of the fill stroke may indicate a volume of air present in the pump chamber 181. Substituting from Equation 9 into Equation 7, the change in volume of the control chamber 171B ΔVd is given by:

$$\Delta Vd = (Vbi + Vdfix)(-1 + (Pdf/Pdi)^{-(1/\gamma)}) \quad (10)$$

Since ΔVr can be calculated from Equation 6, and we know from Equation 5 that ΔVr=(−1)ΔVd, Equation 10 can be re-written as:

$$(-1)\Delta Vr = (Vbi + Vdfix)(-1 + (Pdf/Pdi)^{-(1/\gamma)}) \quad (11)$$

and again as:

$$Vbi = (-1)\Delta Vr/(-1 + (Pdf/Pdi)^{-(1/\gamma)}) - Vdfix \quad (12)$$

Accordingly, the cycler 14 can determine whether there is air in the pump chamber 181, and the approximate volume of the bubble using Equation 12. This calculation of the air bubble volume may be performed if it is found, for example, that the absolute values of ΔVr (as determined from Equation 6) and ΔVd (as determined from Equation 7 using Vdi=Vdfix) are not equal to each other. That is, Vdi should be equal to Vdfix if there is no air present in the pump chamber 181, and thus the absolute value for ΔVd given by Equation 7 using Vdfix in place of Vdi will be equal to ΔVr.

After a fill stroke has been completed, and if air is detected according to the methods described above, it may be difficult to determine whether the air is located on the pump chamber 181 side or the control chamber 171B side of the membrane 15. Air bubbles could be present in the liquid being pumped, or there could be residual air on the control chamber 171B (pneumatic) side of the pump membrane 15 because of a condition (such as, for example, an occlusion) during pumping that caused an incomplete pump stroke, and incomplete filling of the pump chamber 181. At this point, an adiabatic FMS measurement using a negative pump chamber pre-charge can be done. If this FMS volume matches the FMS volume with the positive precharge, then the membrane 15 is free to move in both directions, which implies that the pump chamber 181 is only partially filled (possibly, for example, due to an occlusion). If the value of the negative pump chamber pre-charge FMS volume equals the nominal control chamber 171B air volume when the membrane 15/region 1482 is in contact with the inner wall of the control chamber 171B, then it is possible to conclude that there is an air bubble in the liquid on the pump chamber 181 side of the flexible membrane 15.

In some embodiments, when taking volume measurements, the relative importance of heat transfer can be varied from one measurement to the next. A polytropic model may be used to model the equalization process and capture the effects of different levels of heat transfer. Any models described in in U.S. Pat. No. 10,201,647 to Norris et al., issued Feb. 12, 2019, filed Jun. 5, 2015, entitled "Medical Treatment System and Methods Using a Plurality of Fluid Lines," which is incorporated herein by reference in its entirety may, for example, may be used.

Substantially Instantaneous or Continuous Flow Rate and Stroke Displacement Estimation In some embodiments, the flow rate to or from a pump chamber 181 of a diaphragm pump, and/or the stroke displacement of a pump chamber 181 (i.e. the extent to which the diaphragm has traversed the pump chamber 181) may be estimated while a pumping stroke is occurring. This may be accomplished either during a fluid delivery stroke, or a fluid filling stroke of the diaphragm pump. These estimates may be available during the progression of a pump stroke once sufficient data is collected for controller analysis, the controller then being able to act on continuously updated pressure information to calculate a cumulative volume of fluid moved into or out of the pumping chamber 181. Such real-time information may aid in an early determination of an end of stroke, may reduce the number of partial strokes performed, may permit more accurate delivery of small volumes or increments of fluid, may more efficiently deliver a precise target fluid volume, and may provide for earlier detection of occlusions and other reduced flow conditions, as well aid in priming of a fluid line, etc. This information may also help to increase fluid throughput through a pumping cassette 24.

Flow rate and stroke displacement or stroke progress estimation during a pump stroke may be accomplished by monitoring pressure decay in a control chamber while a pump stroke is in progress. Data produced from monitoring the rate of pressure decay may be used by a controller to determine fluid flow rate through a pumping chamber 181. Since pressure decay during a pump stroke is indicative of a change in volume of the control chamber 171B as the pumping chamber 181 fills with or empties of fluid, monitoring this decay over the course of a pump stroke may allow a controller to estimate stroke displacement as it occurs.

In embodiments in which an on/off, binary, or "bang-bang" pressure controller is used, the pressure controller may need to repeatedly actuate a valve to connect and disconnect a control chamber 171B to a pressure reservoir in order to maintain a desired pressure during pumping. For example, as fluid is pumped out of a pumping chamber 181 during a delivery stroke, the volume of the associated control chamber 171B will increase. This will in turn cause a decay in the pressure of the control chamber 171B. The process or algorithm can be used either with the application of negative pressure to fill the pumping chamber 181 or with the application of positive pressure to evacuate fluid from the pumping chamber 181. The term 'pressure decay' as used herein is meant to refer to a decay in the absolute value of the actual pressure being measured (i.e., a decrease toward ambient pressure in an applied positive pressure, or an increase toward ambient pressure in an applied negative pressure). Once the pressure in the control chamber 171B falls out of an allowed pressure range, the pressure controller may regulate the control chamber 171B pressure by opening a valve to a pressure reservoir. The allowed pressure range may be within a range of a pressure set point. This pressure regulation or maintenance may involve connecting the control chamber 171B to a suitable pressure source for a period of time sufficient to bring the control chamber 171B pressure approximately to a desired value and/or back within the allowed range. The pressure will again decay as more fluid is delivered to or from the pumping chamber 181 and re-pressurization will again be needed. This process will continue until the end of the stroke is reached.

The repeated re-pressurization will generate a pressure regulation waveform that appears substantially saw tooth in nature. An example plot showing a pressure regulation waveform as described above is depicted in FIG. 69. As shown, the waveform oscillates between a lower pressure threshold 2312 and an upper pressure threshold 2310. The pressure decays (see data points 2302-2304) as the stroke progresses, fluid moves out of the pumping chamber 181, and the volume of the control chamber 171B changes. In the example plot in FIG. 69, the control chamber 171B volume is expanding as fluid is pumped out of the pumping chamber 181 of the diaphragm pump to a destination. An end-of-stroke is indicated when the pressure decay levels off 2305, at which point an FMS volume determination can be conducted by fixing the chamber volume 171B (i.e., closing inlet and outlet fluid valves to the pumping chamber 181), and equalizing 2332 the chamber pressure with the pressure of a known reference volume.

Each pressure decay may be monitored such that the volume of the control chamber 171B can be approximately known during the course of a pump stroke. This information may allow a determination of the amount of pump stroke displacement that has occurred when compared with the initial volume of the chamber. The initial volume of the pumping chamber 181 can be determined, for example, by performing a pre-stroke FMS measurement. This method generally involves determining the volume of a closed chamber by measuring its change in pressure when brought into communication with a reference chamber of known volume and pressure. The determination involves closing fluid inlet an outlet valves of the pumping chamber 181 to ensure a constant volume of the control chamber 171B of the pump, and then connecting the control chamber 171B to a reference chamber 174. The process may be modeled as isothermal or adiabatic, depending on the heat transfer properties and dynamics of the system. As mentioned above, the system may also be modeled as a polytropic process to optimize measurement accuracy. Other methods of determining the initial volume of the control chamber 171B can be used. For example, the controller may be programmed to assume that the initial control chamber 171B volume is substantially the control chamber 171B volume physically measured during manufacture of the chambers of the pumping system. This assumption may be employed, for example, when the controller has computed that a preceding end-of-stroke state was fully reached.

The determination of real-time or continuous volume changes in the control and pumping chambers 171B, 181 of a diaphragm pump during a pump stroke is substantially different from previously disclosed pressure-based volume determinations, in that a fluid inlet or outlet valve remains open to allow fluid to continue to flow into or out of the pumping chamber 181. Additionally a reference chamber 174 of known volume and pressure is unnecessary. To distinguish this process from a control chamber 171B/reference chamber 174 equalization process (a 'two-chamber' FMS), the continuous measurement process here described can more aptly be considered a 'one-chamber' FMS. Although the pumping chamber 181 remains open to an inlet or outlet fluid line, the associated control chamber 171B remains a closed system, which allows for determination of a second volume once an initial volume is known. Pressure data is repeatedly sampled while the control chamber 171B volume is isolated from a gas source or sink (i.e., no change in mass in the control volume). Under these circumstances, controller calculations based on an algorithm using a polytropic process may provide more accurate results. The method is only now feasible, because electronic processors capable of rapid data acquisition and computation are now available. For example, a high speed application specific integrated circuit can be employed, or preferably an FPGA device can now be dedicated to this task, relieving a main system processor from having to share its computing resources and reduce its efficiency. A sufficiently robust FPGA in some embodiments can be reconfigurable or reprogrammable for the blocks of time needed to perform on-the-fly or real time volume measurements during a pump stroke, while maintaining some resources for other tasks. Real time or on-the-fly volume measurements may be accomplished by finding the volume of the control chamber 171B at two points between a closure and an opening of the supply valve used to regulate the control or pumping chamber 181 pressure. The volume difference between the two points in time may allow the controller to estimate a relatively real-time flow rate.

As shown in FIG. 69, a high-speed controller can acquire a series of pressure data points 2302, 2303, 2304, each of which allows the controller to successively compute a chamber volume change associated with each point. Assuming that the controller has determined a starting volume of the control chamber 171B, a change in volume at a subsequent pressure decay point can be computed. An ending volume associated with point 2302, for example, may then be used as a starting volume at point 2303 in order to calculate the ending volume at point 2303, and so on.

Figure 70:
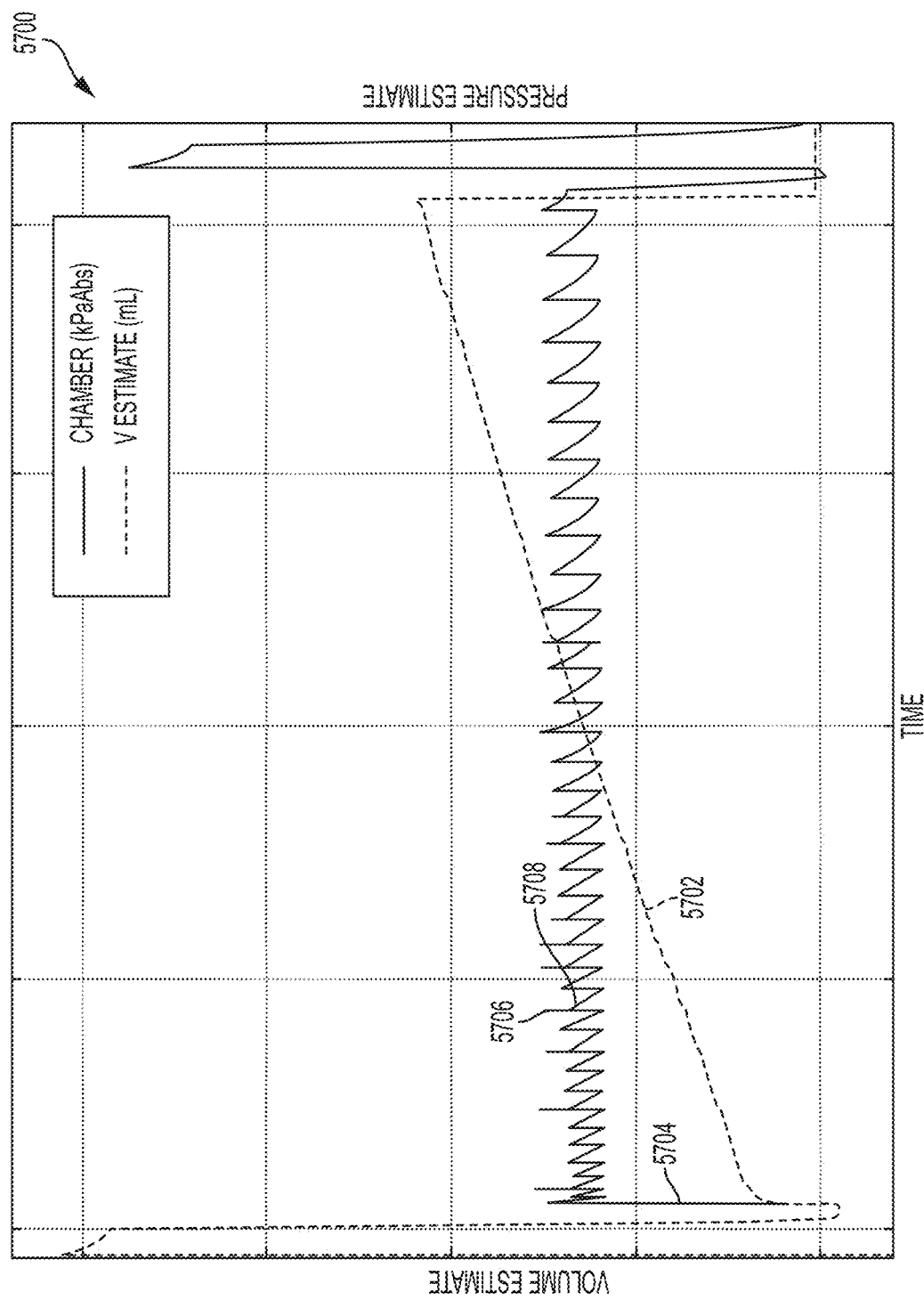
FIG. 70 shows a graph plotting pressure in a control or actuation chamber during a liquid deliver stroke and a cumulative volume estimation plot during the liquid delivery stroke.

FIG. 70 depicts an example graph 5700 with traces representative of pressure in a control chamber 171B and estimated pumped volume from that chamber. The volume estimate trace 5702 is created by sampling pressure data points on each pressure decay 5708 of the pressure trace 5704. As described above, the controller may use the pressure difference between two pressure data points to determine a volume displaced in an associated pumping chamber 181. The controller may then calculate a cumulative volume of fluid moved in or out of the pumping chamber 181. As more and more pressure decay 5708 and re-pressurization events 5706 occur, the cumulative volume indicated by the volume estimate trace 5704 increases. Since the processor is capable of rapidly sampling and analyzing the data points, the volume estimate is able to be updated continuously as shown in the example graph 5700. As a result, the volume delivered to or from the pumping chamber 181 can be accurately estimated while the stroke is in progress. This estimate is generated without halting the pumping of fluid and without the use of a reference chamber 174.

Any number of suitable mathematical methods may be used to model the pressure decay of the control (or pumping) chamber throughout a pump stroke. But it should be understood that a pressure decay curve at one point in the pump stroke may appear quite similar to a pressure decay curve at another point during the pump stroke, yet represent a different amount of volume change in the pumping chamber 181. Programming a controller to analyze the pressure decay curves during a pump stroke by using a polytropic model may help to resolve these potential differences in volume change.

One-chamber FMS—computing real-time or continuous volume changes in the control or pumping chamber 171B, 181 using a polytropic model—may be feasible in systems using either binary or variable orifice valves connecting the pump control chamber 171B to a pressure reservoir (positive or negative pressure). Pressure data can be acquired and analyzed during the time that either type of valve is closed (although this time period is likely much shorter when a vari-valve is used). In either case, the pressure decay during fluid egress (or pressure rise during fluid ingress) can be sampled, the volume change computed, and the process repeated to provide real-time volume change data. In the following description, a polytropic modeling process is applied to a system using binary valves in regulating the pressure in the control or pump chamber 171B, 181. The description applies to other types of valves and pressure regulation protocols.

In general, a one-chamber FMS protocol can be applied to any gas-driven (e.g., air-driven) diaphragm pump having a fluid pumping chamber 181 separated from a control chamber 171B by a flexible diaphragm. During a pump stroke, as fluid either enters or leaves the pumping chamber 181, the control chamber 171B will be a closed system for at least part of the time as the the controller regulates the pressure delivered to the control chamber 171B and diaphragm. A valve connecting the control chamber 171B to a pressure source will close once the pressure in the control chamber 171B reaches or exceeds a high threshold value. The valve will open again (either fully or partially) as the pressure decays from fluid movement into or out of the pumping chamber 181, creating alternating periods during the pump stroke in which the control chamber 171B is closed to air ingress or egress. During these phases in which the control chamber 171B is isolated, a change in pressure reflects a change in the volume of the control chamber 171B and therefore the pumping chamber 181. An initial volume at the beginning of the pressure decay period must be known from a prior measurement, or assumed. A terminal volume can then be calculated from a measured pressure change between the initial and terminal volume. The terminal volume can then be used as the initial volume for the next calculation as the pressure decays further during the control chamber 171B isolation phase. In this way, a controller can rapidly acquire pressure readings during the pressure decay phases of the pump stroke to compute in a nearly continuous manner the change in volume of the pumping chamber 181, and can thus estimate an instantaneous fluid flow rate into or out of the pump. The relationship between pressure and volume of a gas in a closed system is governed by a standard equation describing the behavior of ideal gases, and it may be best to assume a polytropic process in the calculation, in which a polytropic coefficient can vary between 1 and a value representing the heat capacity ratio of the gas used in the pump (adiabatic coefficient for that gas).

A polytropic process is governed by the equation:

$$PV^n = \text{constant}$$

where P=pressure, V=volume, and the polytropic exponent, "n", is a number between 1 and γ (γ being 1.4, the coefficient describing an adiabatic system for most gases including air). Since the right hand side of the equation is a constant, two consecutive points in time can be compared. To compare two consecutive points in time, the following equation may be employed:

$$P_t V_t^n = P_{t-1} V_{t-1}^n$$

where $P_t$ is the pressure at time t, $V_t$ is the volume at time t, $P_{t-1}$ is the pressure at time t−1, and $V_{t-1}$ is the volume at time t−1.

Rearranging the equation to solve for $V_t$ and simplifying yields the following equations:

$$V_t^n = \frac{P_{t-1} V_{t-1}^n}{P_t}$$

$$V_t = \sqrt[n]{\frac{P_{t-1} V_{t-1}^n}{P_t}}$$

$$V_t = \frac{p_{t-1}^{1/n} \times V_{t-1}^{n/n}}{P_t^{1/n}}$$

$$V_t = V_{t-1} \left(\frac{P_{t-1}}{P_t}\right)^{1/n}$$

As shown in the above equations, the current volume of the chamber, $V_t$, can be determined if the volume at the end of the preceding time interval has been determined. This volume may then be used to determine stroke displacement if desired. Additionally, by tracking the amount of time between $V_t$ and $V_{t-1}$, it is possible to determine a rate of flow over that time span. An average flow rate over a portion of the pump stroke may be determined by averaging multiple flow rate determinations using successively paired pressure data values. Additionally, knowing the starting volume and nominal ending volume of the control chamber 171B may provide an independent determination of the amount of time needed to complete the pump stroke. In an example, a data sample set may be acquired every 10 ms and may include 20 data samples. In such embodiments, the amount of time between $V_t$ and $V_{t-1}$ will be 0.5 ms. The preferred data sampling rate will depend, among other things, on the expected duration of a pump stroke, the rate of pressure decay observed by the controller, the degree of measurement error or noise associated with the pressure signal, and the sampling speed and processing capability of the controller (e.g., whether a dedicated FPGA is being used).

In some embodiments, the controller may compute the volume change at each data point sampled. This has the advantage of minimizing the effects of heat transfer between measurement points. On the other hand, the signal noise during measurement may yield a less accurate computation for the change in actual volume. In another embodiment, the processor may sample a set of pressure data points within a time period in which heat transfer is presumed to be at an acceptable level, and the pressure data set may be filtered or smoothed by the processor before an initial smoothed pressure measurement and a final smoothed pressure measurement is used to compute the final volume at the end of the time period. The effects of signal noise on the accuracy of the measurement can thus be reduced.

There are time periods during a pumping stroke in which pressure data acquisition is either not possible or inadvisable. For example, when the pressure supply valve is open and the pump chamber 181 pressure is spiking, fluid flow into or out of the pumping chamber 181 continues. As a first approximation, it may be assumed that the fluid flow rate during this short period of time remains approximately unchanged from the flow rate measured shortly before the opening of the pressure supply valve. The volume change estimated in this manner may then be added to the volume representing the last measured pressure data point to arrive at the initial volume for the next measured pressure data point. Additionally, there may be prescribed points of time during a stroke at which pressure data points may be ignored. For example, depending on the data sampling rate, pressure information immediately preceding a pressure rise during a pressurization event may be inaccurate. Some aliasing may also be present for data points directly following a pressurization event. In an embodiment, data points collected by the controller within a predetermined period of time before and after a pressurization event may be discarded or ignored to further improve the accuracy of the flow determination process.

In embodiments which use an FPGA for pressure data acquisition and analysis, issues stemming from an inferior sampling rate may present less of a concern. In certain embodiments, an FPGA may also have the resource capacity to control the relevant valves in the pumping system. By controlling the pressure supply valves, the FPGA may be able to schedule the sampling of pressure data more efficiently. Synchronization of events may be improved, and aliasing problems with data sampling may be reduced.

Certain assumptions may also be made at the beginning of a pump stroke. A small amount of fluid movement into or out of the pumping chamber is likely to be present prior to the first pressure decay event. Although inertial forces may limit the initial fluid flow, the controller can be programmed to estimate an initial fluid flow and volume change prior to the first data sampling point during pressure decay. Such an assumption may allow for the estimation of changes in chamber volume while pressure decay information at the beginning of the stroke is not available. The amount of fluid assumed to have been moved at the start of a stroke may depend on the pumping pressure applied to the control and pumping chambers 171B, 181. The controller may be programmed to include a pre-determined volume of fluid movement based on the value of the applied pressure. Alternatively, after a number of data points have been sampled to determine an estimated flow rate, the flow rate may be used to extrapolate for the volume moved while the data was unavailable. It may, for example, be assumed that the flow rate over that period of time was substantially equal to the currently estimated flow rate. This assumption that the flow rate is constant may then be used to determine an estimate of the volume moved over the period which data was unavailable.

Figure 71:
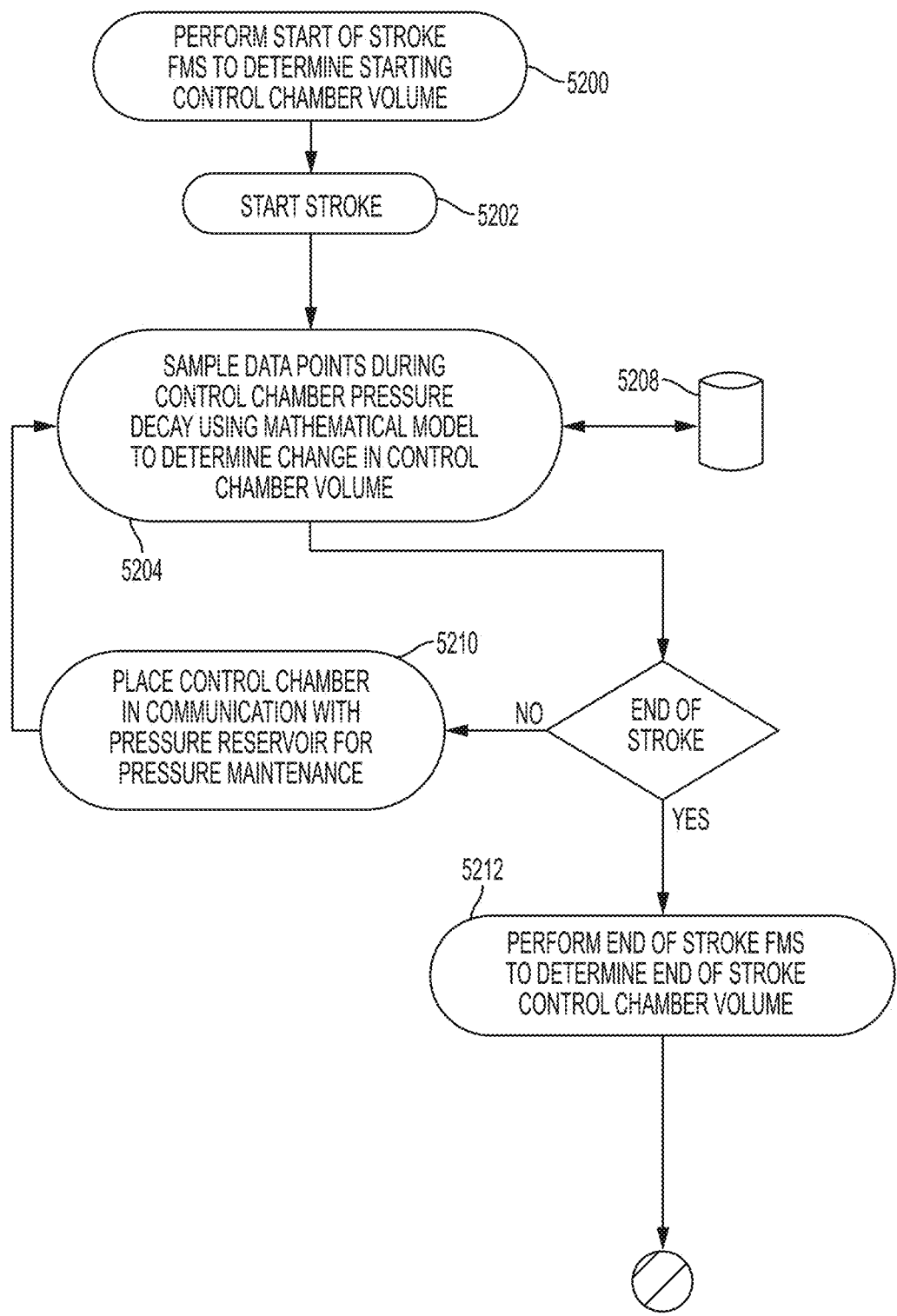
FIG. 71 shows an flowchart outlining a number of steps which may be used to estimate control chamber volume changes over time.

FIG. 71 shows a flowchart detailing an example of a number of steps which may be used to estimate control chamber volume changes during a pump stroke. As shown, the flowchart begins in step 5200, where a pre-stroke FMS measurement is made, which in an embodiment includes freezing the volume of the pumping and control chambers, measuring control chamber pressures and equalizing pressures with a reference volume chamber. This measurement may provide a starting control chamber volume measurement. Alternatively, the starting control chamber volume may be assumed by the controller to be a fixed and known quantity if the controller has calculated that the preceding end-of-stroke of the pumping chamber has been fully completed. A pump stroke may then be started in step 5202. In step 5204, the control chamber pressure decay (or the decay of the absolute value of the pressure) may be monitored as the stroke displaces and causes fluid to move into or out of the pumping chamber. In some specific embodiments, multiple data points may be sampled along each decay curve and the mathematical model described above may be used to determine changes in control chamber volume as the pump stroke proceeds. Data points and volume information may be saved in memory 5208.

Assuming the end of stroke is not detected, once the pressure in the control chamber falls outside of a predetermined range (e.g. falls below a predetermined pressure value), step 5210 may be performed. In step 5210, the pressure controller may perform pressure maintenance on the control chamber (i.e. re-pressurize the control chamber) to bring the control chamber pressure back to approximately a preprogrammed desired value (which may, for example, be at or near a high pressure bound of the range). After completing step 5210, step 5204 may be repeated with the collected data again being saved in memory 5208. This may continue until an end of stroke condition is detected. End of stroke detection is described elsewhere herein.

In the event an end of stroke condition is detected, a post-stroke FMS measurement (determining volume by measuring control gas pressure) may be taken in step 5212. This measurement may be compared to the measurement from step 5200 to check and/or more precisely determine the total volume moved during the stroke. Additionally, this post-stroke FMS measurement may serve as the starting control chamber volume measurement for the next stroke performed by that pump chamber.

Other means of determining that the pump has fully completed its pump stroke may be used. If so, the result of that determination may then be used to initialize the controller to the control chamber's starting volume for the next pump stroke. Methods other than volume determination by pressure measurement may be used to assess the final volume of the control and pumping chambers, whether or not a pump stroke has been fully completed. However the final chamber volume is determined, that value may then be used to initialize the controller as the chamber's starting volume for the next pump stroke.

The polytropic coefficient, "n", of the above described mathematical model may be initialized at a specific value. For example, in some embodiments, the coefficient may be set to 1.4 or γ (representing an adiabatic process for air). The initialized value may differ depending on the embodiment, the type of control fluid, or the intended flow rate. For example, embodiments with a relatively fast flow rate may be more appropriately modeled as an adiabatic system while embodiments with a slower flow rate may be more appropriately modeled as an isothermal system.

The coefficient may then be adjusted to a value yielding greater agreement between the computed real-time flow rate and the measured final volume change at end-of-stroke over a plurality of pump strokes. This may be done by using feedback collected over one or more pump strokes using any suitable software algorithm, or using a controller such as a proportional controller or PID controller. Feedback may be in the form of a calculated delivered volume determined by a comparison of the pre-stroke and post-stroke FMS measurement. The final FMS measurement volume and estimated real-time volume change determined using a current value for "n" may be compared. If the volumes differ by more than a predetermined amount the value for "n" may be adjusted. The new coefficient value may then be saved and used as the initial value for the next pump stroke. In an example, the coefficient "n" may be adjusted using data collected over several pump strokes. For example, values for "n" that would have yielded the final (e.g. FMS measured) volume moved for a number of strokes may be averaged together. In the absence of significant changes in ambient conditions (e.g., fluid or environmental temperature changes), an averaging or other numerical filtering procedure may decrease the time needed to produce accurate flow rate and stroke displacement measurements, as it may not be necessary to have the controller perform repeated comparisons of pre-stroke and post-stroke FMS measurements.

Figure 72:
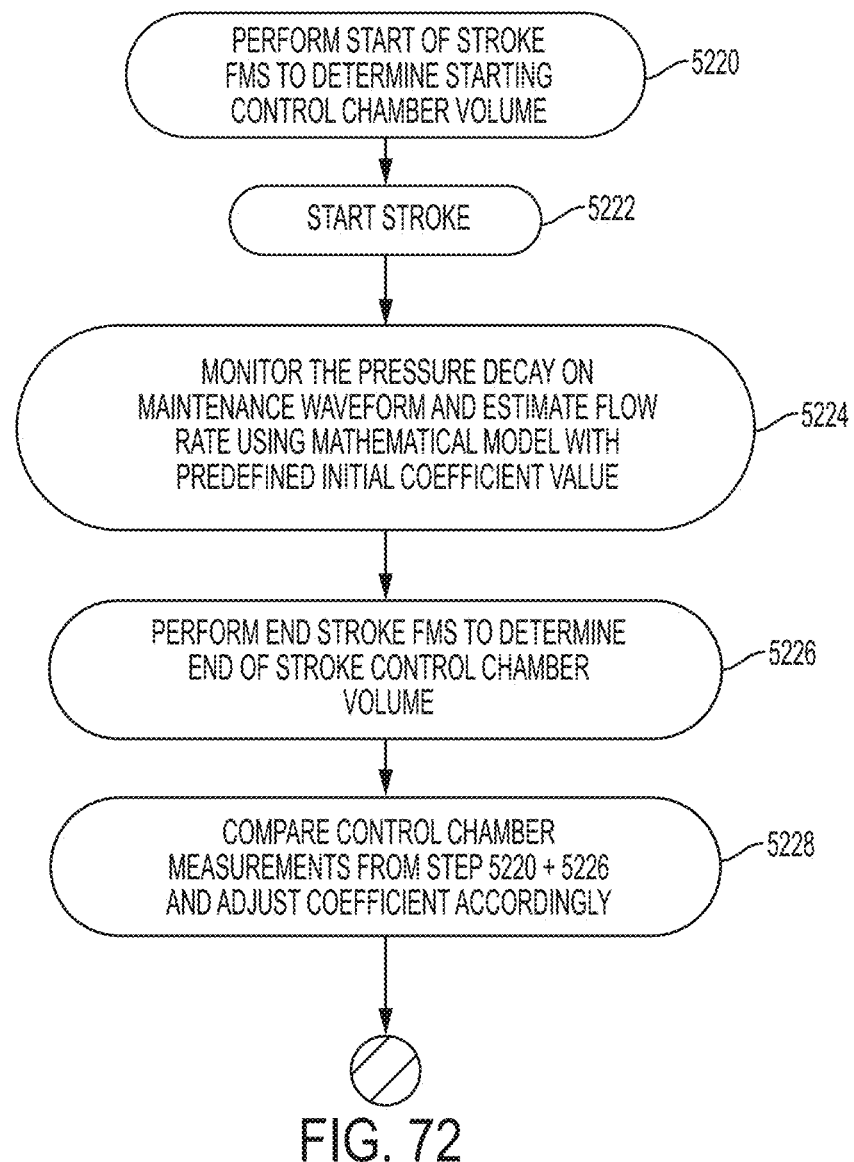
FIG. 72 shows a flowchart outlining a number of steps to adjust an equation used to estimate control chamber volume changes over time during a pump stroke.

FIG. 72 shows a flowchart outlining an example of a number of steps to adjust the coefficient of the mathematical model as described above. As shown, in step 5220, a pre-stroke FMS measurement may be taken to determine a starting volume for a control chamber. The stroke may then begin in step 5222. In step 5224, the pressure decay on the pressure regulation waveform may be monitored. Volume change of the control chamber may be determined using the example mathematical pressure-volume model with a pre-defined initial exponent coefficient value. Once the stroke has completed, in step 5226, a post-stroke FMS measurement may be made to determine the end of stroke control chamber volume. In step 5228, the volume measurements from step 5220 and 5226 may be compared to determine the total control chamber volume change over the stroke. The coefficient may be adjusted based on this comparison to align the two final values if necessary. For example, the coefficient may be adjusted to the value which would have yielded the volume change found by using the FMS measurements.

As mentioned above, a flow rate estimation as a stroke is progressing may be used for a number of purposes including, but not limited to, detection of occlusions, detection of low flow or no flow conditions, detection of end of stroke, detection of fluid line prime state, etc. The flow rate estimation may be monitored to determine if it is likely that an end of stroke condition is present. For example, if the real-time flow rate drops below a predefined threshold (e.g. 15 mL/min), it may be an indication that a pump stroke has been fully completed (i.e. the maximum volume of fluid has been moved given the physical limitations of the pump). If the flow rate estimate drops below the predefined threshold, an FMS measurement may be performed on the chamber and the volume delivered may be verified. If the FMS measurement determines the end of stroke has been reached, the chamber may move onto the next pumping operation (or pump stroke). If an end of stroke condition has not been reached, the controller may undertake a number of actions, including, for example, attempting to resume the pump stroke. Alternatively, the detection of a reduced flow condition may be indicative of an occlusion of the fluid line, an occlusion alert or alarm may be triggered, or a fluid pushback attempt may be made to determine if an occlusion exists.

In some embodiments, the controller may be programmed with an arming routine (a software trigger) to keep it from declaring an end-of-stroke condition prematurely. This may help to avoid false triggering of an end of stroke determination. For example, a lack of cumulative pressure data at the beginning of a stroke may increase the effect of signal noise in a flow rate determination. In an example, the controller may be programmed with a trigger that is armed only after a pre-determined time period has elapsed after the initiation of the pump stroke. In some embodiments the software trigger may be the attainment of a predetermined flow rate value. Or the trigger may be armed after is the controller estimates that a predetermined volume of fluid has been moved. Requiring that the end of stroke detection trigger be armed before an end of stroke condition is detected may help to reduce the number of partial strokes performed and may help to increase throughput of fluid through a pumping cassette. To help prevent a scenario in which the arming criteria is not reached and the end of stroke is never detected, the trigger may be armed after the stroke has been in progress for a predetermined amount of time. In other embodiments, after a predetermined period of time has elapsed since the beginning of the stroke without the arming criteria being met, and end of stroke may automatically be triggered.

Figure 73:
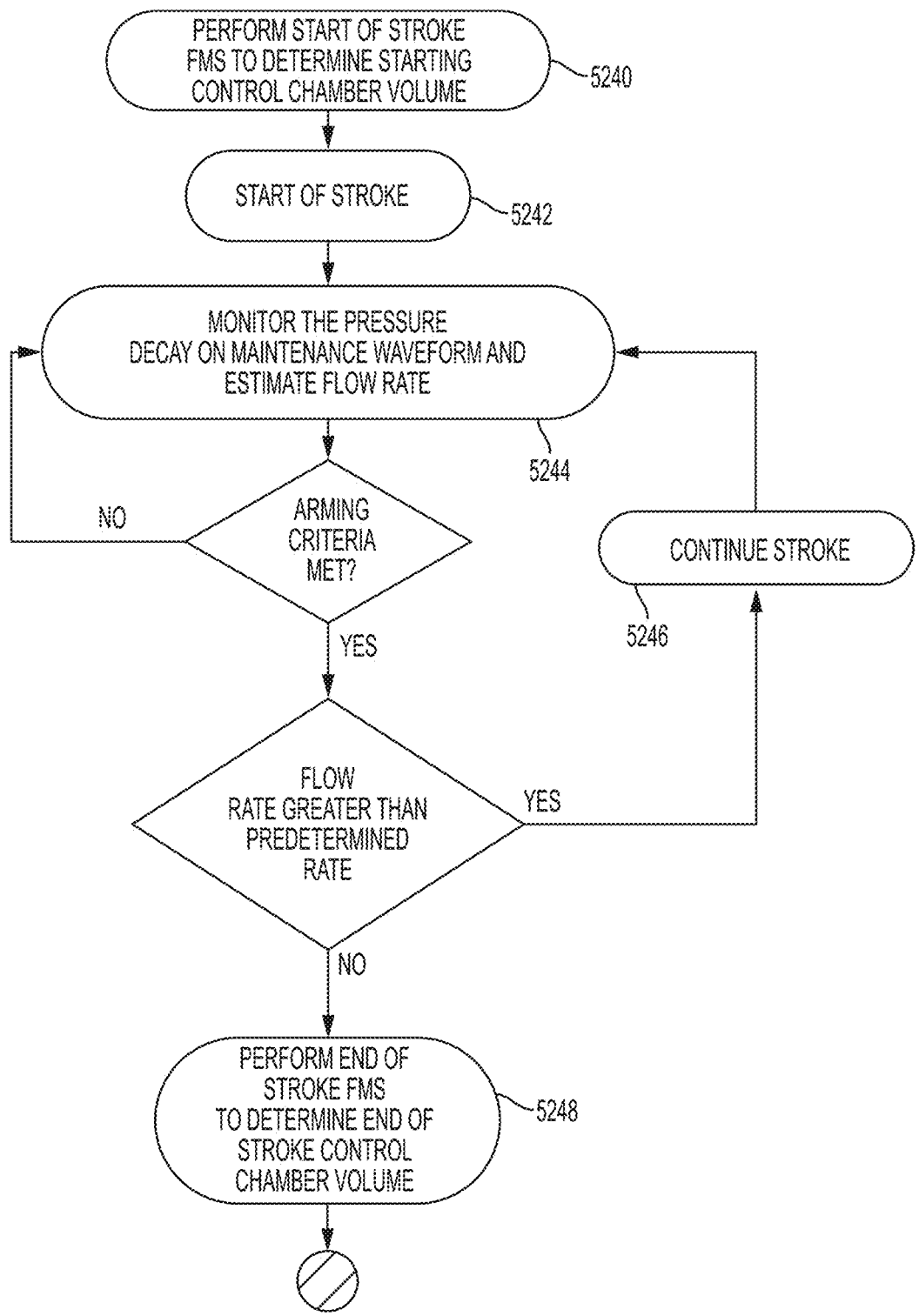
FIG. 73 shows a flowchart outlining a number of steps to detect end of stroke based on flow rate during a stroke.

FIG. 73 shows a flowchart outlining a number of example steps to detect end of stroke based on a real-time flow rate estimation. As shown, in step 5240, a pre-stroke measurement may be performed to determine the starting volume of a control chamber. The pump stroke is then started in step 5242. As the stroke progresses, in step 5244, the pressure decay on the control chamber pressure regulation or maintenance waveform is monitored. A flow rate is estimated based on the pressure decay. When the end of stroke arming criteria is met, the controller determines whether the flow rate is above a pre-established or predetermined flow rate. If the flow rate is above the predetermined flow rate, the pump stroke continues in step 5246 and flow rate estimation continues in step 5244. In the event that the flow rate drops below the predetermined flow rate, in step 5248, the stroke may be ended and an end of stroke FMS measurement may be made to determine the control chamber volume.

In some embodiments, estimation of control chamber volume change over the progression of the stroke may be used to predict the amount of time necessary to complete the stroke. Since the starting volume as well as the nominal or projected end volume of the stroke is known and flow rate may be determined using control chamber volume change, the controller may use this information to estimate how long the entire stroke should take. Correspondingly, the controller can calculate an estimate of how much time is needed to complete the remaining portion of the stroke. Once the predicted end time of the stroke is reached, the stroke may be stopped and an FMS measurement may be made. In the event that the FMS measurement indicates the stroke was a partial stroke, a number of actions may be taken. In some embodiments, a cycler may attempt to retry the stroke. Alternatively, controller detection of a reduced flow condition may be an indication for an occlusion alert or alarm, or a pushback attempt may be made to determine if an end-of-line occlusion can be relieved.

Figure 74:
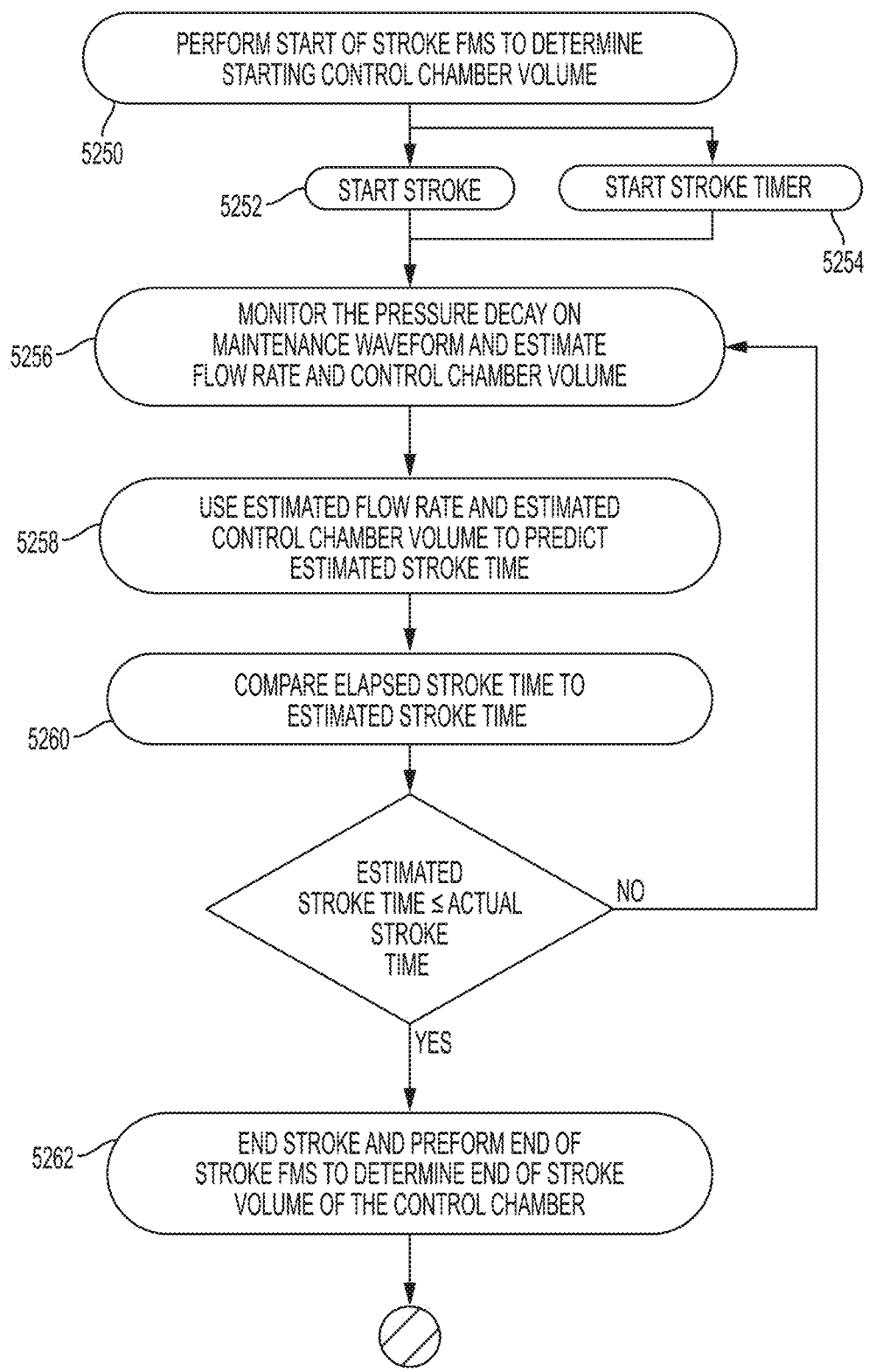
FIG. 74 shows a flowchart outlining a number of steps to determine end of stroke by predicting time necessary to complete a stroke.

FIG. 74 shows a flowchart outlining a number of example steps which may be used to determine end of stroke by predicting time necessary to complete a stroke. As shown, in step 5250, a pre-stroke FMS measurement may be taken to determine the starting volume of a control chamber. A stroke is started in step 5252. When the stroke begins, a stroke timer can be started in step 5254. As the stroke progresses, in step 5256, the pressure decay on the pressure regulation or maintenance waveform for the control chamber is monitored. This may be used to estimate the control chamber volume and flow rate. These estimates may then be used in step 5258 to project an estimated stroke time. The estimated stroke time may be calculated by finding the difference between a current chamber volume and the projected end of stroke chamber volume. The estimated flow rate may then be used to find the amount of time required to complete the stroke. The estimated end-of-stroke time may then be compared to the elapsed stroke time in step 5260. If the estimated end-of-stroke time is longer than the elapsed stroke time, steps 5256, 5258, and 5260 may be repeated. If the estimated end-of-stroke time is less or equal to than the actual elapsed stroke time, the controller may declare an end of stroke condition. In step 5262, the stroke is ended and an FMS measurement may be taken to determine the post-stroke volume of the control chamber. In some embodiments, remaining stroke time estimations may be made until a predetermined amount of stroke time remains or a predetermined amount of stroke displacement has occurred. The controller continues the stroke until that time expires and step 5262 can then be performed.

The availability of real-time flow rate estimation offered by the exemplary mathematical model described above may allow for earlier detection of reduced flow conditions as well. Instead of having a controller wait for a stroke to finish, performing a volume measurement and comparing it to a previous measurement, the controller can be programmed to respond to a real-time flow rate that is less than an expected flow rate threshold. The controller can be programmed to stop the pump stroke at that point to perform a more precise volume measurement (e.g., via an FMS measurement) to verify the flow rate estimate. Thus, reduced flow conditions may be detected without the need to complete prolonged pumping strokes caused by the reduced flow. This may save time, reduce patient discomfort, and may help to increase overall fluid throughput of a pumping cassette. It may also allow a therapy to transition more quickly from the end of a drain phase to the fill phase of the next cycle. This increased efficiency may allow for more therapy time to be allocated to dwells. In one example, the controller may be programmed to declare a reduced flow condition when the flow rate estimate is below a threshold of 50 ml/min. In some embodiments, before a reduced flow condition is declared, the flow rate may have to remain below the threshold for a predefined period of time (e.g. 30 seconds).

Optionally, there may be a plurality of reduced flow condition classifications defined by different flow thresholds. For example, in addition to a low flow threshold (e.g. <50 ml/min) the controller may be programmed to recognize a 'no flow' threshold which is set lower than the low flow threshold (e.g. <15 mL/min).

Figure 75:
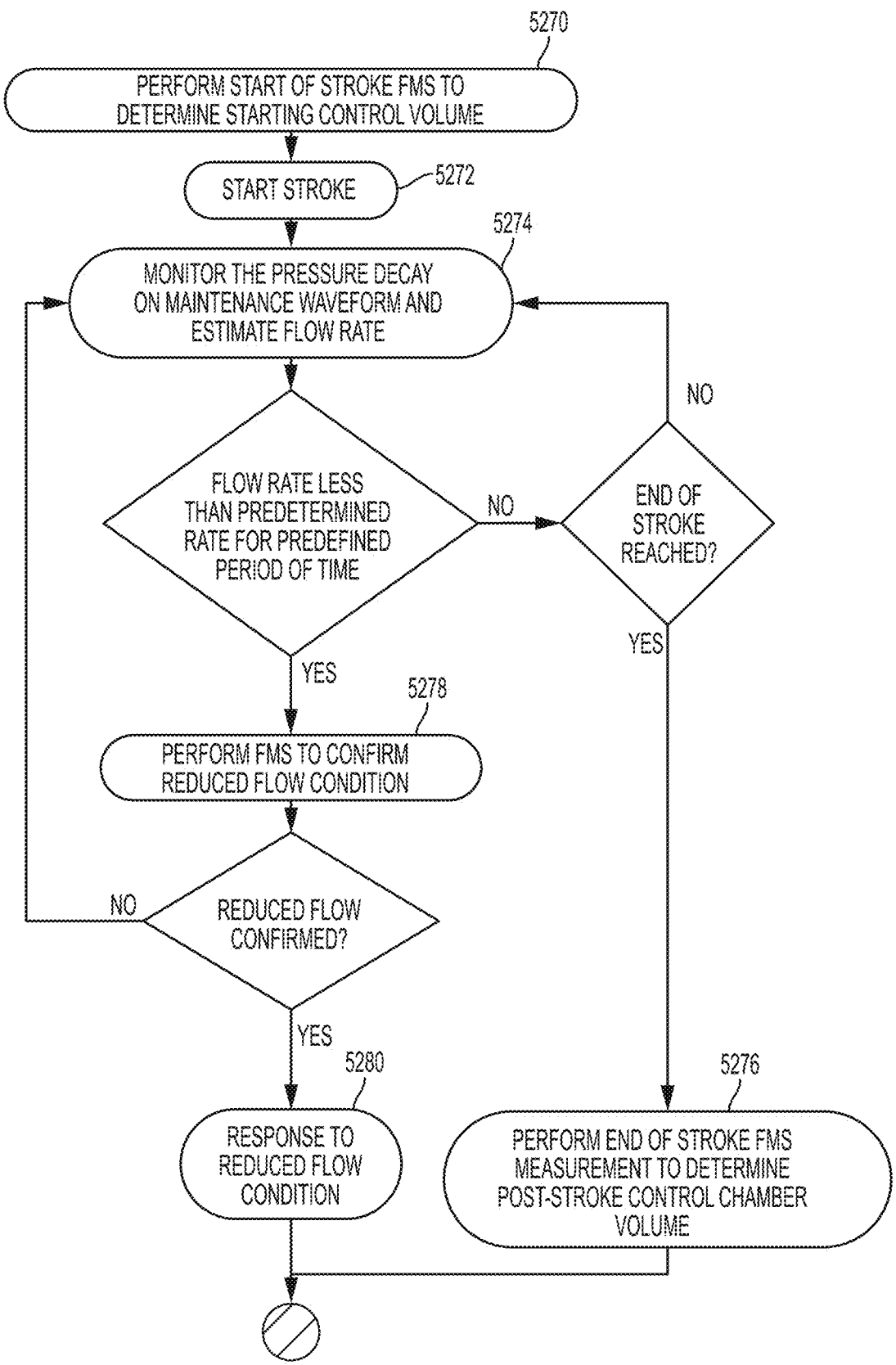
FIG. 75 shows a flowchart outlining a number of steps to detect a reduced flow condition while a pump stroke is in progress.

FIG. 75 shows a flowchart outlining a number of example steps which may be used to detect a reduced flow condition during a pump stroke. As shown, in step 5270 a pre-stroke FMS measurement may be taken to determine the starting volume of a control chamber. A stroke is then started in step

5272. In step 5274, the pressure decay on the pressure regulation or maintenance waveform may be monitored such that real-time control chamber volume change and flow rate may be estimated. The controller continues with the pump stroke as long as the flow rate is greater than a predetermined flow rate for a predetermined period of time. The controller continues to monitor the pressure decay waveforms as described in step 5274. If the end of stroke is reached, an end of stroke FMS measurement may be made in step 5276 to determine the end of stroke control chamber volume. If is the controller determines that the flow rate is less than the predetermined flow rate for a predetermined period of time, an FMS measurement may be made in step 5278 to confirm that a reduce flow condition exists. If the reduced flow condition is not confirmed, the stroke may continue, and the controller continues to compute flow rate based on the control chamber pressure regulation or maintenance waveform as described above in step 5274.

If the reduced flow condition is confirmed by the FMS measurement in step 5278, in step 5280 a reduced flow or occlusion notification, alert, or alarm may be sent to the user. This may be done via a user interface and may be accompanied by an audible message or tone, vibratory indication, etc. The response generated by the cycler controller may be dependent on the flow rate detected. Before indicating an occlusion is present, a pushback of fluid into the fluid reservoir (e.g. peritoneal cavity, heater bag, solution bag, etc. depending on the fluid line) may be triggered. In the event that the pushback attempt is unsuccessful, the controller may issue an occlusion alert.

In some embodiments, in the event a reduced flow condition is detected, a cycler controller may verify whether or not a target volume for a pumping operation (e.g. a drain phase) has been achieved (e.g., a completed peritoneal drain). If the target volume or more has been moved, the controller may declare that the pumping operation has been completed. In some embodiments, a device controller may require a minimum defined time period to have elapsed to ensure that the fluid reservoir (e.g, solution bag, heater bag, or a patient's peritoneum) is substantially empty.

Real-time measurement of fluid flow during a pump stroke can permit the targeting of specific fluid volume deliveries less than a full pump stroke volume, or an integer multiple of a full pump stroke volume. The controller may be programmed to end a stroke when the chamber volume change estimated through pressure measurement indicates that the target volume has been delivered or withdrawn. Upon this occurrence, the controller may initiate an FMS measurement to confirm that the target volume was actually reached. Real-time fluid flow measurement may avoid the need to perform multiple FMS measurements while repeatedly making small displacement partial strokes to avoid over-shooting the target volume. Such a targeting scheme may be particularly desirable in a pediatric application in which the amount of time spent approaching but not over-shooting a target volume would otherwise take a relatively large portion of time in a pumping operation.

Figure 76:
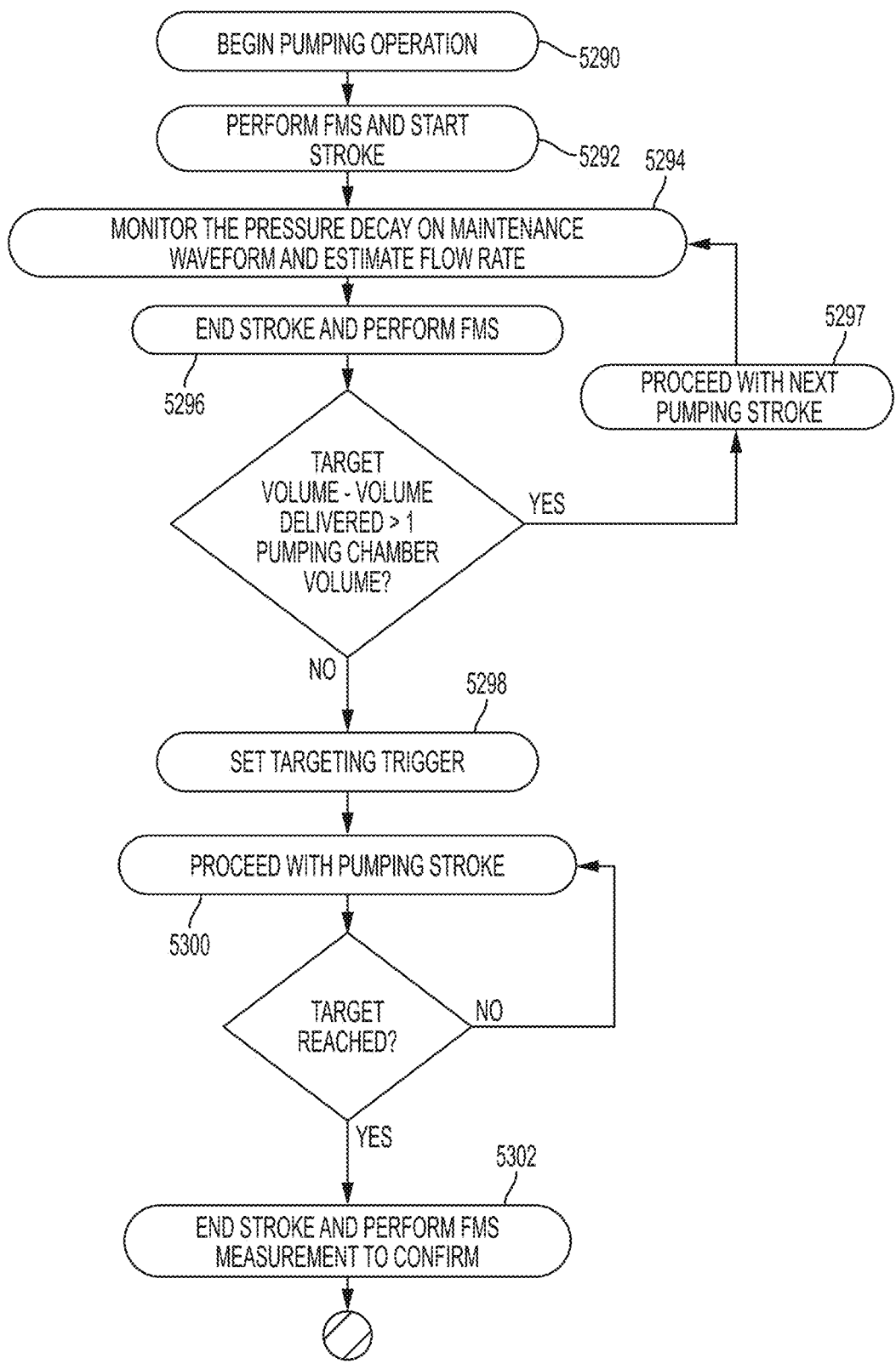
FIG. 76 shows a flowchart outlining a number of steps to determine a target volume of fluid has been moved.

FIG. 76 shows a flowchart outlining a number of example steps that may be used to determine when a target volume of fluid has been moved. As shown, the steps make use of an estimated volume moved based on measurement of pressure decay during a stroke to end the stroke when the target volume is estimated to have been reached. A pumping operation begins at step 5290. This operation may, for example, be a fill phase for a peritoneal dialysis cycle. When the pumping operation begins, an FMS measurement may be made and a pump stroke is started as shown in step 5292. During the stroke, the pressure decay on the pressure regulation or maintenance waveform may be monitored in step 5294. This allows for an estimation of volume displacement and flow rate as the stroke progresses. The stroke may end and a post-stroke FMS measurement may be conducted in step 5296. A cycler controller tracks the computed cumulative volume to see if the difference between the target volume and the total volume of fluid delivered during the pumping operation is greater than a full pump chamber volume. If so, the controller proceeds to command the next pump stroke in step 5297. Steps 5294, 5296, and 5297 may be repeated until the difference between the target volume and total volume pumped is less than the volume of one full pump chamber. At this point, in step 5298, if the delivery of another full chamber volume would cause the target volume to be exceeded, step 5298 is performed.

In step 5298, a targeting trigger may be set as the difference between the total delivered volume for the pumping operation and the target volume for the pumping operation. The pump stroke may then proceed in step 5300 until the controller calculates through pressure decay measurements that the target volume has been reached. At this point, step 5302 may be performed in which the stroke is ended and an FMS measurement may be made to confirm that the target volume of fluid has been moved.

Computing an estimated flow rate from a pressure decay curve during a pump stroke may also allow the controller to close a valve or valves in a preemptive manner in order to more precisely deliver a pre-determined fluid volume. That is, the valve(s) may be closed before the target volume is delivered to account for a delay between the controller command and the valve's mechanical response. The flow which occurs during the period of time required to physically close the valve(s) may then cause the target volume to be substantially met. Specifically, the controller may estimate the amount of time required to physically to close the valve(s). In some embodiments, this estimation may be a preprogrammed value. For example, for a particular valve arrangement the response delay may be approximately 100 ms. Based on a real time computation of the flow rate, the volume of fluid moved during the valve response delay can be estimated. This amount of fluid may be subtracted from the target volume to yield a valve closure trigger volume. Once the valve closure trigger volume has been met, the cycler controller can command the valves to close.

Fluid Line Prime State Using Estimated Flow Rate and Estimated Stroke Displacement In some embodiments, in-stroke computed flow rate and estimated stroke displacement may be used to determine the prime state of a fluid line. This may be accomplished as described in in U.S. Pat. No. 10,201,647 to Norris et al issued Feb. 12, 2019, filed Jun. 5, 2015, entitled "Medical Treatment System and Methods Using a Plurality of Fluid Lines," which is incorporated herein by reference in its entirety.

Set Differentiation

In some embodiments, a controller-computed flow rate and estimated stroke displacement may be used to determine which type of fluid line set is installed in a cycler (the types of fluid line sets may differ in total volume due to variations in tubing length, diameter, size and number of drip chambers, Y-connections or branches, etc.). The controller can also use the same procedure to cross-check previously acquired information about the fluid set. This information may be acquired through a user input via the user interface of the cycler. Additionally, in some embodiments, the controller may acquire this information by using an input device or sensor configured to read a bar code, data matrix or other identification marking.

A preset pumping pressure may be used to pump fluid through the line when computing a flow rate for such a determination. A lower flow rate will indicate a smaller diameter line, or one of greater length. In this manner, a controller may be able to determine, for example, whether an adult set or a pediatric set (which will have smaller fluid conduit) is installed in the medical device. This determination may be made when the medical device is priming the patient line of the set. The medical device may differentiate between sets with different length lines, for example, by monitoring the amount of volume pumped in order to prime the line. Longer lines (e.g. sets which include an extension) will require a larger priming volume than shorter lines. In some embodiments, flow rate data and prime volume data may be analyzed together to differentiate between set types. Flow rate data and prime volume data may be compared to a list of expected values from a number of different sets which may be used in a medical device in order to determine which set is installed in the device.

Figure 77:
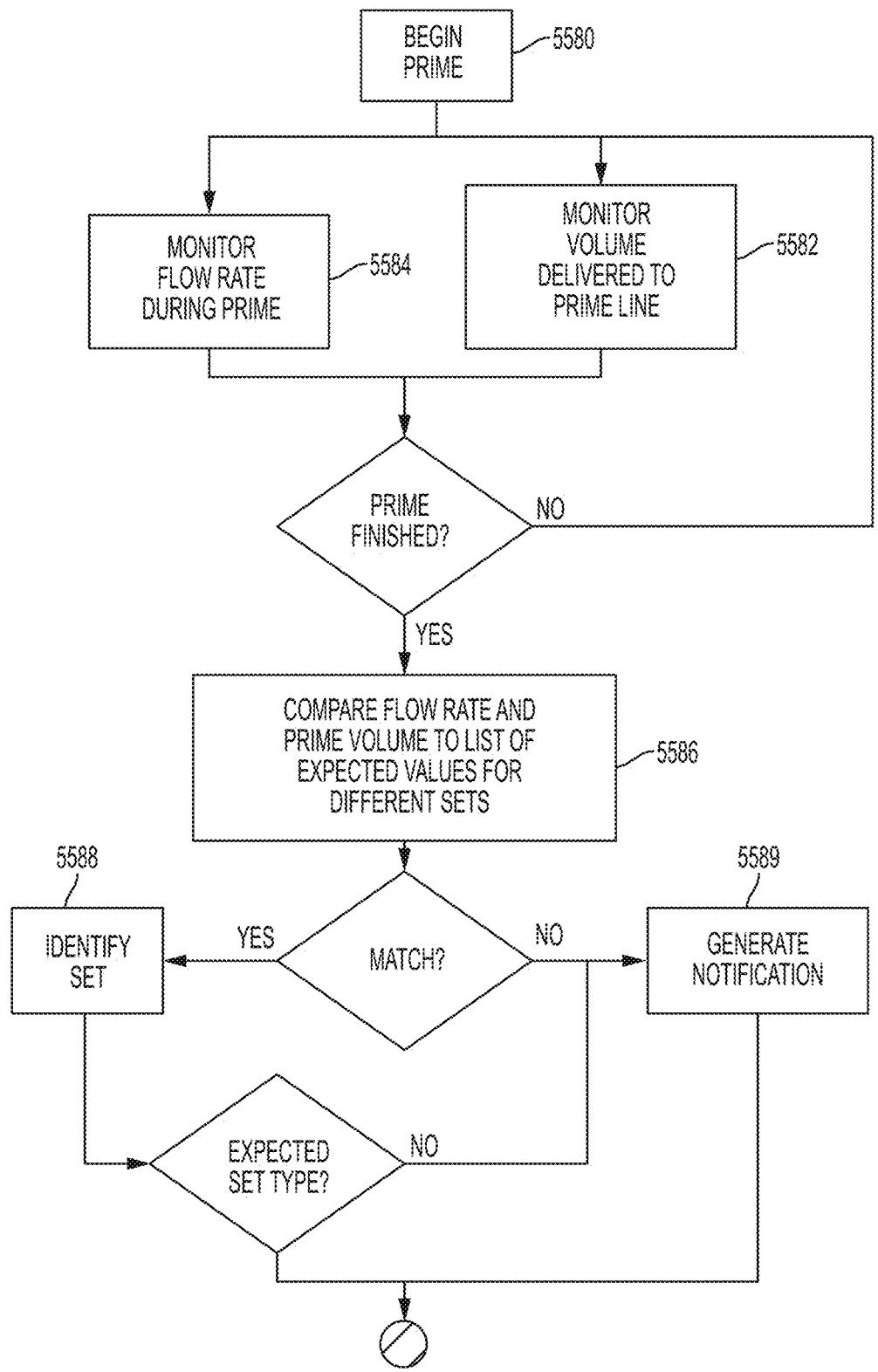
FIG. 77 shows a flowchart outlining steps which may be used by a cycler to differentiate which set of one or more different sets has been installed in a medical device.

FIG. 77 shows a flowchart outlining a number of example steps which may be used by a cycler to differentiate which set of one or more different sets has been installed in a medical device (such as a peritoneal dialysis cycler). In the example embodiment shown in FIG. 77 this determination is made during priming of a line (e.g. the patient line) included in the set. As the line is primed in step 5580, the flow rate during the prime and the volume delivered to the line during the prime are monitored in steps 5584 and 5582 respectively. As described above, a pre-determined pumping pressure may be used to help ensure variations in flow rate between different sets are attributable to the type of installed set.

The medical device may detect the prime status of the line with a prime sensor such as any of those described herein. When the prime is finished, the controller may, in step 5586 compare the flow rate and volume primed to a stored list of expected values for different sets that are available to be installed in the medical device. In some embodiments, these expected values may be determined empirically at the time of manufacture. Optionally, a range of values may be listed for each of the sets. The set type is identified in step 5588. This may be done by determining which set type in the list is closest to the observed flow rate and prime volume values during the prime. If the set type identified in step 5588 does not match previously collected data about the set, the controller may notify the user. This notification may include a visual notification on a user interface and may also be accompanied by an audio tone or alert.

Additionally, if other data has been collected about the set (e.g. from a marking or indicia on the set or from a therapy program) it may be used to verify set type identified in step 5588 is an expected set type. In the event that the set type identified in step 5588 is inconsistent with other previously collect set related data, step 5589 may be performed and the controller may generate a notification for the user.

Noise Reduction Features of the Cycler

A cycler 14 may include one or more features to reduce noise generated by the cycler 14 during operation and/or when idle. Any such features described in in U.S. Pat. No. 10,201,647 to Norris et al., issued Feb. 12, 2019, filed Jun. 5, 2015, entitled "Medical Treatment System and Methods Using a Plurality of Fluid Lines," which is incorporated herein by reference in its entirety may be used.

Control System

The control system 16 described in connection with FIG. 1 has a number of functions, such as controlling dialysis therapy and communicating information related to the dialysis therapy. While these functions may be handled by a single computer or processor, it may be desirable to use different computers for different functions so that the implementations of those functions are kept physically and conceptually separate. For example, it may be desirable to use one computer to control the dialysis machinery and another computer to control the user interface.

Figure 78:
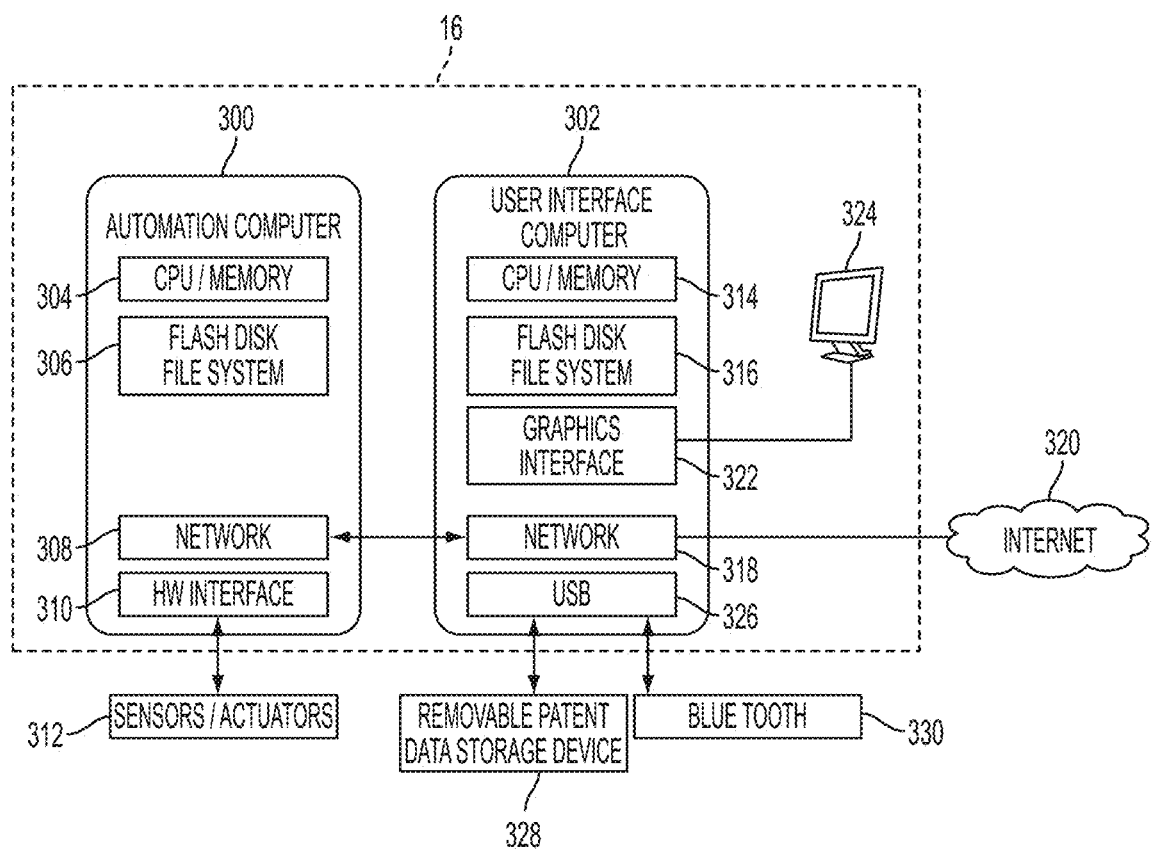
FIG. 78 is a schematic block diagram illustrating an exemplary implementation of control system for an APD system.

FIG. 78 shows a block diagram illustrating an exemplary implementation of control system 16, wherein the control system comprises a computer that controls the dialysis machinery (an "automation computer" 300) and a separate computer that controls the user interface (a "user interface computer" 302). As will be described, safety-critical system functions may be run solely on the automation computer 300, such that the user interface computer 302 is isolated from executing safety-critical functions.

The automation computer 300 controls the hardware, such as the valves, heaters, and pumps that implement the dialysis therapy. In addition, the automation computer 300 sequences the therapy and maintains a "model" of the user interface, as further described herein. As shown, the automation computer 300 comprises a computer processing unit (CPU)/memory 304, a flash disk file system 306, a network interface 308, and a hardware interface 310. The hardware interface 310 is coupled to sensors/actuators 312. This coupling allows the automation computer 300 to read the sensors and control the hardware actuators of the APD system to monitor and perform therapy operations. The network interface 308 provides an interface to couple the automation computer 300 to the user interface computer 302.

The user interface computer 302 controls the components that enable data exchange with the outside world, including the user and external devices and entities. The user interface computer 302 comprises a computer processing unit (CPU)/memory 314, a flash disk file system 316, and a network interface 318, each of which may be the same as or similar to their counterparts on the automation computer 300. The Linux operating system may run on each of the automation computer 300 and the user interface computer 302. An exemplary processor that may be suitable for use as the CPU of the automation computer 300 and/or for use as the CPU of the user interface computer 302 is Freescale's Power PC 5200B®.

Via the network interface 318, the user interface computer 302 may be connected to the automation computer 300. Both the automation computer 300 and the user interface computer 302 may be included within the same chassis of the APD system. Alternatively, one or both computers or a portion of said computers (e.g., display 324) may be located outside of the chassis. The automation computer 300 and the user interface computer 302 may be coupled by a wide area network, a local area network, a bus structure, a wireless connection, and/or some other data transfer medium.

The network interface 318 may also be used to couple the user interface computer 302 to the Internet 320 and/or other networks. Such a network connection may be used, for example, to initiate connections to a clinic or clinician, upload therapy data to a remote database server, obtain new prescriptions from a clinician, upgrade application software, obtain service support, request supplies, and/or export data for maintenance use. According to one example, call center technicians may access alarm logs and machine configuration information remotely over the Internet 320 through the network interface 318. If desired, the user interface computer 302 may be configured such that connections may only be initiated by the user or otherwise locally by the system, and not by remote initiators.

The user interface computer 302 also comprises a graphics interface 322 that is coupled to a user interface, such as the user interface 144 described in connection with FIG. 16. According to one exemplary implementation, the user interface comprises a display 324 that includes a liquid crystal display (LCD) and is associated with a touch screen. For example, a touch screen may be overlaid on the LCD so that the user can provide inputs to the user interface computer 302 by touching the display with a finger, stylus or the like. The display may also be associated with an audio system capable of playing, among other things, audio prompts and recorded speech. The user may adjust the brightness of the display 324 based on their environment and preference. Optionally, the APD system may include a light sensor, and the brightness of the display may be adjusted automatically in response to the amount of ambient light detected by the light sensor.

The brightness of the display may be set by the users for two different conditions: high ambient light and low ambient light. The light sensor will detect the ambient light level and the control system 16 will set the display brightness to the preselected levels for either high or low ambient light based on the measured ambient light. The user may select the brightness level for high and low ambient light by selection a value from 1 to 5 for each condition. The user interface may be a slider bar for each condition. In another example the user may select a number. The control system may set the button light levels to match the display light levels.

The software processes UIC executive 354 or the AC executive 354 may include a low priority sub-process or thread that checks the constant memory registers of the drivers for the touch screen and LCD display. If thread finds that any of the constant values in the memory registers are different from those stored elsewhere in the User Interface computer 302 or automation computer 300, then the thread calls for another software process to reinitialize the drivers for LCD display and/or the touch screen. In one embodiment, the LCD display is driven by a Seiko Epson S1d13513 chip and the touch screen is driven by Wolfson Microelectronics WM97156 chip. Examples of the constant register values include but are not limited to the number of pixels display on the screen, the number colors displayed.

Figure 79:
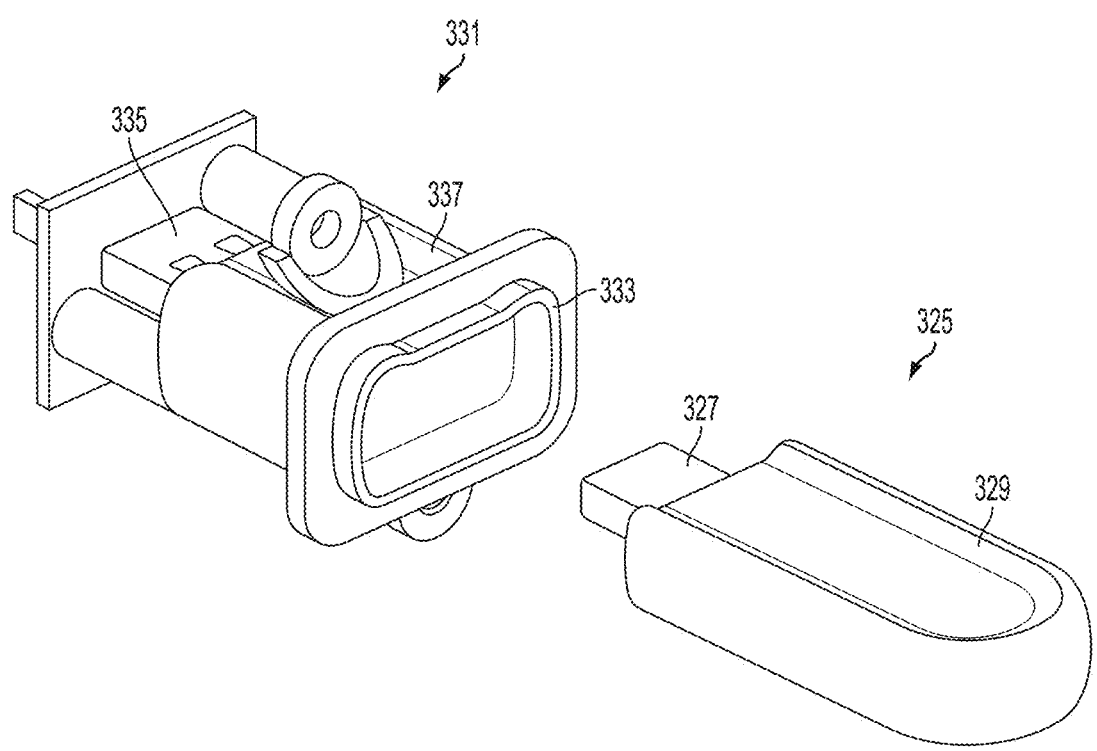
FIG. 79 shows an exemplary patient data key and associated port for transferring patient data to and from the APD system.

In addition, the user interface computer 302 comprises a USB interface 326. A data storage device 328, such as a USB flash drive, may be selectively coupled to the user interface computer 302 via the USB interface 326. The data storage device 328 may comprise a "patient data key" used to store patient-specific data. Data from dialysis therapies and/or survey questions (e.g., weight, blood pressure) may be logged to the patient data key. In this way, patient data may be accessible to the user interface computer 302 when coupled to the USB interface 326 and portable when removed from the interface. The patient data key may be used for transferring data from one system or cycler to another during a cycler swap, transferring new therapy and cycler configuration data from clinical software to the system, and transferring treatment history and device history information from the system to clinical software. An exemplary patient data key 325 is shown in FIG. 79.

As shown, the patient data key 325 comprises a connector 327 and a housing 329 coupled to the connector. The patient data key 325 may be optionally be associated with a dedicated USB port 331. The port 331 comprises a recess 333 (e.g., in the chassis of the APD system) and a connector 335 disposed within the recess. The recess may be defined, at least in part, by a housing 337 associated with the port 331. The patient data key connector 327 and the port connector 335 are adapted to be selectively electrically and mechanically coupled to each other. As may be appreciated from FIG. 79, when the patient data key connector 327 and the port connector 335 are coupled, the housing 329 of the patient data storage device 325 is received at least partially within the recess 333.

The housing 329 of the patient data key 325 may include visual cues indicative of the port with which it is associated and/or be shaped to prevent incorrect insertion. For example, the recess 333 and/or housing 337 of the port 331 may have a shape corresponding to the shape of the housing 329 of the patient data key 325. For example, each may have a non-rectangular or otherwise irregular shape, such as an oblong shape with an upper indentation as shown in FIG. 79. The recess 333 and/or housing 337 of the port 331 and the housing 329 of the patient data key 325 may include additional visual cues to indicate their association. For example, each may be formed of the same material and/or have the same or a similar color and/or pattern.

Figure 80:
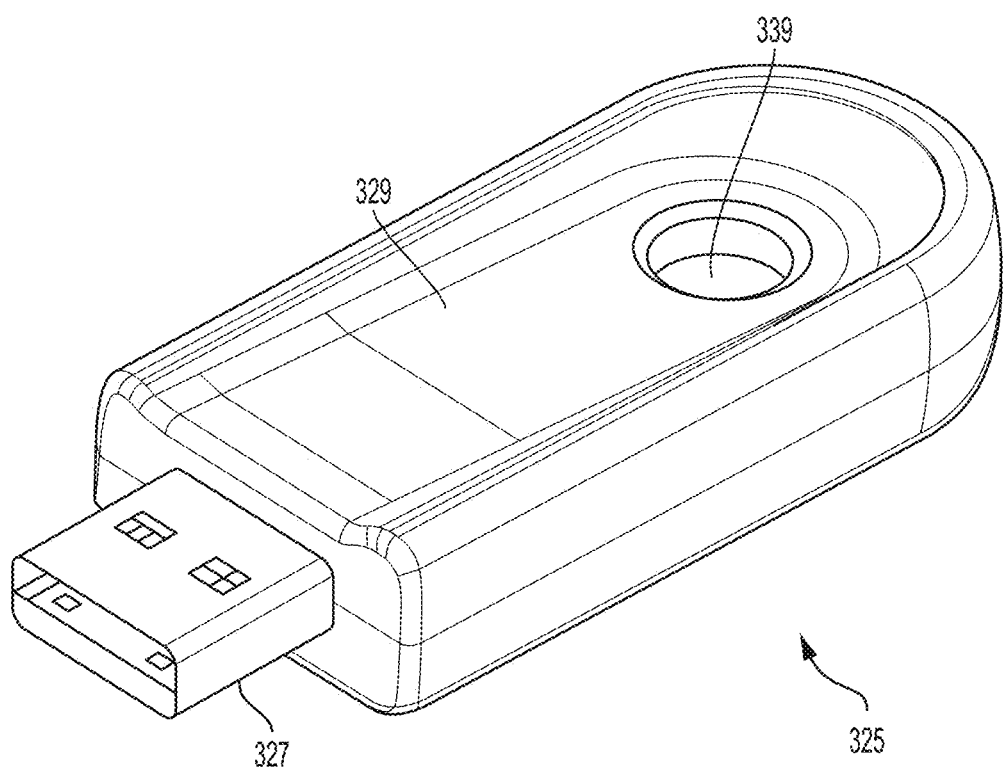
FIG. 80 shows a patient data key with an alternative housing configuration.

In a further embodiment, as shown in FIG. 80, the housing 329 of the patient data key 325 may constructed to be sloped away from connector 327 to carry any liquids that may splash onto the key 325 away from connector 327 and toward the opposite end of the housing 329, where a hole 339 in the housing 329 may help drain the liquid off and away from the patient data key 325 and its coupling with the port connector 335.

Figure 15:
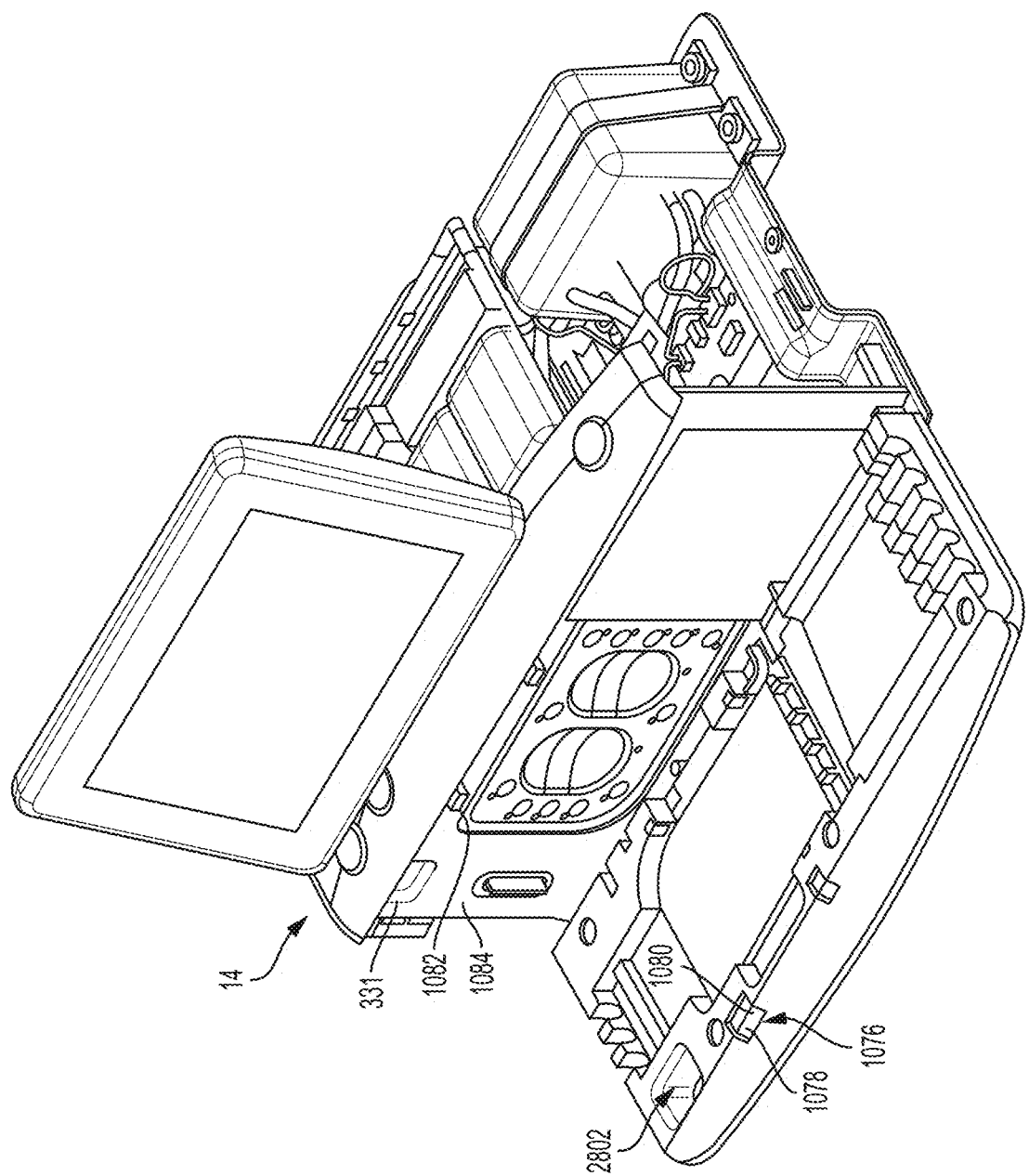
FIG. 15 is a perspective view of a door latch sensor assembly associated with a cycler.

In one embodiment, the port 331 and recess 333 are located on the front panel 1084 of cycler 14 as shown in FIG. 15. The patient data key 325 is inserted in the port 331 before the door 141 is closed and therapy is started. The door 141 includes a second recess 2802 to accommodate the patient data key 325, when the door 141 is closed. Locating the patient data key 325 behind the door 141 assures that all the therapy data may be recorded on to the patient data key 325. This location prevents a user from removing the patient data key 325 mid-therapy.

Alternatively or additionally, the patient data key 325 may comprise a verification code that is readable by the APD system to verify that the patient data key 325 is of an expected type and/or origin. Such a verification code may be stored in a memory of the patient data key 325, and be read from the patient data key 325 and processed by a processor of the APD system. Alternatively or additionally, such a verification code may be included on an exterior of the patient data key 325, e.g., as a barcode or numeric code. In this case, the code may be read by a camera and associated processor, a barcode scanner, or another code reading device.

If the patient data key 325 is not inserted when the system is powered on, an alert may be generated requesting that the key 325 be inserted. However, the system may be able to run without the patient data key 325 as long as it has been previously configured. Thus, a patient who has lost their patient data key 325 may receive therapy until a replacement key 325 can be obtained. Data may be stored directly to the patient data key 325 or transferred to the patient data key 325 after storage on the user interface computer 302. Data may also be transferred from the patient data key 325 to the user interface computer 302.

In addition, a USB Bluetooth adapter 330 may be coupled to the user interface computer 302 via the USB interface 326 to allow, for example, data to be exchanged with nearby Bluetooth-enabled devices. For example, a Bluetooth-enabled scale in the vicinity of the APD system may wirelessly transfer information concerning a patient's weight to the system via the USB interface 326 using the USB Bluetooth adapter 330. Similarly, a Bluetooth-enabled blood pressure cuff may wirelessly transfer information concerning a patient's blood pressure to the system using the USB Bluetooth adapter 330. The Bluetooth adapter 330 may be built-in to the user interface computer 302 or may be external (e.g., a Bluetooth dongle).

The USB interface 326 may comprise several ports, and these ports may have different physical locations and be used for different USB device. For example, it may be desirable to make the USB port for the patient data key 325 accessible from the front of the machine, while another USB port may be provided at and accessible from the back of the machine. A USB port for the Bluetooth connection may be included on the outside of the chassis, or instead be located internal to the machine or inside the battery door, for example.

As noted above, functions that could have safety-critical implications may be isolated on the automation computer. Safety-critical information relates to operations of the APD system. For example, safety-critical information may comprise a state of a APD procedure and/or the algorithms for implementing or monitoring therapies. Non safety-critical information may comprise information that relates to the visual presentation of the screen display that is not material to the operations of the APD system.

By isolating functions that could have safety-critical implications on the automation computer 300, the user interface computer 302 may be relieved of handling safety-critical operations. Thus, problems with or changes to the software that executes on the user interface computer 302 will not affect the delivery of therapy to the patient. Consider the example of graphical libraries (e.g., Trolltech's Qt® toolkit), which may be used by the user interface computer 302 to reduce the amount of time needed to develop the user interface view. Because these libraries are handled by a process and processor separate from those of the automation computer 300, the automation computer is protected from any potential flaws in the libraries that might affect the rest of the system (including safety-critical functions) were they handled by the same processor or process.

Of course, while the user interface computer 302 is responsible for the presentation of the interface to the user, data may also be input by the user using the user interface computer 302, e.g., via the display 324. To maintain the isolation between the functions of the automation computer 300 and the user interface computer 302, data received via the display 324 may be sent to the automation computer 300 for interpretation and returned to the user interface computer 302 for display.

Although FIG. 78 shows two separate computers, separation of the storage and/or execution of safety-critical functions from the storage and/or execution of non safety-critical functions may be provided by having a single computer including separate processors, such as CPU/memory components 304 and 314. Thus, it should be appreciated that providing separate processors or "computers" is not necessary. Further, a single processor may alternatively be used to perform the functions described above. In this case, it may be desirable to functionally isolate the execution and/or storage of the software components that control the dialysis machinery from those that control the user interface, although the disclosure is not limited in this respect.

Other aspects of the system architecture may also be designed to address safety concerns. For example, the automation computer 300 and user interface computer 302 may include a "safe line" that can be enabled or disabled by the CPU on each computer. The safe line may be coupled to a voltage supply that generates a voltage (e.g., 12 V) sufficient to enable at least some of the sensors/actuators 312 of the APD system. When both the CPU of the automation computer 300 and the CPU of the user interface computer 302 send an enable signal to the safe line, the voltage generated by the voltage supply may be transmitted to the sensors/actuators to activate and disable certain components. The voltage may, for example, activate the pneumatic valves and pump, disable the occluder, and activate the heater. When either CPU stops sending the enable signal to the safe line, the voltage pathway may be interrupted (e.g., by a mechanical relay) to deactivate the pneumatic valves and pump, enable the occluder, and deactivate the heater. In this way, when either the automation computer 300 or the user interface computer 302 deems it necessary, the patient may be rapidly isolated from the fluid path, and other activities such as heating and pumping may be stopped. Each CPU can disable the safe line at any time, such as when a safety-critical error is detected or a software watchdog detects an error. The system may be configured such that, once disabled, the safe line may not be re-enabled until both the automation computer 300 and user interface computer 302 have completed self-tests.

Figure 81:
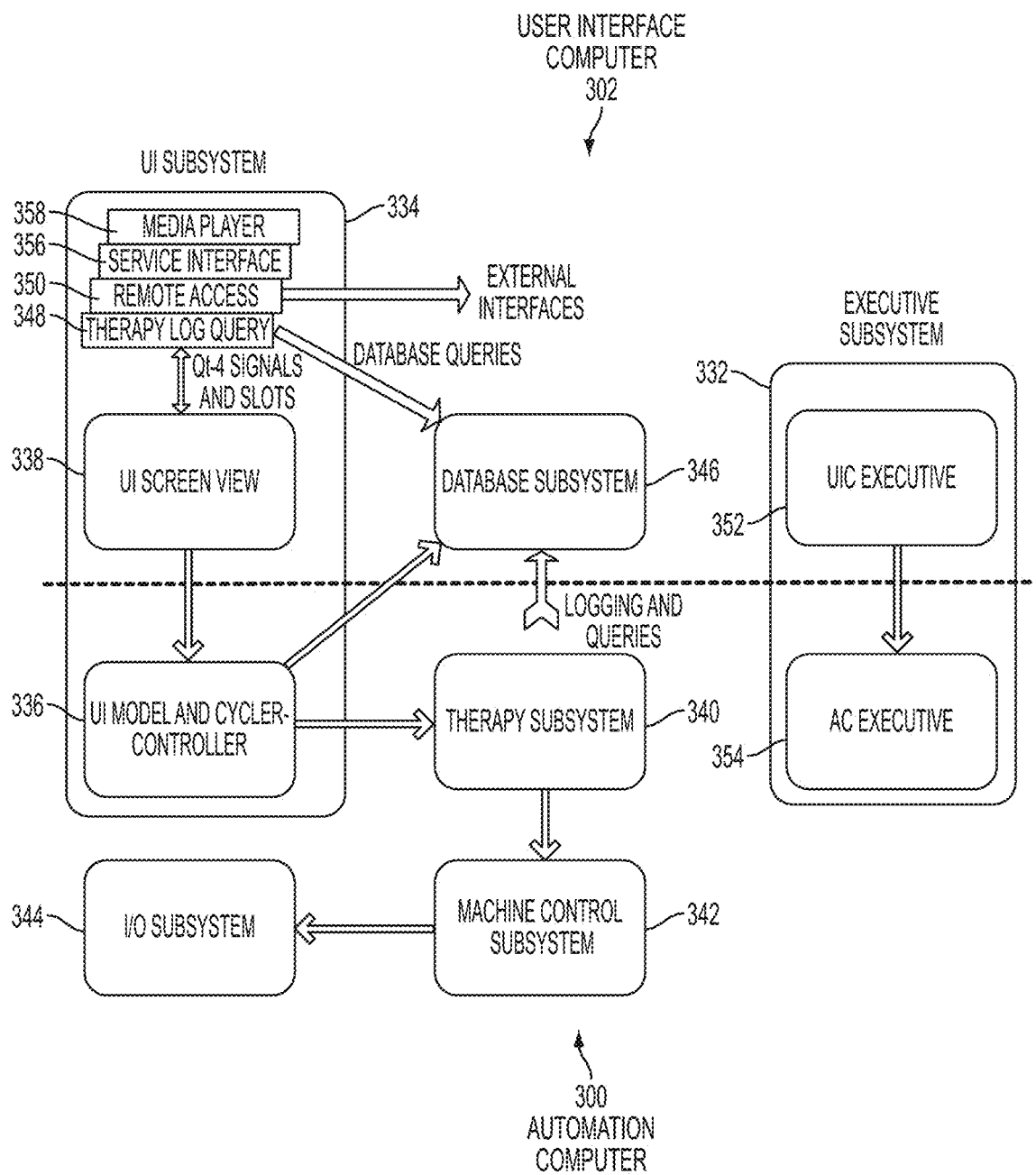
FIG. 81 shows a block diagram of a software subsystems of a user interface computer and automation computer.

FIG. 81 shows a block diagram of the software subsystems of the user interface computer 302 and the automation computer 300. In this example, a "subsystem" is a collection of software, and perhaps hardware, assigned to a specific set of related system functionality. A "process" may be an independent executable which runs in its own virtual address space, and which passes data to other processes using inter-process communication facilities.

The executive subsystem 332 includes the software and scripts used to inventory, verify, start and monitor the execution of the software running on the CPU of the automation computer 300 and the CPU of the user interface computer 302. A custom executive process is run on each of the foregoing CPUs. Each executive process loads and monitors the software on its own processor and monitors the executive on the other processor.

The user interface (UI) subsystem 334, handles system interactions with the user and the clinic. The UI subsystem 334 is implemented according to a "model-view-controller" design pattern, separating the display of the data ("view") from the data itself ("model"). In particular, system state and data modification functions ("model") and cycler control functions ("controller") are handled by the UI model and cycler controller 336 on the automation computer 300, while the "view" portion of the subsystem is handled by the UI screen view 338 on the UI computer 302. Data display and export functionality, such as log viewing or remote access, may be handled entirely by the UI screen view 338. The UI screen view 338 monitors and controls additional applications, such as those that provide log viewing and a clinician interface. These applications are spawned in a window controlled by the UI screen view 338 so that control can be returned to the UI screen view 338 in the case of an alert, an alarm or an error.

The therapy subsystem 340 directs and times the delivery of the dialysis treatment. It may also be responsible for verifying a prescription, calculating the number and duration of therapy cycles based upon the prescription, time and available fluids, controlling the therapy cycles, tracking fluid in the supply bags, tracking fluid in the heater bag, tracking the amount of fluid in the patient, tracking the amount of ultra-filtrate removed from patient, and detecting alert or alarm conditions.

The machine control subsystem 342 controls the machinery used to implement the dialysis therapy, orchestrating the high level pumping and control functionality when called upon by the therapy subsystem 340. In particular, the following control functions may be performed by the machine control subsystem 342: air compressor control; heater control; fluid delivery control (pumping); and fluid volume measurement. The machine control subsystem 342 also signals the reading of sensors by the I/O subsystem 344, described below.

The I/O subsystem 344 on the automation computer 300 controls access to the sensors and actuators used to control the therapy. In this implementation, the I/O subsystem 344 is the only application process with direct access to the hardware. Thus, the I/O subsystem 344 publishes an interface to allow other processes to obtain the state of the hardware inputs and set the state of the hardware outputs.
FPGA In some embodiments, the Hardware Interface 310 in FIG. 83 may be a separate processor from the automation computer 300 and the User Interface 302 that may perform a defined set of machine control functions and provide an additional layer of safety to the cycler controller 16. A second processor, such as a field programmable gate array (FPGA) may increase the responsiveness and speed of the cycler 14 by moving some computing tasks from the automation computer 300 to the hardware interface 310 (e.g., an FPGA), so that the automation computer 300 can devote more resources to fluid management and therapy control, as these comprise resource-intensive calculations. The hardware interface 310 may control the pneumatic valves and record and temporarily store data from the various sensors. The real time control of the valves, pressure levels and data recording by the hardware interface 310 allows the automation computer 300 to send commands and receive data, when the software processes or functions running on the automation computer 300 are ready for them.

A hardware interface processor 310 may advantageously be implemented on any medical fluid delivery apparatus, including (but not limited to) a peritoneal dialysis cycler 14, in which fluid is pumped by one or more pumps and an arrangement of one or more valves from one or more source containers of fluid (e.g., dialysate solution bags, or a heater bag containing fluid to be infused) to a patient or user. It may also be implemented on a fluid delivery apparatus that is configured to pump fluid from a patient or user (e.g., peritoneal dialysis cycler) to a receptacle (e.g., drain bag). A main processor may be dedicated to controlling the proper sequence and timing of pumps and valves to perform specific functions (e.g., pumping from a solution bag to a heater bag, pumping from a heater bag to a user, or pumping from a user to a drain receptacle), and to monitor the volumes of fluid pumped from one location to the next. A secondary (hardware interface) processor (e.g. an FPGA) may correspondingly be dedicated to collect and store data received from various sensors (e.g., pressure sensors associated with the pumps, or temperature sensors associated with a heating system) at an uninterrupted fixed rate (e.g., about 100 Hz or 2000 Hz), and to store the data until it is requested by the main processor. It may also control the pumping pressures of the pumps at a rate or on a schedule that is independent from any processes occurring in the main processor. In addition to other functions (see below) it may also open or close individual valves on command from the main processor.

In one example the Hardware Interface 310 may be a processor that performs a number of functions including but not limited to:
  Acquiring pneumatic pressure sensor data on a predictable and fine resolution time base;
  Storing the pressure data with a timestamp until requested by automation computer 300;
  Validating the messages received from that automation computer 300;
  Providing automated control of one or more pneumatic valves 2660-2667;
  Controlling some valves with a variable pulse width modulation (PWM) duty cycle to provide Pick & Hold functionality and/or control some valves with current feedback;
  Provide automated and redundant safety checking of valve combinations, maximum pressures and temperatures and ability.
  Independent of the other computers 300, 302 putting the cycler 14 into a failsafe mode as needed.
  Monitoring status of buttons on the cycler 14 and controlling the level of button illumination;
  Controlling the Auto Connect screw-drive mechanism 1321 and monitoring the Auto-Connect position sensing;
  Detecting the presence of solution caps 31 and/or spike caps 63;
  Control of the pneumatic pump;
  Control of the prime sensor LED and detector;
  Detecting over-voltages and testing hardware to detect over-voltages;
  Controlling and monitoring one or more fluid detectors;
  Monitoring the latch 1080 and proximity sensor 1076 on the door 141;
  Monitoring critical voltages at the system level.

The Hardware Interface 310 may comprise a processor separate from the processors in the automation computer 300 and user interface 302, A to D converters and one or more IO boards. In another embodiment, the hardware interface is comprised of a FPGA (Field Programmable Gate Array). In one embodiment the FPGA is a SPARTAN® 3A in the 400K gate and 256 ball package made by Xilinx Inc. of California. The Hardware Interface 310 is an intelligent entity that is employed to operate as an independent safety monitor for many of the Control CPU functions. There are several safety critical operations where either the Hardware Interface or the Control CPU serves as a primary controller and the other serves as a monitor.

The hardware interface 310 serves to monitor the following automation computer 300 functions including but not limited to:
  Monitoring the integrity of system control data being received from the automation computer 300;
  Evaluating the commanded valve configurations for combination that could create a patient hazard during therapy;
  Monitoring the fluid and pan temperature for excessive high or low temperatures;
  Monitoring and testing the overvoltage monitor; and
  Provide a means for the automation computer 300 to validate critical data returned from the hardware interface.

Figure 82:
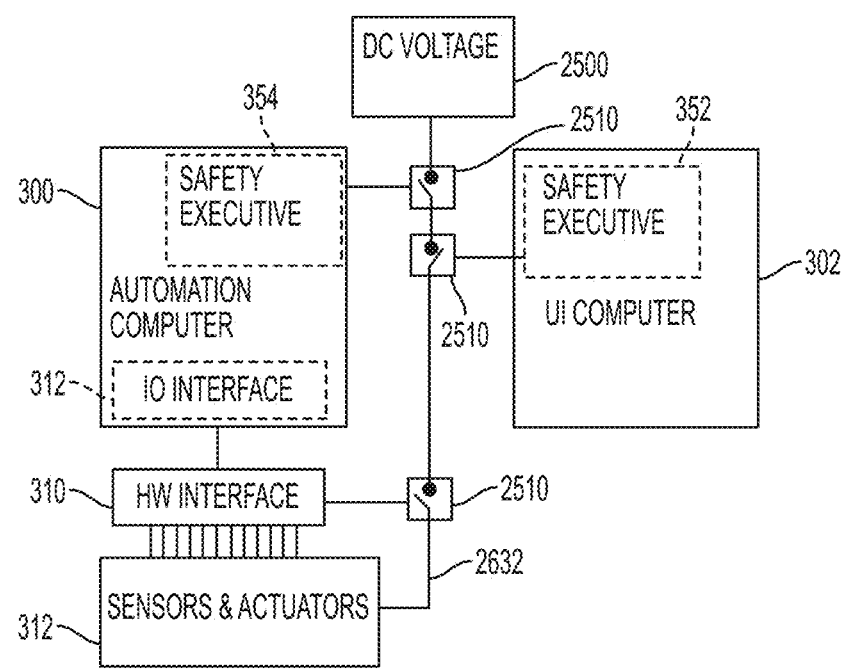
FIG. 82 is a schematic block diagram illustrating an exemplary arrangement of the multiple processors controlling the cycler and the safe line.

FIG. 82 is a schematic representation of one arrangement of the automation computer 300, the UI computer 302 and the hardware interface processor 310. The hardware interface 310 is connected via a communication line to the automation computer 300 and connects to the sensors and actuators 312 in the cycler 14. A voltage supply 2500 provides power for the safety critical actuators that can be enabled or disabled by any of the computers 300, 302, 310. The safety critical actuators include but are not limited to the pneumatic valves, the pneumatic pump and a safety relay on the heater circuit. The pneumatic system is configured to safe condition when unpowered. The pneumatic safe condition may include occluding the lines 28, 34 to the patient, isolating the control chambers 171 and/or closing all the valves 184, 186, 190, 192, on the cassette 24. The safety relay 2030 in the heater circuit 2212 is open, preventing electrical heating, when the relay is unpowered. Each computer 300, 302, 310 controls a separate electrical switch 2510 that can each interrupt power to the valves, pump and safety relay. If any of the three computers detects a fault condition, it can put the cycler 14 in a failsafe condition by opening one of the three switches 2510. The electrical switches 2510 are controlled by the safety executive process 352, 354 in the UI computer 302, and automation computer 300 respectively.

Figure 83:
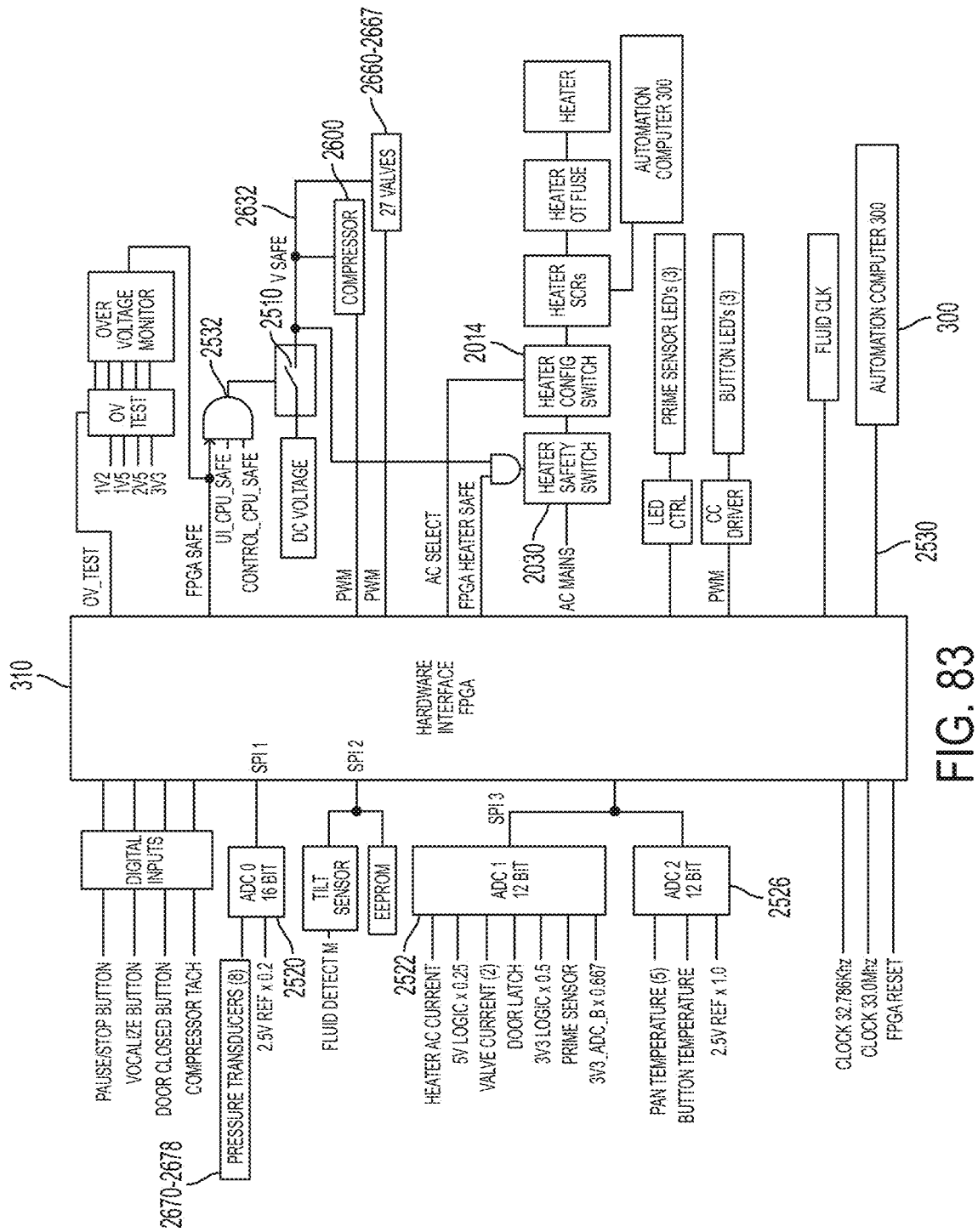
FIG. 83 is a schematic block diagram illustrating exemplary connections between the hardware interface processor and the sensors, the actuators and the automation computer.

FIG. 83 is a schematic illustration of the connections between the Hardware Interface 310, the various sensors, the pneumatic valves, the bag heater and the automation computer 300. The Hardware Interface 300 controls each of the pneumatic valves 2660-2667 and the pneumatic pump or compressor 2600 via pulse-width-modulated DC voltages. FIG. 83 presents an alternative embodiment of the safe line 2632 supplying power to the pneumatic valves 2660-2667, pump 2600 and heater safety relay 2030, in which a single switch 2510 is driven by an AND gate 2532 connected to the three computers 300, 302, 310. The prime sensor is controlled and monitored by the Hardware Interface 310. The brightness of the button LEDs is controlled by the Hardware Interface 310 via a PWM'd voltage.

The data signals from the buttons, pressure sensors, temperature sensors and other elements listed in FIG. 83 are monitored by the Hardware Interface 310, and the data is stored in a buffer memory until called for by the automation computer 300. The digital inputs are connected directly to the Hardware Interface 310. The analog signals from pressure, temperature, current sensors and others are connected to Analog-to-Digital-Converter (ADC) boards that convert the analog signals to digital values and may scale and/or offset the digital values. The outputs of the ADCs are communicated over SPI buses to the Hardware Interface 310. The data is recorded and stored in the buffer at a fixed rate. Some of the data signals may be recorded at a relatively slow rate, including the pressure data on the pressure reservoirs and the fluid trap, temperatures, and current measurements. The low speed data may be recorded at 100 Hz. The adiabatic FMS volume measurement algorithm can be improved with high speed pressure data that is recorded at regular intervals. In a preferred embodiment, the pressure data from the sensors on the control volume 171 and the reference chamber 174 are recorded at 2000 Hz. The data may be stored in random-access-memory (RAM) along with a time stamp. The rate of data collection may preferably proceed independently of the automation computer 300 and of processes or subroutines on the hardware interface. The data is reported to the automation computer 300, when a process calls for that value.

The transfer of data between the hardware interface 310 to the automation computer 300 may occur in a two step process where a data packet transferred and stored in a buffer before being validated and then accepted for use by the receiving computer. In one example, the sending computer transmits a first data packet, followed by a second transmission of the cyclic redundancy check (CRC) value for the first data packet. The receiving computer stores the first data packet in a memory buffer and calculates a new CRC value first data packet. The receiving computer then compares the newly calculated CRC value to the CRC value received and accepts the first data packet if the two CRC values match. The cyclic redundancy check (CRC) is an error-detecting code commonly used in digital networks and storage devices to detect accidental changes to raw data. Blocks of data entering these systems get a short check value attached, based on the remainder of a polynomial division of their contents; on retrieval the calculation is repeated, and corrective action can be taken against presumed data corruption if the check values do not match. The data is not transferred between the automation computer and hardware interface if CRC values do not match. If multiple consecutive data packets fail the CRC test, the receiving computer may signal an alarm and put the machine in a fail-safe condition by de-energizing the safe line 2632. In one example, the alarm condition occurs on the third consecutive failed CRC check.

The automation computer 300 passes commands to open selected valves and set specified pressures in specified volumes to the hardware interface 300. The hardware interface 310 in turn controls the valve position by providing a PWM'd voltage to each valve. The hardware interface 310 opens valves as requested with a pick-and-hold algorithm, where the valve is initially actuated with a high voltage or current, and then held in place with a lower voltage or current. Pick-and-hold operation of valves may advantageously reduce the power draw and the level of heat dissipation inside the cycler 14.

The hardware interface 310 controls the pressure in the specified volume by opening and closing the valves between the specified volume and the appropriate pressure reservoir based on the measured pressure in the specified volume. The hardware interface 310 may also control the pressure in the pressure reservoirs by opening and closing the valves between a pneumatic pump and one of the pressure reservoirs based on the measured pressure in the reservoir. The specified volumes may include each of the control chambers 171, the reference volumes 174, the fluid trap and the positive and negative reservoirs. The hardware interface 310 may control the pressure in each of these specified volumes via a number of control schemes, including but not limited to on-off control, or proportional control of the valve with a PWM signal. In one example, as described above, the hardware interface 310 implements an on-off controller, sometimes referred to as a bang-bang controller, which sets a first and second limit and closes the valve when the pressure exceeds the upper second limit and opens the valve when the pressure is less than the first lower limit. In another example, the hardware interface 310 may operate valves between the specified volume and both pressure reservoirs to achieve a desired pressure. In other examples the automation computer 300 may specify one or more valves and command a specific valve to control the pressure as measured by a specified sensor.

The hardware interface 310 controls the position and operation of the Auto-Connect carriage. The movement and positioning of the Auto-Connect carriage 146 is controlled in real time by the hardware interface 310 based on the measured position of the carriage 146. The automation computer 300 may command a particular function or position for the carriage. The hardware interface 310 carries out the commanded function without burdening memory or processing of the automation computer 300. The positioning of the carriage 146 is controlled with a feedback loop from a position sensor. In addition, the FPGA detects the presence of solution caps 31 and/or spike caps 63 with sensing elements 1112 as described above. Alternatively, the presence of the caps 31 and/or spike caps 63 can be detected by a range of sensing technologies, including but not limited to vision systems, optical sensors that can be blocked by a solution cap 31 and/or spike cap 63, or, for example, a micro-switch on the stripper element 1491.

The hardware interface 310 may implement safety functions independently of the automation computer 300 or the user interface computer 302. The independent action of the hardware interface 310 to disable the safety line 2632 and/or signal an alarm to the safety executives 352, 354 further reduces the possibility of an unsafe condition occurring. The hardware interface 310 may send an alarm and/or de-energize the safe line 2632 for defined valve combinations at any time. Shutting the cycler 14 down based on disallowed valve positions protects the patient and preserves the ability to complete the therapy (after a reset if needed). The hardware interface 310 may also alarm and de-energize the safe line at unsafe conditions including excessive temperature on the heater pan and/or bag button, excessive pressure in control chamber or reservoir. The hardware interface 310 may alarm and de-energize the safe line when water or other liquid is detected in the fluid trap 1722.

Heater Control System

The following descriptions of a heater control system, including (but not limited to) a dual-voltage heater control system and a heater current leakage optimization and safety system may be applied to any device that operates a heater at high (e.g., line) voltages. For example, these heater control systems may be incorporated into the presently disclosed peritoneal dialysis cycler 14 embodiments. In addition, they may be incorporated into peritoneal dialysis systems disclosed in U.S. Pat. No. 5,350,357 to KAMEN DEAN et al., issued Sep. 27, 1994, entitled "Peritoneal dialysis systems employing a liquid distribution and pumping cassette that emulates gravity flow", U.S. Pat. No. 5,431,626 to BRYANT ROBERT J et al., issued Jul. 11, 1995, entitled "Liquid pumping mechanisms for peritoneal dialysis systems employing fluid pressure", U.S. Pat. No. 5,438,510 to BRYANT ROBERT J et al., issued Aug. 1, 1995, entitled "User interface and monitoring functions for automated peritoneal dialysis systems", U.S. Pat. No. 5,474,683 to BRYANT ROBERT J et al., issued Dec. 12, 1995, entitled "Peritoneal dialysis systems and methods employing pneumatic pressure and temperature-corrected liquid volume measurements", and U.S. Pat. No. 5,628,908 to KAMEN DEAN et al., issued May 13, 1997, entitled "Peritoneal dialysis systems and methods employing a liquid distribution and pump cassette with self-contained air isolation and removal", each of which is incorporated by reference in its entirety, or any hemodialysis system, such as a hemodialysis system disclosed in U.S. Pat. No. 8,246,826 to Wilt et al., issued Aug. 21, 2012, entitled "Hemodialysis systems and methods", U.S. Pat. No. 8,357,298 to Demers et al., issued Jan. 22, 2013, entitled "Hemodialysis systems and methods", United States U.S. Pat. No. 8,409,441 to Wilt, issued Apr. 2, 2013, entitled "Blood treatment systems and methods", and U.S. Pat. No. 8,393,690 to Grant et al., issued Mar. 12, 2013, entitled "Enclosure for a portable hemodialysis system," each of which is hereby incorporated by reference herein in its entirety.

The control systems described above may be used to ensure that the solution delivered to a patient is maintained within a pre-determined range of temperatures. During the therapy process, the cycler 14 fills the heater bag 22 with solution from the connected solution containers 20, via a heater bag line 26. The heater bag 22 rests on the heater pan 142 which may include electrical resistance heaters. The heater bag 22 may be covered with an insulated cover 143. A heater controller may function so as to control the thermal energy delivered to the heater pan 142 in order to control the temperature of the solution to a desired set point prior to delivering the solution to the patient. The solution temperature should be within a safe range prior to being delivered to the patient's abdominal cavity in order to avoid injuring or causing discomfort to the patient, or causing hypothermia or hyperthermia. The heater controller may also limit the temperature of the heater pan to touch-safe temperatures. The heater controller is constructed to heat and maintain the solution within a range of acceptable temperatures in a timely manner in order to ensure the most effective therapy.

Figure 84:
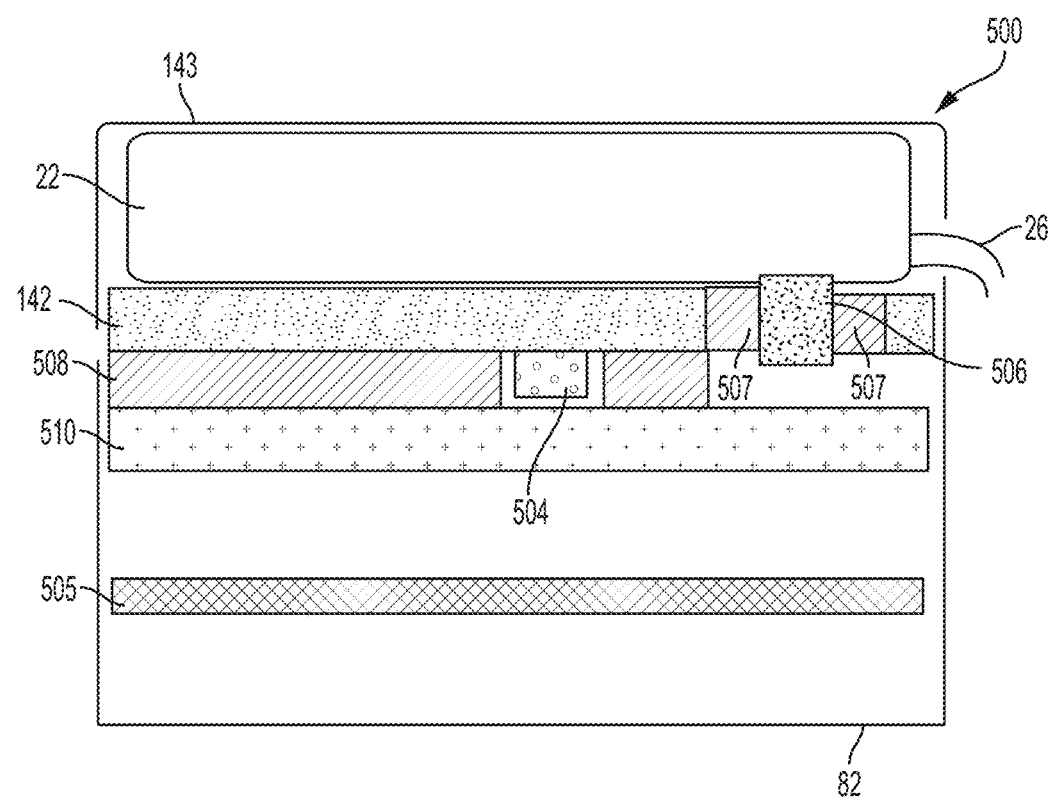
FIG. 84 shows a schematic cross section of the cycler illustrating the components of the heater system for the heater bag.

FIG. 84 is a schematic view of an exemplary embodiment of a solution heater system 500. In this example, the solution heater system 500 is located within the housing 82 of the cycler 14. The housing includes an insulated lid 143 that may be affixed to the top of the housing 82. The housing 82 and the heater lid 143 may therefore define a region that serves to house the components of the solution heater system 500. The solution heater system 500 may include the following elements: housing 82, heater lid 143, heater pan 22, heater elements 508, heater pan temperature sensors 504, button temperature sensor 506, insulating ring 507 and heater control electronics 50. The heater pan 142 is positioned inside the housing 82, and may accommodate a heater bag 22 when positioned on top of the heater tray 142. Preferably, the heater pan 142 is inclined to place the inlet and/or outlet of the heater bag in a dependent position, to help ensure that fluid in the bag 22 is always in contact with the inlet/outlet regardless of the amount of fluid in the bag 22. In an embodiment, there can be up to six or more heater pan temperature sensors 504 (only one exemplary heater pan temperature sensor 504 is shown in FIG. 84) positioned along the floor of the heater pan 142. Additionally, there may be a button temperature sensor 506 positioned within the heater pan 142. The button sensor 506 is positioned to make good thermal contact with the heater bag 22, while being thermally isolated from the heater pan 142 by an insulating ring 507, in order to provide an approximation of the temperature of the fluid or dialysate in the bag. In another embodiment, the button sensor 506 may comprise a pair of thermistors mounted on an aluminum button. The aluminum button is thermally isolated by an insulating ring made of, for example, LEXAN® 3412R plastic or another low thermal conductivity material. The button temperature sensor 506 may be located near the end of the tray where the fluid lines connect to the heater bag 22 in order to better measure the temperature of the fluid within the heater bag 22 when the heater bag 22 is less than approximately one-third full. The button sensor 506 may also be referred to as the fluid or dialysate temperature sensor. There may also be a plurality of heater elements 508 positioned under the heater pan 142, more toward the superior end of the pan 142, with the bag sensor located more toward the dependent portion of the pan 142, in order for the sensor to provide a more accurate reading of the fluid temperature within the bag 22, and to be relatively unaffected by the heater elements 508. The thermal output of the heater elements 508 may be controlled by the heater control electronics 505 to achieve the desired fluid temperature in the heater bag 22. The heater control electronics 505 may include but not be limited to a heater control module 509 that produces a Pulse Width Modulation signal (PWM signal 511, represented in FIG. 85). Electrical hardware in the input-output (IO) subsystem 344 connects electrical power to the heater elements 508 based on the PWM signal 511, and hardware on the IO subsystem 344 reads the output of heater pan temperature sensors 504 and button temperature sensor 506. The PWM signal 511 may control the power supplied to each of the heater elements 508, and consequently the solution heater system 500 may then heat the heater bag 22 to a user-settable comfort temperature, which may be controlled within a preferred safe temperature range. The solution heater system 500 may also limit the surface temperature of the heater pan 142 to a safe-to-touch temperature. The hardware components of the heater control circuitry 505 may be part of controller 16. There may also be insulation 510 positioned below the heater element 508 which functions to thermally isolate the heater pan 142 and heater bag 22 from the electronic and pneumatic components of the cycler 14. Additionally, the heater lid 143 may insulate the heater bag 22 from the surrounding environment. The solution heater system 500 may thus be constructed to bring the solution temperature inside the heater bag 22, as measured by the button temperature sensor 506, to the desired fluid set point temperature 550 (see FIG. 86) as quickly as possible, and maintaining that desired fluid set point temperature 550 through the rest of the therapy cycle. In some embodiments, the temperature sensors connect to the hardware interface 310. The same hardware interface 310 may control a safety relay that disables the heater.

In some embodiments, the heater elements 508 may include thermal switches that open when the temperature of the switch exceeds a first pre-determined value. The switch will close again once the temperature of the switch drops below the second lower pre-determined value. The thermal switch may be incorporated directly into the heater elements 508 or may be mounted on the outside of the heater element 508 or on the heater pan 142. The thermal switches provide an additional layer of protection against unsafe pan 142 temperatures.

Figure 85:
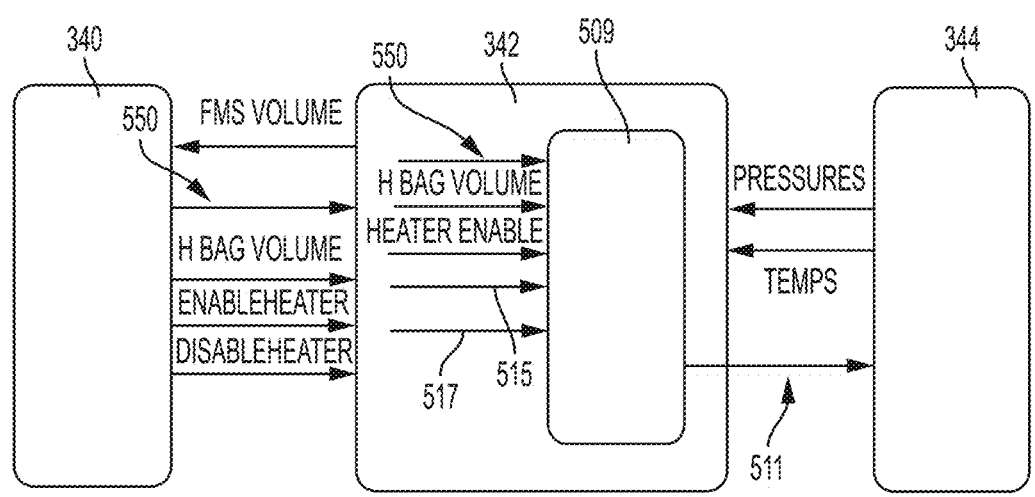
FIG. 85 shows software processes interacting with a heater controller process.

In another example, the thermal switch may be a thermal fuse with a one-time fusible link. A service call will be required to replace the blown thermal fuse, which may advantageously provide an opportunity to inspect and/or test cycler 14 before restarting therapy. FIG. 85 shows a schematic block diagram of the software context of the heater control subsystem. In an embodiment, the logic of the heater control circuitry 505 may be implemented as a heater control module 509 in the machine control subsystem 342 in the APD System software architecture. The heater controller software may be implemented in the controller 16 (FIG. 78) as described below. Additionally, the therapy subsystem 340 may supply information to the machine control subsystem 342 such as the heater bag 22 volume and the set point for the button temperature sensor 506. The heater elements 508 may be enabled by the therapy subsystem 340. The machine control subsystem 342 may also read temperature values from the I/O subsystem 344, which is located below the machine control subsystem 342. Furthermore, the heater controller 509 may output a PWM signal 511 which may then control the power supplied to the heater elements 508.

In an embodiment, the machine control subsystem 342 may be called periodically (e.g., approximately every 10 milliseconds) to service the I/O subsystem 344, update variables, and detect conditions. The machine control subsystem 342 may also send updated signals to the heater control module 509 periodically (e.g., approximately every 10 ms). The updated signals may include the heater bag 22 volume, heater pan temperatures 515, the button temperature 517, the set point temperature 550 and the heater enable function. The heater control module 509 may average some or all of these signals continuously, but only calculate and update its output 511 at a lower frequency (e.g, every 2 seconds).

In another aspect, the solution heater system 500 may be able to control the solution temperature in the heater bag 22 within a given range of a desired fluid set point temperature 550 (see FIG. 85 and FIG. 90-92). Furthermore, the solution heater system 500 has been designed to function within pre-defined specifications under a variety of different operating conditions, such as a relatively wide range of ambient temperatures (e.g., approximately 5° C. to approximately 37° C.), bag fill volumes (e.g., approximately 0 mL to approximately 3200 mL), and solution container 20 temperatures (e.g., between approximately 5° C. and approximately 37° C.). In addition, the solution heater system 500 is capable of functioning within specifications even if the solution in the heater bag 22 and the solution introduced during the replenish cycle may be at different temperatures. The solution heater system 500 has also been designed to function within specifications with heater supply voltages varying as much as +10% of nominal voltage.

The solution heater system 500 may be considered to be an asymmetrical system, in which the solution heater system 500 can increase the solution temperature with the heater elements 508, but relies on natural convection to lower the solution temperature in the heater bag 22. The heat loss may be further limited by the insulation 510 and the insulated cover 143. One possible consequence is that in the event of a temperature overshoot, the APD system 10 may delay a patient fill while the heater bag 22 slowly cools. A possible consequence of placing the heater elements 508 on the heater pan 142 is that the heater pan 142 may be at a substantially higher temperature than that of the heater bag 22 during the heating process. A feedback control on the heater bag 22 temperature as recorded by the button temperature sensor 506, may not turn the heater off soon enough to avoid the thermal energy at a higher temperature in the heater pan 142 from causing the heater bag 22 to overshoot the desired set point temperature 550. Alternatively controlling the heaters 508 to achieve a heater pan temperature 504 that would not cause the heater bag 22 temperature to overshoot may result in a slow heater system and thus delay therapy.

In order to minimize the time for the solution in the heater bag 22 to achieve the set point temperature 550 without overshoot, the heater control module 509 may implement a control loop that varies the electrical power of the heater elements 508 to achieve a desired fluid temperature in the heater bag 22, in part by controlling the equilibrium temperature of the heater pan 142, the heater bag 22 and the fluid within the heater bag 22. In one embodiment, a Proportional-Integral (PI) controller controls an equilibrium temperature 532 that is a function of the temperatures of the heater bag 22 and the heater pan 142 and the volume of solution in the heater bag 22. The equilibrium temperature may be understood to be the temperature that the solution in the heater bag 22 and the heater pan 142 would reach if the heater were turned off and the two components allowed to reach equilibrium. The equilibrium temperature may also be understood as the weighted average of the target temperature for the heater pan 142 and the measured temperature of the solution-filled heater bag 22, weighted by the thermal capacitance of each. The equilibrium temperature may also be calculated as the weighted average of the measured heater pan temperature and the solution temperature, in which the temperatures are weighted by their respective thermal capacitances. In an embodiment, the weighted average temperature of the heater pan 142 and fluid in the heater bag 22 may be calculated as the sum of the target heater pan temperature times the thermal capacitance of the heater pan plus the fluid temperature times the thermal capacitance of the fluid in the heater bag, where the sum is divided by the sum of the thermal capacitance of the heater pan plus the thermal capacitance of the fluid in the heater bag 22. The weighted averages of the heater pan 142 and fluid may be alternatively weighted by the mass of the heater pan 142 and fluid in the bag 22 or the volume of the heater pan 142 and fluid in the bag 22.

Figure 86:
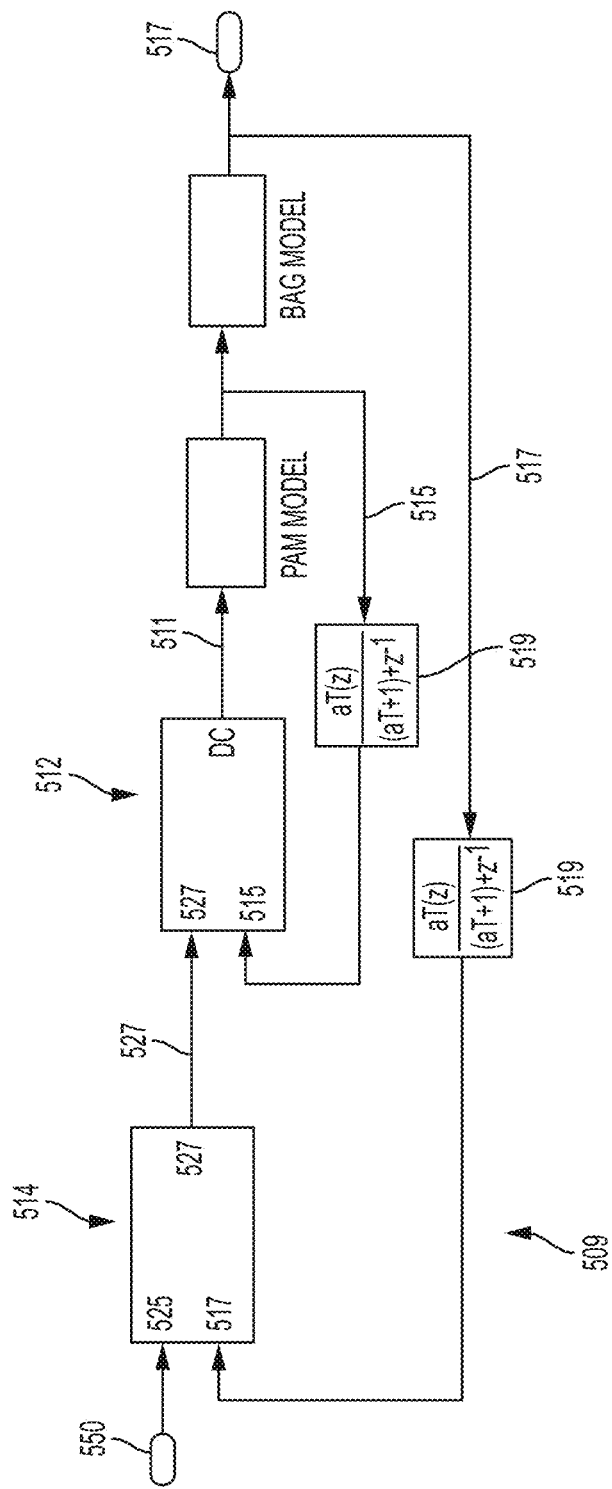
FIG. 86 shows a block diagram of a nested feedback loop to control the heater bag temperature.

The control of the equilibrium temperature may be implemented using a number of control schemes, such as, for example, single feedback loops using proportional, integral and or derivative controllers filters and nested loops. One embodiment of a control scheme using cascaded nested control loops is shown in FIG. 86. The outer loop controller 514 may control the heater bag 22 temperature as measured by the button temperature sensor 506 to the fluid set point temperature 550 by varying the heater pan set point temperature 527 supplied to the inner loop controller 512. Alternatively, the outer loop controller 514 may control the equilibrium temperature of the heater bag 22, fluid and heater pan 142 to the fluid set point temperature 550 by varying the heater pan set point temperature 527. The temperature of the heater bag 22 and fluid may be measured by the button temperature sensor 506 and the heater pan 142 temperature may be measured by one or more of the heater pan temperature sensors 504. The outer loop controller may include one or more of the following elements: proportional controller, integral controller, derivative controller, saturation limits, anti-windup logic and zero-order hold logic elements.

The inner loop controller 512 may control the heater pan 142 temperature to the heater pan set point temperature 527 by varying the thermal output of the heater elements 508. The temperature of the pan 142 may be measured by one or more of the heater pan temperature sensors 504. The inner loop controller may include one or more of the following elements: proportional controller, integral controller, derivative controller, saturation limits, anti-windup logic and zero-order hold logic elements.

An exemplary implementation of the heater control module 509 utilizes a PI regulator cascade-coupled with a Proportional-Integral-Derivative (PID) controller. In the FIG. 86 embodiment, a PID inner loop controller 512 may control the temperature of the heater pan 142, and a PI outer loop controller 514 may control the equilibrium temperature of the heater bag 22, the fluid in the heater bag 22 and the heater pan 142 as measured by the heater pan temperature sensors 504 and button temperature sensor 506. The loop controller 514 differs from a standard PI regulator in that any overshoot of the desired fluid set point 550 by the solution heater system 500 may be minimized by a logic controllable integrator as described below. In an embodiment, the heater pan temperature signal 515 and the button temperature sensor (heater bag 22) signal 517 are low-pass filtered through a pair of control filters 519 at a relatively high frame rate (e.g., a full 100 Hz frame rate), while the heater control module 509 may change the output of the heaters at a lower rate (e.g., rate of ½ Hz).

Figure 87:
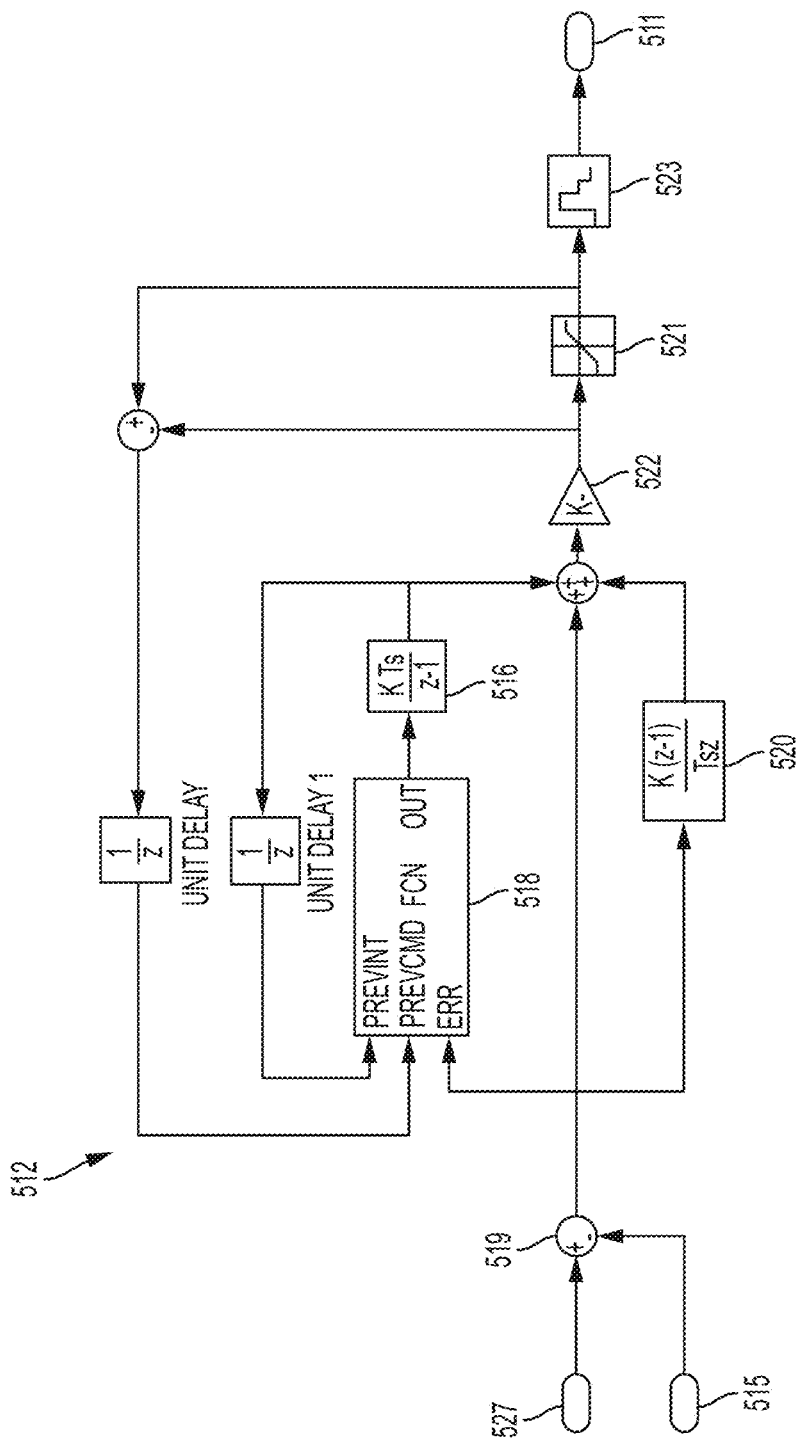
FIG. 87 shows a block diagram of an alternative nested feedback loop to control the heater bag temperature.

FIG. 87 shows a schematic diagram of one embodiment of the inner loop controller 512 (heater pan controller). In this embodiment, the inner loop controller 512 uses a standard PID regulator including but not limited to a differencing element 519 to produce a temperature error and a proportional gain element 522 to create an PWM signal 511. The inner loop controller 512 may further include a discrete-time integrator 516 to reduce the offset error. The inner loop controller 512 may also include an anti-windup logic element 518 to minimize overshoot due a temperature error existing for a long period of time when the output of the inner loop controller 512 is saturated. The inner loop controller 512 may further include a discrete derivative term 520 that acts on the heater pan actual temperature 515 to improve heater responsiveness. The inner loop controller 512 may further include a saturation limit element 521 that sets a maximum and/or minimum allowed heater command or PWM signal 511. The inner loop controller 512 may further include zero-order hold logic 523 to hold the PWM signal 511 constant between controller calculations that occur approximately every 2 seconds.

Figure 88:
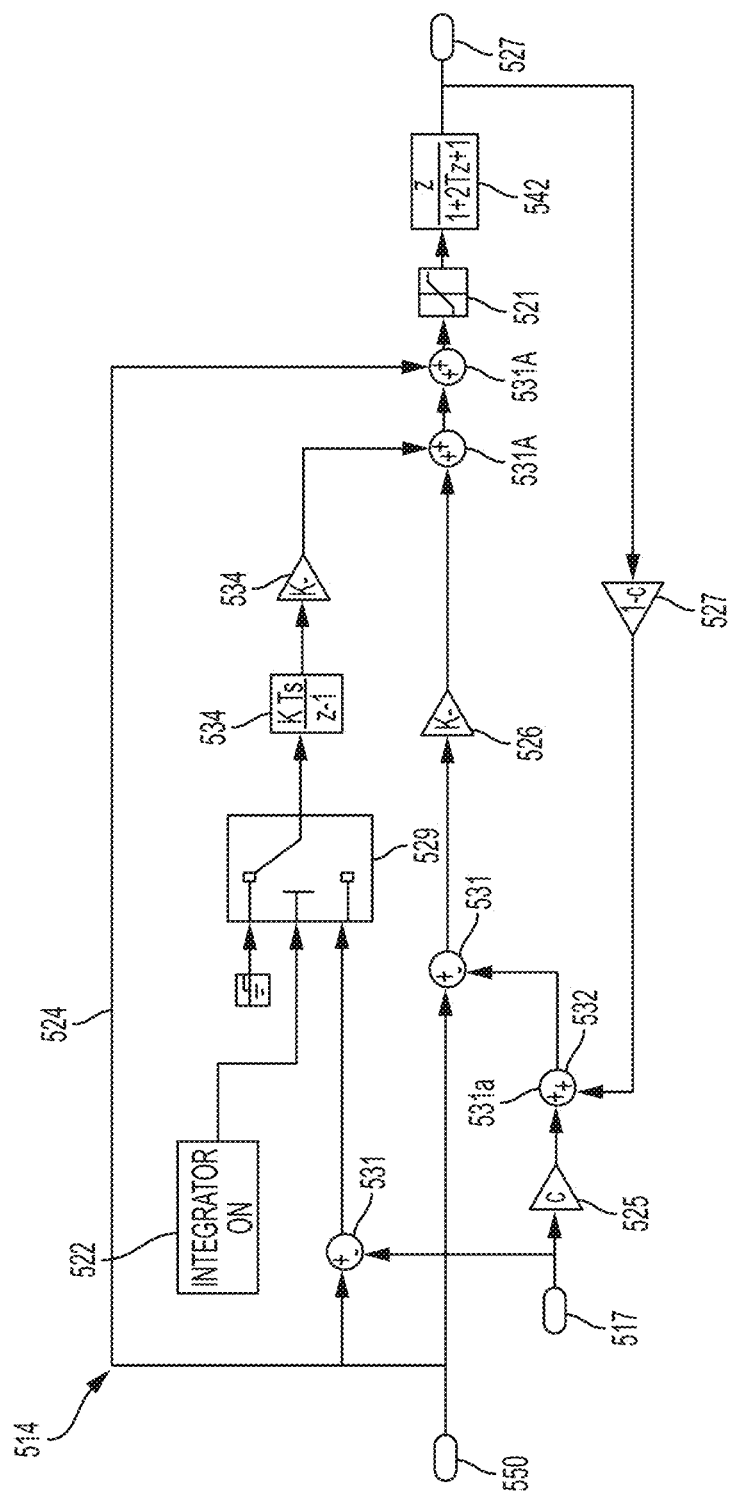
FIG. 88 shows a block diagram of another alternative nested feedback loop to control the heater bag temperature.

FIG. 88 shows a schematic diagram of the outer loop controller 514 (button temperature sensor controller). In this example, the outer loop controller 514 utilizes a modified PI-type regulator, which may include differencing elements 531, an integrator 534 and a proportional gain element 526. The outer loop controller 514 may further include an integrator switching logic 522 and corresponding switch 529, to allow the integrator to be switched on or off by logic in the heater control module 509. The outer loop controller 514 may further include a command feed forward 524 to improve the responsiveness of the outer loop controller 514. The outer loop controller 514 may further include a proportional feedback term 526 to act on a weighted combination of the button temperature sensor target temperature 517 and the heater pan target temperature 527. The resulting measurement is an equilibrium temperature 532 as described above. The outer loop controller 514 may further include a saturation limit element 521 and/or a low pass filter 542. The saturation limit element 521 in the outer loop sets a maximum allowed target pan temperature 527. The low pass filter 542 may be designed to filter out transient control signals at frequencies outside the bandwidth of the solution heater system 500.

The integral elements 534 in the outer loop controller 514 may be turned on by a switch 529 when some or all of the following conditions are present: the rate of change of the button temperature 517 is below a pre-determined threshold, the button temperature 517 is within a pre-determined number of degrees of the fluid set point temperature 550, or the bag 22 volume is greater than a pre-determined minimum and neither of the controllers 512, 514 are saturated. An equilibrium temperature feedback loop may control the transient behavior of the solution heater system 500, and may be dominant when the surrounding ambient temperature is in a normal to elevated range. The action of the integrator 516 may only be significant in colder environments, which may result in a substantial temperature difference between the button sensor actual temperature 517 and the heater pan actual temperature 515 at equilibrium. The feed-forward term 524 may pass the fluid set point temperature 550 through to the heater pan target temperature 527. This action will start the heater pan target temperature 527 at the fluid set point temperature 550, instead of zero, which thereby improves the transient response of the solution heater system 500.

The heater module 509 may also include a check that turns off the PWM signal 511 if the heater pan actual temperature 515 crosses a pre-determined threshold (this threshold may be set to be slightly higher than the maximum allowed heater pan target temperature 527). This check may not be triggered under normal operation, but may be triggered if the heater bag 22 is removed while the temperature of the heater pan 142 is at a pre-determined maximum value.

Figure 89:
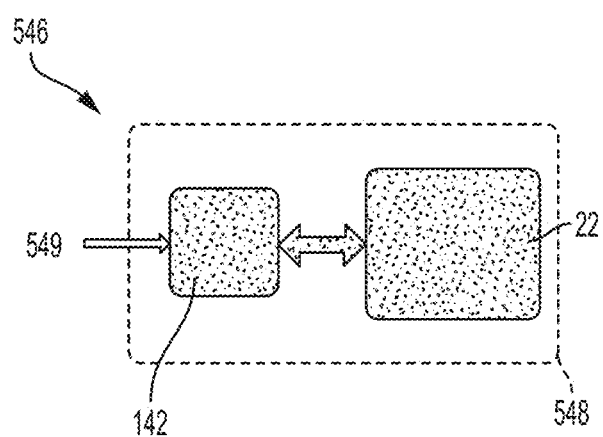
FIG. 89 shows a block diagram of the thermal model of the heater bag and heater tray.

The PI controller 514 may include a proportional term that acts on the equilibrium temperature 532. The equilibrium temperature is the heater bag 22 temperature measured by the button sensor 506 that would result if the heater 508 was turned off and the heater pan 142 and the solution-filled heater bag 22 were allowed to come to equilibrium. The equilibrium temperature can be better understood by referring to FIG. 89, which shows a schematic block diagram of the heater pan 142 and heater bag 22 in a control volume analysis 546. The control volume analysis 546 depicts a model environment in which the equilibrium temperature 532 may be determined. In this illustrative embodiment, the solution heater system 500 may be modeled in as control volume 548, which may comprise at least two thermal masses: the heater pan 142 and the heater bag 22. The boundary of the control volume 548 may be assumed to function as a perfect insulator, in which the only heat transfer is between the heater pan 142 and the heater bag 22. In this model, thermal energy 549 may be added to the system via the heater elements 508, but thermal energy may not be removed from the heater pan 142 and heater bag 22. In this model, as in the solution heater system 500, it is desirable to heat the heater pan 142 just enough that the heater bag 22 reaches its target temperature as the heater pan 142 and heater bag 22 come to equilibrium. Therefore, the equilibrium temperature 532 may be calculated as a function of the initial temperature of the heater bag 22 and the initial temperature of the heater pan 142:

$$E = M_p c_p T_p + V_b \rho_b C_b T_b = (M_p c_p + V_b \rho_b C_b) T_e$$

where $M_P$, $c_p$ are the mass and specific heat of the heater pan 142, $V_P$, $\rho_b$, $c_b$ are the volume, density and specific heat of the solution in the bag 22, $T_p$ and $T_b$ are the temperatures of the heater pan 515 and the button 517 respectively. Solving for the equilibrium temperature yields a linear combination of pan and button temperatures:

$$T_e = cT_b + (1-c)T_p$$

where $$c = \frac{V_b}{k + V_b} \text{ and } k = \frac{M_p C_p}{\rho_b C_b}$$

The constant c is an equilibrium constant, k is the thermal capacitance ratio of the heater pan 142 over the solution. The subscript b denotes the solution in the heater bag 22, while p denotes the heater pan 142.

In this model, allowing the heater module 509 to control the equilibrium temperature 532 during the initial transient may allow for rapid heating of the heater bag 22 while also reducing the heater pan actual temperature 515 sufficiently early to prevent thermal overshoot. The c parameter may be determined empirically. The heater module 509 may set c to a value larger than the measured value to underestimate the total energy required to reach the desired set point 550, further limiting the thermal overshoot of the solution heater system 500.

Figure 90:
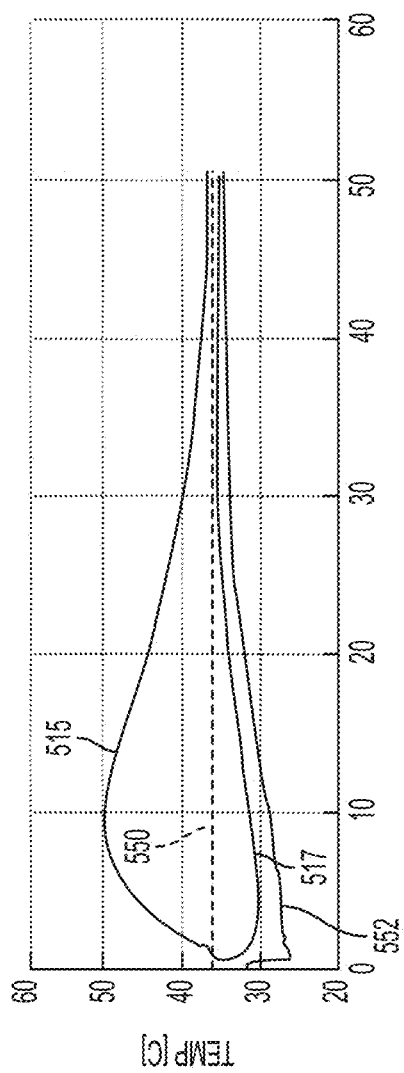
FIG. 90 shows a temperature response of the heater bag and heater tray for nominal conditions.

FIG. 90 shows graphically the performance of solution heater system 500 of the disclosed embodiment operating under normal conditions. The measured temperatures of the heater pan sensors 504, the button temperature sensor 506 and an additional temperature probe are plotted against time. The fluid temperature probe was part of the experimental setup up to verify the control scheme. The fluid probe temperature is shown as line 552. The button temperature is shown as line 517 and the heat pan 142 temperatures are shown as line 515. Line 550 is the target temperature for the button temperature sensor 506. At the start of this trial, the heater bag 22 is substantially empty, the heater is off and fluid is not moving, so that all the temperatures are at a nominal value. At a time T=1, the fluid at 25 C starts to flow into the heater bag 22 bringing down the probe and button temperatures 552, 517, while the heater turns on and increases the heater pan temperature 515. Under normal operation, proportional control of the equilibrium temperature 532 may be sufficient to heat the solution within the heater bag 22 to a temperature close to the desired fluid set point temperature 550. Therefore, in FIG. 90, the solution heater system 500 functions effectively, and the heater pan actual temperature 515, the button sensor actual temperature 517, and a probe temperature 552 all converge to the fluid set point temperature 550 within approximately 50 minutes.

Figure 91:
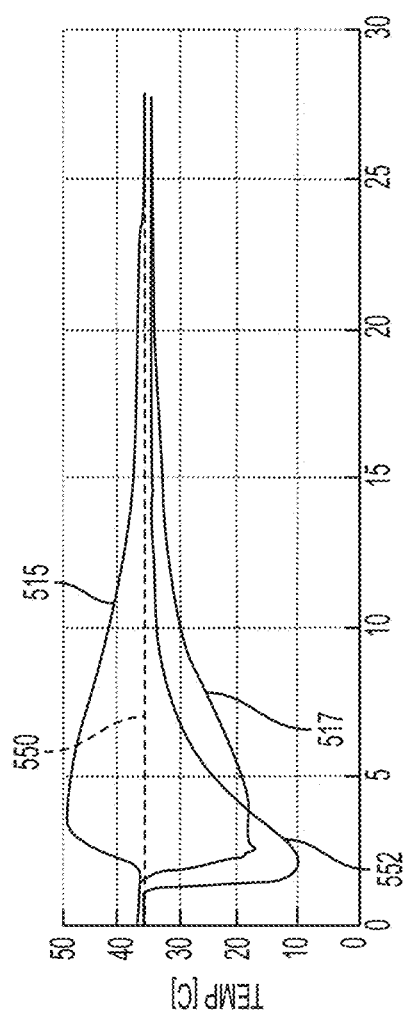
FIG. 91 shows a temperature response of the heater bag and heater tray for warm conditions.

FIG. 91 shows graphically the performance of the solution heater system 500 operated in a high temperature environment in which the ambient temperature is 35° C. As described above, the trial begins with the heater bag 22 being substantially empty. Once the fluid starts to flow and the heater turns on, the probe and button temperatures 552, 517 decrease and the heater pan temperature 515 increases. In a high temperature environment, the solution heater system 500 functions in a manner substantially similar to normal conditions. Thus, proportional control of the equilibrium temperature 532 may again be sufficient to heat the solution within the heater bag 22 to a temperature close to the desired fluid set point temperature 550. In FIG. 90, the solution heater system 500 functions effectively and within desired specifications, and the heater pan actual temperature 515, the button sensor actual temperature 517, and a probe temperature 552 all converge to the desired set point temperature 550 within approximately 30 minutes.

Figure 92:
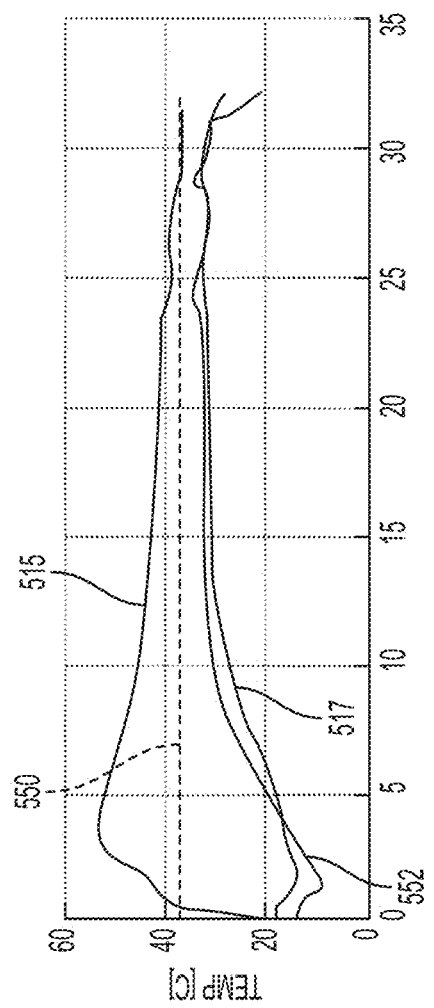
FIG. 92 shows a temperature response of the heater bag and heater tray for cold conditions.

FIG. 92 shows graphically the performance of the solution heater system 500 operated in a cold environment where the ambient temperature is 10 degrees C. and the source fluid is 5 degrees C. As described above, the trial begins with the heater bag 22 being substantially empty. Once the fluid starts to flow and the heater turns on, the probe and button temperatures 552, 517 decrease and the heater pan temperature 515 increases. In a cold environment, setting the desired fluid set point temperature 550 equal to the equilibrium temperature 532 may lead to a steady-state error in the temperature of the button sensor 506. The heat loss in cold environments may necessitate a large temperature difference between the heater pan 142 and the button sensor 506 during thermal equilibrium. Since the equilibrium temperature 532 is a weighted sum of the heater pan 142 and the button sensor 506, the temperature of the button sensor 506 may be below the fluid set point temperature 550 if the temperature of the heater pan 142 is above the desired fluid set point temperature 550 at equilibrium. This may occur even if the equilibrium temperature 532 is equal to the fluid set point temperature 550. To compensate for this steady-state-error an integral term may be added to outer PI controller 514 that acts on the temperature error of the button sensor 506. The integrator 538 may be turned on when one or more of the following conditions are met: a first derivative of the temperature of the button sensor 506 is low; the button sensor 506 is close to the fluid set point temperature 550, the volume of the heater bag 22 exceeds a minimum threshold; and neither inner PID loop 512 or outer PI controller 514 are saturated. In this illustrative embodiment, the switching of the integral term may minimize the effect of the integrator 538 during normal operation and may also minimize the overshoot caused by integration during temperature transients. Therefore, in FIG. 92, the solution heater system 500 functions effectively and within desired specifications, and the heater pan actual temperature 515, the button sensor actual temperature 517, and a probe temperature 552 all converge to the fluid set point temperature 550 within approximately 30 minutes.

In summary, the disclosed temperature controller can achieve good thermal control of a two component system, in which the mass of the first component varies over time, and in which the second component includes a heater or cooler, and both components are in an insulated volume. This thermal control can be achieved by controlling the equilibrium temperature. The temperature controller determines the temperature of both components as well as the mass of the variable component. The temperature controller varies the heating or cooling of the second component to bring the equilibrium temperature to the desired set point temperature. The equilibrium temperature is the thermal capacitance weighted average temperature of the two components. The controller may use a proportional feedback loop to control the equilibrium temperature.

The temperature controller may also include an integral term that responds to the difference between the set point temperature and the temperature of the first component. The integral term optionally may be turned on when some or all of the following conditions are met:

the rate of temperature change of the first component is low;
the temperature of the first part is near the set point temperature;
the volume of the first part exceeds some minimum level;
the control output signal is not saturated.

The temperature controller may also include a feedforward term that adds the set point temperature to the output of the proportional and integral terms.

Further, the temperature controller may be the outer loop controller of a cascade temperature controller in which the outer loop controller includes at least a proportional control term on the equilibrium temperature and outputs a set point temperature for the inner controller. The inner controller controls the temperature of the first component with the heater or cooler elements to the set point temperature produced by the outer controller.

Universal Power Supply

The APD system 10 may include a universal power supply that converts line voltage to one or more levels of DC voltage for some or all of the electro-mechanical elements and electronics in the cycler 14, and provides AC power to the electric heater for the heater pan 142. The electro-mechanical elements in the cycler 14 may include pneumatic valves, electric motors, and pneumatic pumps. The electronics in the cycler 14 may include the control system 16, display 324, and sensors. AC power is supplied to a heater controller to control the temperature of the solution in the heater bag 22 on the heater tray 142 to a desired set point prior to delivering the solution to the user/patient. The universal power supply changes the configuration of two (or more) heater elements 508 to accommodate two ranges of AC line voltages: e.g., a first range of 110±10 volts rms; and a second range of 220±20 volts rms. This arrangement is intended to accommodate using the APD system 10 in a number of different countries. During the start of a therapy session, the APD cycler 14 fills the heater bag 22 with solution from the connected solution containers 20, via a heater bag line 26. In an alternative embodiment, a pre-filled bag of solution may be placed on a heater pan 142 at the start of a therapy.

PWM Heater Circuit

The heater controller in the APD cycler modulates the electrical power delivered to the heater elements 508 attached to the heater pan 142. The APD cycler may be used in various locations around the world and may be plugged into AC mains that supply power from 100 to 230 volts rms. The heater controller and circuits may adapt to the variety of AC voltages while continuing to supply sufficient heater power and not blowing fuses or damaging heater elements in a number of ways.

Figure 93:
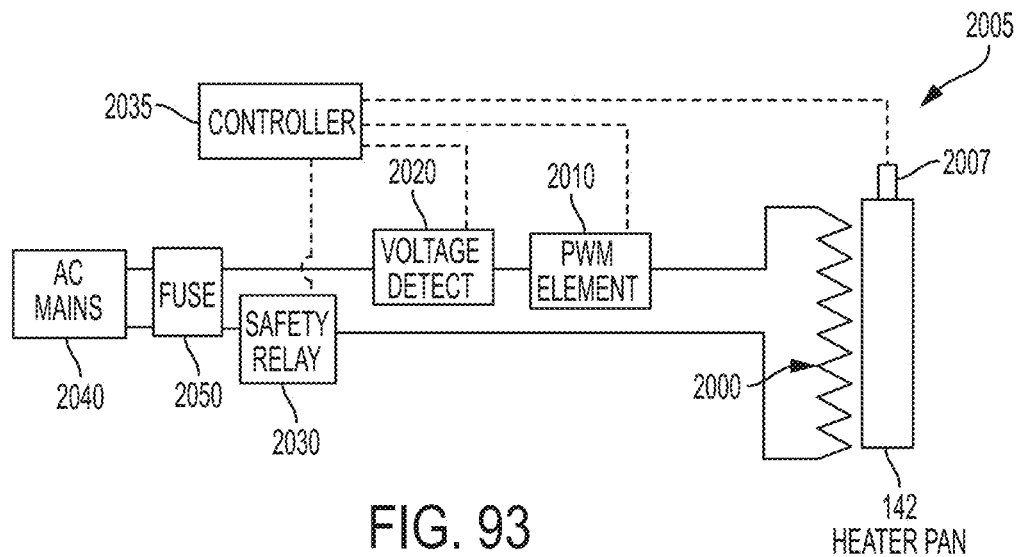
FIG. 93 is a schematic block diagram of one embodiment of a heater control system.

One embodiment of a heater circuit is presented in FIG. 93, where a pulse width modulator (PWM) based circuit 2005 controls the temperature of the heater pan 142 with a pulse-width-modulated (PWM) element 2010 connected between one lead of the AC mains 2040 and the heater element 2000. The controller 2035 is operably connected to the relay 2030 and the PWM element 2010. The controller 2035 monitors the operation of the heater by interrogating the voltage detect 2020 and temperature sensor 2007. The controller 2035 may modulate the amount of power delivered to the heater 2000 via a signal to the PWM element 2010. The PWM or pulse-width-modulated element is closed for some fraction of a fixed period between 0 and 100%. When the PWM element 2010 is closed 0% of the time, no electrical energy flows to the heater 2000. The heater 2000 is continuously connected to the AC mains 2040 when the PWM element is closed 100%. The controller 2035 can modulate the amount of power dissipated by the heater 2000 by setting the PWM element 2010 to a range of values between 0 and 100%, inclusive.

The PWM elements 2010 switch large current flows on and off multiple times a second. PWM elements 2010 are typically some kind of solid state relay (SSR). SSRs for AC voltage typically include a triggering circuit that controls the power switch. The triggering circuit may be, for example, a reed relay, a transformer or an optical coupler. The power switch may be a silicon controlled rectifier (SCR) or a TRIAC. The SCR or TRIAC are also referred to as thyristors. One example of a SSR is the MCX240D5® by Crydom Inc.

In one example, the controller 2035 may modulate the PWM element value in order to control the temperature of the heater pan 142 as measured by temperature sensor 2007. In another example, the controller 2035 may modulate the PWM element value to control the temperature of the fluid in the heater bag 22. In another example the controller 2935 may control the PWM element 2010 to provide a fixed schedule of heater power. The controller 2035 may command a safety relay 2030 that opens the heater circuit and stops the flow of electrical power to the heater 2000. The safety relay 2030 may be controlled by a separate controller (not shown) in order to provide a safety circuit independent of the controller 2035.

The PWM based circuit 2005 may include a voltage detect element 2020 that provides a signal to the controller 2035 indicative of the voltage on the AC mains 2040. In one example, the voltage detect element 2020 may measure the AC potential across the AC mains 2040. In another example the voltage detect element 2020 may measure the current flow through the heater 2000. The controller 2035 may calculate the voltage across the AC mains from a known resistance of the heater element 2000, the PWM element 2010 signal and the measured current.

The PWM based circuit 2005 may vary the maximum allowed duty cycle of PWM element 2010 to accommodate different AC mains voltage. The heater element 2000 may be designed to provide the maximum required power with the lowest possible AC voltage. The controller may vary the duty cycle of the PWM element 2010 to provide a constant maximum heater power for a range of voltages at the AC mains. For example, the voltage supplied to the heater 2000 from a 110 volt AC line may be supplied at a 100% duty cycle, and the same amount of electrical power may be delivered to the heater 2000 from a 220 volt AC line if the PWM element 2010 is set to 25%. The duty cycle of the PWM element 2010 may be further reduced below the maximum value to control the temperature of the heater pan 142.

The temperature of the heater element 2000 and the heater pan 142 may be controlled by the average heater power over a time constant that is a function of the thermal mass of the element and heater pan 142. The average heater power may be calculated from the heater resistance, which is relatively constant, and the rms voltage across the heater element 2000. In a practical sized heater, the PWM frequency is much faster than the time constant of the heater system, so the effective voltage across the heater element is simply the PWM duty cycle multiplied by the rms voltage.

One method to control the heater pan temperature of the circuit in FIG. 93 may direct the controller 2035 to set a maximum PWM duty cycle based on the measured voltage at 2020. The maximum duty cycle may be calculated from the desired maximum heater power, known resistance of the heater element 2000 and the measured voltage. One possible example of the calculation is:

$$PWM_{MAX} = (P_{MAX} * R_{HEATER})^{0.5} / V_{rms}$$

where $PWM_{MAX}$ is the maximum allowed PWM duty cycle, $P_{MAX}$ is the maximum heater power, $R_{HEATER}$ is the nominal resistance of the heater element 2000, and $V_{rms}$ is the supplied voltage as measured by the Voltage Detect 2020. Another example of the calculation is:

$$PWM_{MAX} = P_{MAX} / (I^2 * R_{HEATER})$$

where I is the current flow through heater when the voltage is applied. The controller 2035, after setting the maximum PWM duty cycle, then varies the PWM duty cycle of the PWM element 2010 to control the temperature of the heater pan 142 as measured by a temperature sensor 2007. The controller may control the PWM element to achieve a desired temperature in a number of ways, including, for example, a PID feedback loop, or a PI feedback system.

In an alternative method and configuration, the PWM circuit 2005 does not include the voltage detect 2020. In this alternative method the controller 2035 varies the PWM duty cycle of the PWM element 2010 to achieve the desired heater pan temperature as measured by temperature sensor 2007. The controller 2035 begins the heating cycle at a minimum PWM duty cycle and increases the PWM duty cycle until the temperature sensor reports the desired temperature to the controller 2035. The rate of increase of the PWM rate may be limited or controlled to avoid excessive currents that could trip and blow the fuses 2050. The controller 2035 may alternatively use small gains in a feedback calculation to limit rate of PWM duty cycle increase. Alternatively the controller may use a feed forward control to limit the rate of PWM duty cycle increase.

Dual-Voltage Heater Circuit

Figure 94:
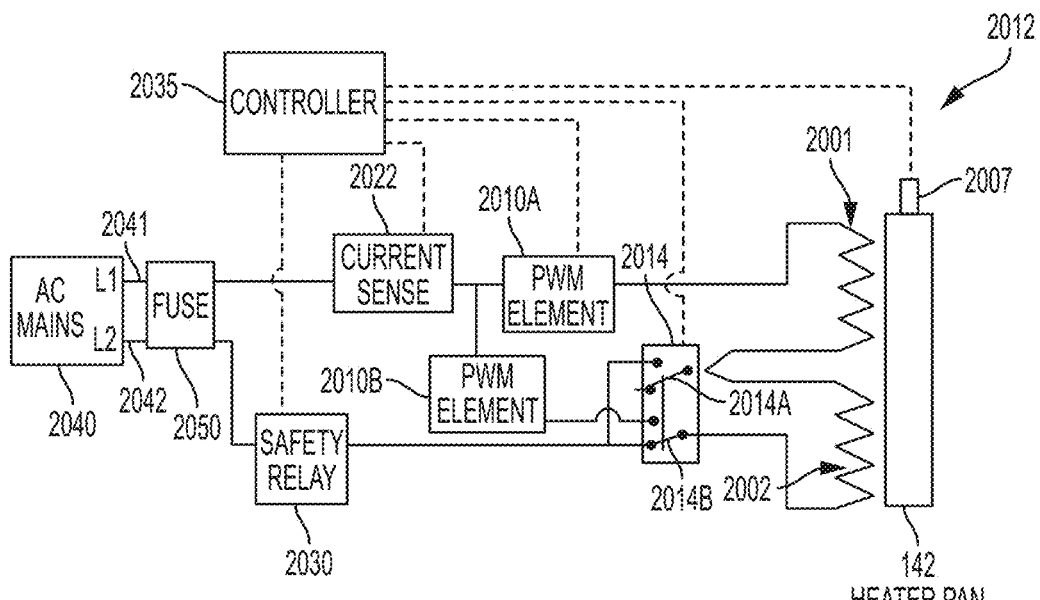
FIG. 94 is a schematic block diagram illustrating a heater circuit configured with a pair of heating elements.

An example of a dual-voltage heater circuit 2012 that changes the resistance of the heater is shown as a schematic block diagram in FIG. 94. The block diagram in FIG. 94 presents one example of a dual-voltage heater circuit 2012 to provide approximately constant heater power for the two standard AC voltages of 110 and 220 volts rms. Dual-voltage heater circuit 2012 limits the maximum current flow by reconfiguring the heater and thus is less sensitive to software errors setting the duty cycle of the PWM element as in circuit 2005. Circuit 2012 lowers the maximum current flows through the PWM element 2010 which allows for smaller and less expensive SSRs. The selection of the heater configuration in circuit 2012 is separated from the heater modulation to improve control and reliability. The PWM elements 2010A, 2010B that modulate the heater power are typically SSR, which typically fail closed, thus providing maximum power. The heater select relay 2014 may be an electromechanical relay, which while less than ideal for high cycle applications, may typically be preferred for safety critical circuits, due in part to the tendency of electromechanical relays to fail open. The selection of the heater configuration by the processor allows more control of heater configuration.

In the event of the AC mains voltage fluctuating, perhaps due to a brown-out, the controller preferably holds the heater configuration constant. In contrast, a circuit that automatically changes the heater configuration based on the instantaneous voltage could fluctuate between heater configurations. This may result in high current flows if the circuit does not respond fast enough to line voltage that returns to its original level from a temporarily lower level. This is more likely to be a problem when only a hardware-enabled circuit is used to respond to voltage fluctuations. A more efficient and reliable solution may be obtained if a programmable controller is used to either analyze the likely cause of the input voltage fluctuation, or to respond only to the measured current flow through the heater averaged over a period of time. In an embodiment, the processor receives input from the user or patient in selecting the heater configuration (parallel or series), and the dual-voltage heater circuit 2012 does not automatically switch between configurations in response to fluctuating line voltage. In another embodiment, the processor measures the current flow in the series configuration (i.e. the higher resistance configuration) at full power, selects a heater configuration appropriate to the AC mains voltage at the start of therapy, and does not change configuration for the duration of therapy.

The dual-voltage heater circuit 2012 may comprise two heater elements 2001, 2002 that can be connected in parallel or in series with one another to provide the same heater power for two different voltages at the AC mains 2040. Each heater element 2001, 2002 may comprise one or more heater sub-elements. The electrical resistance of heater elements 2001, 2002 is preferably approximately equal. The controller 2035 may receive a signal from the current sense 2022 element and control the heater select relay 2014 to connect the heater elements 2001, 2002 in either series or parallel. The controller 2035 may change the electrical arrangement of the two heater elements to limit the current flow resulting from different AC mains voltages. One example of a current sense 2022 element is a current sense transformer AC-1005 made by Acme Electric.

The power in the heater elements 2001, 2002 may be further modulated by the PWM elements 2010A, 2010B controlled by the controller 2035 to achieve a desired temperature as measured by temperature sensor 2007, or to achieve other control goals as described above. The PWM elements 2010A, 2010B may be a solid state relays such as MCX240D5® by Crydom Inc. The safety relay 2030 may be configured to disconnect the heater elements 2001, 2002 from the AC mains 2040. The safety relay 2030 may be controlled by the controller 2035 or another processor or safety circuit (not shown).

The safety relay 2030 and heater select relay 2014 may be solid state or electro-mechanical relays. In a preferred embodiment, the safety relay 2030 and/or heater select relay 2014 are electro-mechanical relays. One example of an electro-mechanical relay is a G2AL-24-DC12 relay made by OMRON ELECTRONIC COMPONENTS and other manufacturers. Electro-mechanical relays are often preferred for safety critical circuits as they are considered to be more robust and more reliable than solid state relays, and have a tendency to fail open. They may also be less susceptible to various failures in the controller software.

In one example, the heater select relay 2014 comprises a double-pole double-throw relay, in which the outputs connect to the heater elements 2001, 2002. The heater select relay 2014, in the non-energized state, connects the heater elements 2001, 2002 in series such that the current flows through one element and then the other. The series configuration may be achieved, in one example circuit, by the following; connect the first end of the heater element 2001 to L1 circuit 2041 via PWM element 2010A; connect the joined ends of heater elements 2001, 2002 to an open circuit via the first pole 2014A; connect second end of heater element 2002 to the L2 circuit 2042 via the second pole 2014B. In an energized state, the heater select relay 2014 connects the heater elements 2001, 2002 in parallel such that approximately half the current flows through each PWM and heater element 2001, 2002. The parallel configuration may be achieved in the same example circuit by the following: connect the first end of the heater element 2001 to L1 circuit 2041 via PWM element 2010A; connect the second end of heater element 2002 to the L1 circuit 2041 via PWM element 2010B; connect the joined ends of heater elements 2001, 2002 to L2 circuit 2042 via the first pole 2014A. The preferred circuit connects the heater elements 2001, 2002 in series in the unpowered condition as it is a safer configuration because the resulting higher resistance will limit current flows and avoid overloading the fuses 2050, or overheating the heating elements 2001, 2002 if connected to a higher voltage AC main.

Figure 95:
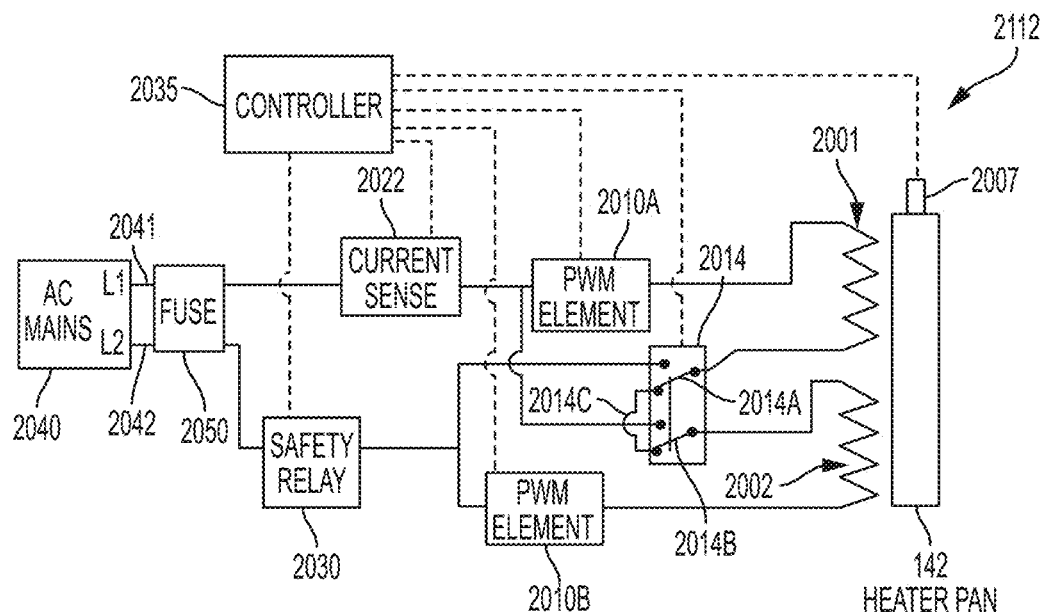
FIG. 95 is a schematic block diagram illustrating a heater circuit configured with a pair of heating elements with reduced potential for current leakage.

Another example of a heater circuit 2112 that changes the effective resistance of the heater by changing the heater configuration is shown in FIG. 95 as a schematic block diagram. The heater circuit 2112 is similar to heater circuit 2012 (shown in FIG. 94) except that heater circuit 2112 provides better leakage current protection in the event that the L1 and L2 power circuits are reversed at the wall socket. The reversal of the L1 and L2 power circuits is possible if the power was incorrectly wired in the building that supplies power to the heater circuit. Wiring in a residential building may not be as reliable as a hospital, where all the electrical system is installed and maintained by qualified personnel.

The electrical components and connections between the PWM elements 2010A, 2010B, the nominal L1 circuit 2041, heater elements 2001, 2002, heater select relay 2014 and the nominal L2 circuit 2042 in heater circuit 2112 are arranged to minimize leakage current regardless of wall socket polarity. In the non-energized state as shown in FIG. 95, the heater select relay 2014 connects the heater elements 2001, 2002 in series with the PWM element 2010A. One possible circuit that connects the heater elements 2001, 2002 in series includes: the first end of heater element 2001 connected to the L1 circuit 2041 via PWM element 2010A; the second end of heater element 2001 connected to the first end of heater element 2002 via the first pole 2014A, a L1 2014C and the second pole 2014B; and the second end of heater element 2002 connected to the L2 circuit 2042 via PWM element 2010B. In the energized state, the heater elements 2001, 2002 and PWM elements 2010A, 2010B are connected in parallel. In an energized state, the heater select relay 2014 connects the heater elements in circuit 2122 in parallel such that approximately half the current flows through each PWM and heater element 2001, 2002. One possible circuit to connect the two heater and PWM elements in parallel includes: the first end of heater element 2001 connected to the L1 circuit 2041 via PWM element 2010A; the second end of heater element 2001 connected via the first pole 2014A to the L2 circuit; the first end of heater element 2002 is connected to the L1 circuit 2041 via the second pole 2014B; the second end of heater element 2002 is connected to the L2 circuit 2042 via the PWM element 2010B. The safety relay 2030 is located on the L2 circuit 2042 and creates a fail-safe condition of no current flow by opening if a fault occurs. The control of the safety relay is described below. The controller 2035 controls the heater configuration to limit the current flow as measured by the current sense 2022 to levels below the current rating for the fuses 2050, heater elements 20001, 2002, the PWM elements 2010A, 2010B and limits total heater power. The controller 2035 varies the duty cycle of the PWM elements 2010A, 2010B to control the heater pan 142 temperature as measured by the sensor 2007.

Dual-Voltage Heater Circuit Implementation

Figure 96:
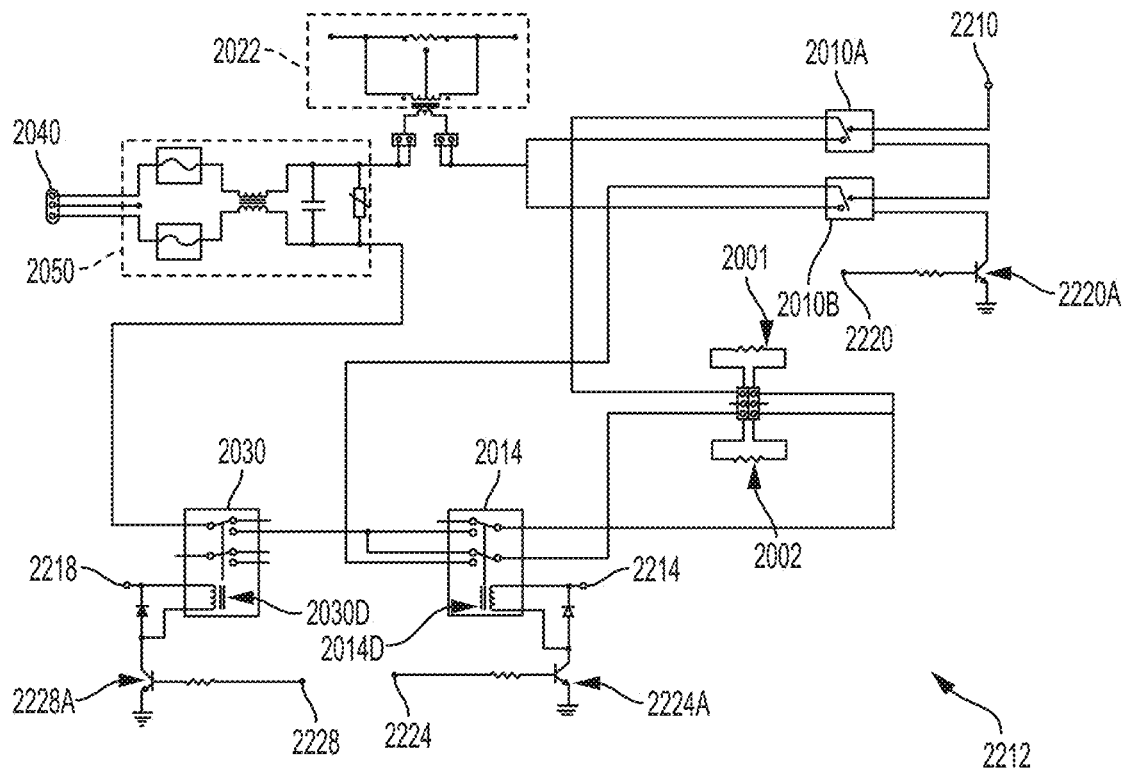
FIG. 96 is a circuit diagram of a heater circuit configured with a pair of heating elements.

A circuit diagram 2212 of one embodiment of the present disclosure is shown in FIG. 96, which is equivalent to heater circuit 2012 in FIG. 94. In the circuit 2212, the heater elements 2001, 2002 are connected in series by the heater select relay 2014 when the relay coil 2014D is not energized. The controller (not shown) connects the heater elements 2001, 2002 and PWM elements 2010A, 2010B in parallel by supplying a signal at node 2224, which closes transistor switch 2224A, and energizing the relay coil using the Vs DC power 2214, The controller modulates the heater power by varying the duty cycle of the PWM elements 2010A, 2010B through a signal at node 2220 and powered with Vsupply 2210. The current flow is measured with the current sense 2022. The safety relay 2030 is normally open. The safety relay 2030 may be controlled by an FPGA board that is separate from the controller. The FPGA board monitors the operation of the APD cycler, including the heater pan temperature and the current sense and several other parameters. The FPGA board may open the relay by removing the signal at node 2228. The safety relay coil 2030D is powered by the Vsafety 2218.

In one example, the voltage supplying Vsupply 2210, Vs 2214, Vsafety 2218 may be the same voltage source. In another example each voltage source may be controllable to provide additional operation control of the heater circuit for added safety. In one example the Vsafety 2218 may be controlled by multiple processors in the APD cycler 14. If any of the processors detects an error and fails, then the Vsafety circuit is opened, the Safety Relay 2030 is opened and heater power is turned off.

Dual-Voltage Heater Circuit Operation

In a typical dual-voltage scenario, a user may wish to use the peritoneal dialysis cycler in either a 110 volt environment or a 220 volt environment (i.e. in most cases a 100% difference in voltage to which the device may be exposed). More generally, however, the dual-voltage heater circuit can be configured for any scenario in which a first voltage and a second higher voltage may be used. The circuit switching system would only be limited by the ability of the controller to discriminate between the current flows resulting from a first voltage or a second voltage being applied to the heater. The elements of the system can include a heater comprising a first heater element connected to a second heater element by a heater select relay, the heater select relay being configured to connect the first heater element either in series or in parallel with the second heater element. A current sense element is configured to measure current flow through the heater. A controller can then be configured to receive the current flow information from the current sense element, and command the heater select relay to switch to either a parallel or series configuration to more closely approximate a current flow that has been pre-determined to provide an optimal degree of heater function and responsiveness. In most cases, it may be safer to have the cycler power up for initial use in a default mode with the heater select relay in a series configuration.

The heater circuit 2212 is operated to provide adequate heater power without allowing damaging currents to flow through the heater elements 2001, 2002 or the fuses 2050. The heater circuit 2212 may be configured before the therapies are run on the APD cycler 14 and not changed during operation regardless of the voltage changes in the AC mains. The control system 16 (in FIG. 78) starts up the heater control circuit 2212 with the heater select relay 2014 un-energized, so the heater elements are connected in series to minimize the current. As one part of the startup processes, software in the automation computer 300 may run a current flow test of the heaters by commanding the PWM elements 2010A, 2010B to 100% duty cycle and the resulting test current is measured by the current sense 2022 and communicated to the automation computer 300. The duty cycle of the PWM elements 2010 may be reset to zero after current flow test.

In one example method, the automation computer 300 evaluates the measured test current against a predetermined value. If the measured test current is above a given value, the automation computer 300 will proceed with the ADP cycler startup procedure. If the measured test current value is below that same given value, then the automation computer 300 will energize the heater select relay to reconfigure the heater elements 2001, 2002 in parallel. The current flow test is repeated and if the new measured test current is above the predetermined value the automation computer 300 will proceed with the ADP cycler startup procedure. If the measure test current from the current flow test with parallel heater elements, is below above the predetermined value, the automation computer 300 will signal an error to the user interface computer 302.

Alternatively, the automation computer 300 may calculate a test voltage based on the measured test current and heater element configuration. If the test voltage is in the range of 180 to 250 volts rms, then the automation computer 300 will proceed with the ADP cycler startup procedure. If the test voltage is in the range of 90 to 130 V rms, then the automation computer 300 will energize the heater select relay to reconfigure the heater elements 2001, 2002 in parallel, repeat the current flow test, and recalculate the test voltage. If the test voltage is in the range of 90 to 130 V rms, the automation computer 300 will proceed with the ADP cycler startup procedure, if not automation computer 300 will signal an error to the user interface computer 302.

In another example method, the automation computer 300 compares the measured test current with the heater elements configured in series to a series-low-range and series-high-range of current values. The series-low-range is consistent with a low AC voltage flowing through the heater elements arranged in series. The series-high-range is consistent with a high AC voltage flowing through the heater elements arranged in series. In an exemplary embodiment, the low AC voltage includes rms values from 100 to 130 volts, while the high AC voltage includes rms values from 200 to 250 volts.

If the measured test current is outside of low-range and the high-range, then the automation computer 300 may determine that the heater circuit is broken and signal an error to the user interface computer 302. If the measured test current is within the high-range, the heater configuration is left unchanged and the startup of the APD cycler 14 may continue. If the measured test current is within the low-range and the heater elements are arranged in series, then the automation computer 300 may reconfigure the heater elements 2001, 2002 to a parallel arrangement by energizing the heater select relay 2014 through a signal at node 2224. The automation computer 300 may control the heater select relay 2014 via a command sent to the hardware interface 310 that in turn provides the signal to actuate the heater select relay 2014.

The automation computer 300 may repeat the current flow test after reconfiguring the heater elements into a parallel arrangement by again commanding the PWM elements 2010A, 2010B to 100% duty cycle and measuring the current flow with the current sense 2022. The measured test current may be evaluated against the parallel-low-range of current values. If the measured test current is within the parallel-low-range values proceed with the ADP cycler startup procedure. If the newly measured test current is outside the parallel-low-range values, then automation computer 300 will signal an error to the user interface computer 302.

The FPGA controller implemented in the hardware interface 310 may be programmed to command the safety relay 2030 to open through a signal at node 2228 while the heater select relay 2014 is switched. The safety relay 2030 may be opened each time the heater select relay 2014 is opened or closed to prevent a short circuit from one pole to the other within the heater select relay 2014.

Dual-Voltage Heater Circuit Operation with User Input

Figure 97:
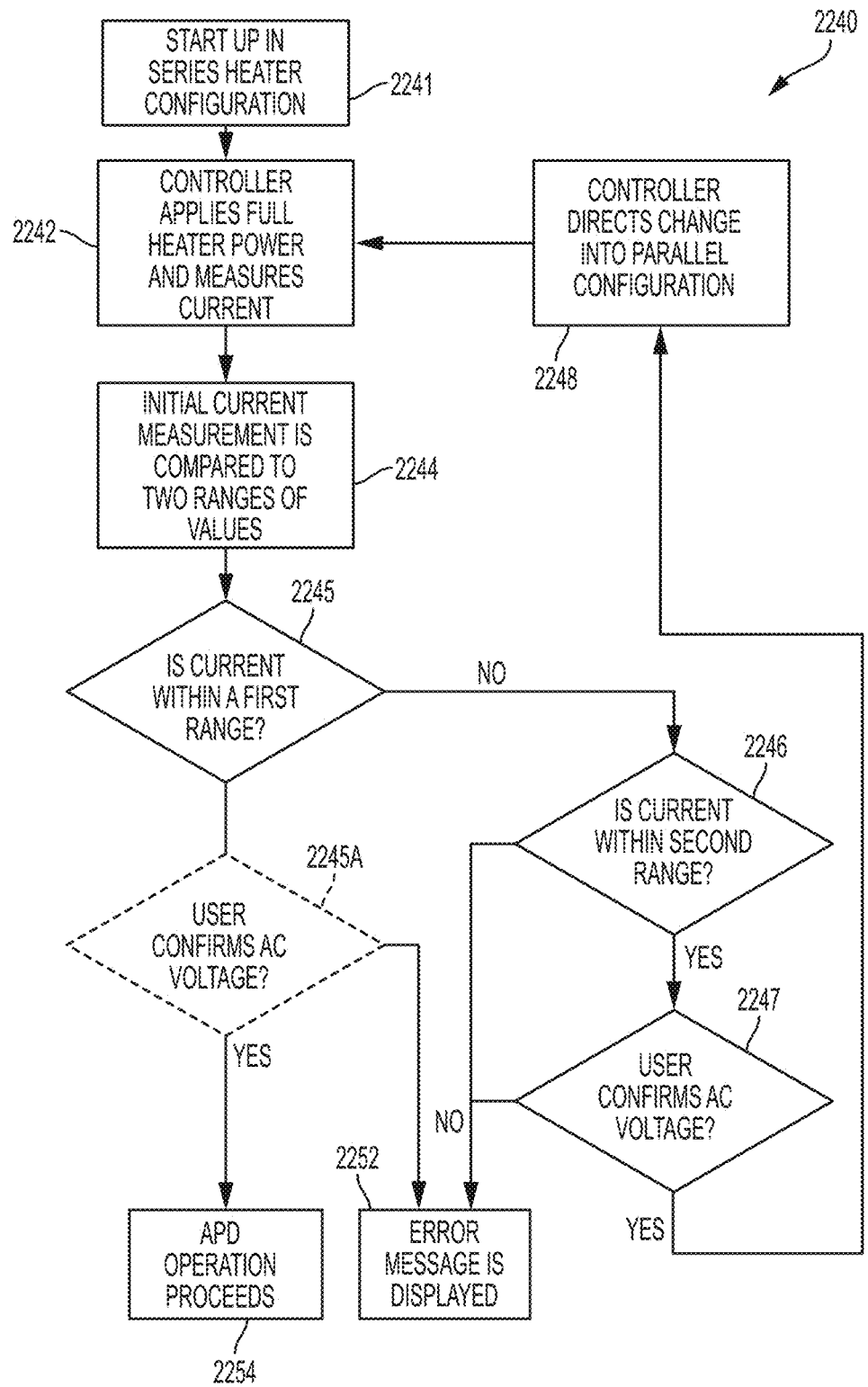
FIG. 97 shows a flow chart outlining a method to select the heater configuration in an APD cycler.

In an alternative embodiment, the automation computer 300 may require user intervention before reconfiguring the heater elements 2001, 2002. Requiring user input provides a valuable safety feature of one embodiment of the present disclosure. FIG. 97 shows a logic flow chart illustrating a method 2240 to include the user in configuring the heater elements appropriately for the available AC voltage. In step 2241, the control system 16 (in FIG. 78) starts up the heater control circuit 2212 (FIG. 96) with the heater select relay 2014 un-energized, so the heater elements are connected in series to minimize the current. In step 2242, the automation computer 300 commands the PWM elements 2010A, 2010B to 100% duty cycle and the current is measured by the current sense 2022 and the measure test current is communicated to the processor. The duty cycle of the PWM elements 2010 may be reset to zero after the test current is measured. In step 2244, the automation computer 300 compares the measured test current to a first range. In step 2245, if the measured test current is within the first range, then the heater configuration is correct and the APD operation proceeds in step 2254. In an alternative embodiment, method 2240 includes step 2245A where the user interface computer 302 ask the user to confirm the AC mains voltage that the automation computer 300 determined from measured test current and the heater configuration before proceeding from step 2245. If the user does not confirm the AC voltage level, method 2240 will proceed to step 2252 and displays an error.

In step 2246, if the measured current is outside the second range, then method 2240 displays an error in step 2252, otherwise the method 2240 proceeds to step 2247. In step 2247, if the user confirms low AC voltage then the heater configuration will be changed in step 2248, otherwise the method 2240 displays an error in step 2252. In step 2248, the automation computer 300 reconfigures the heater elements 2001, 2002 to a parallel arrangement by energizing the heater select relay 2014 through a signal at node 2224. After reconfiguring the heater elements in step 2248, the method 2240 retests the heater in step 2242 and continues through the logic flow chart of method 2240.

Figure 98:
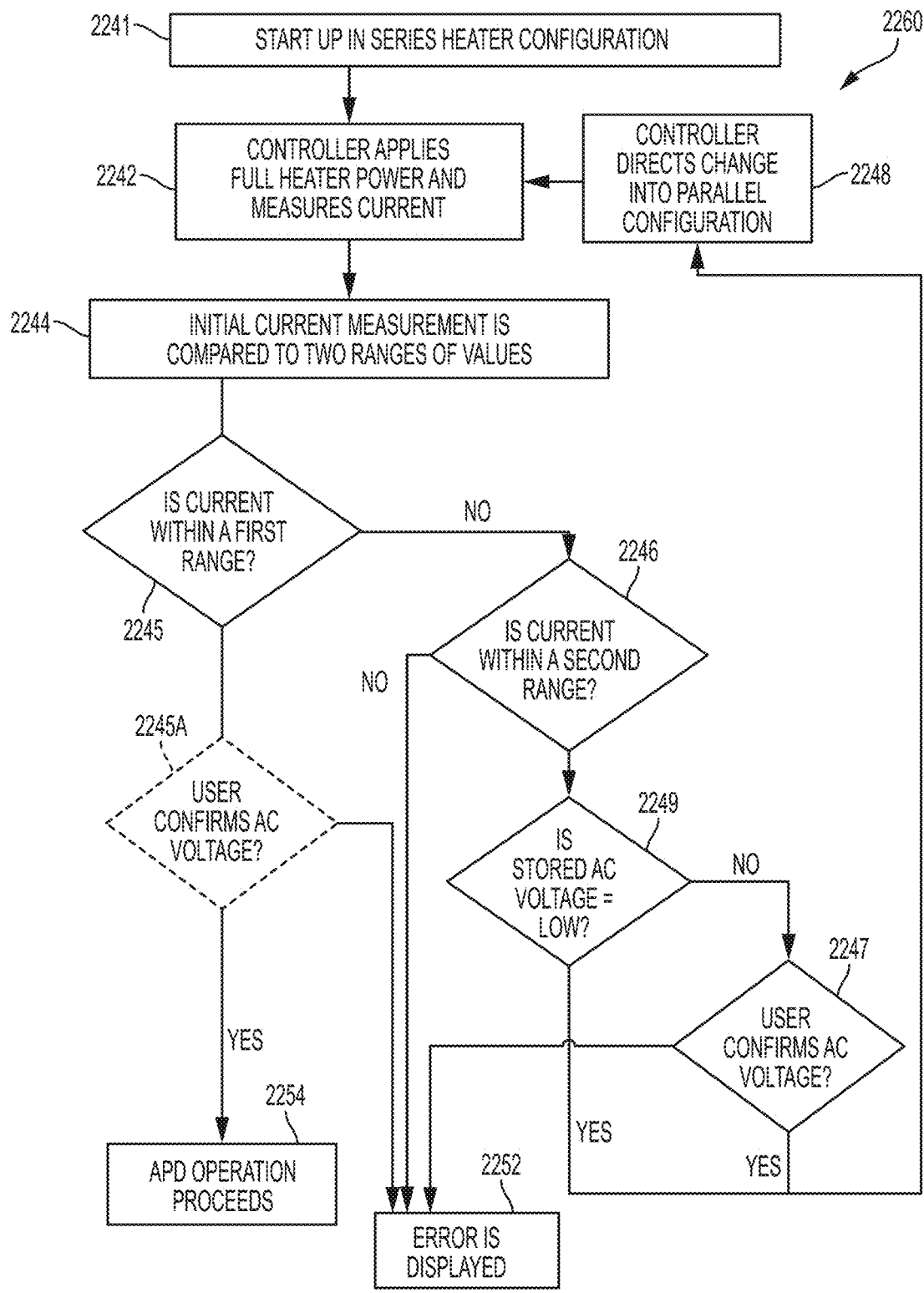
FIG. 98 shows a flow chart outlining a method to select the heater configuration in an APD cycler where a stored value of the AC mains voltage is queried during selection of the heater configuration.

An alternative embodiment, a user or patient may store the AC voltage as high or low in the memory of the control system 16 so that the automation computer 300 need not query the user or patient at each treatment to confirm the AC voltage. FIG. 98 shows a logic flow chart illustrating a method 2260 where the AC voltage value is stored in the memory of the control system 16. The steps 2241 through 2246 are the same as method 2240 described above. In step 2249, the memory is queried for the stored AC voltage value. If the stored AC voltage value is low, then the method 2260 proceeds to step 2248 and reconfigures the heater elements into a parallel arrangement. If the stored AC voltage is high nor zero, then the user interface computer 302 may query the user to confirm a low AC mains voltage. If a user confirms the low AC voltage, then the method 2260 proceeds to step 2248 and reconfigures the heater elements into a parallel arrangement. Step 2248 may also include the setting of the stored AC voltage to low. After reconfiguring the heater elements in step 2248, the method 2260 retests the heater in step 2242 and continues through the logic flow chart of method 2260.

In one example, method 2260 may include a step 2245A which reads from memory or calculates the test voltage from the measured test current and heater configuration and then has the user interface computer 302 asks the user to confirm the test voltage. The method may include a step between 2245 and 2246, where if the heater has been reconfigured to a parallel arrangement and the current is not within the high range, then the method proceeds to step 2252 and shuts down the APD cycler 14.

The methods 2240 and 2260 may evaluate the measured test current by a number of different methods. A preferred method was described above and alternative examples are as are described below. The first range in step 2245 may be a range of current levels that would provide the desired amount of maximum heater power for the current heater element configuration. Alternatively step 2245 may calculate a test voltage from the measured test current and heater element configuration and evaluate if the test voltage is correct for the heater configuration: approximately 110 V rms for parallel configuration and approximately 220 V rms for series configuration. Alternatively step 2245 may test if the measured test current is above a given predetermined value. The second range in step 2246 may be a range of current values corresponding to approximately 110 V rms in a series configuration. Alternatively step 2246 may calculate a test voltage from the measured test current and heater element configuration and evaluate if the test voltage approximately 110 V rms for a series configuration. Alternatively, step 2246 may evaluate if the measure test current is below a given predetermined value.

In another embodiment, the selected AC voltage value in method 2260 may be preloaded in the factory or distribution center based on the expected location of usage. For example, the AC voltage value may be selected for low if the APD cycler will be used in the US, Canada or Japan. For another example, the AC voltage value may be selected for high if the APD cycler will be used in Europe, or Asia.

For machines expected to operate in a given region, this database may be a regional voltage being loaded on the machine at the factory, or loaded by a technician during initial set-up at a place of operation. These regional AC voltage value prescriptions may be entered manually, using a memory stick or similar device, using a personal data key 325 (PDK), a compact disc, bar code reader over the world wide web using an Ethernet or wireless connection or by any other data transfer mechanism obvious to one skilled in the art. In other embodiments, sets of regional voltages may be accessible to control system 16 and may be used to inform a user of the typical operating voltage in his or her area. In one embodiment, prior to accepting a user input in step 2247 to change voltage from a previous setting, a user would be informed of the typical voltage of a region; thus a user unfamiliar with the value of regional voltages would only be required to know his or her current location to provide a safeguard against voltage incompatibility.

In another embodiment, APD cycler 14 would be equipped with a mechanism to determine its current location, for example a GPS tracker, an Ethernet connection and a mechanism to determine the location of the connection, or a mode where user interface 302 can be used to enter the present location, such as country or continent. In an embodiment, after starting up in a series heater configuration and running a current flow test, a user may simply be queried as to his or her present location; if the response to that query matches both the voltage associated with the measured test current and heater configuration and the typical voltage for that region, then treatment is allowed to proceed.

In one embodiment of the present disclosure a manual switch (not shown), or alternately a logic switch, is used to set the APD machine to the appropriate, safe voltage for use. The instantaneous voltage is measured and this measurement, either as the specific value or as a categorical descriptor, is displayed to the user. The user must respond that the measured voltage is within the safe operating range for the machine as currently configured, or alternately must respond by altering the configuration of the machine, before power is allowed to flow to the heating element. The configuration could be altered electronically, for example via the user interface computer 302, or could be performed manually by flipping a switch.

In another embodiment of the present disclosure, a rectifier converts any incoming alternating current (AC) into a single direct current (DC). The heater circuit would resemble heater circuit 2005 in FIG. 93 except the voltage detect 2020 element is replaced with a universal DC supply that rectifies the AC voltage into a selected DC voltage. The electrical power supplied to the heater elements 2001, 2002 may be modulated by a PWM element in the rectifier or by a separate PWM element 2030. The heater circuit may include a safety relay 2010. The single voltage DC power source allows the use of one heater configuration. The PWM element 2030 in this embodiment may comprise one or more IGBT or an MOSFET switches and related electrical hardware. In a preferred embodiment, the incoming alternating current would be converted to direct current in the range of 12V to 48V.

In another embodiment, the heater element 2000 may comprise a Positive Temperature Coefficient (PTC) element that self limits the power dissipated. The internal electrical resistance of a PTC element increases with temperature, so the power level is self limiting. PTC heater elements are commercially available from companies such as STEGO that are rated to run on voltages from 110 to 220 V rms. A heater circuit employing a PTC heating element would resemble heater circuit 2005 with the voltage detect element 2020 removed. The heater power would be controlled with the PWM element 2010 using a Triac. Additional heater circuit embodiments are described in U.S. Pat. No. 10,201,647, to Norris et al., issued Feb. 12, 2019, filed Jun. 5, 2015, and entitled "Medical Treatment System and Methods Using a Plurality of Fluid Lines" which is incorporated herein by reference in its entirety. Aspects of any heater circuits described therein may be used.

Database and User Interface Systems

Referring to FIG. 81, the database subsystem 346, also on the user interface computer 302, stores all data to and retrieves all data from the databases used for the onboard storage of machine, patient, prescription, user-entry and treatment history information. This provides a common access point when such information is needed by the system. The interface provided by the database subsystem 346 is used by several processes for their data storage needs. The database subsystem 346 also manages database file maintenance and back-up.

The UI screen view 338 may invoke a therapy log query application to browse the therapy history database. Using this application, which may alternatively be implemented as multiple applications, the user can graphically review their treatment history, their prescription and/or historical machine status information. The application transmits database queries to the database subsystem 346. The application can be run while the patient is dialyzing without impeding the safe operation of the machine.

The remote access application, which may be implemented as a single application or multiple applications, provides the functionality to export therapy and machine diagnostic data for analysis and/or display on remote systems. The therapy log query application may be used to retrieve information requested, and the data may be reformatted into a machine neutral format, such as XML, for transport. The formatted data may be transported off-board by a memory storage device, direct network connection or other external interface 348. Network connections may be initiated by the APD system, as requested by the user.

The service interface 356 may be selected by the user when a therapy is not in progress. The service interface 356 may comprise one or more specialized applications that log test results and optionally generate a test report which can be uploaded, for example, to a diagnostic center. The media player 358 may, for example, play audio and/or video to be presented to a user.

According to one exemplary implementation, the databases described above are implemented using SQLite®, a software library that implements a self-contained, serverless, zero-configuration, transactional SQL database engine.

The executive subsystem 332 implements two executive modules, the user interface computer (UIC) executive 352 on the user interface computer 302 and the automation computer (AC) executive 354 on the automation computer 300. Each executive is started by the startup scripts that run after the operating system is booted and includes a list of processes it starts. As the executives go through their respective process lists, each process image is checked to ensure its integrity in the file system before the process is launched. The executives monitor each child process to ensure that each starts as expected and continue monitoring the child processes while they run, e.g., using Linux parent-child process notifications. When a child process terminates or fails, the executive either restarts it (as in the case of the UI view) or places the system in fail safe mode to ensure that the machine behaves in a safe manner. The executive processes are also responsible for cleanly shutting down the operating system when the machine is powering off.

The executive processes communicate with each other allowing them to coordinate the startup and shutdown of the various application components. Status information is shared periodically between the two executives to support a watchdog function between the processors. The executive subsystem 332 is responsible for enabling or disabling the safe line. When both the UIC executive 352 and the AC executive 354 have enabled the safe line, the pump, the heater, and the valves can operate. Before enabling the lines, the executives test each line independently to ensure proper operation. In addition, each executive monitors the state of the other's safe line.

The UIC executive 352 and the AC executive 354 work together to synchronize the time between the user interface computer 302 and the automation computer 300. The time basis is configured via a battery backed real-time clock on the user interface computer 302 that is accessed upon startup. The user interface computer 302 initializes the CPU of the automation computer 300 to the real-time clock. After that, the operating system on each computer maintains its own internal time. The executives work together to ensure sufficiently timekeeping by periodically performing power on self tests. An alert may be generated if a discrepancy between the automation computer 300 time and the user interface computer 302 time exceeds a given threshold.

Figure 99:
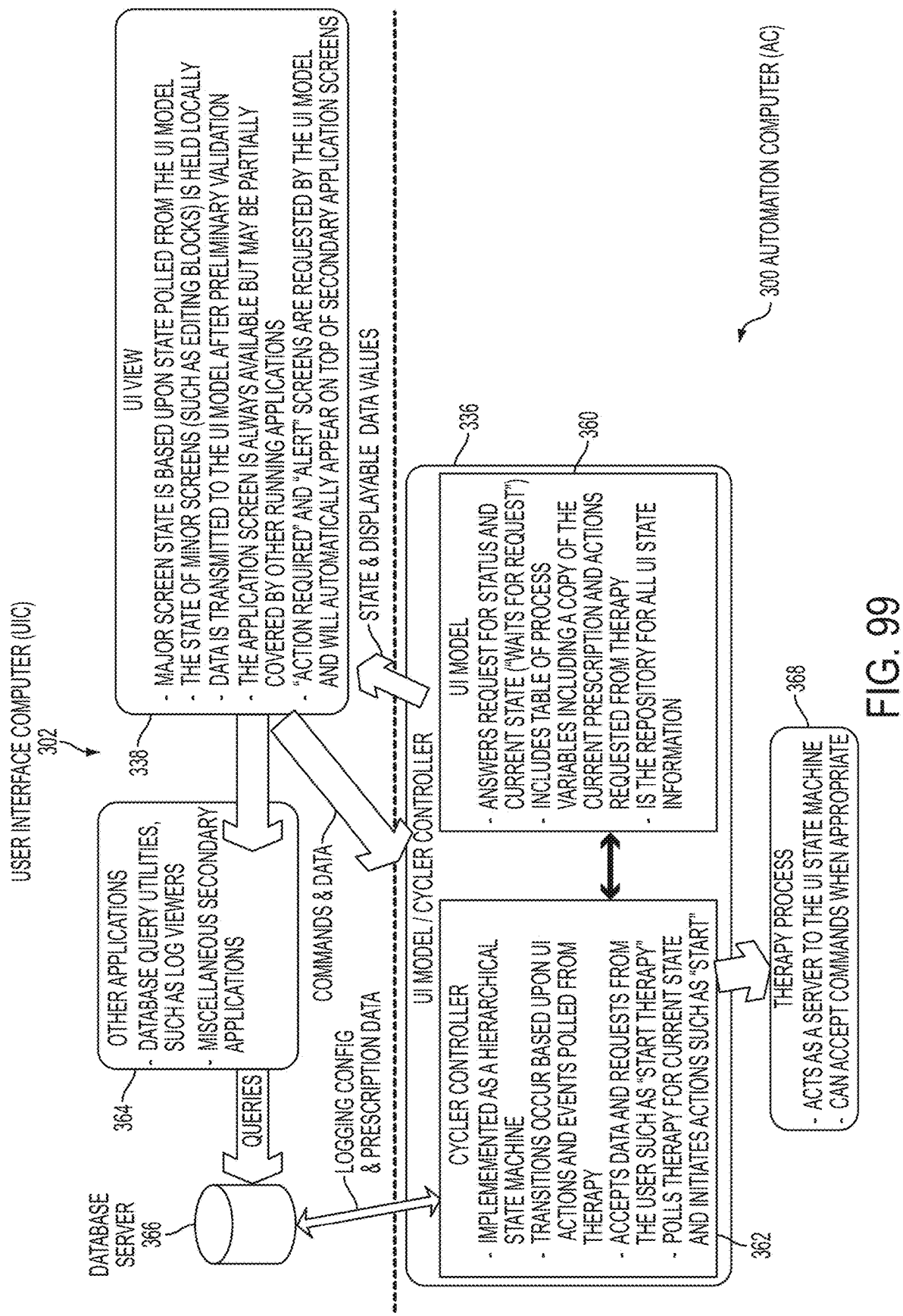
FIG. 99 shows a flow of information between various subsystems and processes of the APD system.

FIG. 99 shows the flow of information between various subsystems and processes of the APD system. As discussed previously, the UI model 360 and cycler controller 362 run on the automation computer 300. The user interface design separates the screen display, which is controlled by the UI view 338, from the screen-to-screen flow, which is controlled by the cycler controller 362, and the displayable data items, which are controlled by the UI model 360. This allows the visual representation of the screen display to be changed without affecting the underlying therapy software. All therapy values and context are stored in the UI model 360, isolating the UI view 338 from the safety-critical therapy functionality.

The UI model 360 aggregates the information describing the current state of the system and patient, and maintains the information that can be displayed via the user interface. The UI model 360 may update a state that is not currently visible or otherwise discernable to the operator. When the user navigates to a new screen, the UI model 360 provides the information relating to the new screen and its contents to the UI view 338. The UI model 360 exposes an interface allowing the UI view 338 or some other process to query for current user interface screen and contents to display. The UI model 360 thus provides a common point where interfaces such as the remote user interface and online assistance can obtain the current operational state of the system.

The cycler controller 362 handles changes to the state of the system based on operator input, time and therapy layer state. Acceptable changes are reflected in the UI model 360. The cycler controller 362 is implemented as a hierarchical state machine that coordinates therapy layer commands, therapy status, user requests and timed events, and provides view screen control via UI model 360 updates. The cycler controller 362 also validates user inputs. If the user inputs are allowed, new values relating to the user inputs are reflected back to the UI view 338 via the UI model 360. The therapy process 368 acts as a server to the cycler controller 362. Therapy commands from the cycler controller 362 are received by the therapy process 368.

The UI view 338, which runs on the UI computer 302, controls the user interface screen display and responds to user input from the touch screen. The UI view 338 keeps track of local screen state, but does not maintain machine state information. Machine state and displayed data values, unless they are in the midst of being changed by the user, are sourced from the UI model 360. If the UI view 338 terminates and is restarted, it displays the base screen for the current state with current data. The UI view 338 determines which class of screens to display from the UI model 360, which leaves the presentation of the screen to the UI view. All safety-critical aspects of the user interface are handled by the UI model 360 and cycler controller 362.

The UI view 338 may load and execute other applications 364 on the user interface computer 302. These applications may perform non-therapy controlling tasks. Exemplary applications include the log viewer, the service interface, and the remote access applications. The UI view 338 places these applications within a window controlled by the UI view, which allows the UI view to display status, error, and alert screens as appropriate. Certain applications may be run during active therapy. For example, the log viewer may be run during active therapy, while the service interface and the remote access application generally may not. When an application subservient to the UI view 338 is running and the user's attention is required by the ongoing therapy, the UI view 338 may suspend the application and regain control of the screen and input functions. The suspended application can be resumed or aborted by the UI view 338.

Figure 100:
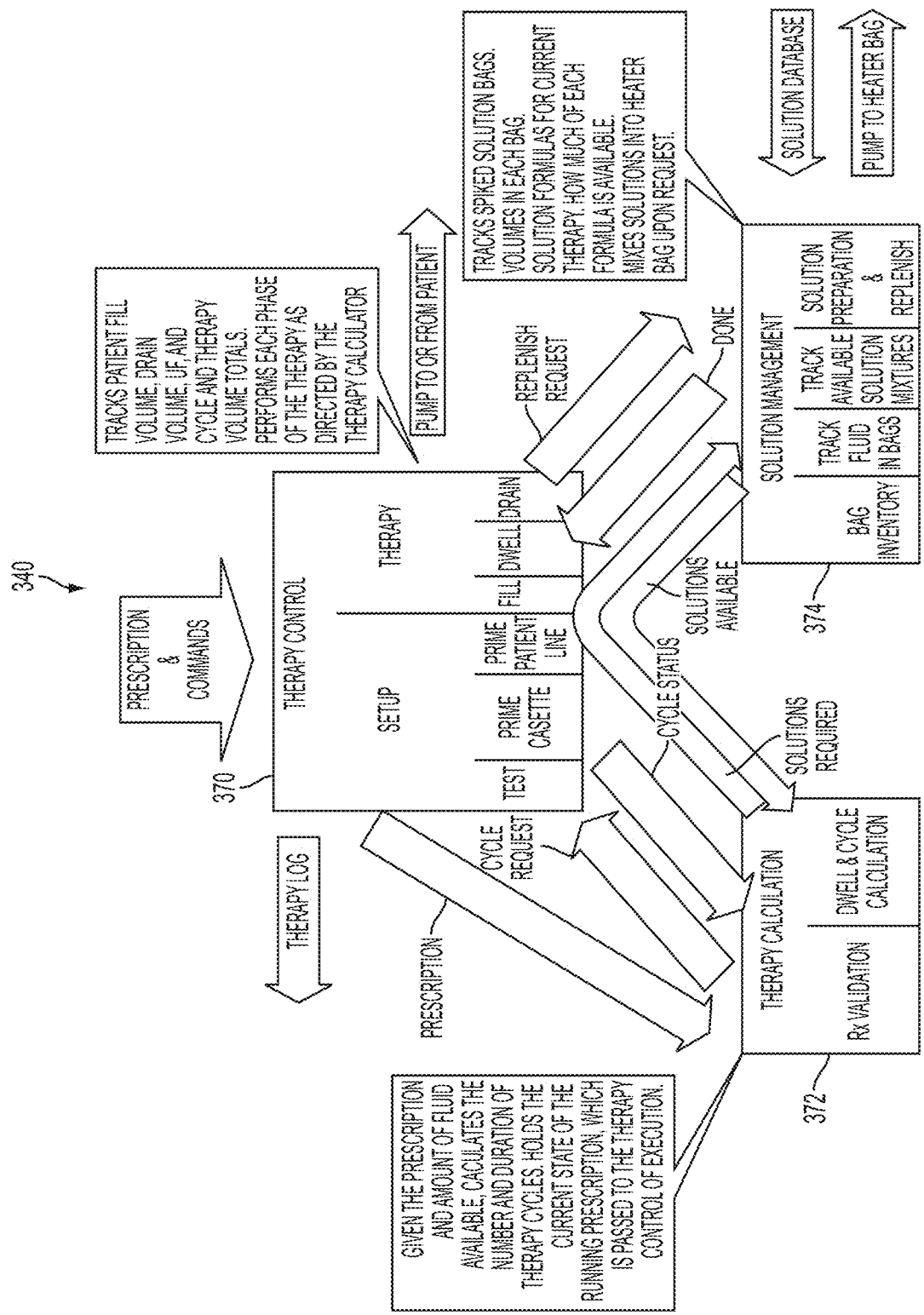
FIG. 100 illustrates an operation of the therapy subsystem of FIG. 99.

FIG. 100 illustrates the operation of the therapy subsystem 340 described in connection with FIG. 81. The therapy subsystem 340 functionality is divided across three processes: therapy control; therapy calculation; and solution management. This allows for functional decomposition, case of testing, and case of updates.

The therapy control module 370 uses the services of the therapy calculation module 372, solution management module 374 and machine control subsystem 342 (FIG. 81) to accomplish its tasks. Responsibilities of the therapy control module 370 include tracking fluid volume in the heater bag 22, tracking fluid volume in the patient, tracking patient drain volumes and ultra filtrate, tracking and logging cycle volumes, tracking and logging therapy volumes, orchestrating the execution of the dialysis therapy (drain-fill-dwell), and controlling therapy setup operations. The therapy control module 370 performs each phase of the therapy as directed by the therapy calculation module 370.

The therapy calculation module 370 tracks and recalculates the drain-fill-dwell cycles that comprise a peritoneal dialysis therapy. Using the patient's prescription, the therapy calculation module 372 calculates the number of cycles, the dwell time, and the amount of solution needed (total therapy volume). As the therapy proceeds, a subset of these values is recalculated, accounting for the actual elapsed time. The therapy calculation module 372 tracks the therapy sequence, passing the therapy phases and parameters to the therapy control module 370 when requested.

The solution management module 374 maps the placement of solution supply bags 20, tracks the volume in each supply bag 20, commands the mixing of solutions based upon recipes in the solution database, commands the transfer of the requested volume of mixed or unmixed solution into the heater bag 22, and tracks the volume of mixed solutions available using the solution recipe and available bag volume.

Figure 101:
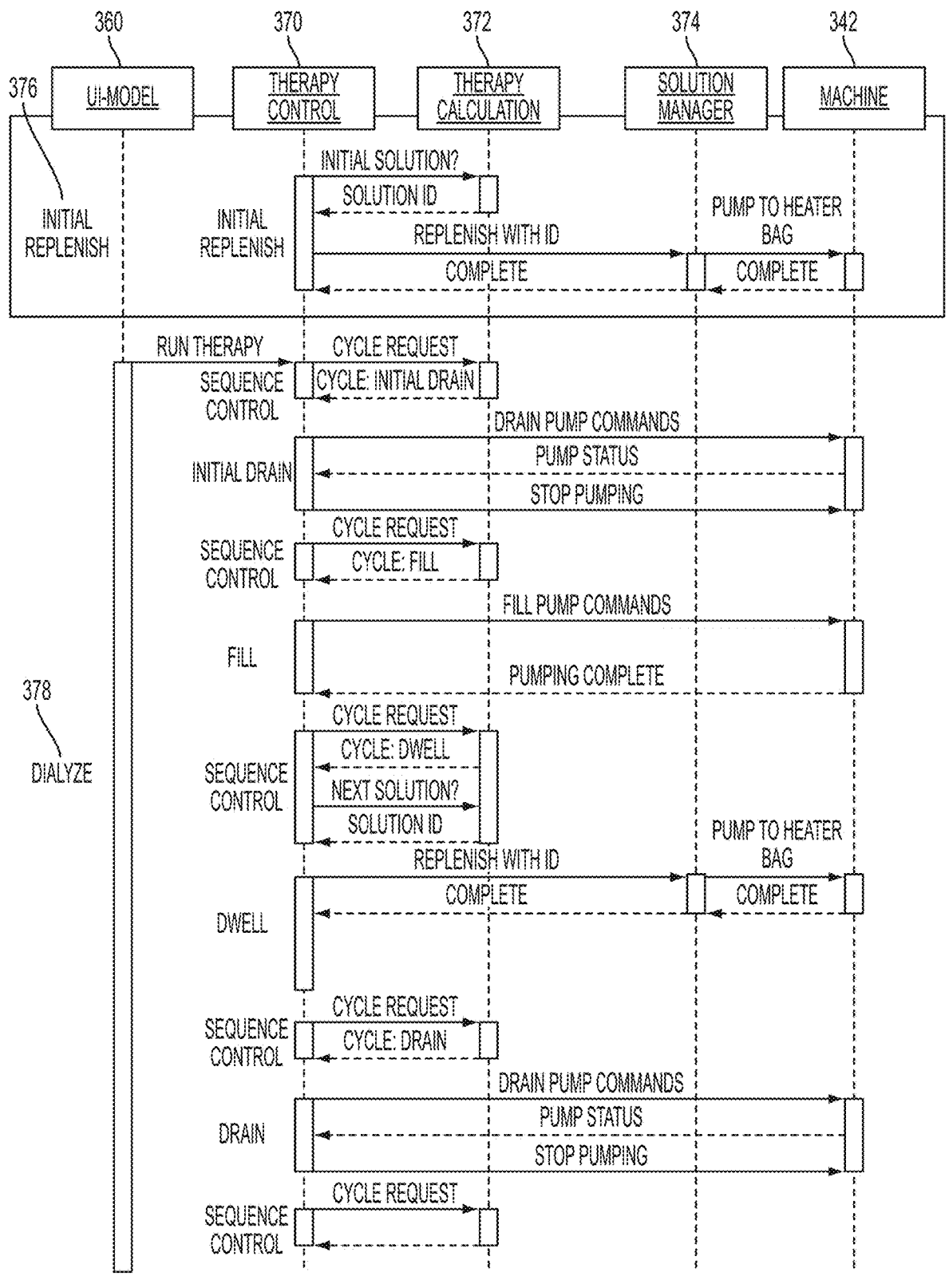
FIG. 101 is a sequence diagram depicting interactions of therapy module processes during initial replenish and dialyze portions of the therapy.

FIG. 101 shows a sequence diagram depicting exemplary interactions of the therapy module processes described above during the initial 'replenish' and 'dialyze' portions of the therapy. During the exemplary initial replenish process 376, the therapy control module 370 fetches the solution ID and volume for the first fill from the therapy calculation module 372. The solution ID is passed to the solution management module 374 with a request to fill the heater bag 22 with solution, in preparation for priming the patient line 34 and the first patient fill. The solution management module 374 passes the request to the machine control subsystem 342 to begin pumping the solution to the heater bag 22.

During the exemplary dialyze process 378, the therapy control module 370 executes one cycle (initial drain, fill, dwell-replenish, and drain) at a time, sequencing these cycles under the control of the therapy calculation module 372. During the therapy, the therapy calculation module 372 is updated with the actual cycle timing, so that it can recalculate the remainder of the therapy if needed.

In this example, the therapy calculation module 372 specifies the phase as "initial drain," and the therapy control module 370 makes the request to the machine control subsystem 342. The next phase specified by the therapy calculation module 372 is "fill". The instruction is sent to the machine control subsystem 342. The therapy calculation module 372 is called again by the therapy control module 370, which requests that fluid be replenished to the heater bag 22 during the "dwell" phase. The solution management module 374 is called by the therapy control module 370 to replenish fluid in the heater bag 22 by calling the machine control subsystem 342. Processing continues with therapy control module 370 calling the therapy calculation module 372 to get the next phase. This is repeated until there are no more phases, and the therapy is complete.

Pump Monitor/Math Repeater

A pump monitor and/or math repeater may be included in certain embodiments and may be similar to those described in U.S. Pat. No. 10,201,647, to Norris et al., issued Feb. 12, 2019, filed Jun. 5, 2015, and entitled Medical Treatment System and Methods Using a Plurality of Fluid Lines which is incorporated herein by reference in its entirety.

Alert/Alarm Functions

Conditions or events in the APD system may trigger alerts and/or alarms that are logged, displayed to a user, or both. These alerts and alarms are a user interface construct that reside in the user interface subsystem, and may be triggered by conditions that occur in any part of the system. These conditions may be grouped into three categories: (1) system error conditions, (2) therapy conditions, and (3) system operation conditions.

"System error conditions" relate to errors detected in software, memory, or other aspects of the processors of the APD system. These errors call the reliability of the system into question, and may be considered "unrecoverable." System error conditions cause an alarm that is displayed or otherwise made known to the user. The alarm may also be logged. Since system integrity cannot be guaranteed in the instance of a system error condition, the system may enter a fail safe mode in which the safe line described herein is disabled.

Each subsystem described in connection with FIG. 81 is responsible for detecting its own set of system errors. System errors between subsystems are monitored by the user interface computer executive 352 and automation computer executives 354. When a system error originates from a process running on the user interface computer 302, the process reporting the system error terminates. If the UI screen view subsystem 338 is terminated, the user interface computer executive 352 attempts to restart it, e.g., up to a maximum of three times. If it fails to restart the UI screen view 338 and a therapy is in progress, the user interface computer executive 352 transitions the machine to a fail safe mode.

When a system error originates from a process running on the automation computer 300, the process terminates. The automation computer executive 354 detects that the process has terminated and transitions to a safe state if a therapy is in progress.

When a system error is reported, an attempt is made to inform the user, e.g., with visual and/or audio feedback, as well as to log the error to a database. System error handling is encapsulated in the executive subsystem 332 to assure uniform handling of unrecoverable events. The executive processes of the UIC executive 352 and AC executive 354 monitor each other such that if one executive process fails during therapy, the other executive transitions the machine to a safe state.

"Therapy conditions" are caused by a status or variable associated with the therapy going outside of allowable bounds. For example, a therapy condition may be caused by an out-of-bounds sensor reading. These conditions may be associated with an alert or an alarm, and then logged. Alarms are critical events, generally requiring immediate action. Alarms may be prioritized, for example as low, medium or high, based on the severity of the condition. Alerts are less critical than alarms, and generally do not have any associated risk other than loss of therapy or discomfort. Alerts may fall into one of three categories: message alerts, escalating alerts, and user alerts.

The responsibility for detecting therapy conditions that may cause an alarm or alert condition is shared between the UI model and therapy subsystems. The UI model subsystem 360 (FIG. 99) is responsible for detecting alarm and alert conditions pre-therapy and post-therapy. The therapy subsystem 340 (FIG. 81) is responsible for detecting alarm and alert conditions during therapy.

The responsibility for handling alerts or alarms associated with therapy conditions is also shared between the UI model and therapy subsystems. Pre-therapy and post-therapy, the UI model subsystem 360 is responsible for handling the alarm or alert condition. During a therapy session, the therapy subsystem 340 is responsible for handling the alarm or alert condition and notifying the UI Model Subsystem an alarm or alert condition exists. The UI model subsystem 360 is responsible for escalating alerts, and for coordinating with the UI view subsystem 338 to provide the user with visual and/or audio feedback when an alarm or alert condition is detected.

"System operation conditions" do not have an alert or alarm associated with them. These conditions are simply logged to provide a record of system operations. Auditory or visual feedback need not be provided.

Actions that may be taken in response to the system error conditions, therapy conditions, or system operation conditions described above are implemented by the subsystem (or layer) that detected the condition, which sends the status up to the higher subsystems. The subsystem that detected the condition may log the condition and take care of any safety considerations associated with the condition. These safety considerations may comprise any one or combination of the following: pausing the therapy and engaging the occluder 147; clearing states and timers as needed; disabling the heater; ending the therapy entirely; deactivating the safe line to close the occluder 147, shut off the heater, and removing power from the valves; and preventing the cycler 14 from running therapies even after a power cycle to require the system to be sent back to service. The UI subsystem 334 may be responsible for conditions that can be cleared automatically (i.e., non-latching conditions) and for user recoverable conditions that are latched and can only be cleared by user interaction.

Each condition may be defined such that it contains certain information to allow the software to act according to the severity of the condition. This information may comprise a numeric identifier, which may be used in combination with a lookup table to define priority; a descriptive name of the error (i.e., a condition name); the subsystem that detected the condition; a description of what status or error triggers the condition; and flags for whether the condition implements one or more actions defined above.

Conditions may be ranked in priority such that when multiple conditions occur, the higher priority condition may be handled first. This priority ranking may be based on whether the condition stops the administration of therapy. When a condition occurs that stops therapy, this condition takes precedence when relaying status to the next higher subsystem. As discussed above, the subsystem that detects a condition handles the condition and sends status information up to the subsystem above. Based on the received status information, the upper subsystem may trigger a different condition that may have different actions and a different alert/alarm associated with it. Each subsystem implements any additional actions associated with the new condition and passes status information up to the subsystem above. According to one exemplary implementation, the UI subsystem only displays one alert/alarm at a given time. In this case, the UI model sorts all active events by their priority and displays the alert/alarm that is associated with the highest priority event.

A priority may be assigned to an alarm based on the severity the potential harm and the onset of that harm. Table 1, below, shows an example of how priorities may be assigned in this manner.

TABLE 1

| POTENTIAL RESULT OF FAILURE TO RESPOND TO THE CAUSE OF ALARM | ONSET OF POTENTIAL HARM | | |
| --- | --- | --- | --- |
| CONDITION | IMMEDIATE | PROMPT | DELAYED |
| death or irreversible injury | high priority | high priority | medium priority |
| reversible injury | high priority | medium priority | low priority |

TABLE 1-continued

| POTENTIAL RESULT OF FAILURE TO RESPOND TO THE CAUSE OF ALARM | ONSET OF POTENTIAL HARM | | |
|---|---|---|---|
| CONDITION | IMMEDIATE | PROMPT | DELAYED |
| minor discomfort or injury | medium priority | low priority | low priority or no alarm signal |

In the context of Table 1, the onset of potential harm refers to when an injury occurs and not to when it is manifested. A potential harm having an onset designated as "immediate" denotes a harm having the potential to develop within a period of time not usually sufficient for manual corrective action. A potential harm having an onset designated as "prompt" denotes a harm having the potential to develop within a period of time usually sufficient for manual corrective action. A potential harm having an onset designated as "delayed" denotes a harm having the potential to develop within an unspecified time greater than that given under "prompt."

Figure 102:
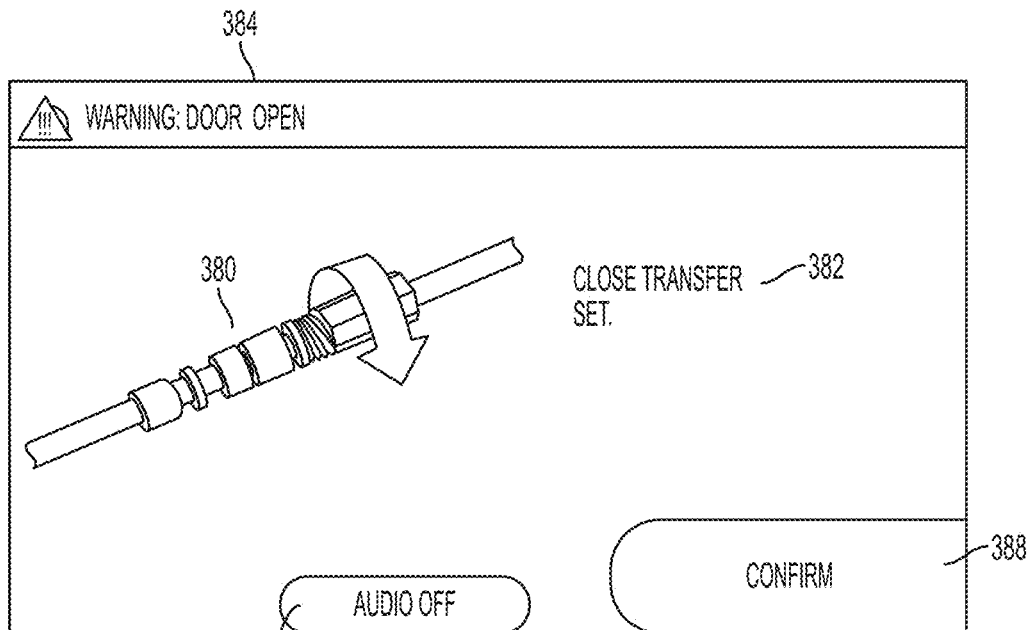
FIGS. 102-107 show screen views relating to alerts and alarms that may be displayed on a touch screen user interface for the APD system.
Figure 103:
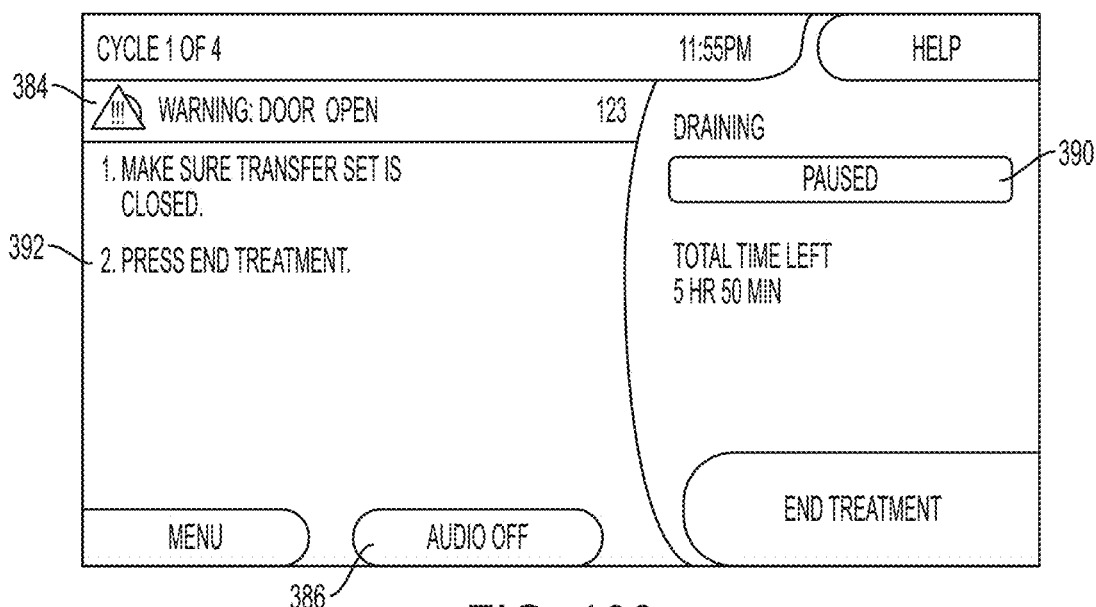

FIGS. 102-107 show exemplary screen views relating to alerts and alarms that may be displayed on a touch screen user interface. FIG. 102 shows the first screen of an alarm, which includes a diagram 380 and text 382 instructing a user to close their transfer set. The screen includes a visual warning 384, and is also associated with an audio warning. The audio warning may be turned off by selecting the "audio off" option 386 on the touch screen. When the user has closed the transfer set, the user selects the "confirm" option 388 on the touch screen. FIG. 103 shows a similar alarm screen instructing a user to close their transfer set. In this case, an indication that draining is paused 390 and an instruction to select "end treatment" are provided 392.

As previously discussed, alerts generally do not have associated risk other than loss of therapy or discomfort. Thus, an alert may or may not cause the therapy to pause. Alerts can be either "auto recoverable," such that if the event clears the alert automatically clears, or "user recoverable," such that user interaction with the user interface is needed to clear the alert. An audible alert prompt, which may have a volume that may be varied within certain limits, may be used to bring an alert to the attention of a user. In addition, information or an instruction may be displayed to the user. So that such information or instruction may be viewed by the user, an auto-dim feature of the user interface may be disabled during alerts.

In order to reduce the amount of disturbance to the user, alerts may be categorized into different types based on how important an alert is and how quick a user response is required. Three exemplary types of alerts are a "message alert," an "escalating alert," and a "user alert." These alerts have different characteristics based on how information is visually presented to the user and how the audible prompt is used.

Figure 104:
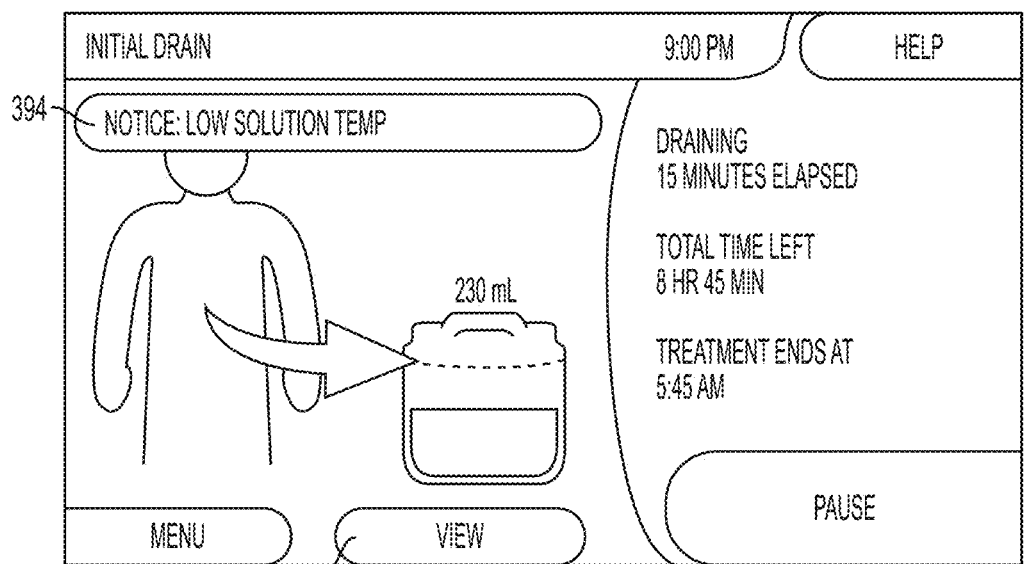
Figure 105:
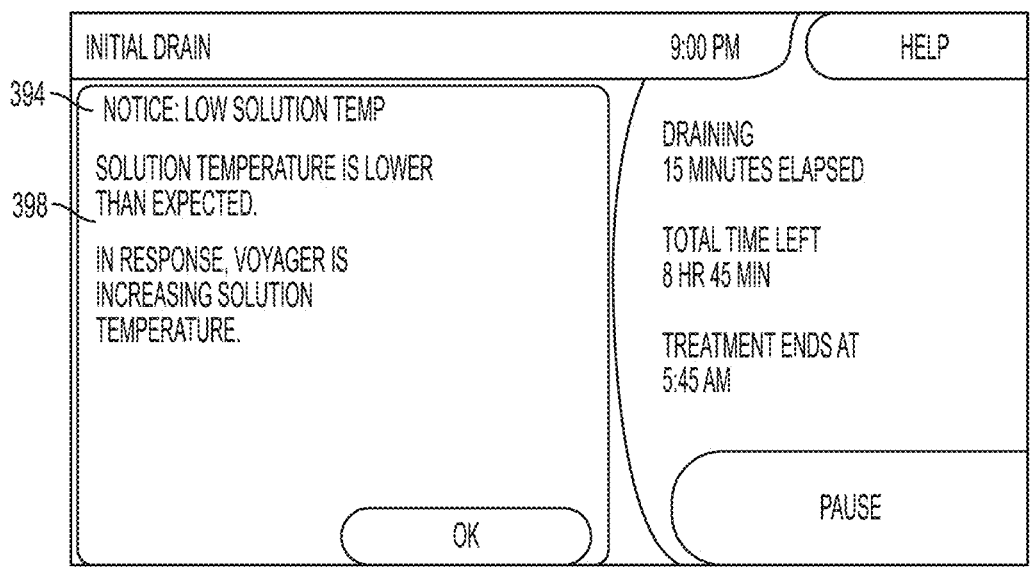

A "message alert" may appear at the top of a status screen and is used for informational purposes when a user interaction is not required. Because no action needs to be taken to clear the alert, an audible prompt is generally not used to avoid disturbing, and possibly waking, the patient. However, an audible alert may be optionally presented. FIG. 104 shows an exemplary message alert. In particular, FIG. 104 shows an under-temperature message alert 394 that may be used to inform a user when the dialysate is below a desired temperature or range. In this case, a user does not need to take any action, but is informed that therapy will be delayed while the dialysate is heated. If the patient desires more information, the "view" option 396 may be selected on the touch screen. This causes additional information 398 concerning the alert to appear on the screen, as shown in FIG. 105. A message alert may also be used when there is a low flow event that the user is trying to correct. In this case, a message alert may be displayed until the low flow event is cleared to provide feedback to the user on whether the user fixed the problem.

Figure 106:
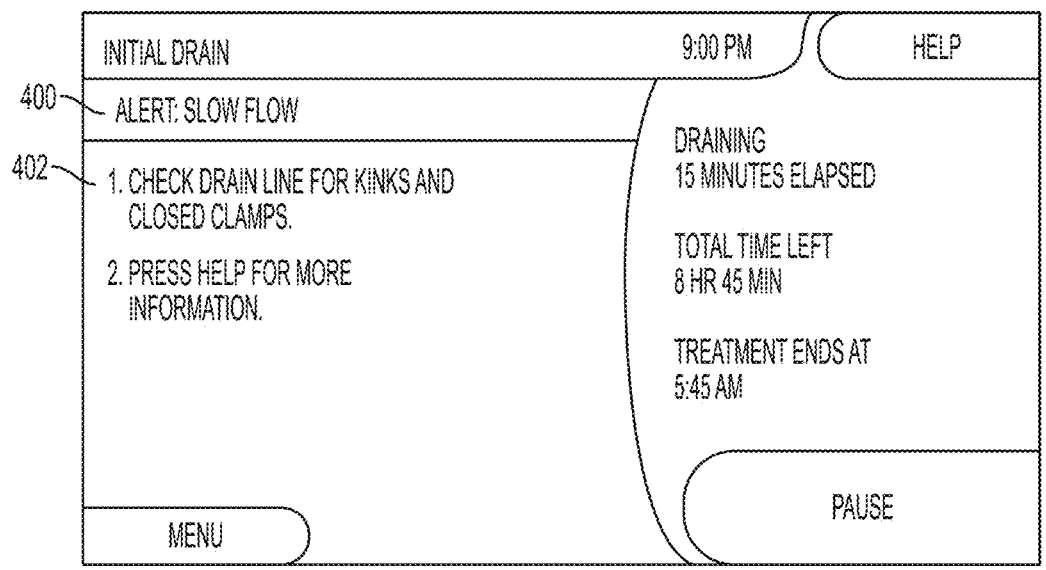
Figure 107:
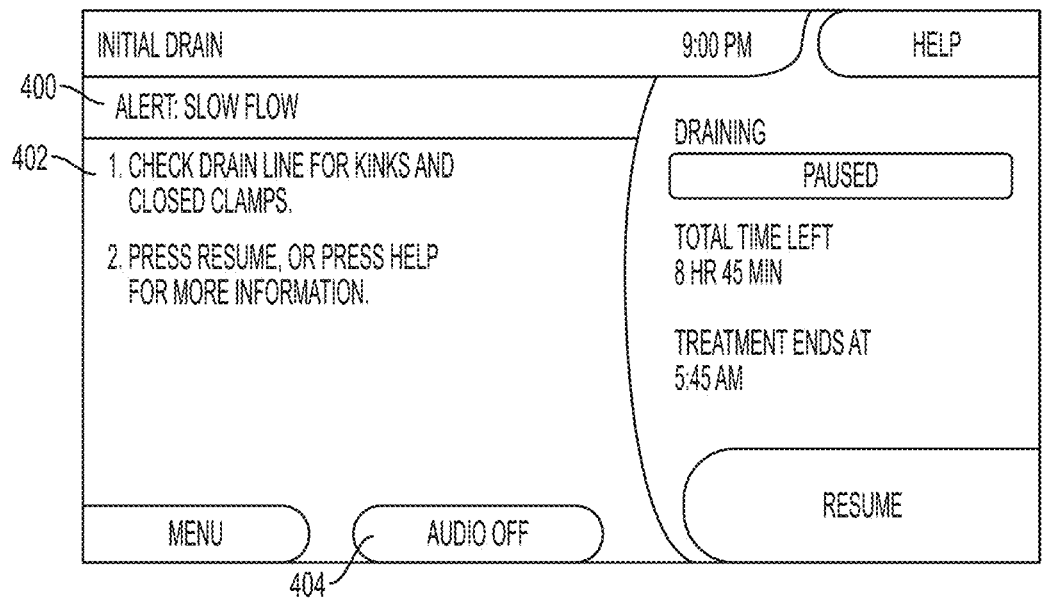

An "escalating alert" is intended to prompt the user to take action in a non-jarring manner. During an escalating alert, a visual prompt may displayed on the touch screen and an audible prompt may be presented (e.g., once). After a given period of time, if the event that caused the alert is not cleared, a more emphatic audible prompt may be presented. If the event causing the alert is not cleared after an additional period of time, the alert is escalated to a "user alert." According to one exemplary implementation of a user alert, a visual prompt is displayed until the alert is cleared and an audible prompt, which can be silenced, is presented. The UI subsystem does not handle the transition to from escalating alert to user alert. Rather, the subsystem that triggered the original event will trigger a new event associated with the user alert. FIG. 106 shows a screen view displaying information concerning an escalating alert. This exemplary alert includes an on-screen alert message 400 and a prompt 402 instructing the user to check the drain line for kinks and closed clamps, as well as and an audible prompt. The audible prompt may be continuous until it is silenced by the user. FIG. 107 shows a screen view including an "audio off" option 404 that may be selected to silence the audible prompt. This alert can be used directly, or as part of the escalating alert scheme.

Each alert/alarm is specified by: an alert/alarm code, which is a unique identifier for the alert/alarm; an alert/alarm name, which is a descriptive name of the alert/alarm; an alert/alarm type, which comprises the type of alert or level of alarm; an indication of whether an audible prompt is associated with the alert/alarm; an indication of whether the alert and associated event can be bypassed (or ignored) by the user; and the event code of the event or events that trigger the alert/alarm.

During alarms, escalating alerts and user alerts, the event code (which may be different from the alert or alarm code, as described above) may be displayed on the screen so that the user can read the code to service personnel if needed. Alternatively or additionally, a voice guidance system may be used so that, once connected to a remote call center, the system can vocalize pertinent information about the system configuration, state, and error code. The system may be connected to the remote call center via a network, telephonic connection, or some other means.

Figure 108:
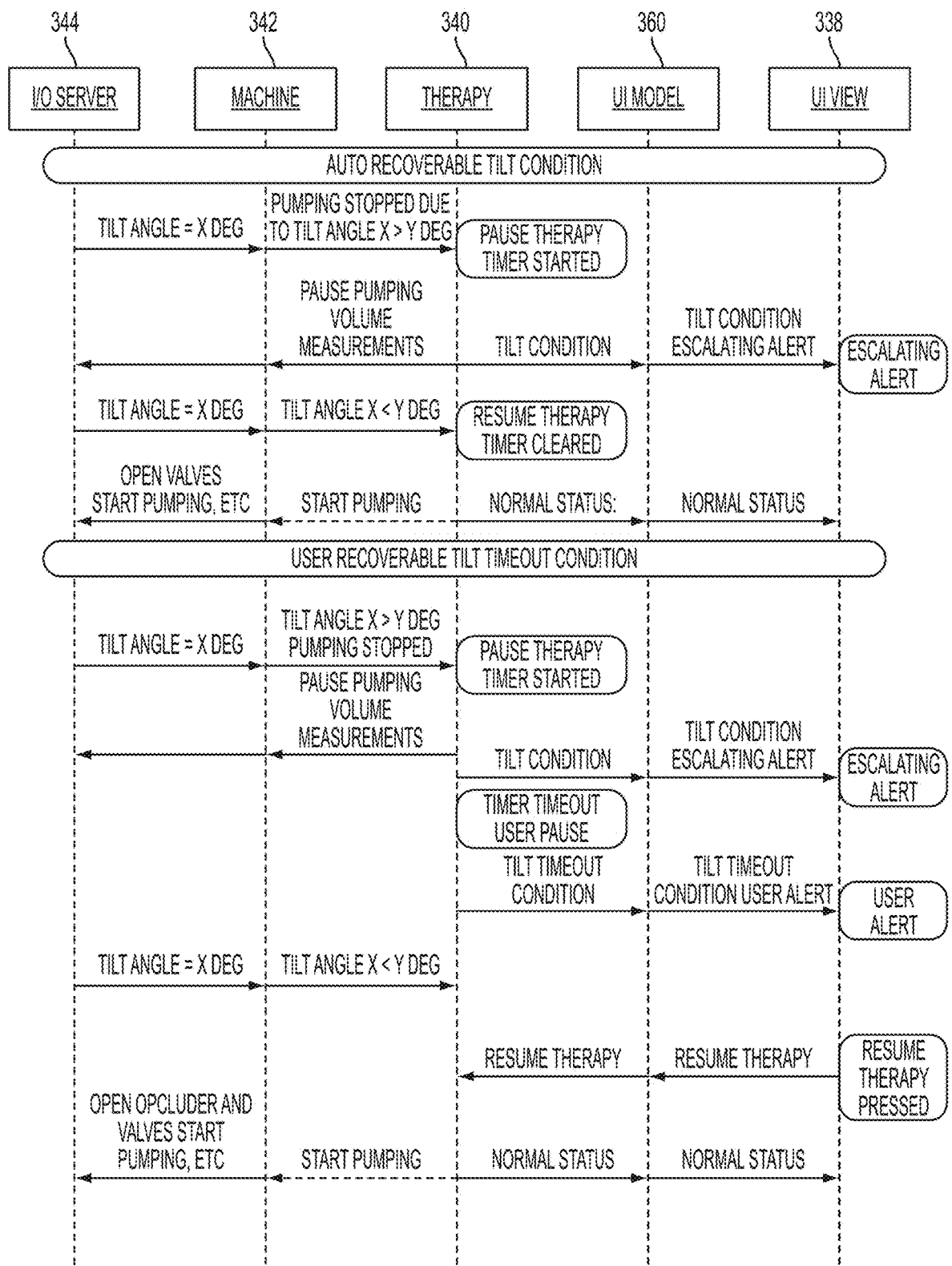
FIG. 108 illustrates component states and operations for error condition detection and recovery.

An example of a condition detected by the therapy subsystem is described below in connection with FIG. 108. The condition results when the APD system is not positioned on a level surface, which is important for air management. More particularly, the condition results when a tilt sensor detects that APD system is tilted beyond a predetermined threshold, such as 35°, with respect to a horizontal plane. As described below, a recoverable user alert may be generated by the therapy subsystem if the tilt sensor senses an angle with an absolute value greater than the predetermined threshold. To avoid nuisance alarms, the user may be directed to level the APD system before therapy begins. The tilt threshold may be lower during this pre-therapy period (e.g., 35°). The user may also be given feedback concerning whether the problem is corrected.

When the tilt sensor detects an angle of tilt exceeding a threshold value during therapy, the machine subsystem 342 responds by stopping the pump in a manner similar to detecting air in the pump chamber. The therapy subsystem 340 asks for status and determines that the machine layer 342 has paused pumping due to tilt. It also receives status information concerning the angle of the machine. At this point, the therapy subsystem 340 generates a tilt condition, pauses therapy, and sends a command to the machine subsystem 342 to pause pumping. This command triggers clean-up, such as taking fluid measurement system (FMS) measurements and closing the patient valve. The therapy subsystem 340 also starts a timer and sends an auto recoverable tilt condition up to the UI model 360, which sends the condition to the UI view 338. The UI view 338 maps the condition to an escalating alert. The therapy subsystem 340 continues to monitor the tilt sensor reading and, if it drops below the threshold, clears the condition and restarts therapy. If the condition does not clear before the timer expires, the therapy subsystem 340 triggers a user recoverable "tilt timeout" condition that supersedes the auto-recoverable tilt condition. It sends this condition to the UI model 360, which sends the condition to the UI view 338. The UI view 338 maps the condition to a user alert. This condition cannot be cleared until a restart therapy command is received from the UI subsystem (e.g., the user pressing the resume button). If the tilt sensor reading is below the threshold, the therapy resumes. If it is not below the threshold, the therapy layer triggers an auto recoverable tilt condition and starts the timer.

Prioritized Audible Signals

The cycler 14 may provide audible signals and voice guidance to the user to communicate a range of information including but not limited to number selection, sound effects (button selection, action selection), machine condition, operational directions, alerts, and alarms. The cycler control system 16 may cause a speaker to annunciate audible signals and vocalizations from stored sound files stored in memory on one or both of the computers 300, 302 in the control system 16. Alternatively, vocalizations may be stored and produced by a specialized voice chip.

In some instances, the cycler 14 may have multiple audible signals to annunciate at the same time or sequentially in a very short time. The annunciation of several signals in a short period of time may overwhelm the user resulting in annoyance or the loss of critical safety information. The cycler control system 16 may assign priorities to each audible signal and suppress the lower priority signals to allow the clear communication of higher priority audible signals. In one instance, the audible signals are prioritized from the highest priority alarm signals to the lowest priority annunciation of a sequence of numbers:

1. Alarms
2. Alerts
3. Sound Effects
4. Voice Guidance
5. Annunciation for a sequence of numbers.

Alarms and alerts are described above. Sound effects may confirm sounds to indicate that a button, or choice has been selected. Sound effects may also announce or confirm a particular action is being taken by the cycler. Voice guidance may include voiced instructions to execute a particular procedure, access help, contact a call center and other directing instructions. Annunciation for a sequence of numbers may include reading back to the user or the call center the number that the user had just keyed in or it may read the user allowable values for requested input.

Battery Operation

The cycler may include a rechargeable lithium ion battery for use as a backup power source. At a minimum this battery helps to ensure that the cycler 14 does not turn off without alerting the user and saving the current state of the treatment. A power management system may be implemented by the cycler 14 when on battery power that is contingent on the amount of charge remaining in the battery. If the battery is sufficiently charged, the cycler 14 can prevent brownouts or short power outages from interfering with the completion of a therapy. The cycler control circuitry can measure the state of charge of the battery, and can correlate the battery charge level with operable states. This information may be obtained empirically through testing, and the correlations between battery charge level and the ability to operate the various subsystems may be stored in memory. The following functions may be associated with the battery charge level:

Level 4: Enough power to perform one cycle of therapy. Implemented if, for example, the charge level of the battery is equal to or greater than approximately 1100 milliamp-hours.

Level 3: Enough power to perform a user drain. Implemented if, for example, the charge level of the battery is equal to or greater than approximately 500 milliamp-hours.

Level 2: Enough power to end therapy, display alert, and guide user through post-therapy breakdown. Implemented if, for example, the charge level of the battery is equal to or greater than approximately 300 milliamp-hours.

Level 1: Enough power to end therapy and display an alert. Implemented if, for example, the charge level of the battery is equal to or greater than approximately 200 milliamp-hours.

Level 0: Not enough power to operate.

If there is enough charge in the battery (Level 4), the cycler 14 will continue with the therapy until the current cycle is finished. This may not include replenishing the heater bag 22 or heating the solution. Therefore, if already in a fill phase, the cycler 14 may continue the therapy if the solution in the heater bag 22 is in the proper temperature range and there is enough solution in the heater bag 22. If the battery only has enough capacity to perform a 20 minute drain (Level 3), the cycler 14 will alert the user, and give the user the option to either drain or end treatment without draining. If the battery only has enough power to alert the user (Level 2) it will not give the user the option to drain and the user will be guided through the post-therapy breakdown. If there is not enough power to guide the user through breakdown (Level 1), the user will be prompted to disconnect and then the cycler 14 will power down. At this battery level the cycler 14 may not have enough power to release the door 141, so the user may not be able to breakdown the therapy. During start up, the cycler 14 can assess the state of the battery, and alert the user if the battery has a fault or if the battery does not have a sufficient charge to at least alert the patient if main power is lost. The cycler 14 may be programmed to not allow the user to start a treatment without the battery having enough capacity to provide and alert and guide the user through post-therapy breakdown (Battery Level 2).

Another example of battery charge levels and available therapy choices or machine actions sets 4 battery charge levels and the available therapy choices or machine actions:

Level 4:

If the fill process has not started, then suspend operation until the AC power is restored. The suspend is limited to 30 mins.

If the fill process has started, then complete cycle including the fill, dwell and drain processes.

The heater bag will not be refilled as there is no heating during battery operation.

End therapy, and guide user through post-therapy breakdown including removal of the of the dialysate delivery set 12*a* from the cycler 14.

Level 3:

If in the fill or drain process, then suspend operation until the AC power is restored. The suspend is limited to 30 mins.

If the drain process has started, then complete the cycle.

The heater bag will not be refilled as there is no heating during battery operation.

End therapy, and guide user through post-therapy breakdown including removal of the of the dialysate delivery set 12*a* from the cycler 14.

Level 2:

End therapy, and guide user through post-therapy breakdown including removal of the of the dialysate delivery set 12*a* from the cycler 14.

Level 1:

End therapy.

Level 0:

Not enough power to operate.

An alert will be displayed to the user or patient at levels 1-4. The control system 16 may extend the cycler 14 operation on battery power by dimming the display screen 324 after a given time period from the last screen touch. In another example the display screen 324 may dim after a given period from the appearance of the most recent message, alert or warning. In one example, the display screen 324 will dim two minutes after the more recent screen touch or last. The display screen 324 may include a message or symbol indicating operation on battery power.

The electrical circuitry connecting the battery to the pneumatic valves may include a regulated voltage boost converter that steps-up the supplied variable battery voltage to a consistent voltage. The supplied battery voltage may drop as the battery is discharged, in one example, a Li-Ion battery at full charge may supply 12.3 volts. The supplied voltage may drop as the battery is depleted to as low as 9 volts when the battery is fully discharged. The pneumatic valves may require a minimum voltage to reliably open fully. In one example, the minimum voltage to reliably open the valve may be 12 volts.

A regulated voltage boost converter may be placed between the supply battery and the valves to assure sufficient voltage to reliably open the valves as battery discharges. The regulated voltage boost converter will output a regulated voltage at a higher value than the variable battery voltage input. In one example, the regulated voltage boost converter may be an integrated chip such as the TPS61175 made by Texas Instruments. A regulated voltage buck/boost converter may also be used between the battery and the valves. The buck/boost converter is able to supply a regulated voltage output from supplied voltages that are higher, equal to, or lower than the input voltage.

In one embodiment, the PWM duty cycle of the valve drivers may vary with the measured battery voltage. The valves may be operated in a pick-and-hold manner, where an initially higher voltage is applied to open the valve and then a lower voltage is applied to hold the valve in desired condition. The PWM duty cycle for the hold function may be scaled inversely with the measure battery voltage to provide a consistent averaged voltage or current to the valves. The PWM duty cycle may be scaled inversely with measured battery voltage for the higher voltage open or pick operation.

Screen Display

As discussed previously, the UI view subsystem 338 (FIG. 99) is responsible for the presentation of the interface to the user. The UI view subsystem 338 is a client of and interfaces with the UI model subsystem 360 (FIG. 99) running on the automation computer 300. For example, the UI view subsystem 338 communicates with the UI model subsystem to determine which screen should be displayed to the user at a given time. The UI view may include templates for the screen views, and may handle locale-specific settings such as display language, skin, audio language, and culturally sensitive animations.

Figure 109:
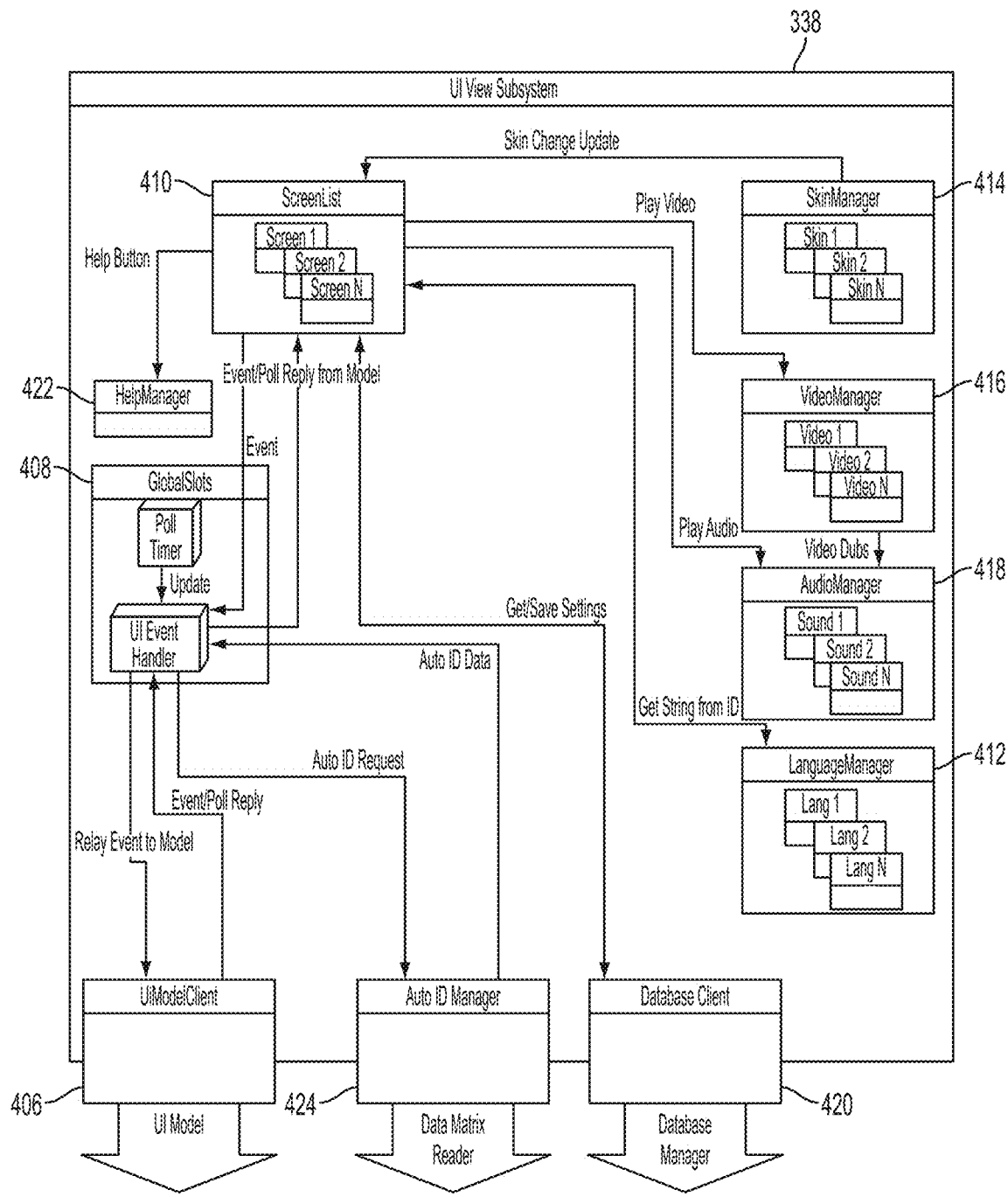
FIG. 109 shows exemplary modules of a UI view subsystem for the APD system.

There are three basic types of events that occur in the UI view subsystem 338. These are local screen events that are handled by the individual screens, model events in which a screen event must propagate down to the UI model subsystem, and polling events that occur on a timer and query the UI model subsystem for status. A local screen event only affects the UI view level. These events can be local screen transitions (e.g., in the case of multiple screens for a single model state), updates to view settings (e.g., locality and language options), and requests to play media clips from a given screen (e.g., instructional animations or voice prompts). Model events occur when the UI view subsystem 338 must consult with the UI model subsystem to determine how to handle the event. Examples that fall into this category are the confirmation of therapy parameters or the pressing of the "start therapy" button. These events are initiated by the UI view subsystem 338, but are handled in the UI model subsystem. The UI model subsystem processes the event and returns a result to the UI view subsystem 338. This result drives the internal state of the UI view subsystem 338. Polling events occur when a timer generates a timing signal and the UI model subsystem is polled. In the case of a polling event, the current state of the UI view subsystem 338 is sent to the UI model subsystem for evaluation. The UI model subsystem evaluates the state information and replies with the desired state of the UI view subsystem 338. This may constitute: (1) a state change, e.g., if the major states of the UI model subsystem and the UI view subsystem 338 are different, (2) a screen update, e.g., if values from the UI model subsystem change values displayed on-screen, or (3) no change in state, e.g., if the state of the UI model subsystem and the UI view subsystem 338 are identical. FIG. 109 shows the exemplary modules of the UI view subsystem 338 that perform the functions described above.

As shown in FIG. 109, the UI model client module 406 is used to communicate events to the UI model. This module 406 is also used to poll the UI model for the current status. Within a responsive status message, the UI model subsystem may embed a time to be used to synchronize the clocks of the automation computer 300 and the user interface computer 302.

The global slots module 408 provides a mechanism by which multiple callback routines (slots) can subscribe to be notified when given events (signals) occur. This is a "many-to-many" relationship, as a slot can be bound to many signals, and likewise a signal can be bound to many slots to be called upon its activation. The global slots module 408 handles non-screen specific slots, such as application level timers for UI model polling or button presses that occur outside of the screen (e.g., the voice prompt button).

The screen list class 410 contains a listing of all screens in the form of templates and data tables. A screen may be made up of a template and an associated data table that will be used to populate that screen. The template may be a window with widgets laid out on it in a generic manner and with no content assigned to the widgets. The data table may include records that describe the content used to populate the widgets and the state of the widgets. A widget state can be checked or unchecked (in the case of a checkbox style widget), visible or hidden, or enabled or disabled. The data table can also describe the action that occurs as a result of a button press. For example, a button on window 'A' derived from template '1' could send an event down to the UI model, whereas that same button on window 'B' also derived from template '1' could simply cause a local screen transition without propagating the event down to the UI model. The data tables may also contain an index into the context-sensitive help system.

The screen list class 410 forwards data from the UI model to the intended screen, selects the proper screen-based data from the UI model, and displays the screen. The screen list class 410 selects which screen to display based on two factors: the state reported by the UI model and the internal state of the UI view. In some cases, the UI model may only inform the UI view that it is allowed to display any screen within a category. For example, the model may report that the machine is idle (e.g., no therapy has been started or the setup phase has not yet occurred). In this case, it is not necessary to confer with the UI model when the user progresses from a menu into its sub-menu. To track the change, the UI view will store the current screen locally. This local sequencing of screens is handled by the table entries described above. The table entry lists the actions that respective buttons will initiate when pressed.

The language manager class 412 is responsible for performing inventory on and managing translations. A checksum may be performed on the list of installed languages to alert the UI view if any of the translations are corrupted and or missing. Any class that wants a string translated asks the language manager class 412 to perform it. Translations may be handled by a library (e.g., Qt®). Preferably, translations are requested as close as possible to the time of rendering. To this end, most screen template member access methods request a translation right before handing it to the widget for rendering.

A skin comprises a style-sheet and images that determine the "look and feel" of the user interface. The style-sheet controls things such as fonts, colors, and which images a widget will use to display its various states (normal, pressed, disabled, etc.). Any displayed widget can have its appearance altered by a skin change. The skin manager module 414 is responsible for informing the screen list and, by extension, the screen widgets, which style-sheet and skin graphics should be displayed. The skin manager module 414 also includes any animated files the application may want to display. On a skin change event, the skin manager will update the images and style-sheet in the working set directory with the proper set, which is retrieved from an archive.

The video manager module 416 is responsible for playing locale-appropriate video given a request to display a particular video. On a locale change event, the video manager will update the videos and animations in the working set directory with the proper set from an archive. The video manager will also play videos that have accompanying audio in the audio manager module 418. Upon playback of these videos, the video manager module 416 will make the appropriate request to the audio manager module 418 to play the recording that belongs to the originally requested video clip.

Similarly, the audio manager module 418 is responsible for playing locale-appropriate audio given a request to play a particular audio clip. On a locale change event, the audio manager will update the audio clips in the working set directory with the proper set from an archive. The audio manager module 418 handles all audio initiated by the UI view. This includes dubbing for animations and sound clips for voice prompts.

The database client module 420 is used to communicate with the database manager process, which handles the interface between the UI view subsystem 338 and the database server 366 (FIG. 99). The UI view uses this interface to store and retrieve settings, and to supplement therapy logs with user-provided answers to questions about variables (e.g., weight and blood pressure).

The help manager module 422 is used to manage the context-sensitive help system. Each page in a screen list that presents a help button may include an index into the context-sensitive help system. This index is used so that the help manager can display the help screen associated with a page. The help screen may include text, pictures, audio, and video.

The auto ID manager 424 is called upon during pre-therapy setup. This module is responsible for capturing an image (e.g., a photographic image) of a solution bag code (e.g., a datamatrix code). The data extracted from the image is then sent to the machine control subsystem to be used by the therapy subsystem to identify the contents of a solution bag 20, along with any other information (e.g., origin) included in the code.

Using the modules described above, the UI view subsystem 338 renders the screen views that are displayed to the user via the user interface (e.g., display 324 of FIG. 78). FIGS. 110-116 show exemplary screen views that may be rendered by the UI view subsystem 338. These screen views illustrate, for example, exemplary input mechanisms, display formats, screen transitions, icons and layouts. Although the screens shown are generally displayed during or before therapy, aspects of the screen views may be used for different input and output functions than those shown.

Figure 110:
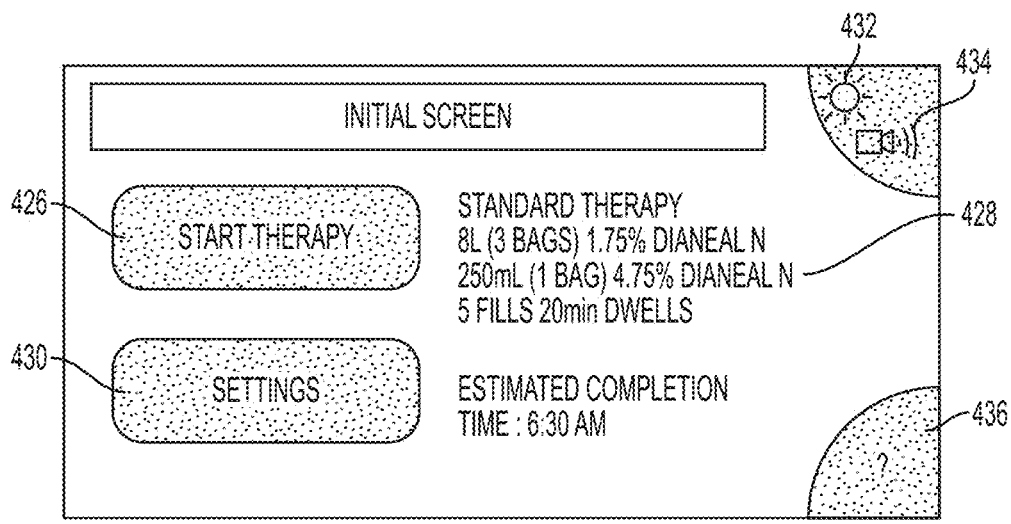
FIG. 110 shows an illustrative user interface initial screen that provides the user the option of selecting between start therapy or settings.

The screen shown in FIG. 110 is an initial screen that provides the user the option of selecting between "start therapy" 426 to initiate the specified therapy 428 or "settings" 430 to change settings. Icons 432 and 434 are respectively provided to adjust brightness and audio levels, and an information icon 436 is provided to allow the user to solicit more information. These icons may appear on other screens in a similar manner.

Figure 111:
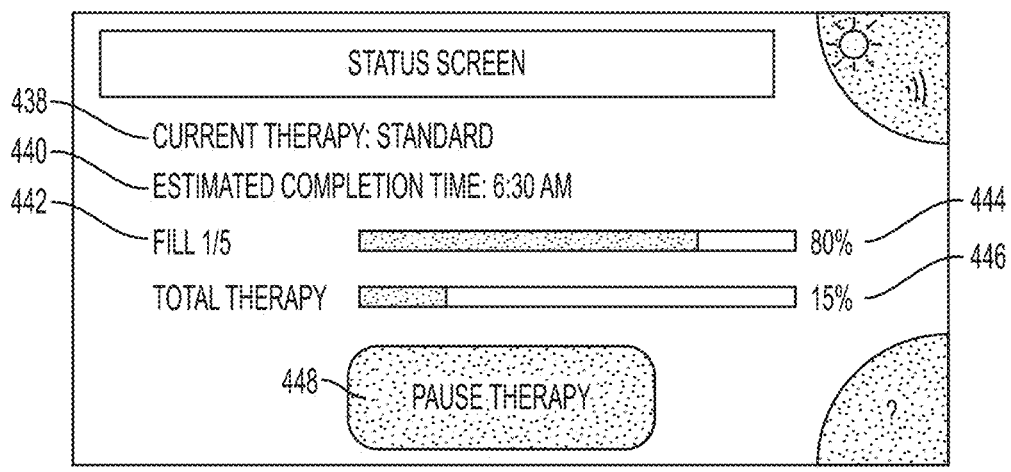
FIG. 111 shows an illustrative user interface status screen that provides information on the status of the therapy.

FIG. 111 shows a status screen that provides information the status of the therapy. In particular, the screen indicates the type of therapy being performed 438, the estimated completion time 440, and the current fill cycle number and total number of fill cycles 442. The completion percentage of the current fill cycle 444 and the completion percentage of the total therapy 446 are both numerically and graphically displayed. The user may select a "pause" option 448 to pause therapy.

Figure 112:
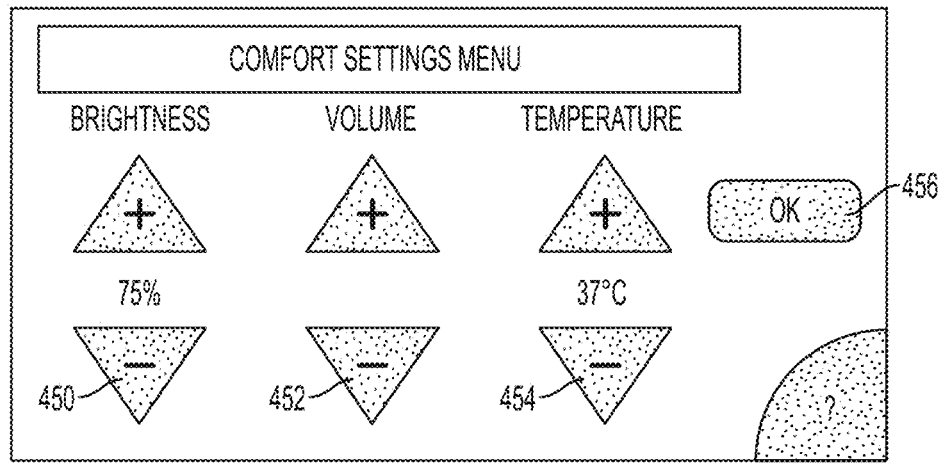
FIG. 112 shows an illustrative user interface menu screen with various comfort settings.

FIG. 112 shows a menu screen with various comfort settings. The menu includes brightness arrows 450, volume arrows 452 and temperature arrows 454. By selecting either the up or down arrow in each respective pair, a user can increase or decrease screen brightness, audio volume, and fluid temperature. The current brightness percentage, volume percentage and temperature are also displayed. When the settings are as desired, a user may select the "OK" button 456.

Figure 113:
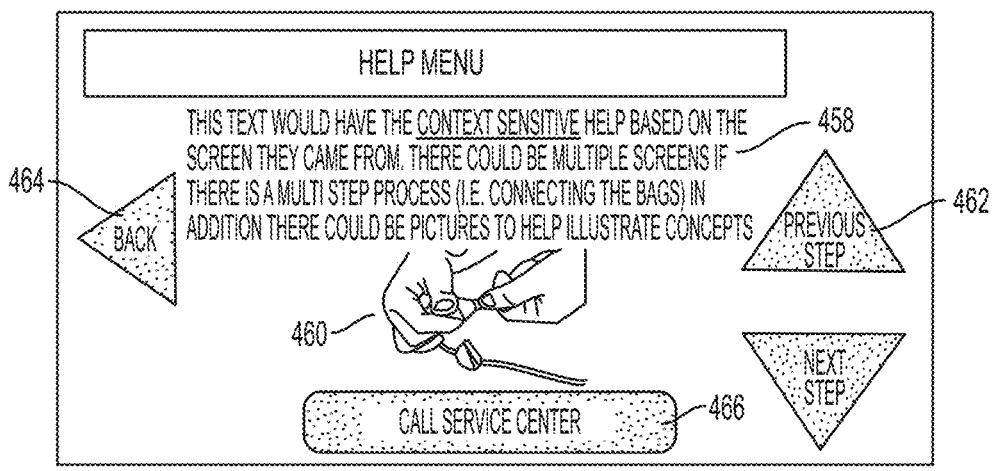
FIG. 113 shows an illustrative user interface help menu screen.

FIG. 113 shows a help menu, which may be reached, for example, by pressing a help or information button on a prior screen. The help menu may include text 458 and/or an illustration 460 to assist the user. The text and/or illustration may be "context sensitive," or based on the context of the prior screen. If the information provided to the user cannot conveniently be provided in one screen, for example in the case of a multi-step process, arrows 462 may be provided to allow the user to navigate backward and forward between a series of screens. When the user has obtained the desired information, he or she may select the "back" button 464. If additional assistance is required, a user may select the "call service center" option 466 to have the system contact the call service center.

Figure 114:
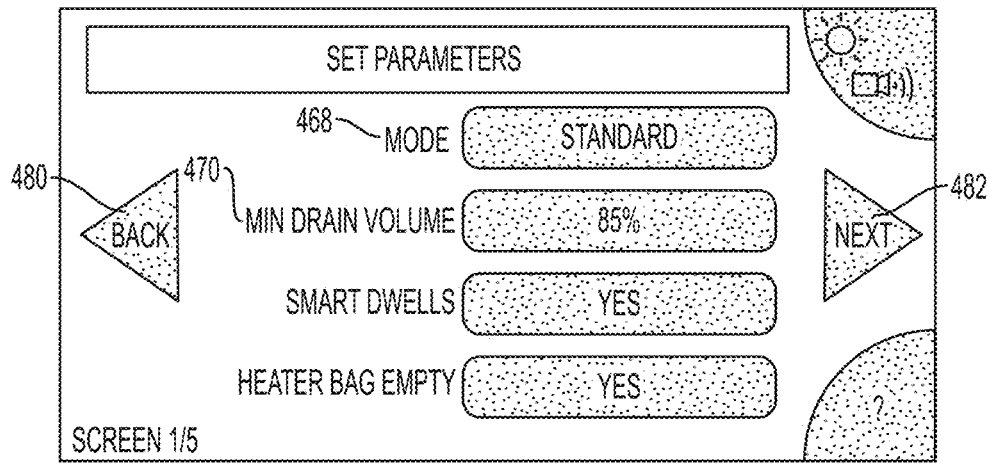
FIG. 114 shows an illustrative user interface screen that allows a user to set a set of parameters.
Figure 115:
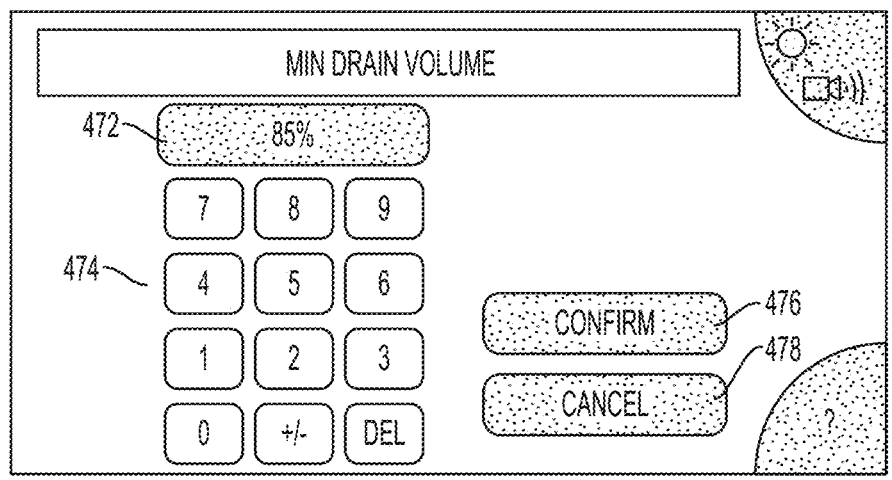
FIG. 115 shows an illustrative user interface screen that allows a user to adjust the minimum drain volume.

FIG. 114 illustrates a screen that allows a user to set a set of parameters. For example, the screen displays the current therapy mode 468 and minimum drain volume 470, and allows a user to select these parameters to be changed. Parameters may be changed in a number of ways, such as by selecting a desired option from a round robin style menu on the current screen. Alternatively, when the user selects a parameter to be changed, a new screen may appear, such as that shown in FIG. 115. The screen of FIG. 115 allows a user to adjust the minimum drain volume by inputting a numeric value 472 using a keypad 474. Once entered, the user may confirm or cancel the value using buttons 476 and 478. Referring again to FIG. 114, a user may then use the "back" and "next" arrows 480, 482 to navigate through a series of parameters screens, each including a different set of parameters.

Figure 116:
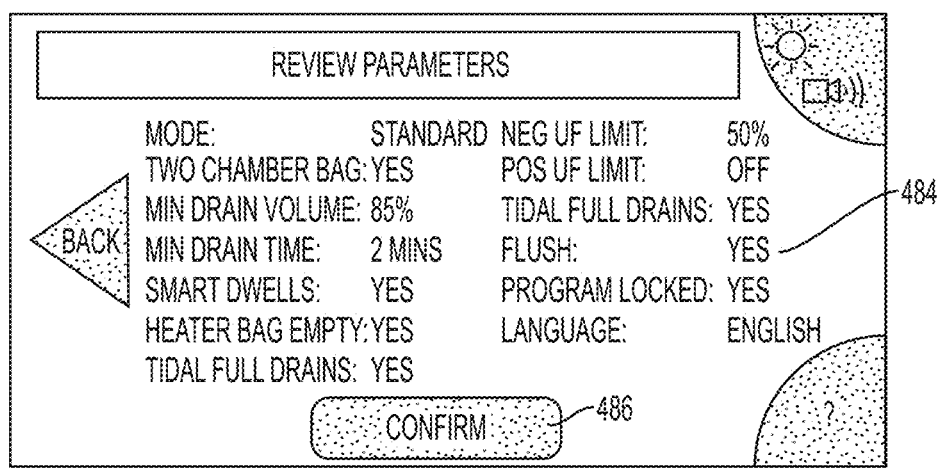
FIG. 116 shows an illustrative user interface screen that allows a user to review and confirm settings.

Once all desired parameters have been set or changed (e.g., when the user has navigated through the series of parameters screens), a screen such as that shown in FIG. 116 may be presented to allow a user to review and confirm the settings. Parameters that have changed may optionally be highlighted in some fashion to draw the attention of the user. When the settings are as desired, a user may select the "confirm" button 486.

Automated Peritoneal Dialysis Therapy Control

Continuous ambulatory peritoneal dialysis ("CAPD") is traditionally performed manually, with a patient or user transferring dialysis solution from a bag into his or her peritoneal cavity, having the fluid dwell in the abdomen for three to six hours, and then allowing the fluid to empty into a collection or drain bag. This is typically done three or four times a day. Automated peritoneal dialysis ("APD") differs from CAPD in that APD is achieved with the aid of a peritoneal dialysis machine ("cycler") that performs a series of fill-dwell-drain cycles during a period of several hours (e.g. when asleep or at night). In APD, the fluid introduced during a fill phase of a cycle, plus any ultrafiltration fluid, may not drain completely during the following drain phase of the cycle. This may be a result of the user's position in bed, leading to sequestration of fluid, for example, in a recess in the peritoneal cavity, and preventing an indwelling catheter from accessing all of the fluid present. In continuous cycling peritoneal dialysis ("CCPD"), the cycler attempts to perform a full drain after a fill and dwell phase in order to prevent accumulation of retained fluid (a residual intraperitoneal volume) with each succeeding cycle. APD generally comprises a plurality of short nighttime exchanges of dialysate while the user is connected to the cycler 14 and asleep. At the end of a nighttime therapy, a volume of dialysis fluid—possibly of different composition—may be left in the peritoneal cavity during the day for continued exchange of solutes, transfer of waste compounds, and ultrafiltration. In intermittent peritoneal dialysis ("IPD"), multiple exchanges of dialysate are performed over a period of time (e.g., at night), without having a prolonged residual (or daytime) dwell cycle.

Therapy with a cycler 14 generally begins with an initial drain phase to attempt to ensure that the peritoneal cavity is empty of fluid. The characteristics of the dialysate solution usually cause some transfer of fluid from the patient's tissues to the intraperitoneal space-ultrafiltration. As therapy proceeds through a series of cycles, fluid may accumulate in the intraperitoneal cavity if the drain phase does not yield the volume of fluid infused during the fill phase, plus the volume of ultrafiltered fluid produced during the time that dialysate solution is in the peritoneal cavity. In some modes, the cycler 14 may be programmed to issue an alarm to the user when the drain volume has not matched the volume of fluid infused plus the expected ultrafiltration ("UF") volume. The expected UF volume is a function of—among other things—the individual patient's physiology, the chemical composition of the dialysate solution, and the time during which the dialysate solution is expected to be present in the peritoneal cavity.

In other modes, the cycler 14 may proceed to the next fill-dwell-drain cycle if a pre-determined amount of drain time has passed and a pre-determined minimum percentage (e.g. 85%) of the preceding fill volume has been drained. In this case, the cycler 14 may be programmed to alarm if the drain flow decreases below a pre-determined rate after the minimum drain time and before the minimum drain percentage has been reached. The cycler 14 may be programmed to alert the user after several minutes (e.g., two minutes) of attempting but failing to maintain a pre-determined flow rate when pumping fluid from the peritoneal cavity. A low-flow condition may be detectable by the cycler 14 because of the increased amount of time required to fill a pump chamber before end-of-stroke is detected by the controller. A zero-flow or no-flow condition may be detectable by the cycler 14 because of the detection by the controller of a premature end-of-stroke state. The duration of the time delay before alerting the user or initiating a new fill-dwell-drain cycle may be programmed to be a few minutes in a low-flow condition (e.g., 2 minutes), and may be shorter (e.g., 30 seconds) in a no-flow condition. A shorter wait-time during a no-flow condition may be preferable, for example, because it may be associated with a greater degree of patient discomfort, or may be the result of a quickly correctable problem, such as a bend in the patient line or catheter. This time delay may be programmed at the cycler 14 manufacturing stage or may be selectable by a clinician as a prescription parameter. The extent of the delay may be governed, among other things, by the countervailing desire of the user or clinician to stay within the targeted total therapy time (keeping in mind that little dialysis is likely to occur when the intraperitoneal volume ("IPV") is low or close to zero). If a full drain is not achieved, the cycler 14 may also track the amount of fluid estimated to be accumulating with each cycle, and issue a warning or alarm if the cumulative IPV exceeds a pre-determined amount. This maximum IPV may be a parameter of the therapy prescription programmed into the cycler 14 by the clinician, taking account of the particular physiological characteristics of the individual patient/user.

One method of dealing with the cumulative retention of fluid during a series of CCPD cycles is to convert the CCPD therapy to a tidal peritoneal dialysis ("TPD") therapy. TPD generally comprises a fill-dwell-drain cycle in which a drain volume is intentionally made a prescribed fraction of the initial fill volume (which may also be initially be entered by the clinician as a prescription parameter). A pre-determined percentage of the infused fluid, or a pre-determined amount of fluid is arranged to remain in the peritoneal cavity during the subsequent fill-dwell-drain cycles during a therapy. Preferably, the subsequent fill volumes are also reduced to match the drain volume (minus the expected UF) in order to maintain a relatively constant residual intraperitoneal volume. For example, an initial fill volume of 3000 ml may be introduced at the beginning of therapy, followed by subsequent drain and fill plus expected UF volumes amounting to only 1500 ml, i.e. 50% of the initial fill volume. The reserve or residual fluid in the peritoneal cavity is then drained completely at the end of therapy. In an alternative mode, a complete drain may be attempted after a pre-determined or prescribed number of fill-dwell-drain cycles (e.g., a complete drain may be attempted after three cycles of tidal therapy, this grouping comprising a therapy "cluster"). TPD may be beneficial in that users may experience less discomfort associated with repeated large fill volumes or repeated attempts to fully empty the peritoneal cavity. Low-flow conditions associated with small intraperitoneal fluid volumes may also be reduced, thus helping to avoid extending the total therapy time. To reduce the discomfort associated with attempting to drain small residual volumes, for example, the tidal drain volume may be set at 75% of the initial fill volume (plus-or-minus expected UF volume), for example, leaving approximately 25% as a reserve or residual volume in the peritoneal cavity for the duration of therapy, or for the duration of a cluster of cycles.

A cycler 14 may also be programmed to convert a CCPD mode of therapy to a TPD mode of therapy during the course of therapy if the user chooses to keep a residual volume of fluid in the peritoneal cavity at the end of the subsequent drain phases (e.g., for comfort reasons). In this case, the cycler 14 is programmed to calculate a choice of residual volumes (or volumes as a percent of initial fill volume) based on the number of extra cycles to be added to the therapy and the volume of remaining dialysate to be infused. For example, the cycler controller can calculate the remaining fill volumes based on the remaining cycles that include an additional one, two or more cycles. Having determined the fill volumes for each of these possibilities, the cycler controller can calculate how much residual volume can be left at the end of each remaining drain phase while ensuring that the IPV remains under a maximum prescribed IPV (Max IPV). The cycler 14 may then present the user with a range of possible residual volumes (as a percentage of the initial fill volume or in volumetric terms) available for each remaining cycle in a therapy extended by one, two or more cycles. The user may make the selection based on the number of extra cycles chosen and the desired amount of post-drain residual volume. Switching to tidal therapy may help to reduce the number of low-drain-flow alerts to the user, which can be particularly advantageous during nighttime therapy.

In switching to tidal mode, the cycler 14 may be programmed to select a reserve or residual volume percentage (volume remaining in the peritoneal cavity as a percent of the fill volume plus expected UF). Alternatively, the reserve volume may be user-selectable or clinician-selectable from a range of values, optionally with the clinician having the ability to select a wider range of possible values than the user. In an embodiment, the cycler 14 may calculate the effects of adding one, two or three additional cycles on the remaining fill volumes and the expected residual IP volume percentage, and give the user or clinician the option of selecting among those calculated values. Optionally, the cycler 14 may be constrained to keep the residual IP volume percentage below a pre-determined maximum value (e.g., a percentage of the initial fill volume plus expected UF, or a percentage of the maximum permissible IPV).

If CCPD is converted to TPD, one or more therapy cycles (fill-dwell-drain cycles) may need to be added to a therapy to use all of the prescribed volume of dialysate for the therapy session. The remaining volume to be infused going forward would then be divided by the remaining number of cycles. Furthermore, the cycler 14 may be programmed to allow the clinician or user to select between extending the targeted total therapy time to accommodate the additional cycles (cycle-based therapy), or to attempt to maintain the targeted therapy time by adjusting the dwell times (i.e., shortening them) if necessary to reduce the fill-dwell-drain cycle durations going forward (time-based therapy).

In an alternative embodiment, the cycler 14 may allow the residual IP volume to fluctuate (optionally within pre-determined limits) from one cycle to the next, depending on how much fluid can be drained within a specified drain time interval. The time available for the drain phase may be limited if the cycler 14 has been programmed to complete the therapy within the previously scheduled time, or the drain phase may be terminated to prevent the cycler 14 from attempting to pull fluid at a slow rate for a prolonged period of time. In switching from CCPD to TPD, if the cycler 14 adds one or more additional cycles to perform a complete therapy with the available dialysate solution, then meeting the scheduled therapy end-time may require shortening the dwell times, or reducing each drain phase, which could cause the residual volume for the tidal mode to vary, depending on the drain flow conditions. As the cycler 14 estimates and tracks the amount of residual volume, it may be programmed to calculate whether the subsequent fill volume plus expected UF volume will reach or exceed a prescribed maximum IPV. If so, the cycler 14 can alert and provide the user with two or more options: the user may terminate treatment, repeat or extend a drain phase in an attempt to lower the residual intraperitoneal volume, or add a cycle to reduce the subsequent fill volumes. After calculating the effect on treatment time of adding an additional one or more cycles (increased number of cycles vs. reduced fill and drain times at lower volumes) the cycler 14 may optionally reduce subsequent dwell times by an amount of time necessary to offset the additional therapy time generated by an additional one or more cycles.

The cycler 14 may be programmed to deliver an optional last-fill phase that delivers fresh dialysate of the same or a different composition to the user's peritoneal cavity for an extended dwell time while not connected to the cycler 14 (e.g., a prolonged dwell phase for a "day therapy," i.e., during the day following a nighttime therapy). At the user's option, the last fill volume may be selected to be less than the fill volumes used during nighttime therapy. The cycler 14 may also optionally prompt the user to select an optional extra last drain to give the user the chance to completely empty the peritoneal cavity prior to the infusion of a last fill volume (which may be carried by the user for a relatively prolonged period of time after the end of nighttime therapy). If this function is enabled, the cycler 14 may prompt the user to sit up or stand, or otherwise move about to mobilize any trapped fluid in the peritoneal cavity during this last drain phase.

The cycler 14 may also be programmed to account for an expected amount of ultrafiltration ("UF") fluid produced during a dwell phase on or off the machine, and to alert the user if a minimum drain volume that includes the volume infused plus this expected UF is not drained either initially at the beginning of therapy, or during a fill-dwell-drain cycle during therapy. In an embodiment, the cycler 14 may be programmed for a minimum initial drain volume and a minimum initial drain time, and to pause or terminate the drain phase if the measured drain flow rate has decreased below a pre-determined threshold value for a pre-determined number of minutes. The minimum initial drain volume may comprise the volume of the last fill phase in the preceding nighttime therapy, plus an expected UF volume from the day therapy dwell phase. If the minimum (or more) initial drain volume is achieved, the minimum initial drain time is reached, and/or the drain flow rate has decreased, the IPV tracked by the cycler controller may be set to zero at the end of the initial drain phase. If not, the cycler 14 may alert the user. The cycler 14 may allow the user to bypass the minimum initial drain volume requirement. For example, the user may have manually drained at some time before initiating APD. If the user elects to forego adherence to the minimum initial drain volume, the cycler 14 may be programmed to perform a full drain at the end of the first cycle regardless of the type of therapy selected by the user. If enabled, this feature helps to ensure that the second fill-dwell-drain cycle begins at an IPV that is as close to zero as possible, helping to ensure that a prescribed maximum IPV should not be exceeded during subsequent cycles of the therapy.

The cycler 14 may also be programmed to allow the user to pause therapy. During a pause, the user may have the option to alter the therapy by reducing the fill volume, reducing therapy time, terminating a planned "day therapy," or ending therapy altogether. In addition, the user may have the option to perform an immediate drain at any time during therapy. The volume of an unscheduled drain may be selected by the user, whereupon the cycler 14 may resume the cycle at the stage at which it was interrupted.

The cycler 14 may be programmed to have a prescriber or "clinician" mode. A software application may be enabled to allow a clinician to create or modify a set of parameters forming the therapy prescription for a particular patient or user, as well as setting the limits within which a user may adjust user-accessible parameters. The clinician mode may also allow a clinician to fix one or more treatment parameters that would otherwise be accessible to a user, as well as lock a parameter to prevent a user from changing it. A clinician mode may be password-protected to prevent unauthorized access. The clinician mode application may be constructed to interface with a database to read and write the parameters comprising a prescription. Preferably, a "user mode" permits a user to access and adjust user-accessible parameters during a pre-therapy startup phase of a therapy. In addition, an "active therapy mode" may optionally be available to a user during therapy, but with access to only a subset of the parameters or parameter ranges available in the user mode. In an embodiment, the cycler controller may be programmed to allow parameter changes during active therapy mode to affect only the current therapy, the parameter settings being reset to previously prescribed values before subsequent therapies. Certain parameters preferably are not user-adjustable at all, user-adjustable with concurrence of a clinician through a prescription setting, or user-adjustable only within a range of values set by a clinician in programming a prescription. Examples of parameters that may not be adjustable solely by the user include, for example, the minimum initial drain volume or time, maximum initial fill volume, and maximum IPV. User-adjustable parameters may include, for example, the tidal drain frequency in a cluster (e.g., adjustable between 1 and 5 cycles), and the percentage of a tidal therapy fill volume to be drained (e.g., adjustable up or down by a pre-determined amount from a default value of, for example, 85%). In an alternative embodiment, the clinician mode may allow a clinician to prevent a user from programming a maximum IPV to be greater than a pre-determined multiple (e.g., 200%) of the initial fill volume assigned to a nighttime fill-dwell-drain cycle.

The cycler 14 may also be programmed to routinely alert the user and to request confirmation when a user-adjustable parameter is entered that is outside of pre-determined ranges. For example, if the maximum IPV has been made user-adjustable in the clinician mode, the cycler 14 may alert the user if he or she attempts to select a Max IPV value outside of a fractional range (e.g., 130-160%) of the programmed fill volume for nighttime therapy.

The cycler 14 may also be programmed to alert the user (and possibly seek confirmation) if the initial drain volume has been made user-adjustable in the clinician mode, and the user selects an initial drain volume below a pre-determined percentage of the fill volume of the last therapy (e.g., if it is adjusted to be less than 70% of the last fill volume). In another example, the cycler 14 may be programmed to alert the user (and possibly seek confirmation) if the total expected UF volume has been made user-adjustable by the clinician mode, and the user selects a total expected UF volume to be below a certain percentage of the total volume processed for a nighttime therapy (e.g., if the total expected UF volume is set at less than 7% of the total nighttime therapy volume). Generally the expected UF volume may be determined empirically by a clinician based on a user's prior experience with peritoneal dialysis. In a further embodiment, the cycler 14 may be programmed to adjust the expected UF volume value according to the actual UF volume in one or more preceding cycles of a therapy. This volume may be calculated in a CCPD mode by calculating the difference between a measured full drain volume and the measured fill volume that preceded it. In some cases, it may be difficult to determine when the peritoneal cavity is fully drained of fluid, and it may be preferable to take an average value of the difference between a full drain volume and a preceding fill volume over a number of cycles.

Some of the programmable treatment settings may include:
- the number of daytime exchanges using the cycler 14;
- the volume of solution to be used for each daytime exchange;
- the total time for a nighttime therapy;
- the total volume of dialysis solution to be used for nighttime therapy (not including a last fill volume if a daytime dwell phase is used);
- the volume of dialysis solution to be infused per cycle;
- in a Tidal therapy, the volume of fluid to be drained and refilled during each cycle (a percentage of the initial fill volume in a nighttime therapy);
- the estimated ultrafiltration volume to be produced during a nighttime therapy;
- the volume of solution to be delivered at the end of a therapy and to be left in the peritoneal cavity for an extended period (e.g, daytime dwell);
- the minimum initial drain volume required to proceed with a therapy;
- the maximum intraperitoneal volume known or estimated to be present that the cycler 14 will allow to reside in the patient's peritoneal cavity which may be based on the measured volumes introduced into the peritoneal cavity, the measured volume removed from the peritoneal cavity, and the estimated volume of ultrafiltration produced during therapy.

Some of the more advanced programmable treatment settings for the cycler 14 may include:
- the frequency of full drains to be conducted during tidal peritoneal dialysis;
- the minimum percentage of the volume delivered to the peritoneum during a day therapy that must be drained before a subsequent fill is allowed;
- prompting the user to perform an extra drain phase at the end of therapy if a pre-determined percentage of the estimated total UF is not collected;
- a minimum length of time required to perform an initial drain before therapy begins;
- a minimum length of time required to perform subsequent drains, either in day-therapy mode or night-therapy mode;
- variable dwell times, adjusted by the cycler controller to maintain a fixed total therapy time when either the fill times or drain times have been changed thus helping to avoid disruptions of the user's schedule;

The cycler 14 can provide the user with alerts or warnings about parameters that have been entered outside a recommended range of values. For example, a warning may be issued if:
- the minimum initial drain volume before a therapy is less than a pre-determined percentage of the currently prescribed last-fill volume at the end of the previous therapy (e.g., <70%);
- the maximum IPV is outside a pre-determined percentage range of the fill volume per cycle (e.g., <130% or >160%);
- the UF volume threshold to trigger an alert to perform an extra drain at the end of therapy is less than a pre-determined percentage of the estimated UF volume per therapy (e.g. <60%);
- the calculated or entered dwell time is less than a pre-determined number of minutes (e.g., <30 minutes);
- the estimated UF volume per therapy is more than a pre-determined percentage of the total dialysis solution volume per therapy (e.g., >25%);
- the sum of all the solution bag 20 volumes for a therapy should be somewhat greater than the volume of solution used during a CCPD therapy session, in order to account for priming of fluid lines and for loss of fluid to drain during air mitigation procedures.

In the clinician mode, in addition to having a selectable maximum IPV, the cycler 14 may be programmed to accept separate minimum drain times for initial drains, day-therapy drains, and night-therapy drains. In the user mode or in the active-therapy mode, the cycler 14 may be programmed to prevent a user from skipping or shortening the initial drain phase at the start of a therapy. In addition, the cycler 14 may permit early termination of the initial drain phase only after a series of escalating low-drain-flow alerts have been issued. An initial alert may instruct the user to change positions or re-position the peritoneal dialysis catheter, which may then be followed by additional alternative instructions if low flow conditions persist, up to a maximum number of alerts. The cycler 14 may also require the user to confirm any change the user makes to the planned therapy, including bypassing a phase. The clinician may specify in a prescription setting to prevent the user from bypassing a drain phase during nighttime therapy. During therapy, the cycler 14 controller may be programmed to not reset the IPV to zero unless the drain volume exceeds the preceding fill volume (to account for the additional IPV produced by ultrafiltration). The cycler 14 may also be programmed to display to the user the estimated IPV during fills, and may notify the user if any drain volume exceeds the fill volume by a pre-determined amount (e.g. drain volume greater than fill volume plus expected UF volume).

The cycler 14 may also be programmed to identify errors in user input and to notify the user of apparent input errors. For example, the number of cycles during a therapy calculated by the cycler, based on the prescription parameters entered by the clinician or user, should be within a pre-determined range (e.g. 1-10). Similarly, the dwell time calculated by the cycler 14 should be greater than zero. In addition, the maximum IPV entered by the user or clinician should be greater than or equal to the fill volume per cycle, plus the expected UF volume. Furthermore, the cycler 14 may be programmed to reject an entered value for maximum IPV that is greater than a pre-determined amount over the fill volume per cycle (e.g., maximum IPV≤200% of initial fill volume). In some cases, it may be desirable for the cycler 14 to be programmed to set the maximum IPV to no greater than the last fill volume if the solution is to remain in the peritoneal cavity for a prolonged period of time, such as during a daytime therapy. In this case, the cycler 14 may be programmed to alert the user if the cycler 14 controller calculates that the last drain volume amounts to less than a complete drain, whereupon the cycler 14 may provide the user with a choice to terminate therapy or undertake another drain phase.

Managing Increasing IPV while Minimizing Alarms

In an embodiment, the cycler 14 may be programmed to track and manage an increasing IPV during a therapy without converting the therapy from continuous cycling peritoneal dialysis ("CCPD") therapy to a standard tidal peritoneal dialysis ("TPD") therapy, which would fix the residual volume to a percentage of the initial fill volume. Rather, an adaptive tidal therapy mode may be initiated, in which the residual volume is allowed to fluctuate or 'float' in response to any slow-drain conditions that may be encountered during any drain phase. The cycler 14 may be programmed to permit this mode to operate as long as any subsequent fill volume plus expected UF does not exceed a prescribed maximum IPV ("Max IPV"). Thus the dwell-phase IPV may be permitted to increase or decrease during a therapy up to a maximum IPV, preferably set by a clinician in the clinician mode. In this adaptive tidal therapy mode, at each drain phase during a therapy, the cycler 14 continues to attempt a complete drain within the allotted time, or as long as a low-flow or no-flow condition has not been detected for a prescribed or pre-set number of minutes. The residual volume at the end of the drain phase is allowed to vary or 'float' as long as it does not exceed an amount that would lead to exceeding the maximum IPV in the next fill phase or during the next dwell phase. In a preferred embodiment, the cycler 14 may be programmed to not issue an alert or alarm to the user as long as it calculates that the subsequent fill phase or dwell phase will not reach or exceed maximum IPV.

The cycler 14 may be programmed to deliver full fill volumes during each cycle of a therapy until the cycler 14 controller calculates that the next fill volume will likely cause the IPV to exceed the maximum IPV. At a convenient time (such as, e.g., the end of a drain phase), the cycler 14 controller may be programmed to calculate a maximum residual IP volume, which represents the maximum permissible residual IP volume at the end of a drain to allow the next cycle to proceed with the previously programmed fill volume. Partial drains will be permitted by the cycler 14 without alarming or issuing an alert as long as the amount of fluid drained brings the residual IPV below the maximum residual IPV. If the estimated or predicted IPV at the end of a drain phase is less than the maximum residual IPV, the cycler 14 can proceed with a full fill phase in the next cycle without risking exceeding the Max IPV. If the estimated IPV at the end of a drain is greater than the maximum residual IPV, the cycler 14 controller may trigger an alert to the user that the subsequent fill plus UF may exceed the maximum IPV. In an embodiment, the cycler 14 may display several options for the user to respond to this alert: it may allow the user to terminate therapy, to attempt another drain phase, or to proceed to enter a revised-cycle therapy mode, in which each subsequent fill volume is reduced and one or more cycles are added to the therapy (thereby ensuring that the remaining volume of fresh dialysate is used during that therapy). In an embodiment, a clinician or user may enable the cycler 14 at the beginning of therapy to automatically enter this revised-cycle therapy mode without having to alert the user during therapy.

In some circumstances, the number of additional cycles may be limited by the planned total therapy time. For example, the duration of night time therapy may be limited by the time at which the user is scheduled to wake up or to get up to go to work. For nighttime therapy, the cycler 14 controller may be programmed, for example, to prioritize the use of all dialysate solution that was planned for therapy in favor of ending therapy at the scheduled time. If the clinician or user has selected the dwell time to be adjustable, then the cycler 14 controller will (1) add one or more cycles to ensure that the fill volume plus expected UF does not exceed maximum IPV; (2) ensure that all of the dialysis solution is used for therapy; and (3) attempt to reach the targeted end-of-therapy time by shortening the dwell times of the remaining cycles. An alternative option available to the user is to extend the end-of-therapy time. In a preferred embodiment, the cycler 14 is programmed to add one or two additional cycles to the therapy to permit a reduced fill volume in order to prevent exceeding the maximum IPV. The cycler 14 controller is programmed to recalculate the maximum residual IPV using the reduced fill volume occasioned by the increased number of cycles. Thus, if a low flow condition during drain occurs at the same IPV, the new higher maximum residual IPV may permit dialysis to proceed without exceeding maximum IPV. If the fill volume cannot be reduced enough by adding a maximum allowable number of extra cycles (e.g., 2 cycles in an exemplary night time therapy scenario), then the cycler 14 may present the user with two options: re-attempt a drain phase, or end therapy. The cycler 14 may be programmed to reset the fill volume again after an adjustment of the fill volume, possibly adding an additional cycle, if a low flow condition at the end of drain is again encountered at an IPV above the newly recalculated and reset maximum residual IPV. Thus the cycler 14 may be programmed to repeatedly adjust the subsequent fill volumes to prevent exceeding maximum IPV if a premature low flow condition is repeatedly encountered.

Replenishment Limitation on Dwell Time Reductions

In an embodiment, if the cycler 14 reduces fill volumes by adding one or more cycles, then it may also reduce the dwell time in order to attempt to keep the therapy session within the total scheduled therapy time. This mode may be useful for nighttime therapy, so that the patient may be reasonably assured that therapy will have ended before a planned time of awakening in the morning. However, the cycler 14 will continue to replenish the heater bag 22 as needed during therapy, the replenishment generally occurring during dwell phases (when the cassette 24 is not otherwise pumping to or from the patient). Therefore, in some circumstances, total therapy time may need to be extended when the required reduction in remaining dwell times leads to a total remaining dwell time that is less than the total estimated time needed to replenish the heater bag 22 with the remaining fresh dialysate. The cycler controller may therefore calculate a maximum dwell time reduction available for the remaining therapy cycles, and extend total therapy time to ensure that the remaining fresh dialysate is properly heated. Because the cycler controller keeps track of the volume of dialysate in the heater bag 22, the temperature of the dialysate in the heater bag 22, and the volume of remaining fresh dialysate that is scheduled to be infused, it can calculate an estimate of the amount of time needed to replenish the heater bag 22 to a pre-determined volume (given its intrinsic pumping capacity), and the time needed to bring the dialysate in the heater bag 22 up to the prescribed temperature before it is infused into the user. In an alternative embodiment, the cycler controller may interrupt pumping operations to or from the user at any time in order to engage the pumps for replenishment of the heater bag 22. The cycler controller may be programmed, for example, to prevent the volume of fluid in the heater bag 22 from dropping below a pre-determined volume at any time during therapy, other than during the last cycle.

In an embodiment, the cycler 14 may be programmed to deliver fluid to the heater bag 22 at a greater flow rate than when it is transferring fluid to or from the user. If binary valves are used to regulate the flow of control fluid or gas between the positive/negative pressure reservoirs and the control or actuation chambers of the cassette 24 pumps, the controller may issue on-off commands to the valves at different pressure levels measured in the control or actuation chambers of the pumps. Thus the pressure threshold in the pump control or actuation chamber at which the controller triggers an 'off' command to the binary valve may have an absolute value that is greater during delivery to or from the heater bag 22 than the corresponding pressure threshold when the cycler 14 is delivering or pulling fluid to or from the user's peritoneal cavity. A higher average pressure applied to the pump membrane may be expected to result in a greater flow rate of the liquid being pumped. A similar approach may be used if variable orifice valves are used to regulate the flow of control fluid or gas between the pressure reservoirs and the control or actuation chambers of the cassette 24 pumps. In this case, the controller may modulate the flow resistance offered by the variable orifice valves to maintain a desired pressure in the pump control chamber within pre-determined limits as the pump membrane is moving through its stroke.

Exemplary Modes of Therapy

Figure 117:
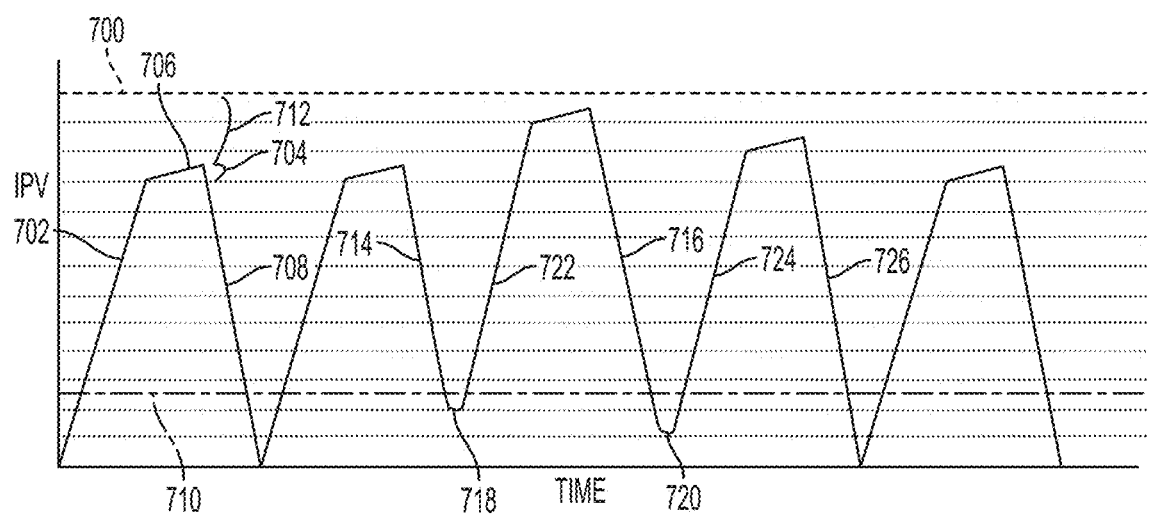
FIG. 117 is an illustration of an adaptive tidal therapy mode during CCPD.

FIG. 117 is a graphical illustration (not to scale in either volumes or time) of an adaptive tidal mode of the cycler 14 when in a CCPD mode. The initial drain at the beginning of therapy is omitted for clarity. The maximum IPV (Max IPV) 700 is a prescription parameter preferably set by the clinician. The initial fill volume 702 is also preferably set by the clinician as a prescription parameter. The expected UF volume is represented by the additional IPV increase 704 during the dwell phase 706. The expected UF volume for an entire therapy may be entered by a clinician into the prescription, and the cycler 14 may then calculate the dwell time per cycle based on the number of cycles during the therapy, and thus the expected UF volume per cycle. It should be noted that ultrafiltration is expected to occur throughout the fill-dwell-drain cycle, and the expected UF volume may include the volume of fluid ultrafiltered throughout the cycle period. In most cases, the dwell time is much larger than the fill or drain times, rendering the ultrafiltration volumes during fill or drain relatively insignificant. The fill and drain times may be adjustable by altering the pressure set points used by the controller to regulate the control valves between the pressure reservoirs and the pumps. However, the adjustability of liquid delivery flow rates and pressures to the user is preferably limited in order to ensure user comfort. Thus the expected UF volume per cycle 704 may be reasonably representative of ultrafiltration during the cycle. The drain phase 708 of the cycle in this example is a full drain, as would occur in a CCPD mode of therapy.

The maximum residual volume 710 can be calculated by the cycler controller once the Max IPV 700, the initial fill volume 702, and the expected UF volume are entered by the clinician. The maximum residual volume 710 is an indication of the 'headroom' 712 available in the peritoneal cavity to accommodate more fluid before reaching Max IPV 700. In an adaptive tidal mode within a CCPD mode of therapy, as long as a drain volume 714, 716 leaves an estimated residual volume 718, 720 less than the maximum residual volume 710, the subsequent fill volume 722, 724 can remain unchanged, because Max IPV 700 is not expected to be breached. As shown in FIG. 117, the occurrence of a low flow condition at the residual volumes 718 and 720 triggers the cycler 14 to initiate the next fill phase 722 and 724. During this form of therapy, the cycler 14 will continue to attempt to perform a full drain 726 within an allotted time assuming a low-flow or no-flow condition is not encountered before the estimated zero IPV is reached. Thus, even if a full drain is not performed (because of a low-flow or no-flow condition), in this case, full fill volumes will continue to be infused, the residual IPV will be allowed to float within a pre-determined range, and the user preferably will not be disturbed by any alarms or alert notifications.

Figure 118:
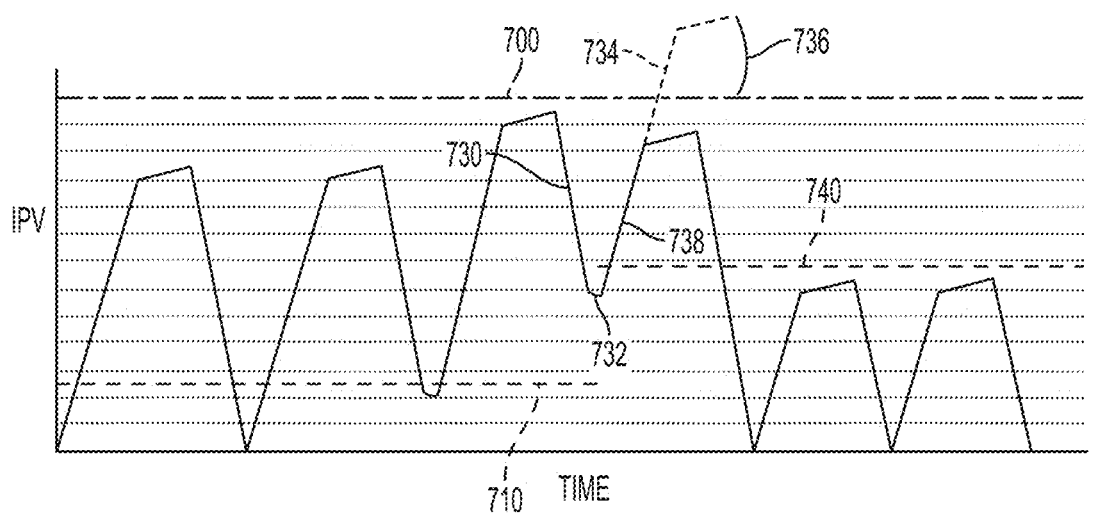
FIG. 118 is an illustration of the implementation of a revised-cycle mode during CCPD.

FIG. 118 is a graphical illustration of how the cycler 14 may handle incomplete drains that fail to reach the maximum residual IPV 710. In this case, the drain phase 730 of the third cycle encounters a low-flow or no-flow condition that prevents the cycler 14 from draining the peritoneal cavity below the maximum residual IPV 710. Given the estimated residual volume 732 (the estimated residual volume after a pre-determined duration of a low-flow condition), the cycler 14 calculates that a subsequent fill phase volume 734 will likely cause the prescribed Max IPV 700 to be reached or exceeded 736. Therefore, at the end of drain phase 730, the cycler 14 may alert the user to this issue. The user may then have the option to terminate therapy, instruct the cycler 14 to re-attempt a drain phase (after possibly changing positions or repositioning the PD catheter), or instruct the cycler 14 to enter into a revised-cycle therapy mode in which the subsequent fill volumes are reduced and one or more cycles added to complete the therapy with the planned total volume of dialysate. To keep within the allotted or prescribed total therapy time, the cycler 14 can calculate the duration of the modified cycles by reducing the fill and drain times to account for the reduced fill and drain volumes, and then determining whether and how much the dwell times need to be reduced to meet the designated ending time of the therapy session.

A user may optionally enable a revised-cycle mode of CCPD at the beginning of a therapy, so that the occurrence of a low-flow condition during therapy can trigger the revised-cycle mode without disturbing the user with an alert or alarm. Otherwise, the user may select the revised-cycle mode upon the occurrence of a low-flow condition above the maximum residual IPV. If the user elects to enter a revised-cycle mode, the cycler controller may calculate the required fill volumes for each of an additional one, two or more cycles (remaining fill volume divided by the remaining planned cycles plus the additional one or more cycles). If one additional cycle yields a fill volume (plus expected UF) low enough to avoid reaching or exceeding Max IPV, the cycler 14 (either automatically or at the user's option) will resume CCPD at that new fill volume 738. Otherwise, the cycler 14 controller will calculate a new fill volume based on an additional two cycles of therapy. (Rarely, more than two additional cycles may be required to ensure that Max IPV is not breached during the remaining therapy. If the additional cycles require a substantial reduction in the remaining dwell times, the cycler 14 may alert the user, particularly if a minimum dwell time has been prescribed, or heater bag 22 replenishment limitations will require a lengthening of the total therapy time). The now-reduced fill volume 738 allows the cycler controller to re-calculate a revised maximum residual IPV 740, which is a function of the sum of the new fill volume plus the expected UF volume per cycle. Any subsequent drain phases that leave an estimated residual IP volume less than the revised maximum residual volume 740 will preferably not trigger any further alerts or alarms to the user, allowing for the adaptive mode of tidal therapy to remain enabled. In an embodiment, the cycler 14 may re-calculate the expected UF volume if it has reduced the duration of the remaining dwell phases in order to stay within the planned total therapy time. Any re-calculated reduction in the expected UF volume may further increase the revised maximum residual IPV. In the example shown in FIG. 118, the cycler 14 continues to perform CCPD mode therapy, and happens to be able to drain fully in the remaining cycles. In order not to further inconvenience the user, the cycler 14 may optionally refrain from making any further adjustments to the therapy (particularly if the total volume of dialysate and the total therapy time have been kept within the prescribed parameters).

Figure 119:
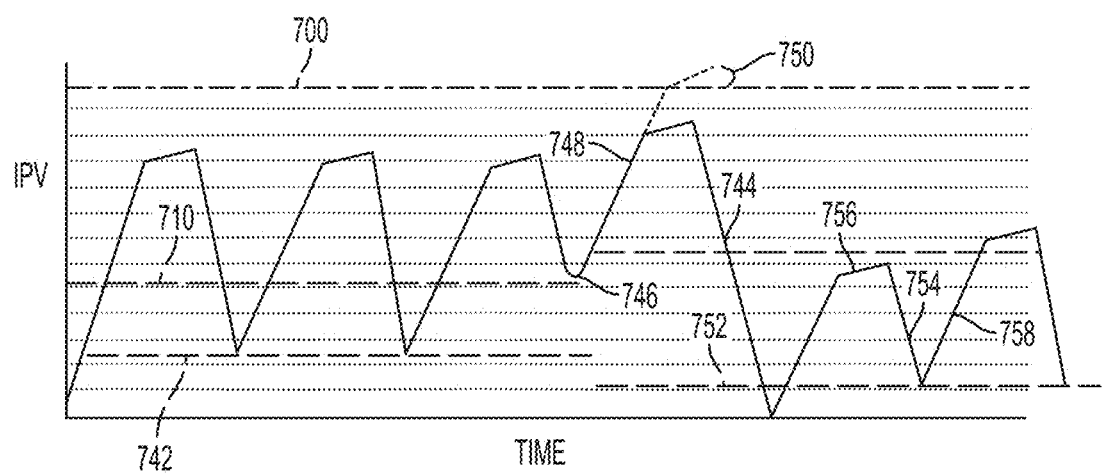
FIG. 119 is an illustration of the implementation of a revised-cycle mode during a tidal therapy.

FIG. 119 illustrates that a planned standard tidal peritoneal dialysis (TPD) therapy may also be subject to a revised-cycle mode of TPD therapy if the cycler controller calculates that the user's Max IPV 700 is likely to be reached or exceeded during therapy. In this example, a user or clinician has selected a standard tidal therapy, in which a planned residual IP volume 742 (in actual volumetric terms or as a percentage of the initial fill volume) has been selected. As an optional feature of the cycler 14, the user or clinician has also chosen to perform a complete drain 744 after every three tidal fill-dwell-drain cycles, comprising a cycle cluster during a therapy session. In this example, a low-flow condition preventing draining below the maximum residual volume 710 occurs at the end of the third cycle 746. At the option of the user or clinician, the cycler 14 either alerts the user to choose to end therapy, repeat a drain phase, or initiate a revised-cycle TPD therapy, or the cycler 14 is allowed to automatically initiate a revised-cycle TPD therapy. In this case, the addition of a sixth cycle with a consequent reduction of the fill volume to a revised fill volume 748, is sufficient to avoid exceeding the Max IPV 700, which otherwise would have occurred 750. In this example, the cycler 14 proceeds to perform a complete drain 744 at the end of a cluster, but resumes a standard TPD therapy thereafter. If the planned residual volume has been specified to be a percentage of the initial fill volume of the cluster, then that percentage may be applied to a revised residual IPV 752. The cycler 14 may then calculate the subsequent drain volumes 754 by calculating the appropriate fraction of the revised fill volume 748 plus expected UF volume in order to drain to the revised residual IPV 752. Any subsequent fill volumes 758 may remain similar to the revised fill volume 748, as long as the cycler 14 calculates that the Max IPV 700 will not be breached. Alternatively, the subsequent fill volumes may be reduced in a manner designed to maintain a relatively constant revised dwell-phase IPV 756. In this case, the cycler controller may be programmed to make the additional calculations necessary to ensure that the entire remaining dialysate solution will be properly divided among a revised fill volume 748 and later fill volumes reduced to maintain a revised dwell-phase IPV 756. In an alternative embodiment, the clinician or user may select the prescribed residual IP volume 742 to be relatively fixed volumetrically throughout therapy. In this case, the cycler controller may convert the percentage value of the residual IP volume 742 into a volumetric value (e.g. in milliliters), and continue to use that targeted residual volume after the revised-cycle mode has been instituted. In any event, the cycler 14 controller may continue to apply the Max IPV 700 limitation in calculating any revised fill volumes.

Figure 120:
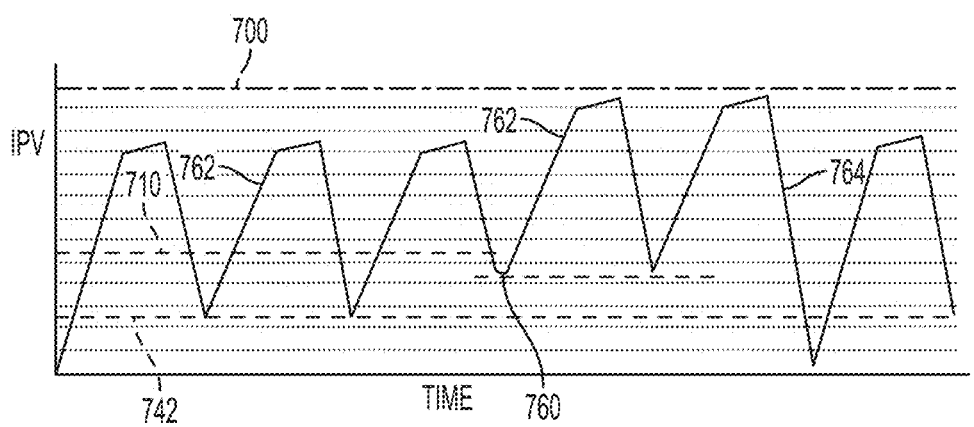

FIG. 120 illustrates how an adaptive tidal therapy mode may be employed during a standard tidal therapy. In this example, a slow-drain condition 760 is encountered below the maximum residual volume 710. As an optional feature of the cycler 14, the user or clinician has also chosen in this example to perform a complete drain 764 after every four tidal fill-dwell-drain cycles, comprising a cycle cluster during a therapy session. In this case, the cycler 14 calculates that the Max IPV 700 will not be reached if the tidal fill volume 762 is maintained. The cycler 14 may be programmed to continue the tidal therapy at a revised residual IP volume 760 in order to avoid another slow-drain condition. Alternatively, the cycler 14 may be programmed to attempt to drain back to the previously prescribed residual IP volume 742. Since tidal therapy can continue without risk of breaching Max IPV 700, the user need not be alerted to the institution of a revised or floating residual volume of the adaptive tidal therapy mode. A full drain 764 is initiated as prescribed, and if successful, the cycler controller may re-institute the originally prescribed tidal therapy parameters. In an embodiment, the cycler 14 may be programmed to alert the user if a full drain cannot be achieved at the end of a tidal therapy cluster.

Adaptive Filling

In some scenarios, variations or alterations from a programmed therapy may cause a cycler 14 to be unable to complete the therapy as prescribed. For example, if more solution volume is used than anticipated during a therapy and the number cycles programmed for the therapy, "n", is maintained, the last fill of the therapy may not be completed as prescribed, because there is not enough solution available to complete at least one fill in the therapy. Generally, a fill volume must be sufficient to result in a minimum volume of intra-peritoneal fluid during a dwell phase. In one example, the cycler 14 may be programmed to adjust each fill cycle volume to ensure that a minimum amount of fluid volume resides in the peritoneal cavity during each dwell phase. A fill volume may need to be greater than anticipated, for example, if a prior fluid drain volume exceeds the expected amount (for example, through the action of the user during therapy), or if the controller exceeds the anticipated drain volume during a previous cycle to avoid exceeding the pre-programmed Max IPV or a newly adjusted Max IPV. In this case, a subsequent fill volume may be greater than anticipated to maintain the pre-determined dwell volume for that cycle. This may potentially reduce the amount of solution available for the last cycle to a fill volume that will fail to provide the required intraperitoneal dwell volume during the last cycle.

To avoid these scenarios, during a therapy, the cycler controller may command that at least one cycle be dropped from the number of cycles programmed for the therapy. Thus, the number of cycles that will occur over the therapy will then be one or more less than "n". A cycle may be dropped, for example, if a fractional or non-integer number of cycles are calculated for a therapy, either at the beginning of therapy or at any time during the therapy. Additionally, it may occur if a user performs a drain during a tidal therapy that deviates from the programmed tidal percentage and/or modulus for the therapy. For example, a user may elect to perform a full drain during a tidal therapy. The controller may then drop a cycle because there may no longer be enough remaining dialysate in the solution bags to complete every programmed cycle of the therapy.

In the event that a cycle is dropped from therapy, the expected times for remaining phases of the therapy may be adjusted, for example, to increase the expected dwell times. This increase in expected dwell times may allow for a larger volume of UF to accumulate in the peritoneal cavity. Ultrafiltration may increase due to the infusion of fresh solution into the peritoneal cavity, when, for example, a user performs a full drain during a tidal therapy, and the peritoneal cavity is subsequently refilled to the initial fill volume with fresh solution. The concentration gradient for certain solutes will be greater and may result in more ultrafiltration during the dwell phase. Additionally, if the controller calculates expected UF per cycle based upon a preprogrammed expected total UF over the therapy, dropping a cycle may cause the controller to recalculate and expect a greater UF volume per cycle. In an embodiment, the controller may recalculate expected ultrafiltrate volume values for the remaining cycle(s) after a cycle is dropped from the therapy, accounting for any reduction in total therapy time, and optionally accounting for increased ultrafiltration from the use of a fresher solution earlier in the therapy.

In some scenarios, this increase may be sufficient to cause an anatomical reservoir volume, or in the specific example, an intraperitoneal volume (IPV) of the patient to exceed a preprogrammed maximum volume during a cycle. This is more likely to occur if the Max IPV volume is set unusually low. Though some embodiments may avoid such a scenario by calculating per cycle UF once at the beginning of therapy, it may be preferable to use an adaptive fill volume which is responsive to such therapy changes. In some embodiments, the number of cycles in the therapy may be kept at the programmed number, "n". The fill volume for the remaining cycles would then be altered from the programmed fill volume for the therapy to ensure that the Max IPV threshold is not exceeded.

Figure 121:
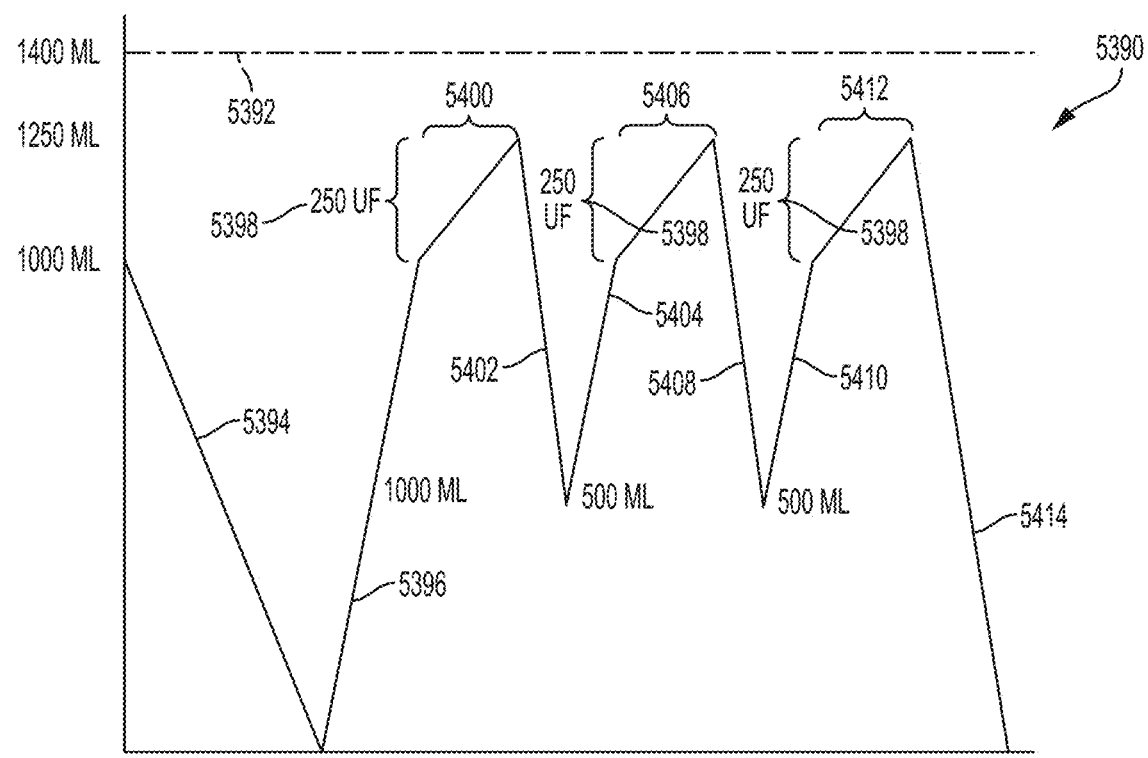

FIG. 121 depicts an example plot 5390 which shows the peritoneal reservoir volume over time for a tidal therapy. The plot is depicted for illustrative purposes and is not to scale. The example tidal therapy is programmed to have a total therapy volume of 2000 mL, an initial fill volume of 1000 mL, and a tidal percentage of 50%. The total expected UF for the therapy is set at 750 mL. The maximum IPV volume 5392 is set at 1400 mL. The therapy is programmed or calculated to have a total of three cycles. In FIG. 121, the therapy proceeds as programmed without a cycle being dropped.

An initial drain 5394 is performed and brings the patient IPV down to 0 mL. The initial fill 5396 of 1000 mL is then delivered to the peritoneal cavity. As shown, the IPV rises after the fill is complete due to the UF volume 5398 accumulating in the peritoneal cavity of the patient. In the example embodiment, 250 mL of UF accumulates per cycle. Though the example plot 5390 appears to depict the UF as accumulating during dwell phase, this is for illustrative purposes only. In reality, this UF would accumulate continuously over the fill, dwell, and drain.

When the first dwell 5400 is completed, 50% of the initial fill volume and the expected UF is drained from the patient in the drain 5402 of the first cycle. This brings the patient IPV to 500 mL. A fill 5404 of 500 mL is then pumped to the patient to bring the patient up to a 1000 mL IPV for the dwell 5406 of the next cycle. When the dwell 5406 completes, this drain and fill process is repeated with drain 5408 and fill 5410. After the dwell 5412 of the last cycle, the patient is fully drained to empty in drain 5414. The total volume delivered over the therapy is 2000 mL as programmed. The maximum IPV threshold 5392 is also not breached at any time during the therapy.

Figure 122:
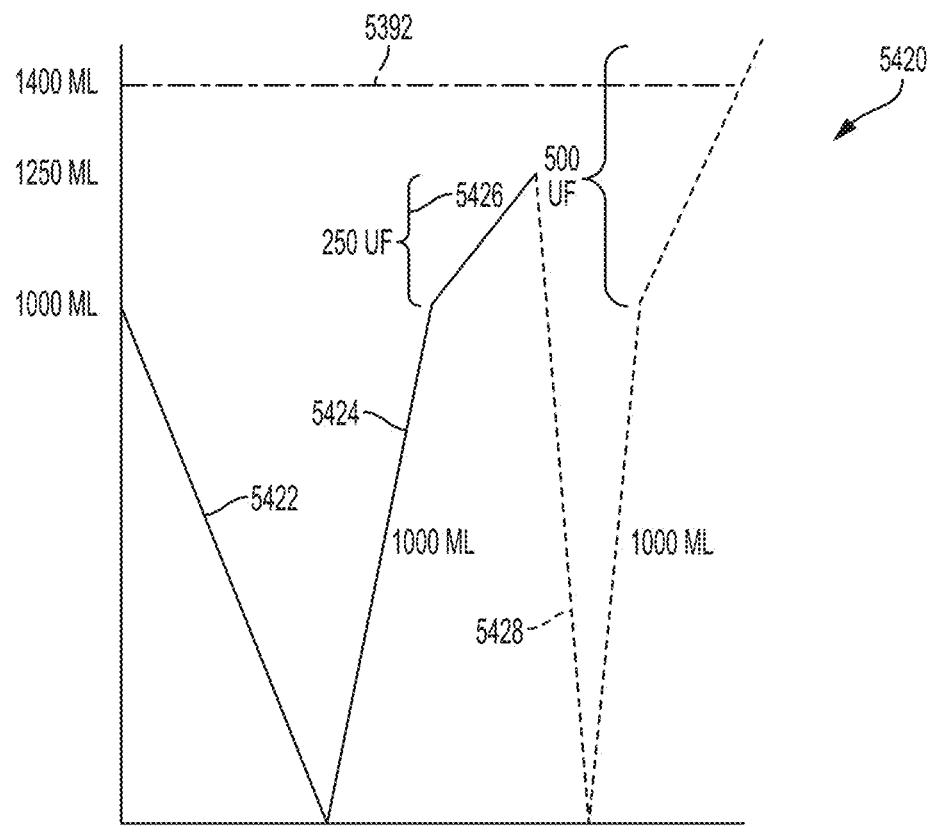

FIG. 122 depicts an example plot 5420 which shows the peritoneal reservoir volume over time for a tidal therapy. This therapy is programmed to have the same parameters as that shown in FIG. 121. The plot 5420 is shown with solid and dashed lines. The solid lines indicate portions of the plot 5420 where the therapy is the same as in FIG. 121. The dashed lines indicate where the plot 5420 departs from the plot 5390 shown in FIG. 121.

To start, an initial drain 5422 drains the patient to empty and then an initial fill 5424 delivers 1000 mL to the patient as in FIG. 121. This leaves 1000 mL of the total therapy volume remaining for the rest of the therapy. While the first dwell 5426 is occurring the 250 mL of UF accumulates. This leaves an expected UF volume for the remaining portion of the therapy of 500 mL.

During the therapy in FIG. 122, a user elects to perform a full drain 5428 after the first dwell 5426. At the end of the full drain 5428, the patient is left in an empty state. The cycler 14 then fills the patient in the second fill 5430 of the therapy. This fill 5430 delivers 1000 mL of solution to the patient in order to keep the dwell volume at the programmed amount. After the second fill 5430, the programmed 2000 mL therapy volume has been used and there may be no more solution remaining to deliver to the patient. As a result, in the example embodiment, this causes a cycle to be dropped from the therapy, shortening the therapy to two cycles. In turn, the remaining expected UF volume of 500 mL is then preferably redistributed to the remaining fill-dwell phase of the second cycle. As shown, this causes the Max IPV threshold 5392, which in this example is set at 1400 mL, to be crossed (fill volume+UF=1500 mL).

In some embodiments, the cycler controller may be configured to recognize and adapt to such a scenario before it occurs. This may be accomplished by having the controller compute before dropping a cycle and performing a fill that the current patient volume plus the next fill volume and the expected UF per cycle does not exceed the Max IPV threshold 5392. If the calculation indicates that the max IPV threshold 5392 will be exceeded, the controller may alter the fill volume so that a breach of the Max IPV threshold 5392 is avoided. This may result in maintaining the "n" number of fills programmed for the therapy (in this example, three fills).

The fill volume may be adapted or changed from the originally programmed volume such that the remaining therapy volume is spread out over the remaining cycles. This may ensure that the fill volume and the expected UF accumulated during a cycle does not exceed the Max IPV threshold 5392. It may also ensure that the full therapy volume of dialysate solution is used. By using the full therapy volume, waste of solution staged for use during the therapy is minimized. The user may be prompted to acknowledge or confirm acceptance of the newly calculated adapted fill volume. In other embodiments, a user may be presented with one or more options to change the therapy, each of which will avoid exceeding the max IPV threshold 5392. The user may select a desired option. The options need not be limited to those described herein.

The following equation may be used to determine an adapted fill volume for a cycle:

$$V_T =$$
$(V_{NEW} * \text{Full Fills Remaining}) + ((\text{Tidal \%} * V_{NEW}) * \text{Tidal Fills Remaining})$ Where $V_T$ is equal to the Therapy Volume Remaining and $V_{NEW}$ is equal to the new fill volume or adapted fill volume for the cycle.

The equation may be rearranged to solve for $V_{NEW}$ to determine the adapted fill volume. Using the example therapy in FIG. 122, when it is detected that a non-adapted fill volume will cause the Max IPV threshold 5392 to be exceeded, $V_{NEW}$ may be determined as follows:

$$1000 \text{ mL} = (V_{NEW} * 1) + ((0.5 * V_{NEW}) * 1)$$

Which simplifies to:

$$1000 \text{ mL} = 1.5 \, V_{NEW}$$

Which may be rearranged to solve for $V_{NEW}$:

$$V_{NEW} = 1000 \text{ mL} / 1.5 = 66\overline{6.6} \text{ mL}$$

The above equation assumes that the tidal percentage is maintained in the remaining cycles of the therapy volume. Optionally, the equation may allow for the tidal percentage to be changed in the remaining cycles of the therapy.

Figure 123:
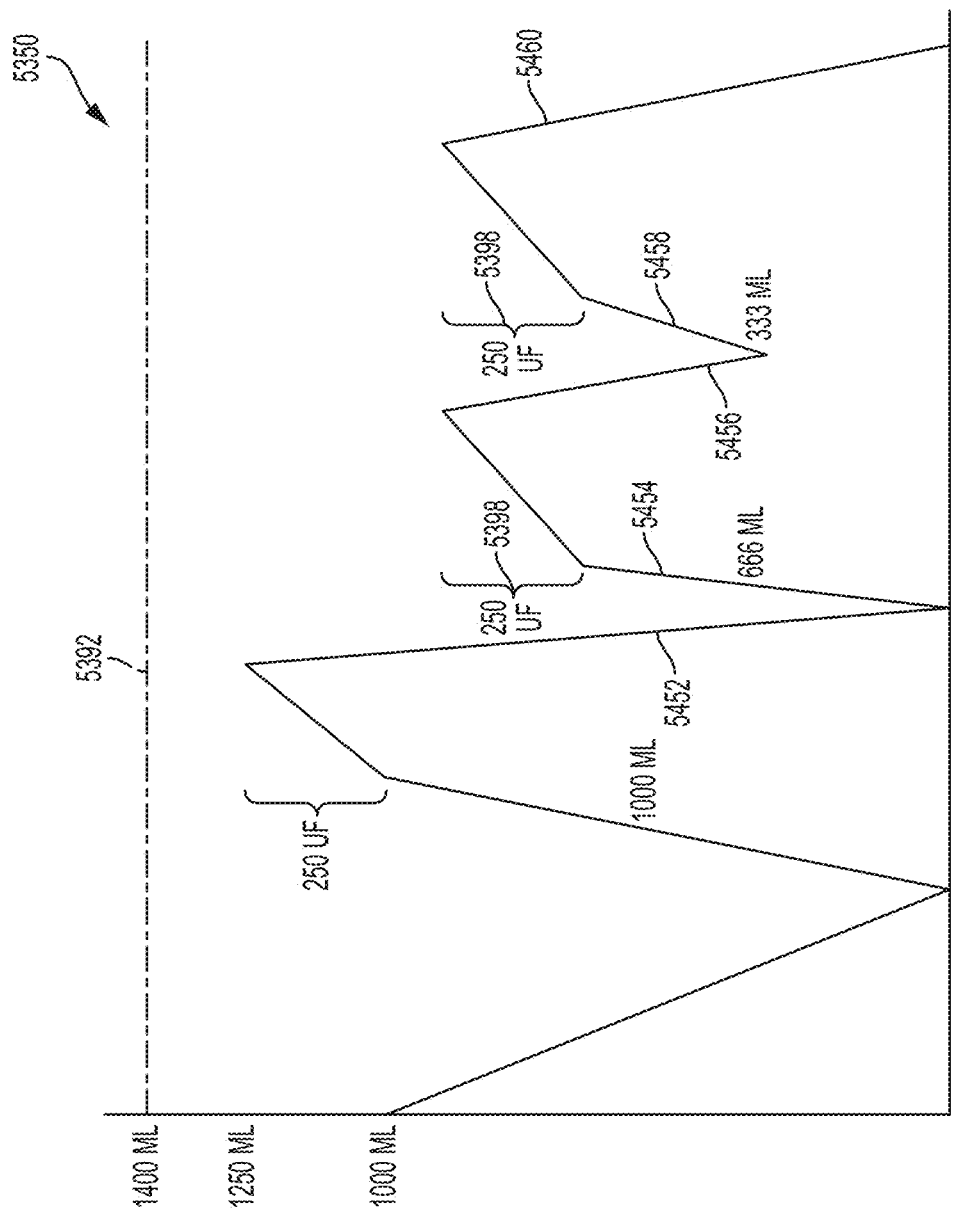

FIG. 123 depicts an example plot 5350 showing the intraperitoneal volume over time for a tidal therapy. The therapy parameters are the same as those programmed in FIGS. 121 and 122. As shown, the fill volume is adapted after a user initiated full drain 5452. The adapted fill volume ensures that the max IPV threshold 5392 is not exceeded during the therapy and that the entirety of the programmed therapy volume is consumed. A cycle is not dropped, as dropping the cycle would not allow the full therapy volume to be used without exceeding the max IPV threshold 5392. Additionally, the tidal percentage is kept at the programmed value in the example plot 5350 shown in FIG. 123.

In some embodiments, a cycle may be dropped and a calculation may then be made to determine if the max IPV threshold 5392 will be breached. The dropped cycle may then be brought back so that the programmed number of cycles for the therapy is maintained. Alternatively, the calculation may be made preemptively before dropping the cycle to determine if dropping the cycle will cause the max IPV threshold 5392 to be exceeded.

Referring back to FIG. 123, calculated above as $V_{NEW}$, the second fill 5454 is 666 mL (rounded for convenience). The 250 mL of UF 5398 accumulated during the cycle does not then cause the max IPV threshold 5392 to be exceeded. During the second drain 5456 the tidal percentage is kept at 50% and the patient is drained to 333 mL. The fill 5458 of the last cycle of 333 mL brings the patient's IPV back to the calculated new fill volume, $V_{NEW}$. Again, the UF 5398 for the last cycle is able to accumulate without the max IPV threshold 5392 being exceeded. The patient is then drained to empty in the drain 5460 of the last cycle to conclude the therapy.

In some embodiments, the controller may adjust the tidal percentage may to keep the IPV of the patient closer to the initial fill volume. Alternatively, in some embodiments the tidal therapy may be converted to a non-tidal therapy after the first adapted fill volume is delivered to the patient. For example, the first adapted fill may be delivered and the dwell may be allowed to elapse. In the following drain, a cycler 14 may only drain the expected UF for the cycle and the therapy may enter a UF maintenance mode. In some embodiments, the expected UF plus an optional extra margin of fluid may be drained. This may allow the next fill to bring the IPV of the patient back to approximately the initial fill volume. Again this should allow for the full therapy volume to be used without the max IPV threshold 5392 for the therapy being exceeded. In another embodiment, the tidal therapy may be converted to a CCPD therapy with the remaining solution volume split between a number of cycles.

In some embodiments, the fill volume may be adapted while still dropping a cycle from the therapy. In such scenarios, the fill volume may be lowered such that the expected UF per cycle after a cycle is dropped does not cause the max IPV threshold 5392 to be exceeded. In some embodiments, the fill volume may be recalculated as:

$$V_{NEW} = \text{Max } IPV - (\text{Expected } UF + \text{Optional Margin})$$

Using this equation and referring to the example therapy described in FIG. 122, after the user elects to perform a full drain, the fill volume may be recalculated based on the new expected UF after the last cycle is dropped. The fill volume may be changed to 825 mL (15% margin on expected UF). Thus the therapy may be completed without the max IPV threshold 5392 being breached. In such embodiments, some solution will be unused at the end of the therapy.

In addition to implementing an adaptive fill volume, the controller can optionally be programmed to perform a fill volume less than the previously programmed fill volume (a 'shorted fill'). This can be useful, for example, if the number of calculated cycles is a non-integer number, which can occur if a programmed therapy volume does not divide evenly into a number of defined cycles. The therapy may perform a shorted fill on the last cycle if a predetermined percentage (e.g. 85%) of the programmed fill volume is available. If the predetermined percentage is not available, the controller can drop the cycle and leave the extra solution unused.

In some cases, if more solution than expected is used during a portion of the therapy, then the remaining solution volume for the last cycle may fall below a predetermined percentage threshold. This can occur in response to a number of factors, such as tolerances in volume targeting (e.g. a small over-delivery may be allowed). Consequently, the controller may drop the last programmed cycle in respose, and may reconfigure the remaining dwell phases to increase the expected UF per cycle. This could cause the Max IPV threshold 5392 to be exceeded.

In some embodiments, this situation may be avoided by preventing the cycler controller from dropping the last cycle of the therapy. The remaining volume in the attached bags may be delivered to the patient for the last fill regardless of what percentage of the programmed fill volume is remaining. Alternatively, if the therapy is a CCPD therapy, the therapy may be converted to a tidal therapy. The tidal percentage may be selected so that the programmed fill volume is maintained without dropping a cycle.

In some embodiments, such a scenario can be avoided by performing the shorted fill at the beginning of therapy (e.g. during the first fill). This may ensure that the remaining therapy volume may be divided between the remaining cycles so that substantially the full programmed fill volume may be delivered to the patient during each cycle. Thus the last fill volume will be expected to be all or nearly all of the programmed fill volume instead of a volume closer to the predetermined percentage threshold. This effectively creates a buffer volume. Whether the last fill cycle is still performed may still be subject to the predetermined percentage of the programmed fill volume threshold. But the likelihood of the threshold not being met may be reduced, owing to the implementation of the buffer fill volume.

The controller can optionally be programmed to assign a range to the threshold fill volume, as a percentage of a programmed fill volume. This range may be viewed as a hysteresis band placed around the predetermined percentage of programmed fill volume threshold. This hysteresis band can be useful in accommodating small differences between expected volume used and actual volume used during a therapy. The controller may be programmed to apply a hysteresis band as a range of percentage values on either or both sides of the predetermined percent threshold. In some embodiments, this hysteresis band may be clinician or user programmable.

Pump Operation Synchronization

In various embodiments, during pumping, pump chambers 181 of a cassette 24 may be synchronized. Any synchronization scheme described in U.S. Pat. No. 10,201,647, to Norris et al., issued Feb. 12, 2019, filed Jun. 5, 2015, and entitled "Medical Treatment System and Methods Using a Plurality of Fluid Lines" which is incorporated herein by reference in its entirety may be used.

Built-in Positive and Negative Pressure Reservoirs

In some embodiments, a pressure reservoir can be molded as a part of the housing of the device. Any such pressure reservoir described in U.S. Pat. No. 10,201,647, to Norris et al., issued Feb. 12, 2019, filed Jun. 5, 2015, and entitled "Medical Treatment System and Methods Using a Plurality of Fluid Lines" which is incorporated herein by reference in its entirety may be used.

Heater Bag Replenish

The heating of fluids to be delivered to a patient consumes a substantial amount of energy. Any medical apparatus configured to infuse a fluid into a patient's body cavity, or intravenously, can be equipped with a controller that improves the efficiency of a heating device acting on a heater bag 22 containing the fluid to be delivered. Although the following description uses a peritoneal dialysis cycler 14 to illustrate the system, it may be applied in a similar manner to any medical infusion apparatus that controls the replenishment of fluid into a heater bag 22, the delivery of heated fluid to a patient, the time during which the fluid remains in the patient, and the withdrawal and draining of the fluid from the patient. Regarding the infusion of dialysate solution, it may also be advantageous in some cases to limit the amount of time the solution is kept at an elevated temperature (e.g., body temperature) while awaiting infusion into the patient.

There are many different types of dialysate solution which may be used with a dialysis machine. These solutions may for example have varying concentrations of osmotic agent, varying types of osmotic agents, different electrolytic components, different pH buffering components, various additives, etc. These differences between solutions may cause the solutions to act differently under various conditions. For this reason, the cycler 14 behavior preferably accommodates the needs of any solution which may be used with the machine. Alternatively, a cycler controller can be programmed to have differing behaviors depending upon the type of solution being used. For example, certain solution types may have a limited useable life once brought to a high temperature to prevent precipitation of solutes in the dialysate. The cycler 14 behavior may be designed to accommodate such a dialysate characteristic As mentioned above, various embodiments of a cycler 14 may include a heater assembly which heats dialysate solution in a heater bag 22 resting on the assembly prior to delivering it to the patient. The heater assembly may comprise a heater pan 142 or trough, sized to accept a solution bag 20 or heater bag 22 that has a volume which is greater than the amount of solution that would be delivered to a normal patient in any one fill operation. In standard practice, the heater bag 22 is typically kept substantially full and the solution contained within the bag 22 is kept within a defined temperature range.

In some embodiments, instead of filling substantially the entire heater bag 22 volume with dialysate and maintaining it at or near that full state, the heater bag 22 may only be partially filled with dialysate. This avoids having a large volume of dialysate remaining heated for several fill, dwell, and drain operations. Thus, the amount of time the dialysate is kept at elevated temperature before delivery to the patient can be minimized.

For example, an amount of solution less than the volume of two programmed fills may be pumped to the heater bag 22. This amount may be referred to as a next cycle fill volume (e.g., volume of fill phase 758, FIG. 119). The next cycle fill volume can comprise an amount of solution needed to complete the next fill of the patient's peritoneal cavity. In some embodiments, a margin or marginal volume of solution may also be added to the next cycle fill volume. Thus the heater bag 22 will be replenished to a volume slightly greater than the solution volume needed to complete the next patient fill. This additional solution may help ensure that the flow rate from the heater bag 22 during a fill of the patient remains relatively high throughout the operation and may serve as a margin in case more solution than anticipated. The marginal volume, may for example, be a preprogrammed, fixed volume or specified as a percentage of the fill volume (or another programmed therapy volume parameter). By replenishing the heater bag 22 in this manner, the amount of time the solution is held at a high temperature before being delivered to a patient may be minimized. In an exemplary embodiment, the replenish volume may be determined as follows:

$$V_R = V_F + \text{Optional Margin} - V_H$$

Where $V_R$ is the determined replenish volume to be transferred to the heater bag 22, $V_F$ is the programmed next fill volume, and $V_H$ is the volume of the heater bag 22 at the beginning of the replenish operation.

The time at which the heater bag 22 is replenished may also be scheduled in a manner which minimizes the amount of time that its contents are kept at an elevated temperature. This may be done by replenishing the heater bag 22 shortly before the next fill operation is scheduled. For example, the heater bag 22 may be refilled near the end of the dwell phase (e.g. dwell phase 756, FIG. 119) of a cycle. In some embodiments, the cycler 14 may determine or estimate an amount of time which will be needed to replenish the heater bag 22 and heat the solution for the next fill.

Heating of the transferred replenish solution can begin as soon as the heater bag 22 replenish operation begins. The controller can be programmed to calculate an estimated heating time required to raise the temperature of the replenished solution in the heater bag 22. In some embodiments, that calculation can be based on the temperature drop of the heater bag 22 as the transfer begins, and/or the volume of replenish solution to be transferred to the heater bag 22. The computation may, for example, include variables such as the initial volume in the heater bag 22, its temperature, and the degree of temperature drop as a pre-determined volume of replenish fluid is transferred into the bag 22. Regardless of how the heating time is computed, if it is estimated by the controller to exceed the replenish volume transfer time, the controller may command the pump to begin the replenish operation before the remaining dwell time becomes less than the estimated time needed to bring the replenish volume to the pre-determined temperature.

Optionally, the cycler 14 may estimate the amount of time which will be needed for the subsequent drain operation after the current dwell. This time estimate may then be added to a transfer time estimate, plus possibly an added time margin in determining how much time is available to heat the fluid in the heater bag 22. The estimate may be taken into account when the cycler 14 is scheduling a replenish. For example, in some embodiments, the replenish may begin when it is determined that a calculated amount of time before the start of the current cycle's drain remains. This amount of time may be calculated as follows:

Time Before Drain (replenish start time)=Optional Margin+Replenish Volume Transfer Time+(if greater than zero (Replenish Volume Heating Time−Drain Time))

Optionally, the controller may compute the contribution that the subsequent drain phase will provide to raise the heater bag 22 fluid to its target temperature (e.g., drain phase 754, FIG. 119). This will allow the controller to initiate heater bag 22 filling later during the dwell phase (e.g., dwell phase 756) by the amount of time available to continue to heat the fluid during the drain phase (e.g. drain phase 754). In some embodiments, at least one estimated amount of time (e.g the replenish/fluid transfer time or heating time) may be inclusive of an added time margin to help ensure that the solution is not less than the programmed temperature by the start of the next cycle. This may help to ensure that a drain is not postponed due to volume transfer in a replenish taking longer than anticipated.

Alternatively, the total volume of the heater bag 22 may be relatively small (e.g. no larger than the volume of about one and a half fills). This may help to ensure that solution in the heater bag 22 is not maintained at high temperature for excessively long periods of time. Instead, the solution in the heater bag 22 will be used over a small number of cycles (e.g. two cycles). In such embodiments, there may be multiple sets available to a user, each of which having differing heater bag 22 sizes. This may allow for a user to perform a therapy with a heater bag 22 which is appropriate for their prescribed fill. In some embodiments, sets with heater bags 22 made of varying materials may also be made available. For example, there may be sets with heater bags 22 which are substantially impermeable to gases such as carbon dioxide.

Figure 124:
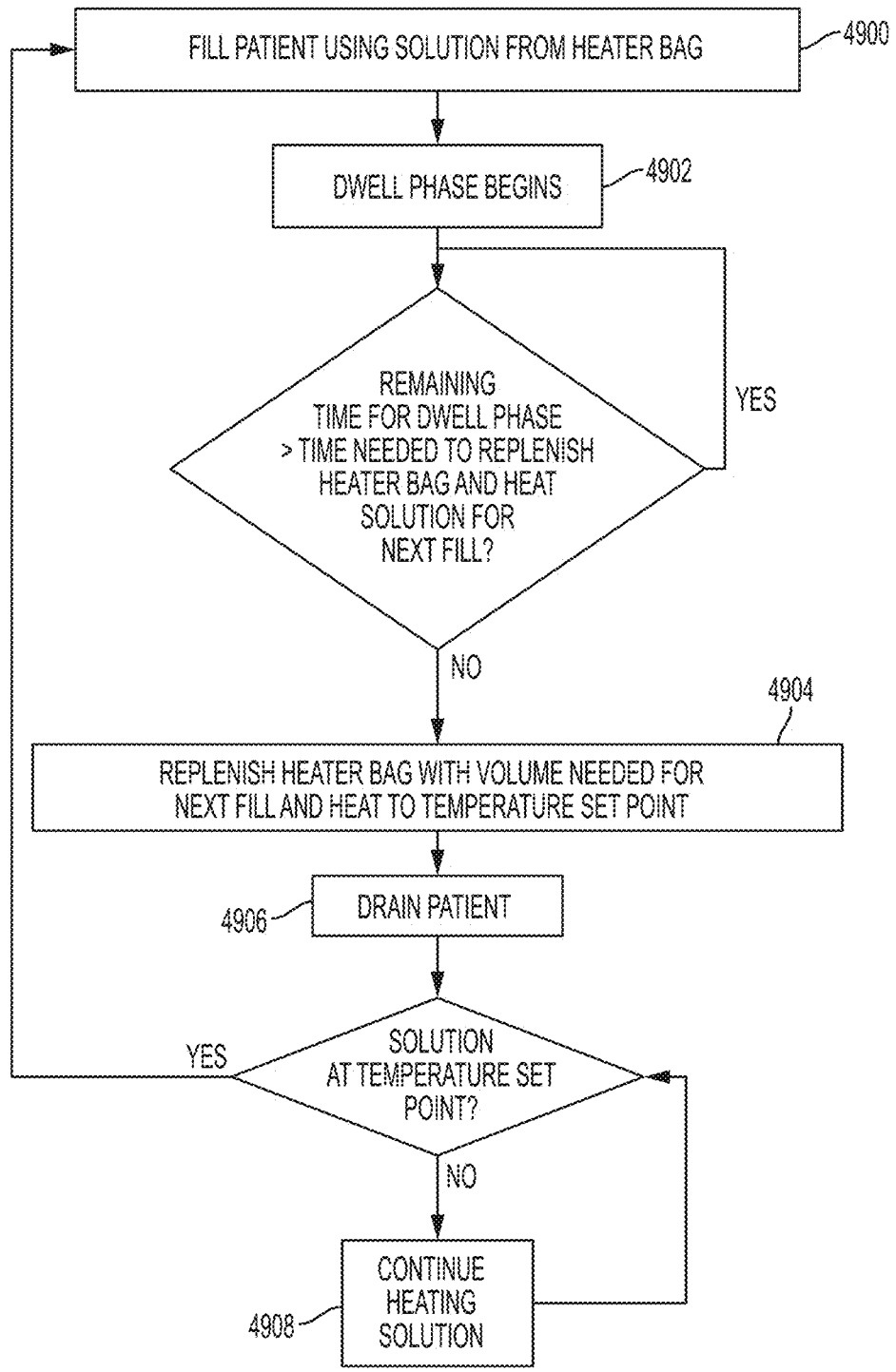

FIG. 124 shows a flowchart outlining number of example steps which may be used to replenish a heater bag with dialysate solution. The steps shown in FIG. 124 help to minimize the amount of time which the solution is heated in the heater bag before delivery to the patient. The flowchart begins after the heater bag has been initially filled and heated at the start of the therapy. As shown, in step 4900 the cycler fills a patient's peritoneal cavity with solution from the heater bag. This may substantially deplete the heater bag to near empty. The dwell phase of the cycle may then begin. The cycler controller monitors the remaining dwell time to ensure that the remaining dwell time is greater than or equal to the time needed to replenish the heater bag and heat solution for the next fill. When the remaining dwell time no longer exceeds the time needed to replenish the heater bag and heat solution for the next fill, step 4904 may be performed. Alternatively, the cycler may schedule the replenish such that there will be enough time to replenish the heater bag and heat the solution. The cycler controller then waits until the scheduled time and proceeds to step 4904.

In step 4904, the cycler replenishes the heater bag with the volume needed for the next fill operation. As mentioned above, the cycler may fill the heater bag to a volume that is greater than is required for the next fill. For example, the heater bag may be filled to the volume needed for the next fill plus an additional marginal volume of 10-25% of the fill volume. The cycler may also begin to heat the solution pumped to the heater bag in the replenish period to within a pre-determined range of a pre-determined temperature set point. This temperature set point may be fixed or programmable by a user, or by a clinician authorized to alter the prescription parameters and settings of the peritoneal dialysis cycler.

After the time allotted for the dwell phase elapses, the cycler proceeds to step 4906 and begins to drain the patient. Optionally, heating of the solution up to within the range of the temperature set point may continue as step 4906 is performed. After the drain operation completes, the cycler returns to step 4900 and refill the patient with solution from the heater bag. If the solution is not within the range of the temperature set point, the cycler may instead continue to heat the solution in step 4908 until the solution is within a range of the desired temperature set point. This will help to ensure that solution significantly above or below the desired temperature is not delivered to a patient.

Solution Expiration Timers

In some embodiments, a cycler 14 may be programmed to determine a solution set up or staged for use in a dialysis therapy has expired. Additionally, a cycler 14 may be programmed to notify a user when a solution has expired. The cycler controller may disallow use of the expired solution and in some embodiments, may require the user to terminate or abort a therapy such that a new therapy with fresh solution may be set up. This may for example be desirable in cyclers 14 in which very long therapies (e.g. up to 48 hours) may be programmed, or in cyclers 14 which allow a user to pause a therapy for long periods of time.

In some embodiments, a cycler 14 may have one or more solution expiration timers that start or may be triggered to start at a predefined point in the therapy. Each of the solution expiration timers may be used for a different solution reservoir. For example, a first solution expiration timer may be used for a first solution reservoir and a second solution expiration timer may be used for a second solution reservoir. The first solution expiration timer may be triggered to start at a first predefined point and the second solution expiration timer may be triggered to start at a second predefined point. A single solution expiration timer may also be used for a number solution reservoirs containing the same type of dialysate solution. A solution expiration timer may allot a predetermined period of time for the therapy to make use of the solution. The predetermined amount of time may vary depending on the type of solution being used. If there are multiple solution expiration timers, the predetermined amount of time may differ for each timer. If the therapy does not use the solution before the time elapses, the solution may be deemed expired by the cycler 14 and treated accordingly. If there are multiple solution expiration timers with different allotted periods of time, one solution expiration timer expiring may cause one or more other solution expiration timer to also expire.

In some embodiments, the amount of time allotted for a solution expiration timer may vary by temperature of the solution. Solution stored in a staged solution bag 20 may be subject to a first solution expiration timer and may then be subject to a different solution expiration timer after being transferred into a heater bag 22. In embodiments in which a cycler 14 heats the solution to a temperature set point defined by the user or a prescriber, the system controller may compute an expiration time for that solution expiration timer based on the value of the temperature set point.

In some embodiments, two solution expiration timers may be used. One solution expiration timer may be for a set of staged solution bags 20 and another solution expiration timer may be for the heater bag 22. The solution bag 20 expiration timer may be programmed to begin when the cycler controller determines that the solution bags 20 have been connected to the set. The heater bag 22 expiration timer may begin each time the heater bag 22 is depleted to a residual volume before it is refilled with fresh solution. For example, in embodiments which schedule replenishes as described above in relation to FIG. 124, the timer may restart at every replenish of the heater bag 22.

In various embodiments, one or more solution expiration times may be established for each type of dialysate compatible for use with the cycler 14. The cycler controller may determine which type of solution is programmed for use with the therapy. Information about the solution used for the therapy may also be read from a barcode or the like on a solution line 30 or may be input by the user via a user interface of the cycler 14. The predetermined period of time allotted for the solution expiration timer may be chosen to match a dialysate solution to be used in the therapy. For example, the cycler controller may match the determined solution type to a predetermined period of time programmed for that solution in a look-up table. If more than one type of solution is to be used for the therapy, the solution with the shortest expiration time may be used to set the predetermined period of time allotted for the solution expiration timer. Multiple solution expiration timers may also be set up so that there is one timer for each of the different solution types used during the therapy.

Alternatively, the one or more solution expiration timer may not be solution specific. In such embodiments, this solution expiration timer may be set such that it would be appropriate for the solution which has the shortest expiration time. The solution expiration times for various solutions may be determined based upon manufacturer recommended values.

If a solution bag 20 expires, the cycler 14 may, for example, no longer draw fluid from that solution bag 20. The therapy may be allowed to continue if other solution bags 20 connected to the set have not yet expired. Additionally, in some embodiments, the user interface of the cycler 14 may notify a user of the solution bag's 20 expiration. In such embodiments, the user may have the option of replacing the solution bag 20.

Alternatively, there may only be a single solution bag 20 expiration timer for all of the solution bags 20 attached to the set 12. In the event that the timer expires, the user may be required to abort the current therapy and begin a new therapy with fresh supplies. If the solution bag 20 expiration timer expires, it may also cause the heater bag 22 expiration timer to expire.

If the heater bag 22 timer expires, the cycler controller may be programmed to not deliver the solution in the heater bag 22 to the user. The cycler 14 may, for example, pump all of the solution in the heater bag 22 to the drain line to discard the solution. The heater bag 22 may then be refilled and the heater bag 22 expiration timer may be restarted. The user may be notified of the heater bag's 22 expiration. Alternatively, if there is not enough solution to refill the heater bag 22, the user may be required to abort the current therapy and begin a new therapy with fresh supplies. In some embodiments, any remaining solution may be delivered to the heater bag 22 and heated. This solution may then be delivered to the patient so that it may dwell in the patient while new supplies are gathered. This may help to minimize loss of therapy.

Figure 125:
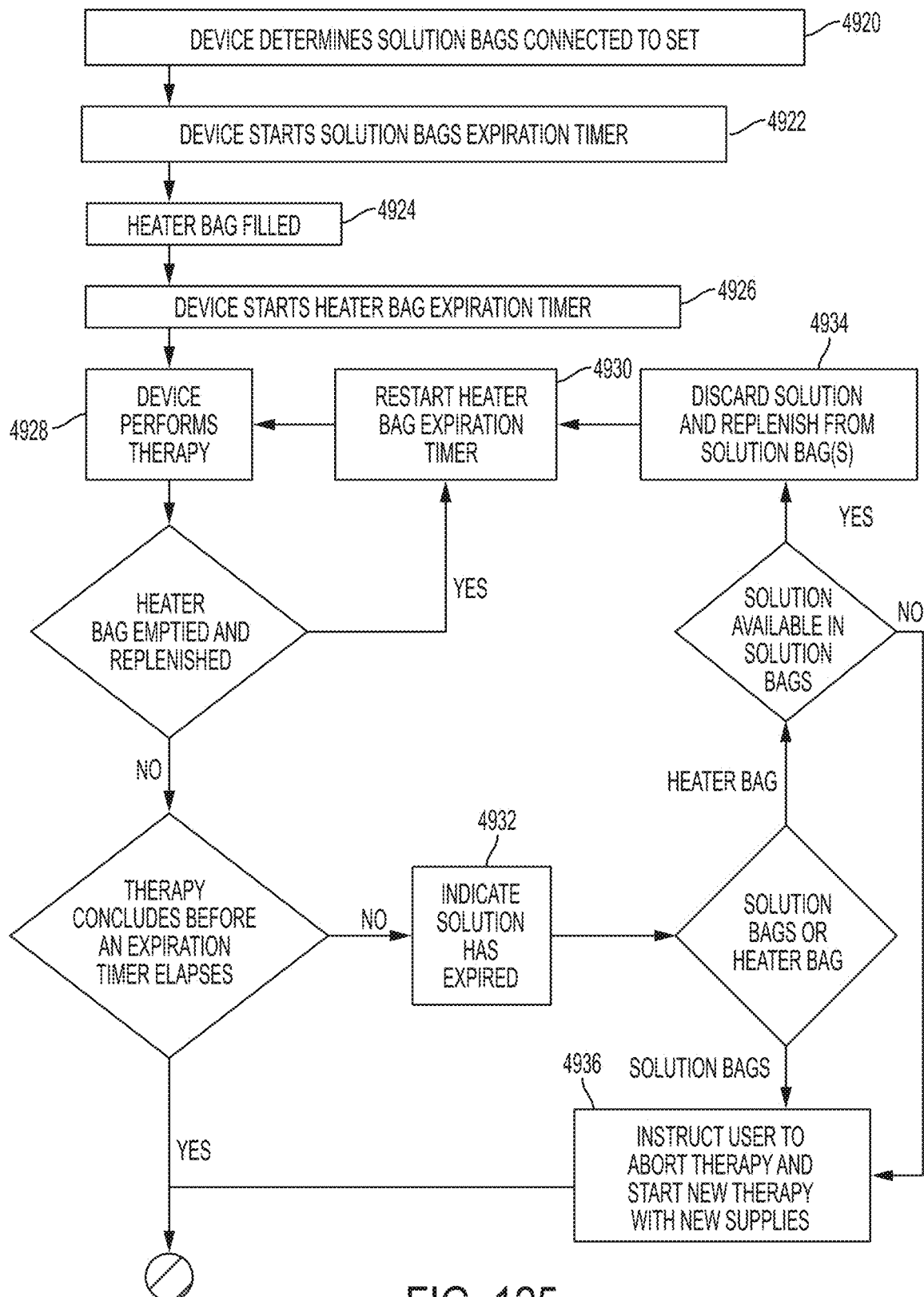

FIG. 125 shows a flowchart outlining a number of example steps which may be employed by a cycler using solution expiration timers. In the example flowchart, the cycler has a solution bag expiration timer and a heater bag expiration timer. As shown, in step 4920 the cycler determines that solution bags have been connected to the set. The cycler may then, in step 4922, begin a solution bag expiration timer. The cycler may then fill the heater bag in step 4924. After the heater bag has been filled, the cycler may start the heater bag expiration timer in step 4926.

In step 4928, the therapy is performed. If during the therapy, the heater bag is emptied and replenished, the heater bag expiration timer may be reset in step 4930. Otherwise, if the therapy concludes before any expiration timers elapse, the therapy may be completed normally. If an expiration timer elapses before the therapy concludes, the cycler may indicate that the solution has expired in step 4932. If it is the heater bag expiration timer that has expired and there is sufficient solution in the solution bags, the cycler may discard the solution in the heater bag and replenish it with solution from the solution bags in step 4934. If there is not enough solution to replenish the heater bag, the cycler may proceed to step 4936 and instruct the user to abort the therapy and start a new therapy with fresh supplies. The cycler may also proceed to step 4936 if it is the solution bag expiration timer that has expired.

Figure 126:
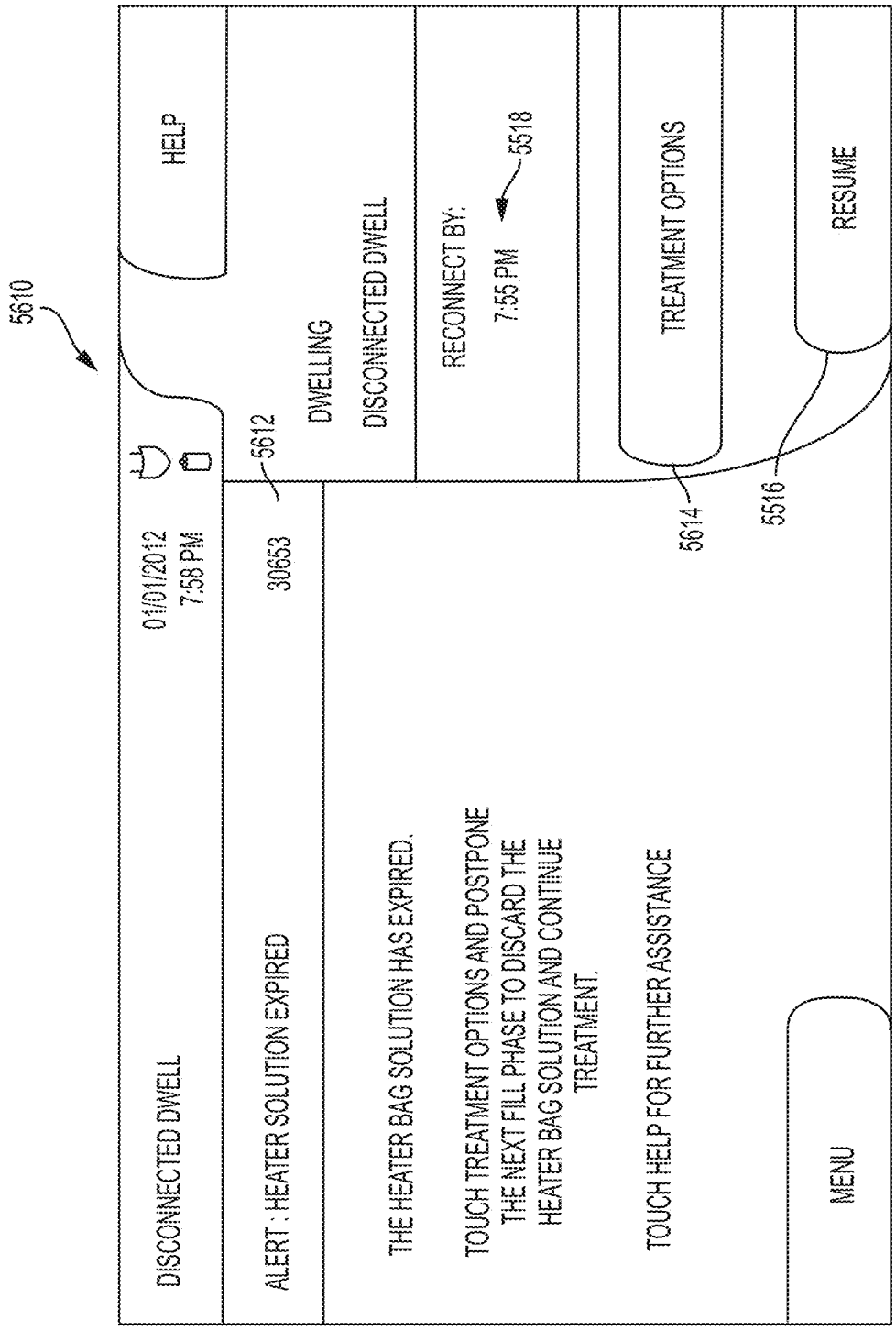

FIG. 126 depicts an example screen 5610 which may be generated by a processor for display on a user interface of a cycler 14. The example screen 5610 indicates to the user that a solution expiration timer has expired. Such a screen may for example be displayed in step 4932 of FIG. 125. In the example embodiment, the solution expiration timer which has expired is the heater bag 22 solution timer.

As shown, the example screen 5610 includes an alert 5612 which declares that solution has expired and provides an error code. The screen 5610 also includes text which informs the user how to resolve the problem. In the example screen 5610, the text instructs the user to postpone a fill phase so that the heater bag 22 solution may be discarded and replaced. A user may be required to navigate to another screen on which they confirm or elect to replace the solution in the heater bag 22. In the example embodiment, such a screen may be navigated to by interacting with a treatment options button 5614 on the screen 5610. In some embodiments, a resume button 5516 on the screen 5610 may be disabled until a user has replaced the solution.

Also shown on the example screen 5610 is a time notification 5518. The time notification 5518 may inform the user when a solution timer is going to expire. The time notification 5518 may be triggered for display when a predetermined amount of time before a solution expiration timer expires is remaining. In some embodiments, for example, in embodiments where a user may disconnect from a cycler 14 during a therapy, the time notification 5518 may inform a user when they must reconnect and continue the therapy to avoid a solution timer from expiring. In the example embodiment, the time notification 5518 is a reconnect by time which informs the user that they had to reconnect by 7:55 PM to avoid the heater bag 22 expiration timer from expiring. As shown by the clock 5620, the reconnect by time passed 3 minutes ago.

Flow Check

In accordance with an aspect of the disclosure, the pressure applied by the pumps to dialysate that is infused into the patient or removed from the patient may be controlled so that patient sensations of "tugging" or "pulling" resulting from pressure variations during drain and fill operations may be minimized. For example, when draining dialysate, the suction pressure (or vacuum/negative pressure) may be reduced near the end of the drain process, thereby minimizing patient sensation of dialysate removal. A similar approach may be used when nearing the end of a fill operation, i.e., the delivery pressure (or positive pressure) may be reduced near the end of fill. Different pressure profiles may be used for different fill and/or drain cycles in case the patient is found to be more or less sensitive to fluid movement during different cycles of the therapy. For example, a relatively higher (or lower) pressure may be used during fill and/or drain cycles when a patient is asleep, as compared to when the patient is awake. The cycler 14 may detect the patient's sleep/awake state, e.g., using an infrared motion detector and inferring sleep if patient motion is reduced, or using a detected change in blood pressure, brain waves, or other parameter that is indicative of sleep, and so on. Alternately, the cycler 14 may simply "ask" the patient—"are you asleep?" and control system operation based on the patient's response (or lack of response).

When draining solution from the peritoneal cavity of a patient it is not unusual for a patient to perceive an uncomfortable tugging sensation. Additionally, this tugging sensation may be more prone to occur when the peritoneal cavity is empty or nearly empty. For this reason, it may be desirable for a cycler 14 to perform a flow check to ensure that the patient is carrying fluid that needs to be removed. Such a flow check may for example be performed before all drains or may be performed prior to certain types of drains. For example, since discomfort is more often reported during initial drains, flow checks may be made before an initial drain is performed by the cycler 14. The flow check may gently attempt to remove fluid from a patient until the controller determines whether or not there is any fluid volume in the patient's peritoneal cavity that requires draining. The cycler 14 may, for example, check to see if a flow rate above a predetermined threshold value can be reached, as this would suggest there is indeed fluid in the patient that should be removed. This may help to minimize or prevent a perceived tugging sensation when there is relatively little fluid, or an insufficient amount of fluid to be drained. The cycler controller may set the pumping pressure for the drain based on the flow rate determined during the flow check. A flow rate above a preset threshold may allow the drain to proceed using a greater force (greater negative pressure).

In prior devices, instead of performing a flow check, the cycler controller would attempt to pull fluid from the peritoneal cavity at a standard or nominal preset pressure. The cycler 14 would be programmed to continue the drain phase until a minimum elapsed drain time or a minimum drain volume was reached. If the resulting flow rate were below a given threshold (e.g. 15 ml/min. over a 45 second period), the cycler 14 would attempt to push fluid back to verify that there was no line occlusion. If no line occlusion was detected, pumping could resume at a lower pressure. If flow remained below a threshold value for another period of time (e.g. 300 seconds), the cycler 14 would either alert the user or allow the user to bypass the remainder of the drain phase. This procedure in some cases could result in episodes of patient discomfort, which now can be mitigated by the flow check procedure.

In some embodiments, a cycler 14 may perform a flow check by attempting to pull fluid from a patient at a flow check pressure. The flow check pressure may be selected so that it is more positive (i.e. closer to atmospheric) than that used during a normal drain operation. For example, the difference between the flow check pressure and the normal drain pressure may be between approximately 2 kPa and 6 kPa. In one example, a flow check pressure may be set at about −6.5 kPa while normal drain pressure may be set at about −9.5 kPa. Other pressure values may be used. The selected pressures may be nominal values that can deviate by a pre-determined margin from the selected pressure while a pumping operation at that pressure is being performed. Additionally, in some embodiments, different flow check pressures may be used for different drains. For example, the flow check pressure used during an initial drain may be weaker (i.e., less negative pressure) than that used during a mid-therapy drain. Selecting the flow check pressure so that it creates a weaker vacuum than the normal draining pressure may feel gentler to the patient. In some embodiments, a user or a clinician may be have the option of setting the flow check pressure.

Figure 127A:
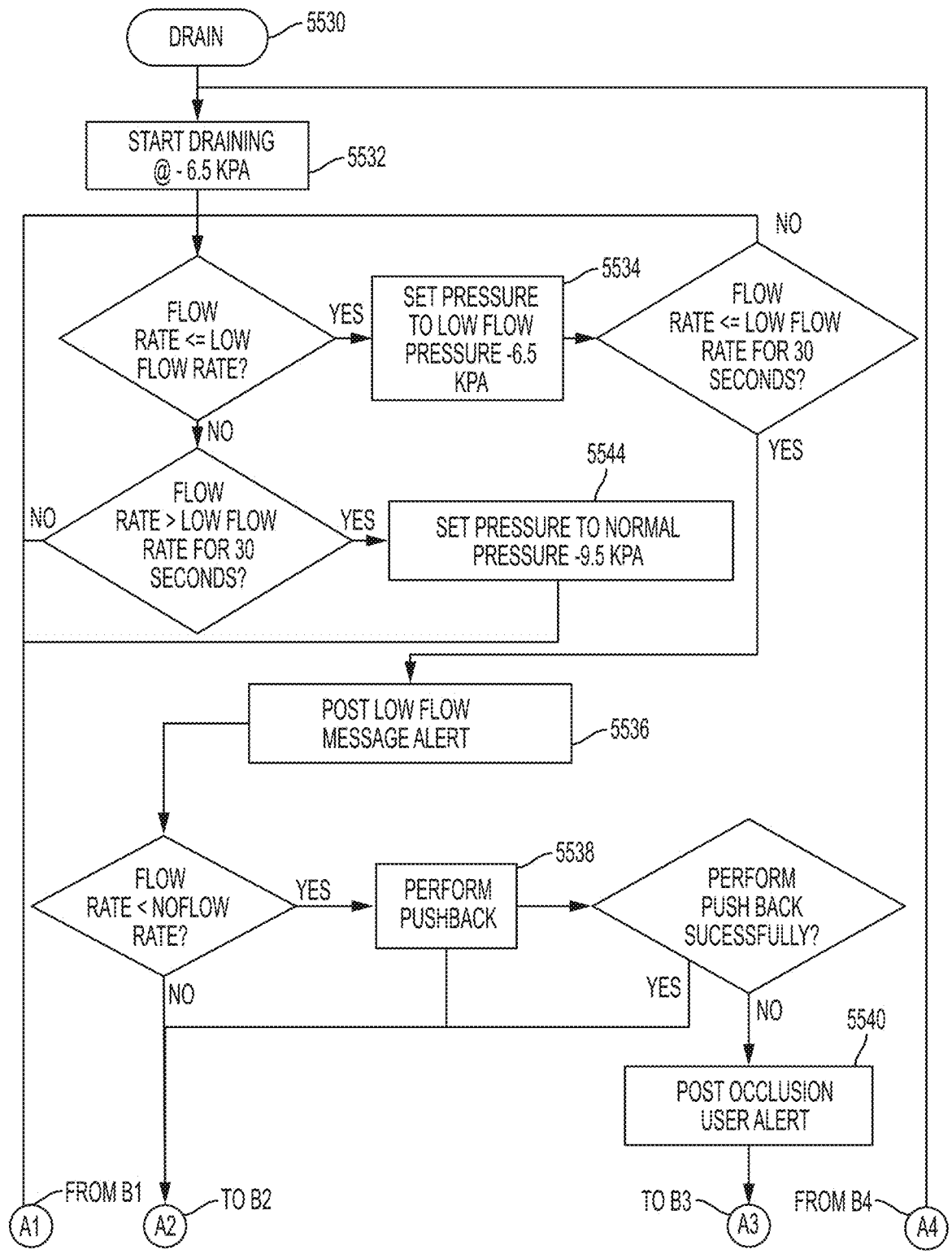
Figure 127B:
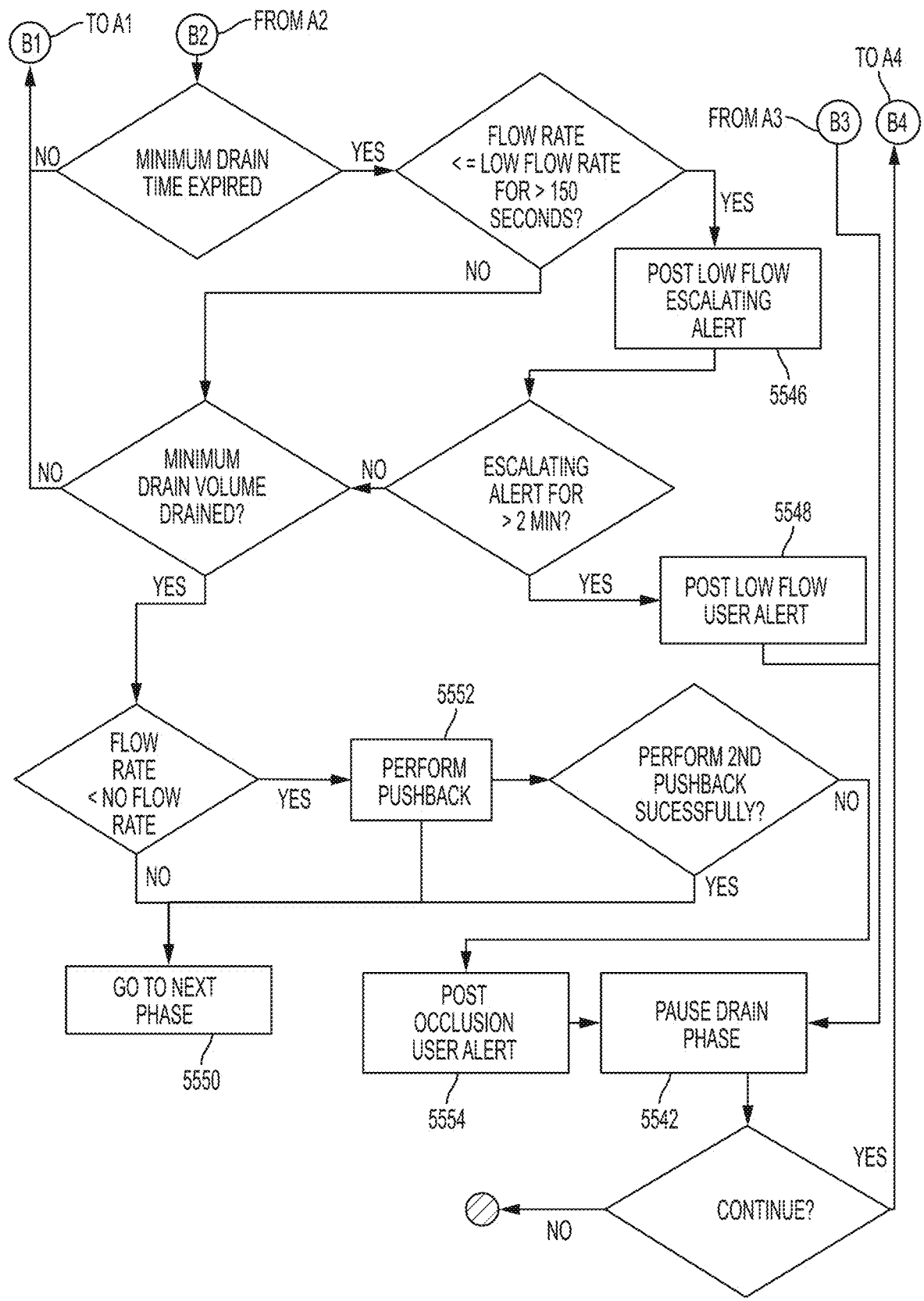

FIGS. 127A and 127B show a flowchart of a cycler 14 performing an initial drain that starts with a flow check. As mentioned above, flow checks may be performed on other drains during a therapy as well. As shown, the drain starts in step 5530. As shown in step 5532, the drain begins with a flow check at a first pressure which is a flow check pressure. In the example embodiment, the drain begins with a drain pressure of −6.5 kPa.

In the event that the flow rate during the flow check is determined to be greater than a flow rate threshold, the cycler 14 may check to see that a flow rate above the threshold is maintained for a predetermined period of time (e.g. 30 seconds). The flow rate threshold may, for example, be a value between approximately 35 ml/min and 75 ml/min. In an embodiment, the flow rate threshold may be approximately 50 ml/min.

If the flow rate is maintained above the threshold, the cycler controller may set the drain pressure to a second pressure considered to be a normal drain pressure in step 5544. This pressure is generally greater (i.e. more negative) than the flow check pressure. In the example embodiment, the normal drain pressure is shown as −9.5 kPa. The flow rate during the drain may continue to be monitored to determine if the flow rate decreases below the flow rate threshold.

In the event that flow rate during the flow check or a drain at normal pressure is determined to be less than or equal to the flow rate threshold, the pressure for the drain operation may be set to a reduced flow pressure in step 5534. In the example embodiment, the reduced flow pressure is the same as the flow check pressure, though this need not always be the case. If the reduced flow condition persists for a predetermined period of time (e.g. 30 seconds), a reduced flow alert may be signaled to a user in step 5536. In some embodiments, this alert may be a silent alert and be displayed as a text notification on the user interface of the cycler 14.

In the event that the flow rate is less than the no flow rate, in some embodiments a push back attempt may be performed in step 5538. In a push back attempt, a cycler 14 may attempt to pump a small volume of fluid into the patient's peritoneal cavity. This may allow the cycler controller to determine if the line is occluded, as the cycler 14 will be unable to deliver the fluid if an occlusion is present. If a low flow condition is related to a peritoneal catheter tip being lodged against a surface or in a tissue recess, the push-back of a small amount of fluid may be sufficient to disengage the catheter tip. The low flow condition may thus be relieved without the cycler controller necessarily having to notify the user. The controller in this case may re-attempt a flow check procedure. In some embodiments, step 5538 may only be performed if the flow rate has been below the low flow rate for a defined period of time (e.g. 30 seconds). In the event that the pushback attempt in step 5538 fails, the cycler 14 may notify the user that an occlusion exists in step 5540. The drain may then be paused in step 5542 and a user may have the option of continuing or bypassing the drain. If a user elects to continue the drain, another flow check may be performed in step 5532 and the flowchart may start over.

If a pushback attempt is successful, or a pushback attempt is unnecessary because the flow rate is greater than the no flow threshold, the cycler 14 may check to see if a minimum drain time has expired or elapsed. This time may, for example, be a clinician programmable parameter. If the minimum drain time has not elapsed, the cycler 14 may continue to monitor the flow rate returning to step 5534 or step 5544 to set the drain pressure accordingly.

If the minimum drain time has expired, the cycler 14 may check to determine if the flow rate has been below or equal to the flow rate threshold for greater than a predetermined period of time. This period of time may also be modifiable by a user such as a clinician. In the example embodiment, the period of time is shown as 150 seconds.

In the event that the flow rate has been at or below the flow rate threshold for more than the predetermined period of time, a reduced flow alert may be signaled to the user in step 5546. This alert may include a text notification displayed on the user interface of a cycler 14 and may be accompanied by an audible noise or tone. If the flow rate persists at or below the flow rate threshold, another reduced flow alert may be signaled to the user in step 5548. This alert may be a higher level alert than that signaled in step 5546. The drain may then be paused in step 5542 and the user may elect to bypass or continue the drain as described above.

In the event that the flow rate is above or rises above the flow rate threshold either before or after step 5546 is to be performed, a cycler controller may check to determine if a minimum pre-determined drain volume has been drained from the patient. If the minimum drain volume has not been met, the cycler 14 may continue to monitor the flow rate returning to step 5534 or step 5544 to set the drain pressure accordingly. If the minimum drain volume has been met the cycler 14 may check to determine if the flow rate is above the no flow rate. If the flow rate is above the no flow rate, the cycler 14 may end the drain and proceed to the next phase of a cycle in step 5550. Since the example flowchart shown in FIGS. 127A and 127B applies to an initial drain, the intraperitoneal volume of the patient may be set to zero in step 5550 as well. In embodiments in which similar logic is used in other therapy drains, the patient volume may not be reset to zero after the drain. In alternative embodiments, if the minimum drain volume has been drained from the patient, the cycler 14 may proceed directly to step 5550.

If the flow rate is determined to be below the no flow rate after the minimum drain volume has been drained from the patient, a cycler controller may command the cycler 14 to perform a pushback in step 5552. In some embodiments, this pushback back may not necessarily be performed. For example, in some embodiments, if a pushback was performed in step 5544, a pushback may not be performed in step 5552. If the pushback is successful, the cycler 14 may end the drain and proceed to the next phase of a cycle in step 5550. If the pushback attempt is unsuccessful, an occlusion alert may be signaled to a user in step 5554. The drain may then be paused in step 5542. A user may then elect to bypass the drain, attempt to resolve the problem and continue with the drain as described above.

In some embodiments, a cycler 14 may be configured to perform either normal drains or soft drains. This may be selectable by a user or caregiver via the user interface of the cycler 14. A processor or controller of the cycler 14 may generate a screen for display on the user interface which allows the user to alter the pumping pressure from a first pumping pressure (e.g. normal pumping pressure) to a second pumping pressure (e.g. soft pumping pressure or weaker pumping pressure). This screen preferably is presented to the user during a drain. The pumping pressure optionally may only be altered for the pumping chamber 181 fill stroke. In response to the user changing the pumping pressure via the user interface, the processor may control the pneumatic circuit of the cycler 14 to apply a different pumping pressure to the pumping chambers 181 of an installed cassette 24.

In some embodiments, this feature may be enabled or disabled by a clinician. For example, a clinician may enable such an option for a patient who reports tugging or discomfort during drains. In various embodiments, this option may only be enabled for certain types of drains. For example, a clinician may have the ability to allow the user to perform soft drains during initial drain.

Such an option may allow the user to switch to a gentler drain in the event that a drain at normal drain pressure is causing discomfort. If an option to select a soft drain or normal drain is available, the cycler 14 should preferably default to performing a normal drain as soft drains may shorten the dwell times for a therapy. The option may, for example, only be made available after a reduced flow condition is detected by the cycler controller. In other embodiments, the user may have an option of selecting between normal drains and soft drains when starting the therapy. In some embodiments, the user may be able to specify specific drains as soft drains and other drains as normal drains.

A soft drain may be at a weaker pressure than that of the normal drain, and may be pre-set or may be user-definable via the user interface. The soft drain may, in some embodiments, use a pumping pressure similar to the pumping pressure used during a flow check or may use the pressure set point defined for the flow check. The soft drain pumping pressure may for example, be weaker than the normal drain pumping pressure by between about 2 and 6 kPa. In some embodiments, a user such as a clinician may define the pressure set points for the normal drain and soft drain. Alternatively, the reduced pumping pressure may be selected from a range of pumping pressures. Optionally, a clinician may be allowed to create another drain profile. For example, a clinician may define a normal drain, softer drain, and softest drain pressure. The user may have the ability to select any of these pre-defined drain types if desired. If a user has set a maximum therapy time for a course of therapy, the controller may not modify the drain pressure unless a reduced flow condition has been detected.

Figure 128:
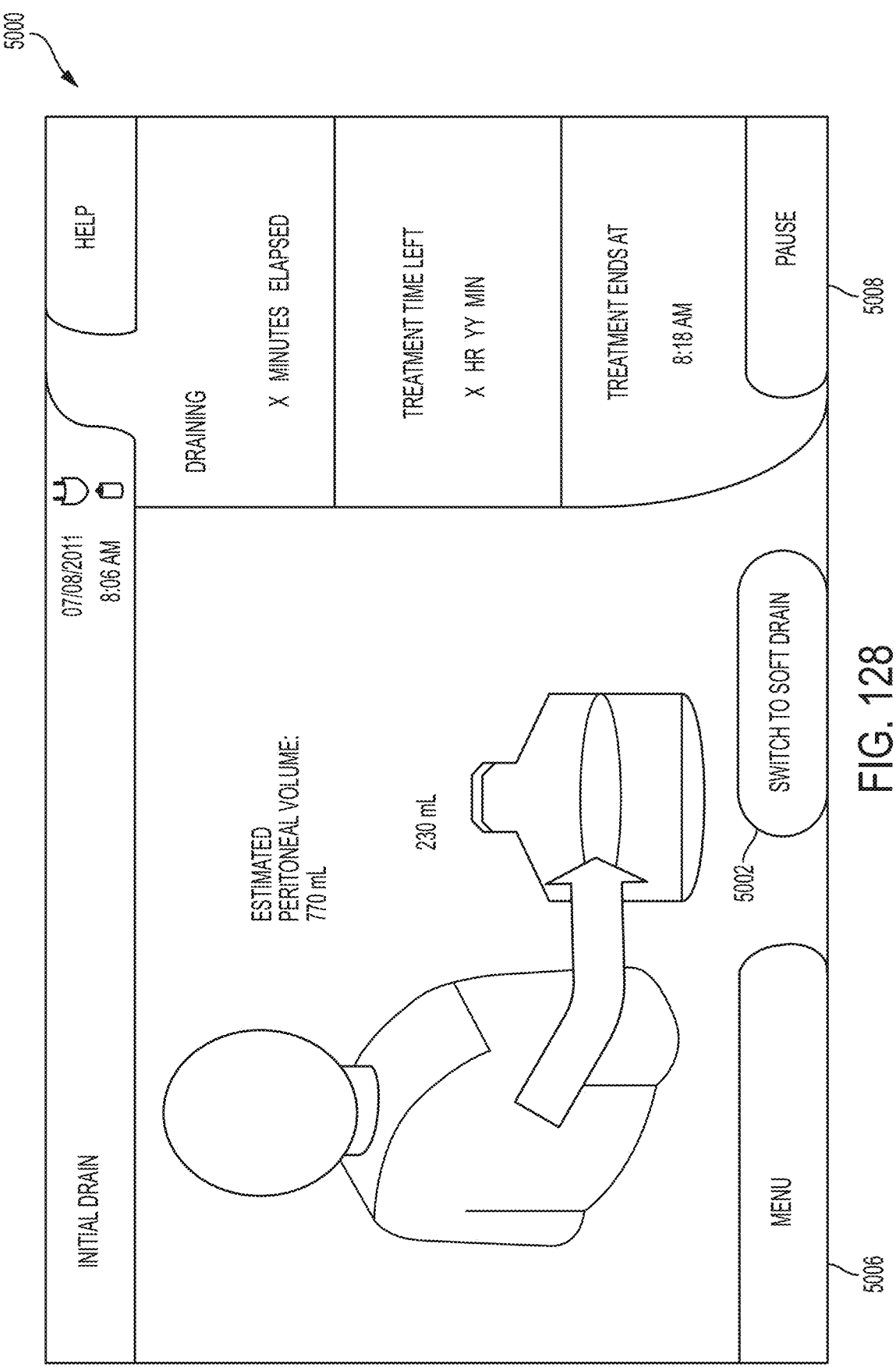

FIG. 128 depicts an example user interface screen which may be displayed on the user interface of a cycler 14 during a drain. Specifically, the screen shown in FIG. 128 is an initial drain screen 5000. As shown, the initial drain screen 5000 includes a variety of information about the drain and the therapy. As shown, the screen also includes a switch to soft drain option 5002. The switch to soft drain option 5002 may, in some embodiments, be selected at any time during the drain. In other embodiments, the switch to soft drain option 5002 may not be enabled or may be grayed out until after a user presses a pause button 5004 to pause the drain. This may help to avoid an accidental button press of the switch to soft drain option 5002 which would slow down the drain operation for no need. In other embodiments, the switch to soft drain option 5002 may not be present on all drain screens. Instead, a user may need to navigate to a switch to soft drain option 5002 by selecting a menu option 5006 on the user interface. When the soft drain option 5002 is selected and the drain pressure is dropped to the soft drain pressure, the user interface may similarly be used to return to a normal drain if desired. As would be appreciated by one skilled in the art, other embodiments may have options for multiple different types of drains such as, e.g., a normal drain, softer drain, and softest drain. In some embodiments, instead of providing a button, the switch to soft drain option 5002 may be implemented in the form of a slider bar. One end of the bar may be the weakest pressure which may be defined for use during a drain. The other end of the bar may be the normal drain pressure. The user may select a desired pressure from anywhere in the range of pressures between each end of the bar. Optionally, the controller may compute the effect on therapy time, pumping time or another measure of the lengthening or shortening the time needed to drain a volume of fluid in response to a change in the pumping pressure, and display information on this effect on the user interface. In an embodiment, the user may be required to confirm on the user interface that a change in pumping pressure is still desired.

The triggering flow rate or the time duration at that lower flow rate may vary, depending on patient-related or clinician-related factors. Additionally, the amount of time which the cycler 14 continues pumping at lower pressure may vary.

In some embodiments, pumping pressure may be adjusted based upon flow rate at any point in a therapy. For example, in the event that a reduced flow rate is determined to exist, the pumping pressure may be lowered to minimize patient discomfort. Such a reduced flow rate condition may, for example, be a low flow condition of, e.g. 50 mL/min. There may be multiple pumping pressures assigned to a variety of flow conditions. For example, there may be a "normal" pumping pressure which is used in normal flow conditions (e.g. flow greater than 50 mL/min). There may be a low flow pressure for flow conditions which are less than the normal flow condition flow rate. There may also be a no flow pumping pressure which may be used in the event that the flow rate is very low (e.g. less than or equal to 15 ml/min).

Pumping pressure need not be assigned based on discretely defined flow conditions (e.g. normal flow, low flow, no flow). Instead, in such embodiments, pumping pressure may be adjusted on a gradient. That is, the pumping pressure may increase or decrease in magnitude in a relatively continuous manner relative to flow rate. The gradient may be linear or non-linear. For example, the magnitude of the increase in pressure may be proportional to the magnitude of the increase in flow rate and the magnitude of the decrease in pressure may be proportional to the magnitude of the decrease in flow rate. The pumping pressure may be adjusted in a substantially continuous fashion as flow rate data becomes available. This continuous adjustment may occur after each stroke or may occur as each stroke progresses if flow rate is estimated during the progression of the stroke. The controller may be programmed to limit the pump pressure variation to within a pre-determined range of pressures. In embodiments in which the pumping pressure used increases or decreases in magnitude relative to the flow rate, a drain operation may still begin with a flow check. That is, the drain operation may start with the negative pressure for the drain phase being set at an initial flow check pressure for a predetermined period of time. This pressure may be selected so that it would be appropriate for a reduced flow condition (e.g. −6.5 kPa) in order to minimize any tugging sensation experienced by the user at the start of the drain operation. If the flow rate falls below a predefined threshold for more than a predetermined period of time, the cycler controller may stop adjustment of the pumping pressure. If the total volume drained during the drain operation is less than the target volume for the drain, a pushback may be performed to check for an occlusion. If the total volume drained has at least reached the target volume for the drain operation then the cycler controller may determine that the drain operation has completed and move onto the next phase of the therapy.

In some embodiments there may be a plurality of different pressures for each defined flow condition. These different pressures may be assigned based upon the source and the destination for the fluid being moved during the pumping stroke. For example, a first pumping pressure may be used when fluid is being filled into a patient's peritoneal cavity at a defined flow rate or flow rate range. A second pressure may be used when fluid is being drained from the patient at a defined flow rate or flow rate range. A third pressure (e.g., closer to the maximal available pressure from the pressure reservoirs) may be selected if no fluid is being pumped to or from a patient (e.g. chamber to drain, chamber to heater bag, heater bag to chamber, etc.), in which case there may be no need to alter the pressure based upon flow rate.

Automated Effluent Sampling

In some embodiments, when programming a therapy, a user may be able to enable/disable or turn on/off an automated sampling parameter. The automated sampling parameter causes a cycler 14 to automatically fill an effluent sampling bag with spent dialysate from a patient during the therapy. The user may be able to define a number of additional parameters which may be used to specify various aspects of the automated sample taken. For example, these additional parameters may be used to define a sample volume to be taken, and when in the therapy a sample is to be taken. They may also be used to define how many samples are to be taken or how many sample bags are to be filled. In some embodiments, these additional parameters may only be enabled or unlocked for editing if the automating sampling parameter has been enabled. In some embodiments, there may be a variety of pre-set sampling regimens with definable parameters from which a user may choose. For example, a sampling regimen may include parameters appropriate for a peritonitis test. A sampling regimen may also include parameters which would be appropriate for a peritoneal equilibration test or peritoneal membrane transport function test.

In one embodiment, an effluent sampling reservoir may be placed into fluid communication with a set 12 installed in the cycler 14. The cycler 14 may pump spent fluid from the connected patient into the effluent sampling reservoir as prescribed by the therapy program. In various embodiments, the user may be asked to identify a fluid port of the dialysis set to which the effluent sampling reservoir has been connected or may be directed to attach the reservoir to a specific port. Alternatively, a set intended to be used in therapies with automated effluent sampling may be provided. In such embodiments, the effluent sampling reservoir may be attached to a specific port on the dialysis set and the cycler controller may command pumping to that port when performing an automated sampling operation. In some embodiments a set 12 may include a connector for an automated sampling reservoir which is unique to the automated sampling reservoir and may only couple to a corresponding unique mating connector on an automated sampling reservoir.

In other embodiments, a feature of a set or fluid line installed in a cycler 14 may be used to determine that the cycler 14 is to take an automated effluent sample. In such embodiments, the feature may, for example be a specific geometry which is sensed by one or more sensor in a cycler 14. When a cycler controller receives data from a sensor indicating that the specific geometry is present, the controller may command the cycler 14 to pump fluid to an effluent sampling reservoir during the therapy. In some embodiments, there may be multiple different geometries which may be detectable by the sensor(s). Each geometry may correspond to effluent sample programs with different sampling parameters. The sensor(s) may be any suitable sensor or combination of sensors, such as, but not limited to a contact sensor (e.g. microswitch), Alternatively, the feature of the set or fluid line may be a magnet or magnetic feature included as part of the cassette 24 or fluid line. When installed in the cycler 14, a hall effect sensor in the cycler 14 may detect the presence of the magnet or magnetic feature. When a cycler controller receives data from the hall effect sensor indicating the magnet or magnetic feature is present, the controller may command the cycler 14 to pump fluid to an effluent reservoir during the therapy.

In another embodiment, a cycler 14 may use an optical sensor to read or decode an identifying mark on a set or a fluid line installed in a cycler 14. The identifying mark may include a code interpretable by the controller that an automated effluent sample is to be taken during a therapy. Additionally, the identifying mark may further be coded to specify various parameters relating to the effluent sample to be taken during the therapy. Such an identifying mark may comprise indicia such as, but not limited to 2-D indicia (e.g. aa barcode, data matrix, etc.), or any other suitable indicia. In some embodiments, the indicia may be included on an identification tag 1100 (see FIG. 20) that may snap onto a portion of the set or fluid line.

Figure 129:
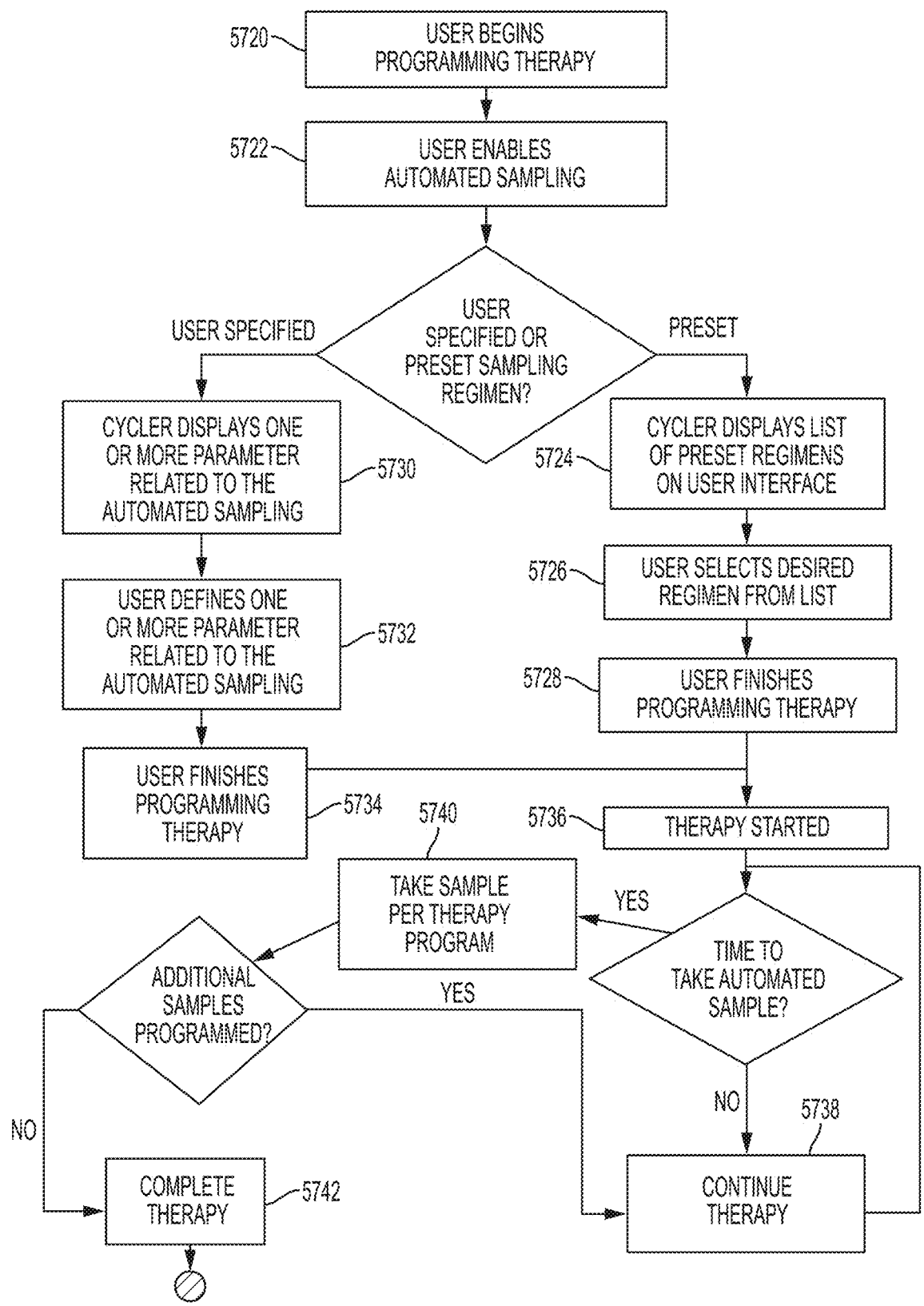

FIG. 129 shows a flowchart outlining steps which may be used to program and collected an automated effluent sample using a cycler. As shown, in step 5720, the user begins programming a therapy. This may involve specifying various therapy parameters such as any of those commonly defined in the art on a user interface of the cycler. In step 5722 a user enables an automated sampling option or parameter. This may be done using a user interface of the cycler. In some embodiments, the user may then choose between a customized or user specified sampling program or a preset sampling program. This may in some embodiments be accomplished by user interaction with a prompt displayed on the user interface of the cycler.

If a user chooses to use a preset sampling program or regimen, the cycler displays a list of one or more preset regimens on the user interface of the device in step 5724. These preset regimens may for example include a peritonitis test, peritoneal equalization test, single sample, etc. In some embodiments, these presets may be tied to other parameters programmed during the therapy. For example, when a preset is selected the amount of fluid to be pumped into the sampling reservoir may be dependent upon the patient fill volume. Additionally, in some instances a user may have to enter one or more additional parameter once a preset has been selected. For example, if a user selects that a single sample is to be collected, the user may be required to define when in the therapy this is to occur. A user may select the desired sampling regimen or program from the list in step 5726. This may be done via any suitable type of interaction with the user interface of the cycler. The user may then finish programming the therapy in step 5728.

If a user chooses to define a user specified or custom sampling regimen, the cycler may display one or more parameters related to the automated sampling on the user interface of the cycler in step 5730. The user may then define one or more parameter related to the automated sampling to be performed by the cycler in step 5732. This may be done via any suitable type of interaction with the user interface of the cycler. The parameters defined may be, but are not limited to any of those mentioned above. The user may then finish programming the therapy in step 5734.

The therapy is started in step 5736. The therapy continues as programmed in step 5738 until it is time for an automated sample to be taken by the cycler. Once it is time for the sample to be taken, the cycler takes the sample as specified by the therapy program in step 5740. If there are additional samples to be taken during the therapy, the cycler proceeds back to step 5738 and continues the therapy until it is time to take another sample. If there are no additional samples to be taken in the therapy, the cycler completes the therapy in step 5742.

Figure 130:
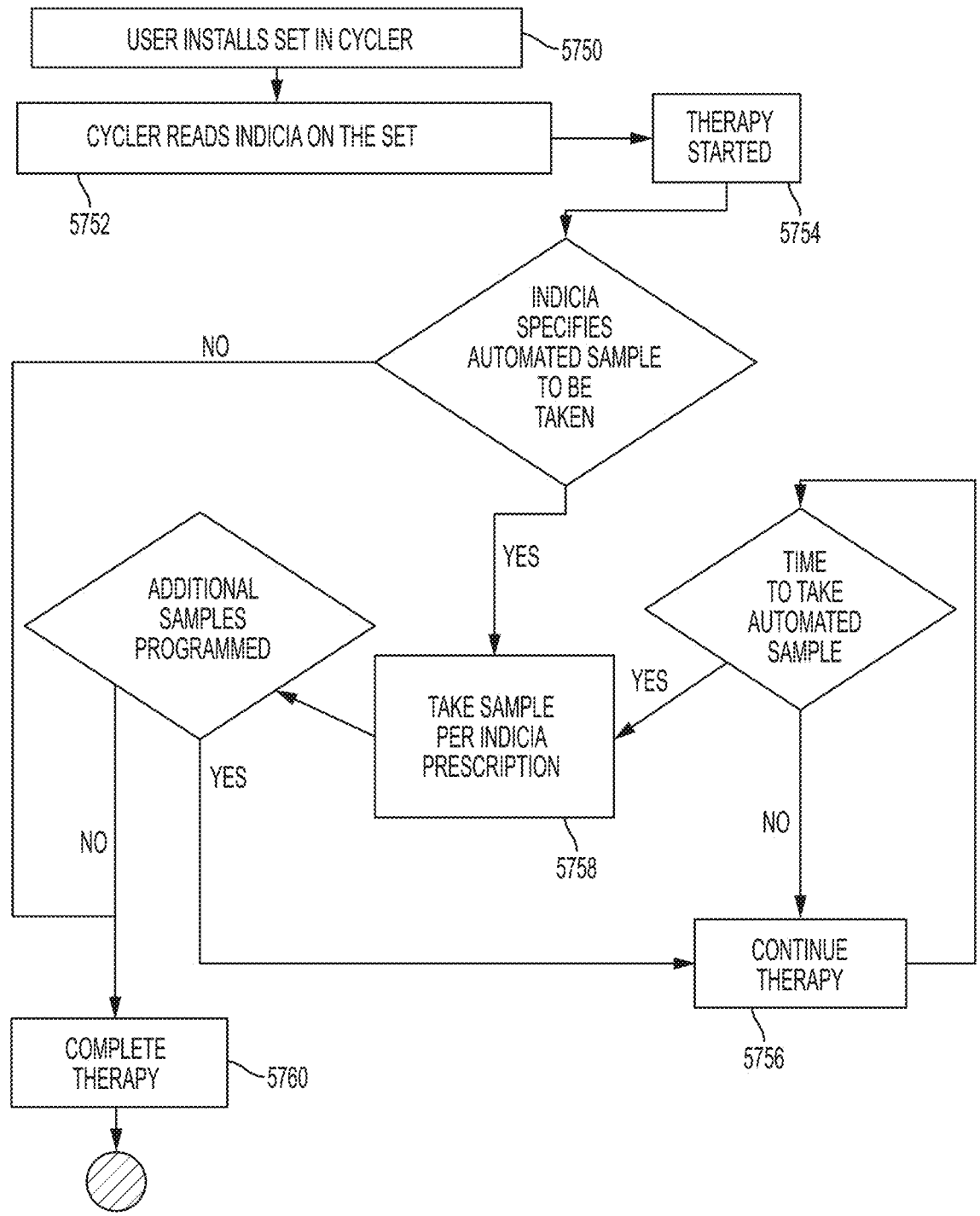

FIG. 130 depicts a flowchart detailing a number of example steps which may be used to program and collected an automated effluent sample using a cycler. In the example embodiment, the cycler includes a sensor which is configured to read an indicia on a set. The indicia on the set may include information about the set or the therapy to be performed. The indicia may also specify whether or not and the manner in which an automated effluent sample is to be taken by the cycler.

As shown, in step 5750, the user installs the set in the cycler. The cycler may then read the indicia on the set 5752. The therapy is started in step 5754. In the event that the indicia indicates that an automated sample is not to be taken during the therapy, the cycler performs and completes the therapy in step 5760.

If the indicia specifies an automated sampling regimen or program, the therapy continues as programmed in step 5756 until it is time for an automated sample to be taken by the cycler. Once it is time for the sample to be taken, the cycler takes the sample as specified by indicia in step 5758. In alternate embodiments, the indicia may specify whether the sample is to be taken and the cycler performs a preprogrammed sampling procedure. If there are additional samples to be taken during the therapy, the cycler proceeds back to step 5756 and continues the therapy until it is time to take another sample. If there are no additional samples to be taken in the therapy, the cycler completes the therapy in step 5760.

Head Height Detection

In some circumstances, it may be useful to determine the heightwise location of the patient relative to the cassette 24 or other portion of the system 10. For example, dialysis patients in some circumstances can sense a "tugging" or other motion due to fluid flowing into or out of the patient's peritoneal cavity during a fill or drain operation. To reduce this sensation, the cycler 14 may reduce the pressure applied to the patient line 34 during fill and/or drain operations. However, to suitably set the pressure for the patient line 34, the cycler 14 may determine the height of the patient relative to the cycler 14, the heater bag 22, drain or other portion of the system. For example, when performing a fill operation, if the patient's peritoneal cavity is located five feet above the heater bag 22 or the cassette 24, the cycler 14 may need to use a higher pressure in the patient line 34 to deliver dialysate than if the patient's peritoneal cavity is located five feet below the cycler 14. The pressure may be adjusted, for example, by alternately opening and closing a binary pneumatic source valve for variable time intervals to achieve the desired target pump chamber pressure. An average desired target pressure can be maintained, for example, by adjusting the time intervals to keep the valve open when the pump chamber pressure is below the target pressure by a specified amount, and to keep the valve closed when the pump chamber pressure is above the target pressure by a specified amount. Any adjustments to maintain the delivery of a complete stroke volume can be made by adjusting the fill and/or delivery times of the pump chamber. If a variable orifice source valve is used, the target pump chamber pressure can be reached by varying the orifice of the source valve in addition to timing the intervals during which the valve is opened and closed. To adjust for patient position, the cycler 14 may momentarily stop pumping of fluid, leaving the patient line 34 in open fluid communication with one or more pump chambers 181 in the cassette (e.g., by opening suitable valve ports in the cassette 24). However, other fluid lines may be closed, such as the upper valve ports 192 for the pump chambers 181. In this condition, the pressure in the control chamber for one of the pumps may be measured. As is well known in the art, this pressure correlates with the "head" height of the patient, and can be used by the cycler 14 to control the delivery pressure of fluid to the patient. A similar approach can be used to determine the "head" height of the heater bag 22 (which will generally be known), and/or the solution containers 20, as the head height of these components may have an effect on pressure needed for pumping fluid in a suitable way. An example head height detection and pressure adjustment method is described in U.S. Pat. No. 6,503,062 entitled Method For Regulating Fluid Pump Pressure, to Gray et al, filed Jul. 10, 2000 which is hereby incorporated by reference herein in its entirety.

A head height detection determination can be used in a variety of applications and the head height detections described may be generalizable to any cassette 24 based pumping system, but are described herein with relation to a dialysis cycler 14. Such a determination may be made at a plurality of times, for instance just after cycler 14 priming, before fluid transfer to and from the patient, or when altered (e.g. decreased) flow conditions are detected. Head height detection may also be performed simultaneously with fluid transfer through a separate chamber of a pumping cassette 24. Head height detection may also be performed for multiple locations of interest within the system simultaneously. The layout of fluid buses in the cassette 24 may be arranged to facilitate this. For example, two locations of interest within the system 10 where simultaneous measurement or measurement and simultaneous volume transfer is desired may communicate with different fluid buses. Locations of interest may also have dedicated fluid pathways to facilitate these simultaneous actions. Where used in a cycler 14 which admixes dialysate instead of using dialysate from a pre-mixed bag, head height detection may be of particular usefulness. For example, head height detection may confirm the components of interest are in an expected location. Since air within a pump chamber 181 may be under varying states of compression due to differences in source head height, this may allow a set of assumptions regarding behavior of any air in a pump chamber 181 to be made. This may help to increase mixing and general volume transfer accuracy as volumetric displacements calculated by the cycler 14 may be captured with more robust reliability.

In embodiments which are configured to perform continuous flow rate and stroke displacement estimation (see, e.g. FIGS. 69-76), the pump membrane or sheeting 151 (see, e.g., FIG. 4) of the sheeting/membrane 15 may be precisely positioned to allow for repeatable determination of both positive and negative head heights over a maximized detection range. Use of a cassette 24, having pre-formed pump sheeting 151 which is flaccid or displaced substantially without stretching through out the stroke may provide further benefit. The pump sheeting 151 target position may be an intermediary location or state between the displacement extremes of the pump sheeting 151 (e.g. a pump chamber 181A, B fully filled and fully delivered pump sheeting 151 position). This may repeatably allow for a single head height determination process to reliably detect the head height of a location of interest.

The maximized detection range may be selected such that the range is most inclusive or entirely inclusive of expected head heights for a location of interest (e.g. patient, heater bag 22, source solution bag 20, other source component). In certain examples, the maximized detection range may be a range which allows for the detection of a maximum positive and negative head height of about the same absolute value (e.g. absolute values within several mm of one another). Depending on the location of interest, the pump chamber sheeting 151 position, and thus detection range, may be adjusted to favor detection of a greater range of either positive or negative head heights.

Figure 131:
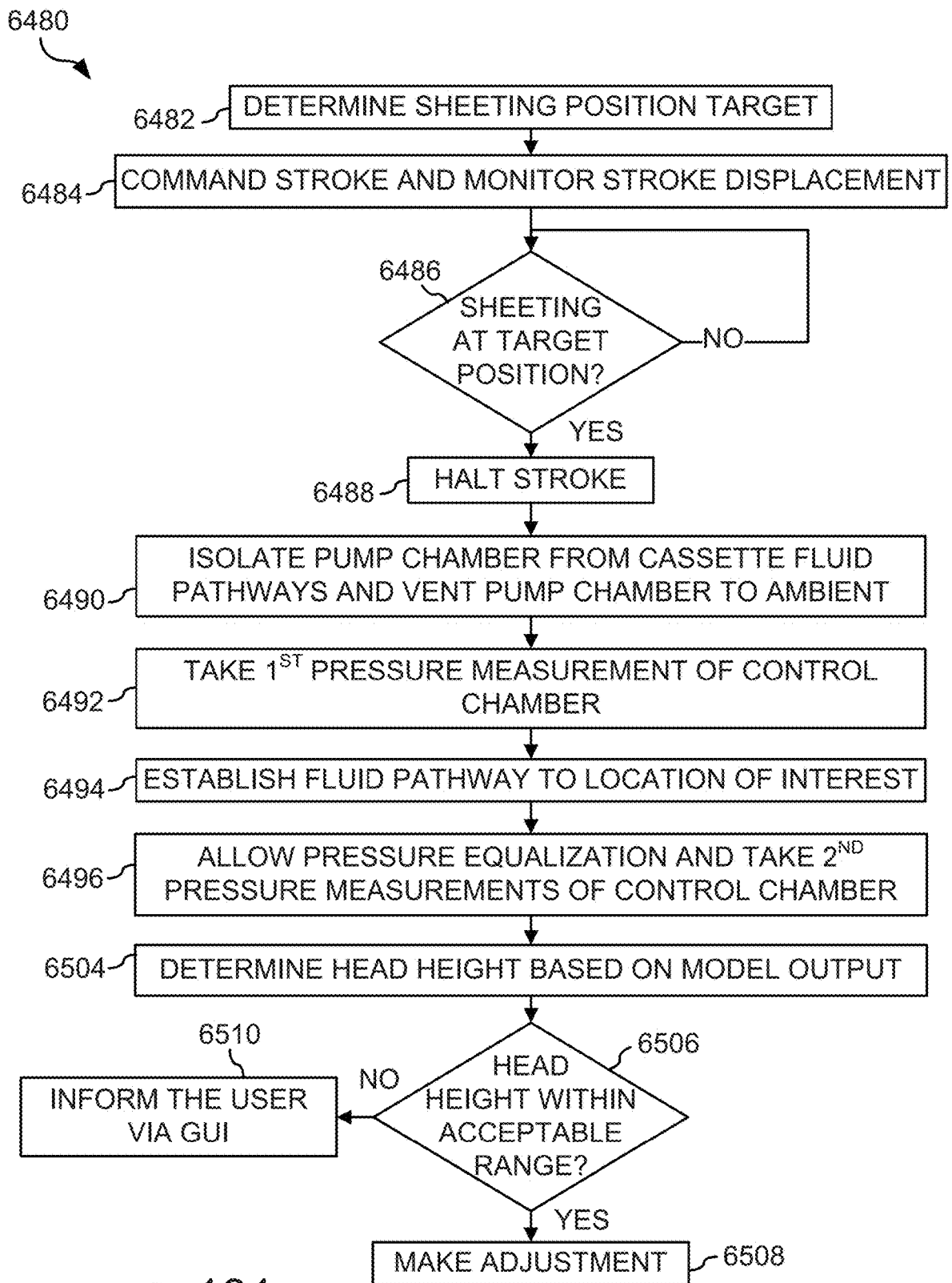

Referring now to the flowchart 6480 depicted in FIG. 131, in block 6482, a controller or control system 16 of the cycler 14 may determine a pump sheeting 151 (see, e.g. FIG. 4) target position. The pump sheeting 151 position target may also be a predetermined position. In some embodiments, a target position may be predetermined for each of a number of locations of interest. The target position used may that associated with the location for which head height is to be determined.

In block 6484, the controller may command the cycler 14 to start a pumping stroke. The pumping stroke may be a fill stroke or delivery stroke depending on the starting position of the pump sheeting 151 with respect to its target position. Stroke displacement, and thus pump sheeting 151 location may also be monitored during the stroke in block 6484. Again, this may be accomplished as described in relation to FIGS. 69-76 for example. If, in block 6486, the controller determines the pump sheeting 151 is at its target position, the stroke may be halted at that point by the controller in block 6488. Optionally, a volume measurement including a pressure equalization of the control chamber 171B volume (whose pressure is known) with a known reference volume 147 (see, e.g., FIG. 67) at known pressure may be performed to verify the pump sheeting 151 is at the target position.

In block 6490, the pump chamber 181A, B may be isolated by closing inlet/outlet cassette fluid valves 190, 192 (see, e.g., FIG. 6) to/from the pump chamber 181A, B. The control chamber 171A, B through which pressure is applied to the pump chamber sheeting 151 may also be vented in block 6490. The control chamber 171A, B may be vented to a venting reservoir such as the ambient atmosphere. Once the control chamber 171A, B has equalized with the venting reservoir, the control chamber 171A, B may be isolated. A first pressure of the control chamber 171A, B may be may be measured in block 6492.

In block 6494, various fluid valves of the cassette 24 may be opened to establish fluid communication between the pump chamber 181A, B and the location of interest. In block 6496, pressure equalization between the control fluid in the control chamber 171A, B and the fluid in the pump chamber 181A, B may occur. In some embodiments, block 6494 may allow for a predefined time period to elapse over which pressure equalization occurs. Alternatively, at least one pressure sensor in communication with the control chamber 171A, B fluid may be monitored. In the latter case, block 6496 may end once the sensor data indicates pressure of the control chamber 171A, B is relatively stable. For example, block 6496 may end once pressure has not deviated greater than a certain amount or outside of a range for a period of time.

A head height of the location of interest may then be determined in block 6504. Head height may be determined by relating the density, acceleration of the fluid due to gravity, and the pressure at the end of block 6496 to the head height of the component of interest. The head height may be equal to the pressure at the end of block 6496 (density*acceleration due to gravity). In some embodiments, the calculated head height may be checked against an acceptable range to ensure the system 10 is properly set up. If, in block 6506, the head height is within the acceptable range, pumping pressures may be adjusted to compensate for the head height in block 6508 as mentioned above. If, in block 6506, the head height is not within the acceptable range, an alert may be generated by a controller for display on a GUI of the cycler 14 in block 6510.

Referring back to block 6482, in some embodiments, multiple models may be employed to determine the target position based on a desired maximized detection range. If, for example, the time needed for pressure in the control chamber 171A, B and pump chamber 181A, B to equalize is above or below a threshold, different models may be used. If below, a first model may be used; If above, a second model may be used. Additional models and thresholds may be included in some embodiments. The first model may be an isothermal model while the second model may be an adiabatic model. The choice of model may be determined based on flow rates from other portions of the therapy or pre therapy. Alternatively, one of the first or second models may be used initially. The controller may reperform the head height determination if warranted by the pressure equalization time.

The first model may operate based on the following example equation:

$$P_f = (P_i(V_{con,i}))/V_{con,f}$$

Where $P_f$ is the final pressure of the control chamber 171A, B volume after equalization in block 6496, $P_i$ is the first pressure from block 6492, $V_{con,i}$ is the initial control chamber 171A, B volume when pump sheeting 151 is at the target position, and $V_{con,f}$ is the final control chamber 171A, B volume.

The second model may operate based on the following example equation:

$$P_f = (P_i(V_{con,i}/V_{con,f})^\gamma$$

Where $\gamma$ is a heat capacity ratio (e.g. 1.4).

By assuming that the pump chamber sheeting 151 transits from the target position to an extreme of travel, these models may be employed to determine the target position based on a desired maximized detection range. For any given target pump sheeting 151 position (and therefore $V_{con,i}$) head height sensitivity ranges may be determined. $P_i$ may be known (e.g. set at 101 kPa, or measured by a sensor communicating with ambient). By assuming the pump sheeting 151 will transit to an extreme of travel, a value for $V_{con,f}$ may also be known. From this, pressure changes needed to bottom out the pump sheeting 151 at an extreme of travel, and therefore head height sensitivity can be determined. Thus, it is possible to choose a pump sheeting 151 target position which has the greatest sensitivity range to different head heights based on observed equalization time.

In the event that a controller determines the head height to be around the edge of a sensitivity range, optionally a second head height detection determination may be made. If the head height is at an edge of the sensitivity range, it can be surmised the pump sheeting 151 had displaced to or near an extreme of travel. In the second head height detection determination, the pump sheeting 151 position target used may be the opposite extreme of travel. This would allow for greater visibility on head heights of the type (e.g. positive or negative) detected in the first head height determination but of greater magnitude.

FIG. 132 shows a number of exemplary actions which may be executed to calculate head height pressure in another embodiment of a head height determination. As shown in FIG. 132, in block 8000 the cassette may primed. In block 8002, a pump chamber may be placed in an initial state where the chamber's sheeting can displace in response to any pressure exerted by the head height of a component of interest. In certain embodiments, the pump sheeting may be placed in a state where it may displace in response to either positive or negative pressure. Thus, if the pump chamber is placed in fluid communication with a system component of interest at either positive or negative head height with respect to the pump chamber, the establishment of fluid communication between the chamber and the component of interest may displace the sheeting. This state may be referred to as an intermediate or mid-stroke state or position. This intermediate position may be determined by the control system as described above or may be preset.

In situations where it is anticipated that the head height of the component of interest will exert a positive pressure on a pump chamber, the pump chamber may be placed in a first biased state in block 8002. The first bias state may be a state which biases the detection range toward detection of positive head heights. For example, the pump chamber may be left in a fully delivered state. Likewise, if it is anticipated that the head height of the component of interest will be negative with respect to a pump chamber, the pump chamber may be placed in a second biased state in block 8002. The second biased state may be a state which biases the detection range toward detection of negative head heights.

In block 8004, the control chamber associated with the pump chamber to be used for measuring head height may be vented. In block 8006, the control system of the cycler may wait for pressure stability within the control chamber to be achieved. In block 8008, the control chamber associated with the pump chamber may be isolated. In block 8010, the control system of the cycler may wait for the pressure to stabilize within the control chamber. In block 8012, the pump chamber may be placed in fluid communication with a system component of interest. In block 8014, control system may detect a number of pressure peaks and predict a final pressure of the control chamber (described in more detail below, e.g., in reference to FIG. 134). In block 8016, the control system may calculate an appropriate head height pressure adjustment based off the final pressure. This adjusted pressure may be used for subsequent fluid transfer to/from the component of interest.

Referring now also to FIG. 133, a consistency check may be used in blocks 8006 and 8010 of FIG. 132 to detect pressure stability in the control chamber associated with the pump chamber to be used for measuring head height of the component of interest. Consistency checks may also be used in the head height determination described in relation to FIG. 131. When at least one pressure consistency criteria is met during the consistency check, the consistency check may be deemed to have passed. During a consistency check, pressure samples may be taken at a set time interval or intervals. In some embodiments, the interval could be set to about 5-30 milliseconds (e.g. ~10 milliseconds). These samples may be numerically processed and analyzed for the presence of a predefined pattern or characteristic. When that predefined pattern or characteristic is detected, a signal may be generated which indicates that stability has been achieved and the head height detection determination may be continue.

To check for consistency, a moving average generated from the sensor data may be employed. For example, the difference (or its absolute value) between two consecutive moving average pressure samples may be calculated. Once the pressure difference is consistently near zero for the first and a number of subsequent moving average pressure samples, a signal may be generated indicating that the pressure stability has been achieved. In some embodiments, a threshold of less than a 0.03 kPa deviation from zero could be used to determine if the pressure difference is sufficiently near zero. The number of pressure samples used in the moving average window could be set to five. If pressure stability is not detected within the time delay period then it may be determined that pressure stability has not been achieved, the end pressure may be noted and the process may repeat. In some embodiments, absence of pressure stability may trigger an error to be generated by the control system or trigger error generation after a retry cap has been exceeded. In some embodiments, the control system may present an alert on a graphical user interface of the cycler asking the user to check the system or stop moving around for a period of time.

FIG. 133 is illustrative of an exemplary consistency check. In block 8018, the cassette may be primed. In block 8020, a timer may begin. The timer may set an amount of time during which it is expected that pressure stability should be achieved. The timer may be between 2-6 seconds (e.g. 3 seconds) in various embodiments. If it is determined, in block 8022, that the timer has elapsed, the control system may execute a predefined error handling protocol in block 8024. For example, the control system may generate an error signal or perform a retry of the consistency check while incrementing a retry counter (this may be limited by a retry cap).

If the preset time limit has not elapsed, the control system may receive pressure data from one or more pressure sensor monitoring the control chamber in block 8026. In block 8028, the control system may apply data smoothing to the pressure data. In some embodiments, a moving average can be used to smooth the data The moving average may employ a moving window size of 3-10 values (e.g. ~5) though this window size may grow or shrink in a relationship to sampling frequency. Any window size sufficient to filter out excessive noise may be utilized.

In block 8030, the control system may determine whether the data conforms to a first consistency criteria. If the data does not conform to the first consistency criteria, then the control system may revert back to block 8022. The first consistency criteria may be a predefined criterion which indicates that the pressure data is relatively steady. For example, in some embodiments, a comparison between two consecutive moving average pressure samples may be made. The two consecutive moving average pressure samples may be the current sample moving average and the directly preceding sample's moving average value. The comparison may be based at least in part on the difference between the consecutive pressure sample moving average values. In specific examples, the difference or an absolute value of the difference may be determined in the comparison. Where a difference is calculated, the first consistency criteria may be deemed satisfied by the controller if the difference (or absolute value thereof) is nearly zero (e.g. less than 0.025-0.02 kPa). Alternatively, the criteria may be defined as a percentage of the measurable range of head heights.

If the data does conform to first consistency criteria, then the controller may require the pressure in the control chamber to remain stable in subsequent sampling. For example, the pressure difference may be required to remain consistently near zero for a number (e.g. 3-10) of subsequent moving average pressure samples. In certain embodiments, the control system may determine that pressure stability has been achieved if comparisons performed after each of five subsequent moving average pressure samples are collected indicate that pressure is steady.

In FIG. 133, the control system may initialize a counter in block 8032. The counter may be set to the desired number (e.g. 5) of moving average sample pressures required before a determination that the pressure is stable may be made. In block 8034, the control system may receive pressure data from one or more pressure sensor monitoring the control chamber, and in block 8036 the control system may increment the counter. In block 8038, the control system may determine whether the data conforms to a second consistency criteria. For example, a comparison value calculated between a new sample and the previous sample may be required to be with a range of about 0.00 kPa to 0.05 kPa (e.g. less than 0.03 kPa). If the data does not conform to the second consistency criteria, then the control system may revert back block 8022. If the data does conform to the second consistency criteria then the control system may determine if the counter is at or below preset limit in block 8040. If the counter is at or below the preset limit, the control system may revert back to block 8034. If the counter is above the preset limit then the control system may proceed to determine head height of a component of interest in block 8042.

As mentioned in relation to block 8014 of FIG. 132, when head height of the component of interest is determined, the determination may be made on an incomplete data set. It may be possible to characterize how the system behaves and, based at least in part on that characterization, generate one or more equations that can predict a final control chamber pressure from a data set which is cut off before a final stabilized pressure is achieved. In certain embodiments, a head height determination conducted in this manner may take about 20%-15% or less of the time necessary to for a control chamber to reach a stabilized pressure. As setup of a therapy is generally performed as a user is readying for bed, minimizing the time required for setup is appreciated in the field as advantageous.

This may allow for rapid head height determinations, speeding up any pretherapy checks in which head height is determined. It may also allow for head height determinations to be made during therapy with minimal impact on the therapy itself. Without significantly increasing setup or therapy time, this may also allow for a head height determination for a component reservoir of interest to be made redundantly as a self check or to generate an average of multiple readings which may afford greater accuracy.

To make a determination of head height with an incomplete data set, the control system may, for example, analyze data from at least one pressure sensor monitoring the control chamber for a number of expected features of a predefined feature set. These expected features and temporal characteristics related thereto (e.g. when they occur and/or the amount time between them) may be used to extrapolate a final, stabilized control chamber pressure once enough features have been detected. This extrapolated pressure may allow for a good estimation of the head height of the component of interest.

For example, in the system 10 shown in FIGS. 1-9, the system 10 may behave similarly to an under-dampened second order system when a head height determination is made. In such examples, the feature set may be informed by characteristics which would be expected in an ideal under dampened second order system. For example, the feature set may include an overshoot pressure peak and an undershoot pressure peak which is smaller in magnitude than the overshoot peak. The control system 16 of the cycler 14 may detect a pressure overshoot and undershoot peak in the control chamber 171 after a pump chamber 181 is placed into communication with the component of interest. Data related to these peaks may then be used to extrapolate the final chamber pressure thus significantly speeding the determination process.

The data may also be used to determine a characteristic of interest other than head height. For example, in certain embodiments, the temporal characteristics related to the feature set may be used as a measure of resistance in the tubing. This may allow for a determination of the length of the fluid line between the cassette 24 and reservoir component of interest. Where line extensions accessories may be used, the number of line extension accessories in use may be determined based on temporal characteristics of the feature set. This type of determination may also allow for line extensions to be used on a wider variety of lines with a reduced impact on therapy time. For example, to increase patient comfort, pumping pressure to and from the patient may be adjusted to provide slower fluid transfer. The pumping pressure used may be selected based on the temporal characteristics to generate a desired pressure at the patient end of the line. This may allow pressure to be kept at or closer to a maximum pumping pressure as the resistance in the line will lead to a reduction in pressure at the patient end. Consequentially, an increase in fluid transfer time may be avoided when a patient line extension or extensions are in use. This may allow for longer dwell periods and more clearance of metabolic waste from the patient over the same programmed therapy time.

Temporal characteristics of the feature set may also be used to determine if a flow impedance is present in the flow path between the cassette 24 and the reservoir component of interest. In certain embodiments, these temporal characteristics may be used to determine if an occlusion or partial occlusion is present. Alternatively, these temporal characteristics may be collected to aid in informing an occlusion or partial occlusion determination.

FIG. 134 includes a flow diagram detailing a number of example actions which may be executed during a head height determination. In block 8044 a cassette is primed and the pump chamber sheeting may be placed in an initialized position. In block 8046 a timer may be started. The timer may set an amount of time during which it is expected that features of the feature set should be observed. The timer may be between 2-6 seconds (e.g. 3 seconds) in various embodiments. If it is determined, in block 8048, that the timer has elapsed, the control system may execute a predefined error handling protocol in block 8050. For example, the control system may generate an error signal or perform a retry of the head height determination while incrementing a retry counter (which may be limited by a retry cap).

When performing a head height detection, the control system can receive pressure data from at least one pressure sensor monitoring the control chamber in block 8052. In certain embodiments, data collected in an initial time window may not be used for analysis to minimize noise concerns. This time window may be up to about 1 second (e.g. ~0.3 seconds), though this value may vary from embodiment to embodiment. In block 8054, the control system may apply data smoothing to data received from the at least one pressure sensor. The data smoothing may be similar to that described in relation to block 8028 of FIG. 133. In block 8056, the control system may compare a number (e.g. 2) of consecutive moving average pressure samples to determine if a first condition exists. In the example embodiment shown in FIG. 134, the control system calculates the difference (or an absolute value thereof) between these moving average samples in block 8056. In block 8058, the system may determine if the first condition exists (e.g. if the difference is less than a predefined limit or not). The predefined limit may, for example, be between 0.005 and 0.04 kPa (e.g. 0.025 kPa). In the example in FIG. 134, if the difference is not less than the predefined limit, the control system may revert back to block 8048. If the difference is less than predefined limit the control system may compare a maximum value of the moving average sample window and the current moving average pressure sample to determine if a second condition exists. FIG. 134, for example, calculates a difference (or the absolute value of that difference) between the maximum moving average sample pressure and the current sample pressure in block 8060. In the example shown in FIG. 134, if a peak has not yet been detected in block 8062, the control system may determine if the difference is less than a second predefined limit in block 8064. The second predefined limit may be smaller than the first predefined limit described above in relation to block 8058. In some embodiments, if the difference is between about 0.000 kPa and 0.020 kPa (e.g., less than about 0.005 kPa), a first peak pressure may be set in block 8066. Where the system can be characterized as an under dampened second order system, the first peak may be an overshoot peak. This pressure peak may be set to the present moving average pressure sample or perhaps an average of the current moving average pressure sample and that directly preceding it. The time taken to reach the pressure overshoot may be also noted in block 8066. The control system may then revert back to block 8048. The control system may also revert back to block 8048 if the difference is not smaller than the second predefined limit in block 8064.

Once the first peak has been detected and control system reaches block 8062 again, the control system may proceed to block 8068. In block 8068, the control system may determine if the amount of time from the first pressure peak is greater than a predefined amount of time. This predefined amount of time may be an empirically determined amount of time which is expected before the next peak occurs. For an ideal under dampened second order system this amount of time should be about the same as the amount of time needed to reach the first peak. For example, the predefined amount of time may be set equal to the time required to reach the first peak less some value (e.g. 0.1-0.4 seconds) which may help account for any deviation from an ideal system. If the predefined amount of time has not yet elapsed, the control system may revert back to block 8048. When the predefined amount of time has elapsed, the control system may determine if the magnitude of the current pressure is greater than that detected for the first peak in block 8070. If the magnitude of the current pressure is greater than that detected in the first peak, the control system may return to block 8066 and reset the first pressure as the current pressure. Again, the elapsed time may also be noted. If, however, the current pressure is lower in magnitude than the first peak pressure, the control system may define a second peak pressure as the current pressure in block 8072. The elapsed time before the detection of the second peak pressure may also be noted. In block 8074, the control system may determine an overshoot percent. The percent overshoot may be determined via an equation such as the following:

$$\text{Percent Overshoot} = (1 - (P_1/P_2) - \alpha)$$

Where $P_1$ is the first peak pressure, $P_2$ is the second peak pressure and $\alpha$ is a correction factor which may be empirically determined. The correction factor may be used to adjust for any deviation from an ideal second order system.

In block 8076, the control system may calculate the head height. In some embodiments, head height itself may not be calculated, but a related value such as pressure due to head height may be calculated (or both may be calculated). This may be determined by predicting a final pressure which would have been present had the pressure been allowed to stabilize after detection of the peaks. The final pressure, $P_{Final}$, may be determined via and equation such as the following:

$$P_{Final} = P_1 / (1 + \text{Percent Overshoot})$$

The starting pressure of the pump chamber may then be subtracted from the final pressure to determine the pressure due to head height. If desired, this pressure may then be converted into a head height in units of distance based on acceleration due to gravity, density of the liquid, and the pressure value as described elsewhere herein.

Point of Care Dialysate Admixture

Referring now to FIG. 135-136, and as mentioned elsewhere herein, the system 10 may be used not only to administer an APD therapy, but may also mix fluids for administration to a patient from a number of component sources 6000. The component sources 6000 may include, but are not limited to fluid dispensing or generating machines and prefilled source reservoirs. In some specific examples, the sources 6000 may include a water purification device 6002 or a combination of such devices, for instance, a reverse osmosis water purification device, other filtration device, or a water distillation device. Each source 6000 may be in fluid communication with a cassette 24 installed in the cycler 14. The cassette 24 may include various ports and/or spikes to which fluid lines providing a fluid path to the cassette 24 from the component sources 6000 are attached. The cycler 14 may operate the cassette 24 to draw from the component sources 6000 and pump components to a mixing reservoir 6004. Alternatively or additionally, components from the component sources 6000 may be mixed within the cassette 24. The system 10 may mix the components in a ratio sufficient to generate one or a number of particular specified solution(s) over the course of a therapy. This may be done using any or any combination of the fluid pumping and FMS techniques described herein. The solutions to be mixed may be common dialysate solutions, but may also be patient specific solutions which are defined by a patient's care giver. After admixture, these solutions may be delivered by the cycler 14 to a patient to perform a dialysis therapy in accordance with any of the various therapy modalities disclosed herein.

Such a system may allow for dialysate solutions to be mixed on an as needed basis shortly before the solutions are to be used. As only an amount of solution sufficient to complete the therapy may be mixed, this may help to reduce waste. Likewise, waste related to shelf life constrains of a mixed solution may be avoided. As the solution is mixed automatically, any variability due to patient directed mixing of solutions can be prevented while at the same time removing this aspect of setup burden from the user. Moreover, such a system may allow for smaller and lighter fluid reservoirs (e.g. bags) which require less storage space and are easier for a patient to move about and setup. This may help to accomplish high levels of compliance to any instruction related to head height based locating of reservoirs as the reservoirs can easily be lifted into place. Such smaller fluid reservoirs may present economic incentives as well as they may be easier to ship and distribute. Further, such a system may mitigate or avert shortages of dialysate solution as well. Where component sources 6000 are concentrates, for example, a manufacturer may produce the same overall volume of fluid, but this fluid may provide for a much a larger number of therapies.

The component sources 6000 may contain any component or mixture of components which may be desirable in a solution useful for a patient with compromised renal function. The component sources 6000 may also include a dialysate reservoir of pre-mixed dialysate or dialysate concentrate and combinations thereof. Each component source 6000 may be, contain, or contain a combination of, without limitation, any of the substances listed in Table 2 as follows:

| | | |
|---|---|---|
| Saccharides | Dextrose | Icodextrin |
| Glucose Polymers | Polyglucose in chains having a weight of ~16,000-16,400 Daltons or greater | Glycerol |
| Calcium ions | Magnesium ions | Potassium ions |
| Chloride ions | Sodium ions | A solution containing ions from at least Group I and/or II element |
| Bicarbonate | Acetate | Lactate |
| Amino Acid(s) | Essential Amino Acid Solution | Non-Essential Amino Acid Solution |
| Histidine | Oligopeptides | Osmotic Agent(s) |
| Phosphate | A solution with an Osmolarity of 300-520 mOsmol/L | Electrolyte Concentrate |
| A solution with an Osmolarity of 250-300 mOsmol/L | Extraneal | Dianeal |
| Purified Water | WFI | Physioneal |
| Physioneal Buffer Solution | Dialysis Buffer Solution | Nutrineal |
| Stay-Safe Dialysate | Delflex Neutral pH Dialysate | Balance Dialysate |
| Bica Vera Dialysate | Gambrosol Dialysate | Citrate |
| 50% or greater Glucose solution | Dialysate | A multi-chamber reservoir with at least two of the chambers containing different solutions |
| Polyelectrolytes | Macromolecules | Maltose |
| Albumin | Antibiotics | Bacteriostatics |
| Insulin | Fibrinolytics | Heparin |
| Chemotherapy Agents | Physiologically Hypertonic Solution | Line Flushing Fluid |

-continued

| Pyrophosphate | Diagnostic Agents | Contrast Media |
| Acid Concentrate | Recombinantly Produced Biomolecules | Peritoneal Equilibrium Testing Solution |
| L-carnitine | Alanyl-glutamine | Pyruvate |
| Xylitol | Dextrans | Hyperbranched Polyglycerol |
| Reguneal | Extraneal | |

The components shown in Table 2 may be supplied in a concentrated or unconcentrated form. The components listed in Table 2 may be supplied in a liquid form or a powdered or lyophilized form which is reconstituted with liquid by the cycler 14. In addition to the components listed in Table 2, any of the components listed in: de Vin, Filip, Peter Rutherford, and Dirk Faict. "Intraperitoneal administration of drugs in peritoneal dialysis patients: a review of compatibility and guidance for clinical use." Peritoneal dialysis international 29.1 (2009): 5-15. which is incorporated herein by reference in its entirety may also be used. Any other additive which may be desirable to add to a dialysate solution may also be included as a source component 6000.

In addition to a purified water supply 6002, in certain embodiments, there may be two components sources 6000 which may respectively contain an acid solution and a buffer solution in liquid state. At least one of these solutions may contain a saccharide such as dextrose which may act as an osmotic agent when delivered to a peritoneal cavity of a patient 6008. There may also optionally be a reservoir of pre-mixed dialysate such as a dialysate bag filled with fluid conforming to a patient's last fill prescription.

The system 10 may also include at least one composition sensor 6006. The composition sensor 6006 may be an assembly of components which monitor the mixture formed from the various component sources 6000 such that the cycler 14 control system 16 may check to ensure that the prescribed solution was properly mixed. Data from the at least one composition sensor 6006 may also be used by the control system 16 to help guide the mixing process and make adjustments to the mixture. Composition sensors 6006 may be contact sensors which are in direct contact with solution during sensing. Alternatively, composition sensors 6006 may be non-contact sensors which are disposed outside of the fluid pathways and capable of sensing fluid composition through a fluid line, fluid bag, cassette body, or cassette membrane for example. Composition sensors 6006 may be entirely included in the cycler 14 as hardware components which interface with a region the disposable set 12. Composition sensors 6006 may also be stand-alone components which are not integral to the cycler 14. Alternatively, at least a portion of a composition sensor 6006 may be included as part of the disposable set 12. Composition sensors 6006 may sense any suitable property of the fluid mixture to verify proper mixing of the desired dialysate. For example, conductivity, pH, spectrophotometric properties, chiral properties, density, optical properties, weight, or other properties may be monitored by a composition sensor 6006. Data from composition sensors 6006 may be communicated to the cycler 14 wirelessly or via wired connection.

At least one temperature sensor 6010 may also be included. A temperature sensor 6010 may be positioned to sense the temperature of fluid from the component sources 6000. A temperature sensor 6010 may also be provided to sense ambient temperature. Temperature data from the at least one temperature sensor 6010 may be leveraged by the control system 16 of the cycler 14 to allow the cycler 14 to operate as not only a volume transfer device but also a mass transfer device. The temperature data may, for example, be used to make a density correction on the fluid being pumped via the cassette 24 (e.g. with a look up table). A continuity equation may also be fed temperature and volume data to determine mass transfer during pumping. Temperature data may also be used to aid in the collection of other data about the solution such as ion concentration data (e.g. pH or conductivity data). The temperature sensor 6010 may be a contact sensor or non-contact sensor and may be included as part of the cycler 14 or at least partially as part of the disposable set 12. A temperature sensor 6010 of the system 10 may be a thermistor, thermocouple or an infrared based optical sensor, for example.

In some embodiments, and as shown in FIG. 136, the at least one composition sensor 6006 and/or the at least one temperature sensor 6010 may be included in an auxiliary sensor assembly 6012. The auxiliary sensor assembly 6012 may communicate with the cycler 14 via a communications module which may be wired or wireless. In some embodiments, the auxiliary sensor assembly 6012 may communicate over Radio frequency, WiFi, Bluetooth, Zigbee, Ethernet, IR, Z-wave, ANT, 802.11.15.4, direct cabled connection, an internet web based service, ultrasonically, etc. An auxiliary sensor assembly 6012 may be powered by an internal power source such as a battery source, may draw power from the cycler 14 or another system 10 component, or may draw power from a wall outlet (via appropriate AC adapter if needed). Such an auxiliary sensor assembly 6012 may allow for backwards compatibility with devices capable of communication with the auxiliary sensor assembly 6012. In some embodiments, the auxiliary sensor assembly 6012 may include a USB interface to the cycler 14 and serve as both a sensor module and communicator between the cycler 14 and another wirelessly connected component of the system 10 (e.g. water purifier 6002). Such an auxiliary sensor assembly 6012 may also be integrated into a patient data key 325 as well.

Referring now also to FIGS. 79-80, a data storage device such as a patient data key 325 may be used to provide at least one formulation parameter to the cycler 14. Such formulation parameters may also be entered manually via a user interface of the cycler 14 or received from a cloud or web based service. The patient data key 325 may, for example, be loaded with a therapy formulation file designed by a clinician for the patient. The patient data key 325 may be provided with various security measures to ensure therapy formulations are only accepted when provided via a medical professional or authorized individual. Where a cloud or web based service is used, the cycler 14 may directly interface with the storage medium (e.g. a server) on which therapy formulation files reside and the use of a patient data key 325 may be optional.

The therapy formulation file may include mixing parameters for any dialysate solutions to be administered to the patient during the course of a therapy. Mixing parameters for only a single dialysate may be specified or alternatively, mixing parameters for multiple dialysates to be used during a therapy such as a first dialysate and a second or last fill dialysate may be defined. Mixing parameters may, for example, be volumetric ratios or volumetric transfer parameters, weight based ratios or weight based transfer parameters, or mass/molar ratios or transfer parameters, but are not limited thereto. Mixing parameters may also be specified as source component reservoir ratios (e.g. one full reservoir of type A, two full reservoirs of type B, and so on). Therapy formulation files may additionally include a parameter set or sets which define usage constraints on a dialysate once it has been mixed. For instance, a therapy formulation file may define an expiration period after which the mixed dialysate is prevented from being provided to the patient. Such an expiration period may be used by an expiration timer implemented by the cycler 14 and described in greater detail in relation to FIG. 126.

Depending on the cycler 14, a therapy formulation file may also specify the expected component sources 6000 to be used with the therapy. If the cycler 14 includes an auto-connect assembly (see FIGS. 17-56), an auto-ID camera 1104 (see, e.g. FIG. 21) may image an identification tag 1100 (see, e.g. FIG. 19) on a solution line 30 attached to the component source 6000. The identification tag 1100 may provide an indication as to the type of solution associated with the line 30, the amount of solution, a date of manufacture, expiration date, an identity of the manufacturer, molar concentrations of various components of the solution, and/or formulation parameters for the therapy. If the identification tag 1100 imaged by the auto-ID camera 1104 does not match an expected component source 6000, the control system 16 of the cycler 14 may prevent the component source 6000 contents from being used in therapy. The control system 16 can be programmed to compute the proper admixture requirements based on the type of dialysate or solution containers connected as well. For example, the control system 16 may determine an amount of each component source 6000 to add depending on their concentrations in order to meet the requirements of the therapy formulation file.

The control system 16 may also check the identification tags 1100 (see, e.g. FIG. 19) to ensure no contraindicated component sources 6000 are attached at the same time. The control system 16 may also perform other checks. For example, the controls system 16 may determine that at least one component source 6000 of a number of required types is present. For example, the control system 16 may ensure an osmotic agent concentrate and a buffer solution are present before initiating therapy.

In another embodiment, formulation parameters may be provided to the cycler 14 via a remote (e.g. telephonic or web/cloud based) care managing system with which the cycler 14 is in communication. Such a system may "push" formulation parameters to the cycler 14 as these parameters become available. Alternatively, the cycler 14 may query the remote system for formulation parameters as part of a pre-therapy startup process. Such a system may collect and provide various therapy information to a remote clinician. This information may be used to adjust formulation parameters or other settings to better suit the needs of individual patients.

Valve Actuation Based Fluid Pumping

For certain applications, a cycler 14 may be required to mix only small volumes of solution for a given therapy. This may, for example, be particularly common when a cycler 14 is used for pediatric patients. As the total mix volume decreases, the amount of each component needed decreases as well. Depending on the therapy, as little as 10 ml or less of fluid from a component source 6000 may be required to mix the prescribed solution. As the required amount of fluid decreases, any targeting error of the cycler 14 may become a larger fraction of the total fluid moved. To deliver such small volumes with high precision, both pump chambers 181 of the cassette 24 as well as various valves of the cassette 24 may be used as fluid pumps.

Figure 137:
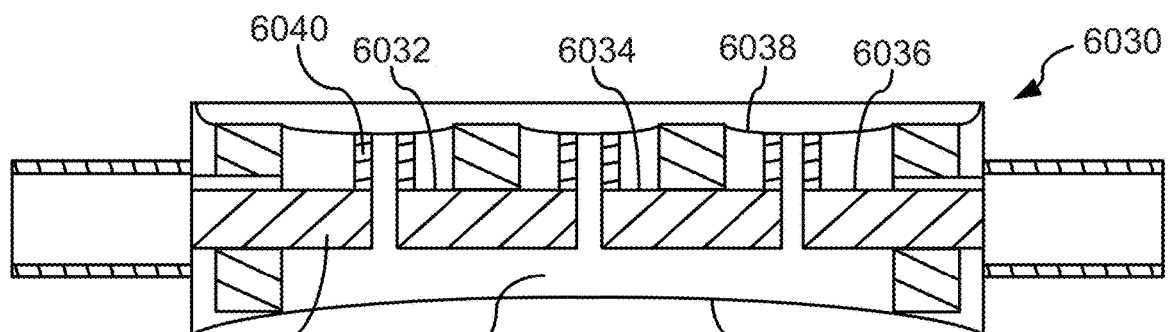

Referring now to FIG. 137, a cross-sectional view of a generic cassette 6030 is shown. The generic cassette 6030 includes three valve stations 6032, 6034, 6036 formed in the cassette body 6031 which are covered with a first flexible membrane 6038. As described above, the flexible membrane 6038 may be actuated (e.g., pneumatically, mechanically, hydraulically etc.) against and away from the valve seats 6040 of each valve station 6032, 6034, 6036 in order to open and close the valves stations 6032, 6034, 6036. In the example illustration, all of the valves stations 6032, 6034, 6036 are shown in a closed configuration in FIG. 137. The cassette 6030 also includes a fluid bus 6042 on the opposing side of the cassette 6030 midbody 6044. A second flexible membrane 6046 is included on this side of the cassette 6030 to seal the fluid bus 6042 as described elsewhere herein. The fluid bus 6042 may be placed into communication with desired valve stations 6032, 6034, 6036 by displacing the first flexible membrane 6038 away from the valve seat 6040 of the desired valve station(s) 6032, 6034, 6036.

When the valves stations 6032, 6034, 6036 move from an open state to a closed state, an amount of fluid displacement may occur. This fluid displacement may be relatively small in scale and on the order of hundredths of a milliliter. Where pump chambers 181 are present, the fluid displacement during valve closure may be between 2 and 3 orders of magnitude smaller than displacement accomplished via a pump chamber stroke. In some specific embodiments the fluid displacement or valve pump stroke volume as the valve station 6032, 6034, 6036 is actuated may be less than around 100-150 microliters. For the cassettes 24 depicted in FIGS. 1-9 a nominal volume displaced during a valve pump stroke may be at or about several dozen microliters (e.g. at or around 70 microliters). Variation from the nominal value valve pump stroke to valve pump stroke may occur on a stroke to stroke basis or from therapy to therapy depending on head height of source reservoirs. In some exemplary cassettes, a valve pump stroke may deliver between about 30-80 microliters. The amount of displacement could be modified to a desired amount by altering the structure of the valve stations 6032, 6034, 6036, or first flexible membrane 6038, or altering the material of the first flexible member 6038. Manipulation of the head height of source reservoirs may also be used to modify or aid in fixing the amount of displacement. In some embodiments, a head height determination which confirms the source components 6000 are at a desired position (or at least with a range of that position) may be used. This may allow for a nominal valve pump stroke volume at that head height to be relied upon for valve stroke based pumping. Via coordinated actuation of valve stations 6032, 6034, 6036, small volumes of fluid can be pumped through the cassette 6030 to desired destinations.

Thus, when valve action is coordinated in a valve pumping sequence or rhythmic pumping pattern, the cassette 6030 can be made to act as a tubeless pneumatic peristaltic pump. Specifically, the cassette 6030 may be made to act as a linear peristaltic pump. Each of the valve stations 6032, 6034, 6036 may serve as a peristaltic actuator similar to those of a linear peristaltic finger pump. As such, each of these valve stations 6032, 6034, 6036 may be referred to as a peristaltic actuator well, peristaltic actuator station, or more generically as a peristaltic translational element station. Likewise portions of the control surface 148 which control actuation of the valve stations 6032, 6034, 6036 may be referred to as peristaltic actuator control regions or translational element control regions. A portion of the cassette body 6031 may serve as the pump platen toward and away from which the translational elements (flexible sheeting 6038 portions over the translation element stations) are displaced. Additionally, the fluid pathway through which the transported fluid travels may be disposed on the opposing side of the platen or cassette body 6031 portion. As a result, the peristaltic action on this fluid pathway via the translational element may be indirect and conveyed via the openings in the valve seats 6040.

Referring to the progression of FIGS. 138-142, three valves stations 6032, 6034, 6036 of the cassette 6030 may be actuated to pump fluid from an inlet 6048 of the cassette 6030 to its outlet 6050. Though the three valve stations 6032, 6034, 6036 are shown as adjacent to one another, this is done to provide a streamlined example. Additional valve stations may be included in a cassette 6030 which are not actuated as part of the valve pumping sequence. Such additional, unused valve stations may be placed between one or more of valve stations 6032, 6034, 6036 if desired. Additionally at least one valve station (not shown) may also be placed in a parallel configuration with the first valve station 6032 and may have an inlet in fluid communication with a source different than that which the inlet 6048 to the first valve station 6032 communicates. A desired valve station of the one or more valve station parallel to the first valve station 6032 may be placed into fluid communication with the common bus 6042 to allow for pumping from a select source of a plurality of sources.

Figure 138:
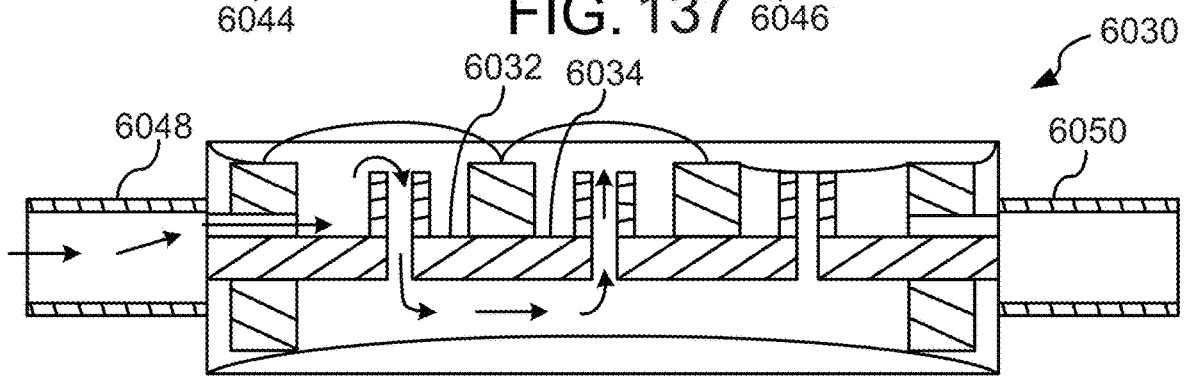
Figure 139:
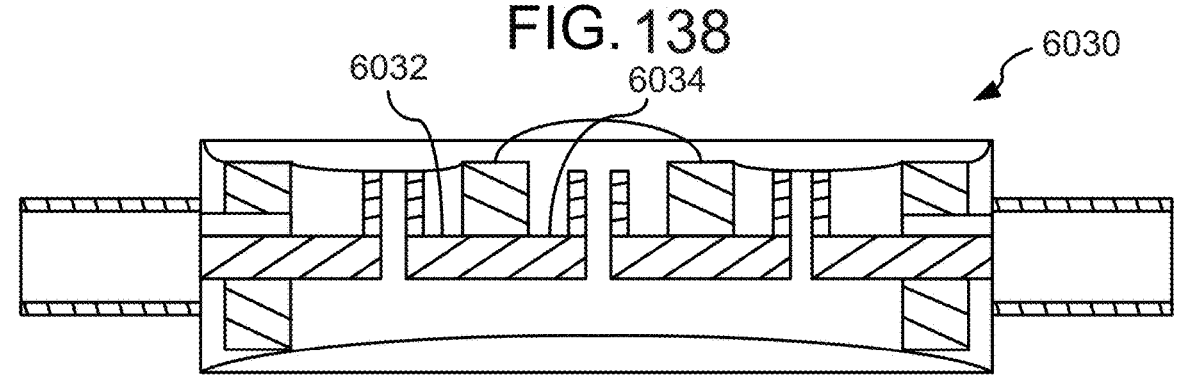

As shown in FIG. 138, a first and second valve station 6032 and 6034 may be opened to perform a fill operation of a valve station. These valve stations 6032, 6034 may be opened in sequence or at substantially the same time. This may cause fluid flow 6035 into these valve stations 6032, 6034. Once the valve fill is complete, the filled valve station 6034 may be isolated by closing the first valve station 6032 as shown in FIG. 139. Thus the second valve station 6034 may serve as an intermediary holding volume during valve based fluid pumping.

Figure 140:
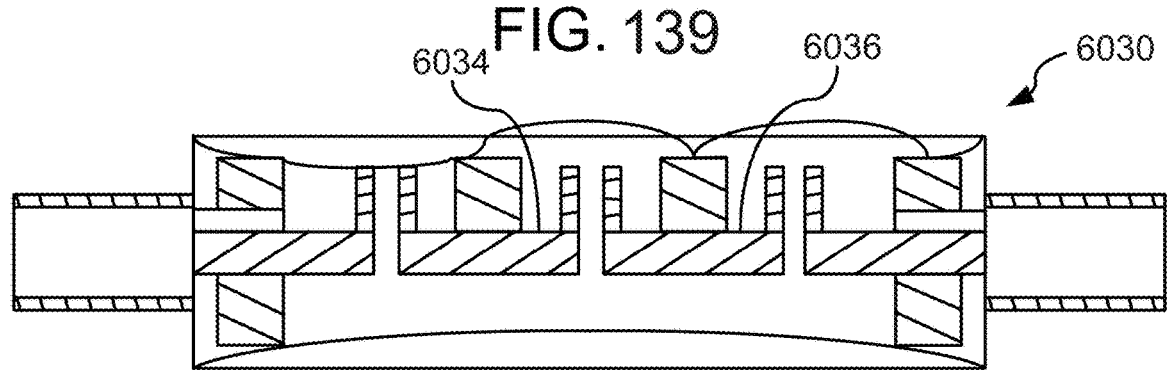
Figure 141:
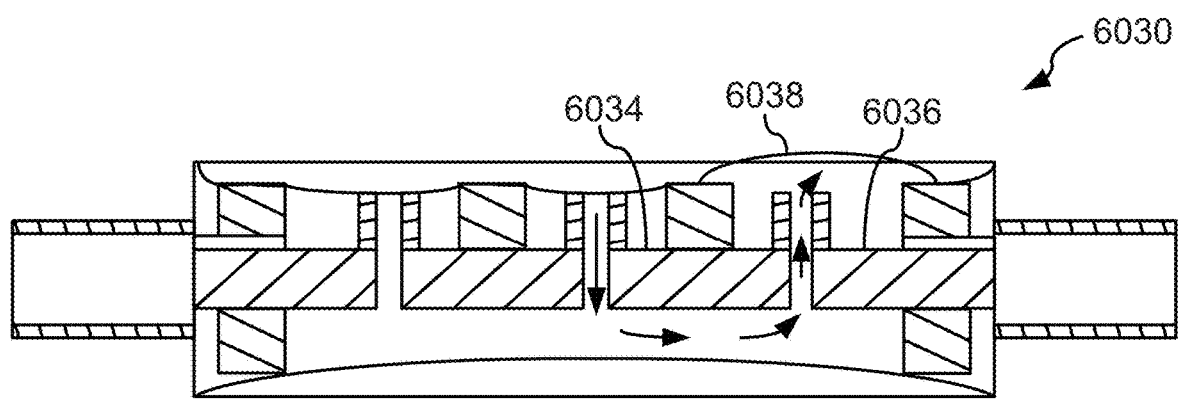
Figure 142:
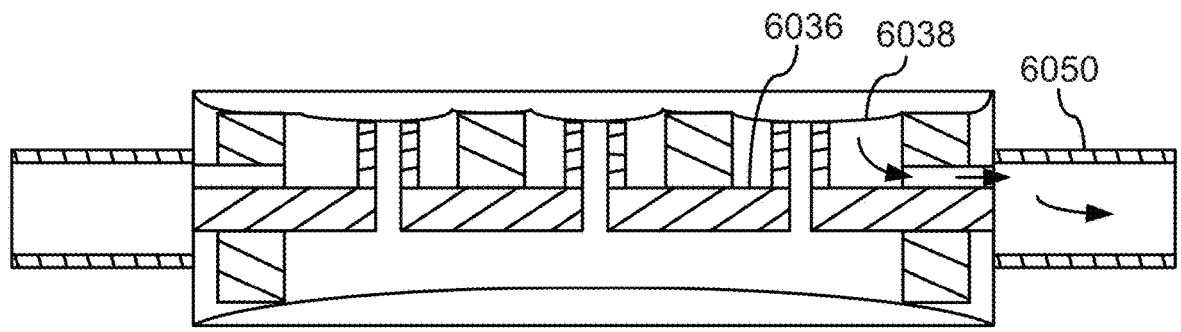

The third valve station 6036 may then be opened to establish fluid communication between the second and third valve station 6034, 6036 as shown in FIG. 140. A valve pump stroke may then be executed by closing the second valve station 6034 as shown in FIG. 141. This will transfer a valve pump stroke volume to the third valve station 6036 from the intermediary holding volume. The third valve station 6036 may then be closed to pump the valve pump stroke volume out the outlet 6050 of the cassette 6030 as depicted in FIG. 142.

Greater volumes per valve pumping sequence may be achieved by utilizing a plurality of valve seats as an intermediary holding volume as shown in the progression of FIGS. 143-146. As shown, the example cassette 6848 includes an additional valve station 6846 and includes four valve stations 6840, 6842, 6844, 6846 in total. Thus, two valve seats are available for use as an intermediary holding volume. Though the four valve stations 6840, 6842, 6844, 6846 are shown as adjacent to one another, this is again done to provide a streamlined example. Additional valve stations may be included in a cassette 6848 which are not actuated as part of the valve pumping sequence. Such additional, unused valve stations may be placed between one or more of valve stations 6840, 6842, 6844, 6846 shown if desired. A greater number of valve stations than shown in FIG. 143-146 may be actuated as part of the rhythmic pumping pattern as well. Three, four, five, or more valve stations may be used as an intermediary pumping volume depending on the cassette 6848 or the pumping volume needed.

Figure 143:
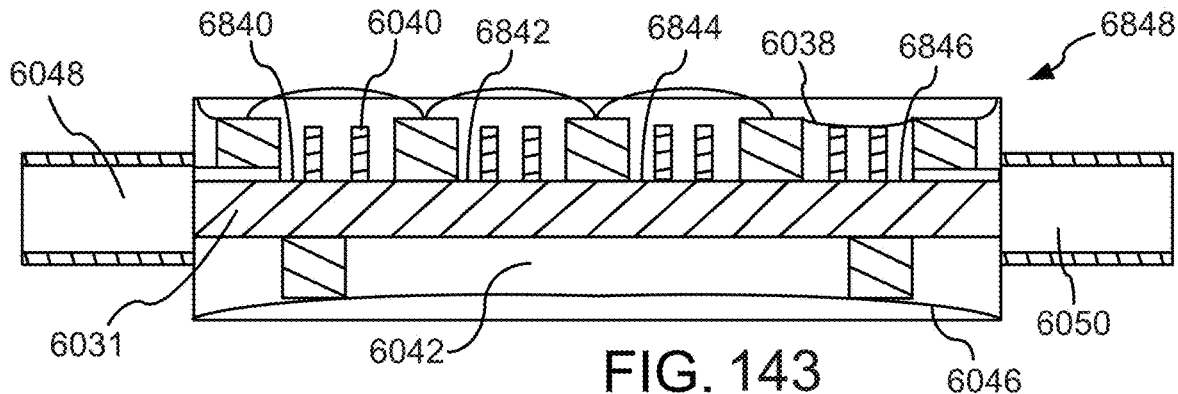
Figure 144:
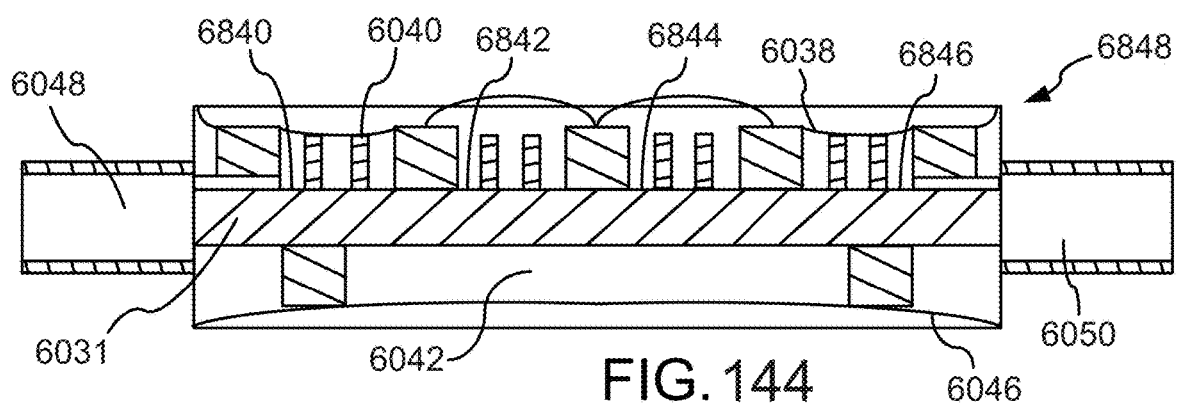

As shown in FIG. 143, a first, second, and third valve station 6840, 6842, 6844 may be opened to perform a fill operation of the valve stations. These valve stations 6840, 6842, 6844 may be opened in sequence or at substantially the same time. This may cause fluid flow into these valve stations 6840, 6842, 6844. Once the valve fills are complete, the filled valve stations 6842, 6844 may be isolated by closing the first valve station 6840 as shown in FIG. 144. Thus the second valve station 6842 and third valve station 6844 may serve as an intermediary holding volume during valve based fluid pumping.

Figure 145:
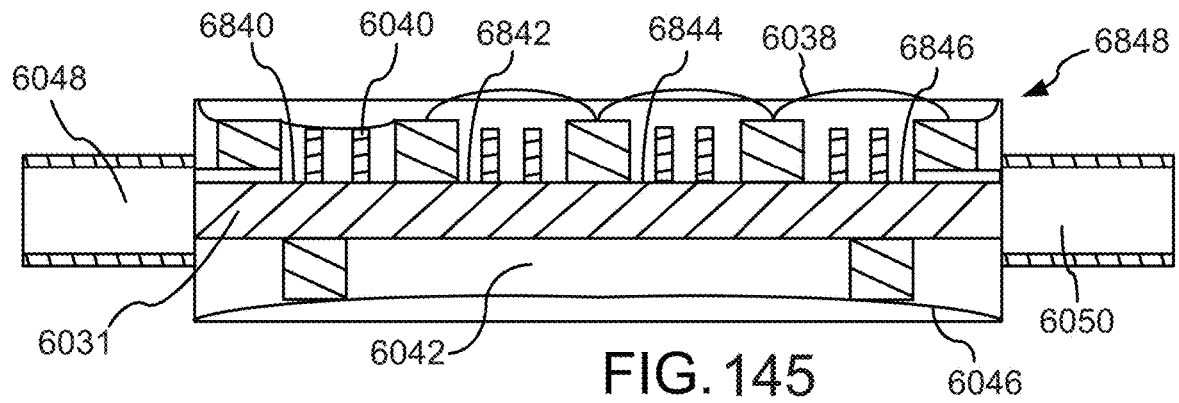
Figure 146:
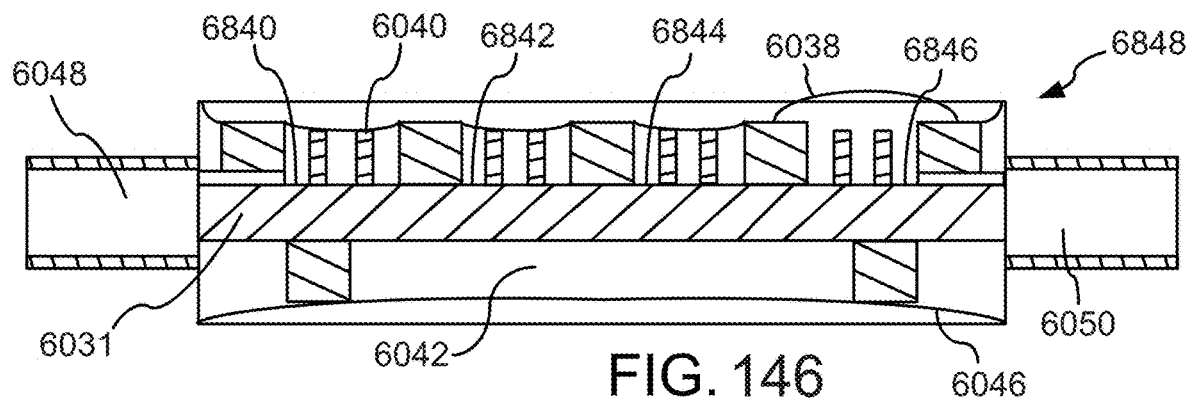

The fourth valve station 6846 may then be opened to establish fluid communication between the second and third valve station 6842, 6844 and the fourth valve station 6846 as shown in FIG. 145. A valve pump stroke may then be executed by closing the valve stations 6842, 6844 as shown in FIG. 146 and eventually valve station 6846 (closure not depicted). This will transfer a valve pump stroke volume from the intermediary holding volume to the outlet 6050 of the cassette 6848. Valve stations 6842, 6844 may be closed at the substantially the same time or in sequence. This may serve to increase the volume pumped in proportion to the number of valve stations used to provide the intermediary holding volume. When two valve stations are used for the intermediary holding volume, the volume transferred may be just under double or approximately double for example.

Alternatively, the valve pump stroke volume may be delivered to a pump chamber 6052 as shown in the progression of FIGS. 147-152. The example cassette 6030 shown in FIGS. 147-152 is depicted schematically, but may be constructed similarly to the cassette shown in FIGS. 137-142. The pneumatic circuit (identified here as an integrated manifold 2700 similar to that in FIG. 62) is also included in FIGS. 147-152. Positive and negative pressure may be applied through the pneumatic circuit to regions of the control surface 148 to open and close valve stations 6032, 6034, 6036, 6053 and actuate the pump chamber 6052.

Figure 147:
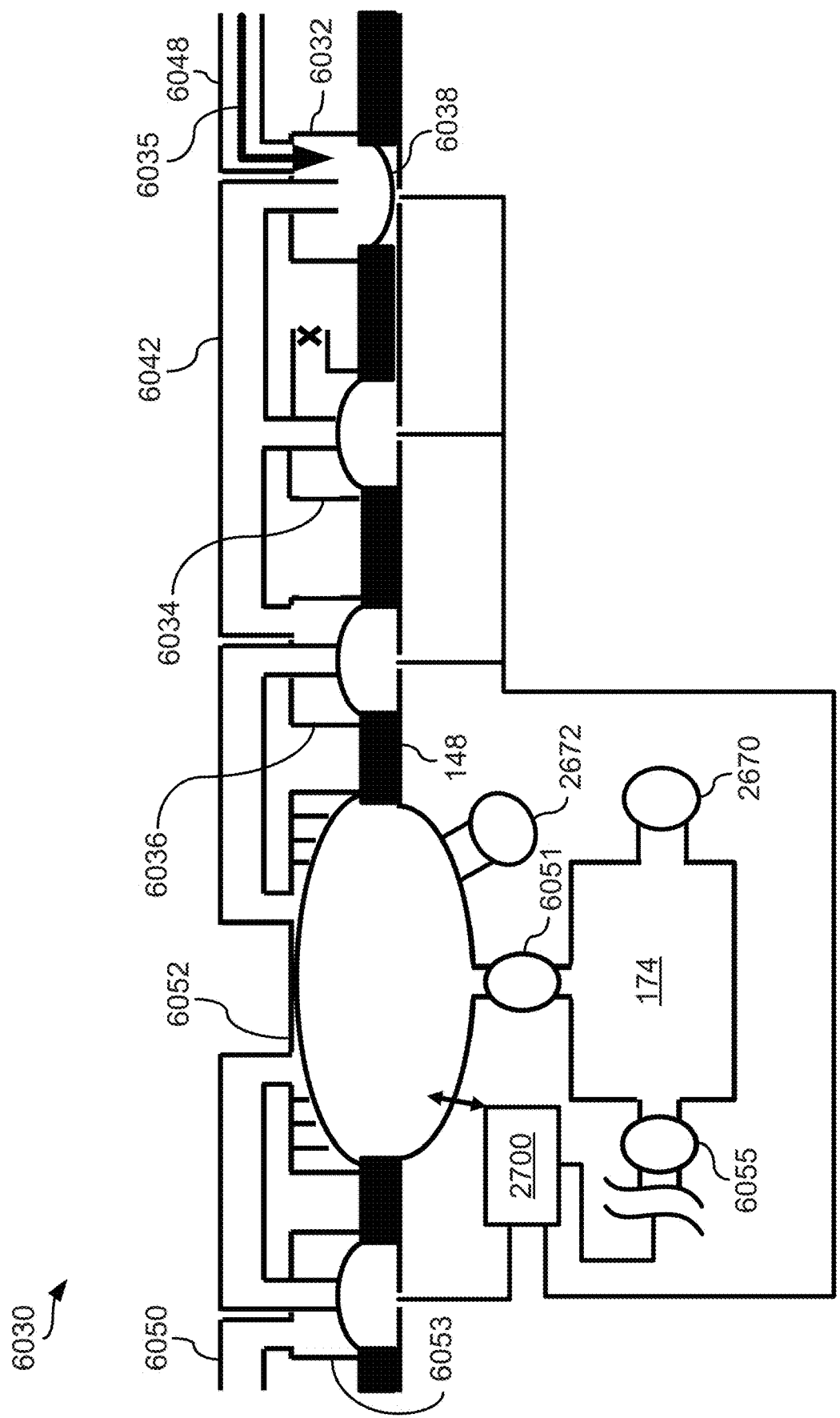
Figure 148:
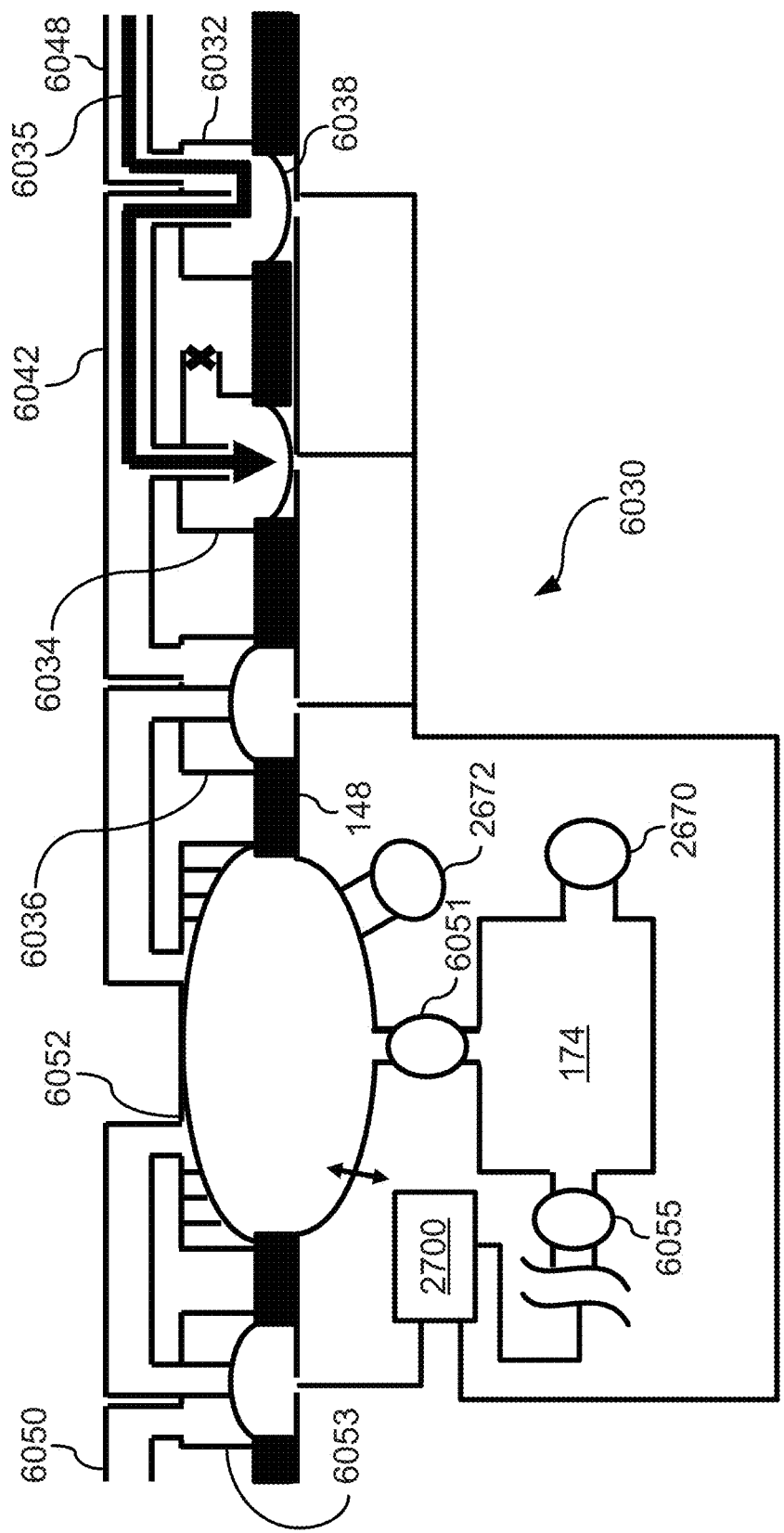

Referring to FIG. 147, a first valve station 6032 may be opened to establish fluid flow 6035 into the first valve station 6032 from the inlet 6048. Referring to FIG. 148, a second valve station 6034 may be opened to cause fluid flow 6035 into the second valve station 6034. Once the valve fill is complete, the filled second valve station 6034 may be isolated to create an intermediary holding volume by closing the first valve station 6032 as shown in FIG. 149.

The third valve station 6036 may then be opened to establish fluid communication between the second and third valve station 6034, 6036 through the fluid bus 6042 as shown in FIG. 150. The second valve station 6034, as shown in FIG. 151, may be closed. This will transfer a valve pump stroke volume to the third valve station 6036 from the intermediary holding volume. The third valve station 6036 may then be closed to pump the valve pump stroke volume to the pump chamber 6052 as shown in FIG. 152. This may be repeated multiple times to move a desired amount of fluid into the pump chamber 6052. Once a desired number of valve pump strokes have been delivered to the pump chamber 6052, the cycler 14 may deliver the pump chamber 6052 to a desired destination. In some embodiments, a volume measurement (described elsewhere herein) may be made to confirm the volume transferred before delivery. To deliver the pump chamber 6052, the chamber outlet valve station 6053 may be opened and positive pressure may be applied to the pump chamber 6052 to push the volume transferred to the pump chamber 6052 by valve stroke pumping to the outlet 6050. Fluid may also be removed from a pump chamber 6052 via valve stroke pumping in a manner similar to as just described. This fluid may be removed from the pump chamber 6052 and delivered back to a component source 6000, mixing reservoir 6004, or to a drain destination depending on the valves stations used and the reservoir connected to the inlet 6048 or outlet 6050 of the cassette 6030.

Executing valve pump strokes to fill or withdraw fluid from a pump chamber 6052 may be done to make fine adjustments to the filled volume of the pump chamber 6052 after the pump chamber 6052 has filled to within a first range of a target volume. For example, when a continuous flow rate and stroke displacement estimator determines the pump chamber 6052 fill volume is within the first range, the control system 16 may command pumping with valve stations 6032, 6034, 6036 of the cassette 6030 until the pump chamber fill volume is within a second range of the target volume. The second range may be substantially tighter (e.g. 20, 30, 40, or up to 50 times tighter) than the first range. In some specific embodiments, the first range may be or be anywhere between +/−~3 ml to +/−1.5 ml and the second range may be or be anywhere between +/−~0.22 ml to +/−~0.07 ml. Valve pumping strokes may be performed in an open loop manner where the number of valve pumping strokes delivered (or removed) from the pump chamber 6052 is equal to:

$$\Delta_v / V_{nom}$$

where Δv is the difference between the target volume and the filled volume and $V_{nom}$ is a nominal valve pump stroke volume. $V_{nom}$ may be an empirically determined value or may be computed from historical valve pump stroke data. The number of valve pumping strokes calculated may be rounded to the nearest whole integer value.

After executing the proper number of valve pump strokes in open loop fashion, a volume measurement of the pumping chamber 6052 may be made as described elsewhere herein. In FIGS. 147-152, pressure transducers 2670, 2672 and a reference chamber 174 which is gated from the pump chamber 6052 via a valve 6051 are included for this purpose. A valve 6055 gating the reference chamber 172 from the pneumatic circuit is also included to facilitate such volume measurement.

The volume measurement may verify that the pump chamber 6052 has been filled to within the second range of the target volume. If necessary, additional valve pump strokes may be performed to add or remove fluid from the pump chamber 6052 after a volume measurement has been taken if the fill volume of the pump chamber 6052 is not within the second range. Once within the second range, the full pump chamber 6052 may then be delivered to a destination such as a mixing reservoir 6004. Valve stroke delivery to or from pump chambers may be performed in a closed loop manner or semi-closed loop manner with volume measurements being respectively taken after each valve pump stroke or after predefined numbers of valves pump strokes as well.

Referring now to FIG. 153, in some embodiments, a continuous stroke displacement estimation (described in greater depth elsewhere herein) may be employed during valve based pumping into or from a pump chamber. This may allow for an estimate of volume pumped into or from a pump chamber during valve stroke pumping. Thus valve stroke pumping may be performed in a closed loop fashion without pausing to perform FMS measurements after each stroke. This may shorten the amount of time needed to accurately fill a pump chamber to a desired volume via valve pump strokes.

FIG. 153 depicts an illustrative graph 6900 showing conceptualized pressure tracing 6902 from a control or actuation chamber of a cycler 14 during filling of a pump chamber via valve pumping. As shown, the pump chamber is pressurized to a negative pressure to encourage flow of fluid into the pump chamber during valve stroke pumping. Due to a reduction of the volume of the control chamber, a pressure decay 6904 occurs each time a valve pump stroke volume is delivered to the pumping chamber. As with other types of pumping, the control chamber may be regulated back to a pressure target 6908 by opening a valve between the control chamber and a pressure source. In the example graph 6900, this pressure maintance is performed each time the pressure decays beyond a predefined pressure limit 6910 and is shown by pressure spikes 6906.

The pressure decays as fluid is delivered to the chamber via valve stroke pumping may be monitored to determine an estimate of the fluid volume delivered to the chamber. This estimate may be generated in any suitable manner. The estimate may be generated as described elsewhere herein, for example, as described in relation to FIGS. 69-72. Once the estimate indicates that the amount of fluid in the pump chamber, an optional FMS measurement (described elsewhere herein) may be conducted to verify the volume contained in the pump chamber. If needed, additional valve pump strokes may be delivered to the pump chamber to meet a target pump chamber fill volume. These valve strokes may also be monitored via continuous pump chamber stroke displacement estimation. Once the value has been determined to be at or within an acceptable range of the target, the pump chamber may be delivered to its destination.

Referring now to FIG. 154, a flowchart 6920 depicting a number of example actions which may be used when delivering valve pump strokes to a pump chamber 181 of a cassette 24 is shown. In some embodiments, the control system 16 of a cycler 14 may command volume measurements to check for air in a pumping chamber 181 while delivering fluid to the pumping chamber 181 via valve pump strokes. The control system 16 may check for air as described under the section heading titled "Air Detection" or as described in U.S. Pat. No. 6,302,653, to Bryant et al., issued Oct. 16, 2001, filed Jul. 20, 1999, and entitled "Methods and Systems for Detecting the Presence of a Gas in a Pump and Preventing a Gas from being Pumped from a Pump" which is incorporated by reference herein in its entirety.

In the event that air is filling a portion of the pump chamber 181 volume, this air may inhibit the displacement of fluid into the pump chamber 181 via valve pump strokes once the combined volume of any air and liquid in the pump chamber 181 is at or near the full pump chamber 181 volume capacity. Since the volume measurement may only capture a measurement of the liquid volume in the pump chamber 181, the control system 16 may not register that the pump chamber 181 is already full. As there may not be an end of stroke detection while displacing fluid into the pump chamber 181 via valve pump strokes, the fullness of the pump chamber 181 may not be quickly detected. Consequently, the control system 16 of the cycler 14 may attempt to continue delivering fluid to the pump chamber 181 via valve pump strokes for a prolonged period without significantly altering the liquid volume in the pump chamber 181. As such, it may be desirable to detect the probable presence of air each time a volume measurement on the pump chamber 181 is made to update the amount of volume displaced into the pump chamber 181. This may increase the reaction speed of the control system 16 and speed volume transfer. This may help to ensure that a supply of properly mixed and heated solution is available for the patient when the patient is ready to be filled during a fill phase of the therapy. As a result, this may help to maximize the amount of time that the patient spends in dwell phases of the therapy and aid in increasing the amount of dialysis performed.

As shown in the flowchart 6920 in FIG. 154, the control system 16 may command a number of valve pump strokes to be delivered to a pumping chamber 181 in block 6922. The control system 16 may keep an estimate of the volume of liquid pumped to the pump chamber 181 via valve pump strokes based on a nominal valve pump stroke volume, the number of valve pump strokes, and the initial volume of the pumping chamber 181. In block 6924, a liquid volume measurement of the pump chamber 181 may be collected. This may be done using a positive pressure precharge as described elsewhere herein (e.g. under the section heading titled "Air Detection"). Typically, this measurement may be taken when the estimated volume pumped to the pump chamber 181 is near a target volume and/or after a pre-defined number of valve pump strokes have been delivered into the pumping chamber 181. If, in block 6926, the pump chamber 181 has been filled to the target volume, the pump chamber 181 may be delivered to a desired destination in block 6928. If, in block 6926, the pump chamber 181 has not been filled to the target volume and there is no indication air may be filling the rest of the pump chamber 181 in block 6930, the control system 16 may command additional valve pumping strokes into the pump chamber 181 and return to block 6922.

If, in block 6926, the pump chamber 181 has not been filled to the target volume and it appears the pump chamber 181 may potentially be full in block 6930, a check for air in the pumping chamber 181 may be made in block 6932. To determine if the pump chamber 181 is potentially full, in various embodiments, the control system 16 may check for conformance to at least one valve pump stroking criteria. For example, the control system 16 may check to see that each valve pump stroke delivered a certain volume of fluid to the pumping chamber 181 and/or that a number of valve pumping strokes into the pump chamber 181 have increased the volume held by the pump chamber 181 by at least some threshold amount. In some examples, the control system 16 may check the volume estimate against the measurement from block 6924 and verify that they are within a range of one another. Alternatively, additionally, or optionally there may be a cap on the number of valve pump strokes needed to displace the target volume of fluid into the pump chamber 181. In the event that one or more such valve pump stroking criteria is breached, the control system 16 may command a check for air in the pump chamber 181 in block 6932. The air check may be done by collecting a measurement of the pump chamber 181 volume using a negative pressure precharge as described elsewhere herein (e.g. under the section heading titled "Air Detection"). This pump chamber 181 volume measurement and the measurement from block 6924 may be compared against one another to determine whether the pump chamber 181 contains a volume of air. The magnitude of the difference between these two measurements may be indicative of the amount of air contained in the pump chamber 181.

The control system 16 may determine there is too much air in the pump chamber 181 in the event that the two measurements differ by more than a predefined threshold amount. Alternatively, the control system 16 may determine there is too much air in the pump chamber 181 if the two volume measurements differ by more than a remaining volume of liquid needed in the pump chamber 181 to reach the target volume. The remaining amount of liquid needed may be determined by subtracting the measurement taken in block 6924 from the target volume. In another embodiment, the control system 16 may determine there is too much air if the negative pressure precharge measurement is different by more than a predetermined volume from a second value representative of a fully liquid filled pump chamber 181. The second value may be a preset value, or it may be a historic value representative of the largest liquid fill volume previously measured for the pump chamber 181.

If, in block 6934, there is not too much air in the pump chamber 181, the control system 16 may command a number of valve pump strokes to the pumping chamber 181 and return to block 6922. In such cases, the slower filling of the pump chamber 181 may be due to a number of factors. For example, if the control system 16 is delivering valve pump strokes to the pumping chamber 181 from a source at a low relative head height, the volume delivered in each valve pump stroke may tend to be smaller. In certain examples, after a number of air checks determine there is not too much air in the pump chamber 181 when pumping from the same source, the control system 16 may decrease the frequency of air checks due to the likelihood that the slower filling is attributable to head height of the source. In embodiments where head height detection is employed to determine the relative location of various sources, the valve stroke pumping criteria may be adjusted depending on the detected head height for each source.

If, in block 6934, there is too much air in the pump chamber 181 the control system 16 may command delivery of the pump chamber 181 in block 6936. The control system 16 may use the measurement from block 6924 and a post pump chamber delivery 181 volume measurement to determine the amount of fluid displaced. A new target fill volume for the pump chamber 181 may be computed by adjusting the previous target fill volume based on the amount of fluid displaced. For example, the amount of fluid displaced may be subtracted from the previous target fill volume to arrive at a new target fill volume. The control system 16 may then command a number of valve pump strokes to the pumping chamber 181 and return to block 6922.

Referring now to FIGS. 155A and 155B a front view and rear view of a two chamber cassette 24 similar to that depicted in FIGS. 1-9 are shown. Such a cassette 24 may support valve stroke pumping from, for example, a source component 6000 to a pump chamber 181C, 181D of the cassette 24. For example, a source component 6000 may be fluidically connected to a source port or source spike 160 of the cassette 24 via a fluid line or flow conduit. In the example, spike caps 63, which may be removed by the cycler 14, are shown covering the spikes 160 of the cassette 24. This connection may place the source components 6000 into communication with source valve wells or stations 185A-185E. The source valve stations 185A-185E may each be placed into or out of fluid communication with a common fluid bus 202 through their respective source valve ports 186 via actuation of a membrane (not shown) covering the cassette 24. The common fluid bus 202 may also be placed into or out of fluid communication with the first pump chamber 181C and second pump chamber 181D via their respective pump valve wells or stations 189C and 189D.

After filling a pump chamber, for example, the second pump chamber 181D to within a first range of the target value, valve pumping strokes may be performed to add or remove fluid from the pump chamber 181D until it is within a second range of the target value. The source valve station 185A-E in communication with the source component of interest may be opened while all other source valve stations 185A-E may remain closed. Additionally, positive pressure may be applied to the membrane over the first pump chamber 181C while its pump valve well 189C is actuated to an open position. The valve station 185A-E may then be actuated closed. This may perform a valve fill stroke of the first pump valve well 189C and isolate that fill stroke volume in the pump valve well 189C. Pump valve well 189C may serve as an intermediary holding volume for the fluid.

While maintaining positive pressure on the first pump chamber 181C, the pump valve well 189D associated with the second pump chamber 181D may be opened. The pump valve well 189C associated with the first pump chamber 181C may be closed. The positive pressure on the membrane (not shown) over the first pump chamber 181C will inhibit fluid flow into the first pump chamber 181C as pump valve well 189C is closed. As a result, substantially all of the fluid moved as the valve well 189C is closing may be transferred to the second pump valve well 189D. This valve well 189D may then be closed to deliver a valve pump stroke to the second pump chamber 181D.

This may be repeated as necessary to place the volume of the second pump chamber 181D within the second range of the target volume. It shall be noted that fluid may be removed from the second pump chamber 181D in a similar manner. As would be appreciated by one skilled in the art, fluid may be pumped to or from the first pump chamber 181C via the cassette 24 valves as well. Additionally, cassettes 24 having a greater number of pump chambers may employ a similar technique to pump to or from select pump chambers of the cassette 24 via cassette 24 valves.

In some embodiments, at least one of the source valve wells 185A-E may not be in communication with a source component 6000. That is, a cassette 24 may include at least one dedicated holding volume valve well which serves as the intermediary holding volume, but otherwise is not involved in the routing of fluid through the set 12. The source port/spike associated with that respective valve well or station 185A-E may be physically blocked off or may not be populated with a fluid line. Alternatively, a spike or port may be absent and the portion of the cassette body forming the walls of the valve well 185A-E may be solid. As a result, the at least one holding volume valve well not in communication with a source component 6000 may be used as the intermediary holding volume when pumping to or from a pump chamber 181C, 181D. Likewise, if an occluder is deployed to prevent flow through a line attached to the valve well's 183, 185 port or spike, that valve well 183, 185 may be used as the intermediary holding volume if it is on the same common bus 202, 200. For example, if an occluder 147 (see, e.g. FIG. 63) is deployed to block flow through the patient line 34, the valve well 183 associated with port 154 could be used as the intermediary volume for valve based pumping along common bus 202. Pump chambers 181C, 181D may also be used as an intermediary holding volume instead of or in addition to at least one valve well 183, 185, 189, 192 of the cassette 24. This may facilitate valve based pumping being performed between two or more common fluid buses 200, 202 of a cassette 24.

Referring now also to FIG. 156, a schematic diagram of an example cassette 6030 is shown. A pump chamber 6052 of the cassette 6030 may be used as a fluid source during valve based pumping instead of directly using a selected source component 6000. This may allow for the volume transfer caused by a valve pump stroke to be controlled and adjusted even when source components may be at different head heights. In the example schematic, the pump chamber 6052 may be filled or delivered by respectively applying negative or positive pressure to a control chamber 171B. This may create a pressure in the pump chamber 6052 on the opposing side of the cassette sheeting 6038. This pressure may be supplied from a pneumatic circuit (identified here as an integrated manifold 2700 similar to that in FIG. 62) though mechanical or hydraulic actuators may be used as well.

After the chamber is full of fluid from the selected source component 6000, pressure may continue to be supplied to the control chamber 171B. When positive pressure (depicted representationally as arrows 6065) is supplied, the pressurized pump chamber 6052 may create an open bias within the cassette 6030 which may aid the valve stations 6032, 6034, 6036 to open more fully when the control surface 148 over the valve stations 6032, 6034, 6036 is subjected to negative pressure. The magnitude of the pressure applied to the pump chamber 6052 via the control chamber 171B may be altered to set or adjust the open bias and thus the valve pump stroke displacement volume.

Referring now also to FIGS. 157A and 157B, a first detailed view 6057 and second detailed view 6059 are respectively shown. The first detailed view 6057 depicts an example view of a portion of a valve station 6034 which may be located at the indicated region 6063 of FIG. 156. In the first detailed view 6057, a valve fill stroke of the valve station 6034 is being performed while the pump chamber 6052 is at a first pressure. The second detail view 6059 is an example view of the portion of the valve station 6034 from the indicated region 6061 of FIG. 156 and also shows a valve fill stroke of the valve station 6034. The pump chamber 6052 is at a second pressure in FIG. 155C. The second pressure, in the example, is greater than the first pressure. The negative pressure applied to the control surface 148 to open the second valve station 6034 is substantially the same in both FIGS. 157A and 157B. Though the second valve station 6034 is shown, this is merely for exemplary purposes and the following description may be generalized to any valve station.

As shown, the cassette sheeting 6038 is displaced a greater distance from the valve seat 6040 of the second valve station 6034 when the pump chamber 6052 is at the second, greater pressure (see FIG. 157B). As a result, in FIG. 157B, the total volume of the second valve station 6034 is greater than the total volume of the second valve station 6034 in FIG. 157A. Consequentially, when the second valve station 6034 is closed by applying positive pressure to the control surface 148, the amount of volume displaced will be greater for the valve station depicted in FIG. 157B.

The valve pump stroke displacement volume may be proportional to the pressure applied to the control chamber 171B for the pump chamber 6052. The pressure of the control chamber 171B then may be selected to control or adjust the valve pump stroke displacement volume. The control chamber 171B may be adjusted between ambient pressure and 25 kPa or greater in some embodiments. The control chamber 171B pressure may be limited to an upper pressure bound which is lower than the valve closure pressure by a predetermined amount. This may allow for an adjustment of valve stroke volumes between when the pump chamber 6052 is subjected to ambient pressure (e.g. 30-70 microliters) and when the pump chamber 6052 is subjected to around 25 kPa (e.g. about 250 microliters) or its upper pressure bound.

In some embodiments, the pump chamber 6052 pressure may be altered dynamically based at least in part on the difference between the current transfer volume and the target transfer volume. Generally, as the current transfer volume gets closer to the target transfer volume, the pump chamber pressure 6052 used may be decreased. When the difference between the current transfer volume and target is within a first range of values, a first pump chamber 6052 pressure may be used. When the difference is within a second range of values, a second pump chamber 6052 pressure may be used. When within a third range, a third pressure may be used and so on. The first range may include current transfer volumes greatest from the target transfer volume. As valve pump strokes are completed, the current transfer volume may enter into the second range and eventually into the third, fourth, fifth, etc. range (if included). The first pressure may be the highest pressure. The pressure may decrease as the current transfer volume progresses into ranges closer to the target transfer volume. As a result, when the current transfer volume is in the first range, each valve pump stroke may transfer a volume larger than that which will be transferred in other ranges for each pump stroke. This may allow for a balance between preventing overshoot of the target transfer volume and quickly reaching the target transfer volume. As mentioned above, the current transfer volume may be tracked in closed loop or semi-closed loop fashion. Alternatively, the valve pump stroke volume may be characterized at each of the first, second, third, etc. pressures to allow for substantially open loop based pumping. In such scenarios, a volume measurement may only be taken when the current transfer volume (e.g. based on accounting from the characterized volumes) is determined to be at or near the target transfer volume. Volume measurements may also be taken when such volume accounting determines the current transfer volume has transitioned from one range to another.

High Precision Volumetric Displacement with Cassette

Depending on the embodiment, the accuracy of the pump chamber volume determinations made via FMS measurements may be greater when the pump chamber volume is within a particular range. This particular range may be a range at which a comparatively large data points have been generated as calibrations have been performed. It may also be a range where the cassette sheeting stretches in a way which is comparatively more deterministic than when the sheeting is at other points in a stroke. For example, volume determinations may be in a highest accuracy range when a pump chamber is nearly full or full. To help increase targeting accuracy, the amount of volume transferred during certain pump strokes may be altered in order to increase the number of pump strokes made in the highest accuracy range. This may involve performing a number of partial pump strokes near the end of a volume transfer.

Referring now to the flowchart 6060 shown in FIG. 158, a pump stroke may be performed by the cycler 14 in block 6062. A number of remaining pump strokes may be determined by the controller 16 in block 6064. If, in block 6066, the number of remaining pump strokes is greater than a predefined number, blocks 6062 and 6064 may be repeated. It shall be appreciated that a volume remaining value instead of a number of remaining pump strokes may alternatively be used in blocks 6064 and 6066.

Once, in block 6066, the number of pump strokes (or volume remaining) is less than a predefined number, the controller 16 may determine a difference between the projected final stroke volume and a nominal stroke volume in block 6068. This may be determined by assuming that pump strokes leading up to the last pump stroke will be of a nominal volume. This nominal volume may be preset or may be determined based on volume measurement data collected over a number of historical pump strokes performed by the cycler 14. After determining this difference, the difference value may be divided by the number of remaining pump strokes in block 6070. This may yield a stroke withholding volume to be applied to each subsequent stroke.

The stroke withholding volume may alter the volume of subsequent strokes such that each of the subsequent strokes is filled to a volume where the volume measurement is in the highest accuracy range. The remaining pump stroke or volume threshold used in 6066 may be selected to ensure that in a worst case scenario (e.g. the projected final stroke volume is a small proportion of the nominal stroke volume) each stroke will be filled to a volume where the measurement would be in the highest accuracy range. For example if the highest accuracy range is bound by a full stroke volume value and the value of full stroke volume minus "X", the threshold may be set such that the withholding volume does not exceed "X". That is, "X" may serve as a maximum withholding volume limit and in turn may dictate the number of strokes for which a withholding volume is to be applied. The stroke threshold used in 6066 may be a full stroke volume/"X".

In block 6072, the next pump stroke may be performed. This stroke may be stopped short of a full stroke by an amount substantially equal to the computed stroke withholding volume. For example, the stroke may be stopped short of the full stroke by an amount as close to the computed stroke withholding volume as a targeting limit of the cycler 14 hardware may allow. A continuous flow rate and stroke displacement estimation (described elsewhere herein) may be used to determine when it is necessary to halt the stroke in order to transfer the proper volume. If additional strokes remain in block 6074, block 6072 may be repeated. In some embodiments, a stroke withholding volume may be recalculated after each stroke taking the previous stroke volume measurements into account. Once all strokes have been completed in block 6074, valve pump strokes optionally may be utilized (described above) to get the total transferred fluid volume within a predefined range of a target in block 6076.

In alternative embodiments, and as shown for example, in the flowchart 6080 of FIG. 159, the withholding volume may also be chosen such that the final pump stroke is a substantially full pump stroke. Blocks 6082, 6084, 6086, and 6088 of FIG. 159 are analogous respectively to blocks 6062, 6064, 6066, and 6068 of FIG. 158. In block 6090, however, the difference between the projected final stroke volume and nominal stroke volume may be divided by the number of remaining strokes minus one. In block 6092, the next pumping stroke may be performed and may be stopped short of a full stroke by an amount substantially equal to the computed stroke withholding volume from block 6090. Strokes may continue to be performed in this manner until the final stroke remains. Once, in block 6094, only the final stroke remains and the last pump stroke may be performed in block 6096. The stroke volume of this stroke should be substantially equal to a full stroke volume. Optionally, valve pump strokes may be utilized to get the total transferred fluid volume within a predefined range of a target.

In some embodiments, the controller 16 may use the cycler 14 to make a plurality of attempts to the fill a pump chamber to a target amount before commanding delivery of the pump chamber to a destination. The controller 16 may command the cycler 14 to fill a pump chamber and deliver all or a portion of the pump chamber back to a source if the chamber was not filled to within a range criteria of the target amount. This range criteria may be no greater than +/−3 ml of the target volume. After returning a portion of the pump chamber to the source, the controller 16 may, if needed, fill the chamber again from the source and determine if the chamber has been filled to the within the range of the target volume. This pumping back and forth to and from the source may continue until the pump chamber has been filled to within the range of the target volume.

Referring now to the flowchart 6100 shown in FIG. 160, a full or partial pump fill stroke may be performed in block 6102. If a full pump stroke is performed, the stroke may be stopped based on a determination made by an end of stroke algorithm (described elsewhere herein). Where a partial stroke is performed, continuous flow rate and stroke displacement estimation may be used to estimate when to stop the fill stroke. In block 6104, a volume measurement of the amount of fluid transferred from the source to the pump chamber may be made. If, in block 6106, the volume measurement indicates that the chamber is not filled to within a range of a target volume, fluid may be delivered back to the source in block 6108. The pump delivery stroke performed in block 6108 may be a full stroke or a partial stroke. Where a partial stroke is preformed a continuous flow rate and stroke displacement estimation may be used to estimate when to stop. A volume measurement may again be taken in block 6110. If, in block 6112, the volume measurement indicates that the chamber is not emptied to within a range of a target volume, the flowchart 6100 may return to block 6102. This filling and emptying of the pump chamber may occur until in block 6106 or block 6112 the volume in the chamber is within the range of the target. Once within the range, the pump chamber may be delivered to the destination in block 6114. Optionally, valve pump strokes may be performed to bring the pump chamber volume closer to the target volume (e.g. within a second, tighter, range of the target volume).

Referring now to the flowchart 6120 shown in FIG. 161, in some embodiments multiple sensors may be used to determine a stroke displacement volume measurement. The measurements made using each sensor may be averaged or otherwise numerically processed to determine a displacement volume of greater accuracy. As shown in block 6122, a fill stroke may be performed with a primary chamber of a cassette 24. The stroke may be a full fill stroke or partial fill stroke. In block 6124, the primary chamber volume may be measured using a first sensor. In some embodiments, this sensor may be used to generate a first volume measurement or may be used to generate a first set of volume measurements for the primary chamber. In block 6126, a fluid pathway from the primary chamber to the secondary chamber of the cassette 24 may be established. All fluid in the primary chamber may be delivered to the secondary chamber in block 6126 as well. In block 6128, the secondary chamber volume may be measured using a second sensor. In some embodiments, this sensor may be used to generate a second volume measurement or may be used to generate a second set of volume measurements taken for the secondary chamber. Where sets of measurements are taken, measurements belonging to the same set may be compared to ensure that they agree within some range of one another.

If, in block 6130, an analysis of the volume measurements from the primary and secondary chambers do not agree (within some predefined range), various error handling may be performed in block 6132. This error handling may include one or more retry in which fluid is delivered back to the primary chamber followed by the flowchart 6120 then restarting from block 6124. Error handling may also include generation of an alert or alarm by the control system 16 perhaps occurring after one or more retry.

If, in block 6130, volume measurements from the primary and secondary chambers agree, the measurements may be used to calculate a fill volume in block 6134. These measurements may be numerically processed (e.g. averaged) to arrive at a chamber fill volume measurement which may be more accurate than a measurement generated using only a single sensor. The secondary chamber may then be actuated to deliver its contents to a destination in block 6136. As with other approaches, additional fluid transfer (e.g. as described in FIGS. 137-154B and FIG. 160) may be made if the chamber volume measurement is not within a range of a target volume before delivery in block 6136.

Other approaches to displacing small amounts of fluid with high precision may include using continuous flow rate and stroke displacement estimation implemented on an FPGA as described above in relation to FIGS. 69-76.

Solutions Assay During Prime

During priming of a cassette 24 installed in a cycler 14, it may be desirable to assay fluid pumped through the cassette 24 to determine its quality, type, or other characteristics of interest. Such an assay may be performed to verify the presence of one or more expected solution or determine the ports on a cassette 24 to which various solution types are attached. The quality of such solutions may also be checked by an assay during priming of the cassette 24. The assay results could for example be compared to nominal values or predefined quality rules associated with the various installed solution types as identified by a user during set up. Alternatively, the solution types and/or nominal values associated with the solution could be collected from an identification tag 1100 imaged by the auto-ID camera 1104 as described elsewhere herein. In some embodiments, the solution types may be unknown and the data collected by the assay sensor or sensor set may be used to determine the solution types present. Such an assay may also be performed to audit the functionality of a source component generating device of the system 10 such as a water purification device 6002. A diluent may be checked by such an assay to ensure that it is being generated in conformance with predefined quality standards.

Referring to FIG. 162, a flowchart 6780 depicting a number of actions which may be executed to assay fluid characteristics during a priming operation of a cassette 24 is depicted. The flowchart 6780 begins after the source components 6000 have been set up, the cassette 24 has been installed in the cycler 14, and various pre-therapy testing has been successful. As shown, in block 6782, the cassette may be primed with a first fluid. The first fluid may be a diluent such as water produced from a water purification device. At least a portion of the fluid used to prime the cassette may be delivered to a drain destination in block 6784. Data related to one or more characteristic of interest of the first fluid may be collected in block 6786 from an assay sensor or sensor set. The assay sensor or sensor set may include any composition sensor or combination of any such sensors described herein.

When fluid is provided to the composition sensor, the fluid may be pumped in a smooth manner. To accomplish this, volume measurements before, after, or both before and after may be omitted. The chambers may be sequenced such that flow to/from the pump chambers past the sensors is substantially continuous. In certain embodiments a continuous flow rate and stroke displacement estimation (described elsewhere herein) may be used. In general, one chamber may be filling while the other is delivering. The flow rate estimation may be used to determine if a first chamber is leading or lagging behind the stroke of the second chamber. The flow rate or one or both chambers may then be adjusted using the flow rate estimator as feedback. This may allow for continuous flow as one chamber may be controlled to be full and ready to transition to a delivery as the delivery stroke on the opposing chamber concludes. This smooth pumping mode may allow for certain types of composition sensors to get more reliable composition readings of the fluid passing the sensor.

In block 6788, the data may be checked against a set of predefined quality rules. In some embodiments, these rules may include a comparison threshold defined with respect to other data generated by the system 10. For example, a comparison between data related to the quality of the water produced by a sensor associated with the water purification device may be checked against data collected from the assay sensor or sensor set to ensure the data is within a threshold range of each other. Other quality rules based on sensed properties of the first fluid (such as any of those properties discussed elsewhere herein) may be implemented as well.

If, in block 6790, the first fluid does not conform to the quality rules, a controller may halt priming of the cassette and generate an alarm for communication to the user in block 6792. If, in block 6790, the first fluid conforms to the quality rules, priming with a next fluid may be performed in block 6794. At least a portion of the next fluid used during priming may be delivered to a drain destination in block 6796. Data from the assay sensor or sensor set may be monitored in block 6798. If, in block 6800, a transition to the next fluid from the previous fluid is detected by the assay sensor or sensor set, data associated with the next fluid may be checked against predefined quality rules for that fluid in block 6802. If, in block 6804, the fluid does not conform to the predefined quality rules, priming may be stopped by the controller and an alert or alarm may be generated in block 6806. The fluid may alternatively be discarded and more of the next fluid may be provided to the assay sensor or sensor set in one or more retry attempt. After a predetermined number of retry attempts have failed, an alarm may be generated in block 6806. If the fluid conforms to the quality rules in block 6804, and all fluids have been primed in block 6808, a mixing operation may begin in block 6810. If additional fluids exist in block 6808, the flowchart 6780 may return to block 6794.

Cassette Bus Flushing

In some embodiments, after a pumping operation has been completed, certain sections or flow paths of the cassette 24 may include contaminating fluid which may not conform to prescribed formulation parameters. When performing a fill stroke from a component source 6000, fluid from the component source 6000 may be required, depending on the cassette 24, to travel through a common channel or bus 200, 202 of the cassette 24 before entering into the pumping chamber 181A, B being actuated. Once the chamber 181A, B has been filled to the appropriate amount, a hold up volume of fluid from the component source 6000 may remain in the common bus 202, 200 or another flow path of the cassette 24. Fluid from one of the component sources 6000 may be used as a flush fluid which is drawn into a chamber 181A, B along with the hold up volume and then pumped to a drain or discard destination. Purified water from a water purification device 6002 may be used as the flush fluid in some embodiments.

Alternatively, since the volume of the common channel or bus 200, 202 is constant, the pumping chamber 181A, B may be stopped short of the target fill volume during the stroke by an amount equal to the hold up volume. The hold up volume, along with the next fluid in the formulation or a flush fluid may then be drawn into a pump chamber during the next fill stroke. The flush fluid may be the diluent used to dilute concentrates in the mixing reservoir 6004. The hold up volume may be subtracted from the chamber fill volume of that stroke to determine the volume of the next fluid (or flush fluid) filled in the chamber. The chamber 181A, B may then be delivered to the mixing reservoir 6004 and the mixing operation may continue.

Referring now to FIG. 163, an example flowchart 6680 detailing a number of acts which may be performed when mixing a prescribed therapy formulation is shown. In the example flowchart 6680, mixing is done to replenish the mixing reservoir after a fill of a patient and the flowchart 6680 begins with the cycler in the dwell state in block 6682. Initial mixing at the start of a therapy may be performed in a similar manner, however, block 6684, in which residual fluid in the mixing reservoir is pumped to drain may not be performed.

In block 6686, the cassette may be flushed with a flush fluid. The flush fluid may be a diluent, perhaps purified water generated by a water purification device of the system. A first portion of the diluent volume specified in the therapy formulation may be delivered to the mixing reservoir in block 6688. This first portion may be a predefined volume (e.g. 300 ml) or may be defined as a percentage of the total diluent volume defined for the therapy. In some embodiments, the first portion may be set as a predefined number of full pump strokes without a specifically defined volume constraint. Thus, so long as volume displacement measurements are taken after each stroke, the volume of diluent transferred may be accounted for during pumping of the first portion. Defining the first portion as a number of full pump strokes and taking a volume displacement measurement after each stroke may allow for the first portion to be transferred quickly without ultimately impacting accuracy.

The cassette may be primed with fluid from a first source component in block 6690. The first source component in the flowchart 6680 is described as a first concentrate (e.g. dextrose), though this component may be any of those described herein (such as those described in Table 2). The cycler may pump the volume of the first source component specified in a therapy formulation to the mixing reservoir in block 6692. If, in block 6694, additional source components are specified in the therapy formulation the cassette may be primed with fluid from the next source component in block 6696. Again, the flowchart 6680 details that the next source component is a concentrate (e.g. an electrolyte), however, any component described herein may be used. The cycler may pump the volume of the next source component specified in the therapy formulation to the mixing reservoir in block 6698. Blocks 6696 and 6698 may be repeated until all source component fluids specified in the therapy formulation have been transferred to the mixing reservoir. Once, in block 6694, all source components have been transferred in their specified amounts, the cassette may be flushed with flush fluid in block 6700. A second portion of diluent may be pumped through the cassette to the mixing reservoir in block 6702. The total volume of diluent specified in the formulation file may be divided between the first and second portion. In such embodiments, the second portion may be all of the remaining diluent necessary to meet the total diluent volume specified in the therapy formulation. In some embodiments, the therapy formulation may include molar ratios for each source component and diluent. The total diluent volume needed for the therapy may be recalculated before delivery of the second portion to the mixing reservoir is completed. The recalculation may be based on the measured volumes or masses of each source component fluid transferred to the mixing reservoir. The recalculated total diluent volume may be a volume which would generate a final mixture in the mixing reservoir that is most closely aligned with the molar ratios specified in the therapy formulation.

The cassette may be primed with the final completed mixture in block 6704. In block 6706 at least one characteristic of interest of the fluid may be sensed. The sensed characteristic may provide insight into the composition of the final mixture. Data from the at least one sensed characteristic may be used by the cycler 14 control system 16 to verify that the final mixture is within acceptable bounds of the therapy formulation parameters. In some embodiments, adjustments may be performed as needed by drawing in additional diluent or source component fluid. Flushing may be performed as needed during the adjustment. Any adjustment may be performed via valve based pumping, pump chamber full or partial strokes or combinations thereof as described elsewhere herein. After adjustment, block 6706 may be repeated.

Referring now to FIGS. 164A-164B, another example flowchart 6720 detailing a number of acts which may be performed when mixing a prescribed therapy formulation is shown. The flowchart 6720 begins with the cycler in a dwell phase in block 6722. In block 6724, a determination may be made as to whether excess solution from a previous fill operation is present in a mixing reservoir of the set installed in the cycler. If excess solution is present, this solution may be pumped to drain in block 6726. In block 6728, the first and second chamber of a cassette installed in the cycler may be filled with a flush fluid (which may be the diluent used during mixing). The first and second chamber may be delivered to a drain destination in block 6730.

In block 6732, at least one of the first and second chambers may be filled with a flush fluid. Any filled chambers of the cassette may be delivered to the mixing reservoir in block 6734. At least one of the first and second chambers of the cassette may be filled from the mixing reservoir in block 6736. Any filled chambers may be delivered to the drain destination in block 6738. If, in block 6740, the dilution of the hold-up volume in the fluid path between the cassette and the mixing reservoir has not been completed the flowchart 6720 may repeat blocks 6732, 6734, 6736, 6738. In some embodiments, multiple chamber volumes may be transferred to the mixing reservoir before retrieving the fluid from the mixing reservoir and delivering it to the drain.

If, in block 6740, the dilution of the hold up volume in the fluid path has been completed a predefined volume of flush fluid (e.g. diluent produced from a water purification device) may be delivered to the mixing reservoir in block 6742. As described in relation to FIG. 163, the predefined volume may be defined as a number of pump strokes. As such, the volume may not be stringently defined and the volume transferred via predefined number of pump strokes may be accounted and stored for later use.

The first or second chamber of the cassette may be filled with a first concentrate in block 6744. At least a portion of the chamber may then be delivered to a drain in block 6746. In block 6748, the volume of first concentrate specified in the therapy formulation file may be transferred through the pumping cassette to the mixing reservoir. The first or second chamber may be filled with a flush fluid in block 6750 and the chamber may be delivered to the drain destination in block 6752. The first or second chamber may be filled with a next concentrate in block 6754. The filled chamber may be delivered to the drain destination in block 6756. In block 6758, a volume of the next concentrate specified in the therapy formulation file may be transferred to the mixing reservoir via the pumping cassette. The first or second chamber may be filled with a flush fluid in block 6760. In block 6762, the filled chamber may be delivered to the drain destination. If, in block 6764, there are additional concentrates specified in the therapy formulation file, the flowchart 6720 may return to block 6754.

If there are not additional concentrates specified in the therapy formulation file in block 6764, a predefined volume of flush fluid may be transferred to the mixing reservoir in block 6766. The predefined volume may be the total volume of diluent defined in the therapy formulation file minus the stored volume of diluent delivered in block 6742. In block 6768, one or more characteristics of interest of the mixture in the mixing reservoir may be sensed to verify the mixture conforms to the mixture specified in the therapy formulation file. As described above with reference to FIG. 163, adjustment and re-verification may be performed under certain circumstances.

Once all mixing per the prescribed therapy formulation has been completed, there may still be a hold up volume of contaminating fluid in certain regions of the cassette 24. This contaminating fluid may be any fluid which does not conform to the prescribed formulation parameters. For example, some portions of the cassette 24 such as a common fluid bus of the cassette 24 and certain valve wells of the cassette 24 may be occupied with flush fluid or source component fluid. Purified water supplied by a water purification device 6002 may be the contaminating fluid, though other fluids such as spent dialysate or anything listed in Table 2 may potentially be present depending on the embodiment or the therapy formulation. If delivered during a fill stage of a therapy cycle, this fluid may dilute or alter the composition of the dialysate mixed for that fill. It may be desirable that this fluid be discarded before any fluid delivery to the patient occurs. In some embodiments, a flush or discarding of this fluid may be performed with a predefined first set of fluids while a flush maybe optional with a second.

Referring now to the flowchart 6300 depicted in FIG. 165, regions filled with non conforming fluid may be flushed with properly mixed dialysate before delivery to the patient occurs. The flowchart 6300 begins with both chambers 181A, 181B in the delivered position. In block 6302, a first chamber 181A, 181B of the cassette 24 may be filled with mixed fluid from a mixing reservoir 6004. The chamber 181A, 181B filled in block 6302 may be the chamber 181A, 181B most distal to the attachment point of the patient line 34 to the cassette 24. In block 6304, valves or access ports leading to the cassette 24 region filled with the non conforming fluid may be opened. This may place the region filled with non conforming fluid into fluid communication with each of the pump chambers 181A, 181B. In the example flowchart 6300, the region is a common fluid bus of the cassette 24, for instance lower fluid bus 202. The region may be a first contaminated region or flow path of a plurality of contaminated flow paths.

In block 6306, the fluid or a portion of the fluid in the first chamber 181A, 181B may be transferred to the second chamber 181A, 181B of the cassette 24. Fluid may be transferred via the region which is filled with non conforming fluid. The amount of fluid transferred may be equal to or slightly greater than a nominal volume of fluid contained in the fluid path established between the two chambers. The fluid transfer may be performed in any suitable manner, though in specific examples may be accomplished by venting the first chamber 181A, 181B to subject it to ambient pressure and drawing a vacuum on the second chamber 181A, 181B. If the cassette 24 layout is such that the region has been completely cleared of non conforming fluid or remaining non conforming fluid will be hydraulically locked from displacing toward the patient, the flowchart 6300 may skip to block 6312. In the latter case, a small, remaining hold up volume of non conforming fluid may still be present in the region of the cassette 24. This volume should, however, only alter the mixed fluid very slowly through diffusion alone and may not present any significant impact to the dialysate formulation.

In other embodiments or if it is desired to remove all non conforming fluid from the region, additional fluid transfers may occur. For example, in block 6308, the first chamber 181A, 181B may be filled with mixed fluid from a mixing reservoir 6004. In block 6310, the first chamber 181A, 181B may be placed into fluid communication with the region and another fluid valve of the region may be opened. It may be desirable that a fluid valve at the terminus of the region (e.g. the fluid valve at the end of a bus) be opened to help ensure the region is completely flushed. In the example flowchart 6300, the fluid valve at a terminus of the common channel is opened placing the common channel in fluid communication with a cassette 24 port leading to one of the source components 6000 (e.g. water purification device 6002). Also in block 6310, a volume substantially equal to or slightly greater than the remaining hold up volume of the region may be delivered into the region. Continuous flow rate and stroke displacement estimation as described elsewhere herein may be used to aid in targeting delivery of the remaining hold up volume to the region.

In block 6312, the second chamber 181A, 181B may be delivered to a drain destination to purge the non conforming fluid from the set 12. Optionally, or depending on the cassette 24 layout, mixed fluid from the first pump chamber 181A, 181B may be pumped to the drain destination as well in block 6314. This may remove any potential remaining non conforming fluid residing in the cassette 24 flowpath leading to the drain destination. To flush the pathway to the drain destination, the entire remaining volume in the first chamber 181A, 181B may be delivered in block 6314 or only a portion sufficient to fill the cassette 24 flowpath to the drain destination.

Accumulator

Referring now to FIG. 166, the system 10 may include at least one accumulator 6850 in some embodiments. An accumulator 6850 may for example be included within the set 12. An accumulator 6350 may be positioned on a diluent or purified water supply conduit within the set 12 such that it is between a water purification device 6002 and the cassette 24 during therapy. Any suitable accumulator 6850 may be used. The accumulator 6850 may be arranged to store a volume of water. The positive pressure of water supplied by the water purification device 6002 may cause water to flow into the accumulator 6850. The accumulator 6850 in this example includes a port 6852. The port 6852 may be fluidly coupled to the water supply conduit so that water may flow between the accumulator 6850 and the water supply conduit. The accumulator 6850 may have any suitable volume and may be arranged to store smaller or larger volumes of water, if desired.

One or more sensor 6851 may be included in the system 10 to monitor flow into the accumulator 6850. The one or more sensor 6851 may be any suitable sensor such as a weight based sensor, flow sensor, pressure sensor, etc. In certain embodiments, redundant sensors 6851 may be used such that their outputs may be compared to verify proper operation. The sensors 6851 may be of the same type or different types depending on the embodiment. The data generated by the one or more sensor 6851 may be used, in conjunction with volume pumping data collected by a cycler 14 to determine when the water purification device 6002 should provide water to the accumulator 6850 or stop providing water to the accumulator 6850. Depending on the water purification device 6002, open loop control may also be employed if the output of the water purification device 6002 can be characterized. In some embodiments, the water purification device 6002 may meter specific volumes of water to the accumulator 6850. The water purification device 6002 may communicate its volume output to the cycler 14.

Data from the at least one sensor 6851 may also be used to inform operation of a failsafe which may be implemented by the attached cycler 14. For example, if the at least one sensor 6851 indicates water is being provided after the cycler 14 commands a stop, an occluder 147 (see, e.g. FIG. 63-66) in the cycler 14 may be deployed to occlude the source lines feeding the cassette 24 or a patient line 34. Similarly, if the at least one sensor 6851 indicates water is being delivered to the accumulator 6850 after the water purification device 6002 communicates it has stopped providing water, cycler 14 may command the occluder 147 be deployed to occlude the source lines. An occluder 147 acting on the patient line 34 may be deployed regardless of the sensor 6851 output when the water purification device 6002 is providing water and only withdrawn when data from the at least one sensor 6851 indicates that water is no longer being provided from the water purification device 6002. In such embodiments, the at least one sensor 6851 may be a pressure sensor which monitors for a rise in pressure indicating that the accumulator 6850 volume is full. Water flow from a water purification device 6002 may be halted when a pressure rise is detected. In some examples, an occluder which is coupled to the water purification device 6002 may instead or additionally be used to prevent flow through the set 12.

In certain examples, the volume of fluid contained in the accumulator 6850 may be tracked by the cycler 14. This volume may be determined based on a volume output communications from the water purification device 6002, sensor 6851 or both. In the event that this volume exceeds a threshold, the cycler 14 may at least partially empty the accumulator 6850 by pumping fluid to a drain destination via the cassette 24. This may, for example, only occur in certain states (e.g. dwell state or a between therapies state where the cycler 14 is waiting for the patient to connect before beginning therapy. Additionally, this may only occur when the cycler 14 is free of alarms or alerts.

Where the accumulator 6850 is included as part of the set 12. The accumulator 6850 may be included in a multi-use segment of the set 12 which is replaced at a lesser frequency than the rest of the set 12. The multi-use segment may be constructed from the same material as the rest of the set 12 or a different material and may connect to the rest of the set 12 via a luer lock connector or similar interface 6854. It may be advantageous to construct the multi-use segment including the accumulator 6850 out of a material or materials which may withstand a heat disinfection. If so constructed, the multi-use segment could be disinfected after a therapy has been performed by exposing it to hot fluid from a heat disinfection cycle already employed by a water purification device 6002. For example, the connector 6854 which couples the multi-use segment to the rest of the set 12 may be attached to a port of the water purification device 6002. The connector 6854 may alternatively be connected to another fluid line from the water purification device 6002 to form a closed fluid circuit. High temperature water may be circulated through the multi-use segment for a predefined period determined to be sufficient to disinfect the segment. Alternatively, an accumulator 6850 may be included as a separate component which is housed in the water purification device 6002 and sterilized during the disinfection cycle of the water purification device 6002.

In the event that part of the set 12 is a multi-use component, the integrity of this portion of the set 12 may be checked after disinfection occurs. Any remaining fluid may be drained from the accumulator 6850 and other portions of the multi-use segment through a drain flow path 6858 of the water purification device 6002. In some embodiments, the fluid may be actively pumped from the accumulator 6850 to the drain. An inlet to the multi-use segment or accumulator 6850 may be closed during this draining. A fluid characteristic sensor 6856 may be disposed on or near the drain flow path 6858. As residual fluid drains from the multi-use segment the fluid characteristic sensor 6856 may monitor the fluid stream for the presence of air. Any suitable sensor may be used as the fluid characteristic sensor 6858. If data from the fluid characteristic sensor indicates greater than a predetermined threshold of air is present during the draining process a fault may be triggered.

Admixing Fluid Handling Set Installation and Integrity Confirmation

Referring now to FIG. 167, a flowchart 6940 detailing a number of example actions which may be used to confirm the installation and integrity of a fluid admixing set is shown. In certain embodiments, when a cycler 14, is set up to perform a therapy in which solutions are to be mixed at the point of care, the cycler 14 may check to ensure that the fluid handling set installed in the cycler 14 is appropriate for such a therapy. Additionally, this check may ensure that the integrity of at least a portion of the set is acceptable. Such a check may be performed prior to therapy a one of a number of other pre-therapy start up procedures. For example, in some embodiments, the control system 16 of the cycler 16 may perform a dry set integrity test and a wet set integrity test which verify that the cycler 14 is functioning properly and the integrity of the cassette 24, its sheeting, and fluid lines and/or bags coupled to the cassette 24 are not compromised. The dry and wet integrity tests may be similar to those performed by the Amia Automated PD System, Kaguya Automated PD System, HomeChoice Automated PD Systems, or as described in U.S. Pat. No. 5,350,357, to Kamen et al., issued Sep. 27, 1994, filed Mar. 3, 1993, and entitled "Peritoneal Dialysis Systems Employing a Liquid Distribution and Pumping Cassette that Emulates Gravity Flow" which is incorporated by reference herein by reference in its entirety and U.S. Pat. No. 6,223,130, to Gray et al., issued Apr. 24, 2001, filed Nov. 16, 1998, and entitled "Apparatus and Method for Detection of a Leak in a Membrane of a Fluid Flow Control System" which is incorporated by reference herein by reference in its entirety.

A mixing fluid set installation and integrity test may be performed as a semi-dry set integrity test which occurs between dry and wet cassette integrity tests. For example, this test may be performed after a dry cassette integrity test has completed and a user has indicated (e.g. via a button press or other interaction with the cycler 14 user interface) that the set has been coupled to a water purification device. Additionally, in some embodiments, the test may be performed after any water quality testing for water produced by the water purification device has completed and has passed (or is indicated to have passed via an interaction with the user interface of the cycler 14). As further described below, the amount of liquid in the set during the semi-dry set integrity test may be minimal and held in a specific segment of the set. As a result, various set integrity tests requiring that the set be dry and not involving the wetted segment of the set may be run after the small volume of water has been delivered into the set. Thus it should be noted that at least some portions of a dry cassette integrity test may be run after the semi-dry test.

Though described in relation to a fluid mixing and handling set, a semi-dry cassette integrity test may be used on various other fluid handling sets. A semi-dry set integrity test may be performed with only a small volume of liquid. This liquid may be present in a single portion of the set or portions of the set while the rest of the set may remain dry. Thus, in the event that the test does not pass, the set will remain nearly entirely dry. As a result, disposal of the set is minimally burdensome. By filling a portion of the set with liquid, the compressibility characteristics of the liquid may be leveraged and certain pathways may be effective blocked off by the liquid. This may, for example, allow for testing of specific segments along particular flow paths as the liquid may be unable to displace when the pressure of the gas in the remaining section of the semi-dry portion of the set is manipulated. For example, a section of a flow path coupled to the cassette which is most distal to the cassette may be filled with liquid. The portion of the set intermediate the cassette and liquid filled distal portion of the flow path may be tested. Additionally, in some embodiments, introduction of the small volume of liquid may cause one or more in line filter included in the set to be placed in a wetted state. Such filters may be included to help protect sterility in portions of the set. Wetting these filters may prevent any air from passing through such filters under the pumping pressures used by the cycler 14. Thus wetting the filters may allow the filters to block off portions of the set. As a result, a semi-dry integrity test may verify the integrity of portions of the set which are meant to be sterile.

In the example shown in FIG. 167, a water purification device coupled to one of the lines of the set may open an outlet valve to fill a portion a flow path including an accumulator 6850. After the flow path between the water purification device and the cassette is in a semi-dry state, the control system 16 of the cycler 14 may command pumping of fluid via the cassette 24 to attempt to pressurize the line under various pressures (e.g. a positive pressure and a negative pressure). The control system 16 may monitor data from a pressure sensor indicative of pressure in a pump chamber of the cassette 24 and compare the data to various pressurization criteria. For example, if the flow path does not negatively pressurize (indicated by a reduced flow condition detected based on data from a sensor which is indicative of the pump chamber pressure as described elsewhere herein) within a number of pump strokes the control system 16 may determine a breach of a pressurization criteria has occurred. Inability to negatively pressurize the flow path may signify that the flow path may be in communication with the atmosphere and integrity of the flow path may be in question.

As shown, in block 6942 of FIG. 167, the control system 16 of the cycler 14 may communicate a dispense command to a water purification device over a communications link. In block 6944, the water device may dispense a volume of liquid into the set. The volume of liquid may be relatively small. For example, the volume of liquid dispensed may be sufficient to fill a portion of a fluid line leading from the water purification device to an accumulator 6850 of the set. The volume may also be sufficient to place any filters included in this fluid line in a wetted state. The volume of water may be less than 250 ml (e.g. 200 mL) in some embodiments. After water delivery to the set is completed communication from the water purification device may be sent to the cycler 14.

In block 6946 the control system 16 of the cycler 14 may command pumping of fluid in a pump chamber 181 of the cassette 24 to the accumulator 6850 via a fluid line 30 coupled to the cassette 24. The fluid in the pump chamber 181 may, in some embodiments, be a volume of gas which is moved to the pump chamber 181 during a previously completed dry cassette integrity test. The accumulator 6850 may be sized to readily accept this fluid without causing pressurization of the intervening flow path. The pressurization criteria used as this fluid is delivered may a positive pressurization check. This may be indicated by a reduced flow condition detected based on data indicative of pump chamber pressure. For example, data from a pressure sensor in a control chamber 171 of the cycler 14 may be monitored and the pressurization criteria may be deemed breached if the data indicates the control chamber pressure is greater than a threshold above ambient pressure after a period of time has elapsed. For example, if the control chamber 171 pressure is not within 5 kPa of ambient pressure after two seconds, the pressurization criteria may be breached.

In the event that the user has installed a fluid handling set which is not intended for point of care fluid mixing (see, e.g. set 12A of FIG. 1A), the fluid pathway may end in a capped connector 35 (see, e.g. FIG. 1A). The capped connector 35 may prevent the transfer of fluid in the pump chamber 181 through the line 30 and the cycler 14 may be unable to complete the delivery stroke or the stroke may not complete in an expected manner. Similarly, if an admixing fluid handling set is installed in the cycler 14, the delivery stroke may be unable to complete or complete as expected in the event that the line is occluded. As a result, the flow path may become positively pressurized breaching the pressurization criteria for this portion of the test. If, in block 6948, this first pressurization criteria is breached, an error may be generated in block 6950. If, in block 6948, the delivery is successful and conformance with the pressurization criteria is detected, the cycler 14 may in block 6952 command pumping of fluid from the accumulator 6850.

In the event that the accumulator 6850 integrity is acceptable, a second, negative pressurization criteria may be expected to be met when pumping fluid form the accumulator 6850. The presence of liquid in the portion of the line between the accumulator 6850 and the water purification device as well as the wetted filters (if included) may prevent air from being drawn into the accumulator 6850 through that line. As a result, no more than a threshold amount of fluid may be expected to be pumped from the accumulator 6850 before a reduced flow condition is detected. In certain embodiments, the second pressurization criteria may be deemed breached if more than a predefined number of pump strokes (e.g. 30) from the accumulator 6850 have been completed and a reduced flow condition has not been detected. In some embodiments, the second pressurization criteria may be deemed to be breached if a reduced flow condition has not been detected after a predefined number of strokes has been exceeded and pressure in a control chamber 171 consistently remains above a predefined value (e.g. −18 kPa) while filling from the accumulator. Additionally, or alternatively, the second pressurization criteria may be deemed to be breached if a reduced flow condition has not been detected after a predefined number of strokes has been exceeded and the decay of pressure in a control chamber 171 is above a predefined value (e.g. 0.24 kPa/2 seconds) while filling from the accumulator. In some embodiments, the pressure decay may be ignored over an initial number of pumping strokes from the accumulator 6850 or an initial amount of time (e.g. 20 seconds) as fluid is pumped from the accumulator 6950. In the event that more than the expected amount of air is able to be pumped from the accumulator 6850 or the second pressurization criteria is otherwise breached, the control system 16 of the cycler 14 may deduce that the integrity of the accumulator 6850 is unacceptable.

If, in block 6954, this second pressurization criteria is not met, the control system 16 of the cycler 14 may generate an error. When an error is generated in block 6954, the control system 16 may prohibit use of that particular fluid handling set for the upcoming therapy. The user may also be notified of this via a message generated for display on the user interface of the cycler 14. If, in block 6954, conformance with the second pressurization criteria is detected, the integrity test may pass and an admixture fluid handling set may be confirmed to be installed in the cycler 14 by the control system 16 in block 6956.

High Pressure Fluid Set Portion with Cassette Based Pumping System

As described in relation to FIG. 62, a cycler 14 may include a number of pressure reservoirs 2620, 2610. These reservoirs 2620, 2610 may include control fluid which is maintained at preset pressure set points by one or more pump 2600. During operation of the cycler 14, the control system 16 may, among other things, open various valves of the pneumatic system of the cycler 14 to apply pressurized control fluid to select regions of a cassette 24. This may cause fluid to be transferred and routed through the cassette 24 via the actuation of cassette 24 pump chambers 181A, B and the opening and closing of cassette 24 valve stations. The preset pressures, however, may impose limitations on the pressures which can be present in other portions of a fluid handling set 12 (see, e.g. FIG. 1). For example, if a certain amount of positive pressure is applied to close a valve station of the cassette 24, that valve station may not reliably close if it comes into communication with a portion of the set 12 at a higher positive pressure than the control fluid. In certain examples, the cassette 24 may tolerate a maximum pressure of between 20-70 kPa (e.g. 28 kPa or 48 kPa). The higher positive pressure may be any pressure above the toleration pressure. In various embodiments, the higher positive pressure may be about 50%, 100%, 250%, 500%, or more greater than the maximum toleration pressure of the cassette 24. In some embodiments, the higher positive pressure may be between about 100 kPa and 300 kPa (e.g. 200 kPa).

Referring now also to the flowchart 6250 of FIG. 168A, to ensure that the valve states of a cassette 24 in a first portion of a set 12 can be reliably known when the set 12 includes a second portion at a higher positive pressure than the control fluid, a sensor (e.g. a pressure transducer)

included in the cycler 14 may be monitored. This sensor may be disposed so as to monitor a pressure in a portion of the cassette 24. For example, a fluid path from a portion of the set 12 containing the high pressure portion to a pump chamber 181A, B of the cassette 24 may be established. The sections may, for example, be separated by an accumulator 6850 as shown in FIG. 166. The pump control chamber pressure sensor 2672 (see, e.g. FIG. 62) may be monitored. If the pump control chamber 171A, 171B (see, e.g., FIG. 62) pressure changes in a manner which indicates the cassette 24 is being subjected to the pressure in the high positive pressure portion of the set 12, the control system 16 of the cycler 14 may issue a failsafe command. The fail safe command may cause the cassette 24 to be isolated from that portion of the set 12 or may cause the high positive pressure source to be turned off (or both). In the event that the quality of a communication line to the high pressure source (e.g. wired or wireless) falls below a threshold or communication is lost, all components of the system 10 may react as if the fail safe command has been issued and received.

As shown in FIG. 168A, in block 6252 a pump chamber 181A, 181B of the cassette 24 may be delivered to a destination and held in the delivered position by continued application of positive pressure to the associated pump control chamber 171A, 171B. This pump chamber 181A, 181B may then be placed into communication with a cassette 24 port having potential exposure to high pressure in the high pressure portion of the fluid handling set 12 in block 6254. The high pressure source which generates the high positive pressure for the high pressure portion of the fluid handling set 12 may be turned on in block 6256.

The control system 16 may monitor data from the pump control chamber pressure sensor 2672 in block 6258. The pressure of the pump control chamber 171A, 171B may also be maintained within a range of a set point by connecting the control chamber 171A, 171B with a positive pressure source (e.g. positive reservoir 2620 of FIG. 62) as needed in block 6258. The set point may be set such that it is higher than that exerted due to the head height of the high pressure portion of the set 12. The head height of fluid in the high pressure portion of the set 12 may be assumed to be ~1 meter. Alternatively, the head height may be determined by the control system 16 as described elsewhere herein. The set point should also be low enough that there is a large buffer between the set point and a pressure at which the valve states of the cassette 24 may not be reliably known. In some examples, the set point may be at or about 10 kPa, 12 kPa, or up to and above 25 kPa. The set point may be set at about 25%-50% of positive pressure reservoir set point or the pressure applied to the cassette 24 valves to maintain them in the closed state.

If, in block 6260, the pump control chamber 171A, 171B pressure rises above a range of the set point, this rise in pressure may be assumed to indicate that the pump chamber 181A, 181B is being pressurized via the high pressure source. The high positive pressure source may be turned off in block 6262. Alternatively or additionally, an occluder may be deployed to isolate the first and second portions of the set 12.

To increase the amount of available detection and reaction time, in some embodiments a plurality of pump chambers 181A, 181B may be placed in the delivered position in block 6252 and placed in communication with the selected port in block 6254. Consequentially, if pump chambers 181A, 181B begin receiving pressure from the high pressure source, the pressure within the cassette 24 will rise more slowly as a larger volume must be pressurized. This may provide additional time for the control system 16 to detect the pressure rise via the pump control chamber sensors 2672. Additionally, the control system 16 may connect additional closed volumes (or volumes which may be closed off from atmosphere via actuation of one or more valve) with the pump control chamber(s) 171A, 171B of interest. For example, a reference chamber 174 (see, e.g., FIG. 62) may be placed into communication with a pump control chamber 171A, 171B. Both the pump control chamber 171A, 171B and the reference chamber 174 may be maintained within the range of the set point as described above. If the pump chamber 181A, 181B begins to be pressurized via the high positive pressure source, the peak pressure in the pump chambers 181A, 181B may be lower before the cassette 24 is isolated from the high pressure source. Where included within the system 10, a second, third, forth, etc. closed volume may also be connected similarly to the reference chamber 174.

Referring now to the flowchart 6400 depicted in FIG. 168B, when it is determined that pressure from the high pressure portion of the set 12 is reaching the cassette 24 in block 6402, the control system 16 of the cycler 14 may establish at least one flow through pathway within the cassette 24. A valve or valves of a pressure distribution module 2700 (see, e.g. FIG. 60) may be toggled via valve state commands from the control system 16 in block 6404 such that a path from an inlet of the cassette 24 is created to one or more outlet of the cassette 24 in block 6406. Such a valve state configuration of the cassette 24 may also be commanded as a failsafe configuration, for example, in the event that communication is lost with the pressure source. This flow through pathway may allow for pressurized fluid to pass through the cassette 24 to a controlled destination as well as help to prevent pressure buildup.

The outlet chosen may, in some embodiments be an outlet to a drain line 28 (see, e.g. FIG. 1) attached to the cassette 24. Alternatively or additionally, an outlet leading to a heater bag 22 of the set 12 may be actuated into and open state. In some embodiments, an outlet to a source component 6000 may also be opened. For example, if a source component 6000 has been emptied by the cycler 14 during an admixture operation, an empty source component 6000 reservoir may serve as a reservoir for excess fluid. The outlet(s) opened may be preordained as a preset parameter. Alternatively, the control system 16 of the cycler 14 may determine the outlet(s). This determination may be made based on a rate of the pressure rise used to determine pressure from the second portion of the set 12 is reaching the cassette 24. If the pressure rise rate is below a first threshold, only one outlet (e.g. any of those just described) may be opened. If the pressure rise rate is above the threshold, additional outlet(s) may be opened. If the pressure change rate rises above a second pressure threshold, additional outlet(s) may be opened. If no source components 6000 are empty, an outlet to a source component 6000 may not be opened. In some embodiments, one or more source component 6000 may be sized to have a maximum fill volume greater than the volume filled during manufacture. In such embodiments, therapy may be terminated and a flowpath to one or more such source component 6000 may be opened to accept the excess fluid.

Optionally, in block 6408, the control system 16 may issue at least one occluder actuation or deployment command. The command may, for example, be a command to cease actively holding open an occluder. This command may cause, in block 6410, one or more of the fluid lines attached to outlets of a cassette 24 to be occluded by the deployment of an occluder 147 (see, e.g., FIG. 63). An occluder 147 associated with a patient line 34 attached to the cassette 24 may, for example, be deployed. An alarm may also be generated by the control system 16 in block 6412. The alarm may be generated at any time after detection of the high positive pressure reaching the cassette 24.

Mass Transfer

Referring now to FIG. 169, in certain scenarios, fluids supplied to a cycler 14 from various component sources 6000 may differ significantly from one another in temperature. As temperature will alter the density of these fluids, relying on volume transfer alone may be insufficient to admix a fluid with a stringent prescription for the molar concentrations of its various components. Some systems 10 may include at least one mass transfer sensor to either directly determine molar concentration of fluid being mixed or indirectly determine these concentrations through volume measurements and another characteristic such as temperature.

In various embodiments, the temperature of incoming source fluid may be controlled, sensed, or both controlled and sensed. Where temperature data is available, this data may be used to determine density of the pumped fluid thus allowing a conversion of the volume transferred to a value of mass transferred. To control the temperature of incoming source fluid, at least one source heater 6270 may be included in the system 10. A source heater 6270 may be an active heating element such as a resistive heater or may be a heat exchanger. In the case of an active heating element, the source heater 6270 may be a heating blanket or pouch which at least partially wraps around or receives reservoirs containing source components 6000. An inline heating agent may be used as well. Any source heaters 6270 may receive power from the cycler 14 and pass data to the cycler 14 via a wired connection 6272.

Referring now also to FIGS. 170-171, a source heater 6270 may also be included in the cycler 14. For example, a heater similar to the connector heater (e.g. described in relation to region 2807 of FIG. 17) may be used as a source heater 6270. A similar heater may be placed in the cycler 14 housing 82 adjacent the control surface 148 which interfaces with the cassette 24. A source heater 6270 may be included in a cap stripper 149 or in place of the cap stripper 149 for example. Whether located in the door 141 or in cycler 14 housing 82, the source heater 6270 may be disposed such that lines from source components 6000 pass the source heater 6270 en route to their respective inlet ports on the cassette 24.

Referring again primarily to FIG. 169, if it is desired to use a heat exchanger for one of the at least one source heater 6270, fluid lines or source flow conduits carrying warm fluid from part of the system 10 may be routed through and or wrapped around reservoirs of source components 6000. These fluid lines may carry fluid from another of the source components 6000 which is at a more predictable temperature. Such lines may be referred to as heat exchanger source lines. For example, the heat exchange source lines may carry fluid generated by a water purification device 6002. In such embodiments, the water purification device 6002 may be arranged to output purified water at a temperature near body temperature (e.g. ~35° C.). The fluid lines may also carry fluid from a heater bag 22 which may be the mixing container 6004 shown in FIG. 169. This fluid may be recirculated between the source components 6000 and heater bag 22 until it is determined that fluid returning to the heater bag 22, is within a range of the temperature of the fluid exiting the heater bag 22. This may be determined by monitoring temperature sensors associated with a heater pan 142 (see, e.g., FIG. 84) of the cycler 14. For example, when the temperature sensors associated with the heater pan 142 read the heater bag 22 solution is steady within a range of a set point, it may be determined that the source components 6000 are at the desired temperature.

Referring now also to FIG. 172, the fluid lines 6280 from the source components 6000 may also or instead be routed to pass through, under, or around the heater bag 22 of the system 10. For example, lines 6280 from the source components 6000 may pass under the heater bag 22 on their way to an inlet port of the cassette 24. Alternatively, fluid lines 6280 or the fluid pathway from source components 6000 may be at least partially physically attached or integrated into the heater bag 22. This may be desirable as it may help to decrease the set up burden for the user. Where the source component 6000 lines 6280 are made at least partially integral with the heater bag 22, the path of the fluid lines 6280 may be preprescribed. In some embodiments, these lines or flow conduits may extend in a straight line path from a first point on the heater bag 22 to a second point on the heater bag 22. Alternatively, and as shown the lines 6280 may be arranged to extend between a first point and a second point on the heater bag 22 in an indirect path which increases or helps maximize heat transfer. For example, the path of the lines 6280 may be preprescribed in a switchback like pattern or path. At least one of the lines 6280 (e.g. a purified water line) may be independent of the heater bag 22 and free of any direct physical attachment to the heater bag 22. The heater pan 142 may also include a recess mimicking the prescribed routing of the fluid line(s) 6280 such that the line(s) 6280 do not prevent the heater bag 22 from making contact with the heater pan 142. The recess may be sized such that when the line 6280 is disposed within the recess, the interface between the line and the heater bag 22 is substantially within the plane of the heater pan 142. Additionally, routing of the fluid line 6280 may ensure regions of the heater bag 22 intended to contact temperature sensors in the heater pan 142 may be free of the fluid line 6280.

Referring now to FIG. 173, it may also be possible for the heater bag 22 to be of multiple layer construction. In the example shown in FIG. 173, the heater bag 22 includes a first layer 6520, second layer 6522, and third layer 6524. The first and second layer 6520, 6522 may be coupled to each other and form a first volume for storing fluid to be delivered to a patient. This volume may be constructed similarly to a conventional heater bag 22. The volume between the first and second layers 6520, 6522 may pre filled with dialysate or filled with dialysate by a cycler 14 (e.g. during an admixture or heater bag replenish). The first and second layers 6520, 6522 may be coupled to form a single interior chamber. In alternate embodiments, the first volume may be a multi chamber volume where each chamber is connectable via manipulation of a frangible or other temporary barrier such as is described elsewhere herein. The first volume may also be constructed similarly to or include aspects of any of the mixing reservoirs 6004 described below in relation to FIGS. 239-247.

The second layer 6522 and third layer 6524 may also be attached to one another to form a second interior volume. The second interior volume may serve as a heat exchange volume. Referring now also to FIG. 174, the second interior volume may be a convoluted pathway 6530 leading from an inlet port 6526 to an outlet port 6528. Fluid may flow along the pathway 6530 and be heated in transit via heat transfer from the heater pan 142 and fluid in the first interior volume. Thus, the second interior volume may form part of a source flow conduit or heat exchange source flow conduit and may be made of a different material than the rest of the source flow conduit.

Walls 6532 forming the convoluted pathway 6530 are depicted in FIG. 174. These walls may be formed by selectively attaching portions the second and third layers 6522, 6524 together. This may be done via heat bonding, solvent bonding, or any other suitable process. The layout of the convoluted pathway 6530 may be selected to maximize transit time from the inlet port 6526 to the outlet 6528. The layout may also be chosen to minimize an amount of hold up volume in the heater bag 22 while still allowing for acceptable heating. In FIG. 174, the convoluted pathway extends from the inlet 6526 to an opposing side of the heater bag 22 before returning to the outlet 6528. The route of the pathway to or from the side of the heater bag 22 opposing the inlet 6526 and outlet 6528 may be in a switchbacked, zigzagged, meandering or serpentine pathway.

Some layouts may include a sensor region 6534. This region may be disposed in the general location of a temperature sensor included in the heater pan 142. The pathway 6530 in the vicinity of the sensor region 6534 may be arranged so as to establish a relatively stagnant fluid pool in the sensor region 6534. This region may be close in temperature to the fluid in the first volume. As a result, this may allow for a temperature sensor to collect measurements of the heater bag 22 temperature while mitigating influence of any cold fluid in the heat exchange volume. Though depicted as connected to the convoluted pathway 6530 in the example embodiment, the sensor region 6534 may also be isolated from fluid flowing in the convoluted pathway 6530.

To facilitate heat transfer to source component fluid, a start up fluid volume generated from a source component reservoir such as a water purification device 6002 (e.g. at 30-40° C.) may be first pumped into the heater bag 22. This may help to quickly get the heater bag 22 up to temperature and may help ensure that the heater bag 22 and source component 6000 fluid lines 6280 have substantially uniform contact with the heater pan 142 before the heat exchange process is begun. The start up fluid volume may be a preset volume or may be a portion of the water volume necessary to admix the desired dialysate solution. The start up fluid volume may be around 100-300 ml for example.

FIGS. 175-177 show respectively back, side, and front views of exemplary cassette 7300. As FIGS. 175-177 show, the cassette 7300 may include an injection molded body having back side 7310 shown in FIG. 175 and front side 7311 shown in FIG. 175. A flexible diaphragm may overlay the front side and back side of cassette 7300. Sensor ports 7305 and 7306 may extend into fluid path 7303 of the exemplary cassette 7300. Sensor ports 7305 and 7306 may be used to insert a sensing probe, thermal well or other sensing element. Exemplary cassette 7300 shows two sensor ports per cassette 7300, but one port, two ports, or more than two ports may be used depending on the configuration of the cassette and the type of sensor or sensors used. Sensor ports 7305 and 7306 may be positioned in the rigid body of cassette 7300. However, in other embodiments, a sensor port 7305 and 7306 may extend though one or more areas of the flexible diaphragm overlying the cassette 7300.

Referring now to FIG. 178, exemplary cassette 7300 is shown with sensor ports 7305 and 7306 extending into fluid path 7303 such that a component 7100 placed in sensor ports 7305 and 7306 would come into direct contact with the dialysate or component(s) thereof contained in or flowing through fluid path 7303. FIG. 178 additionally shows thermal wells 7100 positioned near sensor ports 7305 and 7306.

In this embodiment, cassette 7300 and thermal wells 7100 are separate parts. In some embodiments, the cassette 7300 and the thermal well 7100 are made from different materials. For these embodiments, the thermal well 7100 can be made from any materials, including but not limited to, plastic, metal, ceramic or a combination thereof. The material may depend in some part on the compatibility with the intended dialysate formulation or components in that formulation. In other embodiments, thermal well 7100 could be made from the same material as cassette 7300. In yet further embodiments, thermal well 7100 could be formed as a part of the structure of the rigid body of cassette 7300.

The length and width of the thermal well 7100 utilized with exemplary cassette 7300 can be any length and width having the desired or tolerable accuracy characteristics and which properly positions any sensor or sensing probe utilized with thermal well 7100 sufficiently in contact with the dialysate or component(s) thereof contained in or flowing through fluid path 7306. The length of thermal well 7100 may impact the fluid flow of the dialysate or its components in fluid path 7303 to a certain extent. It also should be understood that the length of the thermal well 7100 may also impact the turbulence of the fluid flow. Thus, the length and width of the thermal well 7100 may be changed to have greater or lesser impact on the fluid flow and turbulence of the fluid, while mitigating the other variables.

The shape of the thermal well 7100 is also a variable. Any shape desired is contemplated. However, the shape of the thermal well 7100, as with the other variables, is determined in part based on the intended use of the sensor apparatus. For purposes of description, an exemplary embodiment is described herein. However, the shape in the exemplary embodiment is not meant to be limiting. All of the various embodiments of thermal wells 7100 described herein may be used in conjunction with cassettes, such as exemplary cassette 7300 or any other cassette described herein.

Referring now FIG. 179 for purposes of description, the thermal well 7100 has been divided into three zones. The top zone 7402 communicates with the sensing probe (not shown); the middle zone 7404 provides the desired length of the thermal well 7100. As described above, the length may dictate the level of protrusion into the fluid path. The length is dictated in part by the desired performance characteristics as discussed above. The middle zone 7404 also isolates the top zone 7402 from ambient. The middle zone 7404 may also serve to locate, fasten or seal the thermal well 7100 into the cassette 7300.

Figure 203:
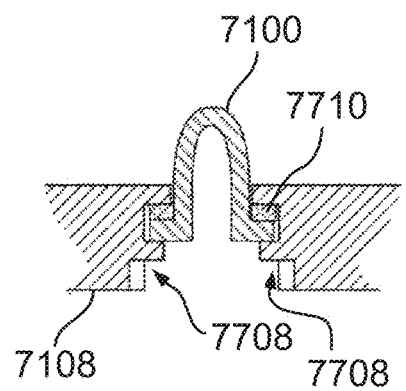
Figure 204:
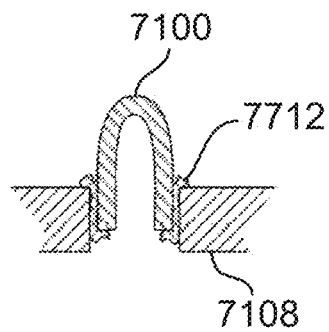

The bottom zone 7406, in some embodiments, may not be necessary (see FIG. 204). Thus, in these embodiments, the middle zone 7404 and the bottom zone 7406 may be a single zone. However, in the exemplary embodiment, the bottom zone 7406 is shaped to aid in press fitting the thermal well into an area in a fluid line 7108 and may locate and/or fasten the thermal well 7100 into the fluid line 7108. In other embodiments, zone 7406 may be formed to facilitate various joining methods (see FIGS. 194-203, 205-212).

Referring now to FIG. 180, a cross section of the exemplary embodiment of the thermal well 7100 is shown. The dimensions of the exemplary embodiment of the thermal well 7100 include a length A of approximately 0.113 inches (with a range from 0-0.379 inches), a radius B of approximately 0.066 inches and a wall thickness C ranging from approximately 0.003-0.009 inches. These dimensions are given for purposes of an exemplary embodiment only. Depending on the variables and the intended use of the sensing apparatus, the thermal well 7100 dimensions may vary, and the various embodiments are not necessarily proportional. In some embodiments, the ratios between any of A, B, and C may be about the same as the ratios resulting from the dimensions just described. In other examples, the ratios may vary.

In some embodiments, the wall thickness can be variable, i.e., the wall thickness varies in different locations of the thermal well 7100. Although these embodiments are shown with variable thicknesses in various locations, this is for description purposes only. Various embodiments of the thermal well 7100 may incorporate varying wall thickness in response to variables. These varying wall thicknesses can be "mixed and matched" depending on the desired properties of the sensing apparatus. Thus, for example, in some embodiments, a thinner zone 7404 may be used with thicker zone 7406 and vice-versa. Any other combination of "thinner" and "thicker" in regards to zones 7402, 7404, 7406 may be used. Also, the terms used to describe the wall thicknesses are relative. Any thickness desired is contemplated. The figures shown are therefore for descriptive purposes and represent two embodiments where many more are contemplated.

Referring now to FIGS. 181 and 182, zone 7402 can be thicker or thinner as desired. The thinner zone 7402, amongst other variables, generally provides for a faster sensing time while a thicker zone may be useful for harsh environments or where sensor damping is desired. Zone 7404 may be thicker, amongst other variables, for greater strength or thinner for, amongst other variables, greater isolation from ambient. Zone 7406 can be thinner or thicker depending on the fastening method used.

FIG. 183 shows thermal wells 7100 installed in an exemplary cassette 7300. Thermal wells 7100 may be installed in the exemplary cassette 7300 by use of the ways described herein, including adhesive, welding (ultrasonic and otherwise), o-ring, retaining plate, and otherwise. Referring now to FIG. 179 for purposes of description, the bottom zone 5406 is shaped to aid in press fitting the thermal well into the sensor port 7305 shown in FIGS. 175-178. FIG. 184 shows thermal well 7100 installed in sensor port 7305 and 7306. As may be best shown by FIG. 185, thermal well 7100 may extend into a fluid path 7303 so that the thermal well 7100 may come into direct contact with any dialysate contained in or flowing through an exemplary cassette 7300.

In certain embodiments of sensor apparatus and sensor apparatus systems used in conjunction with a flexible membrane cassette 7300, a sensing probe may be installed directly into sensing ports 7305 and 7306. In further embodiments of sensor apparatus and sensor apparatus systems used in conjunction with a flexible membrane cassette 7300, a sensing probe may be used with a thermal well 7100.

As can be seen in FIG. 185, dialysate or component(s) thereof is/are in contact with the outside of zone 7402 of the thermal well 7100. Thermal energy is transferred from the dialysate or component(s) thereof to the thermal well 7100. The thermal energy can then be further transferred to the tip 7302 (see, e.g. FIG. 216) of a sensing probe 7890 (see, e.g. FIG. 216). Thermal energy may then conducted to a thermal sensor 7315 (see, e.g. FIG. 216). Heat transfer from the tip 7302 to the thermal sensor 7315 may be improved by the use of a thermal epoxy or thermal grease 7322 (see, e.g. FIG. 216).

Many different embodiments of sensing apparatus may be used in connection with a thermal well 7100 installed in a flexible cassette 7300, including embodiments similar to those described below. While several geometries have been described, many others could be shown to achieve desired performance characteristics.

Referring now to FIG. 186, a sensor apparatus system of the type generally shown may be used in connection with exemplary cassette 7300. In the system, the sensor apparatus is installed in sensor ports 7305 and 7306 extending into fluid path 7303. The sensor apparatus includes the sensing probe 7890 and the thermal well 7100. In this embodiment, the thermal well 7100 and fluid line 7303 is contained in an exemplary cassette 7300. In certain embodiments, exemplary cassette 7300 is intended to be disposable. Sensing probe 7890 is mounted in a reusable portion. Also in the reusable portion is a spring 7801. The spring 7801 and sensing probe 7890 are located in a housing 7800. The housing 7800 can be in any machine, container, device or otherwise. In certain embodiments the reusable portion is contained in or otherwise a part of a pressure applying device (such as the cycler 14 of FIG. 1). The spring 7801 can be a conical, a coil spring, wave spring, or urethane spring. Alternatively, any other apparatus for biasing the sensing probe to ensure an appropriate fit in thermal well 7100 may be used, including the apparatus described below.

In certain embodiments, the thermal well 7100 and the sensing probe 7890 may include alignment features (of the type shown in FIG. 225, 7702, 7704) that aid in the thermal well 7100 and sensing probe 7890 being aligned. The correct orientation of the thermal well 7100 and the sensing probe 7890 may aid in the mating of the thermal well 7100 and the sensing probe 7890 to occur. Referring again to FIG. 186, the configuration of the housing 7800 may provide the sensing probe 7890 with space for lateral movement. This allows the sensing probe 7890 to, if necessary; move laterally in order to align with the thermal well 7100 for mating.

In various embodiments, the sensing probe 7890 is configured with respect to the housing 7800 (as shown in FIG. 186) to facilitate engagement between the sensing probe 7890 and the thermal well 7100 and to aid in establishing full contact of the sensing probe 7890 and the thermal well 7100. Variations of the configurations generally shown in FIGS. 226-228 and described above may be used in conjunction with exemplary cassette 7300.

In other embodiments, the sensing probe 7890 may be aligned and positioned by other housing 7800 configurations. Thus, the embodiments of the housing 7800 shown herein are only some embodiments of housings 7800 in which the sensor apparatus can be used. The sensor apparatus generally depends on being located amply with respect to the dialysate. The configurations that accomplish this can vary depending on the dialysate and the intended use of the sensing apparatus. Further, in some embodiments where the thermal well 7100 is not used, but rather, the sensing probe is used only. The housing 7800 configurations may vary as well.

In embodiments in which cassette 7300 is loaded into a device, such as a pressure applying device or a cycler 14 (as shown in FIG. 1), it may be preferable for sensor ports 7305 and 7306 to be positioned in the bottom edge of cassette 7300 (the bottom edge of the cassette 7300 is shown in FIG. 176). Positioning of the sensor ports 7305 and 7306 along the bottom edge of exemplary cassette 7300 (such that sensor ports 7305 and 7306 and installed thermal wells 7100 extend into the bottom fluid line 7303 of the cassette 7300) may facilitate engagement with the sensor apparatus as shown in, for example, FIG. 186. In certain of these embodiments, the exemplary cassette 7300 with installed thermal wells 7100 may be placed in position over sensor probes 7980, and then rotated vertically down and onto the sensor probes 7890.

The sensing apparatus, in some embodiments, is used to sense conductivity of the dialysate or component(s) thereof within a fluid line within a cassette 7300. In some embodiments, this is in addition to temperature sensing. In those embodiments where both temperature and conductivity sensing is desired, the sensing probe typically includes at least three leads, where two of these leads may be used for temperature sensing and the third used for conductivity sensing.

Referring now to FIG. 187, for conductivity sensing, at least two sensors 7102, 7104 are located in an area containing the dialysate or component(s) thereof. In the embodiment shown, the area containing the dialysate or component(s) thereof is a fluid path 7105 inside a fluid line 7108. The conductivity sensors 7102, 7104 can be one of the various embodiments of sensing probes as described above, or one of the embodiments of the sensor apparatus embodiments (including the thermal well 7100) as described above.

Referring now again to FIG. 186, sensing probes 7000 installed in thermal wells 7100 in sensor ports 7305 and 7306 can be used for sensing the conductivity of the dialysate or component(s) thereof located between sensor ports 7305 and 7306 in fluid line 7303. However, in other embodiments, at least one of the sensors may be any electrical sensor known in the art. Thus, in the systems described herein, conductivity and temperature can be sensed through using either one of the sensor apparatus or one of the sensor probes as described herein and a second capacitance or conductivity sensor or other electrical sensor.

Temperature sensing may be used as a part of various safety apparatuses and procedures. Temperature sensing may be used to measure the temperature of the dialysate or component(s) in a cassette 7300 before the dialysate enters the patient. In other embodiments, temperature sensing may be used to measure the temperature of the dialysate in a cassette 7300 before and after the dialysate enters the patient. Temperature measurements may be sent to a cycler 14 and/or the control system 16. Temperature measurements may be taken at predetermined times, regular, intervals, or on demand. Temperature measurements of the dialysate or component(s) thereof may be displayed to the patient via a graphical user interface. In other embodiments, the temperature measurements are compared against a desired value or against a desired range. In certain embodiments, a cycler 14 or its control system 16 may cause a notice or alarm to be displayed to the patient indicating that the temperature is outside of certain parameters. In other embodiments, a cycler 14 or its control system 16 may not start a PD treatment if the temperature is outside of certain parameters. In other embodiments, a cycler 14 or its control system 16 may stop or delay a PD treatment if the temperature is outside of certain parameters. In various embodiments, the temperature of the dialysate or component(s) thereof may be measured in one fluid path in the cassette 7300, in multiple fluid paths in the cassette 7300, or in all fluid paths in the cassette 7300.

Conductivity sensing may be used (alone or preferably in conjunction with temperature sensing) as a part of various safety apparatuses and procedures. Conductivity sensing may be used to measure the conductivity of the dialysate or component(s) thereof in a cassette 7300 before the dialysate enters the patient to determine if the dialysate solution or component(s) thereof have/has the expected conductivity. Thus conductivity sensing may be used (alone or preferably in conjunction with temperature sensing) to determine if the dialysate prepared in a dialysate preparation system is of the expected conductivity and thus is of the expected formulation, pH, and the like. Conductivity sensing may be used (alone or preferably in conjunction with temperature sensing) to determine if the dialysate in a pre-mixed bag remains stable. In other embodiments, conductivity sensing may be used (alone or preferably in conjunction with temperature sensing) to determine if the patient or caregiver has appropriately removed a seal and properly mixed multiple components of a multi-chamber or multi-component bag.

In certain embodiments, a cycler 14 or its control system 16 may cause a notice or alarm to be displayed to the patient indicating that the conductivity of the dialysate or component(s) is/are outside of certain parameters. A cycler 14 or its control system 16 may cause a notice or alarm to be displayed to the patient indicating that the dialysate may not be safe for PD treatment based on the conductivity of the dialysate or component(s) thereof. In other embodiments, a cycler 14 or its control system 16 may not start a PD treatment if the conductivity of the dialysate or component(s) is/are outside of certain parameters. In other embodiments a cycler 14 or its control system 16 may stop or delay a PD treatment if the conductivity of the dialysate or component(s) thereof is/are outside of certain parameters. In various embodiments, the conductivity of the dialysate or component(s) thereof may be measured in one fluid path in the cassette 7300, in multiple fluid paths in the cassette 7300 or in all fluid paths in the cassette 7300.

A known volume of dialysate or component(s) thereof may be used to determine conductivity. Thus, two sensors may be used and the volume of fluid or dialysate (or component(s) thereof) between the two sensors can be known or determined. Conductivity sensing may be done with the two electrical contacts (as described above), where one or both can be a sensor apparatus. Conductivity sensing may be done by determining the conductivity from each of the sensors and then determining the difference.

If the difference is above a predetermined threshold, indicating an abnormal difference in conductivity between the first and second sensor (the designations "first" and "second" being arbitrary), then it can be inferred that air may be trapped in the dialysate or component(s) thereof and a bubble detection alarm may be generated to indicate a bubble. Thus, if there is a large decrease in conductivity (and likewise, a large increase in resistance) between the first and second sensor, air could be trapped and bubble presence may be detected.

Leaks in a machine, system, device or container may be determined using the conductivity sensing. Where a sensing apparatus is in a machine, device, or system, a lead from the sensor apparatus (or electrical contacts) to an analyzer or control system 16 may be present. The analyzer or control system 16 that analyzes the electrical signals from the contacts may be connected to a metal or conductive portion of the machine, device, system or container. If the control system 16 determines an electrical signal from the machine, then a fluid leak may be inferred.

Alternate embodiments of thermal wells 7100 are described, often in relation to a fluid line 7108. The fluid line 7108 could alternatively be a fluid path 7303 of a cassette 7300. In one exemplary embodiment, a thermal well 7100 is used to accommodate a sensor probe 7000, such as a temperature sensing probe. The thermal well 7100 comes into direct contact with a dialysate or component(s) thereof and the sensing probe 7000 may not. Based on heat transfer dictated in large part by the thermodynamic properties of the thermal well 7100 and sensing probe 7000 construction, the sensing probe 7000 can determine the properties of the dialysate or component(s) thereof without coming into direct contact with the dialysate or component(s) thereof. The accuracy and efficiency of the sensor apparatus arrangement depends on many factors including, but not limited to: construction, material and geometry of both the probe 7000 and the thermal well 7100.

Referring now to FIGS. 188 and 189, two embodiments of the sensor apparatus which includes the thermal well 7100 and the sensing probe 7103, are shown in relation to a fluid line 7108. In these embodiments, the thermal well 7100 is integrated into the fluid line 7108. However, in other embodiment, the thermal well 7100 may be at least partial independent from and not completely integrated into the fluid line 7108. The thermal well 7100 can be made from different materials as compared with the fluid line 7108. In alternate embodiments, the thermal well 7100 is completely independent from any fluid line 7108. The thermal well 7100 can be completely independent and not integrated into any other component(s). The thermal well 7100 can also be integrated partially or entirely into components other than a fluid line 7100 or cassette 7300 flow path 7303. For example, in some embodiments, a thermal well 7100 can be integrated into a container, chamber, machine, protective sleeve, fluid pump, pump cassette, disposable unit, manifold, or other assembly, sub-assembly, or component.

FIGS. 188-191 show relatively embodiments of the sensor apparatus. Thus, for these embodiments, the sensing apparatus includes a thermal well 7100 and a sensing probe 7103 where the thermal well 7100 either is integrated as one continuous part with the fluid line 7108 or is a separate part or independent from the fluid line 7108. Referring now to FIG. 188, a side view showing a thermal well 7100 formed in a fluid line 7108 which provides the space 7105 for dialysate or component(s) thereof to flow through, and a sensing probe 7103 is shown. Data from the sensing probe 7103 is transmitted using at least one lead 7106. An end-on view of FIG. 188 is shown in FIG. 189. In this embodiment, the thermal well 7100 is one piece or integral with the fluid line 7108. The total area of the thermal well 7100 can vary. By varying the geometry of the thermal well 7100, the variables, including, but not limited to, the thermal conductivity characteristic of the thermal well 7100 and thus, the heat transfer between the thermal well 7100 and the sensing probe 7103 may vary. In some embodiments, the fluid line 7108 may be made at least partially (e.g. in the region of a thermal well 7100) from a material having a desired thermal conductivity. The material may vary depending on the purpose. The material can be anything including, but not limited to, any plastic, ceramic, metals or alloys of metals or combinations thereof. Referring now to FIGS. 190 and 191, the fluid line 7108 and the thermal well 7100 may be separate parts and may be made from different materials.

Many embodiments of the sensor apparatus are contemplated. Many of the various embodiments include variations on the materials and the geometries of the thermal well 7100 and/or the sensing probe 7103. These variations are dictated by multiple variables related to the intended use for the sensor apparatus. These variables include but are not limited to: 1) geometry of the thermal well; 2) material composition of the thermal well; 3) material composition of the sensing probe; 4) desired flow rate of the dialysate; 5) length and width of the thermal well; 6) desired accuracy of the sensing probe; 7) wall thicknesses; 8) length and width of the sensing probe; 9) cost of manufacture; 10) dialysate or dialysate component composition and characteristics including tolerance for turbulence; 11) geometry of sensing probe; and 12) desired speed of readings. Thus, the dialysate and the constraints of the desired sensor, for example, the accuracy, time for results and the fluid flow and dialysate or component characteristics are but a sampling of the various constraints that dictate the embodiment used. In most instances, each of the variables will affect at least one part of the embodiment of the sensor apparatus.

Referring now to FIGS. 192-193, two embodiments of the thermal well 7100 are shown independent or as separate parts from the fluid line 7108. These embodiments show two geometries of a thermal well 7100. In FIG. 192, the geometry includes a longer thermal well 7100. In FIG. 193, the thermal well 7100 geometry is shorter. The thermal well 7100 of FIG. 192, in some specific embodiments, projects across about 60% of way across the flow conduit or space for dialysate flow 7105 while that in FIG. 193 projects across about one third of the way across. The length and width of the thermal well 7100 produce varying properties and accuracies of the thermal conductivity between the thermal well 7100 and the sensing probe 7103.

Referring now to FIG. 192 the longer thermal well 5100 may generally provide a greater isolation between the dialysate or component(s) thereof temperature in the fluid line 7108 and the ambient temperature. Although the longer thermal well 7100 geometry shown in FIG. 192 may be more accurate, the embodiment shown in FIG. 193 may be accurate enough for the purpose at hand. Thus, the length and width of the thermal well 7100 can be any length and width having the desired or tolerable accuracy characteristics.

Still referring to FIGS. 192-193, the longer thermal well 7100 shown in FIG. 192 may impact the fluid flow of the dialysate or component(s) thereof in the fluid line 7108 to a greater degree than the embodiment shown in FIG. 193. It should be understood that the length of the thermal well 7100 may also impact the turbulence of the fluid flow. Thus, the length and width of the thermal well 7100 may be changed to have greater or lesser impact on the fluid flow and turbulence of the fluid. The shape of the thermal well 7100 is also a variable. Any shape desired is contemplated. However, the shape of the thermal well 7100, as with the other variables, is determined in part based on the intended use of the sensor apparatus.

Various approaches may be used for embedding or attaching the thermal well 7100 into a fluid line 7108. Referring now to FIGS. 194-212, various configurations for embedding the thermal well 7100 into a fluid line 7108 are shown. For these embodiments, the thermal well 7100 can be made from any materials, including but not limited to, plastic, metal, ceramic or a combination thereof. The material may depend in some part on the compatibility with the intended dialysate or component(s) thereof. The fluid line 7108 may be made at least in part from plastic, metal, or any other material that is suitable with the dialysate or component(s) thereof.

Figure 194:
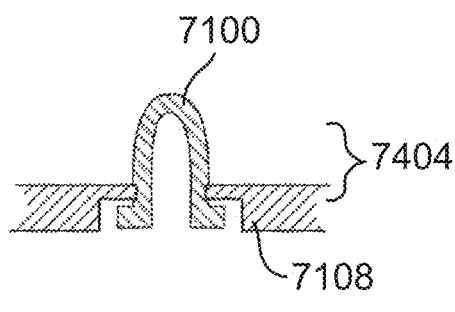
Figure 195:
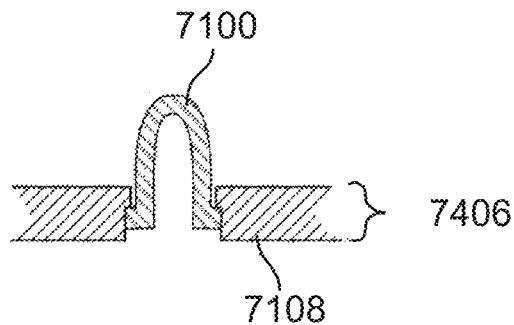
Figure 196:
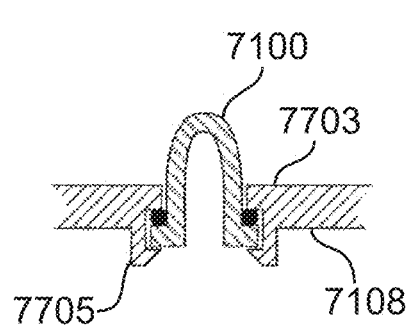
Figure 197:
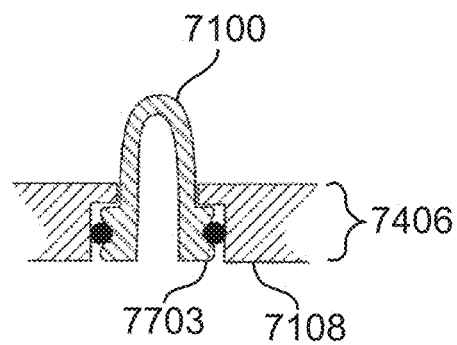
Figure 198:
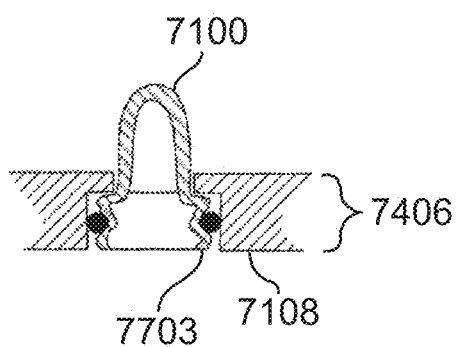

Referring first to FIG. 194, the thermal well 7100 is shown press fit into a fluid line 7108 using zone 7404. In FIG. 195, the thermal well 7100 is shown press fit into a fluid line 7108 using zone 5406. Referring now to FIG. 196, the thermal well 7100 is shown retained in the fluid line 7108 with flexible tabs 7704 in a snap fit arrangement. An O-ring 7703 is also provided. Referring now to FIG. 197, the thermal well 7100 is shown inserted into a fluid line 7108 with an O-ring 7703 in an O-ring groove. The O-ring groove can be cut, formed, spun, cast or injection molded into the thermal well 7100, or formed into the thermal well 7100 by any other method. FIG. 198 shows a similar embodiment to that shown in FIG. 197.

Figure 199:
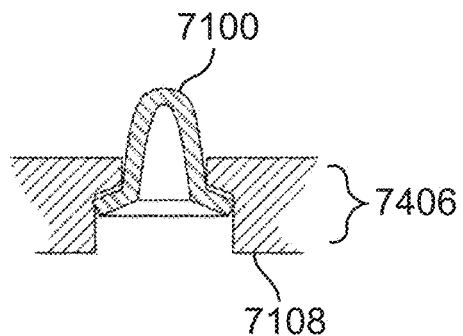
Figure 200:
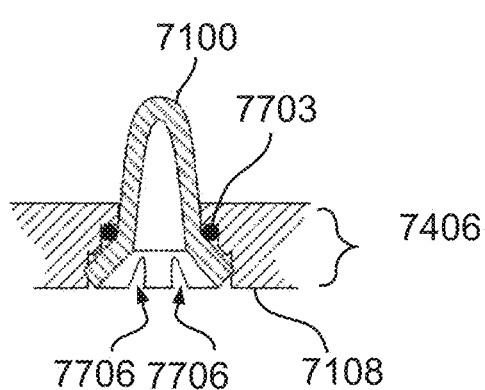

Referring now to FIG. 199, the thermal well 7100 is shown press fit into a fluid line 7108. Zone 7406 includes flexibility allowing the edge of zone 7406 to deform the material of the fluid line 7108. Referring now to FIG. 200, the embodiment shown in FIG. 199 is shown with the addition of an O-ring 7703. Referring now to FIG. 200, the thermal well 7100 includes cuts 7706 on the zone 7406 providing flexibility of the zone 7406 for assembly with a fluid line 7108. An O-ring 7703 is also provided. Although two cuts are shown, a greater number or fewer cuts are used in alternate embodiments.

Figure 202:
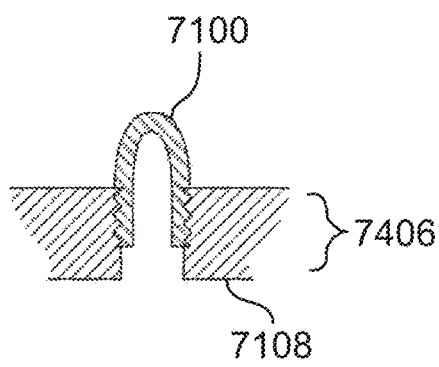
Figure 205:
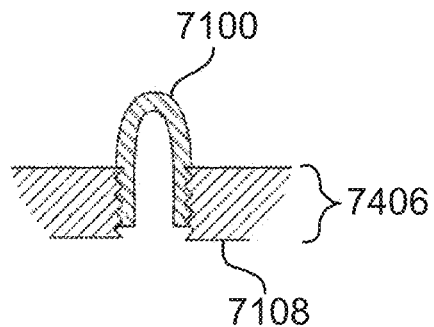

Referring to FIG. 202, the thermal well 7100 is shown insert molded in the fluid line 7108. Zone 7406 is formed to facilitate or enable assembly by insert molding. FIG. 203 shows an embodiment where the thermal well 7100 is attached via a heat stake 7708 to retain the thermal well 7100 in the fluid line 7108. An o-ring 7710 may also be included. The o-ring 7710 may have a rectangular, round, or X-shaped cross section like any other o-ring described herein. Referring now to FIG. 204, a thermal well 7100 may retained in a fluid line 7108 by adhesive 7712. The adhesive can be any adhesive, but in one embodiment, the adhesive is a UV curing adhesive. In alternate embodiments, the adhesive may be any adhesive that is compatible with the dialysate or component(s) thereof. In this embodiment, the thermal well 7100 is shown without a zone 7406. Referring now to FIG. 205, a thermal well 7100 is shown ultrasonically welded in a fluid line 7108. The zone 5406 is fabricated to enable joining by ultrasonic welding.

Figure 206:
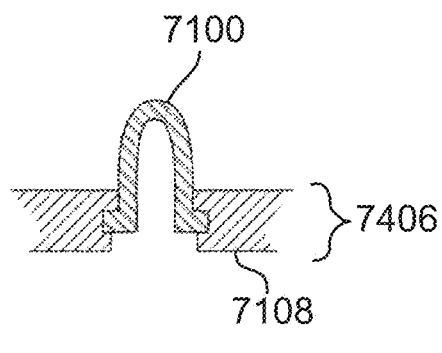
Figure 207:
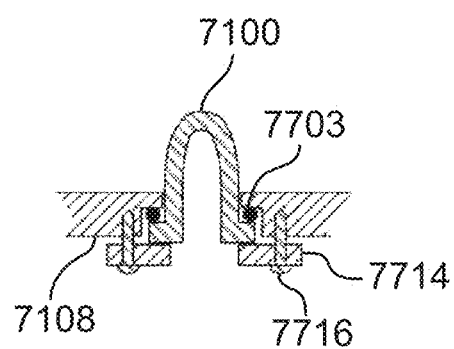
Figure 208:
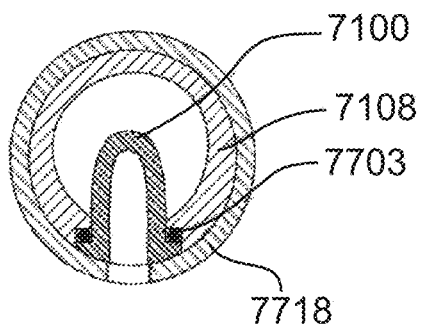
Figure 209:
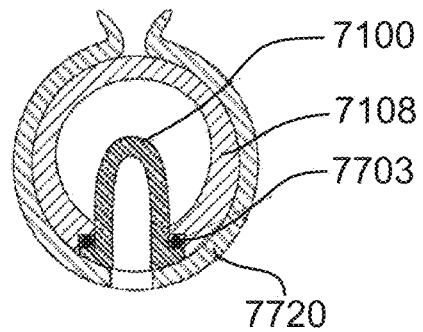

Referring now to FIG. 206, a thermal well 7100 is shown insert molded in the fluid line 7108. Zone 7406 is a flange for the plastic in the fluid line 7108 to flow around. In the embodiment shown, the flange is flat, however, in other embodiments; the flange may be bell shaped or otherwise shaped. Zone 7406 may also include a thread feature or sawtooth shaped exterior surface as shown in FIG. 202. Referring now to FIG. 207, the thermal well 7100 is shown retained in a fluid line 7108 by a retaining plate 7714 and a fastener 7716. O-ring 7703 is also shown. Referring now to FIG. 208, an end-on view is shown of a thermal well 7100 that is retained in a fluid line 7108 by a retaining ring 7718. Referring now to FIG. 209, an end-on view is shown of a thermal well 7100 that is retained in a fluid line 7108 by a clip 7720. An O-ring 7703 is also shown in both FIGS. 208 and 209.

Figure 210:
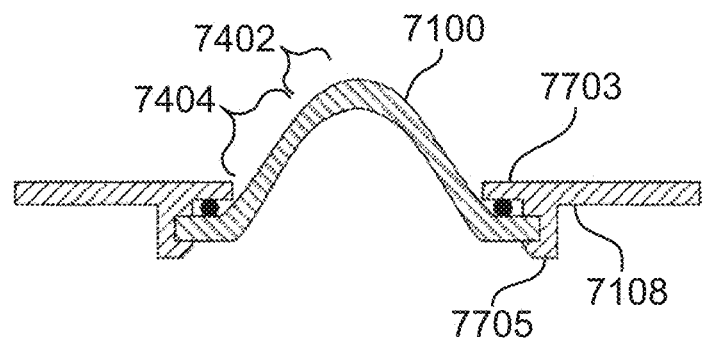

Referring now to FIG. 210, the embodiment of FIG. 196 is shown with an alternate thermal well 7100. In this embodiment of the thermal well 7100, zone 5404 includes a taper that may allow for easier alignment with a sensing probe, better isolation of zone 5402 from ambient and better flow characteristics in the fluid path. The thermal well 7100 is shown retained in the fluid line 7108 using flexible tabs 7705. An O-ring 7703 is also provided.

Figure 211:
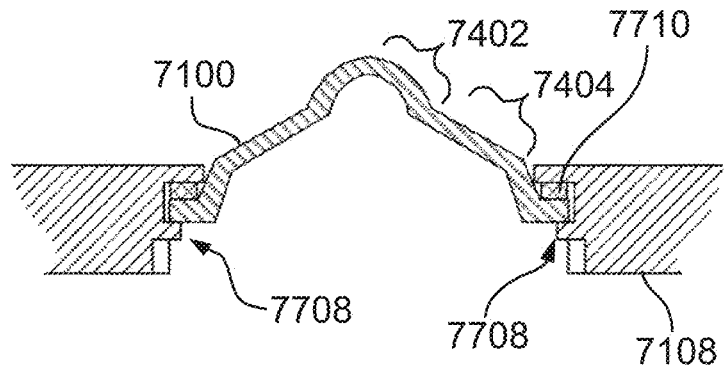

FIG. 211 shows the embodiment of FIG. 203 with an alternate thermal well 7100. The thermal well 7100 shown in this embodiment has a taper in zone 7404 that may allow for easier alignment with a sensing probe, may allow better isolation of zone 7402 from ambient and may allow better flow characteristics in the fluid path. Zone 5402 provides a generally hemispherical contact for effective thermal coupling with a thermal probe. The thermal well 7100 may be attached to the fluid line 7108 via a heat stake 7708. In some embodiments of FIG. 211, an O-ring 7710 may also be included.

Figure 201:
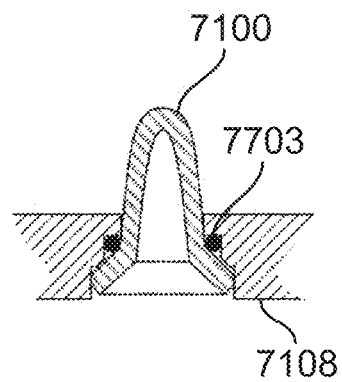

Referring now to FIG. 212, the embodiment of FIG. 201 is shown with an alternate thermal well 7100. FIG. 212 is shown with the addition of an O-ring 7703. Zone 7404 has convolutions or an undulating cross section that may allow better isolation of zone 7402 from ambient. While several geometries have been shown for zone 7404, many others could be shown to achieve desired performance characteristics.

Various embodiments of systems, devices, and methods for sensor interface, including direct sensor contact, sensor interface through the use of a thermal well, or otherwise with various disposable and reusable components are described.

Referring now to FIG. 213, a sectional view of an exemplary embodiment of a sensing probe 7890 is shown. An exploded view of the sensing probe 7890 is shown in FIG. 214. The housing 7804 may be a hollow structure that attaches to a tip 7802. The tip 7802 may be made of a highly thermally conductive material. Thermally conductive materials, for example, copper, silver and steel, can be used, however, depending on the desired use for the sensing probe and the dialysate or component(s) thereof; the materials may be selected to be durable and compatible for the intended use. Additionally, factors such as cost and case of manufacture may dictate a different material selection. In one exemplary embodiment, the tip 5802 is made from copper. In other embodiments, the material can be an alloy of copper or silver, or either solid or an alloy of any thermally conductive material or element, including but not limited to metals and ceramics.

The housing 7804, in the exemplary embodiment, may be made from a thermally insulative material or a thermally and electrically insulative material. The housing 7804 may be made of plastic which is a thermally insulative and electrically insulative material. The tip 7802 either contacts the dialysate or component(s) thereof directly, or else is mated with a thermal well 7100. In the exemplary embodiment, the tip 7802 may be attached to the housing 7804 using a urethane resin or another thermal insulator in between the tip 7802 and the housing 7804. Urethane resin additionally may add structural support. In alternate embodiments, other fabrication and joining methods can be used to join the tip 7802 to the housing 7804.

In the exemplary embodiment, the tip 7802 is shaped to couple thermally with a thermal well 7100. The tip 7802 may be shaped to insulate the thermal sensor 7808 from ambient. In the exemplary embodiment, the tip 7802 may be made from metal. In alternate embodiments, a non-electrically conductive material may be used for the tip. These embodiments may be preferred for use where it is necessary to electrically insulate the thermal well 7100 from the probe. In another alternate embodiment, the tip 7802 may be made from any thermally conductive ceramic.

In the exemplary embodiment, the thermal sensor 7808 is located in the housing 7804 and is attached to the interior of the tip 7802 with a thermally conductive epoxy 7812. In the exemplary embodiment, the epoxy used may THERMALBOND, however, in other embodiments; any thermal grade epoxy can be used. In alternate embodiments, thermal grease may be used. In alternate embodiments, an epoxy or grease is not used. The thermal sensor 7808, may be a thermistor, thermocouple, or any other temperature sensing device. The choice of thermal sensor 7808 may again relate to the intended use of the sensing apparatus.

Leads 7814 from the thermal sensor 7808 may exit the back of the housing 7804. These leads 7814 attach to other equipment used for calculations. A third lead 5816 from the tip 7802 may also be included. The tip 7802, in the exemplary embodiment, includes a tab 5818 for attachment to a lead. The third lead 7816 may be attached to the tip 7802 on the tab 7818. The third lead 7816 is attached to the tip 7802 because in this embodiment, the tip 7802 is metal and the housing 7804 is plastic. In alternate embodiments, the housing 7804 may be metal, and the third lead 7816 may be attached to the housing 7804. Depending on the intended use of the sensing apparatus, the third lead 7816 may not be included. Where a third lead 7816 is not desired, the tip 7802 may not include the tab 7818.

Referring now to FIG. 215 the tip 7302 of a sensing probe is shown. The tip 7302 includes a zone 7304 that may contact either a dialysate or component(s) thereof to be tested or a thermal well 7100. A zone 7307 attaches to the sensor probe housing (not shown). An interior area or receptor 7308 may accommodate the thermal sensor (not shown). In this embodiment, the tip 7302 is made from stainless steel, but can be made from any thermally conductive material, including but not limited to: metals (including copper, silver, steel), ceramics or plastics. In the exemplary embodiment, zone 7307 includes a tab 7312. The tab 7312 may be a region of the tip 7302 which extends proud of an end face 7314 of the tip 7302. Alternatively, and as shown in FIG. 215, the end face 7314 of the tip 7302 may be cut or disposed at an angle oblique to the longitudinal axis of the tip 7302. In such instances, the region of zone 7307 most distal to zone 7304 may be referred to as the tab 7312. A third lead 7816 (see, e.g. FIG. 213) may attach to the tab 7312.

Referring next to FIGS. 216-217, the sensing probe 7890 is shown including the tip 7302 and the housing 7013. In one embodiment, the housing 7013 may be made from any thermally insulative material, including but not limited to, plastic. The housing 7013 may be press fit to the tip 7302, glued, or attached in any other manner. The thermal sensor 7015 may be thermally coupled to the tip 7302 with thermal grade epoxy or, in alternate embodiments, thermal grease 7322. Two leads 7316 from the thermal sensor 7015 may extend to the distal end of the housing 7013. In some embodiments, a third lead 7318 may be attached to the tip 7302 from the tab 7312. As discussed above, in some embodiments where the third lead 7318 is not desired, the tip 7302 does not include a tab 7312. The housing 6012 may include a plastic molded over zone or over molded zone 7320 of the tip 7302, the leads 7316, and third lead 7318 (if present) as shown in FIG. 217.

Referring now to FIG. 218, a side view of a sensing probe 7890 is shown. The sensing probe 7890 includes a housing 7013, a tip 7302, and leads 7316, 7318. A flange 7324 is shown. A flange 6020 may used for mounting and/or attachment to equipment.

Referring now to FIG. 219, a sensing probe 7890 is shown coupled to a thermal well 7100 which is fastened into a fluid line 7108. In the embodiment as shown, two leads 7316 are shown at the distal end of the sensing probe 7890. A third lead 6018 may also be incorporated into the sensing probe 7890. FIG. 220 shows an alternate embodiment where the sensing probe 7890 does not include the third lead 7318.

Referring now to both FIGS. 219 and 220, the tip 7302 of the sensing probe 7890 may be in direct contact with the thermal well 7100 zone 7402. The thermal well 7100 may be hollow, and the inner part of zone 7402 may be formed such that it will be in mating contact with the sensing probe tip 7302. The thermal well 5100 may be designed to have a mating geometry with the sensing probe 7890. Thus, the geometry of the thermal well 7100 may depend on the geometry of the tip 7302 of the sensing probe 7890 and vice-versa. In some specific embodiments, the sensing probe 7890 does not have a tight fit or a perfect mate with the thermal well 7100.

Referring now to FIG. 221, one embodiment of the sensing probe 7890 is shown coupled to a thermal well 7100 which may be fastened into a fluid line 7108. Two leads 7316 are shown at the distal end of the sensing probe 7890. In some embodiments, a third lead 7318 is also incorporated into the sensing probe 7890. FIG. 222 shows an alternate embodiment where the sensing probe 7890 does not include the third lead 7318.

Referring now to FIGS. 221 and 222, the tip 5802 forms an air gap 7324 between the inner zones 7404 and 7406 of the thermal well 7100 and the tip 7302. The air gap 7324 provides an insulative barrier so that only the top of the sensing tip of 7302 is in communication with the top zone 7402 of the thermal well 7100.

Referring now to both FIGS. 219-222, the tip 7302 of the sensing probe 7890 may be in direct contact with the thermal well 7100 zone 7402. The thermal well 7100 may be hollow, and the inner part of zone 7402 may be formed such that it will be in mating contact with the sensing probe tip 7302. The thermal well 5100 may be designed to have a mating geometry with the sensing probe 7890. Thus, the geometry of the thermal well 7100 may depend on the geometry of the tip 7302 of the sensing probe 7890 and vice-versa. In some embodiments, it may be desirable that the sensing probe 7890 does not have a tight fit or a perfect mate with the thermal well 7100.

Referring now to FIG. 223, a sensing probe 7890 and thermal well 7100 are shown coupled together and outside of a fluid line 7108. As described above, the thermal well 7100 can be in a fluid line 7108, a protective sleeve, any disposable, machine, chamber, cassette 7300 or container. A dialysate or component(s) thereof may be in contact with the outside of zone 7402 of the thermal well 7100. Thermal energy is transferred from the dialysate or component(s) thereof to the thermal well 7100 and further transferred to the tip 7302 of the sensing probe 7890. Thermal grease 7322 may be included in some embodiments. Thermal energy is then conducted to the thermal sensor 7315. The thermal sensor 7315 communicates via leads 7316 with equipment that can determine the temperature of the dialysate based on feedback of the thermal sensor 7315. The thermal sensor 7315 may, for example, generate a temperature data signal based on the thermal energy and transmit that signal via leads 7316.

In embodiments where conductivity sensing is also desired, lead 7318 may communicate with equipment that can determine the conductivity of the dialysate or component(s) thereof. With respect to determining the conductivity of the dialysate or component(s) thereof, in addition to the lead 7318, a second electrical lead/contact (not shown) would also be used. The second lead could be a second sensor apparatus or a second probe that is not necessarily the same as the sensor apparatus shown in FIG. 223. Any probe or apparatus capable of sensing capacitance or conductivity of the dialysate or component(s) thereof, including, an electrical contact may be used.

Referring now to FIG. 224, an alternate embodiment showing a sensing probe 7890 coupled to a thermal well 7100 is shown. For purposes of this description, any embodiment of the sensing probe 7890 and any embodiment of the thermal well 7100 can be used. In this embodiment, to increase the thermal coupling between the tip of the sensing probe 7890 and the thermal well 7100, thermal grease 7322 is present at the interface of the tip of the sensing probe 7890 and the zone 7402 of the thermal well 7100. The amount of thermal grease 7322 may be a volume sufficient to only be present in zone 7402. However, in alternate embodiments, larger or smaller volumes of thermal grease 7322 can be used.

Referring now to FIG. 225, a sensor apparatus system 7350 is shown. In the system 7350, the sensor apparatus is shown in a device containing a fluid line 7108. The sensor apparatus includes the sensing probe 7890 and the thermal well 7100. In this embodiment, the thermal well 7100 and fluid line 7108 are a disposable portion of the system 7350 and the sensing probe 7890 is a reusable portion. Also in the reusable portion may be a spring 7700. The spring 7700 and sensing probe 7890 are located in a housing 7709. The housing 7709 can be in any machine, container, device or otherwise. The spring 7700 can be a conical, a coil spring, wave spring, or a urethane spring. The sensing probe 7890 may suspended by a spring 7700 supported by the flange 7326. The spring 7700 allow vertical movement of the sensing probe 7890 when the thermal well 7100 mates with the sensing probe 7890. The spring 7700 aids in establishing and maintaining full contact of the sensing probe 7890 and the thermal well 7100. The mating provides the thermal contact so that the thermal well 7100 and the sensing probe 7890 are thermally coupled.

In this embodiment, the thermal well 7100 and the sensing probe 7890 may include alignment features 7702, 7704 that aid in alignment of the thermal well 7100 and sensing probe 7890 and may aid in the mating of the thermal well 7100 and the sensing probe 7890. The configuration of the space 7707 may provide the sensing probe 7890 with space for lateral movement. This allows the sensing probe 7890 to, if necessary; move laterally in order to align with the thermal well 7100 during mating.

A dialysate or component(s) thereof may flow through the fluid path 7105 and past the thermal well 7100 such that the thermal well 7100 has ample contact with the dialysate or component(s) thereof in the fluid path 7105 and can sense the temperature properties and, in some embodiments, the conductive properties of the dialysate or component(s) thereof. The location of the thermal well 7100 in the fluid path 7105, as described in more detail above, may be related to the desired accuracy, the dialysate and other considerations.

Referring now to FIG. 226, another sensor system 7350 is shown. In this embodiment, the sensing probe 7890 is suspended by a coil spring 7352. A retaining plate 7714 captures the coil spring 7352 to retain the spring 7352 and sensing probe 7890. In one embodiment, the retaining plate 7714 is attached to the housing 7709 using screws. In alternate embodiments, the retaining plate 7714 may be attached to the housing 7709 using any fastening arrangement including but not limited to: adhesive, flexible tabs, press fit, and ultrasonic welding. Aligning features 7356 on the housing 7709 may aid in alignment of the sensing probe 7890 with a thermal well 7100 (not shown in FIG. 226). Lateral movement of the sensing probe 7890 may be provided for by clearance in areas 7358 or displacement paths in the housing 7709.

Referring now to FIG. 227, a sensing probe 7890 is shown in a housing 7709. An alternate embodiment of a spring, a flexible member 7900, is integrated or integral with the sensing probe 7890 to allow vertical movement of the sensing probe 7890 within the housing 7709. A retaining plate 7714 captures the flexible member 7900 to retain the flexible member 7900 and sensing probe 7890. The retaining plate 6902 may be attached to the housing 7709 using screws. However, in alternate embodiments, the retaining plate 7714 is attached to the housing 7709 using any fastening method including but not limited to: adhesive, flexible tabs, press fit, and ultrasonic welding. Lateral movement of the sensing probe 7890 is provided for by clearance in areas 7358 or displacement paths in the housing 7709.

Referring now to FIG. 228, an alternate embodiment of a sensing probe 7890 in a housing 7709 is shown. A flexible member 7900 is attached or part of the housing 7709, and may provide for vertical movement of the sensing probe 7890. In this embodiment, the openings 7904, 7906 in housing 7709 are sized such that the sensing probe 7890 experiences limited lateral movement. The flexible member 7900 may act on the flange 7326 of the sensing probe 7890.

The flange 7326, as shown and described with respect to FIG. 228, can be located in any area desired on the sensing probe 7890. In other embodiments, the sensing probe 7890 may be aligned and positioned by other housing 7709 configurations. Thus, the embodiments of the housing 7709 shown herein are only some embodiments of housings 7709 in which the sensor apparatus can be used.

In each of FIGS. 225-228 a wire 7711 is shown. The wire 7711 may contain the leads. In some embodiments, there are two leads in the wire 7711. Some of these embodiments are for temperature sensing. In other embodiments, the wire 7711 contains three or more leads. Some of these embodiments are for temperature and conductivity sensing. The sensing apparatus, in some embodiments, is used to sense conductivity. In some embodiments, this is in addition to temperature sensing. In those embodiments where both temperature and conductivity sensing is desired, the sensing probe typically includes at least three leads, where two of these leads may be used for temperature sensing and the third used for conductivity sensing.

Referring now to FIG. 229, an alternate embodiment of a sensor apparatus including a sensing probe 7890 and a thermal well 7100 is shown in a fluid line 7108. In this embodiment, the sensing probe 7890 may be constructed of a metal housing. The thermal well 7100 may also be constructed of metal. The thermal well 7100 and the sensing probe 7890 can be made from the same metal or a different metal. The metal, in the preferred embodiment, may be a conductive metal, which may include stainless steel, steel, copper, and silver. A lead 7360 is attached to the sensing probe 7890 housing for conductivity sensing. The thermal sensing leads 7362 are attached to a thermal sensor located inside the sensing probe 7890 housing. The lead 7360 (or the lead for conductivity sensing) can be attached anywhere on the sensing probe 7890 because the sensing probe 7980 is constructed of metal.

Referring now to FIG. 230, a sensing probe or probes 7890 may also extend or be embedded into a source component 6000 reservoir such as a dialysate bag or concentrate bag. Any of the sensing probes 7890 described above may be used. Sensing probes 7890 may pass through the reservoir wall 7891 material and either be in direct contact with the fluid or be assembled into a thermal well 7100 as described above. Sensor probes 7890 could be used to provide either temperature data or both temperature data and conductivity data. As shown, sensor probes 7890 disposed in a source component 6000 reservoir may be located near or adjacent the outlet port of the reservoir. This may help to ensure that the sensor probes 7890 are maintained in communication with fluid within the reservoir even when the reservoir is nearly empty. In some embodiments, a sensing probe 7890 may be included on a component of the system 10 such as the cycler 14 or a water purification device 6002. The source component 6000 may be mated with the probe 7890 during set up of the therapy to take a temperature reading. This reading may be compared to an acceptable temperature range and if within the limits of the range, use of the source component 6000 for the therapy may be allowed. The temperature value read at this time may be used for density corrections for at least a portion of the therapy.

Various embodiments described in relations to FIGS. 175-229 and 230 may provide data which may be used to facilitate use of the cycler 14 as a mass transfer device. Any of the sensor probes 7890 described above may provide temperature data signals via any number of leads to a control system 16 of a cycler 14. These temperature data signals may be analyzed by the cycler 14 control system 16 to determine a temperature value for fluid in proximity to the sensing probe. This temperature value may subsequently be used to determine a density of a source component 6000 fluid being pumped though a cassette 24 placed within the cycler 14. A look up table relating source component 6000 fluid temperatures and their consequent densities may be used for this purpose. In some embodiments, interpolation techniques such as linear interpolation may be used in conjunction with data in a look up table as well. In certain embodiments a continuity equation may be used. Where a continuity equation is used the equation may be generated based on the data similar to that which would be included in a look up table (e.g. using a best fit curve). Direct measurement of a specimen of the fluid across the desired operating range may also be used to generate the continuity equation.

One or more sensing probe(s) may extend into a region of the cassette 24 where temperature sensing is desired. For example, a sensing probe may extend through the cassette body into each of the pump chambers 181A, B of the cassette 24. A temperature reading for each pumping stroke may be taken and used in conjunction with a volume measurement associated with the pump stroke to determine a mass of source component 6000 fluid transferred during the pump stroke. The control system 16 of the cycler 14 may tally the mass of each source component 6000 transferred to a mixing reservoir 6004 (e.g. a heater bag 22) during an admixture operation. Thus, by delivering fluid to the mixing reservoir 6004 and tracking the amount of mass moved on a stroke by stroke basis, the cycler 14 may accurately admix fluids prescribed in a therapy formulation. With such mass transfer accounting, the cycler 14 may adhere to a therapy formulation prescription specified in molar or mass ratios, even if the source components 6000 are each at significantly differing temperatures.

A temperature sensor associated with the cassette 24 may be calibrated as provided in the flowchart 6240 depicted in FIGS. 231A-231B. As shown, in block 6242, a fill stroke may be performed to draw fluid into a pump chamber 181A, B from a source component 6000 (e.g. a water purifier). The temperature of fluid drawn into the pump chamber 181A, B in block 6242 may be measured in block 6244 by a temperature sensor associated with the cassette 24. The pump chamber 181A, B may be delivered to a substantially empty mixing reservoir 6004 such as a heater bag 22 in block 6246. A second temperature measurement of the fluid may be taken by a temperature sensor of the heater pan 142 in block 6248. The first and second temperature measurement may then be compared 6250.

In some embodiments, multiple chambers may be delivered to the heater bag 22 with the temperature of each pumped chamber volume being measured. These measurements may be averaged or otherwise numerically processed to arrive at a source temperature value which serves as the first temperature measurement. After these multiple chambers have been delivered to the heater bag 22, a temperature measurement of fluid in the heater bag 22 may be made and may serve as the second temperature measurement. In certain embodiments, fluid may be transferred into the heater bag 22 and measured to determine the first temperature. Fluid may then be transferred to the cassette 24 for sensing by an uncalibrated sensor to collect the second measurement.

If, in block 6252, the first and second measurements do not agree to within a predefined amount, the cassette temperature sensor may be calibrated based on the heater pan 142 sensor reading in block 6254. Alternatively, additionally, or optionally if the first and second measurement agree within the predefined amount in block 6252, the fluid may be warmed on the heater pan 142 and a third temperature measurement may be taken with the heater pan 142 sensor in block 6256. A pump chamber 181A, B of the cassette 24 may be filled in block 6258. The temperature of the fluid drawn into the pump chamber 181A, B from the mixing reservoir 6004 may be measured by the cassette sensor to generate a fourth temperature measurement in block 6260. The third and fourth temperature measurement may be compared in block 6262. If, in block 6264, these temperatures do not agree within a predefined amount, the cassette sensor may be calibrated based on the heater pan 142 sensor in block 6266. This calibration may account for any delta in measurements between the first and second temperature and any delta between the third and fourth measurements. After calibration or if the sensors agree within the predefined amount, the cycler may proceed to the therapy or additional pre-therapy activities in block 6268.

If there are multiple cassette sensors, each of the cassette sensors may be calibrated based on a heater pan 142 sensor as described in relation to the flowchart 6240 in FIGS. 231A-231B. Additionally, where measurements are taken via a heater pan 142 sensor, it is also possible that these measurements be based off of a plurality of sensors monitoring the heater pan 142 temperature. For example, some or all of the sensors monitoring the heater pan 142 may provide a temperature measurement to a control system 16 of the cycler 14. These measurements may be averaged or otherwise numerically processed to arrive at a mixing reservoir 6004 temperature value. A value determined in such a manner may be used as one or both of the second and third temperature measurements described in the flowchart 6240 shown in FIGS. 231A-231B.

In some embodiments, the temperature calibration may be performed during manufacture. The calibration data may then be applied to the set 12 in a suitable location. For example, the calibration data may be included on a data matrix, QR code, RFID, barcode, or other machine readable form of documentation on the set 12. Where the calibration data is in a printed format, the printed data may be applied to a solution line cap 31, a solution line connector end 30A, a solution line brace 5050 (see, e.g. FIG. 235), identification tag 1100 (see, e.g. FIG. 19), or the solution line 30 itself. This data may then be read by an Auto-ID camera 1104 (see, e.g., FIG. 21) included in the cycler 14. After reading the data, the control system 16 of cycler 14 may use the data to apply a calibration to the sensor(s).

Referring now also to FIGS. 232-233, the temperature of the fluid may be determined through the use of a non-invasive or contactless temperature sensor 6290. The contactless temperature sensor 6290 may be an infrared thermometer such as an IR sensitive imager or imager array and may be positioned within the cycler 14 housing 82 or door 141. The imager(s) may be disposed such that their field of view encompasses a monitored portion of the set 12 such as a fluid line 30. An infrared transparent window 6292 or transparent windows 6292 may be included. The transparent window(s) 6292 may be disposed intermediate the imager(s) and the cassette 24 or one or more lines 30 from the solution components 6000. The imager may also be disposed such that it is not in line with the window 6292. For example, the imager may be provided in a sensing assembly including one or more mirrors or a fiber optic line or bundle allowing the imager to be placed in a wide range of locations within the cycler 14. Alternatively, there may be no window 6292 intermediate the imager and cassette 24 or one or more lines and the imager may be disposed with a direct line of sight to the monitored portion of the set 12.

In FIG. 232, the contactless temperature sensor 6290 is shown disposed within the cycler 14 housing 82 at a location were the field of view is in line with the path of fluid lines 30 leading to cassette 24 inlet ports from the component sources 6000. A transparent window 6292 is disposed between the sensor 6290 and the fluid lines 30. The fluid lines 30 may be made from or include a region which is made from a material which is thermally transparent such that IR radiation may be sensed via the sensor 6290.

As shown in FIG. 233, contactless temperature sensors 6290A-C may also be placed so as to sense the temperature of various regions of the cassette 24. Though three sensors 6290A-C are shown in FIG. 233, not all of these sensors 6290A-C may be included. A contactless temperature sensor 6290A-C may, for example, monitor the temperature in one or more of the pump chambers of the cassette 24 or fluid pathways for the cassette 24. Temperature sensors 6290A-C may sense temperature from either or both the front and back side of the cassette 24.

As shown, a contactless temperature sensor 6290A-C may be included in a pressure delivery module 2700 of the cycler 14. In the example embodiment, a sensor 6290A is shown disposed in the pressure distribution module of the pressure delivery module 2700. This sensor 6290A may be placed in a location which provides a vantage point to the region of the cassette 24 where temperature monitoring is desired. A sensor 6290A may be placed within or in-line with one or both of the control chamber depressions 171A, 171B to monitor the temperature of fluid in the pumping chambers 181A, 181B of the cassette 24. If behind the control chamber depression 171A, 171B a viewing pathway 6294 may extend from the control chamber depression 171A, 171B to the sensor 6290. The view pathway 6294 shown in FIG. 233 is an embrasure.

Where a temperature sensor 6290A-C is placed on the pressure distribution module 2700 side of the cassette 24, the control surface 148 may be or include a transparent window 6292. For instance, the control surface 148 may be constructed of a flexible clear material which is transparent to infrared wavelengths. Alternatively, the control surface 148 may include a transparent window 6292 and be otherwise opaque. Such a window 6292 may be created in a multi material molding process. It may be desirable that the window 6292 material and the rest of the control surface 148 have relatively similar mechanical properties such that they behave similarly when pressure is applied. The transparent window 6292 in FIG. 233 is included in the pump control region 1482 of the control surface 148. This window 6292 may be any shape (e.g. round, ovoid, circular, or polygonal) and may be positioned in the field of view of the temperature sensor. In some embodiments, the entire pump control region 1482 of the control surface may be made of the transparent window 6292 material.

A contactless temperature sensor 6290A-C may also be included in a door 141 of the cycler 14. In the example embodiment, sensors 6290B, C are shown disposed in the piston 6296 which displaces to press the mounting location 145 into contact with the cassette 24. These sensors 6290B-C may be placed in a location which provides a vantage point to the region of the cassette 24 where temperature monitoring is desired. Similar to sensor 6290A, sensor 6290B is disposed so as to be in line with a pumping chamber 181A, B of the cassette 24. Where it is desired to monitor the temperature of fluid in a pump chamber 181A, B only one sensor 6290A, B may be included or only one sensor 6290A, B may be included per pump chamber 181A, B. A sensor 6290C or sensors may also or instead be positioned so as to have a vantage point of a fluid bus or common channel 200, 202 of the cassette 24. Sensor 6290C is disposed in line with the lower fluid bus 202 of the cassette 24 but an additional sensor could be included in line with the upper fluid bus 200 if desired. Sensor 6290C in these positions could monitor the temperature of fluid entering and exiting the pumping chambers 181A, 181B.

Where a temperature sensor 6290A-C is disposed in the door 141, the mounting location 145 may be or include a transparent window 6292. For instance, the mounting location 145 may be constructed of or include a portion which is a compressible clear material which is transparent to infrared wavelengths. Where only partially transparent, the mounting location 145 may be created in a multi material molding process. It may be desirable that the window 6292 material and the rest of the mounting location 145 have relatively similar mechanical properties such that they behave similarly when pressure is applied. If the transparent window 6292 in FIG. 233 is positioned in line with the pump chamber 181A, B of the cassette 24, the pump chamber region of the cassette 24 may include a cassette window 6298 or the entire cassette 24 may be made of a thermally transparent material.

Referring now to FIG. 234, it may also be possible to use a contactless temperature sensor 6290 which is sensitive to visible wavelengths as opposed to infrared wavelengths. Similar to FIG. 232 an imager which serves as the contactless temperature sensor 6290 may be disposed within the cycler housing 82 and have a field of view of a transparent window 6292. A portion of the set 12 may be constructed of a thermochromic material or may be constructed including a thermochromic element 6293A, B. The imager or contactless temperature sensor 6290 may monitor the color of the thermochromic material or element 6293A, B to determine temperature information about fluid within that specific portion of the set 12. In FIG. 234, a number of thermochromic elements 6293A, B are included on each solution line 30.

Two different varieties of thermochromic elements 6293A, B are shown in FIG. 234. Thermochromic element 6293A is shown as a sleeve which surrounds the solution line. The thermochromic element 6293A may clip in place around the solution line 30 or perhaps be overmolded on the solution line 30 (or any other portion of the set 12). A portion of the solution line 30 itself could also be constructed from thermochromic materials. Thermochromic element 6293B is shown as an appliqué which may be placed on the solution line 30 (or any other portion a set 12). The appliqué may include thermochromic or cholesteric liquid crystals or be printed with a thermochromic ink/dye or luecodye. Thermochromic ink or dye may also be printed directly onto the solution line 30. In some embodiments, the solution line 30 may include a portion constructed from a highly thermally conductive at which the thermochromic elements 6292A, B are disposed.

As shown, each of the thermochromic elements 6293A, B includes a number of temperature sensitive regions 6295. Each of the regions 6295 may be sensitive to a different temperature range. The temperature ranges selected may be based on expected temperature ranges of source components 6000. The contactless temperature sensor 6290 may monitor each of the regions 6295. During processing of the image captured by the example contactless temperature sensor 6290, a determination may be made as to how many regions 6295 of a thermochromic element 6293A, B have changed color. The region 6295 with the highest temperature sensitivity to have changed color may indicate the temperature of the fluid within that solution line 30.

Where liquid crystals are used, the temperature sensor may monitor each of the cells or regions 6295. During processing of image data, a determination may be made as to which region or regions have altered in color. Once identified, this data may be used to arrive at a temperature of the fluid in the solution line 30. If each region 6295 supports a full spectrum transition over a temperature range, the color of each region 6295 may also be utilized in determining the fluid temperature. Though individual regions 6295 or cells of liquid crystal with different temperature sensitivities are shown, a continuous zone of liquid crystal with a temperature sensitivity gradient may also be used.

In the example embodiment, the liquid crystal regions 6295 of thermochromic element 6293B are surrounded by a second material. This second material may be a thermochromic region 6295 as well. The surrounding thermochromic region 6295 may, for example, be printed with a thermochromic ink/dye. This region 6295 may have a temperature sensitivity chosen such that it is in its color change state when between the highest and lowest temperature sensitivities of the liquid crystal regions 6295. Thus, the surrounding region 6295 may serve as an indicator which shows whether the temperature of fluid in the solution line 30 is within range of the liquid crystal regions 6295.

Referring now to FIG. 235-236, thermochromic elements 6293C may additionally or instead be included as spiking indicia in embodiments including an automated cap removal and line spiking assembly (see, e.g. FIGS. 16-56). In embodiments including an automated spiking assembly, the force needed to spike solution lines 30 onto a cassette 24 may vary depending on the temperature of the solution lines 30. As solution lines 30 increase or decrease in temperature from an intended use temperature or temperature range, the amount of force needed to puncture their septa 30B may increase. Thus, monitoring one or more thermochromic element 6293C with an imager may allow a determination as to whether a septum 30B may be too hot/cold to spike or how much force should be used in the spiking operation. The color may also be used to provide a temperature input for a mass based fluid transfer operation.

As shown, a number of thermochromic elements 6293C are placed in exemplary locations near the septum 30B of a solution line 30. The thermochromic elements 6293C may be overmolded onto, printed onto, or otherwise supplied or adhered to these locations. Various embodiments may only include one or some of those shown in FIGS. 235-236. Thermochromic elements 6293C may be disposed, for example, on a solution line cap 31, a solution line connector end 30A, a solution line brace 5050, identification tag 1100, or the solution line 30 itself. Any of these components may also be at least partially or entirely constructed from a thermochromic material. Where the identification tag 1100 includes a thermochromic component, the data matrix 1103 may be printed in a thermochromic ink/dye. Where braces 5050 are included, the brace 5050 may be any of those described in U.S. Pat. No. 10,201,647, to Norris et al., issued Feb. 12, 2019, filed Jun. 5, 2015, and entitled "Medical Treatment System and Methods Using a Plurality of Fluid Lines" which is incorporated by reference herein by reference in its entirety.

Referring now to the flowchart 6500 shown in FIG. 237, after a set is installed in a cycler in block 6502, a portion of the set where the thermochromic elements are disposed may, in block 6504, be imaged. A processor may receive the image data and analyze the data to determine temperature information in block 6506. This temperature information may be used to guide a solution line spiking operation. Fluid density determinations may also be at least partially based off a thermochromic element's color. If, in block 6508, the temperature information indicates the solution line septum is not within an expected temperature range, an alert may be generated in block 6510. This alert may, for example, be displayed on a GUI of the cycler. If, in block 6508, the temperature is within range, the spiking force may be adjusted in block 6512 and the solution lines may be spiked in block 6514. In some embodiments, block 6512 may be optional and a pre-set standard spiking force may be used in each spiking operation.

In other embodiments, and referring now to FIG. 238, temperature may be sensed via at least one RFID or NFC based temperature sensor 6540 included as part of a set 12. The RFID temperature sensor 6540 may be included in a passive or active RFID tag, however, passive RFID tags may be preferred. These RFID temperature sensors 6540 may, for example, be embedded within or attached to source component 6000 reservoirs. RFID temperature sensors 6540 may also store a variety of information such as source component type or contents (e.g. chemical composition), source component reservoir volume, lot number, manufacturer, manufacture date, expiration date, and perhaps admixture instructions.

An interrogator 6542 may periodically query the RFID temperature sensors 6540 for temperature data during therapy. This data may be used by a cycler 14 control system 16 to determine a density of fluid being pumped into a mixing reservoir 6004 and may thus facilitate mass based mixing. Preferably, the RFID temperature sensor 6540 may be placed on the reservoir in a location where it may continue to measure the temperature of fluid even when the reservoir is nearly empty. The RFID temperature sensor 6540 may, for example, be placed adjacent an outlet of a source component 6000 reservoir.

The interrogator 6542 may read any additional data on the RFID temperature sensors 6540 as well. This data may, for example, be checked during pre-therapy to ensure that only expected source components 6000 and/or all source components 6000 needed for an admixture formulation prescription are present. Data may also be checked to ensure that the source components 6000 are not expired and that lot numbers associated with the source components 6000 are acceptable (e.g. not recalled or the like). The source component 6000 may also be checked during pre-therapy to ensure the temperature of the source component 6000 is within an acceptable range.

As shown, the interrogator 6542 may be a stand-alone component which may communicate with other components of the system 10 via a wireless communication protocol such as a Bluetooth protocol. Any protocol described above with reference to auxiliary sensor assemblies 6012 may be used. In other embodiments, the interrogator 6542 may be included in a piece of hardware such as a dongle which may plug into a USB or other port of the cycler 14 or another system 10 component. Interrogator 6542 may also be included within, for example, the cycler 14 or a water purification device 6002 of the system 10. In these examples, the interrogator 6542 may read the RFID temperature sensor 6540 through a housing 82 of the cycler 14 or housing of a water purification device 6002. The interrogator 6542 may also draw power from the cycler 14 or water purification device 6002. Data from the RFID temperature sensor 6540 may be collected by the cycler 14 multiple times throughout the therapy to adjust density calculations as the therapy progresses. This data may, for example, be collected on a predetermined schedule or on every withdrawal stroke from a source component 6000. Data from the RFID temperature sensor 6540 may also be collected prior to allowing use of a source component 6000 for the therapy.

The cycler 14 may also include a scale to measure the weight of fluid displaced during pump strokes. The heater pan 142 may double as the pan for the scale allowing the weight of a mixing reservoir 6004 (e.g. heater bag 22) to be measured. Any suitable variety of scale may be used, but in specific embodiments an electromagnetic scale such as an electromagnetic force restoration or compensation scale may be used. Strain based scales such as those incorporating one or more Wheatstone bridge are also possible. In such embodiments, admixture based on a formulation prescription may optionally be performed without the use of fluid volume measurements. Instead, the amount of source components 6000 pumped to the mixing reservoir 6004 may be measured via the scale. Pumping of any particular component may be stopped when the weight measurement from the scale indicates an appropriate mass of the source component 6000 has been transferred to the mixing reservoir 6000.

If the cycler 14 includes an FPGA which controls timing of pneumatic valves involved in the pumping and routing of fluid through the cassette 24, scale data may be supplied to the FPGA to help govern pumping of fluid from the source components 6000. The FPGA may interact directly with the scale sensor hardware without the need for its own operating system. As a result, the FPGA may make and act on decisions in real time allowing for precise control over the amount of mass delivered to the mixing reservoir 6004.

If an FPGA is not used, at least a portion of the pumping operation may be performed using valve pump strokes as described above. During a portion of a mass transfer operation from a source component 6000 to a mixing reservoir 6004, fluid may be pumped in substantially full pump strokes from the cassette pump chambers 181A, B. Once the scale data indicates that the mass transferred is within a range of the target mass, a second portion of the mass transfer operation may begin using valve pump strokes. The range may be defined based on any targeting error limitations imposed by a cycler 14 operating system not operating in real time. The range may be set to a value about equal to the maximum targeting error attributable to this cause.

Scale data may be compared to pumping data to ensure that the data is in agreement. For example, after conducting a pumping stroke, the control system of the cycler 14 may compare the scale measurement change to a nominal mass transferred per pump stroke for a given source component 6000. If the mass transferred is outside of a range of the nominal mass or is outside of the range of the nominal mass for a number of strokes, an error may be triggered by the controls system 16. The range of the nominal mass may be informed by a nominal volume displacement per pump stroke and the density of the source component 6000 at the extremes of an anticipated source component 6000 temperature range. If volume measurement data is also collected, the volume transfer data and the density of the source component 6000 at the extremes of the anticipated source component 6000 temperature range may be used to check the mass transfer measurement.

To prevent outside influences from interfering with the scale measurements, the lid 143 (see, e.g., FIG. 16) may double as a protective shield or guard. The lid 143 may inhibit direct contact with the mixing reservoir 6004 during measurement periods. The lid 143 may be locked during admixture operations. Alternatively, the lid 143 may include or interface with at least one switch or detector which monitors the state of the lid 143. A micro switch or similar mechanically actuated switch assembly may be used to provide an indication of lid 143 state. For example, such a switch may indicate whether or not the lid 143 is in an opened/closed state or locked/unlocked. Additionally, other types of sensors may be used such as Hall effect sensors, optical sensors, capacitive sensors, inertial sensors or tilt sensors, or various encoders may be used. If the control system 16 detects that the lid 143 has been unlocked or opened, pumping may be halted during admixture operations. During other pumping operations such as patient fills or drains, pumping may continue regardless of the lid 143 state.

Mixing Reservoir

The mixing reservoir 6004 may include at least one feature which aids in establishing a uniform dispersal of fluid entering the mixing reservoir 6004. Such a feature may generally be referred to as a dispersal element and may encourage or exert control over the mixing of fluid within the mixing reservoir 6004 via a number of different strategies. Dispersal elements may be constructed so as to create a desired flow type or flow pattern in fluid entering the mixing reservoir 6004.

A dispersal element may act as a turbulence generator which establishes a turbulent stream out of the fluid entering the mixing reservoir 6004. A dispersal element may act as a vortex generator which establishes a vortex within the mixing reservoir 6004. A dispersal element may also act as a laminar flow director. Dispersal elements may also be arranged such that flow entering the bag is laminar but then gets broken into to turbulent flow at a downstream point in the flow path.

A dispersal element may also help to make the flow of fluid into the mixing reservoir more diffuse. For example, the inlet line to the mixing reservoir 6004 may extend into the interior volume of mixing reservoir 6004 and include a plurality of orifices, perforations, or pores through which fluid may be ejected into the mixing reservoir 6004. In some embodiments the inlet line may extend into the mixing reservoir 6004 along a path which may be at least partially predetermined. The orifices or pores may be dimensioned such that mass flow out of the inlet line at a first portion of the tube is substantially the same as mass flow out of the inlet line another portion of the tube located downstream of the first portion.

Referring now to FIGS. 239-240, an exemplary mixing reservoir 6004 is shown. The mixing reservoir 6004 shown is a flaccid walled reservoir or bag which may inflate and deflate in response to fluid transfer to/from the mixing reservoir 6004. In other embodiments, the mixing reservoir 6004 may be any other type of container. The mixing reservoir 6004 is attached to an inlet/outlet line 6420. The inlet/outlet line 6420 may be physically attached to the mixing reservoir 6004 at one or more points or regions along the inlet/outlet 6420 line. In FIG. 239, the inlet/outlet line 6420 is attached to the mixing reservoir 6004 at a first attachment region 6422 and second attachment region 6424. This physical attachment may serve as a constraint which generally maintains an inlet/outlet line 6420 in a defined path. In alternative embodiments, the terminal downstream end of the inlet/outlet line 6420 may be free within the mixing reservoir 6004.

As best shown in FIG. 240, a detailed view of the indicated region of FIG. 239, the inlet/outlet line 6420 may include a number of orifices 6426, 6428, 6430 disposed along a length of the inlet/outlet line 6420 internal to the mixing reservoir 6004. The orifices 6426, 6428, 6430 may provide the only fluid pathways to and from the inlet/outlet line 6420. Alternatively, and where the downstream terminal end of the inlet/outlet line 6240 is free, the terminal end of the inlet/outlet line 6240 may be open to the interior lumen of the inlet/outlet line 6240.

The orifices 6426, 6428, 6430 may be disposed at regular or irregular intervals along the length of the tube. In the example embodiment, sets of orifices 6426, 6428, 6430 are disposed at regular intervals from one another and orifices 6426, 6428, 6430 within each set are also disposed at regular intervals from one another. Orifices 6426, 6428, 6430 or sets of orifices 6426, 6428, 6430 may also be disposed at regular or irregular radial intervals from one another. For example, orifices 6426, 6428, 6430 may be placed every 90 or 120° from one another about the wall of the inlet/outlet line 6420.

During delivery of fluid to the mixing reservoir 6004, as fluid escapes the inlet/outlet line 6420 into the mixing reservoir 6004 from upstream orifices, a pressure drop will occur and the pressure driving the fluid at a downstream orifice will be decreased. In the exemplary embodiment, orifices 6426, 6428, 6430 are sized such that their cross-sectional area increases in proportion to their location with respect to a pump 6432 (e.g. cycler 14 operating a cassette 24). In general, the further downstream from the pump 6432, the greater the cross-sectional area of an orifice or set of orifices 6426, 6428, 6430 may be. Though not shown to scale in FIG. 240, the cross-sectional area of each orifice 6426, 6428, 6430 may be chosen such that substantially uniform mass flow out of the inlet/outlet line 6420 is generated as fluid is delivered to the mixing reservoir 6004.

In alternate embodiments, the size of the orifices 6426, 6428, 6430 may be constant, however, the density of orifices 6426, 6428, 6430 along the length of the inlet/outlet line 6420 may be altered. In general, the number of orifices 6426, 6428, 6430 at an upstream region of the inlet/outlet line 6420 may be less than the number of orifices 6426, 6428, 6430 at a downstream region of the inlet/outlet line 6420. In alternate embodiments, the shape of orifices 6426, 6428, 6430 may vary as well. Orifices 6426, 6428, 6430 may be circular, ovoid, polygonal, star shaped, etc.

Referring now to FIG. 241, in some embodiments, a downstream terminal end 6430 of an inlet/outlet line 6420 to a mixing reservoir 6004 may be constructed as a Venturi type ejector. This portion of the inlet/outlet line 6420 may be disposed within the mixing reservoir 6004 and may leverage the pressure drop within the Venturi to draw surrounding fluid into the inlet/outlet line 6420 fluid stream. As shown, the flow lumen 6422 of the inlet/outlet line 6420 may include a restriction 6424. A number of ports 6426 may be included such that fluid in the mixing reservoir 6004 may be drawn into the inlet/outlet line 6420. The number of ports 6426 may be variable depending on the embodiment. Additionally, the ports may be disposed at regular or irregular intervals about the inlet/outlet line 6420. In the example, there are two ports disposed 180° apart from one another. To further encourage mixing, the end of the inlet/outlet line 6420 may include a number of scallops 6428. The scalloped edge may help to introduce vortex like or turbulent flow to fluid exiting the downstream terminal end 6430 of the inlet/outlet line 6420.

Referring now to FIG. 242, an example mixing reservoir 6004 including a separate inlet line 6432 and an outlet line 6434 is shown. To ensure one directional flow through the inlet 6432 and outlet line 6434, a check valve 6436 may be included in each line 6432, 6434. The inlet and outlet line 6432, 6434 may be disposed offset from and angled with respect to one another. This may help to create a swirling flow within the mixing reservoir 6004 the thus allow the separate inlet 3432 and outlet lines 6434 to act as dispersal elements. In the example embodiment, the inlet line 6432 is positioned so as to expel liquid into the mixing reservoir 6004 in a first direction. The outlet line 6434 is positioned so as to pull liquid out of the mixing reservoir from a second direction. The first direction and second direction in the example embodiment are angled the same amount, though in opposing directions (i.e. one measured clockwise the other counterclockwise) from a medial plane 6438 of the mixing reservoir 6004. Such a mixing reservoir 6004 may be used in conjunction with any of the active mixing strategies described elsewhere in the specification.

Referring now to FIG. 243A-243B, in some scenarios, source components 6000 may each be of different densities and may have a tendency to stratify within the mixing reservoir 6004. To mitigate such stratification, a flow director 6440 may be included on the inlet line to the mixing reservoir 6004 and act as a dispersal element. The flow director 6440 may include a common flow path 6442 which may split into at least first 6444 and second flow paths 6446. Though the example embodiment includes a common flow path 6442 which bifurcates, other embodiments may split the common flow path 6442 into more than two different flow path branches. The first and second flow path 6444, 6446 (and other if included) may be angled with respect to the axis of the common flow path 6442 and may extend in opposing directions as shown. In the example embodiment, the angles of the axes of the first flow path 6444 and second flow path 6446 with respect to the axis of the common flow path 6442 are congruent. Alternatively, no split of the common flow path 6442 may occur. The common flow path 6442 may extend all the way through the flow director 6440.

The flow director 6440 may include a float 6448 which is disposed within a channel 6450. The float 6448 may translate along the channel 6450 in a direction transverse to the common flow path 6442. The float 6448 may be cylindrical or another elongate form with a round or polygonal cross-sectional shape. Alternatively, the float 6448 may be a ball, sphere or spheroid. In some embodiments, the float 6448 may be have a dumbbell or hourglass like shape. The channel 6450 may be shaped to accommodate the desired displacement range of the float 6448.

Depending on the orientation of the mixing reservoir 6004, the float 6448 may rise to a first end 6452 (as shown) or second end 6454 of the channel 6450. When the float 6448 abuts either first end 6452 or second end 6454 of the channel 6450, the float 6448 may respectively block the first flow path 6444 or second flow path 6446. The flow path 6444, 6446, pointed upward will thus be blocked by the float 6448. In alternative embodiments, the float 6448 may be replaced by a sinker (not shown) to create the opposite effect. Where no split occurs and the common flow path 6442 extends through the entirety of the flow director 6440, the location of the float/sinker in the channel 6450 may serve to redirect flow in the common flow path 6442.

Such a flow director 6440 may be advantageous where the installation orientation of the mixing reservoir 6004 is uncontrolled. Where the mixing reservoir 6004 is a heater bag 22, for example, the mixing reservoir 6004 may be installed with a first side or opposing second side facing downward. By installing the flow director 6440 such that the channel 6450 is perpendicular to these sides, the float 6448 may ensure fluid is directed toward the downward facing side of the mixing reservoir 6004 regardless of the installation orientation.

Referring now to FIGS. 244A-244B, in certain embodiments, a flow director 6280 may be configured to redirect flow moving in a first direction, but have substantially no redirecting effect in a second direction. For example, a flow director 6280 may redirect inflow to the mixing reservoir 6004 to help combat potential stratification and aid in uniform mixing. Outflow from the mixing reservoir 6004 may be substantially free from any redirection generated by the flow director 6280. As shown In FIGS. 244A-B, the exemplary flow director 6820 includes a flow path 6822. A flapper 6824 is disposed within the flow path 6822. The flapper 6824 may be anchored into the flow path 6822 via a pivot 6826. The pivot 6826 may be disposed at or near a first end of the flapper 6824.

When outflow 6828 (see FIG. 244A) from the mixing reservoir 6004 is occurring, the flapper 6824 may rotated about the pivot 6826 and align with the direction of flow. When in this aligned state, the flapper 6824 may exert minimal redirecting influence on passing fluid. When inflow 6830 (see FIG. 244B) to the mixing reservoir 6004 is occurring, the flow may crash into a side of the flapper 6824 and cause the flapper 6824 to displace about the pivot 6826 until a second end of the flapper 6824 opposite the first end contacts a wall of the flowpath 6822. This may cause a redirection of flow toward the opposing wall of the flow path 6822.

Referring now to FIG. 245, mixing reservoirs 6004 may include one or more baffle 6460 which may act as a dispersal element. The baffle 6460 may be disposed within the interior volume of the mixing reservoir 6004 and be physically attached to at least one wall of the mixing reservoir 6004. Where the mixing reservoir 6004 is a flaccid bag such as a heater bag 22, a baffle 6460 or baffles 6460 may be welded, heat staked, solvent bonded, etc. to opposing walls of the mixing reservoir 6004 bag material. The baffles 6460 may be shaped and disposed so as to generate mixing of fluid within the mixing reservoir 6004 as fluid delivered to the bag encounters the baffles 6460.

A baffle 6460 may be constructed of a rigid material, or may be constructed of a flexible, flaccid, or bendable material. A baffle 6460 included in a mixing reservoir 6004 may be a solid piece of material having a uniform cross-sectional shape. A baffle 6460 may be substantially planar, curved, cylindrical, round, rectangular, triangular, or chevron shaped in cross-section. Any other shape may also be used. Baffles 6460 may include multiple portions or regions which differ in cross-sectional shape. Baffles 6460 may also differ in cross-sectional shape depending on their location within the mixing reservoir 6004. Some baffles 6460s may include a number of pass throughs or be screen/grate like instead of solid. These pass throughs may facilitate control of flow impedance as liquid moves through a mixing reservoir 6004. In some embodiments, a baffle 6460 may constrain a shape change of a mixing reservoir 6004 as the mixing reservoir 6004 inflates or deflates with fluid. For example, a baffle 6460 or baffles 6460 may be employed to create a quilted or tufted pattern of rises and valleys on the surface of the mixing reservoir 6004 as the mixing reservoir 6004 fills with fluid. This again may help to generate more turbulent flow of fluid within the mixing reservoir 6004.

FIG. 245 shows a baffle 6460 which illustrates a number of the above features. As shown, the baffle 6460 is generally planar. The baffle 6460 includes first regions 6462 which are of a substantially uniform cross sectional shape. A recessed, second region 6464 is also included and has a variable cross sectional shape. Other embodiments may not include a continuously varying cross section, but rather a cross section that changes in stepwise fashion over one or more steps. Though as shown, any cross section within the second region 6464 would have a foot print smaller than that of the first regions 6462, baffles 6460 may include bulged regions as well. Multiple recessed and bulged regions may be included depending on the embodiment.

The baffle 6460 shown in FIG. 245 also includes a number of pass throughs 6466, 6468, 6470. Pass throughs 6466 are spaced at regular intervals and are substantially identical in size. Pass throughs 6466 are round in shape and roughly circular. As illustrated by pass throughs 6468, any other shape may be used. For example, pass throughs 6468 are depicted as elongate polygonal channels though rounded ovoid type channels are also possible. Again, these pass throughs 6468 are roughly the same shape and size and are spaced at regular intervals. Pass throughs 6468 are generally parallel to one another, but may be angled orthogonally toward one another and potentially intersect one another as well. As shown by pass throughs 6470, pass throughs may be irregularly spaced with different sizes and shapes.

Referring now to FIG. 246, baffles 6460 may be provided in a staggered arrangement or pattern within a mixing reservoir 6004. In the example, a first set of baffles 6460 is disposed in line with axis 6472 of the flow lumen of the inlet/outlet line 6420 to the mixing reservoir 6004. A second set of baffles 6460 extends toward the axis 6472 of the flow lumen from a point at or near first and second edges 6474, 6476 of the mixing reservoir 6004. In the exemplary embodiment, the first and second edges 6474, 6476 are generally parallel to the axis 6472 of the flow lumen. Baffles 6460 of the second set of baffles 6460 may be positioned such that they are disposed at between (e.g. at a midpoint) baffles 6460 of the first set. That is, baffles 6460 from the first set may be disposed in alternating fashion with the baffles 6460 of the second set. As shown, all of the baffles 6460 are positioned at roughly the same angle with respect to the axis 6472 of the flow lumen. In the example embodiment, the baffles 6460 are disposed substantially perpendicular to the axis 6472 of the flow lumen.

FIG. 247 depicts another example mixing reservoir 6004 including a number of baffles 6460. The baffles 6460 in FIG. 247 are constructed as chevron structures. The apex of each chevron baffle 6460 points toward a side 6478 of the mixing reservoir 6004 where the inflow from the lumen of the inlet/outlet line 6240 enters the mixing reservoir 6004. In other embodiments, the apexes of the baffles 6460 may not all point in the same direction. In the example, the baffles 6460 are disposed in a staggered "V" formation with a central baffle 6460 positioned in line with the axis 6472 of the flow lumen of the inlet/outlet line 6420. Two additional baffles 6460 are disposed in echelon with respect to the central baffle 6420. In other embodiments, the number of baffles 6460 may differ.

In some embodiments, a single component source 6000 may include a number of different solution components in a single assembly. The single component source 6000 may be a bag type container including a number of partitions to generate isolated reservoirs within the bag. Each solution component may be separated from other solution components within the assembly by permanent barriers and/or temporary removable barriers. This may ensure that each solution component within the component source 6000 is stored together and thus at the same temperature. As such, the effect of temperature on density may be minimized.

An example component source 6000 containing a number of solution components 6000 is shown in FIG. 248. As shown, the component source 6000 is a multi-chamber or reservoir bag. The example embodiment depicts a plurality of solution component reservoirs 6570 within the multichamber bag. Any suitable number of solution component reservoirs 6570 may be included within a source component 6000, however, two are shown in the exemplary embodiment. The solution component reservoirs 6570 may be separated by at least one barrier 6572. The at least one barrier 6572 may be arranged such that it is resistant to a single point failure.

In the example embodiment, the solution component reservoirs 6470 each are partially defined by a portion of a barrier 6572 associated with that solution component reservoir 6570. An interstitial region 6574 may be defined between the barriers 6572 separating two adjacent solution component reservoirs 6570 within the source component 6000. The interstitial region 6574 may be a sealed volume or may be open to the surrounding environment. Where an interstitial region 6574 is included, a two point failure may be necessary for solutions in each of the adjacent solution component reservoirs 6570 to mix prior to therapy. Each barrier 6572 defining the walls of the interstitial region 6574 may need to be compromised before solution in each solution component reservoir 6570 may mix.

Each of the solution component reservoirs may have a dedicated outlet port 6576. The outlet lines 6578 extending from the outlet ports 6580 may include poka-yoke type connectors 6582 which are specific to each solution that may be contained within a solution component reservoir 6570 of the source component 6000. The poka-yoke connectors 6582 may have any specific shape or geometry and only be capable of interfacing with a connector on a set 12 having a cooperating or corresponding shape or geometry. Thus, the poke-yoke connector 6582 may prevent connectors with mismatched geometry from coupling into fluid communication with the respective solution component reservoir 6570. In the example embodiment shown in FIG. 248, the poka-yoke connectors 6582 are schematically drawn as different polygons. This may ensure that a given line attached to the cassette 24 may be attached to a known solution type. The cycler 14 control system 16 may then rely on assumptions about the types of solutions connected to specific ports of the cassette 24 when conducting mixing operations.

Referring now to FIG. 249, in some embodiments, a source component 6000 may include a barrier 6572 between solution component reservoirs 6570 which exists temporarily. This barrier 6572 may be broken, interrupted, or disturbed so as to allow communication from one side of the barrier 6572 to the other. Such a barrier 6572 may be included where it is desirable to keep the solution in the solution component reservoirs 6570 isolated until a point immediately before the therapy.

The barrier 6572 may be a peelable barrier which can be broken or disrupted upon application of a predetermined pressure. The barrier 6572 may also include one or more frangible 6584 which may be broken to establish a flow path between the adjacent solution component reservoirs 6570 within the source component 6000. The one or more frangible may be a pin type frangible. Where peelable barriers are used, the barriers may be formed by creating a deliberately weak seal via heat staking, ultrasonic welding, or application of adhesive. This may allow for solutions to remain separate from one another during shipping and storing, but allow for mixing prior to therapy.

The source component 6000 shown in FIG. 249 includes two solution component reservoirs 6750 separated by a temporary barrier 6572. The solution component reservoirs 6570 are bilaterally disposed about the axis of an outlet port 6580. The outlet port 6580 may be a common outlet port 6580 shared by at least two solution component reservoirs 6570 of the source component 6000. A line barrier 6586 may also be included. The line barrier 6586 may also be formed as a temporary barrier which may include one or more frangible or be peelable. The line barrier 6586 may prevent fluid communication from the solution component reservoirs 6570 into the outlet line 6578 until the line barrier 6586 has been broken or interrupted. To ensure that the solution component reservoirs 6570 have been placed into fluid communication with one another prior to allowing fluid communication with the outlet line 6578, the line barrier 6586 may be more durable than the inter reservoir barrier 6572 between the solution component reservoirs 6750. The line barrier 6586 may, for example, be constructed so as to have a first strength and the inter reservoir barrier 6572 may be constructed to have a second strength. The first strength may be chosen to be a greater than the second. As force is applied to the source component 6000, the second strength will be exceeded before the first strength is exceeded. Thus, as the bag is manipulated, the action of breaking the line barrier 6586 may cause the inter reservoir barrier 6572 to be broken as well. This may help to prevent unmixed fluid from entering the outlet line 6578.

In some embodiments, the line barrier 6586 may include a frangible 6588 in an otherwise permanent partition. The frangible 6588 may be disposed at an intersection point of the line barrier 6586 and the inter reservoir barrier 6572. When intact the frangible 6588 may keep each of the solution component reservoirs 6570 and the outlet line 6578 isolated from one another. When broken, the frangible 6588 may establish fluid communication from both of the solution component reservoirs 6570 to the outlet line 6578. Thus, fluid is drawn from both of the solution component reservoirs 6570 even if the user forgets to break the inter reservoir barrier 6572.

In an alternative embodiment, the line barrier 6586 may be formed from the portion of the inter reservoir barrier 6572 most proximal to the inlet line 6578 of the source component reservoir 6000. In such embodiments, portion of the inter reservoir barrier 6572 proximal to the inlet line may be broader or thicker (thus giving it more strength) than the rest of the inter reservoir barrier 6572. This portion may surround the inlet line 6578 terminus preventing any flow through the inlet line 6578. Such an embodiment would similarly ensure the fluid in each of the two source component reservoirs 6750 is in fluid communication before the access to the inlet line 6578 is created.

Referring now to FIG. 250, each of the solution component reservoirs 6570 may be associated with a dedicated outlet line 6578. These lines may be joined at a line junction 6590. The line junction 6590 may serve as a frangible housing and include an in line frangible 6594. When intact, the inline frangible 6594 may prevent the flow of fluid from the component source 6000 through the line junction 6590. Additionally, the in line frangible 6594 may keep fluid from each of the solution component reservoirs 6570 separated from one another. Once broken, the frangible 6594 may no longer block fluid flow through the line junction and allow fluid from each of the solution component reservoirs 6570 to flow through the common fluid line 6592. Again, this may allow fluid to be drawn from each of the source component reservoirs 6570 even if the user forgets to break the inter reservoir barrier 6572.

Referring now to FIG. 251, an exemplary in line frangible 6594 is depicted. The inline frangible 6594 may include a first section 6596 and a second section 6598. The first section 6596 may be a stationary section 6596 which is not disturbed when the in line frangible 6594 is broken. The first section 6596 may include fluid flow conduits which are in line with and in fluid communication with the dedicated outlet lines 6578 from the solution component reservoirs 6570. The second section 6598 may be a removable section which is loosely attached to the first section 6596. The second section 6598 may be attached so as to block the flow through the flow conduits of the first section 6596. When broken, and referring now also to FIG. 252, the second section 6598 may separate from the first section 6596 allowing flow through the first section 6596 into the common fluid line 6592.

As shown, the common fluid line 6592 is greater in diameter than the outlet lines 6578 from each of the solution component reservoirs 6570. In some embodiments, the cross sectional area of the flow paths within the outlet lines 6578 may be about half the size of the cross sectional area of the common fluid line 6592. In the event that the in line frangible 6594 is improperly broken and one of the fluid flow conduits in the first section 6596 remains blocked, a partial flow condition may be generated. The control system 16 of the cycler 14 may be able to detect the partial flow condition based on flow rates when drawing fluid from the component source 6000.

A flowchart 6600 depicting a number of exemplary acts which may be used to determine if an in line frangible was properly broken is shown in FIG. 253. The flowchart 6600 starts in block 6602 with the in line frangible in a broken state. In block 6604, the cycler may perform a fill stroke from the component source. The flow rate from the component source may be determined in block 6608. If, in block 6608, the flow rate is above a predetermined threshold, the cycler may proceed with a fill of the mixing reservoir in block 6610. In some embodiments, the chamber may be filled and redelivered to the component source a predefined number of times before proceeding to fill the mixing reservoir. This may help to ensure that fluid in the component source is mixed.

If, in block 6608, the flow rate is below the predefined threshold, it may be determined that the frangible was not properly broken and a flow path to a solution component reservoir of the component source is still blocked. In block 6612 an alert may be generated. Additionally, a message may be rendered for display on a graphical user interface of the cycler which instructs the user to check the frangible. The user may check the frangible and attempt to remedy any issue with the frangible. An input (e.g. button press, touch screen interaction) may be received in block 6614 to indicate that the frangible has been checked. The flowchart 6600 may then return to block 6604 and repeat. In some instances, there may be a cap on the allowed number of retires and a retry counter may be incremented each time a retry occurs. After the cap has been reached an error may be generated and the user may be required to install a new set or component source.

Mixing within a mixing reservoir 6004 may also be encouraged by actively causing displacement of fluid within the mixing reservoir 6004. For example, the cycler 14 may actuate the cassette 24 to pump fluid out of the mixing reservoir 6004 and then redeliver the fluid to the mixing reservoir 6004. This may be done repeatedly to cause mixing of fluid within the mixing reservoir 6004. This pumping back and forth from the mixing reservoir 6004 may be performed at mixing pressures which are predefined for the cycler 14. For example, high actuation pressures or maximum pumping pressures for the cycler 14 may be defined as the mixing pressures. In some specific embodiments the mixing pressures may be −25 kPa and +25 kPa. These high actuation pressures may help to ensure that fluid is mixed aggressively or efficiently by the cycler 14. The amount of time between a withdrawal and redelivery or a redelivery and the following withdrawal may also be preset. In some embodiments, there may only be a brief pause or the cycler 14 may switch directly from a withdrawal or redelivery to the subsequent withdrawal or redelivery. In some embodiments, a pause between a delivery and fill stroke of a pump chamber or vice versa may be less than 15% of the time taken to complete one of those strokes. In some embodiments, the control chamber 171 for the pump chamber 181 may be equalized with the reference chamber 174 and then optionally vented to atmosphere between switching from a withdrawal or delivery stroke. In some embodiments, the control chamber 171 may be placed into communication with a vent through the reference chamber 174 without previously equalizing with the reference chamber 174. In some embodiments, while venting to atmosphere the venting valve may be opened and closed so as to gradually vent the control chamber 171. This may limit the amount of noise generated due to relatively large pressure changes as the cycler 14 pumps back and forth from the mixing reservoir 6004. Where the cassette 24 includes multiple pump chambers 181A, B, and the mixing reservoir 6004 is equipped with separate inlet and outlet flow paths, a plurality of pump chambers 181A, B may be operated in phase to fill and redeliver liquid from the component source 6000 simultaneously.

As shown in the flowchart 6550 in FIG. 254, the mixing reservoir 6004 may, in block 6552, be filled with fluid according to mixing parameters defined in a therapy formulation communicated to a cycler 14. Once the mixing reservoir 6004 has been filled per the therapy formulation, mixing may begin. Mixing may also be performed any time after the mixing reservoir 6004 has been filled with fluid from at least two different source components 6000 (e.g. during a dwell phase of therapy after the mixing reservoir 6004 has been replenished for the next fill). In block 6554, fluid may be withdrawn from the mixing reservoir 6004 by applying negative pressure to at least one pump chamber 181A, B of the cassette 24 and opening fluid valves of the cassette 24 to establish a flow path to the mixing reservoir 6004. The control chambers 171B of the cycler 14 may be vented to ambient in block 6556. The fluid in the cassette 24 pump chambers 181A, B may then be redelivered back to the mixing reservoir 6004 in block 6558 by applying positive pressure to the at least one pump chamber 181A, B. A determination, in block 6560, may be made to ascertain if a mixing operation has been completed. If the operation has not been completed, blocks 6554, 6556, 6558 may repeat. If the operation has been completed, the cycler 14 may proceed with therapy in block 6562. It may be determined that the mixing operation has been complete when a number of withdrawals and redeliveries have been executed. The number may be calculated by the control system 16 based on the therapy formulation. For example, the number may be calculated by a formula which makes the number increase proportionally with the total amount of volume in the mixing reservoir 6004. The mixing operation may also be determined to have finished after a predefined volume has been recirculated through the cassette 24 and back to the bag. This volume may also be calculated by a formula which increases the total amount of volume to be recirculated in proportion to the total amount of volume contained in the mixing reservoir 6004. The recirculated volume may be tracked using any volume measurement determination scheme described herein.

The venting in block 6556 may be performed in any number of ways. Preferably, the venting in block 6556 is conducted in a manner which minimizes operational noise. For example, the control chambers 171B of the cycler 14 may be vented directly to atmosphere by opening a vent valve. Alternatively, the control chambers 171B may be equalized with an intermediary volume at a pressure closer to ambient than that control chamber 171B. The intermediary volume may in some embodiments be a reference chamber or volume 174 (see, e.g. FIG. 62). After this equalization, the control chamber 171B may then be vented to ambient by opening a vent valve. When opening the vent valve, the valve may be actuated open at a 100% duty cycle. Alternatively, it may be more desirable to create a more gradual equalization with ambient via the vent valve. In such embodiments, the vent valve may be actuated at a duty cycle less than 100%. This may allow for control over the rate of pressure change during the equalization process. The duty cycle may be preset to a value which has been empirically demonstrated to control the pressure change rate to within a range of desired values. In some embodiments, a pressure data signal from a sensor associated with the control chamber 171B may be monitored and used as an input to a control algorithm which governs the duty cycle of the vent valve. For example, the pressure data signal may be used by the control system in order to achieve a desired rate of pressure change. It should also be appreciated that the rate of pressure change when a control chamber 171B is brought to its fill or deliver pressure after venting may also be controlled using the data signal. Such a control chamber pressure rate controller may be used in any instance where it may be desirable to limit operational noise and is not just limited to being implemented during mixing operations. For example, the rate of pressure change may be controlled for any and/or all venting of control chambers 171B by the cycler 14.

In embodiments where the cycler 14 generates solution mixtures based on a stringently defined therapy formulation, it may be desirable to ensure that the mixing reservoir 6004 is completely empty prior to a new mixture being generated in the mixing reservoir 6004. In the event that some residual fluid from a previous mixture remains in the mixing reservoir 6004, this residual fluid volume may alter the composition of any subsequently generated mixture. Where the mixing reservoir 6004 is a flaccid or collapsible reservoir, at least a portion of the surfaces defining the interior volume of the mixing reservoir 6004 may include a texture or raised pattern. Textures or raised patterns may also be included on mixing reservoirs 6004 which are collapsible, but include on or more rigid portions. When the mixing reservoir 6004 is in a collapsed state, the texture or pattern may form a number of fluid channels which are in fluid communication with an outlet port of the mixing reservoir 6004. Thus, even in the collapsed state, pockets of residual fluid (perhaps of different formulation than the next fluid to be mixed) are inhibited from forming. Such a texture or raised pattern may be included for a heater bag 22 of a set 12 as well.

Referring specifically to FIG. 255, an exemplary mixing reservoir 6004 is shown. The exemplary mixing reservoir 6004 is depicted in a collapsed state. For sake of illustration, the material of the mixing reservoir 6004 is depicted as transparent to reveal features on the interior surfaces of the mixing reservoir 6004 internal volume. This material may be the same material used to construct a heater bag 22 of a set 12. The mixing reservoir 6004 may be made of opaque material as well. As shown, at least a portion of the interior surfaces defining the mixing reservoir's 6004 interior volume are textured. In FIG. 255, substantially the entirety of the surfaces defining the interior volume of the mixing reservoir 6004 are textured. The surface of the mixing reservoir 6004 adjacent the heater pan 142 (see, e.g., FIG. 84) may be left at least partially or entirely plain and untextured to facilitate temperature sensing and heat exchange into the mixing reservoir 6004 depending on the embodiment.

As shown in FIG. 255, the texture may be a Gaussian texture and may project into the interior volume of the mixing reservoir 6004. Isotropic type textures may also be used. In a collapsed state, a network of fluid flow channels may be established within the mixing reservoir 6004. These fluid flow channels may be defined at least in part by the texture. The texture may be generated by an etching or other mold texturing process which is applied to a form 6642 (see, e.g., FIG. 256) for a portion of the mixing reservoir 6004. In some embodiments, the texture may be machined into the forms 6642 for the mixing reservoir 6004 components. Such a Guassian or isotropic texture may allow for the material used to form the mixing reservoir 6004 be pre-textured and then bonded together to construct the interior volume of the mixing reservoir 6004.

Referring now also to FIG. 256A, B, in embodiments where the mixing reservoir 6004 includes at least two sheets 6640A, B which are conjoined to one another, the texture or design may be applied as the sheets 6640A, B are being conjoined. The sheets 6640A, B may, for example, be heat bonded to one another to form the perimeter seal 6650 and interior volume of the mixing reservoir 6004. Each of the forms 6642 may include a heat sealing face 6644 which may be disposed around the periphery of the forms 6642. This heat sealing face 6644 may generate the bond or perimeter seal 6650 around the perimeter of the mixing reservoir 6004. Each of the forms 6642 may also include a central region 6646 which is within the region defined by the heat sealing face 6644. The central region 6646 may include a negative of the desired texture on at least a part of the central region 6646 surface. Each of the forms 6642 may additionally include one or more vacuum ports 6648 which communicates with the central region 6646. The combination of heat and vacuum applied during the conjoining process may cause the texture or pattern to be thermoformed into the mixing reservoir 6004 while the perimeter seal 6650 is formed.

A one step mixing reservoir 6004 and texture/pattern forming process may be desirable for a variety of reasons.

For example, the texture/pattern may be located in specific regions on the mixing reservoir 6004. Additionally, specific regions of the mixing reservoir 6004 may be left bare or plain. For example, regions near the perimeter of the mixing reservoir 6004 may be left bare so as to facilitate the formation of a robust perimeter seal 6650 by the heat sealing face 6644 of the forms 6642. Temperature sensor contact regions of the mixing reservoir 6004 may also be left bare so as to minimize the amount of material and air gap present between the sensor and fluid within the mixing reservoir 6004. Alternatively, the temperature sensor contact region may also be thermoformed, but have a shape which interrupts the pattern/texture. In such embodiments, the temperature sensor contact region may be flat or devoid of bumps, channels, etc. Thermoforming the temperature sensor contact region may be desirable as it may thin the mixing reservoir material in this region minimizing the amount of material separating the temperature sensor from fluid in the mixing reservoir 6004.

The texture/pattern may also be created such that certain features of a texture or pattern having a plurality of features are located in desired locations of the mixing reservoir 6004. For example, features may include, though are not limited to: coarser and finer textures, different pattern sizes (e.g. a size gradient), different texture/pattern density (e.g. density gradient), repeating pattern units which are oriented different angles, pattern interruptions, etc.

As a one step mixing reservoir 6004 and texture/pattern forming process allows for texture or pattern features to be disposed in spatially defined positions within the mixing reservoir 6004, the texture/pattern on each sheet 6640A, B may be offset from one another. The texture/pattern on a second sheet 6640B of the mixing reservoir 6004, may for example, be offset from the texture or pattern on the first sheet 6640A by an offset chosen to prevent an interlocking of the texture/pattern on each sheet 6640A, B when the mixing reservoir 6004 is in a collapsed state. The interlock inhibiting offset may ensure that the network of fluid channels formed when the mixing reservoir 6004 collapses is not blocked by the texture or pattern on an opposing sheet of the mixing reservoir 6004. The offset may be a size based offset. In such examples, the size of the texture/pattern of one of the sheets 6640A, B may be made larger than that of the other sheet 6640A, B. Thus, to the extent one texture/pattern extends into flow channels of the other sheet 6640A, B formed when the mixing reservoir 6004 is in a collapsed state, the flow channels may remain partially open. The offset may also be a spatial shift type offset. The spatial shift may be controlled so as to limit or prevent the texture/pattern on one sheet 6640A, B from extending into the network of flow channels generated by the other sheet 6640A, B when the mixing reservoir 6004 is in a collapsed state.

Referring now to FIG. 257, an example sheet 6640 having a geometric pattern is depicted. The example pattern may be formed in a thermoforming process as described above. As shown, the pattern is formed of repeating pattern units 6652. In the example, the repeating pattern units 6652 are shapes, specifically polygons, which are spaced from one another. In the example, the shapes are hexagons, however, any polygon or round shape may be used. The repeating pattern unit 6652 may also be a dome-like shape.

The shapes may be disposed at even spacing with a constant size gap 6654 between one another or may be spaced with variable size gaps 6654. The spacing gap 6654 between pattern units 6652 (whether constant or variable) may be chosen such that the spacing gap 6654 is smaller than the pattern unit 6652. This may help to prevent interlocking of the pattern on each sheet 6640 of a mixing reservoir as the pattern unit 6652 will not be able to fit into the gap 6654 between pattern units 6652 on the adjacent sheet 6640. The size of the gaps 6654 may be selected to allow for a desired flow rate from the mixing reservoir 6004 to be achieved when the mixing reservoir 6004 reaches a collapsed state and the cycler 14 performs a fill stroke from the mixing reservoir 6004. The gaps 6654 may, for example, be between 10-90% of the width of the repeating pattern units 6652.

FIG. 258 depicts a cross sectional view of a portion of a mixing reservoir 6004 in a collapsed state. As shown, the pattern units 6652 abut one another when the mixing reservoir 6004 is in the collapsed state. The walls of the pattern units 6652 may be strong enough to resist crumpling or collapse under a first negative pressure the mixing reservoir 6004 may be subjected to when a fill stroke of a cassette 24 pumping chamber 171B is performed. In some specific embodiments, the walls of the pattern units 6652 may resist collapse under a pressure of at least −10 to −20 kPa (e.g. −15 kPa). The gaps 6654 may then form the network of fluid flow channels which allow fluid in all parts of the mixing reservoir 6004 to remain in fluid communication with the outlet of the mixing reservoir 6004. This may allow the cycler 14 to continue to withdraw fluid from the mixing reservoir 6004 when the mixing reservoir 6004 is in a nearly empty state. The walls of the pattern units 6652 may have a collapse pressure which is below a second pressure the mixing reservoir 6004 may be subjected to when a fill stroke of a pump chamber 171B is performed. The second pressure may be between −15 and −30 kPa (e.g. −22 kPa). At the collapse pressure, the mixing reservoir 6004 may transition from a collapsed state to a flattened state. In the flattened state the mixing reservoir 6004 may be substantially emptied and the network of fluid channels within the mixing reservoir 6004 may no longer be present.

In some embodiments, the collapse pressure for pattern units 6652 may be variable depending on their location within the mixing reservoir 6004. Specifically, it may be desirable that pattern units 6652 located most distal to the outlet of the mixing reservoir 6004 may have a collapse pressure lower than those located most proximal to the outlet of the mixing reservoir 6004. The collapse pressure may generally increase as proximity to the outlet of the mixing reservoir increases. Where the pattern is generated by thermoforming, this may be accomplished by creating a depth gradient for the negative of the pattern in the forms 6652. The portion of the pattern negative located most distal from the outlet of the mixing reservoir 6004 may be the deepest portion of the negative. The depth of the negative may decrease as proximity to the outlet of the mixing reservoir 6004 increases. Consequently, during vacuum forming, the walls of the pattern units 6652 farther from the outlet to the mixing reservoir 6004 may be thinner than those closer to the outlet. The thinner walls may reach their collapse pressure sooner than the thicker walls closer to the outlet. Thus the portion of the mixing reservoir 6004 farthest from the outlet may be encouraged to transition to a flattened state first. The transition from collapsed to flattened state may then proceed generally from the portion of the bag distal to the outlet toward the outlet. This may help to ensure the mixing reservoir 6004 is completely emptied by the cycler 14 before a new mixture is generated in the mixing reservoir.

Referring now also to FIG. 259, another example sheet 6640 of a mixing reservoir 6004 is depicted. The mixing reservoir 6004 is similar to that shown in FIG. 257, however, a flat temperature sensor contact region 6656 of the mixing reservoir 6004 is included. This temperature sensor contact region 6656 may rest on a temperature sensing portion of the heater pan 142 (see, e.g. FIG. 84). The temperature sensor contact region 6656 may be recessed with respect to the pattern units 6652. In some embodiments, the temperature sensor contact region 6656 may be recessed a greater amount than the gaps 6654. Thus, when the mixing reservoir 6004 is in a collapsed state, the temperature sensor contract region 6656 may define a volume which is in communication with the network of fluid channels formed by the gaps 6654 between the pattern units 6652. This volume may ensure that liquid is present in the vicinity of the temperature sensor while there is still liquid present in the mixing reservoir 6004.

Referring now to FIG. 260, the pattern included in the mixing reservoir 6004 need not be a uniform pattern. For example, the pattern may be a branching tributary type pattern similar to the venation of a leaf. Each branch 6660A, B in the pattern may be thermoformed to establish flow channels when the mixing reservoir 6004 is in a collapsed state. There may be a plurality of branches 6660A, B flow channel sizes. Each branch 6660A, B in the pattern may be in fluid communication (potentially through other branches) to a main branch (not shown) or a hub 6662. The hub 6662 may be located in a temperature sensor contact region of the mixing reservoir 6004 and may be formed similar to the temperature sensor contact region 6656 described above in relation to FIG. 259. The hub 6662 may ensure that, when in the collapsed state, fluid leaving the mixing reservoir 6004 is caused to pass over a region of the mixing reservoir 6004 resting on a temperature sensor of the heater pan 142 (see, e.g., FIG. 84) before exiting the mixing reservoir 6004. This may facilitate temperature sensing of fluid in the mixing reservoir 6004 when the mixing reservoir 6004 is in the collapsed state.

Each successive branch 6660A, B in the pattern may be of smaller caliber than the previous branch 6660A, B. Any branch 6660A, B extending directly from the main branch or hub 6662 may branch at least once before the smallest tributary size is reached. In the example, a plurality of primary branches 6660A extend from the hub 6662. Each of these branches 6660A may have at least one secondary branch 6660B which extends therefrom. In some embodiments, tertiary, quaternary, etc. branches may also be included. The secondary branches 6660B may be extended from the primary branches 6660A in symmetric fashion. That is, secondary branches 6660B (or any tributary branch to a larger branch) may be placed in pairs, extending from substantially the same point on a given primary branch 6660A but to opposite sides of the primary branch 6660A. In other embodiments, secondary branches 6660B may be disposed asymmetrically about a primary branch 6660A. In some embodiments, branching from the primary branches 6660A may not be present. Instead, a number primary branches 6660A may be arranged parallel to accomplish the same.

In some embodiments, the outlet line 6664 to the mixing reservoir 6004 may include an interior portion 6666 which extends into the interior volume of the mixing reservoir 6004. In the example embodiment in FIG. 260, the interior portion 6666 extends to the hub 6662 such that the outlet line may be in direct fluid communication with the hub 6662 volume. Thus, when the mixing reservoir 6004 is in a collapsed state, residual fluid may still be able to be removed from the mixing reservoir 6004 via the outlet line 6664.

Osmotic Agent Concentration Sensor

Referring now to FIG. 261, some embodiments may include a flow composition sensor or concentration sensor 6360 for one or more source component 6000 in a formulation prescription. The source component 6000 may be an osmotic agent which is substantially electrolyte free or may be an agent which, when dissolved, yields a solution with little ionic content. The osmotic agent may be a sugar such as dextrose. The concentration sensor 6360 may sense an optical property of fluid containing the source to determine its concentration. Additionally, the concentration sensor 6360 may be a non-invasive sensor which collects data to determine the concentration without being in direct contact with the solution. Concentration may, for example, be sensed through the wall of a fluid line 6362, fluid containing bag, or other fluid reservoir. In some embodiments, the concentration sensor may be one of those shown and described in U.S. Pat. No. 9,310,314, Filed Feb. 9, 2015, Issued Apr. 12, 2016, and entitled "Apparatus and Methods for Concentration Determination Using Polarized Light" which is hereby incorporated by reference herein in its entirety.

The example concentration sensor 6360 shown in FIG. 261 includes a fluid line holder which may include a base member 6364 and a retainer 6366. Though in the example, the concentration sensor 6360 is shown as a stand alone sensor module, one or both of the base member 6364 and retainer 6366 may be included as part of the cycler 14. For example, either may be formed integral to the housing 82 of the cycler 14. The base member 6364 may include a recess 6372 which is sized to receive the retainer 6366 when the sensor is fully assembled. The base member 6364, retainer 6366 or both may include a channel 6368. In the example embodiment, both the base member 6364 and retainer 6366 include a channel 6368 which cooperate to surround a portion of a fluid line 6362 when the fluid line 6362 has been placed into the concentration sensor 6360.

The base member 6364 and retainer 6366 may include a coupler which, when engaged, holds the base member 6364 and retainer 6366 together. The coupler may also help to provide repeatable positioning of the fluid line 6362. The coupler may be a fastener, clip or clamp, snap fit, friction fit, hook and loop tape, etc. In the example, the coupler is magnetic and one or both of the base member 6364 and retainer 6366 may include at least one magnet 6370 which attracts a piece of metal or magnet in the other of the base member 6364 and retainer 6366. The retainer 6366 and base member 6364 may also be physically attached via a connector in order to prevent loss of one of the components. In some embodiments, the connector may be a hinge (not shown) located on an edge 6374, 6376, 6378 of the receiving recess 6372 of the base member 6364.

The concentration sensor 6360 includes cavities or pathways 6380A, B which terminate at the wall of the channel 6368. The cavities 6380A, B may be disposed on opposing sides of the concentration sensor 6360 and may be positioned such that their termination points at the channel 6368 wall are substantially coaxially. The cavities 6380A, B may house a light emission assembly 6382 and a light detection assembly 6384. The light emission assembly 6382 may project light into the fluid line 6362 as well as detect the intensity of the light being projected into the fluid line 6362. The light detection assembly 6384 may detect the intensity of light which has passed through the fluid line 6362. The amount of light absorbed as it passes through the fluid in the fluid line 6362 may be proportional to the length of the path between the emission assembly 6382 and the detection assembly 6364 as well as the concentration of the source component 6000 of interest. As the concentration detector 6360 keeps the path length constant, variation in the intensity of light received at the detection assembly 6364 should be due to changes in the composition of fluid within the fluid line 6362. The path length may be greater than or equal to 2.5 inches, 3 inches, 4 inches or more.

The light emission assembly 6382 may include an LED and phototransitor. The LED may emit light at a frequency which is absorbed by the source component 6000 of interest. The absorbance may, for example, be due to molecular bond vibration and/or electron energy state promotion. The LED may be a UV/Vis producing LED. The UV/Vis wavelength may be selected to be at or near an absorbance peak (e.g. $\lambda_{max}$) for the source component 6000 of interest. The LED may emit light at a wavelength of 405 nm+/−40 nm for example. Preferably, the LED includes a non-diffusion lens. In some specific examples, the LED may be a VLMU3100 UV Emitter available from Vishay Semiconductors headquartered at Vishay Intertechnology, Inc. 63 Lancaster Avenue Malvern, PA 19355. A UV3TZ-405-15 UV emitter available from Bivar Inc. and headquartered in Irving, CA may also be used.

The phototransitor used in the emission assembly 6382 and the detector assembly 6384 may be the same and may be chosen based on the emission wavelength. The wavelength of maximum sensitivity may be chosen to be the same as or near the emission wavelength of the LED. Where the emitter is a UV/Vis emitter, the phototransitor may be sensitive to a spectral range corresponding to the UV/Vis range or between ~350 nm-950 nm. The phototransitors may, in some specific embodiments, be SFH 3310 Phototransistors available from OSRAM located at 28845 Cabot Drive Novi, MI 48377.

To help prevent a loss in optical signal due to diffraction at the bend regions 6386 of the fluid line 6362, the channel 6368 may be formed to optimize the shape of the bend regions 6386 of the fluid line 6362. When the fluid line 6362 is placed into the channel 6368 and retained by the retainer 6364, the path of the channel 6368 may constrain the fluid line 6362 in a retained configuration. The retained configuration may force the bends regions 6386 of the fluid line 6362 to conform to a specific optimized geometry. The geometry which provides the best signal to noise ratio may be empirically determined.

The angle of the cavities 6380A, B with respect to their termination point at the channel 6368 wall may also be at a detector irradiance optimizing angle which accounts for boundary behaviors (e.g. refraction) of emitted light in the pathway between the emitter 6382 and detector 6384. The detector irradiance optimizing angle may be selected based on anticipated or empirically observed bending of the emitted light path. This angle may be chosen such that the bending redirects emitted light onto the detector 6384. The angle of the cavity 6380A, B for the emitter 6382 and detector 6384 may be the same or may differ depending on the embodiment.

FIG. 262 depicts an example plot 6390 depicting data 6392 collected from a YSI 2300 Glucose analyzer and data 6394 collected from an example concentration sensor 6360 similar to that described in relation to FIG. 261. In the example plot 6390, dialysate solutions including varying concentrations of dextrose were measured. Each data point on the plot 6390 was created from an average of several different data points collected for the same solution. As shown, the example concentration sensor 6360 detected about a 50 mV difference between a 1.5% and 2.5% dextrose solution. An about 135 mV difference was detected between a 2.5% and 4.25% dextrose solution. As would be appreciated by one skilled in the art, a curve fit could be employed to relate the mV reading of the example concentration sensor 6360 to the reference reading provided by the YSI 2300 analyzer.

While aspects of the disclosure have been described in conjunction with specific embodiments thereof, it is evident that many alternatives, modifications, and variations will be apparent to those skilled in the art. Accordingly, embodiments of the disclosure as set forth herein are intended to be illustrative, not limiting. Various changes may be made without departing from the spirit and scope of the disclosure.

What is claimed is:

1. A cassette based fluid pumping system comprising:
a pumping cassette having a first side including a plurality of valve wells and a second side having a fluid bus, the first and second side each covered by a flexible membrane;
a control surface having a plurality of valve well control stations actuatable with respect to the flexible membrane covering the first side of the cassette to open and close the plurality of valve wells when the cassette is mated against the control surface; and
a pressure distribution assembly having a positive and a negative pressure source and a number of pneumatic valves; and
a controller configured to selectively actuate the number of pneumatic valves to apply pressure against the plurality of valve well control stations in a valve pumping sequence causing the plurality of valve wells to be opened and closed in sequence so as to pump fluid through the fluid bus of the pumping cassette from a source to a destination until a volume of the fluid displaced through the fluid bus of the pumping cassette from the source to the destination is within a range of a target volume.

2. The system of claim 1, wherein the destination is selected from a list consisting of a mixing reservoir in fluid communication with the cassette, a heater bag in fluid communication with the cassette, and a pump chamber disposed within the pumping cassette.

3. The system of claim 1, wherein the source is selected from a list consisting of a pump chamber disposed within the pumping cassette, and a source component in fluid communication with the cassette.

4. The system of claim 1, wherein the source is a source component containing one of a component from a list consisting of a buffer solution, an acid solution, a purified water source, and a dialysate concentrate.

5. The system of claim 1, wherein each valve pumping sequence transfers under 150 microliters.

6. The system of claim 1, wherein each valve pumping sequence transfers a nominal volume of 70 microliters.

7. The system of claim 1, wherein at least one of the plurality of valve wells is a dedicated holding volume valve well.

8. The system of claim 1, wherein the pumping cassette includes a pump chamber on the first side of the pumping cassette, the control surface includes a pump chamber control region adjacent the pump chamber when the cassette is mated against the control surface, and the controller is further configured to apply negative pressure to the pump chamber control region via actuation of the pneumatic valves while selectively actuating the plurality of pneumatic valves to apply pressure against the plurality of valve well control stations in a valve pumping sequence.

9. The system of claim 8, wherein the controller configured to monitor the volume of the pump chamber while selectively actuating the plurality of pneumatic valves to apply pressure against the plurality of valve well control stations in a valve pumping sequence via a pressure sensor disposed in a volume bounded at least partially by the pump chamber control region.

10. The system according to claim 1, wherein the pumping cassette is devoid of pump chambers.

11. The system according to claim 1, wherein all of the plurality of valve wells include volcano valves.

12. The system according to claim 1, wherein the plurality of valve wells includes a first valve well, a second valve well, and a third valve well.

13. The system according to claim 1, wherein the control surface is configured to fluidly isolate the plurality of valve wells from each other when the control surface is mated against the flexible membrane covering the first side of the cassette.

\* \* \* \* \*